US007426441B2

(12) United States Patent
Mendrick et al.

(10) Patent No.: US 7,426,441 B2
(45) Date of Patent: *Sep. 16, 2008

(54) METHODS FOR DETERMINING RENAL TOXINS

(75) Inventors: Donna Mendrick, Gaithersburg, MD (US); Mark Porter, Gaithersburg, MD (US); Kory Johnson, Gaithersburg, MD (US); Brandon Higgs, Gaithersburg, MD (US); Arthur Castle, Gaithersburg, MD (US); Michael Elashoff, Gaithersburg, MD (US)

(73) Assignee: Ocimum Biosolutions, Inc., Indianapolis, IN (US)

( * ) Notice: Subject to any disclaimer, the term of this patent is extended or adjusted under 35 U.S.C. 154(b) by 286 days.

This patent is subject to a terminal disclaimer.

(21) Appl. No.: 11/036,196

(22) Filed: Jan. 18, 2005

(65) Prior Publication Data

US 2006/0078900 A1   Apr. 13, 2006

Related U.S. Application Data

(62) Division of application No. 10/152,319, filed on May 22, 2002.

(60) Provisional application No. 60/292,335, filed on May 22, 2001, provisional application No. 60/297,523, filed on Jun. 13, 2001, provisional application No. 60/298,925, filed on Jun. 19, 2001, provisional application No. 60/303,810, filed on Jul. 10, 2001, provisional application No. 60/303,807, filed on Jul. 10, 2001, provisional application No. 60/303,808, filed on Jul. 10, 2001, provisional application No. 60/315,047, filed on Aug. 28, 2001, provisional application No. 60/324,928, filed on Sep. 27, 2001, provisional application No. 60/330,867, filed on Nov. 1, 2001, provisional application No. 60/330,462, filed on Oct. 22, 2001, provisional application No. 60/331,805, filed on Nov. 21, 2001, provisional application No. 60/336,144, filed on Dec. 6, 2001, provisional application No. 60/340,873, filed on Dec. 19, 2001, provisional application No. 60/357,843, filed on Feb. 21, 2002, provisional application No. 60/357,842, filed on Feb. 21, 2002, provisional application No. 60/357,844, filed on Feb. 21, 2002, provisional application No. 60/364,134, filed on Mar. 15, 2002, provisional application No. 60/370,206, filed on Apr. 8, 2002, provisional application No. 60/370,247, filed on Apr. 8, 2002, provisional application No. 60/370,144, filed on Apr. 8, 2002, provisional application No. 60/371,679, filed on Apr. 12, 2002, provisional application No. 60/372,794, filed on Apr. 17, 2002.

(51) Int. Cl.
*G06F 19/00* (2006.01)

(52) U.S. Cl. .............................. 702/19; 435/6; 700/30; 702/22; 707/104.1

(58) Field of Classification Search ....................... None
See application file for complete search history.

(56) References Cited

U.S. PATENT DOCUMENTS

| | | | |
|---|---|---|---|
| 5,811,231 A | 9/1998 | Farr et al. | |
| 5,858,659 A | 1/1999 | Sapolsky et al. | |
| 5,953,727 A | 9/1999 | Maslyn et al. | ............... 707/104 |
| 5,965,352 A | 10/1999 | Stoughton et al. | ............... 435/4 |
| 6,132,969 A | 10/2000 | Stoughton et al. | |
| 6,153,421 A | 11/2000 | Yanagi et al. | |
| 6,160,105 A | 12/2000 | Cunningham et al. | ....... 536/23.1 |
| 6,185,561 B1 | 2/2001 | Balaban et al. | ................. 707/6 |
| 6,203,987 B1 | 3/2001 | Friend et al. | |
| 6,218,122 B1 | 4/2001 | Friend et al. | |
| 6,228,589 B1 | 5/2001 | Brenner | |
| 6,229,911 B1 | 5/2001 | Balaban et al. | ............. 382/128 |
| 6,365,352 B1 | 4/2002 | Yerramilli et al. | |
| 6,372,431 B1 | 4/2002 | Cunningham et al. | |
| 6,403,778 B1 | 6/2002 | Cunningham et al. | |
| 6,421,612 B1 | 7/2002 | Agrafiotis et al. | |
| 6,461,807 B1 | 10/2002 | Friend et al. | |
| 2001/0039006 A1 | 11/2001 | Snodgrass | |
| 2001/0049139 A1 | 12/2001 | Lagasse et al. | |
| 2002/0119462 A1 | 8/2002 | Mendrick et al. | |
| 2002/0142284 A1 | 10/2002 | Raha et al. | |
| 2003/0028327 A1 | 2/2003 | Brunner et al. | |

(Continued)

FOREIGN PATENT DOCUMENTS

WO   WO 93/01205   1/1993

(Continued)

OTHER PUBLICATIONS

"nephrotoxic" definition, Merriam-Webster online dictionary, 2005, on the world wide web at http://www.m-w.com/cgi-bin/dictionary?book=Dictionary&va=nephrotoxic, 2 pages.

(Continued)

*Primary Examiner*—Carolyn L. Smith
(74) *Attorney, Agent, or Firm*—Cooley Godward Kronish LLP

(57) ABSTRACT

The present invention is based on the elucidation of the global changes in gene expression and the identification of toxicity markers in tissues or cells exposed to a known renal toxin. The genes may be used as toxicity markers in drug screening and toxicity assays. The invention includes a database of genes characterized by toxin-induced differential expression that is designed for use with microarrays and other solid-phase probes.

14 Claims, No Drawings

U.S. PATENT DOCUMENTS

| | | |
|---|---|---|
| 2003/0124552 A1 | 7/2003 | Lindemann et al. |
| 2003/0154032 A1 | 8/2003 | Pittman et al. |

FOREIGN PATENT DOCUMENTS

| | | |
|---|---|---|
| WO | WO 94/17208 | 4/1994 |
| WO | WO 95/11755 | 5/1995 |
| WO | WO 97/13877 | 4/1997 |
| WO | WO 97/16732 | 5/1997 |
| WO | WO 99/12118 | 3/1999 |
| WO | WO 99/27090 | 6/1999 |
| WO | WO 99/32660 | 7/1999 |
| WO | WO 99/43345 | 9/1999 |
| WO | WO 99/58670 | 11/1999 |
| WO | WO 00/28092 | 5/2000 |
| WO | WO 00/39336 | 7/2000 |
| WO | WO 00/47761 | 8/2000 |
| WO | WO 00/12760 | 9/2000 |
| WO | WO 00/63435 | 10/2000 |
| WO | WO 01/02609 | 1/2001 |
| WO | WO 01/11076 | 2/2001 |
| WO | WO 01/14425 | 3/2001 |
| WO | WO 01/20043 | 3/2001 |
| WO | WO 01/23886 | 4/2001 |
| WO | WO 01/25473 | 4/2001 |
| WO | WO 01/32928 | 5/2001 |
| WO | WO 01/36684 | 5/2001 |
| WO | WO 01/38579 | 5/2001 |
| WO | WO 01/44512 | 6/2001 |
| WO | WO 01/63279 | 8/2001 |
| WO | WO 02/31704 | 4/2002 |
| WO | WO 03/085083 | 10/2003 |
| WO | WO 03/095624 | 11/2003 |
| WO | WO 03/100030 | 12/2003 |

OTHER PUBLICATIONS

Aardema and MacGregor, Mutation Res., 499:13-25, (2002).
Adamson & Harman et al., Biochem. Pharmacol., 45:2289-2294 (1993).
Affymetrix Rat Toxicology U34 Datasheet, released Aug. 1999.
Afshari et al., Cancer Res., 59: 4759-4760 (1999).
Agha et al., Lipid Peroxidation and Lysosomal Integrity ; 31., 279-285 (1995).
Ahotupa et al., Carcinogenesis., 15: 863-868 (1994).
Ala-Kokko et al., Biochem. J., 244:75-79, (1987).
Al-Bayati & Stohs, Arch. Environ. Contam. Toxicol., 20:361-365 (1991).
Allan et al., J. Biol. Chem.., 276: 27272-27280 (2001).
Amelsen, Jean Claude., Setting death in motion , vol. 395, (1998).
Anderson & Barton, Environ. Health Perspect., 106: 349-355 (1998).
Anderson et al., Toxicol. Appl. Pharmacol., 137: 75-89 (1996).
Anderson, Steven P., Hepatic Expression of Acute-Phase Protein, 26: 226-238 (1999).
Andersson et al; Anthraquinone-induced cell injury; 135: 11-20 (1999).
Anton et al., Cell Biochem. Biophys., 32: 27-36 (2000) Abstract only.
Arano et al ., Arzneim-Forsch./Drug, 46 : 398-400 (1996).
Atchinson et al., Digestive Dis. Sci., 45: 614-620 (2000).
Bajgar et al., Neurochem. Int., 24: 555-558 (1994).
Baker et al., Chem. Res. Toxicol., 14(9): 1218-1231 (2001)
Bandara, et al., Toxicol. Sci., 73:195-206, (2003).
Barner & Gray, Ann. Pharmacother., 32: 70-77 (1998).
Bartosiewicz et al., J. Pharmacol. Exp. Ther., 297: 895-905 (2001).
Beck et al, Arch. Toxicol., 64: 210-217 (1990).
Becker et al., Alzheimer Dis. Assoc. Disord., 10 : 124-131 (1996).
Bedard et al., Antimicrob. Agents Chemother., 43: 557-567 (1999).
Bedossa et al., Hepatology, 19: 1262-1271 (1994).
Beierschmitt, William P., Induction of Hepatic Microsomal Drug-Metabolizing;, 15-21, 2001.
Belury et al., Toxicol. Appl. Pharmacol., 151: 254-261 (1998).

Berbner et al., "induction of cytochrome P450 IA and NDA damage in isolated rainbow trout (Onchorhynchus mykiss) hepatocytes by 2, 3, 7, 8-tetrachlorodibenzo p-dioxin," Biomarkers 4: 214-228 (1999).
Bergeron et al., Xenobiotica, 28: 303-312 (1998).
Berndt et al., Proc. Natl. Acad. Sci. U.S.A.., 95: 12556-12561 (1998).
Birge et al., Toxicol. Appl. Pharmacol., 105: 472-482 (1990).
Bissig et al., "Functional expression cloning of the canalicular sulfate transport system of rat hepatocytes," J Biol Chem 269(4):3017-3021, 1994.
Boelsterli et al., Cell Biol, Toxicol., 3: 231-250 (1987).
Boess, et al., Toxicological Sciences, 73:386-402, (2003).
Bogdan, "Human carbon catabolite repressor protein (CCR4)-associative factor 1: cloning, expression and characterization of its interaction with the B-cell translocation protien BTG1,"Biochem. J. 336:471-481 (1998).
Boon, et al., Proc. Natl. Acad. Sci. USA, 99(17):11287-11292, (2002).
Boorman et al., "Toxicogenomics, Drug Discovery, and the Pathologist," Toxicologic Pathology 30(1): 15-27 (2002).
Bort et al., J. Pharmacol. Exp. Ther., 288: 65-72 (1999).
Bosio and Borlak, Innovations in Pharmaceutical Technology, 65-75, 2001.
Bouchard et al., Liver, 13: 193-202 (1993).
Bramow, Stephan, et al., Pharmacol. & Toxicol., 89:133-139, (2001).
Browne, et al., Targets, 1(2):59-65, (2002).
Bruck et al., Dig. Dis. Sci., 44: 1228-1235 (1999).
Bulera, S.J., et al., Hepatology, 33:1239-1258, (2001).
Burchiel et al., Toxicol. Sci., 59: 193-195 (2001).
Burczynski & Penning, Cancer Res., 60: 908-915 (2000) Abstract only.
Burczynski (Editor), "An Introduction to Toxicogenomics," Wyeth Research, Andover, MA, CRC Press pp. 226-259, (Pub. 2003).
Burczynski et al., Toxicol. Sci., 58:399-415 (2000).
Burris, Hicken and Farr, Genetic Engineering News, May 1, 1999, pp. 42-43, (1999).
Bursch et al., Arch. Toxicol., 69: 253-258 (1995).
Buttar et al., Toxicology., 6: 9-20 (1976).
Butterworth et al., Cancer Res., 49: 1075-1084 (1989).
Cadet, et al., Synapset, 44:211-226 (2002).
Cai et al., J. Med. Chem., 41: 1970-1979 (1998).
Calabrese et al., J. Amer. College Toxicol., 15: 62-69 (1996).
Castell et al., Cell Biol. Toxicol., 13: 331-338 (1997).
Castle, A., et al., "Apex Necrosis," Soc. Of Tox. Mtg. (2004).
Castle, A., et al., "Effects of Multiple Cardiac Apex Necrosis Agents on Genome Wide Expression," Soc. Of Tox. Mtg. (2003) Abstract only.
Castle, A.L., et al., "Liver Toxicity Prediction and Classification Using Microarray Data: . . . ," Soc. Of. Tox. Mtg., (2002).
Castle, Carver & Mendrick, Drug Disc. Today, 7(13):728-736, (2002).
Chan et al., Proc. Natl. Acad. Sci. U.S.A.., 98: 4611-4616 (2001).
Chanda et al., Hepatology, 21: 477-486 (1995).
Chen et al., J. Biol. Chem.., 275: 22619-22622 (2000).
Chen et al., J. Environ. Pathol. Toxicol. Oncol., 14: 83-99 (1995) Abstract only.
Chen, et al., Mol. Carcinog. 30:79-87, (2001).
Chisholm et al., Am. J. Physiol., 276: G1165-G1173 (1999).
Chou et al., Proc. Natl. Acad. Sci. U.S.A.., 98: 8113-8118 (2001).
Christian et al., Toxicol. Appl. Pharmacol., 82: 239-255 (1986).
Clive et al., Fundam. Appl. Toxicol., 3: 587-602 (1983).
Coles et al., Arch. Biochem. Biophys., 264: 253-260 (1988).
Conforti et al., Agents Actions, 40: 176-180 (1993).
Coni et al., Hepatology, 17: 1109-1116 (1993).
Copenhagen et al., Journal of Hepatology; 30:1 pg. (1999).
Corell et al., Acta Pharmacol. Toxicol. (Copenh), 45: 232-239 (1979).
Corton & Stauber, Toxicol. Sci., 58: 217-219 (2000).
Corton et al., Biochimie., 79: 151-162 (1997).
Corton et al., Cancer Lett., 134: 61-71 (1998).
Corton et al., Cancer Lett., 137: 9-15 (1999).
Corton et al., Mol. Pharmacol., 54: 463-473 (1998).
Cronin, M.T.D., IL Farmaco, 56:149-151, (2001).
Crosby et al., Toxicol. Appl. Pharmacol., 169: 205-221 (2000).
Cunningham et al., Ann. N.Y. Acad. Sci., 919: 52-67 (2000).

Cunningham, M.J., J. of Pharmacol. And Toxicol. Methods, 44:291-300, (2000).
Cutler, P., et al., Electrophoresis, 20:3647-3658, (1999).
D'Mello et al., Exp. Toxicol. Pathol., 51: 549-553 (1999).
Daniels, K., "Toxicogenomics: Database Construction, Predictive Modeling & Biomarker Discovery," U.S. Army-13 7th Annual Health Protection Conf. (2004) Abstract only.
Daniels, K., "Toxicogenomics: The Application of Gene Expression in Transforming Toxicology Scrrening," U.S. Army Center for Health Promotion & Preventive Medicine Seminar, (2004).
Database Geneseq [online], "Sindbis virus genomic cDNA PCR primer SEQ ID NO:3," Database Accession No. AAZ92894, retrieved from EBI Accession No. GSN:AAZ92894 (2000).
Database Geneseq 'Online!, "Reverse transcription primer used in cDNA anaysis technique," Database Accession No. AAQ75569, retrieved from EBI Accession No. GSN:AAQ75569 (1995).
Davila et al., Toxicology., 57: 267-286 (1989).
Davis et al., Cancer Res., 60: 2887-2891 (2000).
De Fabiani et al., J. Biol. Chem., 276: 30708-30716 (2001).
Del Giudice et al., IL Farmaco., 51: 693-698 (1996).
Delaney & Timbrell, Xenobiotica, 25: 1399-1410 (1995).
Demeule, Brossard and Beliveau, Am. J. Physiol. Renal Physiol. 277:F832-F840, (1999).
Diel et al., J. Steroid Biochem. Mol. Biol., 7: 1-10 (2000).
Diez-Fernandez, et al., Biochem. Pharmacol., 51:1159-1163, (1996).
Dodds & Rivory, Mol. Pharmacol., 56: 1346-1353 (1999).
Dos Santos et al., J. Am. Soc. Nephrol., 8: 361-367 (1997).
Duivenvoorden et al., Biochem. Biophys. Res. Commun., 215(2): 598-605 (1995).
Dutar et al., Brain Res., 527: 32-40 (1990).
Eadie et al., Med. Toxicol. Adverse Drug Exp., 3: 85-106 (1988).
Eikmans, et al., Kidey Int'l, 62:1125-1135, (2002).
Eldridge et al., Carcinogenesis, 11: 2245-2251 (1990).
Ellis & Isaacs, Cancer Res., 45: 6041-6050 (1985).
Emmison et al., Biochim. Biophys. Acta, 1083: 147-152 (1991).
Enomoto et al., Toxicol. Sci., 59: 169-177 (2001).
Evans & Relling, Science, 286:487-491, (1991).
Falzon et al., Br. J. Exp. Pathol., 66: 527-534 (1985).
Fan & Rozman, Toxicol. Lett., 75: 209-216 (1995).
Fan et al., J. Biol. Chem.., 271: 24698-24710 (1996).
Farag & Hassib, Clin. Sci. (Lond), 84: 387-390 (1993).
Farghali et al., Methods Find. Exp. Clin. Pharmacol., 6: 449-454 (1984).
Farr & Dunn, Toxicol. Sci., 50: 1-9 (1999).
Farr et al., "Concise review: gene expression applied to toxicology," Toxicol Sci 50(1):1-9, 1999.
Fernandez-Tome & Sterin-Speziale, Pharmacology, 48: 341-348 (1994).
Ficazzola et al., Carcinogenesis, 22: 1271-1279 (2001).
Fielden & Zacharewski, Toxicol. Sci., 60: 6-10 (2001).
Fitten et al., J. Gerontol., 42: 681-685 (1987).
Forestier et al., Biochem. Biophys. Res. Commun., 225: 377-383 (1996).
Fracasso et al., Agents Actions, 22: 3-4 (1987).
Fracasso et al., Agents Actions, 31: 313-316 (1990).
Frazier JM, Predictive Toxicodynamics: Empirical/machanistic approaches, Toxicology in Vitro, 1997. pp. 465-472, vol. II.
Froesch et al., J. Biol. Chem.., 274: 6469-6475 (1999).
Frueh et al., Mol. Pharmacol., 51: 363-399 (1997).
Fulgencio et al., Biochem. Pharmacol., 62: 439-446 (2001).
Furr, Ann. N.Y. Acad. Sci., 761: 79-96 (1995).
Furr, Eur. Urol., 29: 83-95 (1996).
Gallagher, et al., Toxicol. And Appl. Pharmacol. 134:81-91, (1995).
Ganem & Jefcoate, Toxicol. Appl. Pharmacol., 150: 68-75 (1998).
Garcia-Allan et al., J. Biochem. Mol. Toxicol.., 14: 65-72 (2000).
Geiger et al., Agents Actions, 38: Spec No: C69-72 (1993) Abstract only.
GenBank Accession No. AA799479 (Apr. 30, 1998).
GenBank Accession No. AA891812 (Jan. 25, 1999).
GenBank Accession No. A1177366 (Jan. 20, 1999).
GenBank Accession No. L23413, Bissig et al., "Rattus norvegicus sulfate anion transporter (sat-1) mRNA," Apr. 12, 1994.
GenBank Accession No. L26268, Raburn et al., "Rattus norvegicus anti-proliferative factor (BTGI) mRNA," Jan. 26, 1996.
GenBank Accession No. M25823 (Apr. 27, 1993).
Genes on Clontech Atlas Human Stress/Toxicology Array from e-mail/ website dated Oct. 29, 1998.
Gerhold et al., Physiol. Genomics, 5: 161-170 (2001).
Ghatineh & Timbrell, Biochem. Soc. Trans., 18: 1217-1218 (1990).
Ghatineh et al., Arch Toxicol., 66: 660-668 (1992).
Gobe, G., et al., J. Am. Soc. Nephrot., 11:454-467, (2000).
Goll et al., Toxicol. Appl. Pharmacol., 160: 21-32 (1999).
Golub et al., "Molecular Classification of Cancer: Class Discovery and Class Prediction by gene Expression monitoring," Science 285:531-537 (1999).
Gombar et al. Assesment of Developmental Toxicity Potential of Chemicals by Quantitative Structure-Toxicity Relationship Models, Chemosphere, 1995, vol. 31, No. 1, pp. 2499-2510.
Gomez-Lechon, et al., Toxicol. Sciences, 65:299-308, (2002).
Gooderham et al., "Molecular and genetic toxicology of 2-amino-1-methyl-6-phenylimidazo[4,5-*b*]pyridine PhIP)," Mutation Research 506-507:91-99 (2001).
Gram & Bentsen, Acta Neurol. Scand. Suppl., 97: 81-90 (1983).
Greaves et al., Cancer Res., 53: 3919-3924 (1993).
Green et al., Toxicol. Appl. Pharmacol., 76: 139-149 (1984).
Grigg, Environmental Health Inst. to use gene chips to evaluate chemicals for potential harm to humans NEIHS, Feb. 29, 2000, entire document.
Guardavaccaro et al., Mol. Cell. Biol., 20: 1797-1815 (2000).
Guarner et al., Liver, 5: 35-39 (1985) Abstract only.
Hamada et al., Hepatology, 21: 1455-1464 (1995).
Hamada et al., J. Hepatol., 30: 807-818 (1999).
Hamadah, et al., Toxicol. Sciences, 67:232-240, (2002).
Hamaya, Y., et al., Anesth. Analg., 90:1177-1183, (2000).
Hargus et al., Chem. Res. Toxicol., 7: 575-582 (1994).
Hargus et al., Chem. Res. Toxicol., 8: 993-996 (1995).
Harries et al., Toxicol. In Vitro, 15: 399-405 (2001).
Harris et al., "Comparison of basal gene expression profiles and effects of hepatocarcinogens on gene expression in cultured primary human hepatocytes and HepG2 cells," Mutation Research 539:79-99 (2004).
Hartmann, et al., J. of Pharma. And Experim. Therap., 303:273-281, (2002).
Hartung & Wendel, Biochem. Pharmacol., 42: 1129-1135 (1991).
Hasegawa et al., Gan To Kagaku Ryoho 30:325-333 abstract (2003).
Hassett et al., Biochem. Pharmacol., 55: 1059-1069 (1998) Abstract only.
Hayashi et al., Biochim. Biophys. Acta., 879: 140-148 (1986) Abstract only.
He et al., J. Biol. Chem.., 276: 20858-20865 (2001).
He, et al., J. Clin. Invest., 108: 1321-1330 (2001).
Hellriegel et al., Biochem. Pharmacol., 52: 1561-1568 (1996).
Henger and Kretzler, et al., Kidney Int'l, 65:904-917, (2004).
Hessel et al., Braz. J. Med. Biol. Res., 29: 793-796 (1996).
Hewitt, et al., J. Am. Soc. Nephrol. 15:1677-1689, (2004) Abstract only.
Higgs, B., et al., "Effects of Rat Gender and Strain on Elucidating Liver Toxicity," Soc. Of Tox. Mtg., (2003) Abstract only.
Hildebrand et al., Arch. Toxicol., 73: 233-245 (1999) Abstract only.
Hillstrom et al., Proc. Soc. Exp. Biol. Med., 200: 122-126, 1992.
Hissink et al., Chem. Res. Toxicol., 9: 1249-1256 (1996).
Hoebe et al., Vet. Q., 22: 21-25 (2000) Abstract only.
Hogstrand et al., "Application of genomics and proteomics for study of the integrated response to zinc exposure in a non-model fish species, the rainbow trout," Comparative Biochemistry and Physiology Part B 133:523-535 (2002).
Hogue, Chemical and Engineering News, 79: 33-34 (2001).
Hoshi et al., Jpn. J. Pharmacol., 50: 289-293 (1989).
Huang, et al., Toxicol. Sciences, 63:196-207, (2001).
Hunter et al., Br. J. Pharmacol., 98: 79-86 (1989).
Hwang, et al., Biochem. And Biophys. Res. Commun., 146(I):87-93, (1987).
Iida, et al., Carcinogenesis, 24(4):757-770, (2003).
Inohara et al., EMBO J., 17: 2526-2533 (1998).

International Search Report in Applicant's corresponding PCT application, WO 02/095000 A3, published Nov. 28, 2002.
International Search Report in Applicants' PCT Application No. PCT/US01/23872, Mar. 21, 2003.
International Search Report in Applicants' PCT Application No. PCT/US05/34780, Mar. 30, 2006.
International Search Report in Applicants' PCT Application No. PCT/US04/39593, Mar. 8, 2006.
International Search Report in Applicants' PCT Application No. PCT/US05/11532, mailed Sep. 13, 2006.
Iredale et al., J. Clin. Invest., 102: 538-549 (1998).
Irizarry et al. (2003), "Summaries of Affymetrix GeneChip probe level data," Nucl. Acids Res 31(4):e15, 8 pp.
Iswaran et al., J. Toxicol. Sci., 22 75-88 (1997).
Itoh et al., Behav. Brain Res., 83: 165-167 (1997).
Itoh et al., Eur. J. Pharmacol., 322: 11-19 (1997).
Izumi et al., J. Biol. Chem.., 272: 7381-7389 (1997).
Jaeschke, et al., Toxicol. Sciences, 65:166-176 (2002).
Jakubczak et al., An Onolytic Adenovirus Selective for Retinoblastoma Tumor Suppressor Protein Pathway-Defective Tumors, Cancer Research, Apr. 1, 2003, vol. 63, pp. 1490-1499.
Jansen, Muller, and Sturm, Hepatology, 34(6):1067-1074 (2001).
Jean et al., Toxicol. Lett., 95: 155-163 (1998).
Jenner & Timbrell, Arch. Toxicol., 68: 349-357 (1994).
Jeon et al., Toxicol. Appl. Pharmacol., 144: 27-35 (1997).
Johnson and McMillian, 23rd Annual Mtg. Of the Amer. College of Toxicology, p. 532 (2002).
Johnson and Wolfgang, Current Topics in Med. Chem., 1(4):233-245, (2001).
Johnson, K., et al., "Predictive Modeling of Hepatotoxicants Using Microarrays and a Linear Discriminant Modeling Approach," ISMB Conf., Aug. 2002, (2002).
Johnston & Kroening, Pharmacol. Toxicol., 83: 231-239 (1998).
Jover et al., Toxic. in Vitro., 6: 47-52 (1992).
Kanaji et al., J. Cell Biol., 151: 277-288 (2000).
Kannan et al., Oncogene., 20: 2225-2234 (2001).
Karam & Ghanayem, Carcinogenesis, 18: 2077-2083 (1997).
Kasper & Mueller, Carcinogenesis, 17: 2271-2274 (1996).
Kawamoto, et al., Gene, 174:151-158 (1996).
Kesterson et al., Hepatology, 4: 1143-1152 (1984).
Kikuchi et al., Gene Expressions and Activities of Protein Phosphatases I alpha, 2A and 2C in Hepatocarcinogenesis and Regeneration After Partial Hepatectomy, Cancer Detection and Prevention, 1997, vol. 21(1), pp. 36-43.
Kim & Ziegler, Drug Metab. Dispos., 28: 1003-1006 (2000).
Kim et al., Drug Metab. Dispos., 26: 66-72 (1998).
Kim et al., Toxicol. Appl. Pharmacol., 102: 34-39 (1990).
Kim et al., Toxicology and Applied Pharmacology 176:118-126 (2001).
Kinbara et al., Scand. J. Gastroenterol., 32: 947-952 (1997).
Kingsley et al., Epilepsia, 21: 699-704 (1980).
Kingsley et al., J. Clin. Pharmacol., 23: 178-185 (1983).
Knapp et al., Am. J. Vet. Res., 56: 801-805 (1995).
Kocarek et al., Mol. Pharmacol., 54: 474-84 (1998).
Koga et al., Fukuoka Igaku Zasshi, 82: 197-206 (1991).
Kondo et al., Cancer Res., 50: 6222-6228 (1990).
Kongo et al., Toxicol. Lett., 105: 103-110 (1999).
Konstandi et al., "Stress-mediated modulation of B(alpha)P-induced hepatic CYPIA1: role of catecholamines," Chemico-Biological Interactions 147:abstract, (2004).
Koopen et al., Hepatology 27: 537-545 (1998).
Koopen et al., J. Lipid. Res., 40: 100-108 (1999).
Kossor et al., Biochem. Pharmacol., 46: 2061-2066 (1993).
Kossor et al., Fundam. Appl. Toxicol., 26: 51-62 (1995).
Kossor et al., Toxicol. Appl. Pharmacol., 119: 108-114 (1993).
Kretz-Rommel & Boelsterli, Toxicol, Appl. Pharmacol., 120: 155-161 (1993).
Kurota and Yamaguchi, Molec. And Cell. Biochem., 151:55-60, (1995).
Kwak et al., Mol. Med., 7: 135-145 (2001).
Kwon, et al., Am. J. Physiol. Renal Physiol. 279:F552-F564, (2000).
Lake et al., Toxicology., 131: 9-20 (1998).
Lake et al., Hepatic Effects of Phthalate Esters and Related., 67: pp. 283-290, (1986).
Lake, Annu. Rev. Pharmacol. Toxicol., 35: 483-507 (1995).
Lang et al., Alcohol Clin. Exp. Res., 22: 823-829 (1998).
Larsen & Jefcoate, Arch. Biochem. Biophys., 321: 467-476 (1995).
Lashkari et al., PNAS 94:13057-13062, (1997).
Laskin et al., Hepatology, 21: 1045-1050 (1995).
Lauredo et al., J. Appl. Physiol., 85: 2298-2304 (1998).
Lazartigues et al., Eur. J. Pharmacol., 361: 61-71 (1998).
LeBlank, G., et al., Cancer Research, 52:510-547, (1992).
Lecureur, V., et al., Toxicology, 153:203-219, (2000).
Lee et al., J. Pharm. Pharmacol., 52: 341-355 (2000).
Lees et al., Lipids, 30: 221-226 (1995).
Leifeld, et al., Amer. J. of Pathol., 154(6):1711-1720, (1999).
Lewis et al., Hepatology, 2: 870-873 (1982).
Li et al., Zhonghua Gan Zang Bing Za Zhi, 9: 103-104 (2001).
Liang et al., Zhonghua Gan Zang Bing Za Zhi, 7: 72-73 (1999).
Liu et al., Infect. Immun., 66: 5089-5098 (1998).
Liu et al., Mol. Cell. Biol., 20: 6105-6113 (2000).
Liu et al., Proc. Natl. Acad. Sci. U.S.A.., 98: 6192-6197 (2001).
Liu et al., SHOCK, 14: 361-365 (2000).
Lock et al., Toxicol. Lett., 10: 427-435 (1982).
Lorenzini et al., Carcinogenesis, 17: 1323-1329 (1996).
Lovett Science, 289: 536-537 (2000).
Lubman, et al., "What do the FDA and Pharma Companies Think of Toxicogenomics" (2002).
Lugovskoy et al., Cell, 99: 747-755 (1999).
Luhe, A., et al., Toxicol. Sciences, 73:315-328, (2003).
Lullmann & Lullmann-Rauch, Toxicol. Appl. Pharmacol., 61: 138-146 (1981).
MacGregor, et al., Toxicol. Sciences, 59:17-36, (2001).
Mahnke et al., Arch. Biochem. Biophys., 337: 62-68 (1997).
Mann, Toxicol. Pathol., 25: 72-79 (1997).
Manoukian & Carson, Drug Saf., 15: 64-71 (1996).
Mansfield, T., et al., Ann. Mtg. Of the Amer. College of Toxicol., p. 516.
Marketing Materials, "Symposium on Toxicogenomics Launches New National Academics Program," Emerging Issues, 2:1-7, (2003).
Markovich et al., "heavy metals mercury, cadmium, and chromium inhibit the activity if the mammalian liver and kidney sulfate transporter sat-1," Toxicol. Appl. Pharmacol. 154:181-187 (1999).
Martelli et al., J. Pharmacol. Exp. Ther., 273: 113-120 (1995).
Masubuchi et al., J. Pharmacol. Exp. Ther., 287: 208-213 (1998).
Masubuchi et al., J. Pharmacol. Exp. Ther., 292: 982-987 (2000).
Mattes, W., & Orr, M., "Concordance of Toxicogenomic Predictions and Mechanistics Analysis for compounds Tested in Both Rat Liver and Primary Rat Hepatocytes," LabFusion 2004 Presentation, (2004).
Mattes, W., et al., "Cross-Species Analysis of Phenobarbital-Induced Gene Expression Changes in Dog and Rat," Soc. Of Toxicol. Mtg. 2003, (2003) Abstract only.
Mattes, W., et al., "Cross-Species Analysis of Phenobarbital-Induced Gene Expression Changes in Dog and Rat," Soc. Of Toxicol. Mtg. 2004, (2004).
Mayeux & Sano, N. Engl. J Med., 341: 1670-1679 (1999).
Mayol et al., Carcinogenesis., 13: 2381-2388 (1992).
Maziasz et al., Toxicol. Appl. Pharmacol., 110: 365-373 (1991).
McKillop et al., Xenobiotica., 28: 465-478 (1998).
MDS Pharma Services Marketing Materials, "Pharmotif Solutions: Smart Decisions in Discovery and New Applications for Existing Drugs," 1-6, (2003).
Mendrick, D. L., ToxExpress, FDA-DIA Pharmacogenomics Workshop May 2002.
Mendrick, D., "Discovery of Relevant biomarkers for Nonclinical and Clinical Applications," American College of Toxicology Mtg. Nov. 8, 2004.
Mendrick, D., "Role of Gene Expression Studies in Nonclinical Toxicogenomics," PhRMA/FDA Genomics (Microarray) Biostatistics Worshop, (2004).
Mendrick, D.L., et al., "Using Gene Markers Indentified From a Large Database Built with Primary Rat Hepatocytes for Prediction of Human Hepatotoxicity," Society of Toxicology Mtg, (2002).

Mendrick, D.L., et al., Cross compound predictions and pathway analysis using gene expression profiles from acetaminophen or carbon tetrachloride, two structurally distinct liver toxicants, Society of Toxicology Mtg, (2002).
Mendrick I, Cysteine Protease Inhibitor (2004).
Mendrick, Extracellular Matrix Protein Dermatopontin., (2004).
Mendrick., Chemokine (2004).
Mendrick., Lipid Transporter (2004).
Mendrick., "General Biological Findings for 80 Genes" (2004).
Mendrick, "Genomic Search for Candidate Biomarkers" (2004).
Menegazzi et al., Hepatology, 25: 585-592 (1997).
Meneses-Lorente, et al., Chem. Res. Toxicol., 16(9):A-H, 1070-1077), (2003).
Metz & Ritter, J. Biol. Chem., 237: 5607-5614 (1998).
Metz et al., Mol. Pharmacol., 58: 319-327 (2000).
Meyer, K., et al., Carcinogenesis, 24(5):975-984, (2003).
Milam and Byard, Toxicol. Appl. Pharmacol., 79: 342-347 (1985).
Minamide et al., J. Pharm. Sci., 87: 640-646 (1998).
Mino et al., J. Histochem. Cytochem., 46: 1151-1160 (1998).
Miracle et al., The Path from Molecular Indicators of Exposure., 12 : 457-462 (2003).
Mitchell & Acosta, J. Toxicol. Environ. Health, 7: 83-92 (1981).
Mitchell et al., Ann. Intern. Med., 84: 181-192 (1976).
Monteith et al., Drug Chem. Toxicol., 19: 71-84 (1996).
Moore et al., Fundam. Appl. Toxicol., 3: 560-568 (1983).
Moran et al., Immunopharmacology, 12: 245-250 (1986).
Morgan, K.T., et al., Toxicol. Pathol., 30(4):435-451, (2002).
Morigasaki et al., Biochem. Biophys. Res. Commun., 273: 261-266 (2000).
Morooka et al., J. Biol. Chem.., 270: 30084-30092 (1995).
Motoki et al., Cancer Lett., 135: 145-150 (1999).
Nakamura, et al., Clinical Immun. And Immunopath., 66(1):33-42, (1993).
Newsholme, et al., Electrophoresis, 21:2122-2128, (2000).
Nguyen et al. (2002), "Tumor classification by partial least squares using microarray gene expression data," Bioinformatics 18(1):39-50.
Nicholls-Grzemski et al., Toxicol. Sci., 56: 220-228 (2000).
Nims et al., Carcinogenesis, 8: 67-71 (1987).
Nordberg & Svensson, Drug Saf., 19: 465-480 (1998).
Nuwaisyr et al., "Microarrays and toxicology : the advent of toxicogenomics," Molecular Carcinogenesis 24(3):153-159, 1999.
Nuwaysir, et al., Cancer Research, 56:3704-3710, (1996).
Oberhammer et al., Hepatology, 23: 329-337 (1996).
O'Brien, et al., Toxicol. And Appl. Pharma., 171:27-37, (2001).
Ohta et al., Biochem. J., 324: 777-782 (1997).
Olden & Guthrie, Mutation Research, 473:3-10, (2001).
Olson et al., Fundam. Appl. Toxicol., 22: 631-640 (1994).
Omiecinski et al., Mol. Pharmacol., 38: 462-470 (1990).
Omiecinski, et al., Toxicol. Sciences, 48:151-156, (1999).
Omogbai et al., Drug Chem. Toxicol., 22: 629-242 (1999).
Ono et al., Biol. Pharm. Bull., 18: 1779-1783 (1995) Abstract only.
Ono et al., Chem. Pharm. Bull. (Tokyo), 43: 1492-1496 (1995).
Orr, M., et al., Concordance of Toxicogenomic Predictions and Mechanistic Analysis for Compounds Tested in Both Rat Liver and Primary Rat Hepatocytes, Soc. Of Toxicol. Mtg., (2004).
Orr, M., et al., "Cross-species Comparisons—Human and Rat," Soc. Of Toxicol. Mtg., (2004).
Orr, M.S., et al., "Microarray Analysis of NRF2 Pathway and Novel Co-Regulated Genes Induced by Acetaminophen," Soc. Of Toxicol. Mtg., (2002).
Orr, M.S., et al., "Predicting Toxicity in Two distinct Sections of the Kidney via Microarray Anaysis," Soc. Of Toxicol. Mtg., (2002).
Orr, M, et al. "Challenges and Limitations of Gene Expression Profiling" 60: 6-10 (2001).
Orr, Michael, "Comparison of Liver Gene Dysregulation" 21: 253-262 (2002).
Orsler et at., Toxicol. Sci., 47: 203-210 (1999).
Outinen et al., Blood, 94: 959-967 (1999).
Owen et al., Biochem. J., 348 Pt 3: 607-614 (2000).
Panduro et al., Nephron, 65: 100-107 (1993).
Park & Pirmohamed, Toxicol. Lett., 120: 281-291 (2001).
Park et al., Pharmacol. Ther., 68: 385-424 (1995).
Passreiter et al., J. Cell Biol., 141: 373-383 (1998).

Peng et al., JBC 271(6): 3324-3327 (1996).
Pennie & Kimber, Toxicology in Vitro, 16:319-326, (2002).
Pennie, et al., Toxicol. Lett., 120: 353-358 (2001).
Pennie, et al., Toxicol. Sci. 54: 277-283 (2000).
Pennie, Toxicol. Lett., 112-113: 473-477 (2000).
Perrone et al., Toxicol. Appl. Pharmacol., 150: 277-286 (1998).
Petricoin III, et al., Nature Genetics Supp., 32:474-479, (2002).
Pfeffer et al., J Immunology 153(4):1789-1797 (1994).
Pischedda et al., Proc. Natl. Acad. Sci. U.S.A., 92: 3511-3515 (1995).
Plant, N., et al., Toxicol. And Applied Pharma., 183:127-134, (2002).
Pohl et al., Arthritis Rheum., 37: 1557 (1994).
Pollenz et al., Toxicol. Sci., 42: 117-128 (1998).
Porter, M., et al., "Determination of Biological Replicate Number for Rat and Human Microarray-Based Predictive and Mechanistics Assays," Soc. Of Toxicol. Mtg., (2003) Abstract only.
Porter, M., et al., "Effects of Hydration, Fasting, and Anesthesia on Baseline Gene Expression," Soc. Of Toxicol. Mtg., (2003) Abstract only.
Porter, M., et al., "Liver Effects at the Gene Expression Level of Food-Tasting, Water Deprivation, and Anesthetic Agent Administration in Untreated Rats," Soc. Of Toxicol. Mtg., (2003) Abstract only.
Porter, M.W., et al., "Comparison of Microarray Data Generated from the Same RNA at 19 Different Processing Sites," Soc. Of Toxicol. Mtg., (2002).
Porter, Mark, "Comparison of Microarray data Generated from the same RNA at 15 Different Processing Sites," Soc. Of Toxicol. Mtg. Oct. 2003, Abstract only.
Poyet & Labrie, Mol. Cell. Endocrinol., 42: 283-288 (1985).
Prevot et al. J. Biol. Chem.., 276: 9640-9648 (2001).
Pumford et al., Drug Metab. Rev., 29: 39-57 (1997).
Raats, et al., Am. J. Pathol. 156: 1749-1765, (2000).
Raburn et al., "Stage-specific expression of B Cell Translocation Gene 1 in rat testis," Endocrinology 136(12):5769-5777, 1995.
Raburn et al., Endocrinology 136(12):5769-5777, 1995. Abstract only.
Rajeski, David, "Exploring the Genomics Frontier," Risk Policy Report, pp. 1-5, (2002).
Ratanasavanh et al., Xenobiotica., 18: 765-771 (1988).
Ray & Jena, Arch. Toxicol., 73: 594-606 (2000).
Raychaudhuri et al., "Basic microarray analysis: grouping and feature reduction," Trends Biotechnol. 19:189-193 (2001).
Raymond et al., J. Toxicol. Environ. Health, 51: 463-476 (1997).
Reilly et al., Biochem. Biophys. Res. Commun., 282: 321-328 (2001).
Rejeski D., Exploring the Genomics Frontier, Aug, 20, 2002.
Reuter et al., Life Sci, 55: 1-8 (1994).
Rice et al., Carcinogenesis., 15: 395-402 (1994).
Rich et al., Nature, 407: 777-783 (2000).
Richert, L., et al., Toxicol. And Appl. Pharmacol., 191:130-146, (2003).
Riekkinen et al., Eur. J. Pharmacol., 322: 1-9 (1997).
Riekkinen et al., Eur. J. Pharmacol., 323: 11-19 (1997).
Riendeau et al., Br. J. Pharmacol., 121: 105-117 (1997).
Rininger et al., Biochem. Pharmacol., 52: 1749-1755 (1996).
Rininger et al., Drug Discov. Today, 5: 560-568 (2000).
Roberts et al., Toxicol. Appl. Pharmacol., 135: 192-199 (1995).
Rockett & Dix, Environ. Health Perspect., 107: 681-685 (1999).
Rodi et al., Toxicol. Pathol., 27: 107-110 (1999) Abstract only.
Rodrigues & Machinist, Toxicol. Appl. Pharmacol., 137: 193-201 (1996).
Ronchetti et al., "Robust Linear Model Selection by Cross-Validation," J. Am. Statistical Assoc. 92:1017-1023 (1997).
Ruepp et al., Toxicol. Sci., 65: 135-150 (2002).
Runge-Morris et al., Drug Metab. Dispos., 26: 795-801 (1998).
Rusyn, et al., Cancer Research, 64:1050-1057. (2004).
Sachidanandam et al., Nature, 409: 928-933 (2001).
Safe, Annu. Rev. Pharmacol. Toxicol., 38: 121-158 (1998).
Salter and Nilsson, Drug Disc. and Dev., 6(1):117-122 (2003).
Sanz, et al., British J. Cancer, 75(4):487-492, (1997).
Scales & Timbrell, J. Toxicol. Environ. Health, 10: 941-953 (1982).
Scali et al., Pharmacol. Res., 36: 463-469 (1997).
Scassa et al., Exp. Cell Res., 244: 460-469 (1998) Abstract only.
Schiaffonati & Tiberio, Liver, 17: 183-191 (1997) Abstract only.

Schiller et al., Toxicol. Appl. Pharmacol., 81: 356-361 (1985).
Schilter, B. et al. Activation of cytochrome P450 gene expression in rat brain by phenobarbital-like inducers. J Pharmacol Exp Ther 294(3):916-22 (Sep. 2000). Abstract only.
Schiodt et al., N. Engl. J. Med., 337: 1112-1117 (1997).
Scholer et al., Am. J. Med., 80: 34-38 (1986).
Schulte-Hermann et al., Cancer Res., 48: 2462-2468 (1988).
Schuppe-Koistinen, et al., Toxicology, 179:197-219, (2002).
Seefeld et al., Arch. Environ. Contam. Toxicol., 9: 317-327 (1980).
Sendo et al., Chem. Pharm. Bull. (Tokyo), 32: 795-796 (1984).
Servais & Galand, Cell Biol. Int Rep., 16: 319-328 (1992).
Shankar, K., et al., "PPAR-a Mediates Diabetes-Induced Resistance Against Acetaminophen Hepatotoxicity: . . . ," Ann. Mtg. Of the Amer. College of Toxicol., p. 526 (2002) Abstract only.
Shannon et al., J. Pharmacol. Exp. Ther., 255: 1071-1077 (1990).
Shao, "Linear Model Selection by Cross-Validation," J. Am. Statistical Assoc. 88:486-494 (1993).
Shervington, Biochem. Mol. Biol. Int., 45: 303-313 (1998) Abstract only.
Shiota et al., Res. Commun. Mol. Pathol. Pharmacol., 94: 141-146 (1996).
Shultz et al., Toxicol. Appl. Pharmacol., 154: 84-96 (1999) Abstract only.
Sidhu & Omiecinski, J. Biochem. Mol. Toxicol., 13: 1-9 (1999) Abstract only.
Sidhu & Omiecinski, J. Biol. Chem., 273: 4769-4775 (1998) Abstract only.
Sidhu et al., Arch. Biochem. Biophys., 301: 103-113 (1993).
Simmons, P.T. & Portier, C.J., Carcinogenesis, 23(6):903-905, (2002).
Sinz & Woolf, Biochem. Pharmacol., 54: 425-427 (1997).
Skouteris and McMenamin, Biochem. J., 281: 729-733 (1992).
Skrtic et al., J. Hepatol., 27: 903-911 (1997).
Smith, Trends Pharmacol. Sci., 22: 281-285 (2001).
Snape et al., Neuopharmacology, 38: 181-193 (1999).
Soffers, A.E.M.F., et al., Toxic. In Vitro, 15:539-551 (2001).
Somani & Dube, Int. J. Clin. Pharmacol. Ther. Toxicol., 27: 367-387 (1989).
Somani, Biopharm. Drug Dispos., 10: 187-203 (1989).
Soni et al., Regul. Toxicol. Pharmacol., 29: 165-174 (1999).
Sprankle, C., et al., Cancer Letters, 101:97-106, (1996).
Stachlewitz et al., J. Pharmacol. Exp. Ther., 282: 1591-1599 (1997).
Steiner, et al., Environ. Health Perspect., 112(12):1236-1248, (2004).
Stohs et al., Biochem. Biophys. Res. Commun., 111:854-859 (1983).
Su, et al., Proc. Natl. Acad. Sci. USA, 99(17):11181-11186, (2002).
Sèurmen & Eryèurek, Toxicology, 75: 63-69 (1992) Abstract only.
Suter, et al., "Toxicogenomics: Correlation of acetaminophen-induced hepatoxicity with gene expression using DNA microarrays," Soc. Of Toxicogenomics Mtg., (2000).
Sutter, et al., Mol. Cancer Therapeutics, 1:1283-1292, (2002).
Suzuki and Sudo, Japan J. Pharmacol., 49:43-51, (1989).
Tamura et al., Toxicology, 63: 199-213 (1996) Abstract only.
Tao, et al., Experimental Hermatology, 31:251-260 (2003).
Tarloff et al., Fundam. Appl. Toxicol., 30: 13-22 (1996).
Tenniswood et al., Mol. Cell. Endocrinol., 37: 153-158 (1984).
Thomas, R.S., et al., Molecular Pharmacol., 60(6):1189-1194, (2001).
Timbrell et al., J. Pharmcol. Exp. Ther., 213: 364-369 (1980).
Timbrell et al., J. Toxicol. Environ. Health, 10: 955-968 (1982).
Timbrell, Arch. Toxicol. Suppl., 2: 1-8 (1979).
Tournier et al., Lab. Invest., 59: 657-665 (1988).
Trauner et al., N. Engl. J. Med., 339: 1217-1227 (1998).
Tu, Y., et al., Proc. Nat'l Acad Sci. USA, 99(22):14031-14036, (2002).
Tucker et al., Fundam. Appl. Toxicol., 3: 579-586 (1983).
Tucker, Am. J. Med., 73: 27-30 (1982).
Tygstrup et al., J. Hepatol., 25: 183-190 (1996).
Tygstrup et al., J. Hepatol., 27: 156-162 (1997).
Tygstrup, et al., Biochem. And Biophys. Res. Commun., 290(1):518-525, (2002).
Uhl et al., Mutat. Res., 468: 213-225 (2000) Abstract only.
van Gijssel et al., Carcinogenesis, 18: 1027-1033 (1997).
Vance et al., Epilepsia, 35: 1016-1022 (1994).

Verstrepen, et al., Kidney Int'l, 43:1267-1279, (1993).
Venturelli et al., Overexpression of DR-nm23, 92: 7435-7439 (1995).
Visen et al., J. Pharmacol. Toxicol. Methods, 40: 173-179 (1998).
Wan et al., Infect. Immun., 63: 2435-2442 (1995).
Wang & Dickinson, Drug Metab. Dispos., 26: 98-104 (1998).
Warling & Ulrich, Annu. Rev. Pharmacol. Toxicol., 40: 335-352 (2000).
Waring et al., Toxicol. Appl. Pharmacol., 175: 28-42 (2001).
Waring et al., Toxicol. Lett., 120: 359-368 (2001).
Waring, et al., Environ. Health Perspect., 111:863-870, (2003).
Waterfield et al., Biochem. Pharmacol., 46: 589-595 (1993).
Weber et al., Fundam. Appl. Toxicol., 21: 523-534 (1993).
Weber et al., Toxicology, 66: 133-144 (1991).
Weisenberg-Boettcher et al., A Novelty Highly Potent, Nov. 12, 1989: 501-509.
Wessely, S., et al., Human & Experimental Toxicology, 18:740-764, (1999).
White et al., Biochem. Pharmacol., 45: 21-30 (1993).
White et al., Carcinogenesis, 13: 2197-2203 (1992).
Wilson, et al. PNAS 96:12833-12838 (1999).
Woodcroft & Novak, Drug Metab. Dispos., 26: 372-378 (1998) Abstract only.
Woodward & Timbrell, Toxicology., 30: 65-74 (1984).
Woolf et al., Drug Metab. Dispos., 21: 874-882 (1993).
Xiong et al., "Feature (Gene) Selection in Gene Expression-Based Tumor Classification," Mol. Genet. Metab. 73:239-247 (2001).
Xiong et al., Life Sci., 65: 421-430 (1999).
Xu, et al., World J. Gastroenterol, 10(2):250-254, (2004).
Yamada et al., Life Sci., 61: 171-179 (1997) Abstract only.
Yamaki et al., "Cellular mechanism of lithiumk-induced nephrogenic diabetes insipidus in rats," Am. J. Physiol. Renal Physiol. 261:F505-F511, (1991).
Yang et al., Am J Physiol 277(1):F10-F16 (1999).
Yata et al., J. Hepatol., 30: 419-424 (1999).
Zarif et al., The Effect of A Selective 5-Lipoxygenase, vol. 20, 217-227 (1996).
Zeeberg, et al., Genome biology, 4:R28:1-8, (2003).
Zhao Y. et al. Activation of Pro-death Bcl-2 Family, vol. 276: 27432-27440 (2001).
Zhou G., et al, Role of AMP-activated protein kinase in mechanism, 108: 1167-1174, 2001.
Bagetta et al., *Biochem. Biophys. Res. Commun.*, 197: 1132-1139 (1993).
Tanaka et al., *Clin. Exp. Pharmacol. Physiol.*, 20: 543-547 (1993).
Wang et al., *Neuroreport.*, 10: 789-793 (1999).
Werner et al., *Mutat. Res.*, 395:179-187 (1997).
Abernathy et al., *Proc. Soc. Exp. Biol. Med.*, 199: 54-58 (1992).
Accatino et al., *Hepatology*, 28: 129-140 (1998).
Akesson & Akesson, *Scand. J. Rheumatol.*, 13: 198-202 (1984).
al Casey et al., *Toxicol. Lett.*, 76: 257-265 (1995).
Ammann et al., *Toxicol. Appl. Pharmacol.*, 149: 217-225 (1998).
Ashby & Lefevre, *J. Appl. Toxicol.*, 20: 35-47 (2000).
Aura et al., *Eur. J. Pharmacol.*, 342: 15-20 (1998).
Ax et al., *Biochem. Pharmacol.*, 59: 293-300 (2000).
Azri-Meehan et al., *Fundam. Appl. Toxicol.*, 22: 172-177 (1994).
Bagetta et al., *Eur. J. Pharmacol.*, 213: 301-304 (1992).
Basnet et al., *Biol. Pharm. Bull.*, 19: 1479-1484 (1996).
Becker et al., *Am. J. Kidney Dis.*, 22: 611-615 (1993).
Becquemont et al., *Fundam. Clin. Pharmacol.*, 10: 156-157 (1996).
Becquemont et al., *Pharmacogenetics*, 7: 251-253 (1997).
Belles et al., *Vet. Hum. Toxicol.*, 40: 269-272 (1998).
Benoit et al., *Biochem. Pharmacol.*, 53: 423-427 (1997).
Bentley et al., *Food Chem. Toxicol.*, 31: 857-907 (1993).
Bergstrom et al., *Annu. Rev. Microbiol.*, 49: 607-639 (1995).
Berson et al., *Gastroenterology*, 110: 1878-1890 (1996).
Berthou et al., *Eur. J. Biochem.*, 232: 179-187 (1995).
Bezek et al., *Xenobiotica*, 26: 935-946 (1996).
Bhagwat et al., *Int. J. Oncol.*, 13: 281-288 (1998).
Blackard et al., *J. Clin. Gastroenterol.*, 26: 57-59 (1998).
Blazka et al., *J. Inflamm.*, 47: 138-150 (1995-96).
Blazka et al., *Res. Commn. Mol. Pathol. Pharmacol.*, 92: 259-273 (1996).
Blazka et al., *Toxicol. Appl. Pharmacol.*, 133: 43-52 (1995).

Bombick & Matsumura, *J. Biochem. Toxicol.*, 2: 141-154 (1987).
Booth et al., *Hepatology*, 23: 771-780 (1996).
Bort et al., *Drug Metab. Dispos.*, 24: 969-975 (1996).
Brown et al., *Arch. Biochem. Biophys.*, 342: 134-142 (1997).
Brown et al., *Environ. Health Perspect.*, 104: 634-6440 (1996).
Bruckner et al., *J. Pharmacol. Exp. Ther.*, 300: 273-281 (2002).
Bulera et al., *Toxicol. Appl. Pharmacol.*, 143: 313-320 (1995).
Burcham & Harman, *J. Biol. Chem.*, 266: 5049-5054 (1991).
Burczynski & Penning, *Cancer Res.*, 60: 908-915 (2000).
Bursch et al., *Arch. Toxicol.*, 59: 221-227 (1986).
Buttery et al., *Lab. Invest.*, 71: 755-764 (1994).
Byard & Dougherty, *In Vitro Cell Dev. Biol.*, 21: 489-494 (1985).
Cabre et al., *Clin. Exp. Pharmacol. Physiol.*, 27: 694-699 (2000).
Calabrese et al., *Food Chem. Toxicol.*, 34: 301-311 (1996).
Carfagna et al., *Toxicol. Appl. Pharmacol.*, 137: 173-181 (1996).
Carpenter-Deyo & Reed, *J. Pharmacol. Exp. Ther.*, 258: 747-752 (1991).
Carriero et al., *Pharmacol. Biochem. Behav.*, 58: 851-858 (1997).
Casley et al., *Pharmacogenetics*, 7:283-293 (1997).
Cattley et al., *Cancer Lett.*, 33: 269-277 (1986).
Cattley et al., *Carcinogenesis*, 9: 1179-1183 (1988).
Chen et al., *Amino Acids*, 18: 319-327 (2000).
Chen et al., *Carcinogenesis*, 21: 1205-1211 (2000).
Chen et al., *J. Environ. Pathol. Toxicol. Oncol.*, 14: 83-99 (1995).
Cheng et al., *Neuroreport.*, 8: 97-101 (1996).
Chico et al., *Exp. Clin. Endocrinol. Diabetes.*, 104: 137-144 (1996).
Cousins et al., *Eur. J. Pharmacol.*, 322: 137-145 (1997).
Cousins et al., *Physiol. Behav.*, 64: 153-158 (1998).
Coyne et al., *Gastroentology*, 75: 76-90 (1978).
Crismon, *Ann. Pharmacother.*, 28: 744-751 (1994).
Cuevas et al., *Clin. Exp, Pharmacol. Physiol.*, 28: 637-642 (2001).
Darbre & King, *J. Steriod Biochem.*, 36: 385-390 (1990).
Davilla et al., *Toxicology.*, 57: 267-286 (1989).
Davis et al., *Biochemistry*, 25: 1632-1636 (1986).
Davydov, *Trends Biochem. Sci.*, 26: 155-1560 (2001).
De Ferrari et al., *J. Neurosci. Res.*, 52: 435-444 (1998).
Delaney & Segel, *South. Med. J.*, 78: 1390-1392 (1985).
DeLeve et al., *Biochem. Pharmacol.*, 53: 1339-1345 (1997).
DeNoble et al., *Pharmacol. Biochem. Behav.*, 36: 957-961 (1990).
Dilworth et al., *Toxicol. In Vitro*, 4: 169-176 (2000).
Dirven et al., *Biochem. Pharmacol.*, 43: 261-299 (1992).
Eri & Tveter, *Eur. Urol.*, 26: 219-226 (1994).
Farghali et al., *Int. J. Immunopharmacol.*, 19: 599-604 (1997).
Farghali et al., *Methods Find. Exp. Clin. Pharmacol.*, 6: 449-454 (1984).
Fariss et al., *Hepatology*, 20: 240-246 (1994).
Fernandez-Salguero & Gonzalez, *Pharmacogenetics*, 5: S123-128.
Friedman et al., *Dig. Dis. Sci.*, 44: 1362-1363 (1999).
Fritz & Kaina, *Biochem. Biophys. Res. Commun.*, 268: 784-789 (2000).
Fujiki, *FEBS Lett.*, 476: 42-46 (2000).
Galisteo et al., *J. Pharmacol. Exp. Ther.*, 294: 160-167 (2000).
Gall et al., *J. Steroid Biochem. Mol. Biol.*, 70:101-108 (1999).
Galli & Mori, *Arch. Toxicol.*, 65: 330-334 (1991).
Garcia-Allan et al., *Arch. Toxicol.*, 71: 409-415 (1997).
Gebhardt et al., *Cell. Biol. Toxicol.*, 12: 57-68 (1996).
Geiger et al., *Agents Actions*, 38: Spec No. C69-72 (1993).
Ghatineh & Timbrell, *Biochem. Soc. Trans.*, 18: 1217-1218 (1990).
Giacobini et al., *Neuropharmacology*, 35: 205-211 (1996).
Giacobini, *Neurochem. Int.*, 32: 413-419 (1998).
Gil et al., *Biochim. Biophys. Acta.*, 1272: 140-146 (1995).
Gomez-Lechon et al., *Altern. Lab. Anim.*, 29: 225-231 (2001).
Gong et al., *Pharmacogenetics*, 11: 357-368 (2001).
Gracon et al., *Alzheimer Dis. Assoc. Disord.*, 12: 93-101 (1998).
Guarner et al., *Liver*, 5: 35-39 (1985).
Gupta et al., *Carcinogenesis*, 6: 933-936 (1985).
Gupta et al., *Toxicol. Appl. Pharmacol.*, 146: 317-327 (1997).
Ha et al., *Biochem. Mol. Biol. Int.*, 29: 387-393 (1993).
Hakansson, *Acta Neurol. Scand. Suppl.*, 149: 7-9 (1993).
Hallak & Giacobini, Neuropharmacology, 26: 521-530 (1987).
Hanson et al., *Lab. Invest.*, 41: 500-503 (1979).
Hartung et al., *Dev. Biol. Stand.*, 86: 85-96 (1996).
Hase et al., *Planta Med.*, 63: 22-26 (1997).
Hassett et al., *Biochem. Pharmacol.*, 55: 1059-1069 (1998).
Hayashi et al., *Biochim. Biophys. Acta.*, 879: 140-148 (1986).
Henderson et al., *Proc. Natl. Acad. Sci. U.S.A.*, 97: 12741-12745 (2000).
Hebst et al., *Am. J. Pathol.*, 150: 1647-1659 (1997).
Hildebrand et al., *Arch. Toxicol.*, 73: 233-245 (1999).
Hill & Roth, *Toxicol. Appl. Pharmacol.*, 148: 169-175 (1998).
Hill et al., *Toxicol. Sci.*, 47: 118-125 (1999).
Hinz et al., *Neurochem. Res.*, 21: 331-337 (1996).
Hoebe et al., *Vet. Q.*, 22: 21-25 (2000).
Hoshi & Fujino, *Chem. Pharm. Bull.*, 38: 3446-3448 (1990).
Hoshi et al., *Jpn. J. Pharmacol.*, 50: 289-293 (1989).
Hussain et al. *Sci. Total Environ.*, 274: 151-160 (2001).
Ibebunjo et al., *Can. J. Anaesth.*, 44: 1021-1026 (1997).
Iimuro et al., *J. Leukoc. Biol.*, 55: 723-728 (1994).
James & Roberts, *Carcinogenesis*, 17:1623-32 (1996).
Jinno, et al., *Arch. Toxicol.*, 71: 550-555 (1997).
Jover et al., *Biochem. Pharmacol.*, 46: 1967-1974 (1993).
Jurima-Romet & Huang, *Biochem. Pharmacol.*, 46: 2163-2170 (1993).
Kaminski & Stevens, *Toxicology*, 75: 175-188 (1992).
Karchner et al., *Mar. Environ. Res.*, 50: 51-56 (2000).
Kasper & Mueller, *Carcinogenesis*, 20: 2185-2188 (1999).
Kato & Yamazoe et al., *Toxicol. Lett.*, 64-65: 661-667 (1992).
Kaufmann et al., *Carcinogenesis*, 9: 779-782 (1988).
Kawai et al., *Infect. Immun.*, 59: 2560-2566 (1991).
Keller et al., *Toxicol. Appl. Phamacol.*, 104: 259-266 (1990).
Kemper, *Prog. Nucleic Acid Res. Mol. Biol.*, 61: 23-64 (1998).
King & Somani, *Life Sci.*, 41: 2007-2015 (1987).
Kishi et al., *Mol. Aspects Med.*, 18: S71-S77 (1997).
Kitteringham et al., *Hepatology*, 32: 321-333 (2000).
Knight et al., *Toxicol. Sci.*, 62: 212-220 (2001).
Kobayashi et al., *Drug Metab. Dispos.*, 26: 1026-1030 (1998).
Kocaoglu et al., *Arch. Immunol. Ther. Exp.*, (*Warsz*), 45: 73-77 (1997).
Krall et al., *Ann. Pharmacother.*, 33: 441-450 (1999).
Kryger et al., *Structure Fold. Des.*, 7: 297-307 (1999).
Kullak-Ublick & Meier, *Clin. Liver Dis.*, 4: 357-385 (2000).
Kunstle et al., *Immunol. Lett.*, 55: 5-10 (1997).
Kuo et al., *J. Pharmacol. Exp. Ther.*, 282: 1072-1083 (1997).
Lacroix et al., *Gene*, 86: 201-207 (1990).
Lagadic-Gossmann et al., *Cell Biol. Toxicol.*, 14: 361-373 (1998).
Lahiri & Farlow, *J. Mol. Neurosci.*, 7: 41-49 (1996).
Lake et al., *Environ. Health Perspect.*, 67: 283-290 (1986).
Lamb et al., *Toxicol. Appl. Pharmacol.*, 101: 106-113 (1989).
Lang et al., *Alcohol Clin. Exp. Res.*, 22: 823-829 (1998).
Larrauri et al., *Mol. Toxicol.*, 1: 301-311 (1987-1988).
Laurent & Fraser, *Faseb J.*, 6: 2397-2404 (1992).
Lemberger et al., *J. Biol. Chem.*, 271: 1764-1769 (1996).
Lèullman-Rauch & Scheid, *Virchows Arch. B Cell Pathol.*, 19: 255-268 (1975).
Li et al., *Biochem. Biophys. Res. Commun.*, 229: 982-999 (1996).
Lin et al., *Chem. Res. Toxicol.*, 9: 1183-1193 (1996).
Liu et al., *Biol. Pharm. Bull.*, 21: 44-49 (1998).
Liu et al., *Cancer Res.*, 52: 4139-4143 (1992).
Lomri et al., *Chem. Res. Toxicol.*, 6: 800-807 (1993).
Lupo et al., *Toxicology.*, 44: 229-239 (1987).
M'Harzi et al., *Pharmacol. Biochem. Behav.*, 56: 663-668 (1997).
Mancy et al., *Biochemistry*, 38: 14264-14270 (1999).
Marsman et al., *Toxicol. Appl. Pharmacol.*, 122: 1-6 (1993).
Martelli et al., *Mutagenesis*, 14: 463-472 (1999).
Matsuda et al., *Bioorg. Med. Chem. Lett.*, 8: 2191-2196 (1998).
Matsuo et al., *Acta Med. Okayama*, 46: 345-354 (1992).
Mayorga et al., *Pharmacol. Biochem. Behav.*, 56: 273-279 (1997).
McGirr et al., *Xenobiotica*, 20: 933-943 (1990).
McMartin et al., *Res. Commun. Chem. Pathol. Pharmacol.*, 31: 99-110 (1981).
Mejdoubi et al., *Biochem. Biophys. Res. Commun.*, 254: 93-99 (1999).
Meyers et al., *J. Pharmacol. Exp. Ther.*, 214: 87-93 (1980).
Migliari et al., *Arch. Ital. Urol. Androl.*, 71: 293-302 (1999).
Miller et al., *Toxicol. Sci.*, 48: 30-37 (1999).
Mizutani & Miyamoto, *Toxicol. Lett.*, 105: 25-30 (1999).

Mohammed et al., *J. Neural. Transm. Park. Dis. Dement. Sect.*, 2: 285-294 (1990).
Monteith et al., *Arch. Toxicol.*, 72: 147-156 (1998).
Mus'ilkov'a & Tucek, *Neurosci. Lett.*, 125: 113-136 (1991).
Nabeshima et al., *Jpn. J. Pharmacol.*, 57: 311-319 (1991).
Nakamura & Lou, *J. Biol. Chem.*, 270: 7347-7353 (1995).
Neghab & Stacey, *Chem. Biol. Interact.*, 99: 179-192 (1996).
Nochi et al., *Biol. Pharm. Bull.*, 18: 1145-1147 (1995).
Nussler et al., *ALTEX*, 18: 91-101 (2001).
O'Hara et al., *Fundam. Appl. Toxicol.*, 13: 605-615 (1989).
O'Hara et al., *J. Appl. Toxicol.*, 11: 147-154 (1991).
Ohuchi et al., *Am. J. Physiol.*, 268 (6 Pt 1) G997-G1003 (1995).
Olivier & Krisans, *Biochim. Biophys. Acta*, 1529: 89-102 (2000).
Olsen et al., *Chem. Biol. Interact.*, 107: 93-108 (1997).
Olson et al., *Fundam. Appl. Toxicol.*, 22: 631-640 (1994).
Ono et al., *Biol. Pharm. Bull.*, 18: 1779-1783 (1995).
Padgham et al., *Biochem. Biophys. Res. Commun.*, 15: 599-605 (1993).
Paoletti et al., *Exp. Neurol.*, 149: 349-355 (1998).
Paolini et al., *Che,. Biol. Interact.*, 95: 127-139 (1995).
Parte et al., *J. Androl.*, 21: 525-533 (2000).
Parzefall et al., *Carcinogenesis*, 22: 519-523 (2001).
Penzes et al., *Gene*, 191: 167-172 (1997).
Peruzzi et al., *Neuroreport.*, 8: 103-108 (1996).
Petrulis & Bunce, *J. Biochem. Mol. Toxicol.*, 14: 73-81 (2000).
Phillips et al., *Carcinogenesis*, 17: 89-94 (1996).
Plant et al., *Carcinogenesis*, 19: 925-931 (1998).
Plymale & de la Iglesia, *J. Appl. Toxicol.*, 19: 31-38 (1999).
Porubek et al., *Drug Metab. Dispos.*, 17: 123-130 (1993).
Porubek et al., *Mol. Pharmacol* 31: 647-653 (1987).
Preece et al., *Arch. Toxicol.*, 64: 49-53 (1990).
Puri et al., *Mutagenesis*, 6: 471-478 (1991).
Qi et al., *Cell. Biochem. Biophys.*, 32: 187-204 (2000).
Rabe et al., *Drug Saf.*, 14: 25-38 (1996).
Riekkinen et al., *Eur. J. Pharmacol.*, 366: 13-18 (1999).
Roberts et al., *Toxicol. Lett.*, 112-113: 49-57 (2000).
Roberts et al., *Toxicol. Lett.*, 50: 283-288 (1990).
Robertson et al., *Arch. Toxicol.*, 72: 362-371 (1998).
Rodi et al., *Toxicol. Pathol.*, 27: 107-110 (1999).
Roskams et al., *Hepatology.*, 24: 524-532 (1996).
Roskams et al., *J. Pathol.*, 185: 290-297 (1998).
Roy, *J. Endocrinol.*, 70: 189-195 (1976).
Runge-Morris et al., *Drug Metab. Dispos.*, 24: 734-737 (1996).
Runge-Morris, *Chem. Biol. Interact.*, 3: 15-27 (1998).
Rusyn et al., *Carcinogenesis*, 20: 2095-2100 (1999).
Sallustio & Holbrook, *Drug Metab. Dispos.*, 29: 1535-1538 (2001).
Scassa et al., *Exp. Cell Res.*, 244: 460-469 (1998).
Schiaffonati & Tiberio, *Liver*, 17: 183-191 (1997).
Schrenk et al., *Arch. Toxicol.*, 65: 114-118 (1991).
Seitz et al., *Chem. Res. Toxicol.*, 11: 513-519 (1998).
Seitz et al., *Hepatology*, 20: 487-493 (1994).
Sèu rmen & Eryèurek, *Toxicology*, 75: 63-69 (1992).
Severson et al., *Can. J. Physiol. Pharmacol.*, 62: 244-247 (1984).
Shackleton et al., *Toxicol. Appl. Pharmacol.*, 130: 294-303 (1995).
Shear et al., *Skin Pharmacol.*, 8: 279-291 (1995).
Shervington, *Biochem. Mol. Biol. Int.*, 45: 303-313 (1998).
Sheweita et al., *Toxicology*, 28: 217-224 (2001).
Shirley et al., *Drug Metab. Dispos.*, 21: 580-586 (1993).
Shultz et al., *Toxicol. Appl. Pharmacol.*, 154: 84-96 (1999).
Sidhu & Omiecinski, *J. Biochem. Mol. Toxicol.*, 13: 1-9 (1999).
Sidhu & Omiecinski, *J. Biol. Chem.*, 273: 4769-4775 (1998).
Smith et al., *J. Neurosci. Res.*, 66: 236-241 (2001).
Smith et al., *J. Pharmacol. Exp. Ther.*, 280: 710-720 (1997).
Styles et al., *Carcinogenesis*, 18: 303-313 (1997).
Sundstrom et al., *Biochem. Pharmacol.*, 37: 1003-1008 (1988).
Takeuchi et al., *Neuropediatrics*, 19: 158-161 (1988).
Tamura et al., *Toxicology*, 63: 199-213 (1996).
Tanaka et al., *J. Physiol. Pharmacol.*, 50: 405-417 (1999).
Tang et al., *Drug Metab. Dispos.*, 27: 365-372 (1999).
Tansey & Shechter, *Prog. Nucleic Acid Res. Mol. Res. Mol. Biol.*, 75: 157-195 (2001).
Tarbet et al., *J. Biol. Chem.*, 266: 16667-16673 (1991).
Tee et al., *Toxicol. Appl. Pharmacol.*, 83: 294-314 (1986).
Theilig et al., *J. Am. Soc. Nephrol.*, 12: 2209-2220 (2001).
Thomas et al., *Oncogene*, 19: 5259-5269 (2000).
Timbrell & Waterfield, *Adv. Exp. Med. Biol.*, 403: 125-134 (1996).
Tithof et al., *Environ. Health Perspect.*, 104:52-58 (1996).
Titorenko & Rachubinski, *Nat. Rev. Mol. Cell. Biol.*, 2: 357-68 (2001).
Tobin et al., *Mol. Endocrinol.*, 14: 741-752 (2000).
Tsokos-Kuhn, *Arch. Biochem. Biophys.*, 265: 415-424 (1988).
Turnbull et al., *Biochem. Pharmacol.*, 32: 1887-1892 (1983).
Uhl et al., *Mutat. Res.*, 468: 213-225 (2000).
Vaananen et al., *Inflammation*, 16: 227-240 (1992).
Varone & Canepa, *Arch. Biochem. Biophys.*, 341: 259-266 (1997).
Villalobos et al., *J. Med. Chem.*, 38: 2802-2808 (1995).
Vinggaard et al., *Toxicol. Appl. Pharmacol.*, 55: 150-160 (1999).
Vonen and Morland, *Arch. Toxicol.*, 56: 33-37 (1984).
Wagstaff & McTavish, *Drugs Aging*, 4: 51-540 (1994).
Wang & Tang, *Eur. J. Pharmacol.*, 349: 137-142 (1998).
Wang et al., *Arch. Toxicol.*, 71: 638-645 (1997).
Watanabe et al., *Biochem. Pharmacol.*, 60: 285-291 (2000).
Watanabe et al., *Free Radic. Biol. Med.*, 30: 1019-1028 (2001).
Weber et al., *Chemosphere*, 30: 2635-2641 (1998).
Weber et al., *Chemosphere*, 30: 629-639 (1995).
Williams et al., *Biochem. Pharmacol.*, 49: 209-17 (1995).
Williams et al., *Drug Chem. Toxicol.*, 21: 449-476 (1998).
Wong et al., *Toxicol. Appl. Pharmacol.*, 153: 109-118 (1998).
Woodcroft & Novak, *Drug Matab. Dispos.*, 26: 372-378 (1998).
Wormser & Calp, *Toxicology.*, 53: 323-329 (1988).
Wroblewski & Olson, *Drug Metab. Dispos.*, 16: 43-51 (1988).
Yamada et al., *Life Sci.*, 61: 171-179 (1997).
Yamamura et al., *Drug Metab. Dispos.*, 27: 724-730 (1999).
Yasuhara et al., *Toxicol. Appl. Pharmacol.*, 79: 453-460 (1985).
Yoshida & Suzuki, *Eur. J. Pharmacol.*, 250: 117-124 (1993).
Yoshida et al., *Eur. J. Pharmacol.*, 214: 247-252 (1992).
Zeiger et al., *Mutat. Res.*, 393: 189-197 (1997).
Zhu et al., *Neurosci. Lett.*, 95: 252-256 (1988).

METHODS FOR DETERMINING RENAL TOXINS

RELATED APPLICATIONS

This is a divisional application of copending application Ser. No. 10/152,319, filed May 22, 2002, which claims priority to U.S. Provisional Applications 60/292,335, filed May 22, 2001; 60/297,523, filed Jun. 13, 2001; 60/298,925, filed Jun. 19, 2001; 60/303,810, filed Jul. 10, 2001; 60/303,807, filed Jul. 10, 2001; 60/303,808, filed Jul. 10, 2001; 60/315,047, filed Aug. 28, 2001; 60/324,928, filed Sep. 27, 2001; 60/330,867, filed Nov. 1, 2001; 60/330,462, filed Oct. 22, 2001; 60/331,805, filed Nov. 21, 2001; 60/336,144, filed Dec. 6, 2001; 60/340,873, filed Dec. 19, 2001; 60/357,843, filed Feb. 21, 2002; 60/357,842, filed Feb. 21, 2002; 60/357,844, filed Feb. 21, 2002; 60/364,134, filed Mar. 15, 2002; 60/370,206, filed Apr. 8, 2002; 60/370,247, filed Apr. 8, 2002; 60/370,144, filed Apr. 8, 2002; 60/371,679, filed Apr. 12, 2002 and 60/372,794, Apr. 17, 2002 all of which are herein incorporated by reference in their entirety. This application is also related to U.S. application Ser. Nos. 09/917,800 and 10/060,087, all of which are herein incorporated by reference in their entirety.

SEQUENCE LISTING SUBMISSION ON COMPACT DISC

The Sequence Listing submitted concurrently herewith on compact disc under 37 C.F.R. §§1.821(c) and 1.821(e) is herein incorporated by reference in its entirety. Three copies of the Sequence Listing, one on each of three compact discs are provided. Copy 1 and Copy 2 are identical. Copies 1 and 2 are also identical to the CRF. Each electronic copy of the Sequence Listing was created on May 22, 2002 with a file size of 3088 KB. The file names are as follows: Copy 1- gl5089us.txt; Copy 2- gl5089us.txt; CRF- gl5089us.txt.

BACKGROUND OF THE INVENTION

The need for methods of assessing the toxic impact of a compound, pharmaceutical agent or environmental-pollutant on a cell or living organism has led to the development of procedures which utilize living organisms as biological monitors. The simplest and most convenient of these systems utilize unicellular microorganisms such as yeast and bacteria, since they are the most easily maintained and manipulated. In addition, unicellular screening systems often use easily detectable changes in phenotype to monitor the effect of test compounds on the cell. Unicellular organisms, however, are inadequate models for estimating the potential effects of many compounds on complex multicellular animals, as they do not have the ability to carry out biotransformations.

The biotransformation of chemical compounds by multicellular organisms is a significant factor in determining the overall toxicity of agents to which they are exposed. Accordingly, multicellular screening systems may be preferred or required to detect the toxic effects of compounds. The use of multicellular organisms as toxicology screening tools has been significantly hampered, however, by the lack of convenient screening mechanisms or endpoints, such as those available in yeast or bacterial systems. Additionally, previous attempts to produce toxicology prediction systems have failed to provide the necessary modeling data and statistical information to accurately predict toxic responses (e.g., WO 00/12760, WO 00/47761, WO 00/63435, WO 01/32928, and WO 01/38579).

SUMMARY OF THE INVENTION

The present invention is based on the elucidation of the global changes in gene expression in tissues or cells exposed to known toxins, in particular renal toxins, as compared to unexposed tissues or cells as well as the identification of individual genes that are differentially expressed upon toxin exposure.

In various aspects, the invention includes methods of predicting at least one toxic effect of a compound, predicting the progression of a toxic effect of a compound, and predicting the renal toxicity of a compound. The invention also includes methods of identifying agents that modulate the onset or progression of a toxic response. Also provided are methods of predicting the cellular pathways that a compound modulates in a cell. The invention also includes methods of identifying agents that modulate protein activities.

In a further aspect, the invention includes probes comprising sequences that specifically hybridize to genes in Tables 1-5. Also included are solid supports comprising at least two of the previously mentioned probes. The invention also includes a computer system that has a database containing information identifying the expression level in a tissue or cell sample exposed to a renal toxin of a set of genes comprising at least two genes in Tables 1-5.

DETAILED DESCRIPTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death, are often characterized by the variations in the expression levels of groups of genes.

Changes in gene expression are also associated with the effects of various chemicals, drugs, toxins, pharmaceutical agents and pollutants on an organism or cell. For example, the lack of sufficient expression of functional tumor suppressor genes and/or the over expression of oncogene/protooncogenes after exposure to an agent could lead to tumorgenesis or hyperplastic growth of cells (Marshall (1991), Cell 64: 313-326; Weinberg (1991), Science 254: 1138-1146). Thus, changes in the expression levels of particular genes (e.g. oncogenes or tumor suppressors) may serve as signposts for the presence and progression of toxicity or other cellular responses to exposure to a particular compound.

Monitoring changes in gene expression may also provide certain advantages during drug screening and development. Often drugs are screened for the ability to interact with a major target without regard to other effects the drugs have on cells. These cellular effects may cause toxicity in the whole animal, which prevents the development and clinical use of the potential drug.

The present inventors have examined tissue from animals (kidney cells) exposed to known renal toxins which induce detrimental kidney effects, to identify global changes in gene expression induced by these compounds (Tables 5-5CC). These global changes in gene expression, which can be detected by the production of expression profiles (an expression level of one or more genes), provide useful toxicity markers that can be used to monitor toxicity and/or toxicity progression by a test compound. Some of these markers may also be used to monitor or detect various disease or physiological states, disease progression, drug efficacy, and drug metabolism.

Identification of Toxicity Markers

To evaluate and identify gene expression changes that are predictive of toxicity, studies using selected compounds with well characterized toxicity have been conducted by the present inventors to catalogue altered gene expression during exposure in vivo and in vitro. In the present study, cephaloridine, cisplatin, puromycin aminonucleoside (PAN), bromoethylamine hydrobromide (BEA), gentamicin, ifosfamide, cyclophosphamide, carboplatin, AY-25329, indomethacin, acyclovir, citrinin, mercuric chloride, diflunisal, cidofovir, pamidronate, lithium, hydralazine, colchicine, sulfadiazine, and adriamycin were selected as known renal toxins.

Cephaloridine is an amphoteric, semi-synthetic, broad-spectrum cephalosporin derived from cephalosporin C. Cephalosporins are β-lactam-containing antibiotics which prevent bacterial growth by inhibiting polymerization of the peptidoglycan bacterial cell wall. The linear glycan chains (composed of N-acetylglucosime and N-acetylmuramic acid) are cross-linked to each other by the coupling of short chains of several amino acids, the coupling resulting from the action of a transpeptidase. It is believed that cephalosporins act by blocking the activity of the transpeptidase (*Goodman & Gilman's The Pharmalogical Basis of Therapeutics* 9$^{th}$ ed., J. G. Hardman et al. Eds., McGraw Hill, N.Y., 1996, pp. 1074-1075, 1089-1095).

Cephaloridine is administered intramuscularly and is used to treat infections of the respiratory tract, gastrointestinal tract and urinary tract, as well as infections of soft tissue, bones and joints. Noted adverse effects include hypersensitivity reactions (such as anaphylactic shock, urticaria and bronchospasm), gastrointestinal disturbances, candidiasis, and cardiovascular and blood toxicity, in particular, toxicity to the hematopoietic system (cells responsible for the formation of red and white blood cells and platelets).

Although cephaloridine may be nephrotoxic at high dosages, it is not as harmful to the kidneys as are the aminoglycosides and polymixins. High dosages of cephaloridine may cause acute renal tubular necrosis (*Cecil Textbook of Medicine.* 20$^{th}$ ed. part XII, p. 586, J. C. Bennett and F. Plum Eds., W.B. Saunders Co., Philadelphia, 1996) or drug-induced interstitial nephritis, which is accompanied by elevated IgE levels, fever, arthralgia and maculopapular rash. Renal biopsopy demonstrates edema and interstitial inflammatory lesions, mainly with lymphocytes, monocytes, eosinophils and plasma cells. Vasculitis of small vessels may develop, leading to necrotising glomerulonephritis (G. Koren, "The nephrotoxic potential of drugs and chemicals. Pharmacological basis and clinical relevance.," *Med Toxicol Adverse Drug Exp* 4(1):59-72, 1989).

Cephaloridine has also been shown to reduce mitochondrial respiration and uptake of anionic succinate and carrier-mediated anionic substrate transport (Tune et al. (1990), *J Pharmacol Exp Ther* 252: 65-69). In a study of oxidative stress and damage to kidney tissue, cephaloridine depleted reduced glutathione (GSH) and produced oxidized glutathione (GSSG) in the renal cortex. This drug also inhibited glutathione reductase and produced malondialdehyde and conjugated dienes (Tune et al. (1989), *Biochem Pharmacol* 38: 795-802). Because cephaloridine is actively transported into the proximal renal tubule, but slowly transported across the lumenal membrane into the tubular fluid, high concentrations can accumulate and cause necrosis. Necrosis can be prevented by administering inhibitors of organic anion transport, although such treatment may be counterproductive, as cephaloridine is passed in and out of the kidney by the renal organic anion transport system (Tune et al. (1980), *J Pharmacol Exp Ther* 215: 186-190).

Cisplatin ($Pt(NH_3)_2(Cl)_2$), a broad-spectrum anti-tumor agent, is commonly used to treat tumors of the testicles, ovaries, bladder, skin, head and neck, and lungs (PDR 47$^{th}$ ed., pp. 754-757, Medical Economics Co., Inc., Montvale, N.J., 1993; *Goodman & Gilman's The Pharmalogical Basis of Therapeutics* 9$^{th}$ ed., pp. 1269-1271, J. G. Hardman et al. Eds., McGraw Hill, N.Y., 1996). Cisplatin diffuses into cells and functions mainly by alkylating the $N^7$ of guanine, a highly reactive site, causing interstrand and intrastrand crosslinks in the DNA that are lethal to cells. The drug is not sensitive to the cell cycle, although its effects are most pronounced in S phase.

Because the drug is cleared from the body mainly by the kidneys, the most frequent adverse effect of cisplatin usage is nephrotoxicity, the severity of which increases with increasing dosage and treatment terms. Other adverse effects include renal tubule damage, myelosuppression (reduced numbers of circulating platelets, leukocytes and erythrocytes), nausea and vomiting, ototoxicity, serum electrolyte disturbances (decreased concentrations of magnesium, calcium, sodium, potassium and phosphate, probably resulting from renal tubule damage), increased serum concentrations of urea and creatinine, and peripheral neuropathies.

In one study on rats (Nonclercq et al. (1989), *Exp Mol Pathol* 51:123-140) administration of cisplatin or carboplatin induced renal injury, carboplatin causing less damage than cisplatin. The most prominent injury was to the straight portion of proximal renal tubule.

In another rat study (Goldstein et al. (1981), *Toxicol Appl Pharmacol* 60: 163-175) animals injected with cisplatin displayed decreased food intake as drug dosage increased. On day 2, the high-dose groups (10-15 mg/kg) exhibited a six or seven-fold elevation in BUN. On day 4, BUN elevation was noted in the 5 mg/kg group. An increase in urine volume was observed beginning on days 3-4, along with decreased urine osmolality in the low-dose groups (2.5 or 5 mg/kg). Another experiment on rats (Agarwal et al. (1995), *Kidney Int* 48: 1298-1307) showed that cisplatin treatment produced elevations in serum creatinine levels, which began on day 3 and progressed for the duration of the study.

PAN ($C_{22}H_{29}N_7O_5$), an antibiotic produced by *Streptomyces alboniger*, inhibits protein synthesis and is commonly used experimentally on rats to mimic human minimal change disease. One study showed that PAN-injected rats demonstrated an increase in levels of serum non-esterified fatty acids, while the serum albumin concentration was negatively affected (Sasaki et al. (1999), *Adv Exp Med Biol* 467: 341-346).

In another rat study, an adenosine deaminase inhibitor prevented PAN nephrotoxicity, indicating that PAN toxicity is linked to adenosine metabolism (Nosaka et al. (1997), *Free Radic Biol Med* 22: 597-605). Another group showed that PAN, when administered to rats, led to proteinuria, a condition associated with abnormal amounts of protein in the urine, and renal damage, e.g. blebbing of glomerular epithelial cells, focal separation of cells from the glomerular basement membrane, and fusion of podocytes (Olson et al. (1981), *Lab Invest* 44: 271-279). In another study on rats, administration of PAN induced glomerular epithelial cell apoptosis in a dose- and time-dependent manner (Sanwal et al. (2001), *Exp Mol Pathol* 70: 54-64).

One study with PAN-injected rats (Koukouritaki et al. (1998), *J Investig Med* 46: 284-289) examined the changes in the expression of the proteins paxillin, focal adhesion kinase, and Rho, all of which regulate cell adhesion to the extracellular matrix. Paxillin levels increased steadily, peaked at day 9 after PAN injection, and then remained elevated even after proteinuria resolved. There was no observed change in expression of either focal adhesion kinase or Rho.

BEA, ($C_2H_6BrN.HBr$), is commonly used experimentally on rats to induce papillary necrosis and renal cortex damage, which is similar to human analgesic nephropathy. BEA-induced papillary necrosis in rats eventually leads to the onset of focal glomerular sclerosis and nephrotic proteinuria (Garber et al. (1999), *Am J Kidney Dis* 33: 1033-1039). Even at low doses (50 mg/kg), BEA can induce an apex limited renal papillary necrosis (Bach et al. (1983), *Toxicol Appl Pharmacol* 69: 333-344). In male Wistar rats, BEA administered at 100 mg/kg was shown to cause renal papillary necrosis within 24 hours (Bach et al. (1991), *Food Chem Toxicol* 29: 211-219). Additionally, Bach et al. showed that there was an increase in urinary triglycerides, and lipid deposits were seen by Oil Red O lipid staining in the cells of the collecting ducts and hyperplastic urothelia adjacent to the necrosed region.

It has also been shown that succinate and citrate concentrations are significantly lower in the urine of BEA-treated rats (Holmes et al. (1995), *Arch Toxicol* 70: 89-95). Moreover, BEA treatment induced glutaric and adipic aciduria, which is symptomatic of an enzyme deficiency in the acyl CoA dehydrogenases. The same study examined urinary taurine levels in desert mice, and in BEA-treated desert mice there was an increase in the urinary taurine level which is indicative of liver toxicity.

Another study on BEA-treated rats showed that there was an increase in the concentrations of creatine in the renal papilla and glutaric acid in the liver, renal cortex, and renal medulla as soon as 6 hours post-treatment (Garrod et al (2001), *Magn Reson Med* 45: 781-790).

Discovered and purified in the early 1960's, gentamicin is a broad-spectrum aminoglycoside antibiotic that is cidal to aerobic gram-negative bacteria and commonly used to treat infections, e.g., those of the urinary tract, lungs and meninges. As is typical for an aminoglycoside, the compound is made of two amino sugar rings linked to a central aminocyclitol ring by glycosidic bonds. Aminoglycosides are absorbed poorly with oral administration, but are excreted rapidly by the kidneys. As a result, kidney toxicity is the main adverse effect, although ototoxicity and neuromuscular blockade can also occur. Gentamicin acts by interfering with bacterial protein synthesis. This compound is more potent than most other antibacterial inhibitors of protein synthesis, which are merely bacteriostatic, and its effects on the body are, likewise, more severe (*Goodman & Gilman's The Pharmalogical Basis of Therapeutics* 9th ed., pp. 1103-1115, J. G. Hardman et al. Eds., McGraw Hill, N.Y., 1996).

Aminoglycosides work rapidly, and the rate of bacterial killing is concentration-dependent. Residual bactericidal activity remains after serum concentration has fallen below the minimum inhibitory concentration (MIC), with a duration that is also dosage/concentration-dependent. The residual activity allows for once-a-day administration in some patients. These drugs diffuse into bacterial cells through porin channels in the outer membrane and are then transported across the cytoplasmic membrane via a membrane potential that is negative on the inside (Goodman & Gilman, supra).

Kidney damage, which can develop into renal failure, is due to the attack of gentamicin on the proximal convoluted tubule, particularly in the S1 and S2 segments. The necrosis, however, is often patchy and focal (Shanley et at (1990), *Ren Fail* 12: 83-87). A rat study by Shanley et al. showed that superficial nephrons are more susceptible to necrosis than juxtamedullary nephrons, although the initial segment of the superficial nephrons is remarkably resistant to necrosis.

Reported enzymatic changes upon gentamicin treatment are increased activities of N-acetyl-beta-D-glucosaminidase and alkaline phosphatase and decreased activities of sphingomyelirase, cathepsin B, $Na^+/K^+$-ATPase, lactate dehydrogenase and NADPH cytochrome C reductase, along with decreased protein synthesis and alpha-methylglucose transport (Monteil et al. (1993), *Ren Fail* 15: 475-483). An increase in gamma-glutamyl transpeptidase activity in urine has also been reported (Kocaoglu et al. (1994), *Arch Immunol Ther Exp (Warsz)* 42: 125-127), and the quantification of this enzyme in urine is a useful marker for monitoring gentamicin toxicity.

One source of renal pathology resulting from gentamicin treatment is the generation of reactive oxygen metabolites. Gentamicin has been shown, both in vitro and in vivo, to be capable of enhancing the production of reactive oxygen species. Iron, a necessary co-factor that catalyzes free-radical formation, is supplied by cytochrome P450 (Baliga et al. (1999), *Drug Metab Rev* 31: 971-997).

A gene delivery experiment in rats, in which the human kallikrein gene was cloned into an adenovirus vector and the construct then co-administered with a gentamicin preparation, showed that kallikrein can protect against gentamicin-induced nephrotoxicity. Significantly increased renal blood flow, glomerular filtration rates and urine flow were observed, along with decreased renal tubular damage, cellular necrosis and lumenal protein casts. Kallikrein gene delivery also caused a decrease in blood urea nitrogen levels and increases in urinary kinin and nitrite/nitrate levels. This study provides evidence that the tissue kallikrein-kinin system may be a key pathway that is perturbed during the induction of nephrotoxicity by gentamicin (Murakami et al. (1998), *Kidney Int* 53: 1305-1313).

Ifosfamide, an alkylating agent, is commonly used in chemotherapy to treat testicular, cervical, and lung cancer. Ifosfamide is slowly activated in the liver by hydroxylation, forming the triazene derivative 5-(3,3-dimethyl-1-triazeno)-imidazole-4-carboxamide (DTIC) (*Goodman & Gilman's The Pharmacological Basis of Therapeutics* 9th ed. p. 1235, J. G. Hardman et al., Eds., McGraw Hill, N.Y., 1996). Cytochrome P450 activates DTIC via an N-demethylation reaction yielding an alkylating moiety, diazomethane. The active metabolites are then able to cross-link DNA causing growth arrest and cell death. Though ifosfamide is therapeutically useful, it is also associated with nephrotoxicity, urotoxicity, and central neurotoxicity.

Mesna, another therapeutic, is often administered concomitantly to prevent kidney and bladder problems from arising (Brock and Pohl (1986), *IARC Sci Publ* 78: 269-279). However, there are documented cases in which tubular toxicity occurred and elevated urinary levels of alanine aminopeptidase and N-acetyl-beta-D-glucosaminidase were found in patients even though mesna was administered alongside ifosfamide (Goren et al. (1987), *Cancer Treat Rep* 71: 127-130).

One study examined 42 patients that had been administered ifosfamide to treat advanced soft-tissue sarcoma (Stuart-Harris et al. (1983), *Cancer Chemother Pharmacol* 11: 69-72). The ifosfamide dosage varied from 5.0 $g/m^2$ to 8.0 $g/m^2$, and all of the patients were given mesna to counteract the negative effects of ifosfamide. Even so, nausea and vomiting were common to all of the patients. Out of the 42 patients, seven developed nephrotoxicity, and two of the cases progressed to fatal renal failure.

In another clinical study, renal tubular function was monitored in 18 neuroblastoma patients (Caron et al. (1992), *Med Pediatr Oncol* 20: 42-47). Tubular toxicity occurred in at least 12 of the patients, and seven of those patients eventually developed Debre-de Toni-Fanconi syndrome, although in 3 cases the syndrome was reversible.

Fanconi syndrome is a disorder marked by dysfunction of the proximal tubules of the kidney. It is associated with aminoaciduria, renal glycosuria, and hyperphosphaturia. Ifosfamide is often used experimentally on rats to induce Fanconi syndrome. In one study, rats that were administered 80 mg/kg of ifosfamide had significantly lower body weight and hematocrit than control rats (Springate and Van Liew (1995), *J Appl Toxicol* 15: 399-402). Additionally, the rats had low-grade glucosuria, proteinuria, and phosphaturia. In a mouse study, ifosfamide induced elevated serum creatinine and urea levels and decreased the clearance rate of creatinine (Badary (1999), *J Ethnopharmacol* 67: 135-142).

Cyclophosphamide, a nitrogen mustard and alkylating agent, is highly toxic to dividing cells and is commonly used in chemotherapy to treat malignant lymphomas, such as non-Hodgkin's lymphomas and Burkitt's lymphoma, multiple myeloma, leukemias, neuroblastomas, ovarian adenocarcinomas and retinoblastomas, as well as breast and lung cancer (*Goodman & Gilman's The Pharmacological Basis of Therapeutics* $9^{th}$ ed., pp. 1234, 1237-1239, J. G. Hardman et al., eds., McGraw Hill, N.Y., 1996; Physicians Desk Reference, $47^{th}$ ed., pp. 744-745, Medical Economics Co., Inc., Montvale, N.J., 1993). Additionally, cyclophosphamide is used as an immunosuppressive agent in bone marrow transplantation and following organ transplantation. Although cyclophosphamide is therapeutically useful against certain types of cancer, it is also associated with cardiotoxicity, nephrotoxicity (including renal tubular necrosis), hemorrhagic cystitis, myelosuppression, hepatotoxicity, impairment of male and female reproductive systems, interstitial pneumonitis and central nervous system toxicity.

Once in the liver, cyclophosphamide is hydroxylated by the cytochrome P450 mixed function oxidase system, producing the active metabolites phosphoramide mustard and acrolein, which cross-link DNA and cause growth arrest and cell death. These metabolites, however, are highly toxic and cause adverse effects in the other organs into which they are transported, such as the kidneys. Acrolein is removed from the kidneys by secretion into the urine, resulting in cystitis (inflammation of the bladder), often hemorrhagic cystitis.

In the kidney, cyclophosphamide induces necrosis of the renal distal tubule. Cyclophosphamide, which is structurally similar to the anti-cancer drug ifosfamide, does not induce damage to the renal proximal tubule nor does it induce Debre-de Toni-Fanconi syndrome (Rossi et al. (1997), *Nephrol Dial Transplant* 12: 1091-1092).

One clinical trial of patients being treated with cyclophosphamide showed that renal damage from the drug leads to a reduced biotransformation rate and low renal clearance of the drug, resulting in a build-up of toxic alkylating metabolic products (Wagner et al. (1980), *Arzneimittelforschung* 30: 1588-1592).

In a study of patients suffering from malignant lymphomas and mammary carcinomas, a direct relationship was found between the dose of cyclophosphamide used in treatment and the concentration of alkylating metabolites in the patients' urine. The upper limit of the dose was determined by the nature and degree of the toxic side effects, rather than by the rate at which the drug could be metabolized (Saul et al. (1979), *J Cancer Res Clin Oncol* 94: 277-286). It is the acrolein itself that is toxic, not the alkylating activity of cyclophosphamide (Brock et al. (1979), *Arzneimittelforschung* 29: 659-661). A study on rats also showed that acrolein from the kidneys can produce hemorrhagic cystitis and that the acrolein concentration is directly related to the frequency and severity of the cystitis (Chijiwa et al. (1983), *Cancer Res* 43: 5205-5209).

Carboplatin, a platinum coordination complex, is commonly used in chemotherapy as an anti-tumor agent. As a chemotherapeutic agent, carboplatin acts similarly to cisplatin. Carboplatin enters the cell by diffusion where it is activated by hydrolysis (*Goodman & Gilman's The Pharmacoloiical Basis of Therapeutics* $9^{th}$ ed., p. 1270-1271, J. G. Hardman et al. Eds., McGraw Hill, N.Y. 1996). Once activated, the platinum complexes are able to react with DNA causing cross-linking to occur. One of the differences between carboplatin and cisplatin is that carboplatin is better tolerated clinically. Some of the side-effects associated with cisplatin, such as nausea, neurotoxicity, and nephrotoxicity, are seen at a lesser degree in patients administered carboplatin. Some other side-effects are hypomagnesaemia and hypokalaemia (Kintzel (2001), *Drug Saf* 24: 19-38).

In one study on male Wistar rats, carboplatin was administered at a dosage of 65 mg/kg (Wolfgang et al. (1994), *Fundam Appl Toxicol* 22: 73-79). After treatment with carboplatin, CGT excretion was increased approximately two-fold.

Another study compared cisplatin and carboplatin when given in combination with vindesine and mitomycin C (Jelic et al. (2001) *Lung Cancer* 34: 1-13). The study showed that carboplatin administered with vindesine and mitomycin C was advantageous in terms of overall survival, although the regimen was more hematologically toxic than when cisplatin was given.

AY-25329, is a phenothiazine that has been shown to be mildly hepatotoxic and to induce nephrosis. Its structure is shown below.

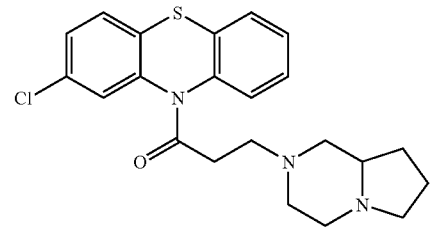

Phenothiazines are a class of psychoactive drugs. They have been used to treat schizophrenia, paranoia, mania, hyperactivity in children, some forms of senility, and anxiety. Some side effects associated with prolonged use of the drugs are reduced blood pressure, Parkinsonism, reduction of motor activity, and visual impairment.

Chlorpromazine (Thorazine or Largactil) is an aliphatic phenothiazine and is widely used for treating schizophrenia and manic depression. Prolactin secretion is increased while taking chlorpromazine, and galactorrhea and gynecomastia have both been associated with the drug. Trifluoperazine is another prescribed phenothiazine. It is used to treat anxiety, to prevent nausea and vomiting, and to manage psychotic disorders. Negative side-effects that have been associated with the drug are liver damage, bone marrow depression, and Parkinsonism.

Acyclovir (9-[(2-hydroxyethyl)methyl]guanine, Zovirax®), an anti-viral guanosine analogue, is used to treat herpes simplex virus (HSV), varicella zoster virus (VZV) and Epstein-Barr virus (EBV) infections. It is transported into cells by the nucleoside transporter that imports guanine, and acyclovir is phosphorylated by virally encoded thymidine kinase (TK). Other kinases convert acyclovir to its activated di- and triphosphate forms, which prevent the polymerization of viral DNA. Acyclovir triphosphate competes with dGTP for the viral polymerase, and acyclovir is preferentially incorporated, but as a monophosphate. As a result, chain elongation ceases (*Fields Virology* 3d ed., Fields et al., eds., pp. 436-440, Lippincott-Raven Publishers, Philadelphia, 1996; *Cecil Textbook of Medicine.* 20$^{th}$ed., part XII, p. 1742, J. C. Bennett and F. Plum Eds., W.B. Saunders Co., Philadelphia, 1996).

The pharmacokinetics of acyclovir show that it has a useful half-life of about three hours and that most of it is excreted in the urine largely unchanged (Brigden et al. (1985), *Scand J Infect Dis Suppl* 47:33-39). Not surprisingly, the most frequent adverse effect of acyclovir treatment is damage to various parts of the kidney, particularly the renal tubules. Crystalluria, or the precipitation of crystals (in this case, crystals of acyclovir), in the lumina of the renal tubules can occur (Fogazzi (1996), *Nephrol Dial Transplant* 11: 379-387). If the drug crystallizes in the renal collecting tubules, obstructive nephropathy and tubular necrosis can result (Richardson (2000), *Vet Hum Toxicol* 42: 370-371). Tissues from biopsies of affected patients showed dilation of the proximal and distal renal tubules, with loss of the brush border, flattening of the lining cells and focal nuclear loss (Becker et al. (1993), *Am J Kidney Dis* 22: 611-615).

Citrinin, a mycotoxin produced by the fungus *Penicillium citrinum*, is a natural contaminant of foods and feeds (Bondy and Armstrong (1998) *Cell Biol. Toxicol.* 14: 323-332). It is known that mycotoxins can have negative effects on the immune system, however citrinin-treated animals have been shown to stimulate responses against antigens (Sharma (1993) *J. Dairy Sci.* 76: 892-897). Citrinin is a known nephrotoxin, and in birds such as chickens, ducklings, and turkeys, it causes diarrhea, increased food consumption and reduced weight gain due to kidney degeneration (Mehdi et al. (1981) *Food Cosmet. Toxicol.* 19: 723-733; Mehdi et al. (1984) *Vet. Pathol.* 21: 216-223). In the turkey and duckling study, both species exhibited nephrosis with the occurrence of hepatic and lymphoid lesions (Mehdi et al., 1984).

In one study, citrinin was administered to rabbits as a single oral dose of either 120 or 67 mg/kg (Hanika et al. (1986) *Vet. Pathol.* 23: 245-253). Rabbits treated with citrinin exhibited renal alterations such as condensed and distorted mitochondria, distended intercellular spaces of the medullary and straight cortical distal tubules, and disorganization of interdigitating processes. In another rabbit study, citrinin-administered rabbits displayed azotaemia and metabolic acidosis (Hanika et al. (1984) *Food Chem. Toxicol.* 22: 999-1008). Renal failure was indicated by decreased creatinine clearance and increased blood urea nitrogen and serum-creatinine levels.

In the past, mercury was an important component of pharmaceuticals, particularly of antiseptics, antibacterials, skin ointments, diuretics and laxatives. Although, mercury has been largely replaced by more effective, more specific and safer compounds, making drug-induced mercury poisoning rare, it is still widely used in industry. Poisoning from occupational exposure and environmental pollution, such as mercury release into public water supplies, remains a concern as wildlife, domestic animals and humans are affected.

Because of their lipid solubility and ability to cross the blood-brain barrier, the most dangerous form of mercury is the organomercurials, the most common of which is methylmercury, a fungicide used for disinfecting crop seeds. In a number of countries, incidents involving large-scale illness and death from mercury poisoning have been reported when mercury-contaminated seeds were planted and the crops harvested and consumed. A second source of organic mercury poisoning results from industrial chemicals containing inorganic mercury, such as mercury catalysts, which form methylmercury as a reaction product. If this waste product is released into reservoirs, lakes, rivers or bays, the surrounding population can become sick or die, particularly those who eat local fish.

The inorganic salt mercuric chloride, $HgCl_2$, as well as other mercuric salts, are more irritating and more toxic than the mercurous forms. Mercuric chloride is used today in industry, for the manufacture of bleach, electronics, plastics, fungicides and dental amalgams. The main source of human exposure is industrial dumping into rivers (Goodman & Gilman's: The Pharmacological Basis of Therapeutics (9th ed.), pp. 1654-1659, McGraw-Hill, N.Y., 1996).

When inorganic mercury salts are ingested, about 10% of the mercuric ions are absorbed by the gastrointenstinal tract, and a considerable portion of the $Hg^{2+}$ can remain bound to the mucosal surfaces. The highest concentration of $Hg^{2+}$ is found in the kidneys, as it is retained there longer than in other tissues. Consequently, the kidneys are the organ most adversely affected by inorganic mercury poisoning. The proximal tubules are the major site of damage, where tubular necrosis results. The mercury affects primarily the S2 and S3 portions of the proximal tubules, but, at high levels of mercury exposure, the S1 and distal portions of the tubules are also damaged. These regions of the nephrons are affected because they contain enzymes (such as gamma-glutamyl-transpeptidase) and transport proteins (such as the basolateral organic anion transport system) involved in mercury uptake (Diamond et al. (1998), *Toxicol Pathol* 26: 92-103).

Urinary markers of mercury toxicity which can be detected in NMR spectra include elevated levels of lactate, acetate and taurine and decreased levels of hippurate (Holmes et al (2000), *Chem Res Toxicol* 13: 471-478). Known changes in gene expression in kidneys exposed to $Hg^{2+}$ include up-regulation of the heat-shock protein hsp72 and of the glucose-regulated protein grp94. The degree of tissue necrosis and level of expression of these proteins is proportional to both the dose of mercury ($Hg^{2+}$) and the length of the exposure time to mercury ($Hg^{2+}$), with hsp72 accumulating in the renal cortex and grp94 accumulating in the renal medulla (Goering et al. (2000), *Toxicol Sci* 53: 447-457).

Diflunisal, a non-steroidal anti-inflammatory drug (NSAID), is a difluorophenyl derivative of salicylic acid (*Goodman & Gilman's The Pharmacological Basis of Therapeutics* 9$^{th}$ed. p. 631, J. G. Hardman et al., Eds., McGraw Hill, N.Y., 1996). It is most frequently used in the treatment of osteoarthritis and musculoskeletal strains. NSAIDs have analgesic, antipyretic and anti-inflammatory actions, however hepatotoxicity is known to be an adverse side effect of NSAID treatment (Masubuchi et al. (1998) *J. Pharmacol. Exp. Ther.* 287: 208-213). Diflunisal has been shown to be less toxic than other NSAIDs, nevertheless over long periods of dosage it can lead to deleterious effects on platelet or kidney function (Bergamo et al. (1989) *Am. J. Nephrol.* 9: 460-463). Other side effects that have been associated with diflunisal treatment are diarrhea, dizziness, drowsiness, gas or heartburn, headache, nausea, vomiting, and insomnia.

Masubuchi et al. compared the hepatotoxicity of 18 acidic NSAIDs. In the study, diflunisal (administered at a concentration of 500 μM) was shown to increase LDH leakage in rat hepatocytes, a marker for cell injury, when compared to the control sample. In addition, treatment with diflunisal led to decreased intracellular ATP concentrations.

One study compared the effects of diflunisal and ibuprofen when given to patients over a two week period (Muncie and Nasrallah (1989) *Clin. Ther.* 11: 539-544). In both the ibuprofen and the diflunisal group, two patients complained of abdominal cramping. The study indicated that even during short-term usage some gastrointestinal effects may occur. The toxic dose used in this study was chosen as one that did not induce significant gastric ulceration in rats. The group of rats given the high dosage of diflunisal had increased concentrations of creatinine which is consistent with renal injury, although dehydration may also cause increases in creatinine concentration.

Cidofovir (Vistide®) is an antiviral cytosine analog used in the treatment of viral infections such as herpesvirus, adenovirus, papillomavirus, poxvirus and hepadnavirus (*Goodman & Gilman's The Pharmacological Basis of Therapeutics* $9^{th}$ ed., p. 1216, J. G. Hardman et al., Eds., McGraw Hill, N.Y., 1996). It is also useful for the treatment of cytomegalovirus (CMV) infection, which is a type of herpesvirus.

Some mild side effects seen in patients receiving cidofovir are nausea, vomiting, and fever. The most serious reported side effect of the drug is kidney toxicity. In response to the threat of nephrotoxicity, it is necessary for patients receiving cidofovir to have their kidneys checked before treatment, and the patients must be monitored during treatment for early symptoms of kidney problems. In addition, cidofovir is given with fluids to help reduce the risk of kidney toxicity. Probenecid, a drug that helps protect the kidneys, is normally administered concomitantly (Lalezari and Kuppermann (1997)*J. Acquir. Immune Defic. Syndr. Hum. Retrovirol.* 14: S27-31).

One study compared the safety and efficacy of cidofovir in the treatment of CMV (Lalezari et al. (1998) *J. Acquir. Immune Defic. Syndr. Hum. Retrovirol.* 17: 339-344). Approximately 40% of the patients exhibited dose-dependent asymptomatic proteinuria and 25% of the patients had elevated serum creatinine levels.

Pamidronate (Aredia®) is a bisphosphonate drug that is clinically used to inhibit bone resorption and make bones more stable. It is used to treat hypercalcemia (too much calcium in the blood) that occurs with some types of cancer. Typically administered by intravenous injection, pamidronate is frequently used in patients with breast cancer or multiple myeloma whose disease has spread to the bones. Some side effects related to pamidronate treatment are abdominal cramps, chills, confusion, fever, muscle spasms, nausea, muscle stiffness, and swelling at the injection site. Patients with kidney problems may be prohibited from using pamidronate as it is excreted through the kidneys.

In one study, rats and mice were given varying doses of labeled pamidronate (Cal and Daley-Yates (1990) *Toxicology* 65: 179-197). Pamidronate treatment led to significant weight loss and a decrease in creatinine clearance. Morphological studies showed a loss of brush border membranes and the presence of focal proximal tubular necrosis.

Another study compared the tolerability of different treatments for hypercalcemia of malignancy by reviewing articles published between 1979 and 1998 (Zojer et al. (1999) *Drug Saf* 21: 389-406). The authors found that elevated serum creatinine level, nausea, and fever were reported following treatment with bisphosphonates such as pamidronate.

Markowitz et al. (2001, *J. Am. Soc. Nephrol.* 12: 1164-1172) tried to determine whether there was a correlation between pamidronate treatment and collapsing focal segmental glomerulosclerosis (FSGS). The authors examined the histories of seven patients who had developed collapsing FSGS, and they found that the only drug treatment in common was the administration of pamidronate. When given at the recommended dose of 90 mg per month, renal toxicity was rare. However, when pamidronate was given at higher doses nephrotoxicity occurred.

Lithium, an alkali metal, is the main pharmacological treatment for bipolar disorders. It is typically given as a salt, such as lithium carbonate or lithium citrate. Some common side effects of lithium treatment are an increase in urination, increase in drinking, dry mouth, weight gain, fine tremor, and fatigue. Some more serious side effects related to lithium treatment are blurred vision, mental confusion, seizures, vomiting, diarrhea, muscle weakness, drowsiness, and coarse tremor (*Goodman & Gilman's The Pharmacological Basis of Therapeutics* $9^{th}$ ed., p. 448, J. G. Hardman et al., Eds., McGraw Hill, N.Y., 1996).

Since lithium is often used on a maintenance basis for a lifelong period, numerous studies have been performed to try and elucidate the effects of lithium on the kidney. One group administered lithium in daily doses within the human therapeutic range to male Wistar rats (Kling et al. (1984) *Lab Invest* 50: 526-535). Rats that were given lithium developed marked polyuria within three weeks of the initial dosing. The rats displayed elevated free water clearance and vasopressin-resistant diabetes insipidus. The cortical collecting tubules displayed morphological changes, e.g. dilation of the tubules, bulging cells lining the tubules, enlarged nuclei, following lithium treatment.

Another study examined a human population that had been given lithium for the treatment of bipolar disorder (Markowitz et al. (2000) *J. Am. Soc. Nephrol.* 11: 1439-1448). The patients had a mean age of 42.5 years and had been undergoing lithium treatment from 2 to 25 years (mean of 13.6 years). Approximately one fourth of the patients had nephrotic proteinuria, almost 90% of them had nephrogenic diabetes insipidus (NDI), and renal biopsies revealed a chronic tubulointerstitial nephropathy in all of the patients. Following cessation of lithium treatment, seven of the patients proceeded to end-stage renal disease.

Even though nephrotoxicity is a known side effect of lithium treatment, some studies have indicated that in actuality it is not all that common (Johnson (1998) *Neuropsychopharmacology* 19: 200-205). One study showed that the NDI-like effect in lithium treatment was easily overcome by increasing the levels of arginine vasopressin (AVP) (Carney et al. (1996) *Kidney Int* 50: 377-383). Other studies have suggested that patients with psychiatric disorders display certain defects in renal function without undergoing lithium treatment (Gitlin (1999) *Drug Saf* 20: 231-243).

Hydralazine, an antihypertensive drug, causes relaxation of arteriolar smooth muscle. Such vasodilation is linked to vigorous stimulation of the sympathetic nervous system, which in turn leads to increased heart rate and contractility, increased plasma renin activity, and fluid retention (*Goodman & Gilman's The Pharmacological Basis of Therapeutics* $9^{th}$ ed., p. 794, J. G. Hardman et al., Eds., McGraw Hill, N.Y., 1996). The increased renin activity leads to an increase in angiotensin 11, which in turn causes stimulation of aldosterone and sodium reabsorption.

Hydralazine is used for the treatment of high blood pressure (hypertension) and for the treatment of pregnant women suffering from high blood pressure (pre-eclampsia or eclampsia). Some common side effects associated with hydralazine use are diarrhea, rapid heartbeat, headache, decreased appetite, and nausea. Hydralazine is often used concomitantly with drugs that inhibit sympathetic activity to combat the mild pulmonary hypertension that can be associated with hydralazine usage.

In one hydralazine study, rats were fed hydralazine and mineral metabolism was monitored (Peters et al. (1988) *Toxi-* col Lett 41: 193-202). Manganese and zinc concentrations were not effected by hydralazine treatment, however tissue iron concentrations were decreased and kidney copper concentrations were increased compared to control groups.

Another study compared the effects of hydrazine, phenelzine, and hydralazine treatment on rats (Runge-Morris et al. (1996) *Drug Metab Dispos* 24: 734-737). Hydralazine caused an increase in renal GST-alpha subunit expression, although unlike hydrazine and phenelzine it did not alter renal cytochrome P4502E1 expression.

Colchicine, an alkoloid of *Colchicum autumale*, is an anti-inflammatory agent used in the treatment of gouty arthritis (*Goodman & Gilman's The Pharmacological Basis of Therapeutics* $9^{th}$ ed., p. 647, J. G. Hardman et al., Eds., McGraw Hill, N.Y., 1996).

An antimitotic agent, colchicine binds to tubulin which leads to depolymerization and disappearance of the fibrillar microtubules in granulocytes and other motile cells. In doing so, the migration of granulocytes into the inflamed area is inhibited. Through a series of events, the inflammatory response is blocked.

Some common, mild side effects associated with colchicine treatment are loss of appetite and hair loss. More severe side effects that warrant cessation of treatment are nausea, vomiting, diarrhea, and abdominal pain. Coichicine overdose can induce multiorgan failure with a high incidence of mortality. In this setting, renal failure is multifactorial and related to prolonged hypotension, hypoxemia, sepsis, and rhabdomyolysis. In rats, less dramatic doses have been shown to inhibit the secretion of many endogenous proteins such as insulin and parathyroid hormone.

One study investigated the effects of colchicine on microtubule polymerization status and post-translational modifications of tubulin in rat seminiferous tubules (Correa and Miller (2001) *Biol Reprod* 64: 1644-1652). Colchicine caused extensive microtubule depolymerization, and total tubulin levels decreased twofold after coichicine treatment. The authors also found that colchicine treatment led to a decrease in tyrosination of the microtubule pool of tubulin which was associated with depolymerization of microtubules.

Sulfadiazine, a sulfonamide, is an antimicrobial agent. It is commonly used concomitantly with pyrimethamine to treat toxoplasmosis, an infection of the brain, in patient suffering from AIDS. These drugs are able to cross the blood-brain barrier and are used at relatively high doses. In addition, sulfadiazine has been shown to be effective at preventing certain types of meningococcal diseases and in treating urinary tract infections.

Sulfonamides in general are structural analogs of para-aminobenzoic acid (PABA). Because they are competitive antagonists of PABA, sulfonamides are effective against bacteria that are required to utilize PABA for the synthesis of folic acid (*Goodman & Gilman's The Pharmacological Basis of Therapeutics* $9^{th}$ ed., p. 1058-1060, J. G. Hardman et al., Eds., McGraw Hill, N.Y., 1996).

The main side effects associated with sulfadiazine treatment are fever and skin rashes. Decreases in white blood cells, red blood cells, and platelets, nausea, vomiting, and diarrhea are some other side effects that may result from sulfadiazine treatment. The most troublesome problem with this drug for HIV/AIDS patients is kidney toxicity. These patients tend to use these drugs for extended periods of time, which puts a constant strain on the kidneys. In addition, kidney stones tend to form in the bladder and ureter thereby blocking the flow of urine. Kidney damage may result, and if left untreated kidney failure may occur. Therefore, patients being treated with sulfadiazine are instructed to increase their fluid intake in order to prevent crystal formation in the kidneys.

One case study examined four HIV-positive patients who had been given sulfadiazine to treat toxoplasmosis (Crespo et al. (2000) *Clin Nephrol* 54: 68-72). All four of the patients, one of whom was a previously healthy person, developed oliguria, abdominal pain, renal failure, and displayed multiple radiolucent renal calculi in echography. Following extensive hydration and alcalinization, the renal function of the patients returned to normal.

Adriamycin, known generically as doxorubicin, is an anthracycline antibiotic produced by the fungus *Streptomyces peucetius*. It is an anti-tumor drug used in the treatment of breast, ovarian, bladder, and lung cancers as well as non-Hodgkin's lymphoma, Hodgkin's disease and sarcoma (*Goodman & Gilman's The Pharmacological Basis of Therapeutics* $9^{th}$ ed., p. 1264-1265, J. G. Hardman et al., Eds., McGraw Hill, N.Y., 1996).

Adriamycin has tetracycline ring structures with the sugar daunosamine attached by glycosidic linkage. It is able to intercalate with DNA, it affects DNA and RNA synthesis, and it can interact with cell membranes and alter their functions. Typically the drug is cell-cycle specific for the S phase of cell division. By binding to the cancer cells' DNA and blocking topoisomerase II, cancer cells are unable to divide and grow.

Some common side effects associated with adriamycin treatment are fatigue, a drop in white blood cell, red blood cell, or platelet count, hair loss, skin discoloration, and watery eyes. More serious side effects include myocardial toxicity, ulceration and necrosis of the colon, and development of a second cancer.

Because of its utility in fighting cancer, numerous studies have been performed in attempts to further understand the mechanisms and effects of adriamycin. In one study, investigators injected mice with a single dose of adriamycin (Chen et al. (1998) *Nephron* 78: 440-452). The mice exhibited signs of combined glomerular albuminuria and immunoglublinuria, progressively elevated levels of nitrite/nitrate in the urine, abnormal renal function, and other symptoms indicative of focal segmental glomerulosclerosis.

In another study, rats were given adriamycin and the effects on angiotensin converting enzyme (ACE) were monitored (Venkatesan et al. (1993) *Toxicology* 85: 137-148). The rats developed glomerular and tubular injury, and serum ACE levels were significantly elevated 20, 25, and 30 days post-treatment. A different study followed rabbits for up to one year that were treated with either adriamycin, nephrectomy, or combinations thereof (Gadeholt-Gothlin et al. (1995) *Urol Res* 23: 169-173). The rabbits that were treated with adriamycin exhibited signs of nephrotoxicity at relatively low doses.

Toxicity Prediction and Modeling

The genes and gene expression information, gene expression profiles, as well as the portfolios and subsets of the genes provided in Tables 1-5, may be used to predict at least one toxic effect, including the nephrotoxicity of a test or unknown compound. As used, herein, at least one toxic effect includes, but is not limited to, a detrimental change in the physiological status of a cell or organism. The response may be, but is not required to be, associated with a particular pathology, such as tissue necrosis. Accordingly, the toxic effect includes effects at the molecular and cellular level. Nephrotoxicity is an effect as used herein and includes but is not limited to the pathologies of nephritis, kidney necrosis, glomerular and tubular injury, and focal segmental glomerulosclerosis. As used herein, a gene expression profile comprises any quantitative representation of the expression of at least one mRNA species in a cell sample or population and includes profiles made by various methods such as differential display, PCR, hybridization analysis, etc.

In general, assays to predict the toxicity or nephrotoxicity of a test agent (or compound or multi-component composition) comprise the steps of exposing a cell population to the test compound, assaying or measuring the level of relative or absolute gene expression of one or more of the genes in Tables 1-5 and comparing the identified expression level(s) to the expression levels disclosed in the Tables and database(s) disclosed herein. Assays may include the measurement of the expression levels of about 2, 3, 4, 5, 6, 7, 8, 9, 10, 15, 20, 25, 30, 50, 75, 100 or more genes from Tables 1-5.

In the methods of the invention, the gene expression level for a gene or genes induced by the test agent, compound or compositions may be comparable to the levels found in the Tables or databases disclosed herein if the expression level varies within a factor of about 2, about 1.5 or about 1.0 fold. In some cases, the expression levels are comparable if the agent induces a change in the expression of a gene in the same direction (e.g., up or down) as a reference toxin.

The cell population that is exposed to the test agent, compound or composition may be exposed in vitro or in vivo. For instance, cultured or freshly isolated renal cells, in particular rat renal cells, may be exposed to the agent under standard laboratory and cell culture conditions. In another assay format, in vivo exposure may be accomplished by administration of the agent to a living animal, for instance a laboratory rat.

Procedures for designing and conducting toxicity tests in in vitro and in vivo systems are well known, and are described in many texts on the subject, such as Loomis et al., Loomis's Esstentials of Toxicology, 4th Ed., Academic Press, New York, 1996; Echobichon, The Basics of Toxicity Testing, CRC Press, Boca Raton, 1992; Frazier, editor, In Vitro Toxicity Testing, Marcel Dekker, New York, 1992; and the like.

In in vitro toxicity testing, two groups of test organisms are usually employed: One group serves as a control and the other group receives the test compound in a single dose (for acute toxicity tests) or a regimen of doses (for prolonged or chronic toxicity tests). Because, in some cases, the extraction of tissue as called for in the methods of the invention requires sacrificing the test animal, both the control group and the group receiving compound must be large enough to permit removal of animals for sampling tissues, if it is desired to observe the dynamics of gene expression through the duration of an experiment.

In setting up a toxicity study, extensive guidance is provided in the literature for selecting the appropriate test organism for the compound being tested, route of administration. dose ranges, and the like. Water or physiological saline (0.9% NaCl in water) is the solute of choice for the test compound since these solvents permit administration by a variety of routes. When this is not possible because of solubility limitations, vegetable oils such as corn oil or organic solvents such as propylene glycol may be used.

Regardless of the route of administration, the volume required to administer a given dose is limited by the size of the animal that is used. It is desirable to keep the volume of each dose uniform within and between groups of animals. When rats or mice are used, the volume administered by the oral route generally should not exceed about 0.005 ml per gram of animal. Even when aqueous or physiological saline solutions are used for parenteral injection the volumes that are tolerated are limited, although such solutions are ordinarily thought of as being innocuous. The intravenous $LD_{50}$ of distilled water in the mouse is approximately 0.044 ml per gram and that of isotonic saline is 0.068 ml per gram of mouse. In some instances, the route of administration to the test animal should be the same as, or as similar as possible to, the route of administration of the compound to man for therapeutic purposes.

When a compound is to be administered by inhalation, special techniques for generating test atmospheres are necessary. The methods usually involve aerosolization or nebulization of fluids containing the compound. If the agent to be tested is a fluid that has an appreciable vapor pressure, it may be administered by passing air through the solution under controlled temperature conditions. Under these conditions, dose is estimated from the volume of air inhaled per unit time, the temperature of the solution, and the vapor pressure of the agent involved. Gases are metered from reservoirs. When particles of a solution are to be administered, unless the particle size is less than about 2 µm the particles will not reach the terminal alveolar sacs in the lungs. A variety of apparatuses and chambers are available to perform studies for detecting effects of irritant or other toxic endpoints when they are administered by inhalation. The preferred method of administering an agent to animals is via the oral route, either by intubation or by incorporating the agent in the feed.

When the agent is exposed to cells in vitro or in cell culture, the cell population to be exposed to the agent may be divided into two or more subpopulations, for instance, by dividing the population into two or more identical aliquots. In some preferred embodiments of the methods of the invention, the cells to be exposed to the agent are derived from kidney tissue. For instance, cultured or freshly isolated rat renal cells may be used.

The methods of the invention may be used generally to predict at least one toxic response, and, as described in the Examples, may be used to predict the likelihood that a compound or test agent will induce various specific kidney pathologies, such as nephritis, kidney necrosis, glomerular and tubular injury, focal segmental glomerulosclerosis, or other pathologies associated with at least one of the toxins herein described. The methods of the invention may also be used to determine the similarity of a toxic response to one or more individual compounds. In addition, the methods of the invention may be used to predict or elucidate the potential cellular pathways influenced, induced or modulated by the compound or test agent due to the similarity of the expression profile compared to the profile induced by a known toxin (see Tables 5-5CC).

Diagnostic Uses for the Toxicity Markers

As described above, the genes and gene expression information or portfolios of the genes with their expression information as provided in Tables 1-5 may be used as diagnostic markers for the prediction or identification of the physiological state of tissue or cell sample that has been exposed to a compound or to identify or predict the toxic effects of a compound or agent. For instance, a tissue sample such as a sample of peripheral blood cells or some other easily obtainable tissue sample may be assayed by any of the methods described above, and the expression levels from a gene or genes from Tables 1-5 may be compared to the expression levels found in tissues or cells exposed to the toxins described herein. These methods may result in the diagnosis of a physiological state in the cell or may be used to identify the potential toxicity of a compound, for instance a new or unknown compound or agent. The comparison of expression data, as well as available sequence or other information may be done by researcher or diagnostician or may be done with the aid of a computer and databases as described below.

In another format, the levels of a gene(s) of Tables 1-5, its encoded protein(s), or any metabolite produced by the encoded protein may be monitored or detected in a sample, such as a bodily tissue or fluid sample to identify or diagnose a physiological state of an organism. Such samples may include any tissue or fluid sample, including urine, blood and easily obtainable cells such as peripheral lymphocytes.

Use of the Markers for Monitoring Toxicity Progression

As described above, the genes and gene expression information provided in Tables 1-5 may also be used as markers for the monitoring of toxicity progression, such as that found after initial exposure to a drug, drug candidate, toxin, pollutant, etc. For instance, a tissue or cell sample may be assayed by any of the methods described above, and the expression levels from a gene or genes from Tables 1-5 may be compared to the expression levels found in tissue or cells exposed to the renal toxins described herein. The comparison of the expression data, as well as available sequence or other information may be done by a researcher or diagnostician or may be done with the aid of a computer and databases.

Use of the Toxicity Markers for Drug Screening

According to the present invention, the genes identified in Tables 1-5 may be used as markers or drug targets to evaluate the effects of a candidate drug, chemical compound or other agent on a cell or tissue sample. The genes may also be used as drug targets to screen for agents that modulate their expression and/or activity. In various formats, a candidate drug or agent can be screened for the ability to stimulate the transcription or expression of a given marker or markers or to down-regulate or counteract the transcription or expression of a marker or markers. According to the present invention, one can also compare the specificity of a drug's effects by looking at the number of markers which the drug induces and comparing them. More specific drugs will have less transcriptional targets. Similar sets of markers identified for two drugs may indicate a similarity of effects.

Assays to monitor the expression of a marker or markers as defined in Tables 1-5 may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, gene chips containing probes to one, two or more genes from Tables 1-5 may be used to directly monitor or detect changes in gene expression in the treated or exposed cell. Cell lines, tissues or other samples are first exposed to a test agent and in some instances, a known toxin, and the detected expression levels of one or more, or preferably 2 or more of the genes of Tables 1-5 are compared to the expression levels of those same genes exposed to a known toxin alone. Compounds that modulate the expression patterns of the known toxin(s) would be expected to modulate potential toxic physiological effects in vivo. The genes in Tables 1-5 are particularly appropriate markers in these assays as they are differentially expressed in cells upon exposure to a known renal toxin. Tables 1 and 2 disclose those genes that are differentially expressed upon exposure to the named toxins and their corresponding GenBank Accession numbers. Table 3 discloses the human homologues and the corresponding GenBank Accession numbers of the differentially expressed genes of Tables 1 and 2.

In another format, cell lines that contain reporter gene fusions between the open reading frame and/or the transcriptional regulatory regions of a gene in Tables 1-5 and any assayable fusion partner may be prepared. Numerous assayable fusion partners are known and readily available including the firefly luciferase gene and the gene encoding chloramphenicol acetyltransferase (Alam et al. (1990), *Anal Biochem* 188: 245-254). Cell lines containing the reporter gene fusions are then exposed to the agent to be tested under appropriate conditions and time. Differential expression of the reporter gene between samples exposed to the agent and control samples identifies agents which modulate the expression of the nucleic acid.

Additional assay formats may be used to monitor the ability of the agent to modulate the expression of a gene identified in Tables 1-5. For instance, as described above, mRNA expression may be monitored directly by hybridization of probes to the nucleic acids of the invention. Cell lines are exposed to the agent to be tested under appropriate conditions and time, and total RNA or mRNA is isolated by standard procedures such those disclosed in Sambrook et al. (Molecular Cloning: A Laboratory Manual, 2nd Ed., Cold Spring Harbor Laboratory Press, Cold Spring Harbor, N.Y., 1989).

In another assay format, cells or cell lines are first identified which express the gene products of the invention physiologically. Cells and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines may be transduced or transfected with an expression vehicle (e.g., a plasmid or viral vector) construct comprising an operable non-translated 5'-promoter containing end of the structural gene encoding the gene products of Tables 1-5 fused to one or more antigenic fragments or other detectable markers, which are peculiar to the instant gene products, wherein said fragments are under the transcriptional control of said promoter and are expressed as polypeptides whose molecular weight can be distinguished from the naturally occurring polypeptides or may further comprise an immunologically distinct or other detectable tag. Such a process is well known in the art (see Sambrook et al., supra).

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells are disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the agent-contacted sample is then compared with the control samples (no exposure and exposure to a known toxin) where only the excipient is contacted with the cells and an increase or decrease in the immunologically generated signal from the agent-contacted sample compared to the control is used to distinguish the effectiveness and/or toxic effects of the agent.

Another embodiment of the present invention provides methods for identifying agents that modulate at least one activity of a protein(s) encoded by the genes in Tables 1-5. Such methods or assays may utilize any means of monitoring or detecting the desired activity.

In one format, the relative amounts of a protein (Tables 1-5) between a cell population that has been exposed to the agent to be tested compared to an un-exposed control cell population and a cell population exposed to a known toxin may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe, such as a specific antibody.

Agents that are assayed in the above methods can be randomly selected or rationally selected or designed. As used herein, an agent is said to be randomly selected when the agent is chosen randomly without considering the specific sequences involved in the association of a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see G. A. Grant in: Molecular Biology and Biotechnology, Meyers, ed., pp. 659-664, VCH Publishers, New York, 1995). A skilled artisan can readily recognize that there is no limit as to the structural nature of the agents of the present invention.

Nucleic Acid Assay Formats

The genes identified as being differentially expressed upon exposure to a known renal toxin (Tables 1-5) may be used in a variety of nucleic acid detection assays to detect or quantify the expression level of a gene or multiple genes in a given sample. The genes described in Tables 1-5 may also be used in combination with one or more additional genes whose differential expression is associate with toxicity in a cell or tissue. In preferred embodiments, the genes in Tables 1-5 may be combined with one or more of the genes described in prior and related application Nos. 60/292,335; 60/297,523; 60/298,925; 60/303,810; 60/303,807; 60/303,808; 60/315,047; 60/324,928; 60/330,867; 60/330,462; 60/331,805; 60/336,144; 60/340,873; 60/357,843; 60/357,842; 60/357,844; 60/364,134; 60/370,206; 60/370,247; 60/370,144; 60/371,679; 60/372,794, 09/917,800 and 10/060,087 all of which are incorporated by reference on page 1 of this application.

Any assay format to detect gene expression may be used. For example, traditional Northern blotting, dot or slot blot, nuclease protection, primer directed amplification, RT-PCR, semi- or quantitative PCR, branched-chain DNA and differential display methods may be used for detecting gene expression levels. Those methods are useful for some embodiments of the invention. In cases where smaller numbers of genes are detected, amplification based assays may be most efficient. Methods and assays of the invention, however, may be most efficiently designed with hybridization-based methods for detecting the expression of a large number of genes.

Any hybridization assay format may be used, including solution-based and solid support-based assay formats. Solid supports containing oligonucleotide probes for differentially expressed genes of the invention can be filters, polyvinyl chloride dishes, particles, beads, microparticles or silicon or glass based chips, etc. Such chips, wafers and hybridization methods are widely available, for example, those disclosed by Beattie (WO 95/11755).

Any solid surface to which oligonucleotides can be bound, either directly or indirectly, either covalently or non-covalently, can be used. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, from 2, 10, 100, 1000 to 10,000, 100,000 or 400,000 or more of such features on a single solid support. The solid support, or the area within which the probes are attached may be on the order of about a square centimeter. Probes corresponding to the genes of Tables 1-5 or from the related applications described above may be attached to single or multiple solid support structures, e.g., the probes may be attached to a single chip or to multiple chips to comprise a chip set.

Oligonucleotide probe arrays for expression monitoring can be made and used according to any techniques known in the art (see for example, Lockhart et al (1996), *Nat Biotechnol* 14:1675-1680; McGall et al. (1996), *Proc Nat Acad Sci USA* 93:13555-13460). Such probe arrays may contain at least two or more oligonucleotides that are complementary to or hybridize to two or more of the genes described in Tables 1-5. For instance, such arrays may contain oligonucleotides that are complementary to or hybridize to at least 2, 3, 4, 5, 6, 7, 8, 9, 10, 20, 30, 50, 70, 100 or more of the genes described herein. Preferred arrays contain all or nearly all of the genes listed in Tables 1-5, or individually, the gene sets of Tables 5-5CC. In a preferred embodiment, arrays are constructed that contain oligonucleotides to detect all or nearly all of the genes in any one of or all of Tables 1-5 on a single solid support substrate, such as a chip.

The sequences of the expression marker genes of Tables 1-5 are in the public databases. Table 1 provides the GenBank Accession Number or NCBI RefSeq ID for each of the sequences. Table 3 provides the LocusLink and Unigene names and descriptions for the human homologues of the genes described in Tables 1 and 2. The sequences of the genes in GenBank and/or RefSeq are expressly herein incorporated by reference in their entirety as of the filing date of this application, as are related sequences, for instance, sequences from the same gene of different lengths, variant sequences, polymorphic sequences, genomic sequences of the genes and related sequences from different species, including the human counterparts, where appropriate. These sequences may be used in the methods of the invention or may be used to produce the probes and arrays of the invention. In some embodiments, the genes in Tables 1-5 that correspond to the genes or fragments previously associated with a toxic response may be excluded from the Tables. p As described above, in addition to the sequences of the GenBank Accession Numbers or NCBI Refeq ID's disclosed in the Tables 1-5, sequences such as naturally occurring variants or polymorphic sequences may be used in the methods and compositions of the invention. For instance, expression levels of various allelic or homologous forms of a gene disclosed in Tables 1-5 may be assayed. Any and all nucleotide variations that do not alter the functional activity of a gene listed in the Tables 1-5, including all naturally occurring allelic variants of the genes herein disclosed, may be used in the methods and to make the compositions (e.g., arrays) of the invention.

Probes based on the sequences of the genes described above may be prepared by any commonly available method. Oligonucleotide probes for screening or assaying a tissue or cell sample are preferably of sufficient length to specifically hybridize only to appropriate, complementary genes or transcripts. Typically the oligonucleotide probes will be at least about 10, 12, 14, 16, 18, 20 or 25 nucleotides in length. In some cases, longer probes of at least 30, 40, or 50 nucleotides will be desirable.

As used herein, oligonucleotide sequences that are complementary to one or more of the genes described in Tables 1-5 refer to oligonucleotides that are capable of hybridizing under stringent conditions to at least part of the nucleotide sequences of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

The phrase "hybridizing specifically to" or "specifically hybridizes" refers to the binding, duplexing, or hybridizing of a molecule substantially to or only to a particular nucleotide sequence or sequences under stringent conditions when that sequence is present in a complex mixture (e.g., total cellular) DNA or RNA.

Assays and methods of the invention may utilize available formats to simultaneously screen at least about 100, preferably about 1000, more preferably about 10,000 and most preferably about 1,000,000 different nucleic acid hybridizations.

As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e., A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

The terms "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases.

While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Typically, stringent conditions will be those in which the salt concentration is at least about 0.01 to 1.0 M $Na^+$ ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical submit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Probe Design

One of skill in the art will appreciate that an enormous number of array designs are suitable for the practice of this invention. The high density array will typically include a number of test probes that specifically hybridize to the sequences of interest. Probes may be produced from any region of the genes identified in the Tables and the attached representative sequence listing. In instances where the gene reference in the Tables is an EST, probes may be designed from that sequence or from other regions of the corresponding full-length transcript that may be available in any of the sequence databases, such as those herein described. See WO 99/32660 for methods of producing probes for a given gene or genes. In addition, any available software may be used to produce specific probe sequences, including, for instance, software available from Molecular Biology Insights, Olympus Optical Co. and Biosoft International. In a preferred embodiment, the array will also include one or more control probes.

High density array chips of the invention include "test probes." Test probes may be oligonucleotides that range from about 5 to about 500, or about 7 to about 50 nucleotides, more preferably from about 10 to about 40 nucleotides and most preferably from about 15 to about 35 nucleotides in length. In other particularly preferred embodiments, the probes are 20 or 25 nucleotides in length. In another preferred embodiment, test probes are double or single strand DNA sequences such as cDNA fragments. DNA sequences are isolated or cloned from natural sources or amplified from natural sources using native nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes may fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample to be screened. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross hybridization to a nucleic acid in the sample other than the target to which the probe is directed. For example, if the target is present the perfect match probes should be consistently brighter than the mismatch probes. In addition, if all central mismatches are present, the mismatch probes can be used to detect a mutation, for instance, a mutation of a gene in the accompanying Tables 1-5. The difference in intensity between the perfect match and the mismatch probe provides a good measure of the concentration of the hybridized material.

Nucleic Acid Samples

Cell or tissue samples may be exposed to the test agent in vitro or in vivo. When cultured cells or tissues are used, appropriate mammalian cell extracts, such as liver extracts, may also be added with the test agent to evaluate agents that may require biotransformation to exhibit toxicity. In a preferred format, primary isolates of animal or human renal cells which already express the appropriate complement of drug-metabolizing enzymes may be exposed to the test agent without the addition of mammalian kidney extracts.

The genes which are assayed according to the present invention are typically in the form of mRNA or reverse transcribed mRNA. The genes may or may not be cloned. The genes may or may not be amplified. The cloning and/or amplification do not appear to bias the representation of genes within a population. In some assays, it may be preferable, however, to use polyA+ RNA as a source, as it can be used with less processing steps.

As is apparent to one of ordinary skill in the art, nucleic acid samples used in the methods and assays of the invention may be prepared by any available method or process. Methods of isolating total mRNA are well known to those of skill in the art. For example, methods of isolation and purification of nucleic acids are described in detail in Chapter 3 of *Laboratory Techniques in Biochemistry and Molecular Biology, Vol. 24*, Hybridization With Nucleic Acid Probes: Theory and Nucleic Acid Probes, P. Tijssen, Ed., Elsevier Press, New York, 1993. Such samples include RNA samples, but also include cDNA synthesized from a mRNA sample isolated from a cell or tissue of interest. Such samples also include DNA amplified from the cDNA, and RNA transcribed from the amplified DNA. One of skill in the art would appreciate that it is desirable to inhibit or destroy RNase present in homogenates before homogenates are used.

Biological samples may be of any biological tissue or fluid or cells from any organism as well as cells raised in vitro, such as cell lines and tissue culture cells. Frequently the sample will be a tissue or cell sample that has been exposed to a compound, agent, drug, pharmaceutical composition, potential environmental pollutant or other composition. In some formats, the sample will be a "clinical sample" which is a sample derived from a patient. Typical clinical samples include, but are not limited to, sputum, blood, blood-cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Forming High Density Arrays

Methods of forming high density arrays of oligonucleotides with a minimal number of synthetic steps are known. The oligonucleotide analogue array can be synthesized on a single or on multiple solid substrates by a variety of methods, including, but not limited to, light-directed chemical coupling, and mechanically directed coupling (see Pirrung, U.S. Pat. No. 5,143,854).

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5' photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In addition to the foregoing, additional methods which can be used to generate an array of oligonucleotides on a single substrate are described in PCT Publication Nos. WO 93/09668 and WO 01/23614. High density nucleic acid arrays can also be fabricated by depositing pre-made or natural nucleic acids in predetermined positions. Synthesized or natural nucleic acids are deposited on specific locations of a substrate by light directed targeting and oligonucleotide directed targeting. Another embodiment uses a dispenser that moves from region to region to deposit nucleic acids in specific spots.

Hybridization

Nucleic acid hybridization simply involves contacting a probe and target nucleic acid under conditions where the probe and its complementary target can form stable hybrid duplexes through complementary base pairing. See WO 99/32660. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization tolerates fewer mismatches. One of skill in the art will appreciate that hybridization conditions may be selected to provide any degree of stringency.

In a preferred embodiment, hybridization is performed at low stringency, in this case in 6×SSPET at 37° C. (0.005% Triton X-100), to ensure hybridization and then subsequent washes are performed at higher stringency (e.g., 1×SSPET at 37° C.) to eliminate mismatched hybrid duplexes. Successive washes may be performed at increasingly higher stringency (e.g., down to as low as 0.25×SSPET at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Signal Detection

The hybridized nucleic acids are typically detected by detecting one or more labels attached to the sample nucleic acids. The labels may be incorporated by any of a number of means well known to those of skill in the art. See WO 99/32660.

Databases

The present invention includes relational databases containing sequence information, for instance, for the genes of Tables 1-5, as well as gene expression information from tissue or cells exposed to various standard toxins, such as those herein described (see Tables 5-5CC). Databases may also contain information associated with a given sequence or tissue sample such as descriptive information about the gene associated with the sequence information (see Tables 1 and 2), or descriptive information concerning the clinical status of the tissue sample, or the animal from which the sample was derived. The database may be designed to include different parts, for instance a sequence database and a gene expression database. Methods for the configuration and construction of such databases and computer-readable media to which such databases are saved are widely available, for instance, see U.S. Pat. No. 5,953,727, which is herein incorporated by reference in its entirety.

The databases of the invention may be linked to an outside or external database such as GenBank (www.ncbi.nlm.nih.gov/entrez.index.html); KEGG (www.genome.ad.jp/kegg); SPAD (www.grt.kuyshu-u.ac.jp/spad/index.html); HUGO (www.gene.ucl.ac.uk/hugo); Swiss-Prot (www.expasy.ch.sprot); Prosite (www.expasy.ch/tools/scnpsitl.html); OMIM (www.ncbi.nlm.nih.gov/omim); and GDB (www.gdb.org). In a preferred embodiment, as described in Tables 1-5, the external database is GenBank and the associated databases maintained by the National Center for Biotechnology Information (NCBI) (www.ncbi.nlm.nih.gov).

Any appropriate computer platform, user interface, etc. may be used to perform the necessary comparisons between sequence information, gene expression information and any other information in the database or information provided as an input. For example, a large number of computer workstations are available from a variety of manufacturers, such has those available from Silicon Graphics. Client/server environments, database servers and networks are also widely available and appropriate platforms for the databases of the invention.

The databases of the invention may be used to produce, among other things, electronic Northerns that allow the user to determine the cell type or tissue in which a given gene is expressed and to allow determination of the abundance or expression level of a given gene in a particular tissue or cell.

The databases of the invention may also be used to present information identifying the expression level in a tissue or cell of a set of genes comprising one or more of the genes in Tables 1-5, comprising the step of comparing the expression level of at least one gene in Tables 1-5 in a cell or tissue exposed to a test agent to the level of expression of the gene in the database. Such methods may be used to predict the toxic potential of a given compound by comparing the level of expression of a gene or genes in Tables 1-5 from a tissue or cell sample exposed to the test agent to the expression levels found in a control tissue or cell samples exposed to a standard toxin or renal toxin such as those herein described. Such methods may also be used in the drug or agent screening assays as described herein.

Kits

The invention further includes kits combining, in different combinations, high-density oligonucleotide arrays, reagents for use with the arrays, protein reagents encoded by the genes of the Tables, signal detection and array-processing instruments, gene expression databases and analysis and database management software described above. The kits may be used, for example, to predict or model the toxic response of a test compound, to monitor the progression of renal disease states, to identify genes that show promise as new drug targets and to screen known and newly designed drugs as discussed above.

The databases packaged with the kits are a compilation of expression patterns from human or laboratory animal genes and gene fragments (corresponding to the genes of Tables 1-5). In particular, the database software and packaged information that may contain the databases saved to a computer-readable medium include the expression results of Tables 1-5 that can be used to predict toxicity of a test agent by comparing the expression levels of the genes of Tables 1-5 induced by the test agent to the expression levels presented in Tables 5-5CC. In another format, database and software information may be provided in a remote electronic format, such as a website, the address of which may be packaged in the kit.

The kits may used in the pharmaceutical industry, where the need for early drug testing is strong due to the high costs associated with drug development, but where bioinformatics, in particular gene expression informatics, is still lacking. These kits will reduce the costs, time and risks associated with traditional new drug screening using cell cultures and laboratory animals. The results of large-scale drug screening of pre-grouped patient populations, pharmacogenomics testing, can also be applied to select drugs with greater efficacy and fewer side-effects. The kits may also be used by smaller biotechnology companies and research institutes who do not have the facilities for performing such large-scale testing themselves.

Databases and software designed for use with microarrays is discussed in Balaban et al., U.S. Pat. No. 6,229,911, a computer-implemented method for managing information, stored as indexed Tables 1-5, collected from small or large numbers of microarrays, and U.S. Pat. No. 6,185,561, a computer-based method with data mining capability for collecting gene expression level data, adding additional attributes and reformatting the data to produce answers to various queries. Chee et al., U.S. Pat. No. 5,974,164, disclose a software-based method for identifying mutations in a nucleic acid sequence based on differences in probe fluorescence intensities between wild type and mutant sequences that hybridize to reference sequences.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Identification of Toxicity Markers

The renal toxins cephaloridine, cisplatin, puromycin aminonucleoside (PAN), bromoethylamine hydrobromide (BEA), gentamicin, ifosfamide, cyclophosphamide, carboplatin, AY-25329, indomethacin, acyclovir, citrin mercuric chloride, diflunisal, cidofovir, pamidronate, lithium, hydralazine, colchicine, sulfadiazine, and adriamycin and control compositions were administered to male Sprague-Dawley rats at various timepoints using administration diluents, protocols and dosing regimes as previously described in the art and previously described in the priority applications discussed above. The low and high dose level for each compound are provided in the chart below.

| Renal Toxin | Low Dose (mg/kg) | High Dose (mg/kg) | Method of Administration |
|---|---|---|---|
| cephaloridine | 100 | 800 | intravenous |
| cisplatin | 1 | 5 | intravenous |
| PAN | 10 | 150 | intravenous |
| BEA | 10 | 200 | intraperitoneal |
| gentamicin | 2 | 80 | intramuscular |
| ifosfamide | 5 | 100 | intraperitoneal |
| cyclophosphamide | 20 | 2000 | intraperitoneal |
| carboplatin | 5 | 50 | intravenous |
| AY-25329 | 25 | 250 | oral gavage |
| indomethacin | 1 | 10 | oral gavage |
| acyclovir | 10 | 100 | intraperitoneal |
| citrinin | 1 | 35 | intraperitoneal |
| mercuric chloride | 0.1 | 1 | intravenous |
| diflunisal | 2 | 400 | oral gavage |
| cidofovir | 10 | 100 | intraperitoneal |
| pamidronate | 1 | 60 | intraperitoneal |
| lithium | 0.3 (nmol/kg) | 3 (nmol/kg) | intraperitoneal |
| hydralazine | 2.5 | 25 | intraperitoneal |
| colchicine | 0.15 | 1.5 | intraperitoneal |

-continued

| Renal Toxin | Low Dose (mg/kg) | High Dose (mg/kg) | Method of Administration |
|---|---|---|---|
| sulfadiazine | 100 | 1000 | intravenous |
| adriamycin | 1.3 | 12.8 | intravenous |

After administration, the dosed animals were observed and tissues were collected as described below:

Observation of Animals

| | |
|---|---|
| 1. Clinical Observations- | Twice daily: mortality and moribundity check. Cage Side Observations - skin and fur, eyes and mucous membrane, respiratory system, circulatory system, autonomic and central nervous system, somatomotor pattern, and behavior pattern. Potential signs of toxicity, including tremors, convulsions, salivation, diarrhea, lethargy, coma or other atypical behavior or appearance, were recorded as they occurred and included a time of onset, degree, and duration. |
| 2. Physical Examinations- | Prior to randomization, prior to initial treatment, and prior to sacrifice. |
| 3. Body Weights- | Prior to randomization, prior to initial treatment, and prior to sacrifice. |

Clinical Pathology

| | |
|---|---|
| 1. Frequency | Prior to necropsy. |
| 2. Number of animals | All surviving animals. |
| 3. Bleeding Procedure | Blood was obtained by puncture of the orbital sinus while under 70% $CO_2$/30% $O_2$ anesthesia. |
| 4. Collection of Blood Samples | Approximately 0.5 mL of blood was collected into EDTA tubes for evaluation of hematology parameters. Approximately 1 mL of blood was collected into serum separator tubes for clinical chemistry analysis. Approximately 200 uL of plasma was obtained and frozen at ~−80° C. for test compound/metabolite estimation. An additional ~2 mL of blood was collected into a 15 mL conical polypropylene vial to which ~3 mL of Trizol was immediately added. The contents were immediately mixed with a vortex and by repeated inversion. The tubes were frozen in liquid nitrogen and stored at ~−80° C. |

Termination Procedures

Terminal Sacrifice

Approximately 3, 6, 24, 48, 72, 120, 144, 168, 336, and/or 360 hours after the initial dose, rats were weighed, physically examined, sacrificed by decapitation, and exsanguinated. The animals were necropsied within approximately five minutes of sacrifice. Separate sterile, disposable instruments were used for each animal, with the exception of bone cutters, which were used to open the skull cap. The bone cutters were dipped in disinfectant solution between animals.

Necropsies were conducted on each animal following procedures approved by board-certified pathologists.

Animals not surviving until terminal sacrifice were discarded without necropsy (following euthanasia by carbon dioxide asphyxiation, if moribund). The approximate time of death for moribund or found dead animals was recorded.

Postmortem Procedures

Fresh and sterile disposable instruments were used to collect tissues. Gloves were worn at all times when handling tissues or vials. All tissues were collected and frozen within approximately 5 minutes of the animal's death. The liver sections and kidneys were frozen within approximately 3-5 minutes of the animal's death. The time of euthanasia, an interim time point at freezing of liver sections and kidneys, and time at completion of necropsy were recorded. Tissues were stored at approximately −80° C. or preserved in 10% neutral buffered formalin.

Tissue Collection and Processing

Liver
1. Right medial lobe—snap frozen in liquid nitrogen and stored at ~−80° C.
2. Left medial lobe—Preserved in 10% neutral-buffered formalin (NBF) and evaluated for gross and microscopic pathology.
3. Left lateral lobe—snap frozen in liquid nitrogen and stored at ~−80° C.

Heart
A sagittal cross-section containing portions of the two atria and of the two ventricles was preserved in 10% NBF. The remaining heart was frozen in liquid nitrogen and stored at ~−80° C.

Kidneys (Both)
1. Left—Hemi-dissected; half was preserved in 10% NBF and the remaining half was frozen in liquid nitrogen and stored at ~−80° C.
2. Right—Hemi-dissected; half was preserved in 10% NBF and the remaining half was frozen in liquid nitrogen and stored at ~−80° C.

Testes (Both)
A sagittal cross-section of each testis was preserved in 10% NBF. The remaining testes were frozen together in liquid nitrogen and stored at ~−80° C.

Brain (Whole)
A cross-section of the cerebral hemispheres and of the diencephalon was preserved in 10% NBF, and the rest of the brain was frozen in liquid nitrogen and stored at ~−80° C.

Microarray sample preparation was conducted with minor modifications, following the protocols set forth in the Affymetrix GeneChip Expression Analysis Manual. Frozen tissue was ground to a powder using a Spex Certiprep 6800 Freezer Mill. Total RNA was extracted with Trizol (Gibco-BRL) utilizing the manufacturer's protocol. The total RNA yield for each sample was 200-500 μg per 300 mg tissue weight. mRNA was isolated using the Oligotex mRNA Midi kit (Qiagen) followed by ethanol precipitation. Double stranded cDNA was generated from mRNA using the SuperScript Choice system (GibcoBRL). First strand cDNA synthesis was primed with a T7-(dT24) oligonucleotide. The cDNA was phenol-chloroform extracted and ethanol precipitated to a final concentration of 1 μg/ml. From 2 μg of cDNA, cRNA was synthesized using Ambion's T7 MegaScript in vitro Transcription Kit.

To biotin label the cRNA, nucleotides Bio-11-CTP and Bio-16-UTP (Enzo Diagnostics) were added to the reaction. Following a 37° C. incubation for six hours, impurities were removed from the labeled cRNA following the RNeasy Mini kit protocol (Qiagen). cRNA was fragmented (fragmentation buffer consisting of 200 mM Tris-acetate, pH 8.1, 500 mM KOAc, 150 mM MgOAc) for thirty-five minutes at 94° C. Following the Affymetrix protocol, 55 μg of fragmented cRNA was hybridized on the Affymetrix rat array set for twenty-four hours at 60 rpm in a 45° C. hybridization oven.

The chips were washed and stained with Streptavidin Phycoerythrin (SAPE) (Molecular Probes) in Affymetrix fluidics stations. To amplify staining, SAPE solution was added twice with an anti-streptavidin biotinylated antibody (Vector Laboratories) staining step in between. Hybridization to the probe arrays was detected by fluorometric scanning (Hewlett Packard Gene Array Scanner). Data was analyzed using Affymetrix GeneChip® version 2.0 and Expression Data Mining (EDMT) software (version 1.0), GeneExpress2000, and S-Plus.

Tables 1 and 2 disclose those genes that are differentially expressed upon exposure to the named toxins and their corresponding GenBank Accession and Sequence Identification numbers, the identities of the metabolic pathways in which the genes function, the gene names if known, and the unigene cluster titles. The model code represents the various toxicity state that each gene is able to discriminate as well as the individual toxin type associated with each gene. The codes are defined in Table 4. The GLGC ID is the internal Gene Logic identification number.

Table 3 discloses those genes that are the human homologues of those genes in Tables 1 and 2 that are differentially expressed upon exposure to the named toxins. The corresponding GenBank Accession and Sequence Identification numbers, the gene names if known, and the unigene cluster titles of the human homologues are listed.

Table 4 defines the comparison codes used in Tables 1, 2, 3, and 5.

Tables 5-5CC disclose the summary statistics for each of the comparisons performed. Each of these tables contains a set of predictive genes and creates a model for predicting the renal toxicity of an unknown, i.e., untested compound. Each gene is identified by its Gene Logic identification number and can be cross-referenced to a gene name and representative SEQ ID NO. in Tables 1 and 2. For each comparison of gene expression levels between samples in the toxicity group (samples affected by exposure to a specific toxin) and samples in the non-toxicity group (samples not affected by exposure to that same specific toxin), the tox mean (for toxicity group samples) is the mean signal intensity, as normalized for the various chip parameters that are being assayed. The non-tox mean represents the mean signal intensity, as normalized for the various chip parameters that are being assayed, in samples from animals other than those treated with the high dose of the specific toxin. These animals were treated with a low dose of the specific toxin, or with vehicle alone, or with a different toxin. Samples in the toxicity groups were obtained from animals sacrificed at the timepoint(s) indicated in the Table 5 headings, while samples in the non-toxicity groups were obtained from animals sacrificed at all time points in the experiments. For individual genes, an increase in the tox mean compared to the non-tox mean indicates up-regulation upon exposure to a toxin. Conversely, a decrease in the tox mean compared to the non-tox mean indicates down-regulation.

The mean values are derived from Average Difference (AveDiff) values for a particular gene, averaged across the corresponding samples. Each individual Average Difference value is calculated by integrating the intensity information from multiple probe pairs that are tiled for a particular fragment. The normalization multiplies each expression intensity for a given experiment (chip) by a global scaling factor. The intent of this normalization is to make comparisons of individual genes between chips possible. The scaling factor is calculated as follows:

1. From all the unnormalized expression values in the experiment, delete the largest 2% and smallest 2% of the values. That is, if the experiment yields 10,000 expression values, order the values and delete the smallest 200 and the largest 200.

2. Compute the trimmed mean, which is equal to the mean of the remaining values.

3. Compute the scale factor SF=100/(trimmed mean).

The value of 100 used here is the standard target value used. Some AveDiff values may be negative due to the general noise involved in nucleic acid hybridization experiments. Although many conclusions can be made corresponding to a negative value on the GeneChip platform, it is difficult to assess the meaning behind the negative value for individual fragments. Our observations show that, although negative values are observed at times within the predictive gene set, these values reflect a real biological phenomenon that is highly reproducible across all the samples from which the measurement was taken. For this reason, those genes that exhibit a negative value are included in the predictive set. It should be noted that other platforms of gene expression measurement may be able to resolve the negative numbers for the corresponding genes. The predictive ability of each of those genes should extend across platforms, however. Each mean value is accompanied by the standard deviation for the mean. The linear discriminant analysis score (discriminant score), as disclosed in the tables, measures the ability of each gene to predict whether or not a sample is toxic. The discriminant score is calculated by the following steps:

Calculation of a Discriminant Score

Let $X_i$ represent the AveDiff values for a given gene across the non-tox samples, i=1 . . . n.

Let $Y_i$ represent the AveDiff values for a given gene across the tox samples, i=1 . . . t.

The calculations proceed as follows:

1. Calculate mean and standard deviation for $X_i$'s and $Y_i$'s, and denote these by $m_X$, $m_Y$, $s_X$, $s_Y$.

2. For all $X_i$'s and $Y_i$'s, evaluate the function $f(z)=((1/s_Y)*\exp(-0.5*((z-m_Y)/s_Y)^2))/(((1/s_Y)*\exp(-0.5*((z-m_Y)/s_Y)^2))+((1/s_X)*\exp(-0.5*((z-m_X)/s_X)^2)))$.

3. The number of correct predictions, say P, is then the number of $Y_i$'s such that $f(Y_i)>0.5$ plus the number of $X_i$'s such that $f(X_i)<0.5$.

4. The discriminant score is then P/(n+t).

Linear discriminant analysis uses both the individual measurements of each gene and the calculated measurements of all combinations of genes to classify samples. For each gene a weight is derived from the mean and standard deviation of the toxic and nontox groups. Every gene is multiplied by a weight and the sum of these values results in a collective discriminate score. This discriminant score is then compared against collective centroids of the tox and nontox groups. These centroids are the average of all tox and nontox samples respectively. Therefore, each gene contributes to the overall prediction. This contribution is dependent on weights that are large positive or negative numbers if the relative distances between the tox and nontox samples for that gene are large and small numbers if the relative distances are small. The discriminant score for each unknown sample and centroid values can be used to calculate a probability between zero and one as to the group in which the unknown sample belongs.

Example 2

General Toxicity Modeling

Samples were selected for grouping into tox-responding and non-tox-responding groups by examining each study individually with Principal Components Analysis (PCA) to determine which treatments had an observable response. Only groups where confidence of their tox-responding and non-tox-responding status was established were included in building a general tox model (Table 5).

Linear discriminant models were generated to describe toxic and non-toxic samples. The top discriminant genes and/or EST's were used to determine toxicity by calculating each gene's contribution with homo and heteroscedastic treatment of variance and inclusion or exclusion of mutual information between genes. Prediction of samples within the database exceeded 80% true positives with a false positive rate of less than 5%. It was determined that combinations of genes and/or EST's generally provided a better predictive ability than individual genes and that the more genes and/or EST used the better predictive ability. Although the preferred embodiment includes fifty or more genes, many pairings or greater combinations of genes and/or EST can work better than individual genes. All combinations of two or more genes from the selected list (Table 5) could be used to predict toxicity. These combinations could be selected by pairing in an agglomerate, divisive, or random approach. Further, as yet undetermined genes and/or EST's could be combined with individual or combination of genes and/or EST's described here to increase predictive ability. However, the genes and/or EST's described here would contribute most of the predictive ability of any such undetermined combinations.

Other variations on the above method can provide adequate predictive ability. These include selective inclusion of components via agglomerate, divisive, or random approaches or extraction of loading and combining them in agglomerate, divisive, or random approaches. Also the use of composite variables in logistic regression to determine classification of samples can also be accomplished with linear discriminate analysis, neural or Bayesian networks, or other forms of regression and classification based on categorical or continual dependent and independent variables.

Example 3

Modeling Methods

The above modeling methods provide broad approaches of combining the expression of genes to predict sample toxicity. One could also provide no weight in a simple voting method or determine weights in a supervised or unsupervised method using agglomerate, divisive, or random approaches. All or selected combinations of genes may be combined in ordered, agglomerate, or divisive, supervised or unsupervised clustering algorithms with unknown samples for classification. Any form of correlation matrix may also be used to classify unknown samples. The spread of the group distribution and discriminate score alone provide enough information to enable a skilled person to generate all of the above types of models with accuracy that can exceed discriminate ability of individual genes. Some examples of methods that could be used individually or in combination after transformation of data types include but are not limited to: Discriminant Analysis, Multiple Discriminant Analysis, logistic regression, multiple regression analysis, linear regression analysis, conjoint analysis, canonical correlation, hierarchical cluster analysis, k-means cluster analysis, self-organizing maps, multidimensional scaling, structural equation modeling, support vector machine determined boundaries, factor analysis, neural networks, bayesian classifications, and resampling methods.

Example 4

Grouping of Individual Compound and Pathology Classes

Samples were grouped into individual pathology classes based on known toxicological responses and observed clinical chemical and pathology measurements or into early and late phases of observable toxicity within a compound (Tables 5A-3CC). The top 10, 25, 50, 100 genes based on individual discriminate scores were used in a model to ensure that combination of genes provided a better prediction than individual genes. As described above, all combinations of two or more genes from this list could potentially provide better prediction than individual genes when selected in any order or by ordered, agglomerate, divisive, or random approaches. In addition, combining these genes with other genes could provide better predictive ability, but most of this predictive ability would come from the genes listed herein.

Samples may be considered toxic if they score positive in any pathological or individual compound class represented here or in any modeling method mentioned under general toxicology models based on combination of individual time and dose grouping of individual toxic compounds obtainable from the data. The pathological groupings and early and late phase models are preferred examples of all obtainable combinations of sample time and dose points. Most logical groupings with one or more genes and one or more sample dose and time points should produce better predictions of general toxicity, pathological specific toxicity, or similarity to known toxicant than individual genes.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

TABLE 1

SUMMARY

| Sequence ID No. | Identifier | GenBank Acc/ Ref. Seq ID | Model Code | Gene Name | Unigene Cluster Title |
|---|---|---|---|---|---|
| 1 | 6949 | AA012785 | q | | ESTs |
| 2 | 25098 | AA108277 | h, v | | |
| 3 | 17312 | AA108308 | r | | ESTs, Highly similar to includes exons 3 through 12 [*M. musculus*] |
| 4 | 16882 | AA684537 | o | | ESTs, Moderately similar to NADH-ubiquinone oxidoreductase subunit CI-SGDH [*H. sapiens*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 5 | 6049 | AA685178 | y | | ESTs, Highly similar to alpha NAC/1.9.2. protein [*M. musculus*] |
| 6 | 4426 | AA685974 | l, m | | ESTs |
| 7 | 21815 | AA686423 | g | | ESTs, Weakly similar to T23657 hypothetical protein M01F1.6 - *Caenorhabditis elegans* [*C. elegans*] |
| 8 | 1600 | AA686470 | i | DNA-damage inducible transcript 3 | DNA-damage inducible transcript 3 |
| 8 | 1599 | AA686470 | i | DNA-damage inducible transcript 3 | DNA-damage inducible transcript 3 |
| 9 | 21997 | AA799325 | u | | ESTs |
| 10 | 18396 | AA799330 | v | | ESTs, Highly similar to AF132951 1 CGI-17 protein [*H. sapiens*] |
| 11 | 6581 | AA799412 | f, l | | ESTs, Weakly similar to ESR1 RAT ESTROGEN RECEPTOR [*R. norvegicus*] |
| 12 | 16538 | AA799449 | k | | ESTs, Weakly similar to nucleosome assembly protein [*R. norvegicus*] |
| 13 | 23294 | AA799472 | u | | ESTs, Moderately similar to CGI-116 protein [*H. sapiens*] |
| 14 | 18290 | AA799497 | r | | ESTs |
| 15 | 18981 | AA799523 | e | | ESTs, Moderately similar to hnRNP protein [*R. norvegicus*] |
| 16 | 20843 | AA799545 | h | | ESTs, Weakly similar to TCPA RAT T-COMPLEX PROTEIN 1, ALPHA SUBUNIT [*R. norvegicus*] |
| 17 | 16993 | AA799560 | b | | ESTs |
| 18 | 16576 | AA799570 | d | | ESTs |
| 19 | 18361 | AA799591 | i | | ESTs, Highly similar to TBB1 RAT TUBULIN BETA CHAIN [*R. norvegicus*] |
| 20 | 17712 | AA799598 | z | | ESTs |
| 22 | 18346 | AA799718 | f | | ESTs |
| 23 | 8768 | AA799726 | l | | ESTs |
| 24 | 11687 | AA799732 | w | | ESTs, Highly similar to Dgcr6 protein [*M. musculus*] |
| 25 | 18349 | AA799744 | u | | ESTs |
| 26 | 17494 | AA799751 | n | | ESTs |
| 27 | 18360 | AA799771 | General | | ESTs |
| 28 | 18880 | AA799801 | w | | ESTs |
| 29 | 20998 | AA799803 | z | | ESTs, Weakly similar to serine protease [*R. norvegicus*] |
| 30 | 21006 | AA799861 | c | | ESTs, Highly similar to IRF7 MOUSE INTERFERON REGULATORY FACTOR 7 [*M. musculus*] |
| 31 | 15011 | AA799893 | General | | ESTs, Highly similar to DDRT helix-destabilizing protein - rat [*R. norvegicus*] |
| 32 | 20811 | AA799899 | a | | ESTs, Highly similar to 60S RIBOSOMAL PROTEIN L18A [*R. norvegicus*] |
| 33 | 23202 | AA799971 | General | | ESTs, Weakly similar S52675 probable membrane protein YDR109c yeast (Saccharomyces cerevisiae) [*S. cerevisiae*] |
| 34 | 4832 | AA800190 | b | | ESTs, Highly similar to glycogen phosphorylase [*R. norvegicus*] |
| 35 | 21656 | AA800202 | d | | ESTs |
| 36 | 18433 | AA800218 | j, y, z | | ESTs, Weakly similar to T15476 hypothetical protein C09F5.2 - *Caenorhabditis elegans* [*C. elegans*] |
| 37 | 6386 | AA800235 | u | | ESTs |
| 38 | 18442 | AA800258 | h, k | | ESTs |
| 39 | 21092 | AA800380 | y | | ESTs, Weakly similar to CORTICOSTEROID 11-BETA-DEHYDROGENASE, ISOZYME 1 [*R. norvegicus*] |
| 40 | 17325 | AA800587 | General | | ESTs, Weakly similar to glutathione peroxidase [*R. norvegicus*] |
| 41 | 13930 | AA800613 | cc, General | | *Rattus norvegicus* gene for TIS11, complete cds |
| 42 | 21372 | AA800693 | v | | ESTs |
| 42 | 21373 | AA800693 | s | | ESTs |
| 43 | 18161 | AA800701 | k | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 44 | 6595 | AA800753 | w | | ESTs |
| 45 | 13348 | AA800928 | General | | ESTs |
| 46 | 23115 | AA801165 | o, y | | ESTs, Highly similar to H2A1 RAT HISTONE H2A.1 [*R. norvegicus*] |
| 47 | 12399 | AA801307 | General | | ESTs |
| 48 | 7543 | AA801395 | General | | ESTs |
| 49 | 24237 | AA817726 | t, General | | ESTs |
| 50 | 11215 | AA817921 | o | | ESTs, Moderately similar to T25763 hypothetical protein F46F11.4 - *Caenorhabditis elegans* [*C. elegans*] |
| 51 | 5985 | AA818005 | g | | ESTs |
| 52 | 11338 | AA818016 | x | | ESTs, Highly similar to rabkinesin-6 [*M. musculus*] |
| 53 | 2845 | AA818026 | k, General | | ESTs, Weakly similar to PRSC MOUSE 26S PROTEASOME REGULATORY SUBUNIT S12 [*M. musculus*] |
| 54 | 16756 | AA818089 | i, k, General | | ESTs, Highly similar to glycyl-tRNA synthetase [*H. sapiens*] |
| 55 | 17771 | AA818224 | e, g, p, General | | ESTs, Highly similar to TBB1 RAT TUBULIN BETA CHAIN [*R. norvegicus*] |
| 56 | 6522 | AA818261 | g, m | | ESTs, Moderately similar to autoantigen p542 [*H. sapiens*] |
| 57 | 5924 | AA818359 | y | | ESTs |
| 58 | 7806 | AA818421 | b, aa | | ESTs |
| 59 | 8237 | AA818512 | v | | ESTs |
| 60 | 17434 | AA818574 | h | | ESTs |
| 61 | 8728 | AA818615 | General | | ESTs |
| 62 | 6054 | AA818658 | b, v, cc, General | Diphtheria toxin receptor (heparin binding epidermal growth factor - like growth factor) | Diphtheria toxin receptor (heparin binding epidermal growth factor - like growth factor) |
| 63 | 11590 | AA818721 | d | | ESTs, Moderately similar to S65785 mel-13a protein - mouse [*M. musculus*] |
| 64 | 4291 | AA818741 | q, General | | ESTs |
| 65 | 4330 | AA818747 | o, General | | ESTs |
| 66 | 19723 | AA818761 | v, General | | ESTs |
| 67 | 13684 | AA818770 | h, j, l, m | | *Rattus norvegicus* serine protease gene, complete cds |
| 68 | 6322 | AA818801 | k | | ESTs |
| 69 | 7690 | AA818875 | General | uroguanylin | uroguanylin |
| 70 | 4952 | AA818907 | q, General | | ESTs |
| 71 | 6094 | AA818911 | t | | ESTs |
| 72 | 10985 | AA818998 | o, General | | ESTs, Weakly similar to HP33 [*R. norvegicus*] |
| 73 | 6120 | AA819008 | t | | ESTs |
| 74 | 2586 | AA819081 | c | | ESTs, Weakly similar testis specific protein [*R. norvegicus*] |
| 76 | 6438 | AA819269 | o | | ESTs |
| 77 | 24721 | AA819306 | d, w | | ESTs |
| 78 | 6250 | AA819376 | o, y | | *Rattus norvegicus* mRNA for inositol hexakisphosphate kinase, complete cds |
| 80 | 6281 | AA819517 | j | | ESTs, Weakly similar to JC5707 HYA22 protein [*H. sapiens*] |
| 81 | 10141 | AA819526 | j | | ESTs |
| 82 | 6551 | AA819558 | t | | ESTs |
| 83 | 6723 | AA819653 | r | | ESTs, Moderately similar to dJ30M3.1 [*H. sapines*] |
| 84 | 14958 | AA819744 | aa | | ESTs |
| 85 | 19433 | AA819776 | v | | ESTs, Weakly similar to HS9B RAT HEAT SHOCK PROTEIN HSP 90-BETA [*R. norvegicus*] |
| 86 | 6204 | AA819889 | aa | | ESTs |
| 87 | 22820 | AA848315 | General | HMm: inosine 5'-phosphate dehydrogenase 2 | ESTs, Weakly similar to guanosine monophosphate reductase [*R. norvegicus*] |
| 88 | 6614 | AA848389 | bb | | ESTs, Weakly similar to T26686 hypothetical protein Y38F1A.6 - *Caenorhabditis elegans* [*C. elegans*] |
| 89 | 21125 | M848437 | General | | ESTs |
| 90 | 23504 | M848496 | q | | ESTs, Moderately similar to IF4B_HUMAN EUKARYOTIC |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 91 | 18532 | AA848675 | g | | TRANSLATION INITIATION FACTOR 4B [*H. sapiens*] ESTs, Weakly similar to FMO1 RAT DIMETHYLANILINE MONOOXYGENASE [*R. norvegicus*] |
| 92 | 21140 | AA848738 | c | | ESTs |
| 93 | 16128 | AA848807 | o | | ESTs, Moderately similar to AF132946 1 CGI-12 protein [*H. sapiens*] |
| 94 | 22923 | AA848929 | g | | ESTs |
| 95 | 17339 | AA849497 | General | | ESTs |
| 96 | 11727 | AA849518 | l | | ESTs |
| 97 | 21275 | AA849796 | i, l, m, General | | ESTs |
| 98 | 16678 | AA849827 | aa | | ESTs |
| 99 | 8515 | AA849917 | e | | ESTs |
| 100 | 18447 | AA849939 | General | | ESTs |
| 101 | 12130 | AA850037 | p | | ESTs |
| 102 | 23981 | AA850040 | x, aa | cyclase-associated protein homologue | cyclase-associated protein homologue |
| 103 | 13615 | AA850364 | t | | ESTs, Moderately similar to RB17 MOUSE RAS-RELATED PROTEIN RAB-17 [*M. musculus*] |
| 105 | 2637 | AA850893 | x | | ESTs, Highly similar to hypothetical protein [*H. sapiens*] |
| 106 | 22093 | AA850909 | d | | ESTs |
| 107 | 21766 | AA850916 | c | | ESTs |
| 108 | 2847 | AA850919 | w | | ESTs, Weakly similar to dithiolethione-inducible gene-1 [*R. norvegicus*] |
| 109 | 12162 | AA850975 | h | | *Rattus norvegicus* mRNA for ras-GTPase-activating protein SH3-domain binding protein, partial cds |
| 110 | 9514 | AA850978 | General | | ESTs |
| 111 | 3924 | AA851017 | e, q | | ESTs, Highly similar to molybdopterin-synthase large subunit [*M. musculus*] |
| 111 | 3925 | AA851017 | o, General | | ESTs, Highly similar to molybdopterin-synthase large subunit [*M. musculus*] |
| 112 | 4490 | AA851184 | a, k | | *Rattus norvegicus* mRNA for cathepsin Y, partial cds |
| 113 | 19187 | AA851230 | General | | ESTs, Weakly similar to T28050 hypothetical protein ZK856.11 - *Caenorhabditis elegans* [*C. elegans*] |
| 114 | 19189 | AA851237 | c | | ESTs, Highly similar to ubiquitin specific protease UBP43 [*M. musculus*] |
| 115 | 15386 | AA851241 | m | | ESTs, Highly similar to hypothetical protein [*H. sapiens*] |
| 116 | 21462 | AA851261 | g, l, General | | ESTs, Weakly similar to A61382 phosphorylation regulatory protein HP-10 [*H. sapiens*] |
| 117 | 21471 | AA851343 | General | | ESTs |
| 118 | 16902 | AA851379 | p | HHs: NADH dehydrogenase (ubiquinone) Fe—S protein 8 (23 kD) (NADH-coenzyme Q reductase) | ESTs, Moderately similar to NUIM__HUMAN NADH-UBIQUINONE OXIDOREDUCTASE 23 KD SUBUNIT PRECURSOR [*H. sapiens*] |
| 119 | 23376 | AA851392 | i, x | | ESTs, Moderately similar to kinesin-like DNA binding protein [*H. sapiens*] |
| 119 | 23377 | AA851392 | x | | ESTs, Moderately similar to kinesin-like DNA binding protein [*H. sapiens*] |
| 120 | 13349 | AA851417 | General | | ESTs |
| 121 | 21527 | AA851733 | r, u | | ESTs |
| 122 | 4048 | AA851814 | i, o, u, General | | *Rattus norvegicus* osteoactivin mRNA, complete cds |
| 123 | 10561 | AA851871 | bb | | ESTs, Highly similar to SSRA HUMAN TRANSLOCON-ASSOCIATED PROTEIN, ALPHA SUBUNIT PRECURSOR [*H. sapiens*] |
| 124 | 17411 | AA858621 | j, y | | *Rattus norvegicus* CaM-kinase II inhibitor alpha mRNA, complete cds |
| 125 | 1801 | AA858636 | k, s, x, bb | | ESTs, Weakly similar to MCM6 RAT DNA REPLICATION LICENSING FACTOR MCM6 [*R. norvegicus*] |
| 126 | 18350 | AA858674 | p | | ESTs |
| 127 | 19484 | AA858693 | e | | ESTs |
| 128 | 6360 | AA858696 | d | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 129 | 17334 | AA858704 | p | | ESTs, Weakly similar to Reg receptor [*R. norvegicus*] |
| 130 | 6380 | AA858758 | q | | ESTs, Weakly similar to dJ413H6.1.1 [*H. sapiens*] |
| 131 | 13219 | AA858759 | a | | ESTs |
| 132 | 6384 | AA858788 | l, m, General | | ESTs |
| 134 | 13412 | AA858830 | p | | ESTs, Highly similar to p40 seven-transmembrane-domain protein [*M. musculus*] |
| 135 | 7279 | AA858892 | f | | ESTs |
| 136 | 18217 | AA858930 | t | | ESTs |
| 137 | 5867 | AA858953 | v, General | HHs: asparaginyl-tRNA synthetase | ASPARAGINYL-TRNA SYNTHETASE, CYTOPLASMIC [*H. sapiens*] |
| 138 | 14479 | AA858969 | r | | ESTs, Moderately similar I56526 interleukin 1 receptor type I - rat [*R. norvegicus*] |
| 139 | 6431 | AA859085 | t | | ESTs |
| 140 | 17361 | AA859114 | o, General | | ESTs |
| 141 | 21025 | AA859241 | General | outer membrane protein | outer membrane protein |
| 142 | 10076 | AA859271 | c | | ESTs |
| 143 | 21791 | AA859333 | k | | ESTs, Weakly similar to CYSR RAT CYSTEINE-RICH PROTEIN 1 [*R. norvegicus*] |
| 144 | 16314 | AA859348 | cc, General | | ESTs |
| 145 | 18862 | AA859520 | f | | ESTs |
| 146 | 15059 | AA859545 | r | | ESTs |
| 147 | 19894 | AA859581 | s | | *Rattus norvegicus* late gestation lung protein 1 (Lgl1) mRNA, complete cds |
| 148 | 14353 | AA859585 | h | | ESTs |
| 149 | 16318 | AA859648 | h | | ESTs, Weakly similar to DnaJ homolog 2 [*R. norvegicus*] |
| 150 | 17316 | AA859652 | General | | ESTs |
| 151 | 19067 | AA859663 | n, q | | ESTs |
| 152 | 22406 | AA859680 | n | | ESTs |
| 153 | 20599 | AA859690 | x | | ESTs |
| 154 | 14261 | AA859693 | u | | ESTs, Weakly similar to YNH2__CAEEL HYPOTHETICAL 31.0 KD PROTEIN R107.2 IN CHROMOSOME III [*C. elegans*] |
| 155 | 14138 | AA859700 | v | HHs: protoporphyrinogen oxidase | ESTs, Highly similar to PPOX MOUSE PROTOPORPHYRINOGEN OXIDASE [*M. musculus*] |
| 155 | 14139 | AA859700 | v | HHs: protoporphyrinogen oxidase | ESTs, Highly similar to PPOX MOUSE PROTOPORPHYRINOGEN OXIDASE [*M. musculus*] |
| 157 | 22374 | AA859804 | l | | ESTs, Weakly similar to IF4E MOUSE EUKARYOTIC TRANSLATION INITIATION FACTOR 4E [*R. norvegicus*] |
| 158 | 22385 | AA859805 | b, k | | ESTs, Moderately similar to LYOX RAT PROTEIN-LYSINE 6-OXIDASE PRECURSOR [*R. norvegicus*] |
| 159 | 22773 | AA859885 | n | | ESTs |
| 160 | 22816 | AA859898 | k, x, z | | ESTs |
| 161 | 11891 | AA859926 | x | | ESTs |
| 162 | 23070 | AA859942 | k | | ESTs, Highly similar to N-myristoyltransferase 1 [*M. musculus*] |
| 163 | 23121 | AA859948 | k | | ESTs |
| 164 | 23166 | AA859954 | cc, General | | ESTs |
| 165 | 18468 | AA859966 | aa | | ESTs, Weakly similar to Edp1 protein [*M. musculus*] |
| 166 | 23336 | AA859981 | q | HHs: inositol(myo)-1(or 4)-monophosphatase 2 | MYO-INOSITOL-1(OR 4)-MONOPHOSPHATASE [*R. norvegicus*] |
| 167 | 4222 | AA860024 | a, bb | | ESTs, Highly similar to EF1G__HUMAN ELONGATION FACTOR 1-GAMMA [*H. sapiens*] |
| 168 | 13974 | AA860030 | u, x, General | | *Rattus norvegicus* mRNA for class I beta-tubulin, complete cds |
| 169 | 7090 | AA860039 | x | Hyaluronan mediated motility receptor (RHAMM) | EST, Hyaluronan mediated motility receptor (RHAMM) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 170 | 23769 | AA860055 | k, x | | ESTs, Moderately similar to T08661 anti-silencing protein ASF1 homolog DKFZp547E2110.1 [*H. sapiens*] |
| 171 | 16323 | AA866240 | w | | EST |
| 172 | 4462 | AA866264 | General | | ESTs, Weakly similar to PE2R RAT 20 ALPHA-HYDROXYSTEROID DEHYDROGENASE [*R. norvegicus*] |
| 173 | 15884 | AA866276 | k | | ESTs, Weakly similar to A60543 protein kinase [*R. norvegicus*] |
| 174 | 17742 | AA866302 | c, y | 4-hydroxyphenylpyruvic acid dioxygenase | 4-hydroxyphenylpyruvic acid dioxygenase |
| 175 | 16333 | AA866414 | a, h | Solute carrier family 4, member 1, anion exchange protein 1 (kidney band 3) | Solute carrier family 4, member 1, anion exchange protein 1 (kidney band 3) |
| 176 | 18918 | AA866444 | p, q | | ESTs, Moderately similar to AF141884 1 oligophrenin-1 like protein [*H. sapiens*] |
| 177 | 16853 | AA866454 | j, l, m, y, z | | ESTs |
| 178 | 18995 | AA866459 | h, m | | ESTs |
| 179 | 16013 | AA866482 | s | | ESTs, Highly similar to FGD1 MOUSE PUTATIVE RHO/RAC GUANINE NUCLEOTIDE EXCHANGE FACTOR [*M. musculus*] |
| 180 | 26036 | AA874849 | r | | |
| 181 | 16059 | AA874857 | h | | ESTs |
| 182 | 16069 | AA874873 | r | | ESTs |
| 183 | 21633 | AA874951 | f | | ESTs, Weakly similar to RNA binding protein [*H. sapiens*] |
| 184 | 16192 | AA874995 | w | | ESTs |
| 185 | 16254 | AA875025 | j | | ESTs, Highly similar to RET3 BOVIN RETINOIC ACID-BINDING PROTEIN I, CELLULAR [*R. norvegicus*] |
| 186 | 16312 | AA875032 | cc, General | | ESTs |
| 187 | 20701 | AA875097 | b | | Rat alpha-fibrinogen mRNA, 3' end |
| 188 | 16416 | AA875098 | bb | | ESTs, Highly similar to ARF3__HUMAN ADP-RIBOSYLATION FACTOR [*R. norvegicus*] |
| 189 | 16419 | AA875102 | bb | | ESTs, Highly similar to RUXE__HUMAN SMALL NUCLEAR RIBONUCLEOPROTEIN E [*M. musculus*] |
| 190 | 15313 | AA875126 | l, m, General | | ESTs |
| 191 | 10936 | AA875146 | w | | ESTs, Weakly similar to AF151834 1 CGI-76 protein [*H. sapiens*] |
| 192 | 18084 | AA875186 | h | | ESTs |
| 193 | 15371 | AA875205 | u | | ESTs, Highly similar to IF39__HUMAN EUKARYOTIC TRANSLATION INITIATION FACTOR 3 SUBUNIT 9 [*H. sapiens*] |
| 194 | 15401 | AA875257 | x, z | | ESTs |
| 195 | 15410 | AA875268 | p, s | HHs: NADH dehydrogenase (ubiquinone) Fe—S protein 7 (20 kD) (NADH-coenzyme Q reductase) | ESTs, Highly similar to NUKM HUMAN, partial CDS [*H. sapiens*] |
| 196 | 15420 | AA875286 | f | | ESTs |
| 197 | 15446 | AA875327 | s, w | | ESTs |
| 198 | 7936 | AA875495 | b, General | | ESTs |
| 199 | 17314 | AA875509 | i, l, m | | ESTs, Highly similar to includes exons 3 through 12 [*M. musculus*] |
| 200 | 24472 | AA875523 | k | | ESTs, Highly similar to MLES RAT MYOSIN LIGHT CHAIN ALKALI, SMOOTH-MUSCLE ISOFORM [*R. norvegicus*] |
| 201 | 15587 | AA875577 | j | | ESTs |
| 202 | 15617 | AA875620 | General | | ESTs |
| 202 | 15618 | AA875620 | General | | ESTs |
| 203 | 5384 | AA891041 | f, cc, General | jun B proto-oncogene | jun B proto-oncogene |
| 204 | 24814 | AA891209 | f, p | | ESTs, Moderately similar to R33729 1, partial CDS [*H. sapiens*] |
| 205 | 21930 | AA891322 | d | | ESTs, Weakly similar to AF151373 1 nucleolin-related protein NRP [*R. norvegicus*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 206 | 17225 | AA891553 | h | | ESTs, Highly similar to eIF3 p66 [*M. musculus*] |
| 207 | 7522 | AA891571 | j, m | | ESTs, Weakly similar to S67314 regulatory protein RMS1 - yeast (*Saccharomyces cerevisiae*) [*S. cerevisiae*] |
| 208 | 9071 | AA891578 | b | | ESTs |
| 209 | 19321 | AA891666 | u | melanoma antigen, family D, 1 | melanoma antigen, family D, 1 |
| 210 | 17693 | AA891737 | j, l, m, n, y, z | | ESTs |
| 211 | 17256 | AA891739 | General | | ESTs, Weakly similar to T22521 hypothetical protein F52H3.5 - *Caenorhabditis elegans* [*C. elegans*] |
| 213 | 18269 | AA891769 | General | | ESTs, Moderately similar to FINC RAT FIBRONECTIN PRECURSOR [*R. norvegicus*] |
| 214 | 9905 | AA891774 | s, bb, D239General | | ESTs |
| 215 | 17061 | AA891812 | d | | ESTs, Highly similar to alpha-adducin, hypertensive phenotype [*R. norvegicus*] |
| 216 | 7050 | AA891824 | h | | *Rattus norvegicus* clone ZG52 mRNA sequence |
| 217 | 4463 | AA891831 | General | | ESTs, Weakly similar to PE2R RAT 20 ALPHA-HYDROXYSTEROID DEHYDROGENASE [*R. norvegicus*] |
| 218 | 14289 | AA891838 | i | | ESTs, Highly similar to muscle protein 684 [*M. musculus*] |
| 219 | 20523 | AA891842 | r, cc | | ESTs |
| 220 | 17779 | AA891914 | g, s, z | | ESTs, Moderately similar to ACY1_HUMAN AMINOACYLASE-1 [*H. sapiens*] |
| 221 | 17438 | AA891943 | General | | ESTs |
| 222 | 22862 | AA891944 | p | | ESTs |
| 223 | 1159 | AA891949 | e, z | | ESTs |
| 224 | 4473 | AA891965 | General | | ESTs, Weakly similar to T31496 hypothetical protein Y116A8C.25 - *Caenorhabditis elegans* [*C. elegans*] |
| 225 | 6362 | AA892053 | f, j, l, m | | ESTs, Highly similar to chromatin structural protein homolog Supt5hp [*M. musculus*] |
| 226 | 9037 | AA892066 | y | | ESTs |
| 227 | 19469 | AA892112 | General | | ESTs, Weakly similar to proline dehydrogenase [*M. musculus*] |
| 228 | 14595 | AA892128 | o, t, v | | ESTs |
| 229 | 16527 | AA892154 | cc | | ESTs |
| 230 | 4482 | AA892173 | bb | | EST |
| 231 | 20917 | AA892238 | h | | ESTs |
| 232 | 2357 | AA892268 | d | | ESTs, Weakly similar to PC4221 protein-tyrosine kinase [*R. norvegicus*] |
| 233 | 18183 | AA892271 | h | | ESTs |
| 234 | 6523 | AA892299 | d | | ESTs |
| 236 | 13647 | AA892367 | a | | ESTs, Highly similar to RL3 RAT 60S RIBOSOMAL PROTEIN L3 [*R. norvegicus*] |
| 237 | 3473 | AA892378 | v | | ESTs, Highly similar to AF151893 1 CGI-135 protein [*H. sapiens*] |
| 238 | 17682 | AA892382 | j, p, s, x, General | | ESTs, Moderately similar to AF185570 1 putative N-acetyltransferase Camello 4 [*R. norvegicus*] |
| 239 | 820 | AA892395 | g, s | Aldolase B, fructose-biphosphate | Aldolase B, fructose-biphosphate |
| 240 | 14754 | AA892414 | u | | ESTs |
| 241 | 17439 | AA892446 | f | | ESTs |
| 242 | 16469 | AA892462 | p | | ESTs, Moderately similar to UCRY_HUMAN UBIQUINOL-CYTOCHROME C REDUCTASE COMPLEX 6.4 KD PROTEIN [*H. sapiens*] |
| 243 | 13609 | AA892468 | i, General | | *Rattus norvegicus* mRNA for prostasin precursor, complete cds |
| 243 | 13610 | AA892468 | n, v, General | | *Rattus norvegicus* mRNA for prostasin precursor, complete cds |
| 244 | 9254 | AA892470 | n, u | | ESTs, Highly similar to HISTONE H2A.Z [*R. norvegicus*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 245 | 11991 | AA892483 | s | | ESTs |
| 246 | 1522 | AA892486 | f | | ESTs, Moderately similar to LYAG MOUSE LYSOSOMAL ALPHA-GLUCOSIDASE PRECURSOR [*M. musculus*] |
| 247 | 11994 | AA892507 | aa | | ESTs, Moderately similar to S63540 protein DS 1, 24K [*H. sapiens*] |
| 248 | 23888 | AA892520 | w | | ESTs |
| 248 | 23889 | AA892520 | h | | ESTs |
| 249 | 8599 | AA892522 | p | | ESTs |
| 250 | 15154 | AA892532 | p | | *R. norvegicus* (Wistar) CaBP1 mRNA |
| 251 | 17468 | AA892545 | r | | ESTs, Highly similar to multi-membrane spanning polyspecific transporter [*M. musculus*] |
| 252 | 11203 | AA892554 | f, h | | ESTs, Highly similar to ras-GTPase-activating protein SH3-domain binding protein [*M. musculus*] |
| 253 | 18906 | AA892561 | a, bb, General | | ESTs, Moderately similar to PTD012 [*H. sapiens*] |
| 254 | 19327 | AA892562 | f, j, y, z | | *R. norvegicus* mRNA for nucleolar protein NAP57 |
| 255 | 18274 | AA892572 | p | | ESTs |
| 256 | 4512 | AA892578 | cc | | ESTs |
| 257 | 15876 | AA892582 | w | | ESTs, Highly similar to RL8_HUMAN 60S RIBOSOMAL PROTEIN L [*R. norvegicus*] |
| 258 | 19085 | AA892598 | General | | ESTs |
| 258 | 19086 | AA892598 | General | | ESTs |
| 259 | 20065 | AA892647 | l | | ESTs, Highly similar to H4_HUMAN HISTONE H4 [*R. norvegicus*] |
| 260 | 20088 | AA892666 | a, n | | ESTs |
| 261 | 23783 | AA892773 | n | | ESTs |
| 262 | 17549 | AA892776 | f, z | | Rat mitochondrial proton/phosphate symporter mRNA, complete cds |
| 263 | 13542 | AA892798 | b | | ESTs |
| 264 | 22537 | AA892799 | General | HHs: glyoxylate reductase/hydroxypyruvate reductase | ESTs, Weakly similar to SERA RAT D-3-PHOSPHOGLYCERATE DEHYDROGENASE [*R. norvegicus*] |
| 264 | 22539 | AA892799 | v | HHs: glyoxylate reductase/hydroxypyruvate reductase | ESTs, Weakly similar to SERA RAT D-3-PHOSPHOGLYCERATE DEHYDROGENASE [*R. norvegicus*] |
| 264 | 22538 | AA892799 | General | HHs: glyoxylate reductase/hydroxypyruvate reductase | ESTs, Weakly similar to SERA RAT D-3-PHOSPHOGLYCERATE DEHYDROGENASE [*R. norvegicus*] |
| 265 | 6951 | AA892820 | h | | ESTs, Weakly similar to S70642 ubiquitin ligase Nedd4 - rat [*R. norvegicus*] |
| 266 | 23322 | AA892821 | j, z | | *Rattus norvegicus* aiar mRNA for androgen-inducible aldehyde reductase, complete cds |
| 267 | 17923 | AA892843 | f | | ESTs, Weakly similar to T29904 hypothetical protein F59A3.3 - *Caenorhabditis elegans* [*C. elegans*] |
| 268 | 22871 | AA892859 | m | | ESTs, Weakly similar to procollagen-lysine 5-dioxygenase [*R. norvegicus*] |
| 269 | 9053 | AA892861 | p, v, General | | ESTs |
| 270 | 16482 | AA892940 | w | | ESTs, Weakly similar to EF2 RAT ELONGATION FACTOR 2 [*R. norvegicus*] |
| 271 | 12020 | AA893035 | j, y | | *Rattus norvegicus* HP33 mRNA, complete cds |
| 272 | 3863 | AA893060 | General | | ESTs |
| 273 | 13332 | AA893080 | i, General | | ESTs |
| 274 | 21305 | AA893082 | General | | ESTs |
| 275 | 16591 | AA893191 | j, z | | ESTs |
| 276 | 17447 | AA893192 | General | | ESTs |
| 277 | 3876 | AA893205 | n | | ESTs |
| 278 | 3878 | AA893230 | General | | ESTs, Weakly similar to CALM_HUMAN CALMODULIN [*R. norvegicus*] |
| 279 | 20986 | AA893242 | q | Acyl CoA synthetase, long chain | Acyl CoA synthetase, long chain |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 280 | 16168 | AA893280 | i, z, General | | ESTs, Moderately similar to adipophilin [*H. sapiens*] |
| 281 | 3886 | AA893289 | j, m, y | | ESTs |
| 282 | 15209 | AA893327 | y | | ESTs |
| 283 | 17800 | AA893436 | cc | | ESTs |
| 284 | 17836 | AA893626 | h | | ESTs, Weakly similar to LIS1 MOUSE PLATELET-ACTIVATING FACTOR ACETYLHYDROLASE IB ALPHA SUBUNIT [*R. norvegicus*] |
| 285 | 9084 | AA893717 | x | | ESTs |
| 286 | 22731 | AA893743 | d | | ESTs |
| 287 | 12031 | AA893860 | v | HHs: threonyl-tRNA synthetase | ESTs, Moderately similar to SYTC_HUMAN THREONYL-TRNA SYNTHETASE, CYTOPLASMIC [*H. sapiens*] |
| 288 | 17897 | AA893905 | k | | ESTs |
| 289 | 3447 | AA893982 | d | | ESTs |
| 290 | 22583 | AA894009 | n | | EST |
| 291 | 10540 | AA894027 | j | | ESTs, Highly similar to A55748 protein kinase [*M. musculus*] |
| 292 | 4569 | AA894059 | x | | ESTs, Weakly similar to APP2 RAT AMYLOID-LIKE PROTEIN 2 PRECURSOR [*R. norvegicus*] |
| 293 | 18419 | AA894130 | d | | |
| 294 | 17336 | AA894297 | j | | ESTs |
| 295 | 19120 | AA894318 | f, j | | ESTs |
| 296 | 19762 | AA899113 | i | | ESTs |
| 297 | 18286 | AA899219 | u | | Rat mRNA for beta-tubulin T beta15 |
| 298 | 22051 | AA899498 | w | | ESTs, Weakly similar to T26581 hypothetical protein Y32B12A.3 - *Caenorhabditis elegans* [*C. elegans*] |
| 298 | 22052 | AA899498 | q | | ESTs, Weakly similar to T26581 hypothetical protein Y32B12A.3 - *Caenorhabditis elegans* [*C. elegans*] |
| 299 | 21628 | AA899563 | aa | | ESTs |
| 300 | 4262 | AA899590 | i | | ESTs |
| 301 | 4661 | AA899709 | t, General | receptor activity modifying protein 3 | receptor activity modifying protein 3 |
| 302 | 21354 | AA899721 | q | | ESTs |
| 303 | 17905 | AA899762 | General | | *Rattus norvegicus* epidermal growth factor receptor related protein (Errp) mRNA, complete cds |
| 304 | 15231 | AA899840 | r | | ESTs |
| 305 | 23778 | AA899854 | c, k, x | topoisomerase (DNA) II alpha | topoisomerase (DNA) II alpha |
| 306 | 22060 | AA899898 | b | | ESTs |
| 307 | 9114 | AA899951 | v, General | | ESTs |
| 308 | 8988 | AA900148 | f | | ESTs |
| 309 | 11841 | AA900247 | v | | *Rattus norvegicus* mRNA for Hsp70/Hsp90 organizing protein |
| 310 | 4725 | AA900290 | cc | | ESTs, Highly similar to ALPHA-2-MACROGLOBULIN PRECURSOR [*R. norvegicus*] |
| 311 | 4747 | AA900465 | General | | ESTs |
| 312 | 20988 | AA900562 | o | | ESTs |
| 313 | 3822 | AA900863 | b, g, General | | ESTs, Weakly similar to nuclear RNA helicase [*R. norvegicus*] |
| 315 | 12420 | AA901017 | b | | ESTs, Weakly similar to T20702 hypothetical protein F10C2.6 - *Caenorhabditis elegans* [*C. elegans*] |
| 316 | 4849 | AA901155 | s | | *Rattus norvegicus* CDK105 mRNA |
| 317 | 3959 | AA901338 | General | | ESTs, Highly similar to IF2B_HUMAN EUKARYOTIC TRANSLATION INITIATION FACTOR 2 BETA SUBUNIT [*H. sapiens*] |
| 318 | 22846 | AA923982 | a, d | | ESTs, Highly similar to ATP-specific succinyl-CoA synthetase beta subunit [*M. musculus*] |
| 319 | 4895 | AA923999 | k | | ESTs |
| 320 | 21546 | AA924188 | cc, General | | ESTs |
| 321 | 24192 | AA924210 | n, General | | ESTs |
| 322 | 4933 | AA924301 | g, l, General | | EST |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 323 | 4944 | AA924405 | l, General | | ESTs, Moderately similar to NO56_HUMAN NUCLEOLAR PROTEIN NOP56 [*H. sapiens*] |
| 324 | 4948 | AA924428 | r | | ESTs |
| 325 | 4949 | AA924432 | General | | ESTs, Weakly similar to NPT2 RAT RENAL SODIUM-DEPENDENT PHOSPHATE TRANSPORT PROTEIN 2 [*R. norvegicus*] |
| 326 | 18891 | AA924598 | e | | ESTs |
| 327 | 22540 | AA924630 | v, General | HHs: glyoxylate reductase/hydroxypyruvate reductase | ESTs, Weakly similar to SERA RAT D-3-PHOSPHOGLYCERATE DEHYDROGENASE [*R. norvegicus*] |
| 327 | 22541 | AA924630 | General | HHs: glyoxylate reductase/hydroxypyruvate reductase | ESTs, Weakly similar to SERA RAT D-3-PHOSPHOGLYCERATE DEHYDROGENASE [*R. norvegicus*] |
| 328 | 14759 | AA924766 | k | | ESTs |
| 329 | 23123 | AA924794 | x | | ESTs |
| 330 | 4067 | AA924813 | g, p | | ESTs |
| 331 | 2888 | AA924902 | r, General | | ESTs |
| 332 | 18130 | AA924964 | d | | ESTs, Highly similar to sec7 domain family member [*H. sapiens*] |
| 333 | 23141 | AA925019 | r | | ESTs |
| 334 | 23195 | AA925026 | General | | ESTs, Weakly similar to MCT7 RAT MAST CELL PROTEASE 7 PRECURSOR [*R. norvegicus*] |
| 335 | 21458 | AA925049 | f, aa, General | | ESTs |
| 336 | 5073 | AA925061 | m | | ESTs, Moderately similar to S20710 hypothetical protein, 16K - mouse [*M. musculus*] |
| 337 | 14790 | AA925087 | o, General | | ESTs |
| 338 | 5089 | AA925126 | g | | EST, Highly similar to T50621 hypothetical protein DKFZp762O076.1 [*H. sapiens*] |
| 339 | 23261 | AA925145 | k, General | | ESTs, Moderately similar to BHMT RAT BETAINE-HOMOCYSTEINE S-METHYLTRANSFERASE [*R. norvegicus*] |
| 340 | 17363 | AA925150 | a | | ESTs, Moderately similar to neurodegeneration-associated protein 1 [*R. norvegicus*] |
| 341 | 23448 | AA925167 | l | | ESTs |
| 342 | 23159 | AA925318 | e | I-kappa-B-beta | I-kappa-B-beta |
| 343 | 21500 | AA925353 | k | | ESTs |
| 344 | 22479 | AA925418 | t | | ESTs |
| 345 | 21151 | AA925539 | b | | ESTs |
| 346 | 16944 | AA925541 | f | heterogeneous nuclear ribonucleoprotein L | heterogeneous nuclear ribonucleoprotein L |
| 346 | 16945 | AA925541 | t | heterogeneous nuclear ribonucleoprotein L | heterogeneous nuclear ribonucleoprotein L |
| 347 | 17514 | AA925554 | bb | HHs: succinate dehydrogenase complex, subunit A, flavoprotein (Fp) | ESTs, Highly similar to DHSA_HUMAN SUCCINATE DEHYDROGENASE [*H. sapiens*] |
| 348 | 5183 | AA925662 | i, General | | ESTs |
| 349 | 23189 | AA925844 | r | | ESTs |
| 350 | 23190 | AA925863 | aa | | ESTs, Highly similar to IMB3_HUMAN IMPORTIN BETA-3 SUBUNIT [*H. sapiens*] |
| 351 | 5252 | AA926051 | General | | EST |
| 352 | 22967 | AA926080 | h, cc | | ESTs |
| 353 | 17157 | AA926129 | b | | ESTs |
| 354 | 13411 | AA926196 | u, General | | ESTs |
| 355 | 5295 | AA926247 | General | putative potassium channel TWIK | putative potassium channel TWIK |
| 356 | 22928 | AA926262 | General | | ESTs, Moderately similar to NEURONAL PROTEIN 3.1 [*M. musculus*] |
| 357 | 8948 | AA926316 | r | | ESTs, Moderately similar to T13963 formin related protein, lymphocyte specific - mouse [*M. musculus*] |
| 358 | 21798 | AA926365 | aa | | ESTs, Moderately similar to AF151827 1 CGI-69 protein [*H. sapiens*] |
| 359 | 9942 | AA942697 | s | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 360 | 6039 | AA942716 | x, General | | ESTs, Highly similar to HN1 [*M. musculus*] |
| 361 | 11174 | AA942745 | g, o, w | | ESTs |
| 362 | 23005 | AA942770 | g | | ESTs |
| 363 | 21318 | AA942774 | General | | ESTs |
| 364 | 6615 | AA942889 | v | | ESTs, Weakly similar to T26686 hypothetical protein Y38F1A.6 - *Caenorhabditis elegans* [*C. elegans*] |
| 365 | 6691 | AA943028 | c | | ESTs, Highly similar to KFMS RAT MACROPHAGE COLONY STIMULATING FACTOR I RECEPTOR PRECURSOR [*R. norvegicus*] |
| 366 | 22142 | AA943066 | p | | ESTs, Weakly similar to p68 RNA helicase [*R. norvegicus*] |
| 367 | 21993 | AA943149 | v, General | | ESTs, Weakly similar to T00084 hypothetical protein KIAA0512 [*H. sapiens*] |
| 368 | 9061 | AA943508 | General | | ESTs, Weakly similar to T08666 hypothetical protein DKFZp547N0510.1 [*H. sapiens*] |
| 369 | 24390 | AA943531 | b, j, n, y | | ESTs, Weakly similar to VIL1 MOUSE VILLIN [*M. musculus*] |
| 370 | 13976 | AA943532 | f, s, x | | *Rattus norvegicus* mRNA for class I beta-tubulin, complete cds |
| 371 | 22248 | AA943537 | cc, General | | *Rattus norvegicus* zyxin mRNA, partial cds |
| 372 | 22257 | AA943558 | m | | ESTs, Highly similar to T2DA_HUMAN TRANSCRIPTION INITIATION FACTOR TFIID 20/15 KDA SUBUNITS [*H. sapiens*] |
| 373 | 12673 | AA943773 | u, cc, General | | ESTs |
| 374 | 13641 | AA944154 | u | | ESTs |
| 375 | 2658 | AA944155 | f | | ESTs |
| 376 | 12770 | AA944161 | d | | ESTs |
| 377 | 20903 | AA944180 | i, x | | ESTs, Highly similar to CKS2 MOUSE CYCLIN-DEPENDENT KINASES REGULATORY SUBUNIT 2 [*M. musculus*] |
| 378 | 13507 | AA944244 | v | | ESTs |
| 379 | 15596 | AA944353 | General | | ESTs |
| 380 | 22681 | AA944413 | i, v, cc, General | | ESTs |
| 381 | 6711 | AA944439 | General | | ESTs, Highly similar to hypothetical protein [*M. musculus*] |
| 382 | 14763 | AA944481 | i, q, General | | ESTs, Weakly similar to FIBA RAT FIBRINOGEN ALPHA/ALPHA-E CHAIN PRECURSOR [*R. norvegicus*] |
| 383 | 22466 | AA944605 | h | | ESTs |
| 384 | 12301 | AA944727 | b | | ESTs, Weakly similar to A44437 regenerating liver inhibitory factor RL/IF-1 - rat [*R. norvegicus*] |
| 385 | 7023 | AA944792 | d, m, aa | HHs: polymerase (RNA) II (DNA directed) polypeptide E (25 kD) | ESTs, Highly similar to RNA polymerase II 23 kD subunit [*H. sapiens*] |
| 386 | 22536 | AA944803 | bb | | ESTs |
| 387 | 22501 | AA944811 | g, l | | ESTs |
| 388 | 23967 | AA944831 | s | | ESTs |
| 389 | 26084 | AA944922 | i | | |
| 390 | 11974 | AA944958 | General | | ESTs |
| 391 | 22547 | AA944970 | aa | | ESTs |
| 392 | 22554 | AA945076 | z, General | | ESTs |
| 393 | 14352 | AA945181 | General | | ESTs |
| 395 | 1798 | AA945569 | General | | *R. norvegicus* alpha-1-macroglobulin mRNA, complete cds |
| 396 | 22050 | AA945604 | i, aa | | ESTs |
| 397 | 19731 | AA945615 | d, o | | ESTs |
| 398 | 22612 | AA945624 | a, General | | ESTs, Weakly similar to DHQU RAT NAD(P)H DEHYDROGENASE [*R. norvegicus*] |
| 399 | 22618 | AA945656 | aa | | ESTs |
| 400 | 11871 | AA945679 | v | | ESTs |
| 401 | 22656 | AA945818 | General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 402 | 6720 | AA945828 | p | | ESTs |
| 403 | 22351 | AA945867 | m | | ESTs |
| 404 | 22665 | AA945877 | f | | ESTs |
| 405 | 24243 | AA945950 | b | | ESTs |
| 406 | 22689 | AA945962 | General | | ESTs |
| 407 | 22692 | AA945986 | d | | ESTs |
| 408 | 22696 | AA945996 | c, General | | ESTs |
| 408 | 22697 | AA945996 | c, o | | ESTs |
| 409 | 22658 | AA945998 | w | | ESTs |
| 410 | 20832 | AA946040 | s | HMm: RIKEN cDNA 2010000G05 gene | ESTs, Highly similar to COXG MOUSE CYTOCHROME C OXIDASE POLYPEPTIDE VIB [*M. musculus*] |
| 411 | 18337 | AA946046 | General | | ESTs |
| 412 | 825 | AA946108 | General | | *Rattus norvegicus* laminin-5 alpha 3 chain mRNA, complete cds |
| 413 | 8639 | AA946221 | e, cc, General | | ESTs |
| 414 | 23237 | AA946224 | f | | ESTs |
| 415 | 15600 | AA946250 | o, aa | | ESTs |
| 416 | 19387 | AA946275 | t | | ESTs, Highly similar to AR21_HUMAN ARP2/3 COMPLEX 21 KD SUBUNIT [*H. sapiens*] |
| 417 | 6351 | AA946344 | d | PCTAIRE-1 protein kinase, alternatively spliced | PCTAIRE-1 protein kinase, alternatively spliced |
| 418 | 22057 | AA946348 | e | | ESTs, Highly similar to autoantigen [*H. sapiens*] |
| 419 | 22069 | AA946349 | aa | | ESTs |
| 420 | 13962 | AA946351 | General | | ESTs |
| 421 | 18280 | AA946361 | g | | ESTs, Highly similar to Ring3 [*M. musculus*] |
| 422 | 18944 | AA946391 | v | | ESTs |
| 424 | 21410 | AA946408 | t | | ESTs, Moderately similar to p18 component of aminoacyl-tRNA synthetase complex [*H. sapiens*] |
| 425 | 643 | AA946439 | o, y | | Rat H4 gene for somatic histone H4 |
| 426 | 20736 | AA946443 | x | | ESTs, Highly similar to NPD1 MOUSE NEURAL PROLIFERATION DIFFERENTIATION AND CONTROL PROTEIN-1 PRECURSOR [*M. musculus*] |
| 427 | 21878 | AA946448 | r | | ESTs |
| 428 | 21947 | AA946451 | bb | | ESTs, Highly similar to AF151863 1 CGI-105 protein [*H. sapiens*] |
| 429 | 17499 | AA946467 | General | | ESTs |
| 430 | 1809 | AA946503 | x, General | | Rat mRNA for alpha-2u globulin-related protein |
| 431 | 23360 | AA955104 | f | | ESTs |
| 432 | 23471 | AA955162 | General | | ESTs |
| 433 | 9452 | AA955206 | b, General | | ESTs |
| 434 | 23512 | AA955282 | General | | ESTs |
| 435 | 22596 | AA955298 | General | | ESTs |
| 436 | 23283 | AA955391 | h | lipoprotein-binding protein | lipoprotein-binding protein |
| 437 | 23546 | AA955393 | General | | ESTs |
| 438 | 12404 | AA955408 | b | | ESTs, Weakly similar to SX10 RAT TRANSCRIPTION FACTOR SOX-10 [*R. norvegicus*] |
| 439 | 23626 | AA955540 | aa | | ESTs |
| 441 | 17540 | AA955914 | bb | | EST, EST, Moderately similar to FBRL MOUSE FIBRILLARIN [*M. musculus*], ESTs, Highly similar to FBRL MOUSE FIBRILLARIN [*M. musculus*] |
| 442 | 24277 | AA955962 | General | | ESTs |
| 443 | 19939 | AA955980 | General | | ESTs, Moderately similar to pescadillo [*H. sapiens*] |
| 444 | 24000 | AA956005 | i | | ESTs, Weakly similar to AF139894 1 RNA-binding protein alpha-CP1 [*M. musculus*] |
| 445 | 11050 | AA956164 | s, v | | ESTs, Weakly similar to TCPA RAT T-COMPLEX PROTEIN 1, ALPHA SUBUNIT [*R. norvegicus*] |
| 446 | 498 | AA956278 | a, General | | ESTs |
| 447 | 23409 | AA956294 | q, x | | ESTs |
| 449 | 23773 | AA956476 | f, x | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 450 | 23799 | AA956530 | d | | ESTs, Highly similar to ET putative translation product [*M. musculus*] |
| 451 | 23800 | AA956534 | aa | | ESTs, Weakly similar to RNG1_HUMAN RING1 PROTEIN [*H. sapiens*] |
| 452 | 23834 | AA956659 | cc, General | | EST |
| 453 | 16425 | AA956688 | f, x | | ESTs, Moderately similar to C8 [*M. musculus*] |
| 454 | 23847 | AA956723 | s | | EST |
| 455 | 23852 | AA956746 | j, l, m, z | | ESTs, Highly similar to Mi-2 protein [*H. sapiens*] |
| 456 | 5989 | AA956907 | g, s | | ESTs, Highly similar to p162 protein [*M. musculus*] |
| 456 | 5990 | AA956907 | General | | ESTs, Highly similar to p162 protein [*M. musculus*] |
| 457 | 23957 | AA957123 | u, General | | ESTs, Weakly similar to AF187065 1 p75NTR-associated cell death executor [*R. norvegicus*] |
| 458 | 22357 | AA957264 | General | | ESTs, Highly similar to hypothetical protein [*H. sapiens*] |
| 459 | 23314 | AA957270 | g, l, m, p, v, cc, General | | ESTs |
| 460 | 23995 | AA957292 | a, b | | ESTs |
| 461 | 2702 | AA957307 | General | HHs: seryl-tRNA synthetase | ESTs, Moderately similar to SYS_HUMAN SERYL-TRNA SYNTHETASE [*H. sapiens*] |
| 462 | 24040 | AA957422 | c | | ESTs, Highly similar to HIGH AFFINITY IMMUNOGLOBULIN EPSILON RECEPTOR GAMMA-SUBUNIT PRECURSOR [*R. norvegicus*] |
| 463 | 12478 | AA957554 | m | | ESTs, Highly similar to P3 MOUSE P3 PROTEIN [*M. musculus*] |
| 464 | 21306 | AA957811 | v | | ESTs |
| 465 | 24183 | AA957889 | t | | ESTs |
| 466 | 24178 | AA957905 | d | | ESTs |
| 467 | 17034 | AA963071 | e | | ESTs, Highly similar to epsilon-COP [*M. musculus*] |
| 468 | 24053 | AA963092 | General | | ESTs, Weakly similar to AF187065 1 p75NTR-associated cell death executor [*R. norvegicus*] |
| 469 | 2767 | AA963201 | o | | ESTs |
| 470 | 2022 | AA963259 | g | | ESTs |
| 471 | 2126 | AA963488 | d | | ESTs |
| 472 | 24246 | AA963703 | b | | ESTs, Highly similar to cell cycle protein p38-2G4 homolog [*H. sapiens*] |
| 473 | 2195 | AA963746 | General | | ESTs |
| 474 | 19370 | AA963797 | i | | ESTs |
| 475 | 2282 | AA964147 | e | | ESTs |
| 476 | 2284 | AA964152 | x | | EST |
| 478 | 2350 | AA964368 | g, General | | ESTs, Highly similar to TGT_HUMAN QUEUINE TRNA-RIBOSYLTRANSFERASE [*H. sapiens*] |
| 479 | 18830 | AA964496 | aa | | ESTs, Highly similar to ATRTC actin beta - rat [*R. norvegicus*] |
| 480 | 2392 | AA964541 | b | | EST |
| 481 | 2395 | AA964554 | General | | ESTs, Highly similar to U3 snoRNP associated 55 kDa protein [*H. sapiens*] |
| 482 | 2410 | AA964589 | i, aa | | EST |
| 483 | 19145 | AA964613 | t | | ESTs |
| 484 | 2424 | AA964617 | g | | ESTs |
| 485 | 3107 | AA964687 | General | | ESTs |
| 486 | 2457 | AA964752 | q, t | | EST |
| 487 | 6778 | AA964763 | b | | ESTs, Highly similar to DRIM protein [*H. sapiens*] |
| 489 | 2468 | AA964807 | l | | ESTs, Weakly similar to T23337 hypothetical protein K05C4.2 - Caenorhabditis elegans [*C. elegans*] |
| 490 | 2469 | AA964814 | w | Glutamate-cysteine ligase (gamma-glutamylcysteine synthetase), regulatory | Glutamate-cysteine ligase (gamma-glutamylcysteine synthetase), regulatory |
| 491 | 12561 | AA964815 | General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 492 | 2326 | AA964892 | aa | | ESTs, Highly similar to PROCOLLAGEN ALPHA 1(IV) CHAIN PRECURSOR [*M. musculus*] |
| 493 | 21339 | AA964962 | General | | ESTs, Highly similar to ABC1 MOUSE ATP-BINDING CASSETTE, SUB-FAMILY A, MEMBER 1 [*M. musculus*] |
| 494 | 21390 | AA964988 | General | | ESTs |
| 495 | 12569 | AA965023 | g | | ESTs |
| 496 | 2583 | AA965166 | bb | | ESTs, Moderately similar to inorganic pyrophosphatase [*H. sapiens*] |
| 497 | 15885 | AA965207 | r | | ESTs, Highly similar to KIAA0958 protein [*H. sapiens*] |
| 499 | 2905 | AA996727 | b, l, m, u, General | | ESTs |
| 500 | 2915 | AA996782 | u, bb | | ESTs, Moderately similar to S27267 lamin A - rat [*R. norvegicus*] |
| 501 | 2920 | AA996813 | d | | ESTs |
| 502 | 19525 | AA996856 | aa, General | | EST |
| 503 | 2984 | AA997015 | c | | ESTs |
| 504 | 2986 | AA997028 | General | | ESTs |
| 505 | 3145 | AA997237 | General | | ESTs |
| 506 | 19249 | AA997342 | m | | ESTs |
| 507 | 16883 | AA997345 | General | | ESTs, Weakly similar to nitrilase homolog 1 [*M. musculus*] |
| 508 | 12598 | AA997362 | s | | ESTs, Moderately similar to LONN_HUMAN MITOCHONDRIAL LON PROTEASE HOMOLOG PRECURSOR [*H. sapiens*] |
| 509 | 3470 | AA997374 | p | | ESTs, Weakly similar to LIS1 MOUSE PLATELET-ACTIVATING FACTOR ACETYLHYDROLASE IB ALPHA SUBUNIT [*R. norvegicus*] |
| 510 | 3180 | AA997425 | t | | ESTs |
| 511 | 3245 | AA997608 | General | | ESTs, Weakly similar to PAI2 RAT PLASMINOGEN ACTIVATOR INHIBITOR-2, TYPE A [*R. norvegicus*] |
| 512 | 3020 | AA997656 | t | | ESTs, Moderately similar to T09071 SH3 domains-containing protein POSH - mouse [*M. musculus*] |
| 513 | 3269 | AA997800 | x, aa | | ESTs, Moderately similar to T30249 cell proliferation antigen Ki-67 - mouse [*M. musculus*] |
| 514 | 3288 | AA997877 | f | | ESTs |
| 515 | 23992 | AA998164 | k, x | Cyclin B1 | Cyclin B1 |
| 516 | 17470 | AA998264 | b | | ESTs, Moderately similar to FLRE_HUMAN FLAVIN REDUCTASE [*H. sapiens*] |
| 517 | 3773 | AA998356 | General | | ESTs, Weakly similar to BCL3_HUMAN B-CELL LYMPHOMA 3-ENCODED PROTEIN [*H. sapiens*] |
| 518 | 19623 | AA998422 | General | | EST |
| 519 | 3572 | AA998516 | x | | ESTs, Highly similar to CGA2 MOUSE CYCLIN A2 [*M. musculus*] |
| 520 | 2782 | AA998565 | c | | ESTs, Moderately similar to CYCLIN-DEPENDENT KINASE INHIBITOR 1C [*M. musculus*] |
| 521 | 26119 | AA998576 | i, r, w, General | | |
| 522 | 22737 | AA998660 | aa | | ESTs |
| 523 | 3696 | AA999030 | e | | ESTs, Moderately similar to AF132966 1 CGI-32 protein [*H. sapiens*] |
| 524 | 3079 | AA999169 | k, x, General | | ESTs |
| 525 | 3081 | AA999171 | e, p, r | Signal transducer and activator of transcription 1 | Signal transducer and activator of transcription 1 |
| 526 | 3082 | AA999172 | General | HHs: guanine monophosphate synthetase | ESTs, Highly similar to GUAA_HUMAN GMP SYNTHASE [*H. sapiens*] |
| 527 | 17337 | AB000717 | k | | ESTs |
| 528 | 1535 | AB000778 | a | Phoshpolipase D gene 1 | Phoshpolipase D gene 1 |
| 529 | 1382 | AB002406 | k | RuvB-like protein 1 | RuvB-like protein 1 |
| 530 | 20184 | AB003753 | d | | |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 531 | 4312 | AB010635 | c, i, j, k, y, z | | *Rattus norvegicus* mRNA for carboxylesterase precursor, complete cds |
| 532 | 21666 | AB012214 | k | HMm: DNA methyltransferase (cytosine-5) 1 | ESTs, Highly similar to JE0378 DNA [*R. norvegicus*] |
| 533 | 15772 | AB015645 | g | | *Rattus norvegicus* mRNA for G protein coupled receptor, complete cds |
| 534 | 1183 | AF013144 | h | | *Rattus norvegicus* MAP-kinase phosphatase (cpg21) mRNA, complete cds |
| 535 | 1582 | AF015911 | h, z | | *Rattus norvegicus* NAC-1 protein (NAC-1) mRNA, complete cds |
| 536 | 11483 | AF020618 | u, cc, General | | ESTs, Moderately similar to MY16 MOUSE MYELOID DIFFERENTIATION PRIMARY RESPONSE PROTEIN MYD116 [*M. musculus*], *Rattus norvegicus* progression elevated gene 3 protein mRNA, complete cds |
| 537 | 20295 | AF024712 | aa | | *Rattus norvegicus* MHC class lb M4 (RT1.M4) pseudogene, complete sequence |
| 538 | 19077 | AF030358 | y, z | | *Rattus norvegicus* chemokine CX3C mRNA, complete cds |
| 539 | 23044 | AF034218 | General | hyaluronidase 2 | hyaluronidase 2 |
| 540 | 25178 | AF035955 | d | | |
| 541 | 1564 | AF035963 | x, bb, General | | *Rattus norvegicus* kidney injury molecule-1 (KIM-1) mRNA, complete cds |
| 542 | 8426 | AF036335 | f | | *Rattus norvegicus* NonO/p54nrb homolog mRNA, partial cds |
| 543 | 21817 | AF036537 | k | | *Rattus norvegicus* homocysteine respondent protein HCYP2 mRNA, complete cds |
| 544 | 21145 | AF038571 | General | Solute carrier family 1 A1 (brain glutamate transporter) | Solute carrier family 1 A1 (brain glutamate transporter) |
| 545 | 22602 | AF044574 | General | putative peroxisomal 2,4-dienoyl-CoA reductase | putative peroxisomal 2,4-dienoyl-CoA reductase |
| 546 | 13464 | AF047707 | h | UDP-glucose: ceramide glycosyltransferase | UDP-glucose: ceramide glycosyltransferase |
| 547 | 24024 | AF052695 | x | cell cycle protein p55CDC | cell cycle protein p55CDC |
| 548 | 12259 | AF061266 | h | transient receptor protein 1 | *Rattus norvegicus* trp1 beta variant mRNA, complete cds |
| 549 | 4589 | AF062389 | y, z | | *Rattus norvegicus* kidney-specific protein (KS) mRNA, complete cds |
| 550 | 16007 | AF062594 | t | nucleosome assembly protein 1-like 1 | *Rattus norvegicus* nucleosome assembly protein mRNA, complete cds |
| 551 | 15761 | AF062741 | u | | *Rattus norvegicus* pyruvate dehydrogenase phosphatase isoenzyme 2 mRNA, complete cds |
| 552 | 17426 | AF073839 | p | | *Rattus norvegicus* bithoraxoid-like protein mRNA, complete cds |
| 553 | 18615 | AF074608 | s | RT1 class lb gene | RT1 class lb gene |
| 554 | 15797 | AF084205 | f | | *Rattus norvegicus* serine/threonine protein kinase TAO1 mRNA, complete cds |
| 555 | 12932 | AF102552 | s | ankyrin 3 (G) | *Rattus norvegicus* 190 kDa ankyrin isoform mRNA, complete cds |
| 556 | 18603 | AI007649 | x | | ESTs, Highly similar to A49013 tumor cell suppression protein HTS1 [*H. sapiens*] |
| 557 | 22733 | AI007668 | r | | ESTs |
| 558 | 22746 | AI007672 | r | | ESTs |
| 559 | 24109 | AI007725 | General | | ESTs |
| 560 | 15848 | AI007820 | n, v | | ESTs, ESTs, Highly similar to HS9B RAT HEAT SHOCK PROTEIN HSP 90-BETA [*R. norvegicus*] |
| 561 | 10108 | AI007857 | f | Hrs | Hrs |
| 562 | 6804 | AI007877 | General | | ESTs |
| 563 | 20099 | AI007893 | f, u | | ESTs |
| 564 | 11368 | AI007948 | d | | ESTs, Weakly similar to T18778 hypothetical protein B0513.2b - *Caenorhabditis elegans* [*C. elegans*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 565 | 15849 | AI008074 | h | | ESTs, ESTs, Highly similar to HS9B RAT HEAT SHOCK PROTEIN HSP 90-BETA [*R. norvegicus*] |
| 566 | 3121 | AI008160 | General | | ESTs, Moderately similar to AF1518411 CGI-83 protein [*H. sapiens*] |
| 567 | 16646 | AI008190 | t | | ESTs, Highly similar to Chain G, G Protein Heterotrimer Gi alpha 1 Beta 1 Gamma 2 With Gdp Bound [*R. norvegicus*] |
| 568 | 12683 | AI008203 | x | | ESTs, Weakly similar to G2/MITOTIC-SPECIFIC CYCLIN B1 [*R. norvegicus*] |
| 569 | 22018 | AI008309 | b | | ESTs, Moderately similar to PIM1 RAT PROTO-ONCOGENE SERINE/THREONINE-PROTEIN KINASE PIM-1 [*R. norvegicus*] |
| 570 | 23917 | AI008441 | n | | ESTs, Highly similar to 6PGD__HUMAN 6-PHOSPHOGLUCONATE DEHYOROGENASE, DECARBOXYLATIN [*H. sapiens*] |
| 571 | 22599 | AI008458 | General | | ESTs |
| 572 | 22698 | AI008578 | p, General | | ESTs |
| 573 | 14405 | AI008579 | r, x | | ESTs |
| 574 | 4086 | AI008629 | x | | ESTs, Moderately similar to JH0446 75K autoantigen [*H. sapiens*] |
| 575 | 3808 | AI008643 | i, v, General | | ESTs, Weakly similar to heat shock protein hsp40-3 [*M. musculus*] |
| 576 | 3931 | AI008697 | l | | ESTs, Weakly similar to T29897 hypothetical protein F38A5.1 - *Caenorhabditis elegans* [*C. elegans*] |
| 577 | 7785 | AI008758 | aa | Dipeptidyl peptidase 4 | Dipeptidyl peptidase 4 |
| 578 | 16701 | AI008838 | q | | ESTs, Weakly similar to LONN__HUMAN MITOCHONDRIAL LON PROTEASE HOMOLOG PRECURSOR [*H. sapiens*] |
| 579 | 21789 | AI008930 | k | | ESTs, Weakly similar to CYSR RAT CYSTEINE-RICH PROTEIN 1 [*R. norvegicus*] |
| 580 | 21895 | AI008971 | General | | ESTs |
| 581 | 410 | AI008974 | i, aa, General | | *R. norvegicus* mRNA encoding 45 kDa protein which binds to heymann nephritis antigen gp330 |
| 582 | 21632 | AI009167 | General | | ESTs, Highly similar to BAG-family molecular chaperone regulator-2 [*H. sapiens*] |
| 583 | 21596 | AI009168 | General | | ESTs |
| 584 | 22801 | AI009197 | General | | ESTs |
| 585 | 11876 | AI009321 | cc, General | | ESTs, Highly similar to similar to human DNA-binding protein 5 [*H. sapiens*] |
| 586 | 2506 | AI009341 | General | | ESTs |
| 587 | 6382 | AI009362 | General | | ESTs |
| 588 | 14370 | AI009427 | k | | ESTs, Highly similar to Lmp10 proteasome subunit [*M. musculus*] |
| 589 | 19275 | AI009460 | x | | ESTs, Highly similar to filamin [*H. sapiens*] |
| 590 | 4154 | AI009467 | g | | ESTs |
| 591 | 3464 | AI009589 | cc | | ESTs |
| 592 | 3926 | AI009592 | e | | ESTs, Highly similar to molybdopterin-synthase large subunit [*M. musculus*] |
| 593 | 19358 | AI009675 | c | | EST |
| 594 | 22545 | AI009747 | g | | ESTs |
| 595 | 15089 | AI009752 | cc, General | | ESTs |
| 596 | 5458 | AI009756 | h | ALG-2 interacting protein 1 | ALG-2 interacting protein 1 |
| 597 | 6844 | AI009770 | e, r, cc | | ESTs |
| 598 | 15627 | AI009810 | aa | | ESTs, Highly similar to RS16__HUMAN 40S RIBOSOMAL PROTEIN S1 [*R. norvegicus*] |
| 599 | 22619 | AI009825 | d | | ESTs |
| 600 | 7857 | AI009898 | j, l, m, z | | ESTs |
| 601 | 13259 | AI009946 | r | | ESTs |
| 602 | 21105 | AI010067 | General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 603 | 24627 | AI010102 | aa | Testis enhanced gene transcript | Testis enhanced gene transcript |
| 604 | 12716 | AI010178 | General | | ESTs, Moderately similar to YA00_HUMAN HYPOTHETICAL PROTEIN CGI-100 PRECURSOR [*H. sapiens*] |
| 605 | 18757 | AI010216 | aa | | ESTs |
| 606 | 2912 | AI010220 | aa, General | | ESTs, Weakly similar to claudin-7 [*R. norvegicus*] |
| 607 | 3316 | AI010237 | t | | ESTs |
| 608 | 15644 | AI010256 | General | | *R. norvegicus* mRNA for histone H3.3 |
| 609 | 657 | AI010262 | b | | *Rattus norvegicus* mRNA for inetrleukin-4 receptor (membrane-bound form), complete cds |
| 610 | 3271 | AI010303 | b | | ESTs |
| 611 | 11081 | AI010407 | bb | | ESTs, Moderately similar to erythroblast macrophage protein EMP [*H. sapiens*] |
| 612 | 16521 | AI010470 | c, s, t, General | Ceruloplasmin (ferroxidase) | Ceruloplasmin (ferroxidase) |
| 613 | 6927 | AI010542 | General | | ESTs |
| 614 | 17524 | AI010568 | a, j, y, General | Growth hormone receptor | Growth hormone receptor |
| 615 | 6946 | AI010642 | n | | ESTs |
| 616 | 23509 | AI010962 | aa | | ESTs, Highly similar to SDP3 [*M. musculus*] |
| 617 | 6044 | AI011285 | t | | ESTs |
| 618 | 13855 | AI011361 | o | | ESTs |
| 619 | 21779 | AI011380 | cc | | ESTs |
| 621 | 12534 | AI011460 | cc | | ESTs |
| 622 | 12629 | AI011492 | e, f | | ESTs, Moderately similar to HYA22 [*H. sapiens*] |
| 623 | 735 | AI011560 | f | | ESTs, Weakly similar to B Chain B, Solution Structure Of The C-Terminal Negative Regulatory Domain Of P53 In A Complex With Ca2+-Bound S100b(Bb) [*R. norvegicus*] |
| 624 | 3941 | AI011598 | General | | ESTs, Moderately similar to LMA5 MOUSE LAMININ ALPHA-5 CHAIN [*M. musculus*] |
| 625 | 17550 | AI011607 | j, General | | ESTs, Weakly similar to JE0360 gamma-Butyrobetaine hydroxylase [*H. sapiens*] |
| 626 | 10636 | AI011634 | e | | ESTs, Weakly similar to I(3)S12 protein [*D. melanogaster*] |
| 627 | 3995 | AI011678 | General | | ESTs |
| 628 | 16112 | AI011706 | h | | ESTs, Weakly similar to SFR5 RAT SPLICING FACTOR, ARGININE/SERINE-RICH 5 [*R. norvegicus*] |
| 629 | 13354 | AI011757 | c | | ESTs, Weakly similar to A35902 Fc gamma [*R. norvegicus*] |
| 630 | 12745 | AI011799 | cc | | ESTs |
| 631 | 18684 | AI011812 | t | | ESTs, Highly similar to AF151842 1 CGI-84 protein [*H. sapiens*] |
| 632 | 4205 | AI011982 | b | | ESTs |
| 633 | 6518 | AI012114 | General | | ESTs, Moderately similar to R29425 1 [*H. sapiens*] |
| 634 | 17407 | AI012145 | General | | ESTs |
| 635 | 13093 | AI012177 | r | | ESTs, Weakly similar to PPP5 RAT SERINE/THREONINE PROTEIN PHOSPHATASE 5 [*R. norvegicus*] |
| 636 | 15395 | AI012216 | f | | ESTs, Moderately similar to Y33K_HUMAN HYPOTHETICAL 33.4 KDA PROTEI [*H. sapiens*] |
| 637 | 21796 | AI012221 | d, General | | ESTs, Weakly similar to S70484 RS43 protein - rat (fragment) [*R. norvegicus*] |
| 638 | 3981 | AI012235 | i, General | | ESTs |
| 639 | 6606 | AI012308 | i, r | | ESTs |
| 640 | 3417 | AI012337 | w | | ESTs, Highly similar to NHPX RAT NHP2/RS6 FAMILY PROTEIN YEL026W HOMOLOG [*R. norvegicus*] |
| 641 | 24200 | AI012356 | b, t, General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 642 | 7471 | AI012379 | cc | | ESTs |
| 643 | 7247 | AI012438 | g | | ESTs |
| 644 | 7127 | AI012464 | p, General | | ESTs |
| 645 | 3304 | AI012471 | b | | ESTs, Weakly similar to T26998 hypothetical protein Y48B6A.6 - *Caenorhabditis elegans* [*C. elegans*] |
| 646 | 2311 | AI012485 | aa | | ESTs |
| 647 | 20817 | AI012589 | g, n, q | glutathione S-transferase, pi 2 | glutathione S-transferase, pi 2 |
| 648 | 3493 | AI012590 | v, General | | ESTs |
| 649 | 8975 | AI012613 | General | | ESTs |
| 650 | 11335 | AI012619 | j | | ESTs, Highly similar to unknown [*H. sapiens*] |
| 651 | 21409 | AI012637 | General | | ESTs |
| 652 | 8015 | AI012638 | aa | | ESTs, Moderately similar to AF151834 1 CGI-76 protein [*H. sapiens*] |
| 653 | 8476 | AI012647 | w | | ESTs, Highly similar to RS20_HUMAN 40S RIBOSOMAL PROTEIN S2 [*R. norvegicus*] |
| 654 | 4232 | AI012958 | e, p, General | | ESTs |
| 655 | 23128 | AI013011 | General | | ESTs |
| 656 | 20086 | AI013260 | General | lamin | lamin |
| 657 | 11969 | AI013273 | k | | ESTs, Highly similar to GLIA DERIVED NEXIN PRECURSOR [*R. norvegicus*] |
| 658 | 26147 | AI013387 | aa | | |
| 659 | 8815 | AI013437 | p | | ESTs |
| 660 | 19722 | AI013508 | k | | *Rattus norvegicus* Hsp70 binding protein HspBP mRNA, complete cds |
| 661 | 6674 | AI013568 | General | | ESTs |
| 662 | 23145 | AI013647 | o, t | | ESTs |
| 663 | 15130 | AI013676 | w | | ESTs |
| 664 | 7274 | AI013715 | aa | | ESTs, Moderately similar to BMP6 RAT BONE MORPHOGENETIC PROTEIN 6 PRECURSOR [*R. norvegicus*] |
| 665 | 7276 | AI013730 | e | | ESTs, Highly similar to KIAA1102 protein [*H. sapiens*] |
| 666 | 7278 | AI013738 | y, z, aa | | ESTs |
| 667 | 22592 | AI013740 | s, x, bb, General | | ESTs, Highly similar to proteolipid protein 2 [*M. musculus*] |
| 668 | 16584 | AI013765 | w | Arrestin, beta 2 | Arrestin, beta 2 |
| 669 | 24143 | AI013804 | j, l | | ESTs, Highly similar to T27225 ADP-ribosylation factor Y57G11C.13 [similarity] - *Caenorhabditis elegans* [*C. elegans*] |
| 670 | 15928 | AI013829 | a, General | | ESTs |
| 671 | 21950 | AI013861 | j | 3-hydroxyisobutyrate dehydrogenase | 3-hydroxyisobutyrate dehydrogenase |
| 672 | 3260 | AI013875 | t | | ESTs |
| 673 | 2708 | AI013882 | d, q | | ESTs, Moderately similar to MSSP [*M. musculus*] |
| 674 | 8585 | AI013886 | i | | ESTs |
| 675 | 7299 | AI013911 | p, r, t, General | | ESTs, Weakly similar to CIRP [*R. norvegicus*] |
| 676 | 15904 | AI013971 | General | | Rat ankyrin binding glycoprotein-1 related mRNA sequence |
| 677 | 12781 | AI014023 | w | | ESTs, Moderately similar to R32184 1 [*H. sapiens*] |
| 678 | 19372 | AI014135 | aa | | *Rattus norvegicus* mRNA for beta-carotene 15,15'-dioxygenase, complete cds |
| 679 | 4241 | AI014140 | w | | ESTs, Highly similar to hypothetical protein [*H. sapiens*] |
| 680 | 15247 | AI014169 | c, u | | *Rattus norvegicus* clone N27 mRNA |
| 681 | 7315 | AI028831 | n | | ESTs, Moderately similar to mitogen-activated protein kinase kinase kinase 6 [*H. sapiens*] |
| 682 | 16631 | AI028856 | General | | ESTs |
| 683 | 23297 | AI028953 | x | | ESTs, Highly similar to S55054 Sm protein G [*H. sapiens*] |
| 684 | 11326 | AI029015 | b | | ESTs |
| 685 | 2866 | AI029058 | n, y | | ESTs |
| 686 | 12812 | AI029126 | General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 687 | 17602 | AI029156 | p | | ESTs |
| 688 | 7392 | AI029185 | aa | | EST |
| 689 | 6517 | AI029264 | d, k, x | | ESTs |
| 690 | 7639 | AI029292 | b | | ESTs |
| 691 | 3874 | AI029428 | i, General | | ESTs, Highly similar to CB80_HUMAN 80 KDA NUCLEAR CAP BINDING PROTEIN [*H. sapiens*] |
| 692 | 12819 | AI029437 | f | | ESTs |
| 693 | 7452 | AI029466 | r | | ESTs |
| 694 | 7493 | AI029608 | b | | ESTs |
| 696 | 7537 | AI029829 | o, General | | ESTs |
| 697 | 2310 | AI029969 | v | | ESTs |
| 698 | 7585 | AI030023 | x | | ESTs |
| 699 | 7586 | AI030024 | b, n | | ESTs |
| 700 | 14492 | AI030091 | cc | | ESTs |
| 701 | 10673 | AI030134 | f | | ESTs, Weakly similar to ankyrin [*R. norvegicus*] |
| 702 | 7615 | AI030163 | o, r | | ESTs |
| 703 | 2370 | AI030179 | General | | ESTs |
| 704 | 7681 | AI030449 | n | | ESTs, Moderately similar to methyltransferase related protein [*M. musculus*] |
| 705 | 11559 | AI030472 | General | | ESTs |
| 706 | 7665 | AI030668 | t, bb | | *Rattus norvegicus* nucleosome assembly protein mRNA, complete cds |
| 707 | 24222 | AI030704 | k | | ESTs |
| 708 | 10740 | AI030743 | h | | EST |
| 709 | 10742 | AI030773 | e | | EST |
| 711 | 16169 | AI030932 | General | | ESTs, Moderately similar to adipophilin [*H. sapiens*] |
| 712 | 19527 | AI030991 | f | | EST |
| 713 | 22614 | AI031004 | r | | ESTs, Highly similar to SX17 MOUSE TRANSCRIPTION FACTOR SOX-17 [*M. musculus*] |
| 714 | 3167 | AI031012 | e | | ESTs, Highly similar to CLPP MOUSE PUTATIVE ATP-DEPENDENT CLP PROTEASE PROTEOLYTIC SUBUNIT, MITOCHONDRIAL PRECURSOR [*M. musculus*] |
| 715 | 5350 | AI043611 | a | | ESTs |
| 716 | 7858 | AI043654 | t | | EST |
| 717 | 10784 | AI043678 | d | | EST |
| 718 | 9180 | AI043694 | aa | | ESTs, Weakly similar to T27134 hypothetical protein Y53C12B.2 - Caenorhabditis elegans [*C. elegans*] |
| 719 | 7867 | AI043695 | aa | HHs: phosphoribosyl pyrophosphate amidotransferase | *Rattus norvegicus* mRNA for amidophosphoribosyltransferase |
| 720 | 7584 | AI043724 | General | | ESTs |
| 721 | 7895 | AI043768 | e | | ESTs, Highly similar to AF151810 1 CGI-52 protein [*H. sapiens*] |
| 722 | 7903 | AI043805 | General | | ESTs |
| 723 | 7913 | AI043849 | cc | | ESTs, Weakly similar to ELL MOUSE RNA POLYMERASE II ELONGATION FACTOR ELL [*M. musculus*] |
| 724 | 3899 | AI043904 | l | | ESTs |
| 725 | 6766 | AI043914 | f | | ESTs |
| 726 | 10818 | AI043990 | g, l, m, General | | ESTs |
| 727 | 7956 | AI044018 | f | | EST |
| 728 | 5393 | AI044170 | p | | EST |
| 729 | 5398 | AI044177 | q | | EST |
| 730 | 5425 | AI044237 | a, d | | ESTs, Weakly similar to AF121893 1 sequence-specific single-stranded-DNA-binding protein [*R. norvegicus*] |
| 731 | 8692 | AI044247 | r | | ESTs, Weakly similar to putative peroxisomal 2,4-dienoyl-CoA reductase [*R. norvegicus*] |
| 732 | 5430 | AI044253 | i | | EST |
| 733 | 5461 | AI044338 | g, p, General | | ESTs |
| 734 | 5464 | AI044345 | i | | ESTs |
| 735 | 3359 | AI044347 | aa | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 737 | 2695 | AI044396 | b | | Rat (clones rLG[08, 14, 25]) interleukin 6 signal transducer mRNA sequence |
| 738 | 5494 | AI044425 | General | | ESTs |
| 740 | 9882 | AI044588 | j, m | | ESTs |
| 741 | 5575 | AI044688 | g | | ESTs |
| 742 | 2348 | AI044794 | General | | ESTs |
| 743 | 18205 | AI044836 | n | | ESTs, Weakly similar to AF165892 1 RNA-binding protein SiahBP [*R. norvegicus*] |
| 744 | 5626 | AI044864 | u | | ESTs |
| 745 | 5630 | AI044869 | f | | ESTs |
| 746 | 5634 | AI044683 | General | | ESTs, Moderately similar to AF151873 1 CGI-115 protein [*H. sapiens*] |
| 747 | 4047 | AI044947 | l, m | | ESTs, Moderately similar to dJ1183I21.1 [*H. sapiens*] |
| 748 | 5654 | AI044976 | w | | EST |
| 749 | 5684 | AI045056 | r | | ESTs |
| 750 | 19235 | AI045074 | General | | ESTs, Highly similar to BGAL MOUSE BETA-GALACTOSIDASE PRECURSOR [*M. musculus*] |
| 751 | 5689 | AI045075 | i, aa, General | | ESTs, Moderately similar to HEM45 [*H. sapiens*] |
| 752 | 5711 | AI045151 | General | | ESTs, Moderately similar to AF118838 1 citrin [*H. sapiens*] |
| 753 | 19237 | AI045153 | c | | ESTs, Weakly similar to TVRTK6 ribosomal protein S6 kinase [*R. norvegicus*] |
| 754 | 9964 | AI045161 | f | | EST |
| 755 | 5735 | AI045223 | f | | ESTs |
| 756 | 5474 | AI045477 | a, General | | ESTs |
| 757 | 5811 | AI045502 | d, e | | ESTs |
| 758 | 5819 | AI045537 | General | | ESTs |
| 759 | 5839 | AI045594 | i | | ESTs |
| 760 | 6808 | AI045600 | s | | ESTs, Highly similar to S30034 translocating chain-associating membrane protein [*H. sapiens*] |
| 761 | 17755 | AI045608 | y | | ESTs |
| 763 | 10020 | AI045632 | a | | ESTs |
| 764 | 5855 | AI045669 | General | | ESTs |
| 765 | 5881 | AI045789 | i | | ESTs, Weakly similar to T12540 hypothetical protein DKFZp434J214.1 [*H. sapiens*] |
| 766 | 5897 | AI045862 | General | | ESTs, Moderately similar to S64732 scaffold attachment factor B [*H. sapiens*] |
| 767 | 5900 | AI045866 | y, z | | ESTs |
| 768 | 7540 | AI045882 | o, t, General | | ESTs, Weakly similar to B48013 proline-rich proteoglycan 2 precursor, parotid - rat [*R. norvegicus*] |
| 769 | 5329 | AI045970 | p | | ESTs |
| 770 | 15093 | AI058285 | d | | ESTs |
| 771 | 8002 | AI058304 | i | | ESTs |
| 772 | 8017 | AI058341 | c | | EST |
| 773 | 6828 | AI058359 | General | | ESTs, Weakly similar to T46465 hypothetical protein DKFZp434A0530.1 [*H. sapiens*] |
| 774 | 8177 | AI058603 | aa | | ESTs |
| 775 | 3090 | AI058730 | aa | | ESTs |
| 776 | 10093 | AI058746 | g | | ESTs |
| 777 | 8143 | AI058759 | General | | ESTs |
| 778 | 18659 | AI058762 | f | | ESTs |
| 779 | 8163 | AI058837 | aa | | ESTs |
| 780 | 4789 | AI058889 | General | | ESTs |
| 781 | 8221 | AI059061 | General | | ESTs |
| 782 | 10159 | AI059147 | d | | EST |
| 783 | 8245 | AI059154 | b | | ESTs, Weakly similar to unnamed protein product [*H. sapiens*] |
| 784 | 8283 | AI059290 | n | | ESTs |
| 785 | 8314 | AI059386 | g, General | | ESTs |
| 786 | 10200 | AI059444 | i | | ESTs |
| 787 | 8347 | AI059519 | s | | ESTs, Weakly similar to EGF RAT PRO-EPIDERMAL GROWTH FACTOR PRECURSOR [*R. norvegicus*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 788 | 18359 | AI059675 | n | | *Rattus norvegicus* transitional endoplasmic reticulum ATPase mRNA, complete cds |
| 789 | 10281 | AI059947 | b, t | | EST |
| 790 | 8494 | AI059968 | aa | | ESTs |
| 791 | 8495 | AI059971 | General | | ESTs, Weakly similar to TNRC MOUSE LYMPHOTOXIN-BETA RECEPTOR PRECURSOR [*M. musculus*] |
| 792 | 8496 | AI059974 | General | | ESTs, Moderately similar to KIAA0978 protein [*H. sapiens*] |
| 793 | 10289 | AI060053 | i | | ESTs, Weakly similar to CGI-142 hypothetical protein [*H. sapiens*] |
| 794 | 8548 | AI060176 | k | | ESTs |
| 795 | 8565 | AI060236 | t | | EST |
| 796 | 18322 | AI060279 | i, y, z | | ESTs |
| 797 | 8745 | AI069939 | r | | ESTs |
| 798 | 8785 | AI070067 | o | | ESTs, Highly similar to rer [*M. musculus*] |
| 799 | 17506 | AI070068 | cc | | ESTs, Weakly similar to 2104282A Gadd45 gene [*R. norvegicus*] |
| 800 | 9067 | AI070087 | General | | ESTs, Weakly similar to NUCL RAT NUCLEOLIN [*R. norvegicus*] |
| 801 | 3551 | AI070122 | e | | ESTs, Moderately similar to CGI-97 protein [*H. sapiens*] |
| 802 | 4967 | AI070179 | k | | ESTs, Moderately similar to GLMB RAT GLIA MATURATION FACTOR BETA [*R. norvegicus*] |
| 803 | 18 | AI070195 | General | | ESTs, Moderately similar to AF132954 1 CGI-20 protein [*H. sapiens*] |
| 804 | 24197 | AI070314 | General | | ESTs, Moderately similar to ARVC_HUMAN ARMADILLO REPEAT PROTEIN DELETED IN VELO-CARDIO-FACIAL SYNDROME [*H. sapiens*] |
| 805 | 8869 | AI070330 | r | | ESTs |
| 806 | 8874 | AI070336 | b, cc | | ESTs |
| 807 | 10417 | AI070410 | m | | ESTs |
| 808 | 8901 | AI070419 | aa | | ESTs, Moderately similar to T08664 Toll protein-like receptor DKFZp547I0610.1 [*H. sapiens*] |
| 809 | 14424 | AI070421 | l, p, General | | ESTs |
| 810 | 10434 | AI070497 | General | | ESTs |
| 811 | 8927 | AI070523 | v | | ESTs |
| 812 | 8946 | AI070611 | q | | ESTs |
| 813 | 8950 | AI070621 | w | | ESTs |
| 814 | 8972 | AI070673 | General | | ESTs |
| 815 | 8981 | AI070715 | bb | | EST |
| 816 | 26184 | AI070784 | i, l | | |
| 817 | 3007 | AI070824 | w | | ESTs, Weakly similar to hypothetical protein [*H. sapiens*] |
| 818 | 8999 | AI070839 | p | | ESTs |
| 819 | 10477 | AI070868 | e, f | bone morphogenetic protein 1 (procollagen C-proetinase) | bone morphogenetic protein 1 (procollagen C-proetinase) |
| 820 | 24301 | AI070911 | k | | ESTs |
| 821 | 8721 | AI071024 | General | | EST |
| 822 | 9212 | AI071098 | x | | ESTs |
| 823 | 1831 | AI071137 | c | | Rat mRNA for cdc25B, complete cds |
| 824 | 11005 | AI071139 | r | | EST |
| 825 | 9104 | AI071173 | j, m | | ESTs, Highly similar to HETEROGENEOUS NUCLEAR RIBONUCLEOPROTEIN G [*M. musculus*] |
| 826 | 9583 | AI071185 | General | | ESTs |
| 827 | 9644 | AI071410 | c | | ESTs |
| 828 | 16058 | AI071490 | General | HHs: serine palmitoyltransferase, long chain base subunit 2 | ESTs, Highly similar to JC5180 serine C-palmitoyltransferase [*M. musculus*] |
| 829 | 11057 | AI071509 | f, o | | ESTs |
| 831 | 5695 | AI071566 | bb | | ESTs, Weakly similar to SYBSR threonine synthase (EC 4.2.99.2) - yeast (Saccharomyces cerevisiae) [*S. cerevisiae*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 832 | 9671 | AI071568 | w | | EST |
| 833 | 22929 | AI071578 | General | | ESTs, Moderately similar to NEURONAL PROTEIN 3.1 [*M. musculus*] |
| 834 | 9673 | AI071581 | General | | ESTs |
| 835 | 9699 | AI071646 | General | | ESTs |
| 837 | 9799 | AI072008 | q, y, z | | ESTs |
| 838 | 9808 | AI072050 | d | | ESTs |
| 839 | 22796 | AI072213 | General | | ESTs |
| 840 | 9271 | AI072405 | v | | ESTs |
| 841 | 10869 | AI072425 | w | | ESTs |
| 842 | 21797 | AI072439 | General | | ESTs, Weakly similar to S70484 RS43 protein - rat (fragment) [*R. norvegicus*] |
| 843 | 9306 | AI072521 | r | | ESTs |
| 844 | 9312 | AI072550 | j | | ESTs |
| 845 | 10893 | AI072559 | x | | EST |
| 846 | 1501 | AI072634 | cc, General | | *Rattus norvegicus* cytokeratin-18 mRNA, partial cds |
| 847 | 6548 | AI072658 | General | | ESTs |
| 848 | 9363 | AI072695 | d | | ESTs, Highly similar to JE0170 dnaJ heat shock protein MCG18 - mouse [*M. musculus*] |
| 850 | 9409 | AI072841 | n | | ESTs, Moderately similar to LMG2 MOUSE LAMININ GAMMA-2 CHAIN PRECURSOR [*M. musculus*] |
| 851 | 9410 | AI072842 | w | | ESTs |
| 852 | 9468 | AI073021 | General | | ESTs |
| 853 | 9518 | AI073223 | f | | EST |
| 854 | 11183 | AI100768 | t | HHs: carbonic anhydrase VIII | ESTs, Weakly similar to CAH2 RAT CARBONIC ANHYDRASE II [*R. norvegicus*] |
| 855 | 9190 | AI100835 | e | | ESTs |
| 856 | 2029 | AI100842 | p | | ESTs |
| 857 | 5687 | AI101006 | e | | ESTs |
| 858 | 15192 | AI101099 | g, cc | | Rat metallothionein-2 and metallothionein-1 genes, complete cds |
| 859 | 17399 | AI101157 | o | | ESTs, Highly similar to ATPK MOUSE ATP SYNTHASE F CHAIN, MITOCHONDRIAL [*M. musculus*] |
| 860 | 9339 | AI101160 | l, m, o | | ESTs, Weakly similar to S46930 teg292 protein - mouse [*M. musculus*] |
| 861 | 6321 | AI101256 | General | | ESTs, Weakly similar to AIF-C1 [*R. norvegicus*] |
| 862 | 5421 | AI101270 | c | | ESTs, Highly similar to GDIS MOUSE RHO GDP-DISSOCIATION INHIBITOR 2 [*M. musculus*] |
| 863 | 11910 | AI101323 | General | | ESTs, Highly similar to ERM_HUMAN ETS-RELATED PROTEIN ERM [*H. sapiens*] |
| 864 | 23140 | AI101608 | e | | ESTs |
| 865 | 4119 | AI101901 | General | | ESTs |
| 866 | 16324 | AI102009 | b | | ESTs, Weakly similar to TRBP MOUSE PROTAMINE-1 RNA BINDING PROTEIN [*M. musculus*] |
| 867 | 18642 | AI102023 | o | | ESTs, Moderately similar to unknown [*H. sapiens*] |
| 868 | 19373 | AI102044 | a | *Drosophila* polarity gene (frizzled) homologue | *Rattus norvegicus* mRNA for beta-carotene 15,15'-dioxygenase, complete cds |
| 869 | 7051 | AI102055 | h | | *Rattus norvegicus* clone ZG52 mRNA sequence |
| 870 | 6544 | AI102064 | c | | ESTs, Weakly similar to AF147718 1 glycine decarboxylase [*R. norvegicus*] |
| 871 | 10227 | AI102248 | w | | ESTs |
| 872 | 23849 | AI102318 | e, q | | ESTs |
| 873 | 11954 | AI102505 | g, j, s | HMm: cytochrome c oxidase, subunit VIIIa | *Rattus norvegicus* liver cytochrome c oxidase subunit VIII (COX-VIII) mRNA, 3' end of cds |
| 874 | 2125 | AI102519 | c, k | | ESTs, Moderately similar to DAP12 [*M. musculus*] |
| 875 | 5967 | AI102520 | y | | ESTs, Moderately similar to AF161588 1 GABA-A receptor-associated protein [*R. norvegicus*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 875 | 5969 | AI102520 | p, w | | ESTs, Moderately similar to AF161588 1 GABA-A receptor-associated protein [*R. norvegicus*] |
| 876 | 11563 | AI102560 | General | | ESTs |
| 877 | 15190 | AI102562 | b, g, n, p, v | | Rat metallothionein-i (mt-1) mrna |
| 878 | 19769 | AI102570 | bb | | EST, Weakly similar to A60716 somatotropin intron-related protein RDE.25 - rat [*R. norvegicus*] |
| 879 | 22487 | AI102578 | General | | ESTs, Highly similar to I49523 Mouse primary response gene B94 mRNA, 3'end - mouse [*M. musculus*] |
| 880 | 19011 | AI102618 | General | | ESTs |
| 881 | 23837 | AI102620 | q, t | | ESTs |
| 882 | 23538 | AI102727 | g, General | solute carrier family 20 (phosphate transporter), member 1 | solute carrier family 20 (phosphate transporter), member 1 |
| 883 | 17234 | AI102741 | c | Tissue inhibitor of metalloproteinase 3 | Tissue inhibitor of metalloproteinase 3 |
| 884 | 5891 | AI102745 | k | | ESTs |
| 885 | 6796 | AI102753 | General | | ESTs |
| 886 | 8837 | AI102849 | o, p | | ESTs |
| 887 | 15861 | AI102868 | i | | ESTs, Weakly similar to phosphoserine aminotransferase [*H. sapiens*] |
| 888 | 3533 | AI102877 | g | | ESTs |
| 889 | 13222 | AI102977 | General | | ESTs, Highly similar to PCAF associated factor 65 beta [*H. sapiens*] |
| 890 | 6806 | AI103018 | o, u | | ESTs |
| 891 | 10659 | AI103059 | w, cc, General | | ESTs |
| 892 | 17400 | AI103097 | e | | ESTs, Highly similar to ATPK MOUSE ATP SYNTHASE F CHAIN, MITOCHONDRIAL [*M. musculus*] |
| 893 | 3584 | AI103106 | x, aa | | ESTs |
| 894 | 13298 | AI103143 | r | | ESTs |
| 895 | 15981 | AI103150 | i, x | | ESTs, Weakly similar to UBC2_HUMAN UBIQUITIN-CONJUGATING ENZYME E2-17 KD [*R. norvegicus*] |
| 896 | 3475 | AI103245 | w | | ESTs, Highly similar to AF151893 1 CGI-135 protein [*H. sapiens*] |
| 898 | 23619 | AI103314 | p | | ESTs |
| 899 | 24181 | AI103320 | e | | ESTs, Moderately similar to T26785 hypothetical protein Y40B1B.7 - Caenorhabditis elegans [*C. elegans*] |
| 901 | 4355 | AI103410 | General | | ESTs |
| 902 | 7622 | AI103472 | General | | ESTs |
| 903 | 20918 | AI103552 | n | | ESTs |
| 904 | 21579 | AI103572 | General | | ESTs |
| 905 | 2222 | AI103631 | o | | ESTs, Highly similar to RIE2 [*M. musculus*] |
| 906 | 2752 | AI103641 | e | | ESTs, Highly similar to sarcosine dehydrogenase [*R. norvegicus*] |
| 907 | 4856 | AI103708 | i | | ESTs |
| 908 | 8990 | AI103719 | l, m, y, z | | |
| 909 | 15942 | AI103738 | r | | ESTs |
| 910 | 22885 | AI103828 | e, General | | ESTs |
| 911 | 15853 | AI103841 | x | Complement component 4 | Complement component 4 |
| 912 | 15050 | AI103911 | j, y | HHs: ubiquinol-cytochrome c reductase, Rieske iron-sulfur polypeptide 1 | Rat Rieske iron-sulfur protein mRNA, complete cds |
| 913 | 12376 | AI103939 | u | | ESTs |
| 914 | 22271 | AI103947 | o, y | | ESTs, Weakly similar to AF151109 1 putative BRCA1-interacting protein [*H. sapiens*] |
| 915 | 20833 | AI104035 | f, q | HMm: RIKEN cDNA 2010000G05 gene | ESTs, Highly similar to COXG MOUSE CYTOCHROME C OXIDASE POLYPEPTIDE VIB [*M. musculus*] |
| 916 | 7010 | AI104099 | w | | ESTs |
| 917 | 22101 | AI104251 | General | | ESTs |
| 918 | 22833 | AI104258 | General | | ESTs |
| 919 | 22211 | AI104279 | g, m | | ESTs, Highly similar to translation initiation factor eIF6 [*M. musculus*] |
| 920 | 10720 | AI104296 | l | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 921 | 15416 | AI104340 | i | | ESTs |
| 922 | 10991 | AI104342 | a | | ESTs |
| 923 | 18831 | AI104357 | p | | ESTs, Highly similar to ATRTC actin beta - rat [*R. norvegicus*] |
| 924 | 7223 | AI104373 | e | | ESTs |
| 925 | 23574 | AI104520 | e, g, s | Cytochrome c oxidase subunit VIa (liver) | Cytochrome c oxidase subunit VIa (liver) |
| 926 | 18509 | AI104528 | q | | ESTs, Weakly similar to NADH: ubiquinone oxidoreductase B17 subunit [*H. sapiens*] |
| 927 | 11680 | AI104605 | v | | ESTs |
| 928 | 12342 | AI104658 | w | | ESTs, Weakly similar to RENAL TRANSCRIPTION FACTOR KID-1 [*R. norvegicus*] |
| 929 | 23689 | AI104685 | r | | Rat mitochondrial succinyl-CoA synthetase alpha subunit (cytoplasmic precursor) mRNA, complete cds |
| 930 | 15377 | AI104821 | o, cc | | ESTs, Moderately similar to T50611 hypothetical protein DKFZp434H2035.1 [*H. sapiens*] |
| 931 | 22957 | AI104897 | General | | ESTs, Moderately similar to meningioma-expressed antigen 11 [*H. sapiens*] |
| 932 | 18451 | AI104953 | o, s | HHs: ATP synthase, H+ transporting, mitochondrial F1 complex, delta subunit | *Rattus norvegicus* delta subunit of F1F0 ATPase gene, complete cds |
| 933 | 24375 | AI104979 | n, General | | ESTs, Moderately similar to nucleolar protein p40 [*H. sapiens*] |
| 934 | 18278 | AI105080 | bb | | ESTs, Moderately similar to SCOT_HUMAN SUCCINYL-COA: 3-KETOACID-COENZYME A TRANSFERASE PRECURSOR [*H. sapiens*] |
| 935 | 2196 | AI105243 | g | | ESTs |
| 936 | 5199 | AI105272 | bb, General | | ESTs, Weakly similar to T21641 hypothetical protein F32B6.2 - *Caenorhabditis elegans* [*C. elegans*] |
| 937 | 12901 | AI105301 | o, s | | ESTs |
| 938 | 7700 | AI105383 | cc, General | | ESTs, Weakly similar to T19707 hypothetical protein C34C6.5 - *Caenorhabditis elegans* [*C. elegans*] |
| 939 | 13343 | AI105398 | u | | ESTs |
| 940 | 22931 | AI105417 | e, General | | ESTs, Moderately similar to NEURONAL PROTEIN 3.1 [*M. musculus*] |
| 941 | 23596 | AI105435 | bb | HMm: glutaryl-Coenzyme A dehydrogenase | ESTs, Highly similar to GCDH MOUSE GLUTARYL-COA DEHYDROGENASE PRECURSOR [*M. musculus*] |
| 942 | 15893 | AI105465 | o | | ESTs, Moderately similar to DHSD_HUMAN SUCCINATE DEHYDROGENASE [*H. sapiens*] |
| 943 | 12660 | AI111492 | c | | ESTs |
| 944 | 4479 | AI111599 | General | | ESTs |
| 945 | 24211 | AI111853 | k | | ESTs, Highly similar to H33_HUMAN HISTONE H3.3 [*R. norvegicus*] |
| 946 | 2539 | AI111960 | r | | ESTs, Weakly similar to FKB5 MOUSE 51 KDA FK506-BINDING PROTEIN [*M. musculus*] |
| 947 | 5729 | AI111990 | k | | EGF-CONTAINING FIBULIN-LIKE EXTRACELLULAR MATRIX PROTEIN 1 PRECURSOR (FIBULIN-3) (FIBL-3) (T16 PROTEIN) [*R. norvegicus*] |
| 948 | 4049 | AI112012 | i, q, u, General | | *Rattus norvegicus* osteoactivin mRNA, complete cds |
| 949 | 12908 | AI112043 | i | | ESTs |
| 950 | 20041 | AI112161 | t | | ESTs |
| 951 | 12937 | AI112462 | General | | ESTs |
| 952 | 3713 | AI112571 | b | | ESTs |
| 953 | 12921 | AI112636 | General | | ESTs, Moderately similar to UDP_HUMAN URIDINE PHOSPHORYLASE [*H. sapiens*] |
| 954 | 12965 | AI112926 | General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 955 | 7499 | AI112986 | General | | ESTs |
| 956 | 4969 | AI113008 | r | | ESTs, Moderately similar to megakaryocyte stimulating factor [*H. sapiens*] |
| 957 | 11817 | AI136295 | f | | ESTs, Highly similar to BC-2 protein [*H. sapiens*] |
| 959 | 11165 | AI136372 | c | | ESTs, Weakly similar to JC4975 plexin 2 precursor - mouse [*M. musculus*] |
| 960 | 4045 | AI136460 | cc | | ESTs |
| 961 | 12782 | AI136493 | k | | ESTs |
| 962 | 6850 | AI136665 | h | ecto-apyrase | ecto-apyrase |
| 963 | 20920 | AI136891 | p, v | butyrate response factor 1 | butyrate response factor 1 |
| 964 | 6552 | AI137062 | o | | ESTs, Highly similar to 6.2 kd protein [*H. sapiens*] |
| 965 | 22722 | AI137211 | i | | ESTs |
| 966 | 13111 | AI137224 | o, General | | ESTs, Highly similar to oxysterol-binding protein [*M. musculus*] |
| 967 | 15969 | AI137302 | e | | ESTs |
| 968 | 14349 | AI137303 | d | | ESTs |
| 969 | 9166 | AI137406 | General | | ESTs |
| 970 | 9525 | AI137516 | r | | ESTs, Weakly similar to ZF37_RAT ZINC FINGER PROTEIN 37 (ZFP-37) [*R. norvegicus*] |
| 971 | 6638 | AI137579 | General | | ESTs |
| 972 | 7414 | AI137586 | General | | ESTs, Highly similar to IMB3_HUMAN IMPORTIN BETA-3 SUBUNIT [*H. sapiens*] |
| 973 | 11321 | AI137752 | z | | ESTs |
| 974 | 23473 | AI137932 | l | | ESTs |
| 975 | 13158 | AI138024 | i | | ESTs |
| 976 | 13467 | AI138034 | cc | UDP-glucose: ceramide glycosyltransferase | UDP-glucose: ceramide glycosyltransferase |
| 977 | 11377 | AI138105 | y | | ESTs |
| 978 | 6790 | AI144801 | d, h | | ESTs |
| 979 | 6506 | AI144919 | j, l, y | | ESTs |
| 980 | 8027 | AI144958 | i | | ESTs |
| 982 | 14458 | AI145095 | General | | ESTs |
| 983 | 7476 | AI145202 | g | | ESTs |
| 984 | 17545 | AI145384 | e | | ESTs, ESTs, Weakly similar to GTP-binding protein [*H. sapiens*] |
| 985 | 17479 | AI145385 | r | | ESTs |
| 986 | 4194 | AI145387 | r | | ESTs |
| 987 | 8634 | AI145722 | g | | ESTs, Weakly similar to T31511 hypothetical protein Y116A8C.9 - *Caenorhabditis elegans* [*C. elegans*] |
| 988 | 8339 | AI145761 | y, General | | ESTs, Weakly similar to T21659 hypothetical protein F32D8.4 - *Caenorhabditis elegans* [*C. elegans*] |
| 989 | 2059 | AI46005 | h, General | | ESTs, Highly similar to pseudouridine synthase 1 [*M. musculus*] |
| 990 | 23224 | AI146033 | o | | *Rattus norvegicus* small zinc finger-like protein (TIM9a) mRNA, partial cds |
| 991 | 5232 | AI168942 | bb | branched chain keto acid dehydrogenase E1, beta polypeptide | branched chain keto acid dehydrogenase E1, beta polypeptide |
| 992 | 18472 | AI168975 | u | | ESTs |
| 992 | 18473 | AI168975 | u | | ESTs |
| 993 | 13235 | AI169020 | r | | ESTs |
| 994 | 11618 | AI169115 | o, y, General | | ESTs |
| 995 | 17386 | AI169144 | o | | ESTs, Weakly similar to T23206 hypothetical protein K01H12.1 - *Caenorhabditis elegans* [*C. elegans*] |
| 996 | 10984 | AI169156 | o, u | | ESTs, Weakly similar to HP33 [*R. norvegicus*] |
| 997 | 8205 | AI169176 | e | | ESTs |
| 998 | 12979 | AI169177 | e | | ESTs, Highly similar to RADIATION-INDUCIBLE IMMEDIATE-EARLY GENE IEX-1 [*M. musculus*] |
| 999 | 2607 | AI169211 | c | | ESTs, Highly similar to A47318 RNA-binding protein Raly - mouse [*M. musculus*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1000 | 22661 | AI169265 | s, z | ATPase, H+ transporting, lysosomal (vacuolar proton pump), subun | ATPase, H+ transporting, lysosomal (vacuolar proton pump), subunit 1 |
| 1001 | 13239 | AI169278 | g, j, l, y, z | | ESTs |
| 1002 | 24162 | AI169279 | m | | ESTS |
| 1003 | 16879 | AI169284 | o | | ESTs, Highly similar to Y069__HUMAN HYPOTHETICAL PROTEIN KIAA0069 [*H. sapiens*] |
| 1004 | 24213 | AI169289 | p | | ESTs, Highly similar to H33__HUMAN HISTONE H3.3 [*R. norvegicus*] |
| 1005 | 13240 | AI169311 | cc | | ESTs |
| 1006 | 5931 | AI169324 | b | | ESTs |
| 1007 | 20891 | AI169337 | d | | ESTs, Highly similar to CGI-117 protein [*H. sapiens*] |
| 1008 | 11979 | AI169365 | cc | | ESTs |
| 1009 | 10947 | AI169372 | s | arachidonic acid epoxygenase | arachidonic acid epoxygenase |
| 1010 | 20697 | AI169494 | o, u | | ESTs |
| 1011 | 8234 | AI169517 | z | | ESTs |
| 1012 | 18343 | AI169648 | o | | ESTs |
| 1013 | 10839 | AI169655 | l, m | | ESTs |
| 1014 | 24146 | AI169668 | j, l | | ESTs, Weakly similar to hypothetical protein [*H. sapiens*] |
| 1015 | 22575 | AI169728 | r | | ESTs, Moderately similar to T47184 hypothetical protein DKFZp434F1526.1 [*H. sapiens*] |
| 1016 | 804 | AI169756 | cc | | ESTs, Highly similar to GENE 33 POLYPEPTIDE [*R. norvegicus*] |
| 1017 | 8213 | AI169883 | p | ferritin light chain 1 | ferritin light chain 1 |
| 1018 | 3916 | AI169947 | i, bb | | ESTs |
| 1019 | 3733 | AI170053 | u, General | | ESTs |
| 1020 | 14179 | AI170224 | cc | | ESTs |
| 1021 | 11406 | AI170263 | r | | ESTs, Moderately similar to class II cytokine receptor 4 [*M. musculus*] |
| 1022 | 3547 | AI170279 | General | | ESTs, Weakly similar to ZNT1 RAT ZINC TRANSPORTER 1 [*R. norvegicus*] |
| 1023 | 11524 | AI170340 | j, y, z | | ESTs, Weakly similar to CL36 RAT LIM DOMAIN PROTEIN CLP-36 [*R. norvegicus*] |
| 1024 | 2729 | AI170363 | e, i | | ESTs |
| 1025 | 18811 | AI170525 | i | | ESTs |
| 1026 | 22524 | AI170542 | h | | ESTs |
| 1027 | 24048 | AI170570 | a, g | | ESTs, Highly similar to CGI-10 protein [*H. sapiens*] |
| 1028 | 5968 | AI170692 | y, aa | | ESTs, Moderately similar to AF161588 1 GABA-A receptor-associated protein [*R. norvegicus*] |
| 1029 | 9757 | AI170693 | b | | ESTs |
| 1030 | 18905 | AI170770 | e, s | | ESTs, Highly similar to NADH-ubiquinone oxidoreductase NDUFS2 subunit [*H. sapiens*] |
| 1031 | 16170 | AI170894 | i | | ESTs, Moderately similar to adipophilin [*H. sapiens*] |
| 1032 | 7089 | AI171185 | c | Hyaluronan mediated motility receptor (RHAMM) | Hyaluronan mediated motility receptor (RHAMM) |
| 1033 | 17591 | AI171354 | b | | ESTs |
| 1034 | 13285 | AI171361 | h | | ESTs, Weakly similar to AIF-C1 [*R. norvegicus*] |
| 1035 | 4428 | AI171362 | a | HHs: NADH dehydrogenase (ubiquinone) Fe—S protein 1 (75 kD) (NADH-coenzyme Q reductase) | ESTs, Moderately similar to NUAM__HUMAN NADH-UBIQUINONE OXIDOREDUCTASE 75 KD SUBUNIT PRECURSOR [*H. sapiens*] |
| 1036 | 18126 | AI171369 | w | | ESTs, Highly similar to S16788 probable reverse transcriptase - rat [*R. norvegicus*] |
| 1037 | 23253 | AI171448 | o | | ESTs, Moderately similar to 68MP MOUSE 6.8 KD MITOCHONDRIAL PROTEOLIPID [*M. musculus*] |
| 1038 | 4584 | AI171492 | m, General | | ESTs |
| 1039 | 11158 | AI171542 | r, s | | ESTs, Moderately similar to NADH: ubiquinone oxidoreductase B22 subunit [*H. sapiens*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1040 | 15345 | AI171587 | l | | ESTs |
| 1041 | 21183 | AI171676 | k | | ESTs |
| 1042 | 8215 | AI171692 | i | ferritin light chain 1 | *Rattus norvegicus* kynurenine aminotransferase/glutamine transaminase K (Kat) gene, complete cds, ferritin light chain 1 |
| 1043 | 11437 | AI171794 | i | | ESTs |
| 1044 | 2625 | AI171800 | cc | | ESTs |
| 1045 | 23579 | AI171802 | v | | ESTs |
| 1046 | 11708 | AI171807 | l, t | | ESTs |
| 1047 | 17204 | AI171844 | s, y, z | HMm: RIKEN cDNA 2410043G19 gene | *Rattus norvegicus* F1-ATPase epsilon subunit mRNA, nuclear gene encoding mitochondrial protein, complete cds |
| 1048 | 4420 | AI171916 | m | | ESTs |
| 1049 | 3266 | AI171948 | l, m | | ESTs, Highly similar to T08675 hypothetical protein DKFZp564F0522.1 [*H. sapiens*] |
| 1050 | 19012 | AI172056 | t | | ESTs |
| 1051 | 11205 | AI172057 | a, q, bb | | ESTs |
| 1052 | 6057 | AI172102 | b | | ESTs, Weakly similar to T33238 hypothetical protein T10H9.3 - *Caenorhabditis elegans* [*C. elegans*] |
| 1053 | 19128 | AI172103 | m | | ESTs |
| 1054 | 15673 | AI172107 | z | | Rat mRNA for 5E5 antigen, complete cds |
| 1055 | 6630 | AI172184 | n | | ESTs |
| 1056 | 11968 | AI172208 | bb | | ESTs, Weakly similar to FETA RAT ALPHA-FETOPROTEIN PRECURSOR [*R. norvegicus*] |
| 1057 | 6974 | AI172263 | l, m | | ESTs |
| 1058 | 23313 | AI172271 | d | | ESTs |
| 1059 | 2140 | AI172272 | General | | ESTs, Moderately similar to A53004 transcription elongation factor S-II - rat [*R. norvegicus*] |
| 1060 | 15382 | AI172302 | l, p, General | | ESTs, Weakly similar to S43056 hypothetical protein - mouse [*M. musculus*] |
| 1061 | 18689 | AI172329 | l | | ESTs |
| 1062 | 17887 | AI172414 | o | | *Rattus norvegicus* apoptosis-regulating basic protein mRNA, complete cds |
| 1063 | 3042 | AI172447 | General | | ESTs, Highly similar to A44437 regenerating liver inhibitory factor RL/IF-1 - rat [*R. norvegicus*] |
| 1064 | 17291 | AI172491 | bb | HMm: isocitrate dehydrogenase 2 (NADP+), mitochondrial | ESTs, Weakly similar to IDHC RAT ISOCITRATE DEHYDROGENASE [*R. norvegicus*] |
| 1065 | 26222 | AI172506 | p | | |
| 1066 | 13095 | AI172595 | r | | ESTs |
| 1067 | 8795 | AI172618 | General | | ESTs |
| 1068 | 6454 | AI175342 | j, l, m, y | | ESTs, Weakly similar to T31067 BIR repeat containing ubiquitin-conjugating enzyme BRUCE - mouse [*M. musculus*] |
| 1070 | 4445 | AI175466 | x | | ESTs, Highly similar to RRAS MOUSE RAS-RELATED PROTEIN R-RAS [*M. musculus*] |
| 1071 | 3418 | AI175475 | m | | ESTs, Highly similar to NHPX RAT NHP2/RS6 FAMILY PROTEIN YEL026W HOMOLOG [*R. norvegicus*] |
| 1072 | 18507 | AI175551 | bb | | ESTs, Moderately similar to AF145050 1 translation elongation factor 1-delta subunit [*R. norvegicus*] |
| 1073 | 10217 | AI175628 | w | | ESTs |
| 1074 | 7262 | AI175833 | j, m, x | | ESTs |
| 1075 | 19004 | AI175875 | r | | ESTs |
| 1076 | 22352 | AI175959 | l, General | | ESTs |
| 1077 | 7022 | AI176041 | h, n | | ESTs, Highly similar to pirin [*H. sapiens*] |
| 1078 | 21467 | AI176061 | t | | ESTs, Weakly similar to tazarotene-induced gene 2 [*H. sapiens*] |
| 1079 | 18581 | AI176160 | General | | ESTs |
| 1080 | 14159 | AI176169 | g | | ESTs |
| 1081 | 21742 | AI176172 | w | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1082 | 10182 | AI176185 | v | | ESTs, Highly similar to P55-C-FOS PROTO-ONCOGENE PROTEIN [R. norvegicus] |
| 1083 | 22765 | AI176265 | General | | ESTs |
| 1084 | 6905 | AI176275 | a | | ESTs, Weakly similar to GSHH RAT PHOSPHOLIPID HYDROPEROXIDE GLUTATHIONE PEROXIDASE [R. norvegicus] |
| 1085 | 12999 | AI176276 | cc | | UAP1_HUMAN UDP-N-ACETYLHEXOSAMINE PYROPHOSPHORYLASE [H. sapiens] |
| 1086 | 16438 | AI176294 | e | | ESTs, Highly similar to SMD2_HUMAN SMALL NUCLEAR RIBONUCLEOPROTEIN SM D2 [H. sapiens] |
| 1087 | 21130 | AI176298 | y | | ESTs |
| 1088 | 3014 | AI176362 | e | | ESTs |
| 1089 | 15015 | AI176363 | r | | ESTs |
| 1090 | 19006 | AI176393 | x | | ESTs |
| 1091 | 20001 | AI176396 | o | | ESTs, Moderately similar to QPS1 [H. sapiens] |
| 1092 | 12174 | AI176435 | j, m | | ESTs |
| 1093 | 15191 | AI176456 | b, o, t, v, cc | | Rat metallothionein-2 and metallothionein-1 genes, complete cds |
| 1094 | 24236 | AI176473 | d, General | | ESTs |
| 1095 | 16518 | AI176546 | v | | ESTs, Moderately similar to HS9B RAT HEAT SHOCK PROTEIN HSP 90-BETA [R. norvegicus] |
| 1096 | 2161 | AI176592 | General | | ESTs |
| 1097 | 12436 | AI176610 | General | | ESTs, Weakly similar to S63220 probable membrane protein YNL247w - yeast (Saccharomyces cerevisiae) [S. cerevisiae] |
| 1098 | 2536 | AI176616 | l, v, General | | ESTs |
| 1099 | 18525 | AI176792 | u | | ESTs |
| 1100 | 23449 | AI176828 | g | | ESTs |
| 1101 | 23299 | AI176839 | General | | ESTs |
| 1102 | 3580 | AI176848 | e | | ESTs |
| 1103 | 22103 | AI176849 | d, General | | ESTs |
| 1104 | 16036 | AI176855 | f | | ESTs |
| 1105 | 15588 | AI176916 | General | | ESTs, Highly similar to phosphomannomutase Sec53p homolog [M. musculus] |
| 1106 | 16917 | AI176951 | t | | ESTs |
| 1107 | 16124 | AI176963 | cc | | Rattus norvegicus transcription factor MRG1 mRNA, complete cds |
| 1108 | 15146 | AI176969 | b, General | | ESTs |
| 1109 | 5786 | AI177058 | f | | ESTs, Weakly similar to PSE-binding factor PTF delta subunit [H. sapiens] |
| 1110 | 2852 | AI177059 | c | | ESTs |
| 1112 | 3156 | AI177092 | g | | ESTs, Highly similar to AF139894 1 RNA-binding protein alpha-CP1 [M. musculus] |
| 1113 | 14384 | AI177096 | a | HMm: adenine phosphoribosyl transferase | Rat adenine phosphoribosyltransferase (APRT) gene, complete cds |
| 1114 | 13310 | AI177119 | General | | ESTs, Weakly similar to C1QB RAT COMPLEMENT C1Q SUBCOMPONENT, B CHAIN PRECURSOR [R. norvegicus] |
| 1115 | 24049 | AI177341 | g, p, s, u | | ESTs, Highly similar to CGI-10 protein [H. sapiens] |
| 1116 | 15964 | AI177360 | o, General | | ESTs |
| 1117 | 14989 | AI177366 | u | Integrin, beta 1 | Integrin, beta 1 |
| 1118 | 7975 | AI177374 | aa | | ESTs |
| 1119 | 3006 | AI177395 | k | | Rattus norvegicus substrate binding subunit of type II 5'-deiodinase D2p29 mRNA, complete cds |
| 1120 | 17570 | AI177683 | r | | Rattus norvegicus mRNA for hnRNP protein, partial |
| 1121 | 9521 | AI177706 | b | | ESTs |
| 1122 | 14425 | AI177755 | g, General | | ESTs |
| 1123 | 10611 | AI177790 | j, m | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1124 | 5356 | AI177813 | cc | | ESTs, Moderately similar to S27962 modulator recognition factor 1 [*H. sapiens*] |
| 1125 | 11791 | AI177843 | General | | ESTs, Highly similar to SAS_HUMAN SARCOMA AMPLIFIED SEQUENCE [*H. sapiens*] |
| 1126 | 14484 | AI177867 | General | | ESTs, Weakly similar to putative eps protein [*R. norvegicus*] |
| 1127 | 5780 | AI177869 | General | | ESTs, Weakly similar to DRAL [*R. norvegicus*] |
| 1128 | 19184 | AI178025 | General | | ESTs, Highly similar to TGIF MOUSE 5'-TG-3' INTERACTING FACTOR [*M. musculus*] |
| 1129 | 6059 | AI178245 | c, General | | ESTs, Moderately similar to C17orf1 protein [*H. sapiens*] |
| 1130 | 23248 | AI178267 | y | | ESTs, Weakly similar to hypothetical protein [*H. sapiens*] |
| 1131 | 4073 | AI178272 | o | | ESTs, Weakly similar to YAE6_YEAST HYPOTHETICAL 13.4 KD PROTEIN IN ACS1-GCV3 INTERGENIC REGION [*S. cerevisiae*] |
| 1132 | 7838 | AI178291 | e | | ESTs |
| 1133 | 18996 | AI178326 | y | | ESTs |
| 1134 | 22488 | AI178392 | b | | ESTs, Highly similar to I49523 Mouse primary response gene B94 mRNA, 3'end - mouse [*M. musculus*] |
| 1135 | 18800 | AI178504 | n, p, aa | | ESTs |
| 1136 | 22197 | AI178527 | g, General | | ESTs |
| 1137 | 3401 | AI178684 | bb | | ESTs, Highly similar to MCM3 MOUSE DNA REPLICATION LICENSING FACTOR MCM3 [*M. musculus*] |
| 1138 | 17713 | AI178700 | m | | ESTs |
| 1139 | 14874 | AI178735 | e | | ESTs |
| 1140 | 23567 | AI178746 | v, General | | ESTs |
| 1141 | 18907 | AI178971 | c | | *Rattus norvegicus* alpha-globin (GloA) gene, complete cds |
| 1142 | 20991 | AI178979 | i | | ESTs |
| 1143 | 5887 | AI179099 | q, t | | ESTs, Moderately similar to Vanin-1 [*M. musculus*] |
| 1144 | 8477 | AI179167 | b, e, General | | ESTs |
| 1145 | 3348 | AI179288 | u, v | | ESTs |
| 1146 | 13608 | AI179314 | e | | ESTs |
| 1147 | 8849 | AI179315 | g, p | | ESTs |
| 1148 | 13611 | AI179378 | v, General | | *Rattus norvegicus* mRNA for prostasin precursor, complete cds |
| 1149 | 15438 | AI179399 | m, x | collagen type V, alpha 2 | collagen type V, alpha 2 |
| 1150 | 13614 | AI179407 | e, t, General | | ESTs, Moderately similar to RB17 MOUSE RAS-RELATED PROTEIN RAB-17 [*M. musculus*] |
| 1151 | 15042 | AI179422 | b, General | | ESTs |
| 1152 | 2768 | AI179481 | i, General | | ESTs |
| 1153 | 24041 | AI179580 | b, i | | ESTs |
| 1154 | 19822 | AI179599 | o, General | | *R. norvegicus* mRNA for ras-related GTPase Rab29 |
| 1155 | 23270 | AI179601 | q, General | | ESTs |
| 1156 | 5901 | AI179605 | e | | ESTs |
| 1157 | 16081 | AI179610 | g, i, p | Heme oxygenase | Heme oxygenase |
| 1158 | 14564 | AI179717 | k | | ESTs |
| 1159 | 7918 | AI179750 | General | | ESTs |
| 1160 | 6647 | AI179795 | g | | ESTs |
| 1161 | 9097 | AI179875 | o, General | hypothetical protein LOC56728 | hypothetical protein LOC56728 |
| 1162 | 23989 | AI179953 | a | | ESTs, Highly similar to GAP JUNCTION BETA-2 PROTEIN [*R. norvegicus*] |
| 1163 | 12899 | AI179967 | b | | ESTs |
| 1164 | 1687 | AI179971 | c | Hemoglobin, alpha 1 | Hemoglobin, alpha 1 |
| 1165 | 22569 | AI179979 | General | | ESTs |
| 1166 | 23514 | AI179986 | o, General | HHs: phosphoserine phosphatase | ESTs, Highly similar to L-3-phosphoserine phosphatase [*H. sapiens*] |
| 1167 | 15892 | AI179988 | c, General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1168 | 12402 | AI180004 | g | | ESTs, Highly similar to Unknown [*H. sapiens*] |
| 1169 | 5443 | AI180165 | General | | ESTs, Moderately similar to testis specific DNAj-homolog [*M. musculus*] |
| 1170 | 5481 | AI180170 | General | | ESTs, Highly similar to A Chain A, The Crystal Structure Of Human Eukaryotic Release Factor Erf1- Mechanism Of Stop Codon Recognition And Peptidyl-Tma Hydrolysis [*H. sapiens*] |
| 1171 | 24028 | AI180239 | i | | ESTs |
| 1172 | 17089 | AI180281 | g | | ESTs, Moderately similar to JC4978 oxidative stress protein A170 - mouse [*M. musculus*] |
| 1173 | 3701 | AI180306 | aa | | ESTs, Moderately similar to Y273_HUMAN HYPOTHETICAL PROTEIN KIAA0273 [*H. sapiens*] |
| 1174 | 3352 | AI180334 | m | | ESTs |
| 1175 | 24368 | AI180392 | l, m | | ESTs, Highly similar to AF114169 1 nucleotide-binding protein short form [*M. musculus*] |
| 1176 | 14337 | AI180414 | c | | ESTs, Moderately similar to SPA1 MOUSE GTPASE-ACTIVATING PROTEIN SPA-1 [*M. musculus*] |
| 1177 | 19080 | AI227647 | j, y, z | | *Rattus norvegicus* chemokine CX3C mRNA, complete cds |
| 1178 | 22838 | AI227667 | aa | | ESTs |
| 1179 | 6765 | AI227761 | i, General | | ESTs, Highly similar to T00367 hypothetical protein KIAA0665 [*H. sapiens*] |
| 1180 | 24054 | AI227867 | General | | ESTs, Weakly similar to AF187065 1 p75NTR-associated cell death executor [*R. norvegicus*] |
| 1181 | 7324 | AI227885 | i | | ESTs |
| 1182 | 23898 | AI227987 | d | | ESTs |
| 1183 | 1651 | AI228068 | n, w | Peptidylglycine alpha- amidating monooxygenase | Peptidylglycine alpha-amidating monooxygenase |
| 1184 | 14237 | AI228128 | e | | EST |
| 1185 | 14242 | AI228197 | General | | ESTs, Weakly similar to C21I_HUMAN PUTATIVE PROTEIN C21ORF18 [*H. sapiens*] |
| 1186 | 16913 | AI228236 | o | | ESTs |
| 1187 | 22915 | AI228299 | r | | ESTs, Highly similar to p97 homologous protein [*H. sapiens*] |
| 1188 | 8917 | AI228301 | General | | ESTs |
| 1189 | 15879 | AI228313 | r, General | | ESTs |
| 1190 | 13727 | AI228326 | o, General | | ESTs, Weakly similar to AFG1_YEAST AFG1 PROTEIN [*S. cerevisiae*] |
| 1191 | 6102 | AI228335 | General | | ESTs |
| 1192 | 13730 | AI228356 | a | | ESTs, Weakly similar to S70642 ubiquitin ligase Nedd4 - rat [*R. norvegicus*] |
| 1193 | 13745 | AI228494 | b, cc | | EST |
| 1194 | 4217 | AI228587 | s | | ESTs, Weakly similar to M172_HUMAN MEMBRANE COMPONENT, CHROMOSOME 17, SURFACE MARKER 2 [*H. sapiens*] |
| 1195 | 16053 | AI228596 | cc | | ESTs, Weakly similar to T16757 hypothetical protein R144.3 - *Caenorhabditis elegans* [*C. elegans*] |
| 1196 | 3557 | AI228672 | e | | ESTs |
| 1197 | 11605 | AI228682 | e | | ESTs |
| 1198 | 13203 | AI228728 | r | | ESTs |
| 1199 | 13771 | AI228848 | g | | ESTs, Highly similar to protein inhibitor of activated STAT protein PIAS1 [*H. sapiens*] |
| 1200 | 5918 | AI229036 | r | | ESTs |
| 1201 | 8235 | AI229154 | k | | ESTs |
| 1202 | 16203 | AI229196 | r | Vesicle-associated membrane protein (synaptobrevin 2) | Vesicle-associated membrane protein (synaptobrevin 2) |
| 1203 | 13826 | AI229304 | a | | ESTs |
| 1204 | 13144 | AI229320 | g | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1205 | 4640 | AI229404 | x, aa | | ESTs |
| 1206 | 23563 | AI229421 | l | | ESTs, Moderately similar to MKK2 MOUSE MAP KINASE-ACTIVATED PROTEIN KINASE 2 [*M. musculus*] |
| 1207 | 15426 | AI229497 | s | | ESTs, Moderately similar to NADH-ubiquinone oxidoreductase PDSW subunit [*H. sapiens*] |
| 1208 | 15193 | AI229508 | bb | | ESTs |
| 1209 | 19243 | AI229638 | x | | ESTs, Highly similar to KITH RAT THYMIDINE KINASE, CYTOSOLIC [*R. norvegicus*] |
| 1210 | 23078 | AI229647 | p | | ESTs |
| 1211 | 3099 | AI229680 | o | HHs: NADH dehydrogenase (ubiquinone) Fe—S protein 3 (30 kD) (NADH-coenzyme Q reductase) | ESTs, Highly similar to NADH: ubiquinone oxidoreductase NDUFS3 subunit [*H. sapiens*] |
| 1212 | 19508 | AI229698 | bb | | Sprague-Dawley D-beta-hydroxybutyrate dehydrogenase mRNA, complete cds |
| 1213 | 13977 | AI229707 | x | | *Rattus norvegicus* mRNA for class I beta-tubulin, complete cds |
| 1214 | 23983 | AI229708 | v | | ESTs, Moderately similar to NADC_HUMAN NICOTINATE-NUCLEOTIDE PYROPHOSPHORYLASE [*H. sapiens*] |
| 1215 | 2688 | AI229793 | e | | ESTs |
| 1216 | 13874 | AI229832 | g | | ESTs, Weakly similar to KIAA0859 protein [*H. sapiens*] |
| 1217 | 12587 | AI229979 | General | | ESTs, Weakly similar to MOT2 RAT MONOCARBOXYLATE TRANSPORTER 2 [*R. norvegicus*] |
| 1218 | 20591 | AI229993 | l, m | | ESTs |
| 1219 | 24042 | AI230002 | a, b, d, General | | ESTs |
| 1220 | 13880 | AI230042 | u | | *Rattus norvegicus* mRNA for voltage-gated ca channel, complete cds |
| 1221 | 17672 | AI230074 | d | HMm: NADH dehydrogenase (ubiquinone) 1 alpha subcomplex, 1 | ESTs, Highly similar to NIMM MOUSE NADH-UBIQUINONE OXIDOREDUCTASE MWFE SUBUNIT [*M. musculus*] |
| 1222 | 3652 | AI230113 | General | | *Rattus norvegicus* hfb2 mRNA, complete cds |
| 1223 | 18650 | AI230121 | aa | | ESTs, Weakly similar to HS9B RAT HEAT SHOCK PROTEIN HSP 90-BETA [*R. norvegicus*] |
| 1224 | 13025 | AI230173 | c | | ESTs, Moderately similar to CHD3_HUMAN CHROMODOMAIN HELICASE-DNA-BINDING PROTEIN 3 [*H. sapiens*] |
| 1225 | 4280 | AI230247 | z | selenoprotein P, plasma, 1 | selenoprotein P, plasma, 1 |
| 1226 | 18528 | AI230284 | General | | ESTs |
| 1227 | 7084 | AI230362 | p | | ESTs, Moderately similar to T46458 hypothetical protein DKFZp434M102.1 [*H. sapiens*] |
| 1228 | 20895 | AI230549 | b, n | | ESTs |
| 1229 | 12961 | AI230554 | General | | ESTs |
| 1230 | 15636 | AI230616 | r | | *Rattus norvegicus* mRNA for galectin-2 related protein, complete cds |
| 1231 | 4121 | AI230647 | j, m | | ESTs |
| 1232 | 14388 | AI230702 | General | | ESTs, Highly similar to HN1 [*M. musculus*] |
| 1233 | 18529 | AI230716 | x, General | | ESTs |
| 1234 | 13618 | AI230724 | General | | *Rattus norvegicus* phosphoinositide phosphatase SAC1 mRNA, complete cds |
| 1235 | 8304 | AI230746 | cc | | ESTs |
| 1236 | 4731 | AI230773 | e | | ESTs |
| 1237 | 14430 | AI230798 | c, k, x | | ESTs, Moderately similar to CDN3_HUMAN CYCLIN-DEPENDENT KINASE INHIBITOR 3 [*H. sapiens*] |
| 1238 | 16627 | AI230822 | bb | HHs: Alg5, S. cerevisiae, homolog of | ESTs, Highly similar to AF102850 1 dolichyl-phosphate beta-glucosyltransferase [*H. sapiens*] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1239 | 3125 | AI231028 | General | | *Rattus norvegicus* mRNA for brain 4.1(S), complete cds |
| 1240 | 633 | AI231127 | k | | ESTs |
| 1241 | 20846 | AI231140 | p | | ESTs, Highly similar to RL2B_HUMAN 60S RIBOSOMAL PROTEIN L23A [*R. norvegicus*] |
| 1242 | 6743 | AI231219 | d | | ESTs |
| 1244 | 26292 | AI231391 | k | | |
| 1245 | 12343 | AI231433 | w | | ESTs |
| 1246 | 7337 | AI231465 | aa | | ESTs |
| 1247 | 16321 | AI231506 | General | | ESTs |
| 1248 | 8004 | AI231532 | j, l | | ESTs, Highly similar to Z183_HUMAN ZINC FINGER PROTEIN 183 [*H. sapiens*] |
| 1249 | 15171 | AI231792 | g | | ESTs, Moderately similar to BAG-family molecular chaperone regulator-3 [*H. sapiens*] |
| 1250 | 6193 | AI231797 | i | | ESTs |
| 1252 | 14227 | AI231999 | u | | ESTs, Moderately similar to tumor protein D53 [*M. musculus*] |
| 1253 | 24501 | AI232006 | w, y, bb | | *Rattus norvegicus* translation elongation factor 1-delta subunit mRNA, partial cds |
| 1254 | 3434 | AI232014 | g, q, z, cc, General | | ESTs |
| 1255 | 19094 | AI232021 | n, General | | ESTs, Highly similar to Human Translation Initiation Factor Eif1, Nmr, 29 Structures [*H. sapiens*] |
| 1256 | 14020 | AI232076 | u | | ESTs |
| 1257 | 6726 | AI232157 | d | | ESTs |
| 1258 | 11549 | AI232174 | l, m | | ESTs |
| 1259 | 23125 | AI232266 | j, s | | ESTs |
| 1260 | 2085 | AI232270 | bb | | ESTs, Moderately similar to JC4914 anti-sigma cross-reacting protein homolog I beta precursor [*H. sapiens*] |
| 1261 | 2913 | AI232272 | o | | ESTs, Weakly similar to T25417 hypothetical protein T28D6.9 - *Caenorhabditis elegans* [*C. elegans*] |
| 1262 | 14304 | AI232281 | g | | ESTs, Weakly similar to KIAA0971 protein [*H. sapiens*] |
| 1263 | 15955 | AI232294 | u, bb, General | | ESTs |
| 1264 | 15122 | AI232303 | y | | ESTs, Weakly similar to Sid1669p [*M. musculus*] |
| 1265 | 4716 | AI232313 | y | purinergic receptor P2X, ligand-gated ion channel 4 | purinergic receptor P2X, ligand-gated ion channel 4 |
| 1266 | 15246 | AI232332 | t, u | | ESTs |
| 1267 | 24321 | AI232340 | o | Stromal cell-derived factor 1 | Stromal cell-derived factor 1 |
| 1268 | 16172 | AI232341 | d | | ESTs, Weakly similar to YQ42_CAEEL HYPOTHETICAL 40.0 KD PROTEIN C13B9.2 IN CHROMOSOME III [*C. elegans*] |
| 1269 | 11411 | AI232346 | h | | ESTs |
| 1270 | 19287 | AI232379 | f | Platelet-derived growth factor receptor alpha | Platelet-derived growth factor receptor alpha |
| 1271 | 5601 | AI232461 | n, General | | ESTs, Weakly similar to FMO1 RAT DIMETHYLANILINE MONOOXYGENASE [*R. norvegicus*] |
| 1272 | 14051 | AI232489 | l, m | | ESTs, Weakly similar to PIR1 [*H. sapiens*] |
| 1273 | 5572 | AI232490 | i, t | | ESTs, Moderately similar to A27340 complement C7 precursor [*H. sapiens*] |
| 1274 | 11157 | AI232494 | cc | | ESTs |
| 1275 | 8709 | AI232534 | o | | ESTs, Weakly similar to DnaJ homolog 2 [*R. norvegicus*] |
| 1276 | 20350 | AI232552 | j, v, y | | EST |
| 1277 | 14069 | AI232631 | e | | ESTs |
| 1278 | 4440 | AI232643 | w | | ESTs |
| 1279 | 17695 | AI232784 | e | | ESTs, Weakly similar to putative peroxisomal 2,4-dienoyl-CoA reductase [*R. norvegicus*] |
| 1280 | 15796 | AI232874 | v | | ESTs |
| 1281 | 12467 | AI232924 | General | | ESTs |
| 1282 | 12873 | AI232984 | i | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1283 | 5355 | AI233031 | r | | ESTs |
| 1284 | 18794 | AI233121 | c | | ESTs, Moderately similar to MHC class I [*M. musculus*] |
| 1285 | 3823 | AI233147 | b, g, General | | ESTs, Weakly similar to nuclear RNA helicase [*R. norvegicus*] |
| 1286 | 11967 | AI233155 | c, k, General | | ESTs |
| 1287 | 11561 | AI233182 | d | | ESTs |
| 1288 | 3471 | AI233183 | g | | ESTs, Highly similar to PM1_HUMAN PROTEIN PM [*H. sapiens*] |
| 1289 | 21948 | AI233191 | i | | ESTs, Weakly similar to T15919 hypothetical protein EEED8.9 - *Caenorhabditis elegans* [*C. elegans*] |
| 1290 | 13598 | AI233194 | g, p, y | | ESTs |
| 1291 | 15552 | AI233195 | y | | ESTs, Highly similar to Bodenin [*M. musculus*] |
| 1292 | 17907 | AI233224 | bb | | *Rattus norvegicus* epidermal growth factor receptor related protein (Errp) mRNA, complete cds |
| 1293 | 14111 | AI233269 | cc | | ESTs |
| 1294 | 12894 | AI233365 | d | | ESTs, Weakly similar to T24956 hypothetical protein T16G1.10 - *Caenorhabditis elegans* [*C. elegans*] |
| 1295 | 7161 | AI233407 | General | | ESTs, Weakly similar to S44853 K12H4.3 protein - *Caenorhabditis elegans* [*C. elegans*] |
| 1296 | 15906 | AI233425 | q | | ESTs |
| 1297 | 14120 | AI233433 | d | | ESTs |
| 1298 | 14095 | AI233468 | a, d | | ESTs |
| 1299 | 3075 | AI233494 | u, aa | | ESTs, Weakly similar to I38079 OXA1 homolog [*H. sapiens*] |
| 1300 | 6046 | AI233530 | General | | ESTs |
| 1301 | 18900 | AI233570 | General | | PSD8_HUMAN 26S PROTEASOME REGULATORY SUBUNIT S14 [*H. sapiens*] |
| 1302 | 7888 | AI233583 | General | HHs: arginyl-tRNA synthetase | ESTs, Moderately similar to SYR_HUMAN ARGINYL-TRNA SYNTHETASE [*H. sapiens*] |
| 1303 | 16709 | AI233602 | General | Adenosin kinase | Adenosin kinase |
| 1304 | 5163 | AI233712 | y | | ESTs, Highly similar to P2CD_MOUSE PROTEIN PHOSPHATASE 2C DELTA ISOFORM (PP2C-DELTA) (P53-INDUCED PROTEIN PHOSPHATASE 1) (PROTEIN PHOSPHATASE MAGNESIUM-DEPENDENT 1 DELTA) [*M. musculus*] |
| 1305 | 7243 | AI233717 | General | | ESTs, Moderately similar to ERHUAH coatomer complex alpha chain homolog [*H. sapiens*] |
| 1306 | 3816 | AI233729 | g | | ESTs, Highly similar to PSD5_HUMAN 26S PROTEASOME SUBUNIT S5B [*H. sapiens*] |
| 1307 | 13023 | AI233740 | d, h, General | | ESTs, Weakly similar to ALDR RAT ALDOSE REDUCTASE [*R. norvegicus*] |
| 1308 | 14871 | AI233743 | g | | ESTs |
| 1309 | 7469 | AI233767 | cc | | ESTs, Highly similar to Gene product with similarity to KIAA0154 [*H. sapiens*] |
| 1310 | 7804 | AI233771 | b | | ESTs |
| 1311 | 13563 | AI233773 | e | | ESTs, Weakly similar to T24413 hypothetical protein T04A11.2 - *Caenorhabditis elegans* [*C. elegans*] |
| 1312 | 2154 | AI233818 | k, cc | | ESTs |
| 1313 | 16616 | AI234079 | h | | ESTs |
| 1314 | 13393 | AI234100 | a, d, General | cysteine rich protein | cysteine rich protein |
| 1315 | 7071 | AI234162 | r | | ESTs |
| 1316 | 14677 | AI234620 | General | | EST |
| 1317 | 4443 | AI234629 | m | | ESTs, Weakly similar to transcription factor C1 [*M. musculus*] |
| 1318 | 22453 | AI234678 | b | | ESTs |
| 1319 | 23964 | AI234748 | t, General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1320 | 19581 | AI234753 | f | | EST |
| 1321 | 22152 | AI234822 | o, General | DEXRAS1 (Dexras1) | DEXRAS1 (Dexras1) |
| 1322 | 18942 | AI234865 | d | | ESTs, Weakly similar to S12207 hypothetical protein [*M. musculus*] |
| 1323 | 22662 | AI234939 | aa | ATPase, H+ transporting, lysosomal (vacuolar proton pump), subun | ATPase, H+ transporting, lysosomal (vacuolar proton pump), subunit 1 |
| 1324 | 3875 | AI235047 | o, General | | ESTs, Highly similar to CB80_HUMAN 80 KDA NUCLEAR CAP BINDING PROTEIN [*H. sapiens*] |
| 1325 | 19479 | AI235135 | o | | EST |
| 1326 | 14906 | AI235192 | g | | ESTs, Highly similar to ABF2_HUMAN ATP-BINDING CASSETTE, SUB-FAMILY F, MEMBER 2 (IRON INHIBITED ABC TRANSPORTER 2) [*H. sapiens*] |
| 1327 | 14718 | AI235210 | e | | ESTs |
| 1328 | 15004 | AI235224 | b, General | | *Rattus norvegicus* tissue inhibitor of metalloproteinase-1 (TIMP1), mRNA, complete cds |
| 1329 | 6632 | AI235277 | v | | ESTs |
| 1330 | 14722 | AI235284 | x, z | | ESTs, Weakly similar to single-pass transmembrane protein [*R. norvegicus*] |
| 1331 | 1462 | AI235585 | u, General | | Rat mRNA for preprocathepsin D (EC 3.4.23.5) |
| 1332 | 21061 | AI235631 | l, m | | ESTs |
| 1333 | 14665 | AI235646 | m | MAD homolog 4 (*Drosophila*) | MAD homolog 4 (*Drosophila*) |
| 1334 | 19940 | AI235689 | General | | ESTs, Moderately similar to pescadillo [*H. sapiens*] |
| 1335 | 5698 | AI235692 | u | | ESTs |
| 1336 | 23745 | AI235732 | k | | ESTs, Highly similar to NID2 MOUSE NIDOGEN-2 PRECURSOR [*M. musculus*] |
| 1337 | 11164 | AI235739 | General | | ESTs, Moderately similar to A56716 aromatic ester hydrolase [*H. sapiens*] |
| 1338 | 5212 | AI235745 | d | | ESTs |
| 1339 | 14768 | AI235912 | h | | ESTs, Weakly similar to hypothetical protein [*H. sapiens*] |
| 1340 | 14776 | AI235950 | m | | ESTs |
| 1341 | 3091 | AI236027 | n, General | | ESTs |
| 1342 | 14861 | AI236045 | r | | ESTs |
| 1343 | 14862 | AI236048 | e | | EST |
| 1344 | 16943 | AI236097 | p | | ESTs, Highly similar to E25B protein [*M. musculus*] |
| 1345 | 8336 | AI236101 | l | | ESTs, Highly similar to JC7107 development related unidentified 27K protein - mouse [*M. musculus*] |
| 1346 | 23230 | AI236146 | v | | ESTs |
| 1347 | 22855 | AI236150 | e | | ESTs, Highly similar to JC7301 Down syndrome critical region protein 5 alpha [*H. sapiens*] |
| 1348 | 14594 | AI236152 | i | | ESTs |
| 1349 | 18406 | AI236168 | r | | ESTs |
| 1350 | 15051 | AI236332 | General | | ESTs, Highly similar to ATDA MOUSE DIAMINE ACETYLTRANSFERASE [*M. musculus*] |
| 1351 | 19298 | AI236338 | bb | | ESTs, Weakly similar to NHPX RAT NHP2/RS6 FAMILY PROTEIN YEL026W HOMOLOG [*R. norvegicus*] |
| 1352 | 10667 | AI236366 | b | siah binding protein 1; FBP interacting repressor; pyrimidine tr | siah binding protein 1; FBP interacting repressor; pyrimidine tract binding splicing factor; Ro ribonucleoprotein-binding protein 1 |
| 1353 | 10774 | AI236397 | f | | ESTs |
| 1354 | 9407 | AI236402 | aa | | ESTs |
| 1355 | 26335 | AI236460 | General | | *Rattus norvegicus* retinol dehydrogenase type II mRNA, complete cds |
| 1356 | 17950 | AI236590 | t, General | | ESTs |
| 1357 | 18259 | AI236601 | h, v | | ESTs |
| 1358 | 11445 | AI236613 | j, y | | ESTs |
| 1359 | 17248 | AI236635 | o, aa | | ESTs, Highly similar to SCF complex protein Skp1 [*M. musculus*] |
| 1360 | 16859 | AI236753 | t, General | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1361 | 5208 | AI236754 | g | | ESTs, Weakly similar to hT41 [*H. sapiens*] |
| 1362 | 24388 | AI236772 | e, General | | ESTs |
| 1363 | 15850 | AI236795 | n, v, w | | ESTs, ESTs, Highly similar to HS9B RAT HEAT SHOCK PROTEIN HSP 90-BETA [*R. norvegicus*] |
| 1364 | 14800 | AI236856 | w | | ESTs |
| 1366 | 11404 | AI237002 | m | spermidine synthase | spermidine synthase |
| 1367 | 18151 | AI237212 | o, General | | ESTs, Highly similar to hepatitis B virus X interacting protein [*H. sapiens*] |
| 1368 | 21553 | AI237535 | t, General | estrogen-responsive uterine transcript | estrogen-responsive uterine transcript |
| 1369 | 11208 | AI237586 | z | | ESTs, Moderately similar to INIB RAT INTERFERON-INDUCIBLE PROTEIN [*R. norvegicus*] |
| 1370 | 21893 | AI237713 | i, k, aa | | ESTs, Moderately similar to Y101__HUMAN HYPOTHETICAL PROTEIN KIAA0101 [*H. sapiens*] |
| 1371 | 14842 | AI237724 | r | | ESTs |
| 1372 | 3467 | AI237835 | General | | ESTs, Moderately similar to MXI1 RAT MAX INTERACTING PROTEIN 1 [*R. norvegicus*] |
| 1373 | 25840 | AI638972 | u | | |
| 1374 | 17108 | AI639017 | n | | ESTs, Highly similar to G9A [*M. musculus*] |
| 1375 | 16676 | AI639082 | c, k, x | mini chromosome maintenance deficient 6 (*S. cerevisiae*) | mini chromosome maintenance deficient 6 (*S. cerevisiae*) |
| 1376 | 12400 | AI639107 | k | | ESTs |
| 1377 | 19952 | AI639108 | q, v | | ESTs |
| 1379 | 25907 | AI639167 | o, w | | ESTs |
| 1381 | 18533 | AI639231 | n | | ESTs, Highly similar to T46480 hypothetical protein DKFZp434L1850.1 [*H. sapiens*] |
| 1382 | 18353 | AI639233 | t, aa | decorin | decorin |
| 1384 | 15330 | AI639285 | General | | ESTs |
| 1385 | 20026 | AI639354 | g | | EST |
| 1386 | 25971 | AI639365 | r | | |
| 1388 | 19152 | AI639387 | u, General | | ESTs |
| 1390 | 18338 | AI639422 | y | | ESTs, Moderately similar to CAQC RAT CALSEQUESTRIN, CARDIAC MUSCLE ISOFORM PRECURSOR [*R. norvegicus*] |
| 1392 | 20082 | AI639488 | i, m | | EST, Highly similar to A42772 mdm2 protein - rat [*R. norvegicus*] |
| 1394 | 20056 | AI639504 | a, bb, General | | ESTs, Weakly similar to T13607 hypothetical protein EG: 87B1.3 - fruit fly [*D. melanogaster*] |
| 1395 | 4713 | AI639518 | q | | ESTs, Highly similar to RPB8__HUMAN DNA-DIRECTED RNA POLYMERASES I, II, AND III 17.1 KD POLYPEPTIDE [*H. sapiens*] |
| 1396 | 14332 | AJ001044 | bb | protein phosphatase 1, regulatory (inhibitor) subunit 5 | protein phosphatase 1, regulatory (inhibitor) subunit 5 |
| 1397 | 7602 | AJ001929 | k | reticulocalbin | reticulocalbin |
| 1398 | 9867 | AJ005424 | u | | *Rattus norvegicus* mRNA for BMK1/ERK5 protein, partial |
| 1400 | 16351 | AJ011811 | General | claudin 7 | claudin 7 |
| 1401 | 20116 | AJ011969 | l, General | growth differentiation factor 15 | growth differentiation factor 15 |
| 1402 | 17635 | AJ223355 | v, w | | *Rattus norvegicus* mRNA for mitochondrial dicarboxylate carrier |
| 1403 | 18686 | D00729 | q | dodecenoyl-Coenzyme A delta isomerase (3,2 trans-enoyl-Coenyme A | Rat mRNA for delta3, delta2-enoyl-CoA isomerase, dodecenoyl-Coenzyme A delta isomerase (3,2 trans-enoyl-Coenyme A isomerase) |
| 1404 | 5049 | D10655 | n, w | dihydrolipoamide acetyltransferase | dihydrolipoamide acetyltransferase |
| 1405 | 25257 | D13623 | j | | |
| 1405 | 15281 | D13623 | h | | ESTs |
| 1406 | 11434 | D14014 | cc | | ESTs |
| 1407 | 1613 | D14076 | x | | Rat mRNA for testicular dynamin, complete cds |
| 1408 | 1728 | D16479 | q | HHs: hydroxyacyl-Coenzyme A dehydrogenase/3-ketoacyl- | Rat mRNA for mitochondrial long-chain 3-ketoacyl-CoA thiolase beta- |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| | | | | Coenzyme A thiolase/enoyl-Coenzyme A hydralase (trifunctional protein), beta subunit | subunit of mitochondrial trifunctional protein, complete dds |
| 1409 | 3015 | D16554 | c, s, v, z | | Rat mRNA for polyubiquitin (four repetitive ubiquitins in tandem), complete cds |
| 1410 | 472 | D26111 | d, s, bb | | *R. norvegicus* mRNA for chloride channel (putative) 2313bp |
| 1412 | 16233 | D29960 | j, l | | *Rattus norvegicus* mRNA for alphaB crystallin-related protein, complete cds |
| 1413 | 9029 | D30804 | n | | ESTs, Highly similar to PRC6 RAT PROTEASOME SUBUNIT RC6-1 [*R. norvegicus*] |
| 1414 | 1485 | D38222 | y, z | | *Rattus norvegicus* tyrosine phosphatase-like protein IA-2a mRNA, partial cds |
| 1415 | 9135 | D45247 | s | proteasome beta type subunit 5 | ESTs, Highly similar to PRCE RAT PROTEASOME EPSILON CHAIN PRECURSOR [*R. norvegicus*] |
| 1416 | 16354 | D50564 | u | HHs: mercaptopyruvate sulfurtransferase | *Rattus norvegicus* mRNA for mercaptopyruvate sulfurtransferase, complete cds |
| 1417 | 1884 | D50695 | l, m, bb | | *Rattus norvegicus* mRNA for proteasomal ATPase (Tat-binding protein7), complete cds |
| 1418 | 21147 | D63772 | General | Solute carrier family 1 A1 (brain glutamate transporter) | Solute carrier family 1 A1 (brain glutamate transporter) |
| 1419 | 826 | D82928 | f | HHs: CDP-diacylglycerol-inositol 3-phosphatidyltransferase (phosphatidylinositol synthase) | Rat mRNA for phosphatidylinositol synthase, complete cds |
| 1420 | 25306 | D84485 | u | | |
| 1421 | 18867 | D88250 | t | | *Rattus norvegicus* mRNA for serine protease, complete cds |
| 1423 | 22543 | H31117 | r, v General | | |
| 1424 | 12360 | H31456 | w | | ESTs |
| 1425 | 20514 | H31489 | h, j | | ESTs |
| 1426 | 11358 | H31610 | h | | ESTs, Highly similar to mtprd [*M. musculus*] |
| 1427 | 4360 | H31813 | bb, General | | ESTs, Moderately similar to T14781 hypothetical protein DKFZp586B1621.1 [*H. sapiens*] |
| 1428 | 9343 | H32169 | l | | ESTs, Moderately similar to COF1 RAT COFILIN, NON-MUSCLE ISOFORM [*R. norvegicus*] |
| 1429 | 4386 | H33093 | h, w | | EST |
| 1430 | 4415 | H33636 | h | | ESTs |
| 1431 | 15374 | H34186 | l | | ESTs, Highly similar to IF39_HUMAN EUKARYOTIC TRANSLATION INITIATION FACTOR 3 SUBUNIT 9 [*H. sapiens*] |
| 1432 | 17159 | J00797 | u, General | alpha-tubulin | alpha-tubulin |
| 1433 | 16260 | J01878 | f | | Rat brain-specific identifier sequence RNA, clone p1b224 |
| 1434 | 17284 | J02827 | bb | Branched chain alpha-ketoacid dehydrogenase subunit E1 alpha | Branched chain alpha-ketoacid dehydrogenase subunit E1 alpha |
| 1435 | 15017 | J03752 | n | | Rat glutathione S-transferase mRNA, complete cds |
| 1436 | 44 | J03819 | p, s | Thyroid hormone receptor, beta (avian erythroblastic leukemia viral (v-erb-a) oncogene homolog 2) | Thyroid hormone receptor, beta (avian erythroblastic leukemia viral (v-erb-a) oncogene homolog 2) |
| 1437 | 21014 | J03914 | e, r, General | Glutathione-S-transferase, mu type 2 (Yb2) | Glutathione-S-transferase, mu type 2 (Yb2) |
| 1438 | 20429 | J05035 | f | Steroid-5-alpha-reductase, alpha polypeptide 1 (3-oxo-5 alpha-steroid delta 4-dehydrogenase alpha 1) | Steroid-5-alpha-reductase, alpha polypeptide 1 (3-oxo-5 alpha-steroid delta 4-dehydrogenase alpha 1) |
| 1439 | 1247 | J05181 | j, l, m, s, y, z | Glutamylcysteine gamma synthetase light chain | Glutamylcysteine gamma synthetase light chain |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1440 | 10464 | J05510 | n, u, General | Inositol 1,4,5-triphosphate receptor type 1 | Rat inositol-1,4,5-triphosphate receptor mRNA, complete cds |
| 1441 | 20149 | K03243 | q | | |
| 1442 | 17758 | K03249 | q | | Rat peroxisomal enoyl-CoA: hydrotase-3-hydroxyacyl-CoA bifunctional enzyme mRNA, complete cds |
| 1443 | 381 | L00124 | w | Elastase 2, pancreatic | Elastase 2, pancreatic |
| 1444 | 2048 | L00382 | k, x | | |
| 1445 | 10500 | L04619 | s | | |
| 1447 | 108 | L14002 | p | | *Rattus norvegicus* clone 15 polymeric immunoglobulin receptor mRNA, 3'UTR microsatellite repeats |
| 1448 | 25366 | L14003 | t | | |
| 1449 | 109 | L14004 | c, p | | *Rattus norvegicus* clone 15 polymeric immunoglobulin receptor mRNA, 3'UTR microsatellite repeats |
| 1450 | 20414 | L14323 | General | Phospholipase C-beta1 | Phospholipase C-beta1 |
| 1451 | 25369 | L14937 | y | | |
| 1452 | 16119 | L16532 | k | 2',3'-Cyclic nucleotide 3'-phosphodiesterase | 2',3'-Cyclic nucleotide 3'-phosphodiesterase |
| 1453 | 25377 | L25387 | h | | |
| 1453 | 12058 | L25387 | h | | ESTs, Highly similar to A53047 6-phosphofructokinase [*R. norvegicus*] |
| 1455 | 21146 | L35558 | General | Solute carrier family 1 A1 (brain glutamate transporter) | Solute carrier family 1 A1 (brain glutamate transporter) |
| 1456 | 106 | L37203 | w | | *Rattus norvegicus* guanylyl cyclase (GC-D) mRNA, complete cds |
| 1458 | 13682 | L38482 | f, j, k, m, z | | *Rattus norvegicus* serine protease gene, complete cds |
| 1459 | 6405 | L38615 | p | Glutathione synthetase gene | Glutathione synthetase gene |
| 1461 | 15189 | M11794 | n, v | | |
| 1462 | 17086 | M13011 | j | | Rat c-ras-H-1 gene, complete cds |
| 1464 | 21053 | M15481 | o | | Rat insulin-like growth factor-I mRNA, 3' end |
| 1465 | 25405 | M18330 | j, l | | |
| 1466 | 25415 | M19648 | a | | |
| 1468 | 14967 | M22366 | w | | |
| 1469 | 20481 | M22631 | bb | Propionyl Coenzyme A carboxylase, alpha polypeptide | |
| 1471 | 15048 | M24542 | q | HHs: ubiquinol-cytochrome c reductase, Rieske iron-sulfur polypeptide 1 | Rat Rieske iron-sulfur protein mRNA, complete cds |
| 1472 | 20921 | M29853 | m | | Rat cytochrome P-450 isozyme 5 (P450 IVB2) mRNA, complete cds |
| 1473 | 1224 | M31931 | u | Cytochrome P450, an olfactory-specific steroid hydroxylase | Cytochrome P450, an olfactory-specific steroid hydroxylase |
| 1474 | 15579 | M33648 | q | | Rat mitochondrial 3-hydroxy-3-methylglutaryl-CoA synthase mRNA, complete cds |
| 1474 | 15580 | M33648 | q | | Rat mitochondrial 3-hydroxy-3-methylglutaryl-CoA synthase mRNA, complete cds |
| 1475 | 17211 | M34331 | g, n, q, v | | ESTs, Weakly similar to KRAB-zinc finger protein KZF-1 [*R. norvegicus*] |
| 1476 | 20699 | M35601 | b, x, bb | | Rat alpha-fibrinogen mRNA, 3' end |
| 1476 | 20700 | M35601 | b, t, bb | | Rat alpha-fibrinogen mRNA, 3' end |
| 1477 | 9223 | M36151 | o | | Rat mRNA for MHC class II antigen RT1.B-1 beta-chain, *Rattus norvegicus* MHC class II antigen RT1.B beta chain mRNA, partial cds |
| 1479 | 1585 | M57728 | j, m, y | | Rat general mitochondrial matrix processing protease (MPP) mRNA, 3' end |
| 1480 | 24844 | M58040 | c | transferrin receptor | transferrin receptor |
| 1481 | 25057 | M58495 | h | | |
| 1482 | 457 | M60666 | d, General | Tropomyosin 1 (alpha) | Tropomyosin 1 (alpha) |
| 1483 | 1223 | M75281 | f | | Rat cystatin S (CysS) gene, complete cds |
| 1484 | 5733 | M81855 | i, k, aa | P-glycoprotein/multidrug resistance 1 | P-glycoprotein/multidrug resistance 1 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1485 | 4198 | M83143 | m | | Rat beta-galactoside-alpha 2,6-sialyltransferase mRNA |
| 1485 | 4199 | M83143 | m | | Rat beta-galactoside-alpha 2,6-sialyltransferase mRNA |
| 1486 | 24651 | M83678 | k, x, z | RAB13 | RAB13 |
| 1487 | 1430 | M84648 | General | Dopa decarboxylase (aromatic L-amino acid decarboxylase) | Dopa decarboxylase (aromatic L-amino acid decarboxylase) |
| 1488 | 25467 | M93297 | c | ornithine aminotransferase | ornithine aminotransferase |
| 1489 | 729 | M95762 | a, y | | *Rattus norvegicus* GABA transporter GAT-2 mRNA, complete cds |
| 1490 | 23698 | NM_012489 | q | *Rattus norvegicus* Acetyl-CoA acyltransferase, 3-oxo acyl-CoA thiolase A, peroxisomal (Acaa), mRNA. Length = 1619 | Acetyl-CoA acyltransferase, 3-oxo acyl-CoA thiolase A, peroxisomal |
| 1490 | 23699 | NM_012489 | q | *Rattus norvegicus* Acetyl-CoA acyltransferase, 3-oxo acyl-CoA thiolase A, peroxisomal (Acaa), mRNA. Length = 1619 | Acetyl-CoA acyltransferase, 3-oxo acyl-CoA thiolase A, peroxisomal |
| 1491 | 7062 | NM_012495 | q | *Rattus norvegicus* Aldolase A, fructose-bisphosphate (Aldoa), mRNA. Length = 1442 | Aldolase A, fructose-bisphosphate |
| 1492 | 15511 | NM_012498 | u | *Rattus norvegicus* Aldehyde reductase 1 (low Km aldose reductase) (5.8 kb Pstl fragment, probably the functional gene) (Akr1b1), mRNA. Length = 1339 | Aldehyde reductase 1 (low Km aldose reductase) (5.8 kb Pstl fragment, probably the functional gene) |
| 1494 | 7427 | NM_012515 | General | *Rattus norvegicus* Benzodiazepin receptor (peripheral) (Bzrp), mRNA. Length = 781 | Benzodiazepin receptor (peripheral) |
| 1495 | 24433 | NM_012527 | i | *Rattus norvegicus* Cholinergic receptor, muscarinic 3 (Chrm3), mRNA. Length = 3578 | Cholinergic receptor, muscarinic 3 |
| 1496 | 4467 | NM_012529 | d | *Rattus norvegicus* Creatine kinase, brain (Ckb), mRNA. Length = 1146 | Creatine kinase, brain |
| 1497 | 16520 | NM_012532 | General | *Rattus norvegicus* Ceruloplasmin (ferroxidase) (Cp), mRNA. Length = 3700 | Ceruloplasmin (ferroxidase) |
| 1498 | 225 | NM_012544 | x, z | *Rattus norvegicus* Angiotensin I-converting enzyme (Dipeptidyl carboxypeptidase 1) (Ace), mRNA. Length = 4142 | Dipeptidyl carboxypeptidase 1 (Angiotensin I-converting enzyme) |
| 1499 | 1431 | NM_012545 | General | *Rattus norvegicus* Dopa decarboxylase (aromatic L-amino acid decarboxylase) (Ddc), mRNA. Length = 1954 | Dopa decarboxylase (aromatic L-amino acid decarboxylase) |
| 1500 | 23868 | NM_012551 | l, m, v, General | *Rattus norvegicus* Early growth response 1 (Egr1), mRNA. Length = 3112 | Early growth response 1 |
| 1500 | 23872 | NM_012551 | l, v, cc, General | *Rattus norvegicus* Early growth response 1 (Egr1), mRNA. Length = 3112 | Early growth response 1 |
| 1500 | 23869 | NM_012551 | v, General | *Rattus norvegicus* Early growth response 1 (Egr1), mRNA. Length = 3112 | Early growth response 1 |
| 1501 | 19407 | NM_012554 | z | *Rattus norvegicus* Enolase 1, alpha (Eno1), mRNA. Length = 1725 | Enolase 1, alpha |
| 1501 | 19408 | NM_012554 | n, s, y, z | *Rattus norvegicus* Enolase 1, alpha (Eno1), mRNA. Length = 1725 | Enolase 1, alpha |
| 1502 | 21836 | NM_012555 | k | *Rattus norvegicus* Ets avian erythroblastosis virus E2 oncogene homolog 1 (tumor progression locus 1) (Ets1), mRNA. Length = 4991 | Ets avian erythroblastosis virus E2 oncogene homolog 1 (tumor progression locus 1) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1503 | 16895 | NM_012558 | g, s | *Rattus norvegicus* Fructose-1,6-biphosphatase (Fbp1), mRNA. Length = 1357 | Fructose-1,6-biphosphatase |
| 1504 | 25317 | NM_012559 | bb | *Rattus norvegicus* Fibrinogen, gamma polypeptide (Fgg), mRNA. Length = 1358 | |
| 1504 | 6477 | NM_012559 | b, bb | *Rattus norvegicus* Fibrinogen, gamma polypeptide (Fgg), mRNA. Length = 1358 | Fibrinogen, gamma polypeptide |
| 1504 | 6478 | NM_012559 | bb | *Rattus norvegicus* Fibrinogen, gamma polypeptide (Fgg), mRNA. Length = 1358 | Fibrinogen, gamma polypeptide |
| 1505 | 11731 | NM_012561 | k | *Rattus norvegicus* Follistatin (Fst), mRNA. Length = 1035 | Follistatin |
| 1507 | 4254 | NM_012564 | a | *Rattus norvegicus* Group-specific component (vitamin D-binding protein) (Gc), mRNA. Length = 1676 | Group-specific component (vitamin D-binding protein) |
| 1508 | 16026 | NM_012578 | r | *Rattus norvegicus* Histone H1-0 (H1f0), mRNA. Length = 1779 | Histone H1-0 |
| 1508 | 16024 | NM_012578 | r | *Rattus norvegicus* Histone H1-0 (H1f0), mRNA. Length = 1779 | Histone H1-0 |
| 1508 | 16025 | NM_012578 | r | *Rattus norvegicus* Histone H1-0 (H1f0), mRNA. Length = 1779 | Histone H1-0 |
| 1509 | 16080 | NM_012580 | g, m | *Rattus norvegicus* Heme oxygenase (Hmox1), mRNA. Length = 870 | Heme oxygenase |
| 1510 | 15098 | NM_012588 | bb | *Rattus norvegicus* insulin-like growth factor-binding protein (IGF-BP3) (Igfbp3), mRNA. Length = 2352 | Insulin-like growth factor-binding protein (IGF-BP3) |
| 1511 | 4450 | NM_012592 | bb | *Rattus norvegicus* Isovaleryl Coenzyme A dehydrogenase (Ivd), mRNA. Length = 2104 | Isovaleryl Coenzyme A dehydrogenase |
| 1511 | 4451 | NM_012592 | i, bb | *Rattus norvegicus* Isovaleryl Coenzyme A dehydrogenase (Ivd), mRNA. Length = 2104 | Isovaleryl Coenzyme A dehydrogenase |
| 1511 | 4452 | NM_012592 | bb | *Rattus norvegicus* Isovaleryl Coenzyme A dehydrogenase (Ivd), mRNA. Length = 2104 | Isovaleryl Coenzyme A dehydrogenase |
| 1512 | 17198 | NM_012593 | a, x | *Rattus norvegicus* Kallikrein 1, renal/pancreas/salivary (Klk1), mRNA. Length = 786 | Kallikrein 1, renal/pancreas/salivary |
| 1512 | 17197 | NM_012593 | x | *Rattus norvegicus* Kallikrein 1, renal/pancreas/salivary (Klk1), mRNA. Length = 786 | Kallikrein 1, renal/pancreas/salivary |
| 1513 | 18749 | NM_012600 | a, h | *Rattus norvegicus* Malic enzyme 1, soluble (Me1), mRNA. Length = 1761 | Malic enzyme 1, soluble |
| 1514 | 2628 | NM_012603 | General | *Rattus norvegicus* Avian myelocytomatosis viral (v-myc) oncogene homolog (Myc), mRNA. Length = 2168 | Avian myelocytomatosis viral (v-myc) oncogene homolog |
| 1514 | 2629 | NM_012603 | x, General | *Rattus norvegicus* Avian myelocytomatosis viral (v-myc) oncogene homolog (Myc), mRNA. Length = 2168 | Avian myelocytomatosis viral (v-myc) oncogene homolog |
| 1515 | 16849 | NM_012608 | n, o, q | *Rattus norvegicus* Membrane metallo-endopeptidase (neutral endopeptidase/enkephalinase) (Mme), mRNA. Length = 3243 | Membrane metallo-endopeptidase (neutral endopeptidase/enkephalinase) |
| 1517 | 15540 | NM_012620 | General | *Rattus norvegicus* serine (or cysteine) proteinase inhibitor. clade E (nexin, plasminogen activator inhibitor type 1), member 1 (Serpine1), mRNA. Length = 3053 | Plasminogen activator inhibitor |
| 1518 | 24568 | NM_012630 | General | *Rattus norvegicus* Prolactin receptor (Prlr), mRNA. Length = 1635 | Prolactin receptor |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1518 | 24566 | NM_012630 | General | *Rattus norvegicus* Prolactin receptor (Prlr), mRNA. Length = 1635 | Prolactin receptor |
| 1519 | 18553 | NM_012631 | k | *Rattus norvegicus* Prion protein, structural (Pmp), mRNA. Length = 765 | Prion protein, structural |
| 1520 | 1844 | NM_012637 | General | *Rattus norvegicus* protein tyrosine phosphatase, non-receptor type 1 (Ptpn1), mRNA. Length = 4127 | ESTs, Protein-tyrosine phosphatase |
| 1521 | 24668 | NM_012642 | f | *Rattus norvegicus* Renin (Ren), mRNA. Length = 1059 | Renin |
| 1522 | 18632 | NM_012645 | a | *Rattus norvegicus* RT1 class lb gene (RT1Aw2), mRNA. Length = 1540 | RT1 class lb gene |
| 1523 | 25435 | NM_012647 | g | *Rattus norvegicus* Sodium channel. voltage-gated, type II, alpha polypeptide (Scn2a1), mRNA. Length = 8553 | |
| 1524 | 9423 | NM_012649 | b, cc | *Rattus norvegicus* Ryudocan/syndecan 4 (Sdc4), mRNA. Length = 2462 | Ryudocan/syndecan 4 |
| 1525 | 24496 | NM_012654 | n | *Rattus norvegicus* Solute carrier family 9 (sodium/hydrogen exchanger 3), antiporter 3, Na+/H+ (amiloride insensitive) (Slc9a3), mRNA. Length = 5153 | Solute carrier family 9 (sodium/hydrogen exchanger 3), antiporter 3, Na+/H+ (amiloride insensitive) |
| 1526 | 7101 | NM_012679 | x, bb, General | *Rattus norvegicus* Clusterin (Clu), mRNA. Length = 1638 | Testostrone-repressed prostate message 2 |
| 1527 | 24707 | NM_012693 | i | *Rattus norvegicus* Cytochrome P450 IIA2 (Cyp2a2), mRNA. Length = 2259 | Cytochrome P450 IIA2 |
| 1528 | 1850 | NM_012696 | t | *Rattus norvegicus* T-kininogen, see also D11Elh1 and D11Mit8 (Kng), mRNA. Length = 1417 | T-kininogen |
| 1528 | 1854 | NM_012696 | t | *Rattus norvegicus* T-kininogen, see also D11Elh1 and D11Mit8 (Kng), mRNA. Length = 1417 | K-kininogen, differential splicing leads to HMW Kngk, T-kininogen |
| 1529 | 1603 | NM_012697 | General | *Rattus norvegicus* Organic cation transporter (Slc22a1), mRNA. Length = 1882 | Organic cation transporter |
| 1530 | 1372 | NM_012734 | u | *Rattus norvegicus* Hexokinase 1 (Hk1), mRNA. Length = 3653 | Hexokinase 1 |
| 1531 | 1478 | NM_012744 | bb, General | *Rattus norvegicus* Pyruvate carboxylase (Pc), mRNA. Length = 3945 | Pyruvate carboxylase |
| 1532 | 343 | NM_012747 | h, t | *Rattus norvegicus* Signal transducer and activator of transcription 3 (Stat3), mRNA. Length = 2924 | Signal transducer and activator of transcription 3 |
| 1533 | 8829 | NM_012749 | General | *Rattus norvegicus* Nucleolin (Ncl), mRNA. Length = 2142 | Nucleolin |
| 1534 | 20828 | NM_012752 | General | *Rattus norvegicus* CD24 antigen (Cd24), mRNA. Length = 1703 | CD24 antigen |
| 1534 | 20829 | NM_012752 | i, General | *Rattus norvegicus* CD24 antigen (Cd24), mRNA. Length = 1703 | CD24 antigen |
| 1534 | 20830 | NM_012752 | i, General | *Rattus norvegicus* CD24 antigen (Cd24), mRNA. Length = 1703 | CD24 antigen |
| 1535 | 15174 | NM_012756 | b | *Rattus norvegicus* Insulin-like growth factor 2 receptor (Igf2r), mRNA. Length = 8810 | Insulin-like growth factor 2 receptor |
| 1536 | 21685 | NM_012760 | j, m, n | *Rattus norvegicus* Lost on transformation 1 (Lot1), mRNA. Length = 5028 | Lost on transformation 1 |
| 1537 | 18068 | NM_012762 | t | *Rattus norvegicus* Interleukin 1beta converting enzyme (Casp1), mRNA. Length = 1209 | Interleukin 1beta converting enzyme |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1538 | 1246 | NM_012770 | a, General | *Rattus norvegicus* Guanylate cyclase, soluble, beta 2 (GTP pyrophosphate - lyase) (Gucy1b2), mRNA. Length = 2335 | Guanylate cyclase, soluble, beta 2 (GTP pyrophosphate - lyase) |
| 1539 | 1348 | NM_012776 | f | *Rattus norvegicus* adrenergic receptor kinase, beta 1 (Adrbk1), mRNA. Length = 2683 | G-protein-linked receptor kinase (beta adrenergic receptor kinase 1) |
| 1540 | 18135 | NM_012791 | w | *Rattus norvegicus* dual-specificity tyrosine-(Y)-phosphorylation regulated kinase 1a (Dyrk1a), mRNA. Length = 2840 | Dual Specificity Yak1-related kinase, ESTs |
| 1541 | 16947 | NM_012793 | p, bb | *Rattus norvegicus* Guanidinoacetate methyltransferase (Gamt), mRNA. Length = 924 | Guanidinoacetate methyltransferase |
| 1542 | 960 | NM_012796 | u | *Rattus norvegicus* glutathione S-transferase, theta 2 (Gstt2), mRNA. Length = 1258 | glutathione S-transferase, theta 2 |
| 1543 | 260 | NM_012798 | f, u | *Rattus norvegicus* MAL protein gene (Mal), mRNA. Length = 2268 | MAL protein gene |
| 1544 | 556 | NM_012803 | d | *Rattus norvegicus* Protein C (Proc), mRNA. Length = 1543 | Protein C |
| 1545 | 21729 | NM_012804 | q | *Rattus norvegicus* ATP-binding cassette, sub-family D (ALD), member 3 (Abcd3), mRNA. Length = 3324 | ATP-binding cassette, sub-family D (ALD), member 3 |
| 1546 | 15032 | NM_012816 | General | *Rattus norvegicus* alpha-methylacyl-CoA racemase (Amacr), mRNA. Length = 1504 | Methylacyl-CoA racemase alpha |
| 1547 | 24895 | NM_012817 | General | *Rattus norvegicus* Insulin-like growth factor-binding protein 5 (Igfbp5), mRNA. Length = 1630 | Insulin-like growth factor-binding protein 5 |
| 1548 | 18109 | NM_012823 | u, General | *Rattus norvegicus* Annexin A3 (Anx3), mRNA. Length = 1454 | ESTs, Weakly similar to LURT3 annexin III - rat [*R. norvegicus*] |
| 1549 | 373 | NM_012833 | h, l, q, General | *Rattus norvegicus* ATP-binding cassette, sub-family C (CFTR/MRP), member 2 (Abcc2), mRNA. Length = 4918 | Canalicular multispecific organic anion transporter |
| 1550 | 2855 | NM_012838 | e | *Rattus norvegicus* Cystatin beta (Cstb), mRNA. Length = 590 | Cystatin beta |
| 1551 | 11136 | NM_012839 | s | *Rattus norvegicus* Cytochrome C, expressed in somatic tissues (Cycs), mRNA. Length = 318 | Cytochrome C, expressed in somatic tissues |
| 1552 | 20885 | NM_012842 | a | *Rattus norvegicus* Epidermal growth factor (Egf), mRNA. Length = 4801 | Epidermal growth factor |
| 1552 | 20884 | NM_012842 | a, bb | *Rattus norvegicus* Epidermal growth factor (Egf), mRNA. Length = 4801 | Epidermal growth factor |
| 1553 | 18770 | NM_012857 | e | *Rattus norvegicus* Lysosomal associated membrane protein 1 (120 kDa) (Lamp1), mRNA. Length = 2006 | Lysosomal associated membrane protein 1 (120 kDa) |
| 1554 | 20674 | NM_012861 | i | *Rattus norvegicus* O6-methylguanine-DNA methyltranferase (Mgmt), mRNA. Length = 812 | ESTs, Weakly similar to S21348 probable pol polyprotein-related protein 4 - rat [*R. norvegicus*], O6-methylguanine-DNA methyltranferase |
| 1555 | 13151 | NM_012862 | a, r, General | *Rattus norvegicus* Matrix Gla protein (Mgp), mRNA. Length = 521 | Matrix Gla protein |
| 1556 | 24617 | NM_012870 | General | *Rattus norvegicus* tumor necrosis factor receptor superfamily, member 11b (osteoprotegerin) (Tnfrsf11b), mRNA. Length = 2432 | Osteoprotegerin |
| 1557 | 20945 | NM_012875 | a, v | Ribosomal protein L39 (Rpl39), mRNA. Length = 324 | Ribosomal protein L39 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1558 | 15872 | NM_012879 | o, r | *Rattus norvegicus* Solute carrier family 2 A2 (gkucose transporter, type 2) (Slc2a2), mRNA. Length = 2573 | Solute carrier family 2 A2 (gkucose transporter, type 2) |
| 1559 | 495 | NM_012880 | z | *Rattus norvegicus* Superoxide dismutase 3 (Sod3), mRNA. Length = 1729 | Superoxide dimutase 3 |
| 1559 | 494 | NM_012880 | c | *Rattus norvegicus* Superoxide dismutase 3 (Sod3), mRNA. Length = 1729 | Superoxide dimutase 3 |
| 1560 | 23651 | NM_012881 | d, u, General | *Rattus norvegicus* Sialoprotein (osteopontin) (Spp1), mRNA. Length = 1457 | Sialoprotein (osteopontin) |
| 1562 | 19477 | NM_012891 | q | *Rattus norvegicus* Acyl-Coa dehydrogenase, Very long chain (Acadvt), mRNA. Length = 2117 | EST, Moderately similar to ACDV RAT ACYL-COA DEHYDROGENASE, VERY-LONG-CHAIN SPECIFIC, MITOCHONDRIAL PRECURSOR [*R. norvegicus*] |
| 1563 | 18564 | NM_012899 | v, General | *Rattus norvegicus* aminolevulinate, delta-, dehydratase (Alad), mRNA. Length = 1116 | Delta - aminolevulinic acid dehydratase |
| 1564 | 7197 | NM_012904 | f, r, cc, General | *Rattus norvegicus* Annexin 1 (p35) (Lipocortin 1) (Anxa1), mRNA. Length = 1402 | Annexin 1 (p35) (Lipocortin 1) |
| 1564 | 7196 | NM_012904 | v, cc, General | *Rattus norvegicus* Annexin 1 (p35) (Lipocortin 1) (Anxa1), mRNA. Length = 1402 | Annexin 1 (p35) (Lipocortin 1) |
| 1565 | 20202 | NM_012909 | b, r | *Rattus norvegicus* Aquaporin 2 (Aqp2), mRNA. Length = 939 | Aquaporin 2 |
| 1566 | 16581 | NM_012911 | c, j | *Rattus norvegicus* Arrestin, beta 2 (Arrb2), mRNA. Length = 1758 | Arrestin, beta 2 |
| 1566 | 16582 | NM_012911 | c | *Rattus norvegicus* Arrestin, beta 2 (Arrb2), mRNA. Length = 1758 | Arrestin, beta 2 |
| 1567 | 24431 | NM_012912 | General | *Rattus norvegicus* Activating transcription factor 3 (Atf3), mRNA. Length = 1893 | Activating transcription factor 3 |
| 1568 | 18118 | NM_012913 | p | *Rattus norvegicus* ATPase, Na+K+ transporting, beta polypeptide 3 (Atp1b3), mRNA. Length = 1818 | ATPase, Na+K+ transporting, beta polypeptide 3 |
| 1569 | 6108 | NM_012915 | n | *Rattus norvegicus* ATPase inhibitor (rat mitochondrial IF1 protein) (Atpi), mRNA. Length = 833 | ATPase inhibitor (rat mitochondrial IF1 protein) |
| 1570 | 20757 | NM_012923 | c, i, aa | *Rattus norvegicus* Cyclin G1 (Ccng1), mRNA. Length = 3169 | Cyclin G1 |
| 1570 | 20755 | NM_012923 | i | *Rattus norvegicus* Cyclin G1 (Ccng1), mRNA. Length = 3169 | Cyclin G1 |
| 1571 | 2830 | NM_012925 | f | *Rattus norvegicus* CD59 antigen (Cd59), mRNA. Length = 1523 | CD59 antigen |
| 1571 | 2831 | NM_012925 | f | *Rattus norvegicus* CD59 antigen (Cd59), mRNA. Length = 1523 | CD59 antigen |
| 1572 | 1977 | NM_012930 | q | *Rattus norvegicus* Carnitine palmitoyltransferase 2 (Cpt2), mRNA. Length = 2296 | Carnitine palmitoyltransferase 2 |
| 1573 | 18694 | NM_012931 | j, l, m, z | *Rattus norvegicus* v-crk-associated tyrosine kinase substrate (Crkas), mRNA. Length = 3335 | v-crk-associated tyrosine kinase substrate |
| 1574 | 13723 | NM_012935 | n | *Rattus norvegicus* Crystallin, alpha polypeptide 2 (Cryab), mRNA. Length = 528 | Crystallin, alpha polypeptide 2, ESTs |
| 1575 | 9109 | NM_012939 | j, y, z | *Rattus norvegicus* Cathepsin H (Ctsh), mRNA. Length = 1362 | Cathepsin H |
| 1575 | 19398 | NM_012939 | aa | *Rattus norvegicus* Cathepsin H (Ctsh), mRNA. Length = 1362 | EST |
| 1576 | 223 | NM_012945 | b, cc | *Rattus norvegicus* Diphtheria toxin receptor(heparin binding epidermal growth | Diphtheria toxin receptor (heparin binding epidermal growth factor - like growth factor) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| | | | | factor - like growth factor) (Dtr), mRNA. Length = 1550 | |
| 1577 | 15058 | NM_012950 | cc | *Rattus norvegicus* Thrombin receptor (F2r), mRNA. Length = 3418 | Thrombin receptor |
| 1579 | 19111 | NM_012963 | g | *Rattus norvegicus* High mobility group 1 (Hmg1), mRNA. Length = 1225 | High mobility group 1 |
| 1580 | 19374 | NM_012964 | x | *Rattus norvegicus* Hyaluronan mediated motility receptor (RHAMM) (Hmmr), mRNA. Length = 2049 | Hyaluronan mediated motility receptor (RHAMM) |
| 1581 | 2554 | NM_012967 | t | *Rattus norvegicus* Intercellular adhesion molecule 1 (Icam1), mRNA. Length = 2602 | Intercellular adhesion molecule 1 |
| 1581 | 2555 | NM_012967 | t, cc, General | *Rattus norvegicus* Intercellular adhesion molecule 1 (Icam1), mRNA. Length = 2602 | Intercellular adhesion molecule 1 |
| 1582 | 24528 | NM_012973 | c | *Rattus norvegicus* Potassium (K+) channel protein, slowly activating (Isk) (Kcne1), mRNA. Length = 585 | Potassium (K+) channel protein, slowly activating (Isk) |
| 1583 | 956 | NM_012976 | c | *Rattus norvegicus* Lectin, galactose binding, soluble 5 (Galectin-5) (Lgals5), mRNA. Length = 872 | Lectin, galactose binding, soluble 9 (Galectin-9) |
| 1584 | 16417 | NM_012991 | g | *Rattus norvegicus* Nucleoprotein 50 kD (Nup50), mRNA. Length = 3027 | Nuclear pore associated protein |
| 1585 | 17393 | NM_012992 | d | *Rattus norvegicus* Nucleoplasmin-related protein (Nuclear protein B23 (Npm1), mRNA. Length = 1232 | Nucleoplasmin-related protein (Nuclear protein B23 |
| 1586 | 23544 | NM_013013 | s | *Rattus norvegicus* Prosaposin (sulfated glycoprotein, sphingolipid hydrolase activator) (Psap), mRNA. Length = 2175 | Prosaposin (sulfated glycoprotein, sphingolipid hydrolase activator) |
| 1587 | 1588 | NM_013026 | k | *Rattus norvegicus* Syndecan 1 (Sdc1), mRNA. Length = 2410 | Syndecan 1 |
| 1588 | 17894 | NM_013027 | m | *Rattus norvegicus* Selenoprotein W muscle 1 (Sepw1), mRNA. Length = 664 | Selenoprotein W muscle 1 |
| 1589 | 18300 | NM_013030 | s, v, General | *Rattus norvegicus* Solute carrier family 17 (sodium/hydrogen exchanger), member 2 (Slc34a1), mRNA. Length = 2440 | *Rattus norvegicus* mRNA for NaPi-2 alpha, complete cds |
| 1589 | 18076 | NM_013030 | g, s, z | *Rattus norvegicus* Solute carrier family 17 (sodium/hydrogen exchanger), member 2 (Slc34a1), mRNA. Length = 2440 | Solute carrier family 17 (sodium/hydrogen exchanger), member 2 |
| 1589 | 18078 | NM_013030 | s | *Rattus norvegicus* Solute carrier family 17 (sodium/hydrogen exchanger), member 2 (Slc34a1), mRNA. Length = 2440 | *Rattus norvegicus* mRNA for NaPi-2 alpha, complete cds, Solute carrier family 17 (sodium/hydrogen exchanger), member 2 |
| 1589 | 18077 | NM_013030 | e, s, z | *Rattus norvegicus* Solute carrier family 17 (sodium/hydrogen exchanger), member 2 (Slc34a1), mRNA. Length = 2440 | Solute carrier family 17 (sodium/hydrogen exchanger), member 2 |
| 1591 | 730 | NM_013040 | w | *Rattus norvegicus* ATP-binding cassette, sub-family C (CFTR/MRP), member 9 (Abcc9), mRNA. Length = 5000 | Sulfonylurea receptor 2 |
| 1592 | 17401 | NM_013043 | i, o, General | *Rattus norvegicus* Transforming growth factor beta stimulated clone 22 (Tgfb 1i4), mRNA. Length = 1666 | Transforming growth factor beta stimulated clone 22 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1593 | 16684 | NM_013052 | General | *Rattus norvegicus* Tyrosine 3 monooxygenase/tryptophan 5-mnooxygenase activation protein, eta polypeptide (Ywhah), mRNA. Length = 1689 | Tyrosine 3-monooxygenase/tryptophan 5-monooxygenase activation protein, eta polypeptide |
| 1594 | 14421 | NM_013053 | u | *Rattus norvegicus* Tyrosine 3 monooxygenase/tryptophan 5-monooxygenase activation protein, theta polypeptide (Ywhaq), mRNA. Length = 2099 | Tyrosine 3-monooxygenase/tryptophan 5-monooxygenase activation protein, theta polypeptide |
| 1595 | 15254 | NM_013058 | k | *Rattus norvegicus* Inhibitor of DNA binding 3, dominant negative helix-loop-helix protein (Id3), mRNA. Length = 568 | Inhibitor of DNA binding 3, dominant negative helix-loop-helix protein |
| 1596 | 14997 | NM_013059 | s, z | *Rattus norvegicus* Tissue-nonspecific ALP alkaline phosphatase (Alpl), mRNA. Length = 2415 | Tissue-nonspecific ALP alkaline phosphatase |
| 1596 | 14996 | NM_013059 | General | *Rattus norvegicus* Tissue-nonspecific ALP alkaline phosphates (Alpl), mRNA. Length = 2415 | Tissue-nonspecific ALP alkaline phosphatase |
| 1597 | 25676 | NM_013069 | aa | *Rattus norvegicus* CD74 antigen (invariant polpypeptide of major histocompatibility class II antigen-associated) (Cd74), mRNA. Length = 1150 | |
| 1597 | 16924 | NM_013069 | o | *Rattus norvegicus* CD74 antigen (invariant polpypeptide of major histocompatibility class II antigen-associated) (Cd74), mRNA. Length = 1150 | CD74 antigen (invariant polpypeptide of major histocompatibility class II antigen-associated) |
| 1598 | 24748 | NM_013070 | h, q | *Rattus norvegicus* Utrophin (Utrn), mRNA. Length = 10,705 | Utrophin |
| 1599 | 1529 | NM_013082 | d, General | *Rattus norvegicus* Ryudocan/syndecan 2 (Sdc2), mRNA. Length = 2153 | Ryudocan/syndecan 2 |
| 1600 | 1521 | NM_013091 | j, l, z, General | *Rattus norvegicus* Tumor necrosis factor receptor superfamily, member 1a (Tnfr1), mRNA. Length = 2130 | Tumor necrosis factor receptor |
| 1601 | 1685 | NM_013096 | c, aa | *Rattus norvegicus* Hemoglobin, alpha 1 (Hba1), mRNA. Length = 556 | Hemoglobin, alpha 1 |
| 1601 | 26150 | NM_013096 | c, i | *Rattus norvegicus* Hemoglobin, alpha 1 (Hba1), mRNA. Length = 556 | |
| 1601 | 1688 | NM_013096 | p | *Rattus norvegicus* Hemoglobin, alpha 1 (Hba1), mRNA. Length = 556 | Hemoglobin, alpha 1 |
| 1601 | 1689 | NM_013096 | c, p | *Rattus norvegicus* Hemoglobin, alpha 1 (Hba1), mRNA. Length = 556 | Hemoglobin, alpha 1 |
| 1601 | 1684 | NM_013096 | c, s, aa | *Rattus norvegicus* Hemoglobin, alpha 1 (Hba1), mRNA. Length = 556 | Hemoglobin, alpha 1 |
| 1602 | 20886 | NM_013097 | u, x, bb | *Rattus norvegicus* Deoxyribonuclease I (Dnase1), mRNA. Length = 1143 | Deoxyribonuclease I |
| 1602 | 20887 | NM_013097 | u, x, bb | *Rattus norvegicus* Deoxyribonuclease I (Dnase1), mRNA. Length = 1143 | Deoxyribonuclease I |
| 1603 | 1321 | NM_013098 | c | *Rattus norvegicus* Glucose-6-phosphatase (G6pc), mRNA. Length = 2237 | Glucose-6-phosphatase |
| 1604 | 15296 | NM_013102 | l, m | *Rattus norvegicus* FK506-binding protein 1 (12 kD) (Fkbp1a), mRNA. Length = 554 | FK506-binding protein 1 (12 kD) |
| 1606 | 23709 | NM_013113 | o, s, z, aa | *Rattus norvegicus* ATPase Na+/K+ transporting beta 1 polypeptide (Atp1b1), mRNA. Length = 2528 | ATPase Na+/K+ transporting beta 1 polypeptide |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1606 | 23711 | NM_013113 | p | *Rattus norvegicus* ATPase Na+/K+ transporting beta 1 polypeptide (Atp1b1), mRNA. Length = 2528 | ATPase Na+/K+ transporting beta 1 polypeptide |
| 1606 | 23710 | NM_013113 | s | *Rattus norvegicus* ATPase Na+/K+ transporting beta 1 polypeptide (Atp1b1), mRNA. Length = 2528 | ATPase Na+/K+ transporting beta 1 polypeptide |
| 1607 | 1976 | NM_013118 | u | *Rattus norvegicus* Guanylate cyclase activator 2 (guanylin) (Guca2a), mRNA. Length = 567 | Guanylate cyclase activator 2 (guanylin) |
| 1609 | 870 | NM_013130 | h | *Rattus norvegicus* MAD (mothers against decapentaplegic, *Drosophila*) homolog 1 (Madh1), mRNA. Length = 2002 | MAD (mothers against decapentaplegic, *Drosophila*) homolog 1 |
| 1610 | 16650 | NM_013132 | u, General | *Rattus norvegicus* Annexin V (Anx5), mRNA. Length = 1417 | Annexin V |
| 1611 | 650 | NM_013134 | h | *Rattus norvegicus* 3-hydroxy-3-methylglutaryl-Coenzyme A reductase (Hmgcr), mRNA. Length = 2664 | 3-hydroxy-3-methylglutaryl-Coenzyme A reductase |
| 1611 | 651 | NM_013134 | h, j, i | *Rattus norvegicus* 3-hydroxy-3-methylglutaryl-Coenzyme A reductase (Hmgcr), mRNA. Length = 2664 | 3-hydroxy-3-methylglutaryl-Coenzyme A reductase |
| 1612 | 1712 | NM_013138 | General | *Rattus norvegicus* Inositol 1,4,5-triphosphate receptor 3 (Itpr3), mRNA. Length = 8806 | Inositol 1,4,5-triphosphate receptor 3 |
| 1613 | 16982 | NM_013144 | o, v, General | *Rattus norvegicus* Insulin-like growth factor binding protein 1 (Igfbp1), mRNA. Length = 1500 | Insulin-like growth factor binding protein 1 |
| 1614 | 21683 | NM_013154 | t, cc, General | *Rattus norvegicus* CCAAT/enhancerbinding, protein (C/EBP) delta (Cebpd), mRNA. Length = 1200 | CCAAT/enhancerbinding, protein (C/EBP) delta |
| 1614 | 21682 | NM_013154 | cc | *Rattus norvegicus* CCAAT/enhancerbinding, protein (C/EBP) delta (Cebpd), mRNA. Length = 1200 | CCAAT/enhancerbinding, protein (C/EBP) delta |
| 1615 | 3431 | NM_013156 | b, g, n | *Rattus norvegicus* Cathepsin L (Ctsl), mRNA. Length = 1386 | Cathepsin L |
| 1615 | 25567 | NM_013156 | v, General | *Rattus norvegicus* Cathepsin L (Ctsl), mRNA. Length = 1386 | |
| 1615 | 3430 | NM_013156 | General | *Rattus norvegicus* Cathepsin L (Ctsl), mRNA. Length = 1386 | Cathepsin L |
| 1616 | 1309 | NM_013159 | w | *Rattus norvegicus* Insulin degrading enzyme (Ide), mRNA. Length = 4276 | Insulin degrading enzyme |
| 1616 | 1310 | NM_013159 | w | *Rattus norvegicus* Insulin degrading enzyme (Ide), mRNA. Length = 4276 | Insulin degrading enzyme |
| 1617 | 21723 | NM_013174 | w | *Rattus norvegicus* Transforming growth factor, beta 3 (Tgfb3), mRNA. Length = 2633 | Transforming growth factor, beta 3 |
| 1618 | 1314 | NM_013181 | m | *Rattus norvegicus* Protein kinase, cAMP dependent, regulatory, type 1 (Prkar1a), mRNA. Length = 1433 | Protein kinase, cAMP dependent, regulatory, type 1 |
| 1619 | 17357 | NM_013183 | p, bb, General | *Rattus norvegicus* Meprin 1 beta (Mep1b), mRNA. Length = 2290 | Meprin 1 beta |
| 1620 | 1300 | NM_013190 | y | *Rattus norvegicus* Phosphofructokinase, liver, B-type (Pfkl), mRNA. Length = 2740 | Phosphofructokinase, liver, B-type |
| 1621 | 16448 | NM_013197 | c | *Rattus norvegicus* Aminolevulinate synthase 2, delta (Alas2), mRNA. Length = 1899 | Aminolevulinate synthase 2, delta |
| 1622 | 20856 | NM_013200 | b | *Rattus norvegicus* Carnitine palmitoyltransferase 1 beta, muscle isoform (Cpt1b), mRNA. Length = 2826 | Carnitine palmitoyltransferase 1 beta, muscle isoform |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1623 | 397 | NM_013214 | f | *Rattus norvegicus* acyl-CoA hydrolase (RBACH), mRNA. Length = 1523 | *Rattus norvegicus* brain cytosolic acyl coenzyme A thioester hydrolase mRNA, complete cds, acyl-CoA hydrolase |
| 1624 | 20864 | NM_013215 | g, n, y | *Rattus norvegicus* aflatoxin B1 aldehyde reductase (AFAR), mRNA. Length = 1272 | aflatoxin B1 aldehyde reductase |
| 1625 | 20728 | NM_013217 | v | *Rattus norvegicus* afadin (AF 6), mRNA. Length = 5957 | afadin |
| 1626 | 1396 | NM_013222 | j | *Rattus norvegicus* augmenter of liver regeneration (ALR), mRNA. Length = 1226 | augmenter of liver regeneration |
| 1627 | 815 | NM_013224 | w | *Rattus norvegicus* ribosomal protein S26 (Rps26), mRNA. Length = 435 | ribosomal protein S26 |
| 1628 | 18305 | NM_013226 | v | *Rattus norvegicus* ribosomal protein L32 (Rpl32), mRNA. Length = 465 | |
| 1629 | 21078 | NM_016986 | d | *Rattus norvegicus* Acyl-Coenzyme A dehydrogenase, C-4 to C-12 straight-chain (Acadm). mRNA. Length = 1866 | Acyl-Coenzyme A dehydrogenase, C-4 to C-12 straight-chain |
| 1630 | 24649 | NM_016988 | v | *Rattus norvegicus* Acid phosphatase 2, lysozymal (Acp2), mRNA. Length = 2009 | Acid phosphatase 2, lysozymal |
| 1631 | 15239 | NM_016989 | q, w | *Rattus norvegicus* adenylate cyclase activating polypeptide 1 (Adcyap1), mRNA. Length = 2681 | *R. norvegicus* (Sprague Dawley) ribosomal protein L15 mRNA |
| 1632 | 45 | NM_016996 | General | *Rattus norvegicus* Calcium-sensing receptor (hypocalciuric hypercalcemia 1, severe neonatal hyperparathyroidism) (Casr), mRNA. Length = 4113 | Calcium-sensing receptor (hypocalciuric hypercalcemia 1, severe neonatal hyperparathyroidism) |
| 1633 | 20714 | NM_016999 | t | *Rattus norvegicus* Cytochrome P450, subfamily IVB, polypeptide 1 (Cyp4b1), mRNA. Length = 2462 | Cytochrome P450, subfamily IVB, polypeptide 1 |
| 1633 | 20713 | NM_016999 | t | *Rattus norvegicus* Cytochrome P450, subfamily IVB, polypeptide 1 (Cyp4b1), mRNA. Length = 2462 | Cytochrome P450, subfamily IVB, polypeptide 1 |
| 1633 | 20711 | NM_016999 | q, t | *Rattus norvegicus* Cytochrome P450, subfamily IVB, polypeptide 1 (Cyp4b1), mRNA. Length = 2462 | Cytochrome P450, subfamily IVB, polypeptide 1 |
| 1633 | 20715 | NM_016999 | q, t | *Rattus norvegicus* Cytochrome P450, subfamily IVB, polypeptide 1 (Cyp4b1), mRNA. Length = 2462 | Cytochrome P450, subfamily IVB, polypeptide 1 |
| 1634 | 1698 | NM_017000 | e, n, p, General | *Rattus norvegicus* Diaphorase (NADH/NADPH) (Dia4), mRNA. Length = 1396 | Diaphorase (NADH/NADPH) |
| 1635 | 1399 | NM_017006 | h, n General | *Rattus norvegicus* Glucose-6-phosphate dehydrogenase (G6pd), mRNA. Length = 2324 | Glucose-6-phosphate dehydrogenase |
| 1637 | 18989 | NM_017013 | n | *Rattus norvegicus* Glutathione-S-transferase, alpha type (Yc?) (Gsta2), mRNA. Length = 830 | Glutathione-S-transferase, alpha type (Yc?) |
| 1638 | 21013 | NM_017014 | e, f | *Rattus norvegicus* Glutathione-S-transferase, mu type 2 (Yb2) (Gstm2), mRNA. Length = 1055 | Glutathione-S-transferase, mu type 2 (Yb2) |
| 1638 | 21015 | NM_017014 | e, General | *Rattus norvegicus* Glutathione-S-transferase, mu type 2 (Yb2) (Gstm2), mRNA. Length = 1055 | Glutathione-S-transferase, mu type 2 (Yb2) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1639 | 11836 | NM_017023 | b | *Rattus norvegicus* Potassium inwardly-rectifying channel, subfamily J (Kcnj1), mRNA. Length = 2069 | Potassium inwardly-rectifying channel, subfamily J |
| 1639 | 5475 | NM_017023 | b | *Rattus norvegicus* Potassium inwardly-rectifying channel, subfamily J (Kcnj1), mRNA. Length = 2069 | ESTs, Potassium inwardly-rectifying channel, subfamily J |
| 1639 | 25546 | NM_017023 | b, bb | *Rattus norvegicus* Potassium inwardly-rectifying channel, subfamily J (Kcnj1), mRNA. Length = 2069 | |
| 1640 | 17807 | NM_017025 | i, General | *Rattus norvegicus* Lactate dehydrogenase A (Ldha), mRNA. Length = 1609 | Lactate dehydrogenase A |
| 1641 | 24597 | NM_017040 | u | *Rattus norvegicus* Protein phosphatase 2 (formerly 2A), catalytic subunit, beta isoform (Ppp2cb), mRNA. Length = 1843 | Protein phosphatase 2 (formerly 2A), catalytic subunit, beta isoform |
| 1642 | 24696 | NM_017048 | f, j, z | *Rattus norvegicus* Solute carrier family 4, member 2, anion exchange protein 2 (Slc4a2), mRNA. Length = 4057 | Solute carrier family 4, member 2, anion exchange protein 2 |
| 1643 | 24695 | NM_017049 | u | *Rattus norvegicus* Solute carrier family 4, member 3, anion exchange protein 3 (Slc4a3), mRNA. Length = 3877 | Solute carrier family 4, member 3, anion exchange protein 3 |
| 1644 | 20876 | NM_017050 | j, n, z | *Rattus norvegicus* Superoxide dismutase 1, soluble (Sod1), mRNA. Length = 650 | Superoxide dimutase 1, soluble |
| 1645 | 910 | NM_017059 | f, l, m | *Rattus norvegicus* Bcl2-associated X protein (Bax), mRNA. Length = 579 | Bcl2-associated X protein |
| 1645 | 912 | NM_017059 | l | *Rattus norvegicus* Bcl2-associated X protein (Bax), mRNA. Length = 579 | Bcl2-associated X protein |
| 1646 | 1946 | NM_017061 | h | *Rattus norvegicus* Lysyl oxidase (Lox), mRNA. Length = 4557 | Lysyl oxidase |
| 1646 | 1942 | NM_017061 | t, General | *Rattus norvegicus* Lysyl oxidase (Lox), mRNA. Length = 4557 | Lysyl oxidase |
| 1646 | 1943 | NM_017061 | t | *Rattus norvegicus* Lysyl oxidase (Lox), mRNA. Length = 4557 | Lysyl oxidase |
| 1647 | 6062 | NM_017066 | d | *Rattus norvegicus* Pleiotrophin (Heparine binding factor, Hbnf, in the mouse) (Ptn), mRNA. Length = 1246 | Pleiotrophin (Heparine binding factor, Hbnf, in the mouse) |
| 1648 | 6654 | NM_017068 | w | *Rattus norvegicus* Lysosomal-associated membrane protein 2 (Lamp2), mRNA. Length = 1548 | Lysosomal-associated membrane protein 2 |
| 1649 | 11153 | NM_017073 | s | *Rattus norvegicus* Glutamine synthetase (glutamate-ammonia ligase) (Glul), mRNA. Length = 2793 | Glutamine synthetase (glutamate-ammonia ligase) |
| 1650 | 923 | NM_017076 | General | *Rattus norvegicus* Tumor-associated glycoprotein pE4 (Tage4), mRNA. Length = 2171 | Tumor-associated glycoprotein pE4 |
| 1651 | 1523 | NM_017079 | s | *Rattus norvegicus* CD1D antigen (Cd1d), mRNA. Length = 1835 | CD1D antigen |
| 1652 | 23660 | NM_017080 | s | *Rattus norvegicus* Hydroxysteroid dehydrogenase, 11 beta type 1 (Hsd11b1), mRNA. Length = 1265 | Hydroxysteroid dehydrogenase, 11 beta type 1 |
| 1653 | 275 | NM_017081 | b, d, General | *Rattus norvegicus* Hydroxysteroid dehydrogenase, 11 beta type 2 (Hsd11b2), mRNA. Length = 1864 | Hydroxysteroid dehydrogenase, 11 beta type 2 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1654 | 16211 | NM_017082 | j, s, z | *Rattus norvegicus* Urmodulin (Tamm-Horsfall protein) (Umod), mRNA. Length = 2227 | Urmodulin (Tamm-Horsfall protein) |
| 1655 | 1552 | NM_017084 | j | *Rattus norvegicus* Glycine methyltransferase (Gnmt), mRNA. Length = 988 | Glycine methyltransferase |
| 1655 | 1550 | NM_017084 | y | *Rattus norvegicus* Glycine methyltransferase (Gnmt), mRNA. Length = 988 | Glycine methyltransferase |
| 1656 | 22552 | NM_017087 | a, k, x | *Rattus norvegicus* Small proteoglycan I (biglycan), bone (BSPG1) (bone/cartilage proteclycan 1 precursor) (Bgn), mRNA. Length = 2446 | Small proteoglycan I (biglycan), bone (BSPG1) (bone/cartilage proteclycan 1 precursor) |
| 1657 | 8888 | NM_017090 | m | *Rattus norvegicus* guanylate cyclase 1, soluble, alpha 3 (Gucy1a3), mRNA. Length = 4775 | Guanylate cyclase, soluble, alpha 1 (GTP pyrophosphate - lyase) |
| 1658 | 10887 | NM_017094 | a, General | *Rattus norvegicus* Growth hormone receptor (Ghr), mRNA. Length = 2950 | Growth hormone receptor |
| 1659 | 4393 | NM_017101 | a, y | *Rattus norvegicus* Peptidylprolyl isomerase A (cyclophilin A) (Ppia), mRNA. Length = 743 | Peptidylprolyl isomerase A (cyclophilin A) |
| 1660 | 24770 | NM_017111 | d | *Rattus norvegicus* solute carrier family (organic anion transporter) member 1 (Slc21a1), mRNA. Length = 2758 | solute carrier family (organic anion transporter) member 1 |
| 1661 | 20745 | NM_017113 | e | *Rattus norvegicus* granulin (Gm), mRNA. Length = 2113 | granulin |
| 1661 | 20746 | NM_017113 | a | *Rattus norvegicus* granulin (Gm), mRNA. Length = 2113 | granulin |
| 1662 | 1375 | NM_017122 | w | *Rattus norvegicus* hippocalcin (Hpca), mRNA. Length = 1561 | hippocalcin |
| 1663 | 12903 | NM_017124 | k | *Rattus norvegicus* CD37 antigen (Cd37), mRNA. Length = 1158 | CD37 antigen |
| 1664 | 24885 | NM_017138 | r | *Rattus norvegicus* laminin receptor 1 (Lamr1), mRNA. Length = 1018 | laminin receptor 1 |
| 1664 | 24886 | NM_017138 | d, q | *Rattus norvegicus* laminin receptor 1 (Lamr1), mRNA. Length = 1018 | laminin receptor 1 |
| 1665 | 15363 | NM_017147 | n, u | *Rattus norvegicus* cofilin 1, non-muscle (Cfl1), mRNA. Length = 1039 | cofilin 1, non-muscle |
| 1666 | 13392 | NM_017148 | u, General | *Rattus norvegicus* cysteine rich protein 1 (Csrp1), mRNA. Length = 1403 | cysteine rich protein |
| 1667 | 5351 | NM_017150 | q | *Rattus norvegicus* ribosomal protein L29 (Rpl29), mRNA. Length = 630 | ribosomal protein L29 |
| 1668 | 16954 | NM_017151 | a, n | *Rattus norvegicus* ribosomal protein S15 (Rps15), mRNA. Length = 487 | ribosomal protein S15 |
| 1669 | 21643 | NM_017152 | g | *Rattus norvegicus* ribosomal protein S17 (Rps17), mRNA. Length = 466 | ribosomal protein S17 |
| 1670 | 1694 | NM_017153 | a, q | *Rattus norvegicus* ribosomal protein S3a (Rps3a), mRNA. Length = 880 | ribosomal protein S3a |
| 1671 | 17104 | NM_017160 | bb, General | *Rattus norvegicus* ribosomal protein S6 (Rps6), mRNA. Length = 801 | ribosomal protein S6 |
| 1671 | 17106 | NM_017160 | u | *Rattus norvegicus* ribosomal protein S6 (Rps6), mRNA. Length = 801 | ribosomal protein S6 |
| 1671 | 17107 | NM_017160 | d, e | *Rattus norvegicus* ribosomal protein S6 (Rps6), mRNA. Length = 801 | ribosomal protein S6 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1672 | 17686 | NM_017165 | n, q | *Rattus norvegicus* glutathione peroxidase 4 (Gpx4), mRNA. Length = 872 | glutathione peroxidase 4 |
| 1673 | 20702 | NM_017166 | c | *Rattus norvegicus* Leukemia-associatedcytosolic phosphoprotein stathmin (Lap18), mRNA. Length = 1054 | Leukemia-associated cytosolic phosphoprotein stathmin |
| 1674 | 3513 | NM_017177 | r | *Rattus norvegicus* choline/ethanolamine kinase (Chetk), mRNA. Length = 1679 | choline/ethanolamine kinase |
| 1675 | 19031 | NM_017180 | v, General | *Rattus norvegicus* T-cell death associated gene (Tdag), mRNA. Length = 1353 | T-cell death associated gene |
| 1676 | 15437 | NM_017187 | x, z | *Rattus norvegicus* high mobility group box 2 (Hmgb2), mRNA. Length = 1072 | high mobility group protein 2 |
| 1676 | 15433 | NM_017187 | y | *Rattus norvegicus* high mobility group box 2 (Hmgb2), mRNA. Length = 1072 | high mobility group protein 2 |
| 1676 | 15434 | NM_017187 | x, z | *Rattus norvegicus* high mobility group box 2 (Hmgb2), mRNA. Length = 1072 | high mobility group protein 2 |
| 1677 | 24437 | NM_017190 | p | *Rattus norvegicus* Myelin-associated glycoprotein (Mag), mRNA. Length = 2474 | Myelin-associated glycoprotein |
| 1678 | 1542 | NM_017193 | j, l, m, z | *Rattus norvegicus* kynurenine aminotransferase II (Kat2), mRNA. Length = 1828 | kynurenine aminotransferase II |
| 1679 | 14695 | NM_017202 | q, s | *Rattus norvegicus* cytochrome c oxidase, subunit IVa (Cox4a), mRNA. Length = 696 | cytochrome c oxidase, subunit IV |
| 1679 | 14694 | NM_017202 | s, z | *Rattus norvegicus* cytochrome c oxidase, subunit IVa (Cox4a), mRNA. Length = 696 | cytochrome c oxidase, subunit IV |
| 1680 | 1428 | NM_017213 | m | *Rattus norvegicus* outer dense fiber of sperm tails 2 (Odf2), mRNA. Length = 2451 | outer dense fiber of sperm tails 2 |
| 1681 | 1622 | NM_017216 | g, j, s, z | *Rattus norvegicus* solute carrier family 3, member 1 (Slc3a1), mRNA. Length = 2305 | solute carrier family 3, member 1 |
| 1682 | 13642 | NM_017220 | v | *Rattus norvegicus* 6-pyruvoyl tetrahydropterin synthase (Pts), mRNA. Length = 1176 | ESTs |
| 1682 | 19976 | NM_017220 | w | *Rattus norvegicus* 6-pyruvoyl tetrahydropterin synthase (Pts), mRNA. Length = 1176 | ESTs |
| 1683 | 1510 | NM_017224 | General | *Rattus norvegicus* organic cationic transporter-like 1 (Orctl1), mRNA. Length = 2227 | organic cationic transporter-like 1 |
| 1684 | 1811 | NM_017228 | j, l, m, z | *Rattus norvegicus* dentatorubral pallidoluysian atrophy (Drpla), mRNA. Length = 4387 | dentatorubral pallidoluysian atrophy |
| 1686 | 17563 | NM_017245 | a, c, e, q | *Rattus norvegicus* eukaryotic translation elongation factor 2 (Eef2), mRNA. Length = 2626 | eukaryotic translation elongation factor 2 |
| 1687 | 17502 | NM_017248 | r | *Rattus norvegicus* heterogeneous nuclear ribonucleoprotein A1 (Hnrpa1), mRNA. Length = 1696 | heterogeneous nuclear ribonucleoprotein A1 |
| 1687 | 17501 | NM_017248 | x | *Rattus norvegicus* heterogeneous nuclear ribonucleoprotein A1 (Hnrpa1), mRNA. Length = 1696 | heterogeneous nuclear ribonucleoprotein A1 |
| 1688 | 19 | NM_017258 | v, General | *Rattus norvegicus* B-cell translocation gene 1, anti-proliferative (Btg1), mRNA. Length = 1464 | B-cell translocation gene 1, anti-proliferative |
| 1689 | 15300 | NM_017259 | i, v, cc, General | *Rattus norvegicus* B-cell translocation gene 2, anti-proliferative (Btg2), mRNA. Length = 2519 | B-cell translocation gene 2, anti-proliferative |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1689 | 15301 | NM_017259 | l, m, v, aa, cc, General | *Rattus norvegicus* B-cell translocation gene 2, anti-proliferative (Btg2), mRNA. Length = 2519 | B-cell translocation gene 2, anti-proliferative |
| 1689 | 15299 | NM_017259 | l, y, cc, General | *Rattus norvegicus* B-cell translocation gene 2, anti-proliferative (Btg2), mRNA. Length = 2519 | B-cell translocation gene 2, anti-proliferative |
| 1690 | 15224 | NM_017264 | d | *Rattus norvegicus* protease (prosome, macropain) 28 subunit, alpha (Psme1), mRNA. Length = 921 | protease (prosome, macropain) 28 subunit, alpha |
| 1691 | 3987 | NM_017280 | bb | *Rattus norvegicus* proteasome (prosome, macropain) subunit, alpha type 3 (Psma3), mRNA. Length = 897 | proteasome (prosome, macropain) subunit, alpha type 3 |
| 1692 | 1447 | NM_017281 | l | *Rattus norvegicus* proteasome (prosome, macropain) subunit, alpha type 4 (Psma4), mRNA. Length = 1121 | proteasome (prosome, macropain) subunit, alpha type 4 |
| 1693 | 15535 | NM_017283 | s, bb | *Rattus norvegicus* proteasome (prosome, macropain) subunit, alpha type 6 (Psma6), mRNA. Length = 932 | proteasome (prosome, macropain) subunit, alpha type 6 |
| 1694 | 12349 | NM_017290 | General | *Rattus norvegicus* ATPase, Ca++ transporting, cardiac muscle, slow twitch 2 (Atp2a2), mRNA. Length = 5648 | ATPase, Ca++ transporting, cardiac muscle, slow twitch 2 |
| 1695 | 15819 | NM_017298 | p | *Rattus norvegicus* calcium channel, voltage-dependent, L type, alpha 1D subunit (Cacna1d), mRNA. Length = 7986 | calcium channel, voltage-dependent, L type, alpha 1D subunit |
| 1696 | 23825 | NM_017299 | v | *Rattus norvegicus* solute carrier family 19 (sodium/hydrogen exchanger), member 1 (Slc19a1), mRNA. Length = 2402 | solute carrier family 19 (sodium/hydrogen exchanger), member 1 |
| 1696 | 23826 | NM_017299 | v | *Rattus norvegicus* solute carrier family 19 (sodium/hydrogen exchanger), member 1 (Slc19a1), mRNA. Length = 2402 | solute carrier family 19 (sodium/hydrogen exchanger), member 1 |
| 1697 | 14003 | NM_017305 | j, l, m, y, z | *Rattus norvegicus* glutamate-cysteine ligase, modifier subunit (Gclm), mRNA. Length = 1382 | Glutamate-cysteine ligase (gamma-glutamylcysteine synthetase), regulatory |
| 1698 | 26109 | NM_017306 | q, s | *Rattus norvegicus* dodecenoyl-Coenzyme A delta isomerase (3,2 trans-enoyl-Coenyme A isomerase) (DCI), mRNA. Length = 972 | EST |
| 1698 | 18687 | NM_017306 | q, t | *Rattus norvegicus* dodecenoyl-Coenzyme A delta isomerase (3,2 trans-enoyl-Coenyme A isomerase) (DCI), mRNA. Length = 972 | Rat mRNA for delta3, delta2-enoyl-CoA isomerase, dodecenoyl-Coenzyme A delta isomerase (3,2 trans-enoyl-Coenyme A isomerase) |
| 1699 | 18142 | NM_017314 | g, s, aa | *Rattus norvegicus* ubiquitin C (Ubc), mRNA. Length = 2545 | ubiquitin C |
| 1700 | 1894 | NM_017320 | t | *Rattus norvegicus* cathepsin S (Ctss), mRNA. Length = 1330 | cathepsin S |
| 1701 | 20809 | NM_017326 | u | *Rattus norvegicus* calmodulin (RCM3), mRNA. Length = 1112 | calmodulin |
| 1702 | 355 | NM_017334 | cc | *Rattus norvegicus* transcriptional repressor CREM (CREM), mRNA. Length = 436 | |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1703 | 16148 | NM_017340 | q, s | *Rattus norvegicus* acyl-coA oxidase (RATACOA1), mRNA. Length = 3741 | acyl-coA oxidase |
| 1703 | 16150 | NM_017340 | a | *Rattus norvegicus* acyl-coA oxidase (RATACOA1), mRNA. Length = 3741 | acyl-coA oxidase |
| 1704 | 20849 | NM_017343 | r, u, General | *Rattus norvegicus* myosin regulatory light chain (MRLCB), mRNA. Length = 1139 | Rat mRNA for myosin regulatory light chain (RLC) |
| 1704 | 20848 | NM_017343 | b, General | *Rattus norvegicus* myosin regulatory light chain (MRLCB), mRNA. Length = 1139 | Rat mRNA for myosin regulatory light chain (RLC) |
| 1705 | 606 | NM_017350 | b | *Rattus norvegicus* urinary plasminogen activator receptor 2 (uPAR-2), mRNA. Length = 1272 | urinary plasminogen activator receptor 2 |
| 1706 | 1581 | NM_017365 | General | *Rattus norvegicus* PDZ and LIM domain 1 (elfin) (Pdlim1), mRNA. Length = 1392 | LIM protein |
| 1707 | 455 | NM_019131 | x | *Rattus norvegicus* Tropomyosin 1 (alpha) (Tpm1), mRNA. Length = 1004 | Tropomyosin 1 (alpha) |
| 1707 | 456 | NM_019131 | y, z | *Rattus norvegicus* Tropomyosin 1 (alpha) (Tpm1), mRNA. Length = 1004 | Tropomyosin 1 (alpha) |
| 1708 | 4532 | NM_019134 | b | *Rattus norvegicus* Solute carrier family 12, member 1 (bumetanide-sensitive sodium-[potassium]- chloride cotransporter) (Slc12a1), mRNA. Length = 4595 | Solute carrier family 12, member 1 (bumetanide-sensitive sodium-[potassium]- chloride cotransporter) |
| 1709 | 1608 | NM_019166 | j, y, z | *Rattus norvegicus* synaptogyrin 1 (Syngr1), mRNA. Length = 879 | ESTs, Moderately similar to synaptogyrin [*R. norvegicus*], synaptogyrin 1 |
| 1710 | 7489 | NM_019169 | c, General | *Rattus norvegicus* synuclein, alpha (Snca), mRNA. Length = 1018 | synuclein, alpha |
| 1711 | 17066 | NM_019170 | p | *Rattus norvegicus* carbonyl reductase (Cbr), mRNA. Length = 1018 | carbonyl reductase |
| 1712 | 23924 | NM_019174 | bb | *Rattus norvegicus* carbonic anhydrase 4 (Ca4), mRNA. Length = 1205 | ESTs, Highly similar to CARBONIC ANHYDRASE IV PRECURSOR [*R. norvegicus*] |
| 1713 | 24019 | NM_019186 | t | *Rattus norvegicus* ADP-ribosylation-like 4 (Arl4), mRNA. Length = 1067 | ADP-ribosylation-like 4 |
| 1714 | 22063 | NM_019195 | d | *Rattus norvegicus* integrin-associated protein (Cd47), mRNA. Length = 1053 | integrin-associated protein |
| 1715 | 2079 | NM_019220 | j, k, z | *Rattus norvegicus* amino-terminal enhancer of split (Aes), mRNA. Length = 1356 | related to *(Drosophila* groucho gene |
| 1716 | 16284 | NM_019229 | l, m | *Rattus norvegicus* solute carrier family 12, member 4 (Slc12a4), mRNA. Length = 3726 | solute carrier family 12, member 4 |
| 1717 | 985 | NM_019233 | b, cc | *Rattus norvegicus* small inducible cytokine subfamily A20 (Scya20), mRNA. Length = 816 | small inducible cytokine subfamily A20 |
| 1718 | 15503 | NM_019237 | k, x | *Rattus norvegicus* procollagen C-proteinase enhancer protein (Pcolce), mRNA. Length = 1547 | procollagen C-proteinase enhancer protein |
| 1718 | 15504 | NM_019237 | k, x | *Rattus norvegicus* procollagen C-proteinase enhancer protein (Pcolce), mRNA. Length = 1547 | procollagen C-proteinase enhancer protein |
| 1719 | 17908 | NM_019242 | l, v, cc, General | *Rattus norvegicus* interferon-related developmental regulator 1 (Ifrd1), mRNA. Length = 1736 | interferon-related developmental regulator 1 |
| 1720 | 11218 | NM_019247 | c | *Rattus norvegicus* paired-like homeodomain transcription factor 3 (Pitx3), mRNA. Length = 1253 | paired-like homeodomain transcription factor 3 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1721 | 15259 | NM_019259 | d, f | *Rattus norvegicus* complement component 1, q subcomponent binding protein (C1qbp), mRNA. Length = 1124 | complement component 1, q subcomponent binding protein |
| 1722 | 21443 | NM_019262 | aa, General | *Rattus norvegicus* complement component 1, q subcomponent, beta polypeptide (C1qb), mRNA. Length = 1136 | complement component 1, q subcomponent, beta polypeptide |
| 1722 | 21444 | NM_019262 | t, General | *Rattus norvegicus* complement component 1, q subcomponent, beta polypeptide (C1qb), mRNA. Length = 1136 | complement component 1, q subcomponent, beta polypeptide |
| 1723 | 117 | NM_019266 | o, bb | *Rattus norvegicus* sodium channel, voltage-gated, type VIII, alpha polypeptide (Scn8a), mRNA. Length = 6586 | sodium channel, voltage-gated, type VIII, alpha polypeptide |
| 1724 | 1145 | NM_019280 | w | *Rattus norvegicus* gap junction membrane channel protein alpha 5 (Gja5), mRNA. Length = 3115 | gap junction membrane channel protein alpha 5 |
| 1725 | 22220 | NM_019286 | c | *Rattus norvegicus* Alcohol dehydrogenase 3 (Adh3), mRNA. Length = 1131 | Alcohol dehydrogenase (class I), alpha polypeptide |
| 1726 | 10015 | NM_019289 | l, m, t, x, General | *Rattus norvegicus* Actin-related protein complex 1b (Arpc1b), mRNA. Length = 1430 | Actin-related protein complex 1b |
| 1726 | 10016 | NM_019289 | bb, General | *Rattus norvegicus* Actin-related protein complex 1b (Arpc1b), mRNA. Length = 1430 | Actin-related protein complex 1b |
| 1727 | 21651 | NM_019296 | c, f, x | *Rattus norvegicus* Cell division cycle control protein 2 (Cdc2a), mRNA. Length = 1184 | Cell division cycle control protein 2 |
| 1728 | 20751 | NM_019301 | s | *Rattus norvegicus* Complement receptor related protein (Cr1), mRNA. Length = 1811 | Complement receptor related protein |
| 1729 | 645 | NM_019345 | bb | *Rattus norvegicus* solute carrier family 12, member 3 (Slc12a3), mRNA. Length = 4361 | solute carrier family 12, member 3 |
| 1730 | 1301 | NM_019349 | c | *Rattus norvegicus* Serine/threonine kinase 2 (Stk2), mRNA. Length = 4194 | Rat liver stearyl-CoA desaturase mRNA, complete cds |
| 1731 | 3776 | NM_019354 | a, u | *Rattus norvegicus* Uncoupling protein 2, mitochondrial (Ucp2), mRNA. Length = 1575 | Uncoupling protein 2, mitochondrial |
| 1732 | 4592 | NM_019356 | General | *Rattus norvegicus* eukaryotic translation initiation factor 2, subunit 1 (alpha) (Eif2s1), mRNA. Length = 1377 | eukaryotic translation initiation factor 2, subunit 1 (alpha) |
| 1733 | 1324 | NM_019371 | w | *Rattus norvegicus* factor-responsive smooth muscle protein (SM-20), mRNA. Length = 2825 | factor-responsive smooth muscle protein |
| 1734 | 19577 | NM_019377 | e | *Rattus norvegicus* 14-3-3 protein beta-subtype (Ywhab), mRNA. Length = 2756 | ESTs, Moderately similar to S12207 hypothetical protein [*M. musculus*] |
| 1735 | 24626 | NM_019381 | s | *Rattus norvegicus* Testis enhanced gene transcript (Tegt), mRNA. Length = 940 | Testis enhanced gene transcript |
| 1736 | 744 | NM_019622 | p | *Rattus norvegicus* espin (Espn), mRNA. Length = 2786 | espin |
| 1737 | 20716 | NM_019623 | c | *Rattus norvegicus* cytochrome P450 4F1 (Cyp4f1), mRNA. Length = 1977 | cytochrome P450 4F1 |
| 1738 | 20709 | NM_019904 | x | *Rattus norvegicus* beta-galactoside-binding lectin (Lgals1), mRNA. Length = 519 | beta-galactoside-binding lectin |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1739 | 574 | NM_019905 | u, General | *Rattus norvegicus* calpactin I heavy chain (Anxa2), mRNA. Length = 1395 | *Rattus norvegicus* clone BB.1.4.1 unknown Glu-Pro dipeptide repeat protein mRNA, complete cds, calpactin I heavy chain, hydroxyacid oxidase 3 (medium-chain) |
| 1740 | 9096 | NM_019908 | j | *Rattus norvegicus* hypothetical protein LOC56728 (LOC56728), mRNA. Length = 858 | hypothetical protein LOC56728 |
| 1741 | 20457 | NM_020073 | i, General | *Rattus norvegicus* parathyroid hormone receptor (LOC56813), mRNA. Length = 2065 | parathyroid hormone receptor |
| 1741 | 20458 | NM_020073 | General | *Rattus norvegicus* parathyroid hormone receptor (LOC56813), mRNA. Length = 2065 | parathyroid hormone receptor |
| 1741 | 20460 | NM_020073 | General | *Rattus norvegicus* parathyroid hormone receptor (LOC56813), mRNA. Length = 2065 | parathyroid hormone receptor |
| 1742 | 18713 | NM_020075 | r | *Rattus norvegicus* eukaryotic initiation factor 5 (eIF-5) (Eif5), mRNA. Length = 3504 | eukaryotic initiation factor 5 (eIF-5) |
| 1742 | 18715 | NM_020075 | r | *Rattus norvegicus* eukaryotic initiation factor 5 (eIF-5) (Eif5), mRNA. Length = 3504 | eukaryotic initiation factor 5 (eIF-5) |
| 1743 | 20493 | NM_020076 | p | *Rattus norvegicus* 3-hydroxyanthranilate 3,4-dioxygenase (Haao), mRNA. Length = 1254 | 3-hydroxyanthranilate 3,4-dioxygenase |
| 1744 | 16375 | NM_020976 | g | *Rattus norvegicus* kidney-specific membrane protein (NX-17), mRNA. Length = 1181 | kidney-specific membrane protein |
| 1745 | 20816 | NM_021261 | k, General | *Rattus norvegicus* thymosin, beta 10 (Tmsb10), mRNA. Length = 539 | thymosin beta-10 |
| 1746 | 15335 | NM_021264 | a | *Rattus norvegicus* ribosomal protein L35a (Rpl35), mRNA. Length = 348 | ribosomal protein L35a |
| 1747 | 18729 | NM_021578 | k, z | *Rattus norvegicus* transforming growth factor beta-1 gene (Tgfb1), mRNA. Length = 1585 | transforming growth factor beta-1 gene |
| 1748 | 19060 | NM_021587 | cc | *Rattus norvegicus* transforming growth factor-beta (TGF-beta) masking protein large subunit (Ltbp1), mRNA. Length = 6244 | transforming growth factor-beta (TGF-beta) masking protein large subunit |
| 1749 | 17324 | NM_021593 | o, General | *Rattus norvegicus* kynurenine 3-hydroxylase (Kmo), mRNA. Length = 1733 | kynurenine 3-hydroxylase |
| 1750 | 19679 | NM_021653 | General | *Rattus norvegicus* Thyroxine deiodinase, type I (Dio1), mRNA. Length = 2106 | Thyroxine deiodinase, type I |
| 1750 | 19678 | NM_021653 | a, v, General | *Rattus norvegicus* Thyroxine deiodinase, type I (Dio1), mRNA. Length = 2106 | Thyroxine deiodinase, type I |
| 1751 | 19665 | NM_021688 | u, General | *Rattus norvegicus* putative potassium channel TWIK (Kcnk1), mRNA. Length = 1582 | putative potassium channel TWIK |
| 1752 | 19667 | NM_021690 | m | *Rattus norvegicus* cAMP-regulated guanine nucleotide exchange factor I (cAMP-GEFI) (Epac), mRNA. Length = 3373 | cAMP-regulated guanine nucleotide exchange factor I (cAMP-GEFI) |
| 1754 | 22916 | NM_021740 | a | *Rattus norvegicus* prothymosin alpha (Ptma), mRNA. Length = 1182 | prothymosin alpha |
| 1755 | 19710 | NM_021744 | t | *Rattus norvegicus* CD14 antigen (Cd14), mRNA. Length = 1591 | CD14 antigen |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1755 | 19711 | NM_021744 | t | *Rattus norvegicus* CD14 antigen (Cd14), mRNA. Length = 1591 | CD14 antigen |
| 1756 | 19712 | NM_021745 | r | *Rattus norvegicus* farnesoid X activated receptor (LOC60351), mRNA. Length = 2070 | farnesoid X activated receptor |
| 1757 | 1962 | NM_021750 | j, k, y, z | *Rattus norvegicus* cysteine-sulfinate decarboxylase (Csad), mRNA. Length = 2413 | *Rattus norvegicus* cca2 mRNA, complete cds |
| 1757 | 19824 | NM_021750 | a, bb | *Rattus norvegicus* cysteine-sulfinate decarboxylase (Csad), mRNA. Length = 2413 | cysteine-sulfinate decarboxylase |
| 1758 | 25198 | NM_021754 | h | *Rattus norvegicus* Nopp140 associated protein (Nap65), mRNA. Length = 1980 | Nopp140 associated protein |
| 1758 | 20035 | NM_021754 | b, n, s, v, General | *Rattus norvegicus* Nopp140 associated protein (Nap65), mRNA. Length = 1980 | Nopp140 associated protein |
| 1759 | 20090 | NM_021757 | m | *Rattus norvegicus* pleiotropic regulator 1 (Plrg1), mRNA. Length = 1545 | pleiotropic regulator 1 |
| 1760 | 17885 | NM_021765 | aa | *Rattus norvegicus* beta prime COP (Copb), mRNA. Length = 3025 | beta prime COP |
| 1762 | 20161 | NM_021836 | cc, General | *Rattus norvegicus* jun B proto-oncogene (Junb), mRNA. Length = 1035 | jun B proto-oncogene |
| 1764 | 1203 | NM_021997 | k, z | *Rattus norvegicus* cytoplasmic linker 2 (Cyln2), mRNA. Length = 4847 | cytoplasmic linker 2 |
| 1765 | 23151 | NM_022005 | b | *Rattus norvegicus* FXYD domain-containing ion transport regulator 6 (Fxyd6), mRNA. Length = 1711 | FXYD domain-containing ion transport regulator 6 |
| 1767 | 17101 | NM_022179 | bb | *Rattus norvegicus* Hexokinase 3 (Hk3), mRNA. Length = 3692 | Hexokinase 3 |
| 1767 | 17100 | NM_022179 | bb | *Rattus norvegicus* Hexokinase 3 (Hk3), mRNA. Length = 3692 | Hexokinase 3 |
| 1768 | 20257 | NM_022180 | w, General | *Rattus norvegicus* Hepatic nuclear factor 4(alpha transcription factor 4) (Hnf4a), mRNA. Length = 1446 | Hepatic nuclear factor 4 (alpha transcription factor 4) |
| 1768 | 25699 | NM_022180 | i | *Rattus norvegicus* Hepatic nuclear factor 4(alpha transcription factor 4) (Hnf4a), mRNA. Length = 1446 | Hepatic nuclear factor 4 (alpha transcription factor 4) |
| 1768 | 10860 | NM_022180 | p | *Rattus norvegicus* Hepatic nuclear factor 4(alpha transcription factor 4) (Hnf4a), mRNA. Length = 1446 | ESTs |
| 1769 | 23780 | NM_022183 | k, x | *Rattus norvegicus* topoisomerase (DNA) II alpha (Top2a), mRNA. Length = 6052 | topoisomerase (DNA) II alpha |
| 1770 | 20312 | NM_022224 | o | *Rattus norvegicus* resiniferatoxin-binding, phosphotriesterase-related protein (Rpr1), mRNA. Length = 1050 | resiniferatoxin-binding, phosphotriesterase-related protein |
| 1771 | 6585 | NM_022266 | d, p, cc | *Rattus norvegicus* connective tissue growth factor (Ctgf), mRNA. Length = 2345 | connective tissue growth factor |
| 1772 | 17161 | NM_022298 | i, v, cc, General | *Rattus norvegicus* alpha-tubulin (Tuba1), mRNA. Length = 1617 | alpha-tubulin |
| 1772 | 17162 | NM_022298 | u | *Rattus norvegicus* alpha-tubulin (Tuba1), mRNA. Length = 1617 | alpha-tubulin |
| 1772 | 17160 | NM_022298 | u | *Rattus norvegicus* alpha-tubulin (Tuba1), mRNA. Length = 1617 | alpha-tubulin |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1772 | 17158 | NM_022298 | q | *Rattus norvegicus* alpha-tubulin (Tuba1), mRNA. Length = 1617 | alpha-tubulin |
| 1773 | 11454 | NM_022381 | i, aa, General | *Rattus norvegicus* Proliferating cell nuclear antigen (Pcna), mRNA. Length = 1160 | Proliferating cell nuclear antigen |
| 1773 | 11455 | NM_022381 | l, General | *Rattus norvegicus* Proliferating cell nuclear antigen (Pcna), mRNA. Length = 1160 | Proliferating cell nuclear antigen |
| 1774 | 13480 | NM_022390 | s | *Rattus norvegicus* quinoid dihydropteridine reductase (Qdpr), mRNA. Length = 1307 | quinoid dihydropteridine reductase |
| 1775 | 15184 | NM_022391 | z | *Rattus norvegicus* pituitary tumor-transforming 1 (Pttg1), mRNA. Length = 974 | pituitary tumor transforming gene |
| 1776 | 22413 | NM_022392 | h | *Rattus norvegicus* growth response protein (CL-6) (LOC64194), mRNA. Length = 2410 | growth response protein (CL-6) |
| 1776 | 22414 | NM_022392 | n | *Rattus norvegicus* growth response protein (CL-6) (LOC64194), mRNA. Length = 2410 | growth response protein (CL-6) |
| 1777 | 22499 | NM_022393 | t | *Rattus norvegicus* macrophage galactose N-acetyl-galactosamine specific lectin (Mgl), mRNA. Length = 1358 | Gal/GalNAc-specific lectin |
| 1779 | 24537 | NM_022399 | e | *Rattus norvegicus* calreticulin (Calr), mRNA. Length = 1882 | calreticulin |
| 1779 | 24539 | NM_022399 | y | *Rattus norvegicus* calreticulin (Calr), mRNA. Length = 1882 | calreticulin |
| 1780 | 1141 | NM_022401 | o, General | *Rattus norvegicus* plectin (Plec1), mRNA. Length = 15,231 | plectin |
| 1781 | 1069 | NM_022402 | g | *Rattus norvegicus* acidic ribosomal protein P0 (Arbp), mRNA. Length = 1046 | acidic ribosomal protein P0 |
| 1782 | 8211 | NM_022500 | j, n, s | *Rattus norvegicus* ferritin light chain 1 (Ftl1), mRNA. Length = 552 | ferritin light chain 1 |
| 1782 | 8212 | NM_022500 | n, s | *Rattus norvegicus* ferritin light chain 1 (Ftl1), mRNA. Length = 552 | ferritin light chain 1 |
| 1783 | 6815 | NM_022503 | s | *Rattus norvegicus* cytochrome c oxidase subunit VIIa 3 (Cox7a3), mRNA. Length = 460 | cytochrome c oxidase subunit VIIa 3 |
| 1784 | 4259 | NM_022504 | q, w | *Rattus norvegicus* ribosomal protein L36 (Rpl36), mRNA. Length = 364 | ribosomal protein L36 |
| 1785 | 1611 | NM_022509 | j | *Rattus norvegicus* survival motor neuron (Smn), mRNA. Length = 1243 | survival motor neuron |
| 1786 | 2236 | NM_022512 | y, z | *Rattus norvegicus* short chain acyl-coenzyme A dehydrogenase (Acads), mRNA. Length = 1749 | short chain acyl-coenzyme A dehydrogenase |
| 1787 | 3026 | NM_022514 | a | *Rattus norvegicus* ribosomal protein L27 (Rpl27), mRNA. Length = 463 | ribosomal protein L27 |
| 1787 | 3027 | NM_022514 | a, q, r, aa | *Rattus norvegicus* ribosomal protein L27 (Rpl27), mRNA. Length = 463 | ribosomal protein L27 |
| 1788 | 2696 | NM_022515 | a, d | *Rattus norvegicus* ribosomal protein L24 (Rpl24), mRNA. Length = 541 | ribosomal protein L24 |
| 1788 | 2697 | NM_022515 | n, w, aa | *Rattus norvegicus* ribosomal protein L24 (Rpl24), mRNA. Length = 541 | ribosomal protein L24 |
| 1789 | 3900 | NM_022516 | h | *Rattus norvegicus* polypyrimidine tract binding protein (Ptb), mRNA. Length = 2697 | polypyrimidine tract binding protein |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1790 | 4151 | NM_022518 | o | *Rattus norvegicus* ADP-ribosylation factor 1 (Arf1), mRNA. Length = 900 | ADP-ribosylation factor 1 |
| 1791 | 4242 | NM_022521 | c | *Rattus norvegicus* ornithine aminotransferase (Oat), mRNA. Length = 1938 | ornithine aminotransferase |
| 1792 | 4412 | NM_022523 | o | *Rattus norvegicus* platelet endothelial tetraspan antigen-3 (Cd151), mRNA. Length = 1668 | platelet endothelial tetraspan antigen-3 |
| 1793 | 6641 | NM_022533 | General | *Rattus norvegicus* plasmolipin (Z49858), mRNA. Length = 1475 | plasmolipin |
| 1794 | 8097 | NM_022536 | a | *Rattus norvegicus* cyclophilin B (Ppib), mRNA. Length = 840 | cyclophilin B |
| 1795 | 8597 | NM_022538 | c, r, u | *Rattus norvegicus* phosphatidate phosphohydrolase type 2 (Ppap2), mRNA. Length = 871 | phosphatidate phosphohydrolase type 2 |
| 1795 | 8598 | NM_022538 | u | *Rattus norvegicus* phosphatidate phosphohydrolase type 2 (Ppap2), mRNA. Length = 871 | phosphatidate phosphohydrolase type 2 |
| 1796 | 9296 | NM_022541 | o | *Rattus norvegicus* small zinc finger-like protein DDP2 (Ddp2), mRNA. Length = 494 | small zinc finger-like protein DDP2 |
| 1797 | 21063 | NM_022585 | h | *Rattus norvegicus* ornithine decarboxylase antizyme inhibitor (Oazi), mRNA. Length = 4269 | ornithine decarboxylase antizyme inhibitor |
| 1799 | 20781 | NM_022591 | z | *Rattus norvegicus* telomerase protein component 1 (Tlp1), mRNA. Length = 8216 | telomerase protein component 1 |
| 1800 | 20803 | NM_022592 | n | *Rattus norvegicus* transketolase (Tkt), mRNA. Length = 2098 | transketolase |
| 1801 | 20925 | NM_022594 | q | *Rattus norvegicus* enoyl hydratase-like protein, peroxisomal (Ech1), mRNA. Length = 1097 | enoyl hydratase-like protein, peroxisomal |
| 1802 | 20944 | NM_022597 | aa | *Rattus norvegicus* cathepsin B (Ctsb), mRNA. Length = 1904 | cathepsin B |
| 1803 | 21024 | NM_022599 | o, General | *Rattus norvegicus* synaptojanin 2 binding protein (Synj2bp), mRNA. Length = 5215 | outer membrane protein |
| 1804 | 2250 | NM_022643 | General | *Rattus norvegicus* Testis-specific histone 2b (Th2b), mRNA. Length = 470 | ESTs, Highly similar to 0506206A histone H2B [*R. norvegicus*] |
| 1805 | 17567 | NM_022672 | a, y | *Rattus norvegicus* ribosomal protein S14 (Rps14), mRNA. Length = 492 | ribosomal protein S14 |
| 1806 | 17661 | NM_022674 | bb | *Rattus norvegicus* H2A histone family, member Z (H2afz), mRNA. Length = 811 | H2A histone family, member Z |
| 1807 | 24563 | NM_022676 | b | *Rattus norvegicus* protein phosphatase 1, regulatory (inhibitor) subunit 1A (Ppp1r1a), mRNA. Length = 619 | protein phosphatase 1, regulatory (inhibitor) subunit 1A |
| 1807 | 24564 | NM_022676 | b, x | *Rattus norvegicus* protein phosphatase 1, regulatory (inhibitor) subunit 1A (Ppp1r1a), mRNA. Length = 619 | protein phosphatase 1, regulatory (inhibitor) subunit 1A |
| 1808 | 20506 | NM_022686 | l | *Rattus norvegicus* germinal histone H4 gene (Hist4), mRNA. Length = 377 | germinal histone H4 gene |
| 1809 | 20508 | NM_022688 | g | *Rattus norvegicus* preoptic regulatory factor-1 (Porf1), mRNA. Length = 689 | preoptic regulatory factor-1 |
| 1810 | 17586 | NM_022694 | k | *Rattus norvegicus* p105 coactivator (U83883), mRNA. Length = 3166 | p105 coactivator |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1811 | 17730 | NM_022697 | a | *Rattus norvegicus* ribosomal protein L28 (Rpl28), mRNA. Length = 466 | ribosomal protein L28 |
| 1811 | 17729 | NM_022697 | q | *Rattus norvegicus* ribosomal protein L28 (Rpl28), mRNA. Length = 466 | ribosomal protein L28 |
| 1812 | 154 | NM_022849 | t | *Rattus norvegicus* crp-ductin (Crpd), mRNA. Length = 4344 | crp-ductin |
| 1813 | 127 | NM_022855 | h | *Rattus norvegicus* casein kinase 1 gamma 3 isoform (Csnk1g3), mRNA. Length = 2547 | casein kinase 1 gamma 3 isoform |
| 1814 | 152 | NM_022858 | j | *Rattus norvegicus* HNF-3/forkhead homolog-1 (Hfh1), mRNA. Length = 1760 | HNF-3/forkhead homolog-1 |
| 1816 | 18101 | NM_022948 | z | *Rattus norvegicus* tricarboxylate carrier-like protein (Loc65042), mRNA. Length = 2699 | tricarboxylate carrier-like protein |
| 1816 | 18103 | NM_022948 | u | *Rattus norvegicus* tricarboxylate carrier-like protein (Loc65042), mRNA. Length = 2699 | tricarboxylate carrier-like protein |
| 1817 | 21491 | NM_022951 | w | *Rattus norvegicus* putative protein phosphatase 1 nuclear targeting subunit (Ppp1r10), mRNA. Length = 4131 | putative protein phosphatase 1 nuclear targeting subunit |
| 1818 | 15742 | NM_022958 | y | *Rattus norvegicus* phosphatidylinositol 3-kinase (Pik3c3), mRNA. Length = 2752 | phosphatidylinositol 3-kinase |
| 1819 | 9286 | NM_023027 | t, w | *Rattus norvegicus* tRNA selenocysteine associated protein (Secp43), mRNA. Length = 864 | tRNA selenocysteine associated protein |
| 1820 | 23215 | NM_023102 | z | *Rattus norvegicus* casein kinase 1 gamma 2 isoform (Csnk1g2), mRNA. Length = 1572 | casein kinase 1 gamma 2 isoform |
| 1821 | 21238 | NM_024125 | cc, General | *Rattus norvegicus* Liver activating protein (LAP, also NF-IL6, nuclear factor-IL6, previously designated TCF5) (Cebpb), mRNA. Length = 1408 | Liver activating protein (LAP, also NF-IL6, nuclear factor-IL6, previously designated TCF5) |
| 1821 | 21239 | NM_024125 | cc, General | *Rattus norvegicus* Liver activating protein (LAP, also NF-IL6, nuclear factor-IL6, previously designated TCF5) (Cebpb), mRNA. Length = 1408 | Liver activating protein (LAP, also NF-IL6, nuclear factor-IL6, previously designated TCF5) |
| 1822 | 353 | NM_024127 | i, n, General | *Rattus norvegicus* DNA-damage-inducible transcript 1 (Gadd45a), mRNA. Length = 711 | DNA-damage-inducible transcript 1 |
| 1822 | 354 | NM_024127 | i, n, General | *Rattus norvegicus* DNA-damage-inducible transcript 1 (Gadd45a), mRNA. Length = 711 | DNA-damage-inducible transcript 1 |
| 1822 | 352 | NM_024127 | h, General | *Rattus norvegicus* DNA-damage-inducible transcript 1 (Gadd45a), mRNA. Length = 711 | DNA-damage-inducible transcript 1 |
| 1823 | 17227 | NM_024131 | x | *Rattus norvegicus* D-dopachrome tautomerase (Ddt), mRNA. Length = 628 | D-dopachrome tautomerase |
| 1824 | 1598 | NM_024134 | l | *Rattus norvegicus* DNA-damage inducible transcript 3 (Ddit3), mRNA. Length = 806 | DNA-damage inducible transcript 3 |
| 1825 | 1162 | NM_024153 | d | *Rattus norvegicus* adrenodoxin reductase (Fdxr), mRNA. Length = 1786 | adrenodoxin reductase |
| 1826 | 7863 | NM_024156 | c | *Rattus norvegicus* annexin VI (Anxa6), mRNA. Length = 2739 | *Rattus norvegicus* mRNA for H(+)-transporting ATPase, complete cds |
| 1827 | 22079 | NM_024157 | x | *Rattus norvegicus* complement factor I (Cfi), mRNA. Length = 2021 | complement factor I |
| 1828 | 16476 | NM_024162 | General | *Rattus norvegicus* heart fatty acid binding protein (Fabp3), mRNA. Length = 666 | heart fatty acid binding protein |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1829 | 17765 | NM_024351 | b, s, v | *Rattus norvegicus* heat shock 70 kD protein 8 (Hspa8), mRNA. Length = 2073 | Heat shock cognate protein 70 |
| 1830 | 8879 | NM_024360 | h | *Rattus norvegicus* hairy and enhancer of split 1, (*Drosophila*) (Hes1), mRNA. Length = 1453 | hairy and enhancer of split 1, (*Drosophila*) |
| 1831 | 20772 | NM_024363 | x | *Rattus norvegicus* heterogeneous nuclear ribonucleoproteins methyltransferase-like 2 (*S. cerevisiae*) (Hrmt1I2), mRNA. Length = 1201 | heterogeneous nuclear ribonucleoproteins methyltransferase-like 2 (*S. cerevisiae*) |
| 1832 | 2812 | NM_024386 | c | *Rattus norvegicus* 3-hydroxy-3-methylglutaryl CoA lyase (Hmgcl), mRNA. Length = 1390 | 3-hydroxy-3-methylglutaryl CoA lyase |
| 1833 | 335 | NM_024387 | j, y | *Rattus norvegicus* heme oxygenase-2 non-reducing isoform (Hmox2), mRNA. Length = 1815 | heme oxygenase-2 non-reducing isoform |
| 1834 | 21 | NM_024388 | cc | *Rattus norvegicus* immediate early gene transcription factor NGFI-B (Nr4a1), mRNA. Length = 2488 | immediate early gene transcription factor NGFI-B |
| 1834 | 22 | NM_024388 | cc | *Rattus norvegicus* immediate early gene transcription factor NGFI-B (Nr4a1), mRNA. Length = 2488 | immediate early gene transcription factor NGFI-B |
| 1836 | 9929 | NM_024392 | f | *Rattus norvegicus* peroxisomal multifunctional enzyme type II (Hsd17b4), mRNA. Length = 2535 | peroxisomal multifunctional enzyme type II |
| 1837 | 3582 | NM_024396 | aa | *Rattus norvegicus* ATP-binding cassette, sub-family A (ABC1), member 2 (Abca2), mRNA. Length = 8040 | ATP-binding cassette, sub-family A (ABC1), member 2 |
| 1838 | 19993 | NM_024398 | e, p, s, aa | *Rattus norvegicus* mitochondrial aconitase (nuclear aco2 gene) (Aco2), mRNA. Length = 2744 | mitochondrial aconitase (nuclear aco2 gene) |
| 1839 | 10789 | NM_024399 | o | *Rattus norvegicus* aspartoacylase (Aspa), mRNA. Length = 1552 | aspartoacylase |
| 1840 | 22626 | NM_024400 | cc, General | *Rattus norvegicus* a disintegrin and metalloproteinase with thrombospondin motifs 1 (ADAMTS-1) (Adamts1), mRNA. Length = 4878 | a disintegrin and metalloproteinase with thrombospondin motifs 1 (ADAMTS-1) |
| 1841 | 13633 | NM_024403 | g, General | *Rattus norvegicus* activating transcription factor ATF-4 (Atf4), mRNA. Length = 1173 | activating transcription factor ATF-4 |
| 1841 | 13634 | NM_024403 | g, General | *Rattus norvegicus* activating transcription factor ATF-4 (Atf4), mRNA. Length = 1173 | activating transcription factor ATF-4 |
| 1842 | 23387 | NM_024404 | b, General | *Rattus norvegicus* RNA binding protein p45AUF1 (Hnrpd), mRNA. Length = 1240 | RNA binding protein p45AUF1 |
| 1843 | 21038 | NM_024484 | h | *Rattus norvegicus* aminolevulinic acid synthase 1 (Alas 1), mRNA. Length = 2052 | aminolevulinic acid synthase 1 |
| 1844 | 1853 | NM_030826 | s | *Rattus norvegicus* Glutathione peroxidase 1 (Gpx1), mRNA. Length = 1539 | ESTs, Glutathione peroxidase 1 |
| 1845 | 15111 | NM_030827 | e, General | *Rattus norvegicus* glycoprotein 330 (Lrp2), mRNA. Length = 15.438 | glycoprotein 330 |
| 1845 | 15112 | NM_030827 | y, z | *Rattus norvegicus* glycoprotein 330 (Lrp2), mRNA. Length = 15.438 | glycoprotein 330 |
| 1845 | 15110 | NM_030827 | General | *Rattus norvegicus* glycoprotein 330 (Lrp2), mRNA. Length = 15.438 | glycoprotein 330 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1846 | 808 | NM_030837 | k, m | *Rattus norvegicus* kidney specific organic anion transporter (Slc21a4), mRNA. Length = 2772 | kidney specific organic anion transporter |
| 1847 | 4057 | NM_030844 | k | *Rattus norvegicus* islet cell autoantigen 1.69 kDa (Ica1), mRNA. Length = 2094 | islet cell autoantigen 1, 69 kDa |
| 1848 | 1221 | NM_030845 | t | *Rattus norvegicus* gro (Gro1), mRNA. Length = 929 | gro |
| 1849 | 21509 | NM_030847 | x | *Rattus norvegicus* epithelial membrane protein 3 (Emp3), mRNA. Length = 737 | epithelial membrane protein 3 |
| 1850 | 1928 | NM_030872 | v | *Rattus norvegicus* pyruvate dehydrogenase kinase 2 subunit p45 (PDK2) (Pdk2), mRNA. Length = 2207 | pyruvate dehydrogenase kinase 2 subunit p45 (PDK2) |
| 1851 | 17342 | NM_030873 | u | *Rattus norvegicus* profilin II (Pfn2), mRNA. Length = 1966 | profilin II |
| 1852 | 24648 | NM_030985 | u | *Rattus norvegicus* Angiotensin II receptor, type 1 (AT1A) (Agtr1a), mRNA. Length = 1450 | Angiotensin II receptor, type 1 (AT1A) |
| 1852 | 25453 | NM_030985 | General | *Rattus norvegicus* Angiotensin II receptor, type 1 (AT1A) (Agtr1a), mRNA. Length = 1450 | |
| 1853 | 21802 | NM_030987 | h | *Rattus norvegicus* Guanine nucleotide-binding protein beta 1 (Gnb1), mRNA. Length = 2837 | Guanine nucleotide-binding protein beta 1 |
| 1854 | 23109 | NM_031000 | f, s, z | *Rattus norvegicus* aldo-keto reductase family 1, member A1 (aldehyde reductase) (Akr1a1), mRNA. Length = 1124 | aldo-keto reductase family 1, member A1 (aldehyde reductase) |
| 1855 | 134 | NM_031003 | a, u | *Rattus norvegicus* 4-aminobutyrate aminotransferase (Abat), mRNA. Length = 1726 | 4-aminobutyrate aminotransferase |
| 1856 | 25461 | NM_031009 | o | *Rattus norvegicus* angiotensin II type-1 receptor (Agtr1), mRNA. Length = 2156 | angiotensin II type-1 receptor |
| 1857 | 1845 | NM_031010 | t | *Rattus norvegicus* arachidonate 12-lipoxygenase (Alox12), mRNA. Length = 2048 | arachidonate 12-lipoxygenase |
| 1857 | 25517 | NM_031010 | c, t | *Rattus norvegicus* arachidonate 12-lipoxygenase (Alox12), mRNA. Length = 2048 | arachidonate 12-lipoxygenase |
| 1858 | 16562 | NM_031020 | f | *Rattus norvegicus* p38 mitogen activated protein kinase (Mapk14), mRNA. Length = 3132 | p38 mitogen activated protein kinase |
| 1859 | 1480 | NM_031021 | f | *Rattus norvegicus* casein kinase II beta subunit (Csnk2b), mRNA. Length = 1984 | casein kinase II beta subunit |
| 1860 | 1719 | NM_031024 | n | *Rattus norvegicus* drebrin A (Dbn1), mRNA. Length = 2697 | drebrin A |
| 1861 | 1350 | NM_031030 | h | *Rattus norvegicus* cyclin G-associated kinase (Gak), mRNA. Length = 4454 | cyclin G-associated kinase |
| 1862 | 16775 | NM_031031 | General | *Rattus norvegicus* L-arginine: glycine amidinotransferase (Gatm), mRNA. Length = 2260 | L-arginine: glycine amidinotransferase |
| 1863 | 691 | NM_031034 | w | *Rattus norvegicus* guanine nucleotide binding protein (G protein) alpha 12 (Gna 12), mRNA. Length = 1423 | guanine nucleotide binding protein (G protein) alpha 12 |
| 1864 | 15886 | NM_031035 | z | *Rattus norvegicus* GTP-binding protein (G-alpha-i2) (Gnai2), mRNA. Length = 1748 | GTP-binding protein (G-alpha-i2) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1866 | 3608 | NM_031044 | k, General | *Rattus norvegicus* histamine N-methyltransferase (Hnmt), mRNA. Length = 1225 | histamine N-methyltransferase |
| 1866 | 3610 | NM_031044 | d, General | *Rattus norvegicus* histamine N-methyltransferase (Hnmt), mRNA. Length = 1225 | histamine N-methyltransferase |
| 1867 | 15137 | NM_031051 | s | *Rattus norvegicus* macrophage migration inhibitory factor (Mif), mRNA. Length = 551 | macrophage migration inhibitory factor |
| 1868 | 514 | NM_031056 | General | *Rattus norvegicus* matrix metalloproteinase 14, membrane-inserted (Mmp14), mRNA. Length = 2448 | matrix metalloproteinase 14, membrane-inserted |
| 1869 | 17269 | NM_031057 | General | *Rattus norvegicus* methylmalonate semialdehyde dehydrogenase gene (Mmsdh), mRNA. Length = 2059 | methylmalonate semialdehyde dehydrogenase gene |
| 1870 | 11849 | NM_031065 | a | *Rattus norvegicus* ribosomal protein L10a (Rpl10a), mRNA. Length = 710 | ribosomal protein L10a |
| 1871 | 1855 | NM_031074 | h | *Rattus norvegicus* nucleoporin 98 (Nup98), mRNA. Length = 3237 | nucleoporin 98 |
| 1872 | 4683 | NM_031083 | d | *Rattus norvegicus* phosphatidylinositol 4-kinase (Pik4cb), mRNA. Length = 3205 | phosphatidylinositol 4-kinase |
| 1873 | 15202 | NM_031093 | a | *Rattus norvegicus* - ral simian leukemia viral oncogene homolog A (ras related) (Rala), mRNA. Length = 952 | #NAME? |
| 1873 | 15201 | NM_031093 | a, n | *Rattus norvegicus* - ral simian leukemia viral oncogene homolog A (ras related) (Rala), mRNA. Length = 952 | #NAME? |
| 1874 | 12639 | NM_031099 | aa | *Rattus norvegicus* ribosomal protein L5 (Rpl5), mRNA. Length = 1069 | ribosomal protein L5 |
| 1875 | 20812 | NM_031100 | a | *Rattus norvegicus* ribosomal protein L10 (Rpl10), mRNA. Length = 769 | ribosomal protein L10 |
| 1876 | 16938 | NM_031103 | w | *Rattus norvegicus* ribosomal protein L19 (Rpl19), mRNA. Length = 703 | ribosomal protein L19 |
| 1877 | 19268 | NM_031104 | q | *Rattus norvegicus* ribosomal protein L22 (Rpl22), mRNA. Length = 465 | ribosomal protein L22 |
| 1878 | 16929 | NM_031108 | q | *Rattus norvegicus* mRNA for ribosomal protein S9 (Rps9), mRNA. Length = 688 | mRNA for ribosomal protein S9 |
| 1879 | 10878 | NM_031110 | q, bb | *Rattus norvegicus* ribosomal protein S11 (Rps11), mRNA. Length = 534 | ribosomal protein S11 |
| 1880 | 19162 | NM_031111 | aa | *Rattus norvegicus* ribosomal protein S21 (Rps21), mRNA. Length = 359 | ribosomal protein S21 |
| 1880 | 19161 | NM_031111 | a, bb | *Rattus norvegicus* ribosomal protein S21 (Rps21), mRNA. Length = 359 | ribosomal protein S21 |
| 1881 | 24615 | NM_031112 | a, y | *Rattus norvegicus* ribosomal protein S24 (Rps24), mRNA. Length = 466 | ribosomal protein S24 |
| 1882 | 20839 | NM_031113 | a, q | *Rattus norvegicus* ribosomal protein S27a (Rps27a), mRNA. Length = 552 | ribosomal protein S27a |
| 1883 | 19040 | NM_031114 | l, m, General | *Rattus norvegicus* S-100 related protein, clone 42C (S100A10), mRNA. Length = 573 | S-100 related protein, clone 42C |
| 1884 | 16349 | NM_031115 | u | *Rattus norvegicus* secretin receptor (Sctr), mRNA. Length = 1796 | secretin receptor |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1885 | 14970 | NM_031127 | General | *Rattus norvegicus* sulfite oxidase (Suox), mRNA. Length = 1777 | sulfite oxidase |
| 1886 | 1814 | NM_031134 | n, q | *Rattus norvegicus* thyroid hormone receptor alpha (Thra1), mRNA. Length = 2460 | thyroid hormone receptor |
| 1887 | 13359 | NM_031135 | General | *Rattus norvegicus* TGFB inducible early growth response (Tieg), mRNA. Length = 3115 | TGFB inducible early growth response |
| 1888 | 15052 | NM_031136 | a | *Rattus norvegicus* thymosin beta-4 (Tmsb4x), mRNA. Length = 686 | thymosin beta-4 |
| 1888 | 19359 | NM_031136 | a | *Rattus norvegicus* thymosin beta-4 (Tmsb4x), mRNA. Length = 686 | EST |
| 1889 | 15185 | NM_031140 | General | *Rattus norvegicus* vimentin (Vim), mRNA. Length = 1796 | vimentin |
| 1890 | 21625 | NM_031144 | a, e | *Rattus norvegicus* cytoplasmic beta-actin (Actx), mRNA. Length = 1128 | cytoplasmic beta-actin |
| 1891 | 238 | NM_031152 | bb | *Rattus norvegicus* RAB11a, member RAS oncogene family (Rab11a), mRNA. Length = 895 | RAB11a, member RAS oncogene family |
| 1891 | 240 | NM_031152 | bb | *Rattus norvegicus* RAB11a, member RAS oncogene family (Rab11a), mRNA. Length = 895 | RAB11a, member RAS oncogene family |
| 1892 | 15277 | NM_031237 | g | *Rattus norvegicus* ubiquitin-conjugating enzyme E2D 3 (homologous to yeast UBC4/5) (Ube2d3), mRNA. Length = 1531 | ubiquitin-conjugating enzyme E2D 3 (homologous to yeast UBC4/5) |
| 1893 | 18083 | NM_031315 | q | *Rattus norvegicus* acyl-CoA thioesterase 1, cytosolic (Cte1), mRNA. Length = 1591 | *R. norvegicus* mRNA for mitochondrial very-long-chain acyl-CoA thioesterase |
| 1893 | 1858 | NM_031315 | q | *Rattus norvegicus* acyl-CoA thioesterase 1, cytosolic (Cte1), mRNA. Length = 1591 | *R. norvegicus* mRNA for mitochondrial very-long-chain acyl-CoA thioesterase, acyl-CoA thioesterase 1, cytosolic |
| 1894 | 15663 | NM_031318 | General | *Rattus norvegicus* t-complex testis expressed 1 (Tctex1), mRNA. Length = 698 | t-complex testis expressed 1 |
| 1895 | 1422 | NM_031324 | bb, General | *Rattus norvegicus* prolyl endopeptidase (Prep), mRNA. Length = 2743 | prolyl endopeptidase |
| 1896 | 18597 | NM_031325 | g, bb | *Rattus norvegicus* UDP-glucose dehydrogeanse (Ugdh), mRNA. Length = 2318 | UDP-glucose dehydrogeanse |
| 1897 | 11259 | NM_031327 | i, cc, General | *Rattus norvegicus* cysteine rich protein 61 (Cyr61), mRNA. Length = 1871 | cysteine rich protein 61 |
| 1898 | 4235 | NM_031330 | General | *Rattus norvegicus* heterogeneous nuclear ribonucleoprotein A/B (Hnrpab), mRNA. Length = 3061 | heterogeneous nuclear ribonucleoprotein A/B |
| 1899 | 18375 | NM_031331 | l, m | *Rattus norvegicus* proteasome (prosome, macropain) 26S subunit, non-ATPase, 4 (Psmd4), mRNA. Length = 1334 | proteasome (prosome, macropain) 26S subunit, non-ATPase, 4 |
| 1900 | 3519 | NM_031334 | cc | *Rattus norvegicus* E-cadherin (Cdh1), mRNA. Length = 4396 | E-cadherin |
| 1901 | 20698 | NM_031357 | b | *Rattus norvegicus* ceroid-lipofuscinosis, neuronal 2 (Cln2), mRNA. Length = 2485 | |
| 1903 | 634 | NM_031509 | n | *Rattus norvegicus* Glutathione-S-transferase, alpha type (Ya) (Gsta1), mRNA. Length = 1178 | Glutathione-S-transferase, alpha type (Ya) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1903 | 25525 | NM_031509 | n | *Rattus norvegicus* Glutathione-S-transferase, alpha type (Ya) (Gsta1), mRNA. Length = 1178 | Glutathione-S-transferase, alpha type (Ya) |
| 1903 | 25069 | NM_031509 | b, n, w | *Rattus norvegicus* Glutathione-S-transferase, alpha type (Ya) (Gsta1), mRNA. Length = 1178 | |
| 1903 | 635 | NM_031509 | z | *Rattus norvegicus* Glutathione-S-transferase, alpha type (Ya) (Gsta1), mRNA. Length = 1178 | Glutathione-S-transferase, alpha type (Ya) |
| 1904 | 848 | NM_031517 | t | *Rattus norvegicus* Met proto-oncogene (Met), mRNA. Length = 4189 | Met proto-oncogene |
| 1905 | 1872 | NM_031523 | a | *Rattus norvegicus* Nerve growth factor, gamma polypeptide (Ngfg), mRNA. Length = 873 | Nerve growth factor, gamma polypeptide |
| 1905 | 16245 | NM_031523 | a, d, u | *Rattus norvegicus* Nerve growth factor, gamma polypeptide (Ngfg), mRNA. Length = 873 | *Rattus norvegicus* (clone RSKG50) kallikrein mRNA, 3' end |
| 1905 | 16244 | NM_031523 | a | *Rattus norvegicus* Nerve growth factor, gamma polypeptide (Ngfg), mRNA. Length = 873 | *Rattus norvegicus* (clone RSKG50) kallikrein mRNA, 3' end |
| 1906 | 9370 | NM_031527 | w | *Rattus norvegicus* Protein phosphatase type 1 alpha, catalytic subunit (Ppp1ca), mRNA. Length = 1392 | Protein phosphatase type 1 alpha, catalytic subunit |
| 1907 | 20448 | NM_031530 | General | *Rattus norvegicus* Small inducible gene JE (Scya2), mRNA. Length = 780 | Small inducible gene JE |
| 1907 | 20449 | NM_031530 | General | *Rattus norvegicus* Small inducible gene JE (Scya2), mRNA. Length = 780 | Small inducible gene JE |
| 1908 | 14633 | NM_031533 | u | *Rattus norvegicus* Androsterone UDP-glucuronosyltransferase (Ugt2b2), mRNA. Length = 1593 | Androsterone UDP-glucuronosyltransferase |
| 1909 | 16048 | NM_031541 | f | *Rattus norvegicus* CD36 antigen (collagen type I receptor, thrombospondin receptor)-like 1 (scavanger receptor class B type 1) (Cd36l1), mRNA. Length = 2497 | CD36 antigen (collagen type I receptor, thrombospondin receptor)-like 1 (scavanger receptor class B type 1) |
| 1910 | 4011 | NM_031543 | c, q | *Rattus norvegicus* Cytochrome P450, subfamily 2e1 (ethanol-inducible) (Cyp2e1), mRNA. Length = 1624 | Cytochrome P450, subfamily 2e1 (ethanol-inducible) |
| 1910 | 4010 | NM_031543 | c, q | *Rattus norvegicus* Cytochrome P450, subfamily 2e1 (ethanol-inducible) (Cyp2e1), mRNA. Length = 1624 | Cytochrome P450, subfamily 2e1 (ethanol-inducible) |
| 1910 | 4012 | NM_031543 | q | *Rattus norvegicus* Cytochrome P450, subfamily 2e1 (ethanol-inducible) (Cyp2e1), mRNA. Length = 1624 | Cytochrome P450, subfamily 2e1 (ethanol-inducible) |
| 1911 | 28 | NM_031546 | General | *Rattus norvegicus* Regucalcin (Rgn), mRNA. Length = 1605 | Regucalcin |
| 1912 | 24640 | NM_031548 | h, cc | *Rattus norvegicus* Sodium channel, nonvoltage-gated 1, alpha (epithelial) (Scnn1a), mRNA. Length = 3081 | Sodium channel, nonvoltage-gated 1, alpha (epithelial) |
| 1913 | 17149 | NM_031549 | x | *Rattus norvegicus* Transgelin (Smooth muscle 22 protein) (Tagln), mRNA. Length = 1186 | Transgelin (Smooth muscle 22 protein) |
| 1913 | 17151 | NM_031549 | x | *Rattus norvegicus* Transgelin (Smooth muscle 22 protein) (Tagln), mRNA. Length = 1186 | Transgelin (Smooth muscle 22 protein |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1914 | 13105 | NM_031552 | w | *Rattus norvegicus* Adducin 3, gamma (Add3), mRNA. Length = 2246 | Adducin 3, gamma |
| 1915 | 15411 | NM_031559 | d, r | *Rattus norvegicus* Carnitine palmitoyltransferase 1 alpha, liver isoform (Cpt1a), mRNA. Length = 4377 | Carnitine palmitoyltransferase 1 alpha, liver isoform |
| 1916 | 16164 | NM_031563 | a, y | *Rattus norvegicus* Y box protein 1 (Ybx1), mRNA. Length = 1489 | Y box protein 1 |
| 1917 | 9621 | NM_031570 | bb | *Rattus norvegicus* ribosomal protein S7 (Rps7), mRNA. Length = 650 | ribosomal protein S7 |
| 1917 | 9620 | NM_031570 | w, bb | *Rattus norvegicus* ribosomal protein S7 (Rps7), mRNA. Length = 650 | ribosomal protein S7 |
| 1918 | 546 | NM_031573 | f | *Rattus norvegicus* Phosphorylase kinase, gamma 1 (Phkg1), mRNA. Length = 1388 | phosphorylase kinase gamma |
| 1919 | 1921 | NM_031576 | f | *Rattus norvegicus* P450 (cytochrome) oxidoreductase (Por), mRNA. Length = 2441 | P450 (cytochrome) oxidoreductase |
| 1919 | 1920 | NM_031576 | r | *Rattus norvegicus* P450 (cytochrome) oxidoreductase (Por), mRNA. Length = 2441 | P450 (cytochrome) oxidoreductase |
| 1920 | 24219 | NM_031579 | i, General | *Rattus norvegicus* protein tyrosine phosphatase 4a1 (Ptp4a1), mRNA. Length = 2638 | protein tyrosine phosphatase 4a1 |
| 1921 | 770 | NM_031584 | k, x | *Rattus norvegicus* solute carrier family 22, member 2 (Slc22a2), mRNA. Length = 2152 | solute carrier family 22, member 2 |
| 1922 | 18008 | NM_031588 | cc | *Rattus norvegicus* neuregulin 1 (Nrg1), mRNA. Length = 3272 | potassium channel, subfamily K, member 3 |
| 1922 | 18005 | NM_031588 | h | *Rattus norvegicus* neuregulin 1 (Nrg1), mRNA. Length = 3272 | potassium channel, subfamily K, member 3 |
| 1922 | 18011 | NM_031588 | cc, General | *Rattus norvegicus* neuregulin 1 (Nrg1), mRNA. Length = 3272 | potassium channel, subfamily K, member 3 |
| 1923 | 1584 | NM_031595 | k | *Rattus norvegicus* proteasome (prosome, macropain) 26S subunit, ATPase 3 (Psmc3), mRNA. Length = 1627 | proteasome (prosome, macropain) 26S subunit, ATPase 3 |
| 1924 | 24235 | NM_031614 | v | *Rattus norvegicus* thioredoxin reductase 1 (Txnrd1), mRNA. Length = 3360 | thioredoxin reductase 1 |
| 1924 | 24234 | NM_031614 | General | *Rattus norvegicus* thioredoxin reductase 1 (Txnrd1), mRNA. Length = 3360 | thioredoxin reductase 1 |
| 1925 | 1639 | NM_031627 | j, l, v | *Rattus norvegicus* nuclear receptor subfamily 1, group H, member 3 (Nr1h3), mRNA. Length = 1723 | nuclear receptor subfamily 1, group H, member 3 |
| 1926 | 1727 | NM_031642 | m, General | *Rattus norvegicus* core promoter element binding protein (Copeb), mRNA. Length = 1356 | core promoter element binding protein |
| 1927 | 20766 | NM_031643 | y | *Rattus norvegicus* mitogen activated protein kinase kinase 2 (Map2k2), mRNA. Length = 1182 | mitogen activated protein kinase kinase 2 |
| 1929 | 1993 | NM_031655 | k, l, m, General | *Rattus norvegicus* latexin (Lxn), mRNA. Length = 1087 | latexin |
| 1930 | 2057 | NM_031660 | e | *Rattus norvegicus* cyclic AMP phosphoprotein, 19 kD (Arpp19-pending), mRNA. Length = 339 | cyclic AMP phosphoprotein, 19 kD |
| 1931 | 15039 | NM_031672 | k, General | *Rattus norvegicus* solute carrier family 15 (H+/peptide transporter), member 2 (Slc15a2), mRNA. Length = 3923 | solute carrier family 15 (H+/peptide transporter), member 2 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1932 | 15175 | NM_031682 | bb | *Rattus norvegicus* hydroxyacyl-Coenzyme A dehydrogenase, type II (Hadh2), mRNA. Length = 917 | hydroxyacyl-Coenzyme A dehydrogenase, type II |
| 1933 | 1004 | NM_031685 | v | *Rattus norvegicus* golgi SNAP receptor complex member 2 (Gosr2), mRNA. Length = 683 | golgi SNAP receptor complex member 2 |
| 1934 | 19727 | NM_031687 | a, q, s | *Rattus norvegicus* ubiquitin A 52 residue ribosomal protein fusion product 1 (Uba52), mRNA. Length = 467 | ubiquitin A-52 residue ribosomal protein fusion product 1 |
| 1935 | 20404 | NM_031700 | j, r, y | *Rattus norvegicus* claudin 3 (Cldn3), mRNA. Length = 1192 | claudin 3 |
| 1935 | 20405 | NM_031700 | o, r | *Rattus norvegicus* claudin 3 (Cldn3), mRNA. Length = 1192 | claudin 3 |
| 1936 | 811 | NM_031705 | General | *Rattus norvegicus* dihydropyrimidinase (Dpys), mRNA. Length = 2091 | dihydropyrimidinase |
| 1936 | 812 | NM_031705 | o, v, bb, General | *Rattus norvegicus* dihydropyrimidinase (Dpys), mRNA. Length = 2091 | dihydropyrimidinase |
| 1937 | 16204 | NM_031706 | q, bb | *Rattus norvegicus* ribosomal protein S8 (Rps8), mRNA. Length = 696 | ribosomal protein S8 |
| 1937 | 16205 | NM_031706 | a, y | *Rattus norvegicus* ribosomal protein S8 (Rps8), mRNA. Length = 696 | ribosomal protein S8 |
| 1938 | 24081 | NM_031708 | m | *Rattus norvegicus* glycoprotein 110 (Gp110-pending), mRNA. Length = 1444 | glycoprotein 110 |
| 1939 | 16918 | NM_031709 | a, q | *Rattus norvegicus* ribosomal protein S12 (Rps12), mRNA. Length = 499 | ribosomal protein S12 |
| 1940 | 1081 | NM_031712 | General | *Rattus norvegicus* PDZ domain containing 1 (Pdzk1), mRNA. Length = 2005 | PDZ domain containing 1 |
| 1941 | 1340 | NM_031715 | b, n, u, cc, General | *Rattus norvegicus* phosphofructokinase, muscle (Pfkm), mRNA. Length = 2757 | phosphofructokinase, muscle |
| 1942 | 23884 | NM_031731 | j, s | *Rattus norvegicus* alcohol dehydrogenase family 3, subfamily A2 (Aldh3a2), mRNA. Length = 2977 | alcohol dehydrogenase family 3, subfamily A2 |
| 1943 | 10241 | NM_031740 | d | *Rattus norvegicus* UDP-Gal: betaGlcNAc beta 1,4-galactosyltransferase, polypeptide 6 (B4galt6), mRNA. Length = 5729 | UDP-Gal: betaGlcNAc beta 1,4-galactosyltransferase, polypeptide 6 |
| 1944 | 1214 | NM_031741 | r | *Rattus norvegicus* solute carrier family 2 (facilitated glucose transporter), member 5 (Slc2a5), mRNA. Length = 2169 | solute carrier family 2 (facilitated glucose transporter), member 5 |
| 1944 | 1215 | NM_031741 | r | *Rattus norvegicus* solute carrier family 2 (facilitated glucose transporter), member 5 (Slc2a5), mRNA. Length = 2169 | solute carrier family 2 (facilitated glucose transporter), member 5 |
| 1945 | 20724 | NM_031753 | h | *Rattus norvegicus* activated leukocyte cell adhesion molecule (Alcam), mRNA. Length = 2866 | activated leukocyte cell adhesion molecule |
| 1946 | 20753 | NM_031763 | y | *Rattus norvegicus* platelet-activating factor acetylhydrolase beta subunit (PAF-AH beta)(Pafah1b1), mRNA. Length = 1233 | platelet-activating factor acetylhydrolase beta subunit (PAF-AH beta) |
| 1946 | 20752 | NM_031763 | h | *Rattus norvegicus* platelet-activating factor acetylhydrolase beta subunit (PAF-AH beta) (Pafah1b1), mRNA. Length = 1233 | platelet-activating factor acetylhydrolase beta subunit (PAF-AH beta) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1947 | 14953 | NM_031774 | p | *Rattus norvegicus* rab acceptor 1 (prenylated) (Rabac1), mRNA. Length = 861 | rab acceptor 1 (prenylated) |
| 1948 | 14184 | NM_031776 | t, General | *Rattus norvegicus* guanine deaminase (Gda), mRNA. Length = 1568 | guanine deaminase |
| 1948 | 14185 | NM_031776 | d, o, t General | *Rattus norvegicus* guanine deaminase (Gda), mRNA. Length = 1568 | guanine deaminase |
| 1949 | 1169 | NM_031789 | c | *Rattus norvegicus* NF-E2-related factor 2 (Nfe2l2), mRNA. Length = 2307 | NF-E2-related factor 2 |
| 1950 | 16155 | NM_031810 | d, z | *Rattus norvegicus* defensin beta 1 (Defb1), mRNA. Length = 416 | defensin beta 1 |
| 1950 | 16156 | NM_031810 | d | *Rattus norvegicus* defensin beta 1 (Defb1), mRNA. Length = 416 | defensin beta 1 |
| 1951 | 17194 | NM_031814 | z | *Rattus norvegicus* G protein-coupled receptor kinase-associated ADP ribosylation factor GTPase-activating protein (GIT1)(Git1), mRNA. Length = 3236 | G protein-coupled receptor kinase-associated ADP ribosylation factor GTPase-activating protein (GIT1) |
| 1952 | 17535 | NM_031816 | bb | *Rattus norvegicus* retinoblastoma binding protein 7 (Rbbp7), mRNA. Length = 1947 | retinoblastoma binding protein 7 |
| 1953 | 2655 | NM_031821 | i, l, m, aa | *Rattus norvegicus* serum-inducible kinase (Snk), mRNA. Length = 2781 | serum-inducible kinase |
| 1954 | 10167 | NM_031830 | i | *Rattus norvegicus* reggie1-1 (Flot2), mRNA. Length = 2629 | reggie1-1 |
| 1955 | 22321 | NM_031832 | o, t, u, General | *Rattus norvegicus* IgE binding protein (Lgals3), mRNA. Length = 948 | IgE binding protein |
| 1956 | 4748 | NM_031834 | e, t | *Rattus norvegicus* sulfotransferase family 1A, phenol-preferring, member 1 (Sult1a1), mRNA. Length = 1227 | minoxidil sulfotransferase |
| 1956 | 4749 | NM_031834 | e, t | *Rattus norvegicus* sulfotransferase family 1A, phenol-preferring, member 1 (Sult1a1), mRNA. Length = 1227 | minoxidil sulfotransferase |
| 1957 | 7914 | NM_031835 | e | *Rattus norvegicus* beta-alanine-pyruvate aminotransferase (AGT2), mRNA. Length = 2151 | beta-alanine-pyruvate aminotransferase |
| 1958 | 8385 | NM_031836 | h | *Rattus norvegicus* vascular endothelial growth factor (Vegf), mRNA. Length = 645 | vascular endothelial growth factor |
| 1958 | 8384 | NM_031836 | h | *Rattus norvegicus* vascular endothetial growth factor (Vegf), mRNA. Length = 645 | vascular endothelial growth factor |
| 1959 | 10268 | NM_031838 | a | *Rattus norvegicus* ribosomal protein S2 (Rps2), mRNA. Length = 819 | ribosomal protein S2 |
| 1959 | 10269 | NM_031838 | aa | *Rattus norvegicus* ribosomal protein S2 (Rps2), mRNA. Length = 819 | ribosomal protein S2 |
| 1959 | 10267 | NM_031838 | n, aa | *Rattus norvegicus* ribosomal protein S2 (Rps2), mRNA. Length = 819 | ribosomal protein S2 |
| 1960 | 15077 | NM_031841 | b | *Rattus norvegicus* stearoyl-CoA desaturase 2 (Scd2), mRNA. Length = 5055 | stearoyl-CoA desaturase 2 |
| 1961 | 16726 | NM_031855 | x | *Rattus norvegicus* Ketohexokinase (Khk), mRNA. Length = 1342 | Ketohexokinase |
| 1962 | 25802 | NM_031969 | a | *Rattus norvegicus* Calmodulin 1 (phosphorylase kinase, delta) (Calm1), mRNA. Length = 3513 | Calmodulin 1 (phosphorylase kinase, delta) |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1962 | 19191 | NM_031969 | c | *Rattus norvegicus* Calmodulin 1 (phosphorylase kinase, delta) (Calm1), mRNA. Length = 3513 | Calmodulin 1 (phosphorylase kinase, delta) |
| 1962 | 19195 | NM_031969 | r | *Rattus norvegicus* Calmodulin 1 (phosphorylase kinase, delta) (Calm1), mRNA. Length = 3513 | Calmodulin 1 (phosphorylase kinase, delta) |
| 1962 | 19190 | NM_031969 | p | *Rattus norvegicus* Calmodulin 1 (phosphorylase kinase, delta) (Calm1), mRNA. Length = 3513 | Calmodulin 1 (phosphorylase kinase, delta) |
| 1963 | 17734 | NM_031970 | v, General | *Rattus norvegicus* Heat shock 27 kDa protein (Hsp27), mRNA. Length = 787 | ESTs, Heat shock 27 kDa protein |
| 1964 | 1475 | NM_031971 | v | *Rattus norvegicus* Heat shock protein 70-1 (Hspa1a), mRNA. Length = 2455 | ESTs, Highly similar to S10A RAT S-100 PROTEIN, ALPHA CHAIN [*R. norvegicus*], Heat shock protein 70-1 |
| 1965 | 15470 | NM_031978 | f | *Rattus norvegicus* 26S proteasome, subunit p112 (PSMD1), mRNA. Length = 3089 | 26S proteasome, subunit p112 |
| 1966 | 18502 | NM_031984 | c | *Rattus norvegicus* cerebellar Ca-binding protein, spot 35 protein (Calb1), mRNA. Length = 2280 | cerebellar Ca-binding protein, spot 35 protein |
| 1967 | 19768 | NM_031986 | v, aa, General | *Rattus norvegicus* syntenin (Sdcbp), mRNA. Length = 2077 | syntenin |
| 1968 | 723 | NM_032084 | n | *Rattus norvegicus* chimerin (chimaerin) 2 (Chn2), mRNA, Length = 1118 | chimerin (chimaerin) 2 |
| 1969 | 17935 | NM_032615 | a | *Rattus norvegicus* membrane interacting protein of RGS16 (Mir16), mRNA. Length = 1203 | membrane interacting protein of RGS16 |
| 1970 | 16831 | NM_033095 | n | *Rattus norvegicus* Crystallin, gamma polypeptide 4 (Crygd), mRNA. Length = 634 | |
| 1971 | 25468 | NM_033234 | c, z | *Rattus norvegicus* Hemoglobin, beta (Hbb), mRNA. Length = 620 | |
| 1971 | 25469 | NM_033234 | c | *Rattus norvegicus* Hemoglobin, beta (Hbb), mRNA. Length = 620 | |
| 1971 | 17832 | NM_033234 | c, p | *Rattus norvegicus* Hemoglobin, beta (Hbb), mRNA. Length = 620 | Rat major beta-globin mRNA, complete cds |
| 1971 | 17829 | NM_033234 | c, z | *Rattus norvegicus* Hemoglobin, beta (Hbb), mRNA. Length = 620 | Rat major beta-globin mRNA, complete cds |
| 1972 | 4723 | NM_033235 | z | *Rattus norvegicus* Malate dehydrogenase-like enzyme (Mdhl), mRNA. Length = 1266 | *Rattus norvegicus* cytosolic malate dehydrogenase (Mdh) mRNA, complete cds |
| 1973 | 1409 | NM_033349 | p, General | *Rattus norvegicus* Hydroxyacyl glutathione hydrolase (Hagh), mRNA. Length = 783 | *Rattus norvegicus* round spermatid protein RSP29 gene, complete cds |
| 1974 | 19998 | NM_033352 | General | *Rattus norvegicus* ATP-binding cassette, sub-family D (ALD), member 2 (Abcd2), mRNA. Length = 5531 | PDZ domain containing 1 |
| 1975 | 1410 | NM_052798 | d | *Rattus norvegicus* Kidney 1 (Kid1), mRNA. Length = 2563 | Rat zinc finger protein (kid-1) mRNA, complete cds |
| 1976 | 15028 | NM_052809 | f | *Rattus norvegicus* cytosolic cysteine dioxygenase 1 (Cdo1), mRNA. Length = 1458 | Rat cysteine dioxygenase mRNA, complete cds |
| 1977 | 5176 | NM_053297 | u | *Rattus norvegicus* Pyruvate kinase 3 (Pkm2), mRNA. Length = 1973 | Rat mRNA for pituitary pyruvate kinase |
| 1978 | 7660 | NM_053299 | i | *Rattus norvegicus* ubiquitin D (Ubd), mRNA. Length = 684 | ESTs, Weakly similar to polyubiquitin [*R. norvegicus*] |
| 1979 | 5117 | NM_053310 | p | *Rattus norvegicus* homer, neuronal immediate early gene, 3 (Homer3), mRNA. Length = 1207 | *Rattus norvegicus* mRNA for Vesl-3, complete cds |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 1981 | 17473 | NM_053319 | a, v | *Rattus norvegicus* dynein, cytoplasmic, light chain 1 (Pin), mRNA. Length = 505 | *Rattus norvegicus* protein inhibitor of neuronal nitric oxide synthase (PIN) mRNA, complete cds |
| 1982 | 25480 | NM_053329 | g | *Rattus norvegicus* insulin-like growth factor binding protein, acid labile subunit (Igfals), mRNA. Length = 1812 | |
| 1982 | 21977 | NM_053329 | y | *Rattus norvegicus* insulin-like growth factor binding protein, acid labile subunit (Igfals), mRNA. Length = 1812 | *Rattus norvegicus* insulin-like growth factor binding protein complex acid-labile subunit gene, complete cds |
| 1983 | 14926 | NM_053330 | f | *Rattus norvegicus* ribosomal protein L21 (Rpl21), mRNA. Length = 554 | *Rattus norvegicus* ribosomal protein L21 mRNA, complete cds |
| 1983 | 14929 | NM_053330 | e, General | *Rattus norvegicus* ribosomal protein L21 (Rpl21), mRNA. Length = 554 | *Rattus norvegicus* ribosomal protein L21 mRNA, complete cds |
| 1984 | 16407 | NM_053332 | c, e | *Rattus norvegicus* cubilin (intrinsic factor-cobalamin receptor) (Cubn), mRNA. Length = 10,872 | *Rattus norvegicus* intrinsic factor-B12 receptor precursor (CUBILIN) mRNA, complete cds |
| 1985 | 15790 | NM_053341 | j, x | *Rattus norvegicus* regulator of G-protein signaling 19 (Rgs19), mRNA. Length = 1607 | regulator of G-protein signaling 19 |
| 1986 | 6154 | NM_053356 | p | *Rattus norvegicus* procoilagen, type I, alpha 2 (Col1a2), mRNA. Length = 4474 | procoilagen, type I, alpha 2 |
| 1987 | 9215 | NM_053374 | i | *Rattus norvegicus* interferon gamma inducing factor binding protein (Igifbp), mRNA. Length = 626 | interferon gamma inducing factor biniding protein |
| 1988 | 6416 | NM_053380 | General | *Rattus norvegicus* solute carrier family 34 (sodium phosphate), member 2 (Slc34a2), mRNA. Length = 3950 | solute carrier family 34 (sodium phosphate), member 2 |
| 1989 | 19113 | NM_053395 | a | *Rattus norvegicus* small muscle protein, X-linked (Smpx), mRNA. Length = 892 | *Rattus norvegicus* SMPX protein (Smpx) mRNA, complete cds |
| 1990 | 2242 | NM_053433 | n, General | *Rattus norvegicus* flavin-containing monooxygenase 3 (Fmo3), mRNA. Length = 2037 | flavin-containing monooxygenase 3 |
| 1991 | 5561 | NM_053438 | y | *Rattus norvegicus* zinc finger protein 103 (Zfp103), mRNA. Length = 3258 | zinc finger protein 103 |
| 1992 | 14670 | NM_053439 | n, General | *Rattus norvegicus* RAN, member RAS oncogene family (Ran), mRNA. Length = 1084 | RAN, member RAS oncogene family |
| 1993 | 17102 | NM_053440 | w | *Rattus norvegicus* superiorcervical ganglia, neural specific 10 (Scgn10), mRNA. Length = 1654 | superiorcervical ganglia, neural specific 10 |
| 1994 | 24762 | NM_053442 | General | *Rattus norvegicus* solute carrier family 8 (cationic amino acid transporter, y+ system), member 7 (Lat4), mRNA. Length = 4117 | solute carrier family 8 (cationic amino acid transporter, y+ system), member 7 |
| 1995 | 8085 | NM_053453 | General | *Rattus norvegicus* regulator of G-protein signaling protein 2 (Rgs2), mRNA. Length = 1629 | regulator of G-protein signaling protein 2 |
| 1996 | 4622 | NM_053463 | d | *Rattus norvegicus* nucleobindin (Nucb), mRNA. Length = 2303 | nucleobindin |
| 1997 | 21866 | NM_053472 | p | *Rattus norvegicus* cytochrome c oxidase subunit IV isoform 2 precursor (CoxIV-2), mRNA. Length = 704 | cytochrome c oxidase subunit IV isoform 2 precursor |
| 1998 | 9573 | NM_053475 | h | *Rattus norvegicus* protein tyrosine phosphatase type IVA, member 2 (Ptp4a2), mRNA. Length = 1095 | protein tyrosine phosphatase type IVA, member 2 |
| 1999 | 16137 | NM_053480 | k | *Rattus norvegicus* DNA polymerase alpha subunit II (Pola2), mRNA. Length = 1836 | DNA polymerase alpha subunit II |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2000 | 15556 | NM_053483 | y | *Rattus norvegicus* karyopherin (importin) alpha 2 (Kpna2), mRNA. Length = 1886 | karyopherin (importin) alpha 2 |
| 2001 | 16394 | NM_053485 | General | *Rattus norvegicus* calcium binding protein A6 (calcyclin) (S100a6), mRNA. Length = 291 | calcium binding protein A6 (calcyclin) |
| 2002 | 4290 | NM_053487 | j, y | *Rattus norvegicus* peroxisomal membrane protein Pmp26p (Peroxin-11) (Pex11a), mRNA. Length = 1194 | peroxisomal membrane protein Pmp26p (Peroxin-11) |
| 2004 | 18826 | NM_053523 | d | *Rattus norvegicus* homocysteine-inducible, endoplasmic reticulum stress inducible, ubiquitin-like domain member 1 (Herpud1), mRNA. Length = 1857 | *Rattus norvegicus* SUP mRNA, complete cds |
| 2005 | 7764 | NM_053525 | aa | *Rattus norvegicus* ATP-dependent, RNA helicase (Rok1), mRNA. Length = 2175 | *Rattus norvegicus* rROK1L mRNA for ROK1-like protein, complete cds |
| 2006 | 14199 | NM_053538 | c | *Rattus norvegicus* lysosomal-associated protein transmembrane 5 (Laptm5), mRNA. Length = 1309 | *Rattus norvegicus* gcd-10S mRNA, complete cds |
| 2007 | 1058 | NM_053539 | c, d | *Rattus norvegicus* isopentenyl-diphosphate delta isomerase (Idi1), mRNA. Length = 1182 | *Rattus norvegicus* isopentenyl diphosphate: dimethylallyl diphosphate isomerase mRNA, complete cds |
| 2008 | 4327 | NM_053563 | General | *Rattus norvegicus* nuclear RNA helicase, DECD variant of DEAD box family (Ddxl), mRNA. Length = 1511 | *Rattus norvegicus* nuclear RNA helicase mRNA, complete cds |
| 2009 | 1342 | NM_053573 | h | *Rattus norvegicus* olfactomedin related ER localized protein (Olfm1), mRNA. Length = 2759 | *Rattus norvegicus* neuronal olfactomedin-related ER localized protein (D2Sut1e) mRNA, complete cds |
| 2010 | 19254 | NM_053576 | h, s | *Rattus norvegicus* thiol-specific antioxidant protein (Prdx5), mRNA. Length = 1414 | *Rattus norvegicus* mRNA for thiol-specific antioxidant protein (1-Cys peroxiredoxin) |
| 2010 | 19253 | NM_053576 | h | *Rattus norvegicus* thiol-specific antioxidant protein (Prdx5), mRNA. Length = 1414 | *Rattus norvegicus* mRNA for thiol-specific antioxidant protein (1-Cys peroxiredoxin) |
| 2011 | 3049 | NM_053582 | p, cc, General | *Rattus norvegicus* glucocorticoid-inducible protein (gis5), mRNA. Length = 1869 | *Rattus norvegicus* gis5 mRNA for glucocorticoid-inducible protein, complete cds |
| 2011 | 3050 | NM_053582 | o, General | *Rattus norvegicus* glucocorticoid-inducible protein (gis5), mRNA. Length = 1869 | *Rattus norvegicus* gis5 mRNA for glucocorticoid-inducible protein, complete cds |
| 2012 | 21423 | NM_053586 | s, y | *Rattus norvegicus* cytochrome c oxidase subunit Vb (Cox5b), mRNA. Length = 485 | Rat mRNA for cytochrome c oxidase subunit VIa |
| 2013 | 21445 | NM_053587 | t, v | *Rattus norvegicus* S100 calcium-binding protein A9 (calgranulin B) (S100a9), mRNA. Length = 494 | *Rattus norvegicus* intracellular calcium binding protein (MRP14) mRNA, complete cds |
| 2014 | 20871 | NM_053591 | j, l | *Rattus norvegicus* dipeptidase 1 (Dpep1), mRNA. Length = 2179 | Rat dipeptidase (dpep1) mRNA, complete cds |
| 2014 | 20870 | NM_053591 | l | *Rattus norvegicus* dipeptidase 1 (Dpep1), mRNA. Length = 2179 | Rat dipeptidase (dpep1) mRNA, complete cds |
| 2015 | 21044 | NM_053594 | d | *Rattus norvegicus* protein tyrosine phosphatase, receptor type, R (Ptprr), mRNA. Length = 3565 | *Rattus norvegicus* mRNA for tyrosine phosphatase CBPTP, complete cds |
| 2016 | 21709 | NM_053596 | k | *Rattus norvegicus* endothelin converting enzyme 1 (Ece1), mRNA. Length = 4469 | Rat mRNA for endothelin-converting enzyme, complete cds |
| 2016 | 21708 | NM_053596 | z | *Rattus norvegicus* endothelin converting enzyme 1 (Ece1), mRNA. Length = 4469 | Rat mRNA for endothelin-converting enzyme, complete cds |
| 2017 | 1597 | NM_053611 | t | *Rattus norvegicus* nuclear proten 1 (Nupr1), mRNA. Length = 602 | *Rattus norvegicus* p8 mRNA, complete cds |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2018 | 5565 | NM_053618 | General | *Rattus norvegicus* Bardet-Biedl syndrome 2 (human) (Bbs2), mRNA. Length = 2573 | *Rattus norvegicus* BBS2 (Bbs2) mRNA, complete cds |
| 2019 | 13004 | NM_053623 | t | *Rattus norvegicus* fatty acid-Coenzyme A ligase, long chain 4 (Facl4), mRNA. Length = 4862 | *Rattus norvegicus* mRNA for Acyl-CoA synthetase, complete cds |
| 2020 | 1127 | NM_053626 | g | *Rattus norvegicus* D-amino acid oxidase (Dao1), mRNA. Length = 1646 | *Rattus norvegicus* mRNA for D-amino-acid oxidase, complete cds |
| 2021 | 18644 | NM_053648 | n | *Rattus norvegicus* beta-carotene 15,15'-dioxygenase (Bcdo), mRNA. Length = 2207 | *Rattus norvegicus* mRNA for beta-carotene 15,15'-dioxygenase, complete cds |
| 2022 | 21637 | NM_053653 | p | *Rattus norvegicus* vascular endothelial growth factor C (Vegfc), mRNA. Length = 1596 | ESTs, Highly similar to VEGC MOUSE VASCULAR ENDOTHELIAL GROWTH FACTOR C PRECURSOR [*M. musculus*] |
| 2023 | 3454 | NM_053662 | cc | *Rattus norvegicus* cyclin L (Ccnl), mRNA. Length = 2092 | *Rattus norvegicus* cyclin ania-6a mRNA, complete cds |
| 2024 | 16121 | NM_053698 | h, j, z | *Rattus norvegicus* Cbp/p300-interacting transactivator, with Glu/Asp-rich carboxy-terminal domain, 2 (Cited2), mRNA. Length = 1155 | *Rattus norvegicus* transcription factor MRG1 mRNA, complete cds |
| 2024 | 16122 | NM_053698 | h, j, z | *Rattus norvegicus* Cbp/p300-interacting transactivator, with Glu/Asp-rich carboxy-terminal domain, 2 (Cited2), mRNA. Length = 1155 | *Rattus norvegicus* transcription factor MRG1 mRNA, complete cds |
| 2025 | 25379 | NM_053713 | General | *Rattus norvegicus* Kruppel-like factor 4 (gut) (Klf4), mRNA. Length = 2393 | |
| 2025 | 13622 | NM_053713 | General | *Rattus norvegicus* Kruppel-like factor 4 (gut) (Klf4), mRNA. Length = 2393 | ESTs, Moderately similar to zinc finger protein [*R. norvegicus*] |
| 2026 | 15376 | NM_053747 | h | *Rattus norvegicus* ubiquilin 1 (Ubqln1), mRNA. Length = 2131 | *Rattus norvegicus* mRNA for DA41, complete cds |
| 2027 | 1218 | NM_053748 | b | *Rattus norvegicus* dipeptidylpeptidase III (Dpp3), mRNA. Length = 2632 | *Rattus norvegicus* mRNA for dipeptidyl peptidase III, complete cds |
| 2028 | 1137 | NM_053763 | y | *Rattus norvegicus* cytochrome P450, 40 (25-hydroxyvitamin D3 1 alpha-hydroxylase) (Cyp40), mRNA. Length = 2426 | *Rattus norvegicus* 25-hydroxyvitamin D 1-hydroxylase (CYP1) mRNA, complete cds |
| 2029 | 15996 | NM_053769 | cc | *Rattus norvegicus* protein tyrosine phosphatase, non-receptor type 16 (Ptpn16), mRNA. Length = 1104 | *Rattus norvegicus* protein tyrosine phosphatase mRNA, complete cds |
| 2030 | 8652 | NM_053774 | g | *Rattus norvegicus* ubiquitin specific protease 2 (Usp2), mRNA. Length = 1857 | *Rattus norvegicus* deubiquitinating enzyme Ubp69 (ubp69) mRNA, complete cds |
| 2031 | 14664 | NM_053806 | General | *Rattus norvegicus* potassium channel, subfamily K, member 6 (TWIK-2) (Kcnk6), mRNA. Length = 2243 | ESTs |
| 2032 | 4361 | NM_053812 | k | *Rattus norvegicus* BCL2-antagonist/killer 1 (Bak1), mRNA. Length = 1923 | *Rattus norvegicus* BAK protein (Bak) mRNA, complete cds |
| 2034 | 15002 | NM_053819 | b, x, bb, General | *Rattus norvegicus* tissue inhibitor of metalloproteinase 1 (Timp1), mRNA. Length = 740 | *Rattus norvegicus* tissue inhibitor of metalloproteinase-1 (TIMP1), mRNA, complete cds |
| 2034 | 15003 | NM_053819 | b, l, x, bb, General | *Rattus norvegicus* tissue inhibitor of metalloproteinase 1 (Timp1), mRNA. Length = 740 | *Rattus norvegicus* tissue inhibitor of metalloproteinase-1 (TIMP1), mRNA, complete cds |
| 2035 | 16173 | NM_053822 | t | *Rattus norvegicus* S100 calcium-binding protein A8 (calgranulin A) (S100a8), mRNA. Length = 361 | *Rattus norvegicus* intercellular calcium binding protein (MRP8) mRNA, complete cds |
| 2036 | 17154 | NM_053835 | j, z | *Rattus norvegicus* clathrin, light polypeptide (Lcb) (Cltb), mRNA. Length = 982 | Rat clathrin light chain (LCB2) mRNA, complete cds, Rat clathrin light chain (LCB3) mRNA, complete cds |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2037 | 20868 | NM_053843 | t | *Rattus norvegicus* Fc receptor, IgG, low affinity III (Fcgr3), mRNA. Length = 1318 | Rat Fc-gamma receptor mRNA, complete cds |
| 2037 | 20869 | NM_053843 | t | *Rattus norvegicus* Fc receptor, IgG, low affinity III (Fcgr3), mRNA. Length = 1318 | Rat Fc-gamma receptor mRNA, complete cds |
| 2040 | 714 | NM_053863 | y | *Rattus norvegicus* solute carrier family 28 (sodium-coupled nucleoside transporter), member 1 (Slc28a1), mRNA. Length = 2401 | *Rattus norvegicus* Sprague-Dawley sodium-dependent nucleoside transporter (rCNT1) mRNA, complete cds |
| 2041 | 19781 | NM_053883 | b | *Rattus norvegicus* dual specificity phosphatase 6 (Dusp6), mRNA. Length = 2104 | *Rattus norvegicus* dual-specificity protein tyrosine phosphatase (rVH6) mRNA, complete cds |
| 2041 | 19780 | NM_053883 | b | *Rattus norvegicus* dual specificity phosphatase 6 (Dusp6), mRNA. Length = 2104 | *Rattus norvegicus* dual-specificity protein tyrosine phosphatase (rVH6) mRNA, complete cds |
| 2042 | 1454 | NM_053887 | General | *Rattus norvegicus* mitogen activated protein kinase kinase kinase 1 (Map3k1), mRNA. Length = 5180 | *Rattus norvegicus* MAP kinase kinase kinase 1 (MEKK1) mRNA, complete cds |
| 2043 | 1660 | NM_053891 | g | *Rattus norvegicus* cyclin-dependent kinase 5, regulatory subunit 1 (p35) (Cdk5r), mRNA. Length = 1208 | *Rattus norvegicus* P35 mRNA, complete cds |
| 2044 | 712 | NM_053896 | k | *Rattus norvegicus* aldehyde dehydrogenase family 1, subfamily A2 (Aldh1a2), mRNA. Length = 2240 | *Rattus norvegicus* aldehyde dehydrogenase mRNA, complete cds |
| 2045 | 753 | NM_053897 | k | *Rattus norvegicus* coagulation factor II (thrombin) receptor-like 1 (F2rl1), mRNA. Length = 1428 | *Rattus norvegicus* proteinase-activated receptor-2 mRNA, complete cds |
| 2046 | 794 | NM_053902 | General | *Rattus norvegicus* kynureninase (L-kynurenine hydrolase) (Kynu), mRNA. Length = 1765 | *Rattus norvegicus* L-kynurenine hydrolase mRNA, complete cds |
| 2047 | 17937 | NM_053911 | f | *Rattus norvegicus* pleckstrin homology, Sec7 and coiled/coil domains 2 (Pscd2), mRNA. Length = 1561 | *Rattus norvegicus* sec7B mRNA, complete cds |
| 2048 | 8188 | NM_053927 | General | *Rattus norvegicus* erythrocyte membrane protein band 4.1-like 3 (Epb4l3), mRNA. Length = 4543 | *Rattus norvegicus* mRNA for type II brain 4.1, complete cds |
| 2050 | 1628 | NM_053936 | h | *Rattus norvegicus* endothelial differentiation, lysophosphatidic acid G-protein-coupled receptor, 2 (Edg2), mRNA. Length = 1543 | *Rattus norvegicus* putative G-protein coupled receptor GPCR91 (Gpcr91) mRNA, complete cds |
| 2051 | 13954 | NM_053955 | General | *Rattus norvegicus* crystallin, mu (Crym), mRNA. Length = 1227 | *Rattus norvegicus* CDK108 mRNA |
| 2052 | 408 | NM_053961 | General | *Rattus norvegicus* endoplasmic retuclum protein 29 (Erp29), mRNA. Length = 4529 | *R. norvegicus* mRNA encoding 45 kDa protein which binds to heymann nephritis antigen gp330 |
| 2052 | 19991 | NM_053961 | a | *Rattus norvegicus* endoplasmic retuclum protein 29 (Erp29), mRNA. Length = 4529 | mitochondrial aconitase (nuclear aco2 gene) |
| 2052 | 16190 | NM_053961 | q | *Rattus norvegicus* endoplasmic retuclum protein 29 (Erp29), mRNA. Length = 4529 | ESTs, Weakly similar to ECHM RAT ENOYL-COA HYDRATASE, MITOCHONDRIAL PRECURSOR [*R. norvegicus*] |
| 2052 | 21355 | NM_053961 | j, l, y, z | *Rattus norvegicus* endoplasmic retuctum protein 29 (Erp29), mRNA. Length = 4529 | ESTs |
| 2055 | 15136 | NM_053971 | aa | *Rattus norvegicus* ribosomal protein L6 (Rpl6), mRNA. Length = 963 | *R. norvegicus* mRNA for ribosomal protein L6 |
| 2055 | 15135 | NM_053971 | d | *Rattus norvegicus* ribosomal protein L6 (Rpl6), mRNA. Length = 963 | *R. norvegicus* mRNA for ribosomal protein L6 |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2056 | 1764 | NM_053974 | h | *Rattus norvegicus* eukaryotic translation initiation factor 4E (Eif4e), mRNA. Length = 1647 | *R. norvegicus* mRNA eIF-4E |
| 2057 | 1292 | NM_053980 | l | *Rattus norvegicus* ADP-ribosylation factor related protein 1 (Arfrp1), mRNA. Length = 943 | *R. norvegicus* (Sprague Dawley) ARP1 mRNA for ARF-related protein |
| 2058 | 15468 | NM_053982 | q | *Rattus norvegicus* ribosamal protein S15a (Rps15a), mRNA. Length = 449 | *R. norvegicus* mRNA for ribosomal protein S15a |
| 2059 | 15642 | NM_053985 | General | *Rattus norvegicus* H3 histone, family 3B (H3f3b), mRNA. Length = 1107 | *R. norvegicus* mRNA for histone H3.3 |
| 2060 | 21066 | NM_054001 | t | *Rattus norvegicus* CD36 antigen (collagen type I receptor, thrombospondin receptor)-like 2 (Cd36l2), mRNA. Length = 1938 | Rat lysosomal membrane protein (LIMPII) mRNA, complete cds |
| 2061 | 17326 | NM_054008 | o | *Rattus norvegicus* Rgc32 protein (Rgc32), mRNA. Length = 889 | *Rattus norvegicus* RGC-32 (RGC-32) mRNA, complete cds |
| 2061 | 17327 | NM_054008 | cc | *Rattus norvegicus* Rgc32 protein (Rgc32), mRNA. Length = 889 | *Rattus norvegicus* RGC-32 (RGC-32) mRNA, complete cds |
| 2061 | 17329 | NM_054008 | g, o, cc | *Rattus norvegicus* Rgc32 protein (Rgc32), mRNA. Length = 889 | *Rattus norvegicus* RGC-32 (RGC-32) mRNA, complete cds |
| 2062 | 25253 | NM_057099 | j, i, m, p, z | *Rattus norvegicus* proteasome (prosome, macropain) subunit, beta type 6 (Psmb6), mRNA. Length = 760 | |
| 2062 | 22849 | NM_057099 | j, l | *Rattus norvegicus* proteasome (prosome, macropain) subunit, beta type 6 (Psmb6), mRNA. Length = 760 | ESTs, Highly similar to PROTEASOME DELTA CHAIN PRECURSOR [*R. norvegicus*] |
| 2063 | 19657 | NM_057103 | b, cc | *Rattus norvegicus* A kinase (PRKA) anchor protein (gravin) 12 (Akap12), mRNA. Length = 5236 | *Rattus norvegicus* PKC binding protein and substrate mRNA, complete cds |
| 2064 | 5492 | NM_057105 | w | *Rattus norvegicus* UDP glycosyltransferase 1 family, polypeptide A6 (Ugt1a6), mRNA. Length = 1593 | ESTs, UDP-glucuronosyltransferase 1 family, member 1 |
| 2064 | 15126 | NM_057105 | r | *Rattus norvegicus* UDP glycosyltransferase 1 family, polypeptide A6 (Ugt1a6), mRNA. Length = 1593 | *Rattus norvegicus* UDP-glucuronosyltransferase UGT1A7 mRNA, complete cds, UDP-glucuronosyltransferase 1 family, member 1 |
| 2064 | 15125 | NM_057105 | s | *Rattus norvegicus* UDP glycosyltransferase 1 family, polypeptide A6 (Ugt1a6), mRNA. Length = 1593 | *Rattus norvegicus* UDP-glucuronosyltransferase UGT1A7 mRNA, complete cds, UDP-glucuronosyltransferase 1 family, member 1 |
| 2066 | 15391 | NM_057114 | n | *Rattus norvegicus* peroxiredoxin 1 (Prdx1), mRNA. Length = 882 | Rat mRNA for HBP23 (heme-binding protein 23 kDa), complete cds |
| 2067 | 727 | NM_057123 | m | *Rattus norvegicus* protease (prosome, macropain) 26S subunit, ATPase 1 (Psmc1), mRNA. Length = 1556 | *Rattus norvegicus* mRNA for proteasomal ATPase (S4), complete cds |
| 2068 | 915 | NM_057124 | s | *Rattus norvegicus* pyrimidinergic receptor P2Y, G-protein coupled, 6 (P2ry6), mRNA. Length = 1922 | Rat mRNA for novel G protein-coupled P2 receptor, complete cds |
| 2069 | 15151 | NM_057131 | k | *Rattus norvegicus* phosphoribosyl pyrophosphate synthetase-associated protein 2 (Prpsap2), mRNA. Length = 1612 | *Rattus norvegicus* mRNA for 41-kDa phosphoribosylpyrophosphate synthetase-associated protein, complete cds |
| 2070 | 1892 | NM_057144 | b | *Rattus norvegicus* cysteine-rich protein 3 (Csrp3), mRNA. Length = 853 | *R. norvegicus* mRNA for muscle LIM protein |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2071 | 12333 | NM_057155 | f | *Rattus norvegicus* X-prolyl aminopeptidase (aminopeptidase P) 2, membrane-bound (Xpnpep2), mRNA. Length = 2828 | *Rattus norvegicus* membrane-bound aminopeptidase P mRNA, complete cds |
| 2071 | 12331 | NM_057155 | v, General | *Rattus norvegicus* X-prolyl aminopeptidase (aminopeptidase P) 2, membrane-bound (Xpnpep2), mRNA. Length = 2828 | *Rattus norvegicus* membrane-bound aminopeptidase P mRNA, complete cds |
| 2071 | 12332 | NM_057155 | f, General | *Rattus norvegicus* X-prolyl aminopeptidase (aminopeptidase P) 2, membrane-bound (Xpnpep2), mRNA. Length = 2828 | *Rattus norvegicus* membrane-bound aminopeptidase P mRNA, complete cds |
| 2072 | 17477 | NM_057194 | a, General | *Rattus norvegicus* phospholipid scramblase 1 (Plscr1), mRNA. Length = 1569 | *Rattus norvegicus* phospholipid scramblase PLSCR mRNA, complete cds |
| 2073 | 15408 | NM_057197 | p, t | *Rattus norvegicus* 2,4-dienoyl CoA reductase 1, mitochondrial (Decr1), mRNA. Length = 1109 | *Rattus norvegicus* mRNA for 2,4-dienoyl-CoA reductase precursor, complete cds |
| 2073 | 15409 | NM_057197 | t | *Rattus norvegicus* 2,4-dienoyl CoA reductase 1, mitochondrial (Decr1), mRNA. Length = 1109 | *Rattus norvegicus* mRNA for 2,4-dienoyl-CoA reductase precursor, complete cds |
| 2074 | 7866 | NM_057198 | h | *Rattus norvegicus* phosphoribosyl pyrophosphate amidotransferase (Ppat), mRNA. Length = 2934 | *Rattus norvegicus* mRNA for amidophosphoribosyltransferase |
| 2075 | 14125 | NM_057208 | h, j, y, z | *Rattus norvegicus* tropomyosin 3, gamma (Tpm3), mRNA. Length = 1101 | *Rattus norvegicus* tropomyosin non-muscle isoform NM1 (TPM-gamma) mRNA, complete cds, *Rattus norvegicus* tropomyosin non-muscle isoform NM3 (TPM-gamma) mRNA, complete cds |
| 2076 | 1743 | NM_057210 | k, s | *Rattus norvegicus* synaptic vesicle glycoprotein 2 a (Sv2a), mRNA. Length = 3844 | *Rattus norvegicus* synaptic vesicle protein (SV2) mRNA, complete cds |
| 2077 | 10498 | NM_078617 | a | *Rattus norvegicus* ribosomal protein S23 (Rps23), mRNA. Length = 432 | *R. norvegicus* (Sprague-Dawley) ribosomal protein S23 mRNA |
| 2078 | 8820 | NM_080399 | n | *Rattus norvegicus* Smhs1 protein (Smhs1), mRNA. Length = 1107 | ESTs |
| 2079 | 15701 | NM_080581 | j, m, y, z | *Rattus norvegicus* ATP-binding cassette, sub-family C (CFTR/MRP), member 3 (Abcc3), mRNA. Length = 5174 | *Rattus norvegicus* mRNA for multidrug resistance-associated protein (MRP)-like protein-2 (MLP-2), complete cds |
| 2079 | 20105 | NM_080581 | aa | *Rattus norvegicus* ATP-binding cassette, sub-family C (CFTR/MRP), member 3 (Abcc3), mRNA. Length = 5174 | ESTs |
| 2080 | 16109 | NM_080585 | c | *Rattus norvegicus* N-ethylmaleimide sensitive fusion protein attachment protein alpha (Napa), mRNA. Length = 1505 | *Rattus norvegicus* mRNA for alpha-soluble NSF attachment protein |
| 2081 | 1757 | NM_080766 | d | *Rattus norvegicus* Neuroblastoma RAS viral (v-ras) oncogene homolog (Nras), mRNA. Length = 3350 | *R. norvegicus* N-ras gene for p21 protein |
| 2082 | 7108 | NM_080778 | y | *Rattus norvegicus* nuclear receptor subfamily 2, group F, member 2 (Nr2f2), mRNA. Length = 1572 | *Rattus norvegicus* ovalbumin upstream promoter beta nuclear receptor rCOUPb mRNA, complete cds |
| 2083 | 132 | NM_080782 | k | *Rattus norvegicus* cyclin-dependent kinase inhibitor 1A (P21) (Cdkn1a), mRNA. Length = 495 | *Rattus norvegicus* p21 (WAF1) mRNA, complete cds |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2083 | 133 | NM_080782 | l | *Rattus norvegicus* cyclin-dependent kinase inhibitor 1A (P21) (Cdkn1a), mRNA. Length = 495 | *Rattus norvegicus* p21 (WAF1) mRNA, complete cds |
| 2084 | 20122 | NM_080887 | General | *Rattus norvegicus* thioredoxin-like (32 kD) (Txnl), mRNA. Length = 1061 | ESTs, Highly similar to thioredoxin-related protein [*M. musculus*] |
| 2085 | 6143 | NM_080892 | e | *Rattus norvegicus* selenium binding protein 2 (Selenbp2), mRNA. Length = 1685 | ESTs, Moderately similar to selenium-binding protein [*H. sapiens*] |
| 2086 | 9952 | NM_080902 | h | *Rattus norvegicus* hypoxia induced gene 1 (Hig1), mRNA. Length = 355 | ESTs, Moderately similar to AF077034 1 HSPC010 [*H. sapiens*] |
| 2087 | 17546 | NM_130401 | b | *Rattus norvegicus* membrane-associated protein 17 (Map17), mRNA. Length = 816 | ESTs, Moderately similar to DD96 homolog [*R. norvegicus*] |
| 2088 | 21695 | NM_130411 | c, x | *Rattus norvegicus* coronin, actin binding protein 1A (Coro1a), mRNA. Length = 1386 | ESTs, Weakly similar to coronin-like protein [*R. norvegicus*] |
| 2089 | 21391 | NM_130416 | x, General | *Rattus norvegicus* annexin A7 (Anxa7), mRNA. Length = 2912 | ESTs, Weakly similar to ANX4 RAT ANNEXIN IV [*R. norvegicus*] |
| 2090 | 20694 | NM_130430 | General | *Rattus norvegicus* proteasome (prosome, macropain) 26S subunit, non-ATPase, 9 (Psmd9), mRNA. Length = 1448 | EST |
| 2090 | 19818 | NM_130430 | cc | *Rattus norvegicus* proteasome (prosome, macropain) 26S subunit, non-ATPase, 9 (Psmd9), mRNA. Length = 1448 | EST |
| 2090 | 18810 | NM_130430 | e, s | *Rattus norvegicus* proteasome (prosome, macropain) 26S subunit, non-ATPase, 9 (Psmd9), mRNA. Length = 1448 | mitochondrial H+-ATP synthase alpha subunit |
| 2091 | 18293 | NM_130433 | q | *Rattus norvegicus* acetyl-Coenzyme A acyltransferase 2 (mitochondrial 3-oxoacyl-Coenzyme A thiolase) (Acaa2), mRNA. Length = 1619 | Rat mRNA for 3-oxoacyl-CoA thiolase |
| 2092 | 25064 | S45392 | a, n | | |
| 2093 | 3244 | S63519 | u | | ESTs |
| 2094 | 25501 | S63521 | q | | |
| 2095 | 16248 | S68135 | h | | Rat brain glucose-transporter protein mRNA, complete cds |
| 2096 | 18647 | S69316 | q | | ESTs, Weakly similar to HS9B RAT HEAT SHOCK PROTEIN HSP 90-BETA [*R. norvegicus*] |
| 2097 | 24351 | S74257 | v | | ESTs, Weakly similar to ABD4 MOUSE ATP-BINDING CASSETTE, SUB-FAMILY D, MEMBER 4 [*M. musculus*] |
| 2098 | 25066 | S75280 | d | | |
| 2099 | 1460 | S76054 | j, l, m, x, y, General | | ESTs, Highly similar to K2C8 RAT KERATIN, TYPE II CYTOSKELETAL 8 [*R. norvegicus*] |
| 2100 | 25539 | S76742 | v | | |
| 2101 | 16400 | S76779 | c | | Rat apolipoprotein e mma |
| 2102 | 24469 | S77858 | n | | ESTs, Highly similar to MLES RAT MYOSIN LIGHT CHAIN ALKALI, SMOOTH-MUSCLE ISOFORM [*R. norvegicus*] |
| 2103 | 25545 | S77900 | k, s | | |
| 2103 | 21583 | S77900 | k | | ESTs |
| 2104 | 10260 | S81497 | s | | ESTs |
| 2105 | 3609 | S82579 | k | histamine N-methyltransferase | histamine N-methyltransferase |
| 2106 | 111 | U02506 | u | | *Rattus norvegicus* clone 15 polymeric immunoglobulin receptor mRNA, 3'UTR microsatellite repeats |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2107 | 14959 | U03390 | a, q, General | | Rattus norvegicus Sprague Dawley protein kinase C receptor mRNA, complete cds |
| 2109 | 2010 | U05675 | b, x, bb | | Rattus norvegicus Sprague-Dawley fibrinogen B beta chain mRNA, complete cds |
| 2110 | 15462 | U06230 | d | protein S | protein S |
| 2112 | 1583 | U07201 | s, General | Asparagine synthetase | Asparagine synthetase |
| 2113 | 627 | U09229 | h | | Rattus norvegicus New England Deaconess transcription factor mRNA, partial cds |
| 2114 | 809 | U17035 | General | | Rattus norvegicus interferon inducible protein 10 (IP-10) mRNA, complete cds |
| 2115 | 16675 | U17565 | k, x, bb | mini chromosome maintenance deficient 6 (S. cerevisiae) | mini chromosome maintenance deficient 6 (S. cerevisiae) |
| 2116 | 25587 | U20110 | r | | |
| 2117 | 90 | U20796 | r | | Rattus norvegicus nuclear receptor Rev-ErbA-beta mRNA, partial cds |
| 2118 | 25589 | U21718 | h, aa | | |
| 2119 | 22196 | U21719 | h | | ESTs |
| 2120 | 17118 | U25746 | s | | Rattus norvegicus RNA helicase with arginine-serine-rich domain mRNA, complete cds |
| 2121 | 1537 | U27518 | g, h, n | | Rattus norvegicus UDP-glucuronosyltransferase mRNA, complete cds |
| 2122 | 1558 | U28504 | bb | | Rattus norvegicus Na+/Pi cotransporter-1 mRNA, complete cds |
| 2123 | 16193 | U30831 | n | | Rattus norvegicus B/K protein mRNA, complete cds |
| 2124 | 17480 | U31598 | z | | R. norvegicus mRNA for RT1.Ma |
| 2125 | 18302 | U33500 | General | | Rattus norvegicus retinol dehydrogenase type II mRNA, complete cds |
| 2126 | 25599 | U34897 | y | | |
| 2127 | 1394 | U37099 | h | | Rattus norvegicus GTP-binding protein (rab 3C) mRNA, complete cds |
| 2128 | 244 | U38376 | n | | EST, Weakly similar to actin-filament binding protein Frabin [R. norvegicus], Rattus norvegicus cytosolic phospholipase A2 mRNA, complete cds |
| 2129 | 1623 | U41164 | h | | Rattus norvegicus Cys2/His2 zinc finger protein (rKr1) mRNA, complete cds |
| 2130 | 15851 | U42719 | f, t, x, General | Complement component 4 | Complement component 4 |
| 2131 | 17886 | U47315 | s, z | | Rattus norvegicus apoptosis-regulating basic protein mRNA, complete cds |
| 2132 | 21654 | U53184 | i, t, General | estrogen-responsive uterine transcript | estrogen-responsive uterine transcript |
| 2133 | 1439 | U57391 | w | | Rattus norvegicus FceRI gamma-chain interacting protein SH2-B (SH2-B) mRNA, complete cds |
| 2134 | 725 | U62316 | bb | solute carrier family 16 (monocarboxylic acid transporters), mem | solute carrier family 16 (monocarboxylic acid transporters), member 7 |
| 2137 | 2153 | U75404 | b, cc, General | | ESTs |
| 2139 | 4956 | U76714 | j, y | | Rattus norvegicus cell adhesion regulator (CAR1) mRNA, complete cds |
| 2140 | 4477 | U77829 | l, m | | ESTs |
| 2141 | 21703 | U82591 | z | | Rattus norvegicus RCL (Rcl) mRNA, complete cds |
| 2142 | 977 | U89744 | s | | Rattus norvegicus putative cell surface antigen mRNA, complete cds |
| 2143 | 23282 | U90725 | h | lipoprotein-binding protein | lipoprotein-binding protein |
| 2144 | 22005 | U96490 | m | | Rattus norvegicus liver mRNA, complete cds |
| 2146 | 819 | X02284 | j, z | Aldolase B, fructose-biphosphate | Aldolase B, fructose-biphosphate |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2147 | 818 | X02291 | e, j, z | Aldolase B, fructose-biphosphate | Aldolase B, fructose-biphosphate |
| 2148 | 20818 | X02904 | n, q | glutathione S-transferase, pi 2 | glutathione S-transferase, pi 2 |
| 2149 | 16401 | X04979 | c | | Rat apolipoprotein e mrna |
| 2150 | 20513 | X05684 | o, r | Pyruvate kinase, liver and RBC | Pyruvate kinase, liver and RBC |
| 2151 | 25084 | X06769 | cc | | |
| 2152 | 672 | X13722 | h | | Rat mRNA for LDL-receptor |
| 2153 | 25675 | X14181 | n | | |
| 2153 | 20810 | X14181 | n, q, w | | ESTs, Highly similar to 60S RIBOSOMAL PROTEIN L18A [R. norvegicus] |
| 2154 | 18541 | X14671 | y | | ESTs, Highly similar to RL26 RAT 60S RIBOSOMAL PROTEIN L26 [R. norvegicus] |
| 2155 | 25679 | X15013 | q | | |
| 2155 | 19244 | X15013 | c, q, w | | ESTs, Highly similar to RL7A_HUMAN 60S RIBOSOMAL PROTEIN L7A [R. norvegicus] |
| 2156 | 15626 | X17665 | a | | ESTs, Highly similar to RS16_HUMAN 40S RIBOSOMAL PROTEIN S1 [R. norvegicus] |
| 2157 | 1893 | X51529 | t | phospholipase A2, group IIA (platelets, synovial fluid) | phospholipase A2, group IIA (platelets, synovial fluid) |
| 2158 | 25686 | X51536 | bb | | |
| 2158 | 10819 | X51536 | aa, bb | | ESTs, Highly similar to RS3 MOUSE 40S RIBOSOMAL PROTEIN S3 [R. norvegicus] |
| 2159 | 18250 | X51706 | a, q, w | ribosomal protein L9 | ESTS, Highly similar to RL9 RAT 60S RIBOSOMAL PROTEIN L9 [R. norvegicus] |
| 2160 | 20872 | X51707 | a | ribosomal protein S19 | ESTs, Highly similar to RS19 RAT 40S RIBOSOMAL PROTEIN S19 [R. norvegicus] |
| 2161 | 516 | X52711 | c | | Rat mRNA for Mx1 protein |
| 2162 | 25689 | X52815 | g | | |
| 2163 | 20427 | X53378 | w | | *Rattus norvegicus* ribosomal protein S13 (RPS13) mRNA, 3' end |
| 2164 | 18606 | X53504 | General | | ESTs, Highly similar to 60S RIBOSOMAL PROTEIN L12 [R. norvegicus] |
| 2165 | 1463 | X54467 | d, u, General | | Rat mRNA for preprocathepsin D (EC 3.4.23.5) |
| 2166 | 24577 | X55153 | a, v | | ESTs, Highly similar to 60S ACIDIC RIBOSOMAL PROTEIN P2 [R. norvegicus] |
| 2167 | 10344 | X57405 | j, m | (*Drosophila* Notch homolog 1 | LOCUS NOTCH HOMOLOG PROTEIN 1 PRECURSOR [R. norvegicus] |
| 2168 | 15106 | X57529 | g, n, q | | ESTs, Highly similar to RS18_HUMAN 40S RIBOSOMAL PROTEIN S18 [R. norvegicus] |
| 2169 | 5667 | X58200 | q, bb | ribosomal protein L23 | |
| 2169 | 18611 | X58200 | a, v | ribosomal protein L23 | ESTs, Highly similar to RL23_HUMAN 60S RIBOSOMAL PROTEIN L23 [R. norvegicus] |
| 2170 | 17175 | X58389 | w | | *R. norvegicus* ASI mRNA for mammalian equivalent of bacterial large ribosomal subunit protein L22 |
| 2171 | 25702 | X58465 | w | | |
| 2171 | 10109 | X58465 | c, q | Ribosomal protein S5 | Ribosomal protein S5 |
| 2172 | 25705 | X59375 | c, i, aa, General | | |
| 2173 | 25709 | X59737 | u | | |
| 2174 | 18354 | X59859 | General | decorin | decorin |
| 2174 | 18355 | X59859 | t | decorin | decorin |
| 2175 | 21657 | X61381 | General | | *Rattus norvegicus* interferon-inducible protein variant 10 mRNA, complete cds |
| 2176 | 25718 | X62145 | bb, General | ribosomal protein L8 | |
| 2176 | 15875 | X62145 | a, q, v | ribosomal protein L8 | ESTs, Highly similar to RL8_HUMAN 60S RIBOSOMAL PROTEIN L [R. norvegicus] |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2177 | 13646 | X62166 | bb | | ESTs, Highly similar to RL3 RAT 60S RIBOSOMAL PROTEIN L3 [*R. norvegicus*] |
| 2178 | 25721 | X62325 | p | | |
| 2179 | 16012 | X62875 | m, s, z | | ESTs, Highly similar to HIGH MOBILITY GROUP PROTEIN HMG-Y [*M. musculus*] |
| 2180 | 25730 | X63369 | cc | | |
| 2181 | 25089 | X63594 | General | | |
| 2181 | 25090 | X63594 | cc, General | | |
| 2182 | 20844 | X65228 | n, w | | ESTs, Highly similar to RL2B_HUMAN 60S RIBOSOMAL PROTEIN L23A [*R. norvegicus*] |
| 2183 | 20879 | X65296 | j, y | carboxylesterase 1 | carboxylesterase 1 |
| 2184 | 25736 | X68782 | c | | |
| 2185 | 16426 | X70369 | c | procollagen, type III, alpha 1 | procollagen, type III, alpha 1 |
| 2186 | 16300 | X70706 | u | plastin 3 (T-isoform) | plastin 3 (T-isoform) |
| 2187 | 24232 | X75207 | c | cyclin D1 | cyclin D1 |
| 2188 | 16272 | X76456 | n, p | | *R. norvegicus* (Sprague Dawley) alpha albumin gene |
| 2189 | 25741 | X76489 | u | | |
| 2190 | 23302 | X78949 | h | prolyl 4-hydroxylase alpha subunit | prolyl 4-hydroxylase alpha subunit |
| 2191 | 25747 | X81448 | General | | |
| 2192 | 24115 | X81449 | u | | ESTs, Highly similar to K1CS RAT KERATIN, TYPE I CYTOSKELETAL 19 [*R. norvegicus*] |
| 2193 | 25754 | X89696 | g | | |
| 2194 | 25097 | X90642 | y, z | | |
| 2195 | 12978 | X96437 | cc, General | | ESTs, Highly similar to RADIATION-INDUCIBLE IMMEDIATE-EARLY GENE IEX-1 [*M. musculus*] |
| 2197 | 4594 | Y07704 | c | | *Rattus norvegicus* mRNA Best5 protein |
| 2198 | 25777 | Y08355 | g, p, General | oxidative stress induced | oxidative stress induced |
| 2199 | 15986 | Y09945 | bb, General | | *Rattus norvegicus* mRNA for putative integral membrane transport protein (UST1r) |
| 2200 | 20890 | Y13275 | k | | *Rattus norvegicus* mRNA for D6.1A protein |
| 2201 | 21914 | Y13336 | d | | *Rattus norvegicus* DAD-1 gene |
| 2202 | 406 | Z11995 | o, General | | *R. norvegicus* mRNA encoding 45 kDa protein which binds to heymann nephritis antigen gp330 |
| 2203 | 18352 | Z12298 | t | decorin | decorin |
| 2204 | 17481 | Z49761 | k | | *R. norvegicus* mRNA for RT1.Ma |
| 2205 | 8664 | Z75029 | r, v | Heat shock protein 70-1 | ESTs, Moderately similar to T17342 hypothetical protein DKFZp586K1924.1 [*H. sapiens*], Heat shock protein 70-1 |
| 2206 | 2459 | AA964755 | cc | | ESTs |
| 2207 | 23830 | AA956638 | aa | | ESTs |
| 2208 | 6100 | X73524 | x | desmin | desmin |
| 2209 | 439 | Z22607 | w | Bone morphogenetic protein 4 | Bone morphogenetic protein 4 |
| 2210 | 8665 | AI071965 | v | Heat shock protein 70-1 | ESTs, Moderately similar to T17342 hypothetical protein DKFZp586K1924.1 [*H. sapiens*], Heat shock protein 70-1 |
| 2211 | 155 | U32681 | t | crp-ductin | crp-ductin |
| 2212 | 19252 | AA892041 | s | HMm: peroxiredoxin 5 | *Rattus norvegicus* mRNA for thiol-specific antioxidant protein (1-Cys peroxiredoxin) |
| 2213 | 15582 | AI232320 | q | | Rat mitochondrial 3-hydroxy-3-methylglutaryl-CoA synthase mRNA, complete cds |
| 2214 | 17541 | M26125 | n | Epoxide hydrolase 1 (microsomal xenobiotic hydrolase) | Epoxide hydrolase 1 (microsomal xenobiotic hydrolase) |
| 2215 | 18609 | M30689 | j | | Rat Ly6-B antigen mRNA, complete cds |
| 2216 | 6262 | AI177125 | g | | ESTs |
| 2217 | 23859 | AI072161 | f | | ESTs |

TABLE 1-continued

SUMMARY

| Sequence ID No. | Identifier | GenBank Acc/ Ref. Seq ID | Model Code | Gene Name | Unigene Cluster Title |
|---|---|---|---|---|---|
| 2218 | 21011 | H32189 | e | Glutathione-S-transferase, mu type 2 (Yb2) | Glutathione-S-transferase, mu type 2 (Yb2) |
| 2220 | 2572 | AI177143 | b | | ESTs |
| 2221 | 25419 | M22922 | a | | |

TABLE 2

PATHWAYS

| Sequence ID No. | Identifier | GenBank Acc/ Ref. Seq. ID No. | Model Code | Pathways |
|---|---|---|---|---|
| 1 | 6949 | AA012785 | q | |
| 2 | 25098 | AA108277 | h, v | |
| 3 | 17312 | AA108308 | r | |
| 4 | 16882 | AA684537 | o | |
| 5 | 6049 | AA685178 | y | |
| 6 | 4426 | AA685974 | l, m | |
| 7 | 21815 | AA686423 | g | |
| 8 | 1600 | AA686470 | i | |
| 8 | 1599 | AA686470 | i | |
| 9 | 21997 | AA799325 | u | |
| 10 | 18396 | AA799330 | v | |
| 11 | 6581 | AA799412 | f, l | |
| 12 | 16538 | AA799449 | k | |
| 13 | 23294 | AA799472 | u | |
| 14 | 18290 | AA799497 | r | |
| 15 | 18981 | AA799523 | e | |
| 16 | 20843 | AA799545 | h | |
| 17 | 16993 | AA799560 | b | |
| 18 | 16576 | AA799570 | d | |
| 19 | 18361 | AA799591 | i | |
| 20 | 17712 | AA799598 | z | |
| 22 | 18346 | AA799718 | f | |
| 23 | 8768 | AA799726 | l | |
| 24 | 11687 | AA799732 | w | |
| 25 | 18349 | AA799744 | u | |
| 26 | 17494 | AA799751 | n | |
| 27 | 18360 | AA799771 | General | |
| 28 | 18880 | AA799801 | w | |
| 29 | 20998 | AA799803 | z | |
| 30 | 21006 | AA799861 | c | |
| 31 | 15011 | AA799893 | General | |
| 32 | 20811 | AA799899 | a | |
| 33 | 23202 | AA799971 | General | |
| 34 | 4832 | AA800190 | b | |
| 35 | 21656 | AA800202 | d | |
| 36 | 18433 | AA800218 | j, y, z | |
| 37 | 6386 | AA800235 | u | |
| 38 | 18442 | AA800258 | h, k | |
| 39 | 21092 | AA800380 | y | |
| 40 | 17325 | AA800587 | General | |
| 41 | 13930 | AA800613 | cc, General | |
| 42 | 21372 | AA800693 | v | |
| 42 | 21373 | AA800693 | s | |
| 43 | 18161 | AA800701 | k | |
| 44 | 6595 | AA800753 | w | |
| 45 | 13348 | AA800928 | General | |
| 46 | 23115 | AA801165 | o, y | |
| 47 | 12399 | AA801307 | General | |
| 48 | 7543 | AA801395 | General | |
| 49 | 24237 | AA817726 | t, General | |
| 50 | 11215 | AA817921 | o | |
| 51 | 5985 | AA818005 | g | |
| 52 | 11338 | AA818016 | x | |
| 53 | 2845 | AA818026 | k, General | |
| 54 | 16756 | AA818089 | i, k, General | |
| 55 | 17771 | AA818224 | e, g, p, General | |
| 56 | 6522 | AA818261 | g, m | |
| 57 | 5924 | AA818359 | y | |
| 58 | 7806 | AA818421 | b, aa | |

TABLE 2-continued

| | | | PATHWAYS | |
|---|---|---|---|---|
| Sequence ID No. | Identifier | GenBank Acc/ Ref. Seq. ID No. | Model Code | Pathways |
| 59 | 8237 | AA818512 | v | |
| 60 | 17434 | AA818574 | h | |
| 61 | 8728 | AA818615 | General | |
| 62 | 6054 | AA818658 | b, v, cc, General | |
| 63 | 11590 | AA818721 | d | |
| 64 | 4291 | AA818741 | q, General | |
| 65 | 4330 | AA818747 | o, General | |
| 66 | 19723 | AA818761 | v, General | |
| 67 | 13684 | AA818770 | h, j, l, m | |
| 68 | 6322 | AA818801 | k | |
| 69 | 7690 | AA818875 | General | |
| 70 | 4952 | AA818907 | q, General | |
| 71 | 6094 | AA818911 | t | |
| 72 | 10985 | AA818998 | o, General | |
| 73 | 6120 | AA819008 | t | |
| 74 | 2586 | AA819081 | c | |
| 76 | 6438 | AA819269 | o | |
| 77 | 24721 | AA819306 | d, w | |
| 78 | 6250 | AA819376 | o, y | |
| 80 | 6281 | AA819517 | j | |
| 81 | 10141 | AA819526 | j | |
| 82 | 6551 | AA819558 | t | |
| 83 | 6723 | AA819653 | r | |
| 84 | 14958 | AA819744 | aa | |
| 85 | 19433 | AA819776 | v | |
| 86 | 6204 | AA819889 | aa | |
| 87 | 22820 | AA848315 | General | Purine metabolism |
| 88 | 6614 | AA848389 | bb | |
| 89 | 21125 | AA848437 | General | |
| 90 | 23504 | AA848496 | q | |
| 91 | 18532 | AA848675 | g | |
| 92 | 21140 | AA848738 | c | |
| 93 | 16128 | AA848807 | o | |
| 94 | 22923 | AA848929 | g | |
| 95 | 17339 | AA849497 | General | |
| 96 | 11727 | AA849518 | i | |
| 97 | 21275 | AA849796 | i, l, m, General | |
| 98 | 16678 | AA849827 | aa | |
| 99 | 8515 | AA849917 | e | |
| 100 | 18447 | AA849939 | General | |
| 101 | 12130 | AA850037 | p | |
| 102 | 23981 | AA850040 | x, aa | |
| 103 | 13615 | AA850364 | t | |
| 105 | 2637 | AA850893 | x | |
| 106 | 22093 | AA850909 | d | |
| 107 | 21766 | AA850916 | c | |
| 108 | 2847 | AA850919 | w | |
| 109 | 12162 | AA850975 | h | |
| 110 | 9514 | AA850978 | General | |
| 111 | 3924 | AA851017 | e, q | |
| 111 | 3925 | AA851017 | o, General | |
| 112 | 4490 | AA851184 | a, k | |
| 113 | 19187 | AA851230 | General | |
| 114 | 19189 | AA851237 | c | |
| 115 | 15386 | AA851241 | m | |
| 116 | 21462 | AA851261 | g, l, General | |
| 117 | 21471 | AA851343 | General | |
| 118 | 16902 | AA851379 | p | Oxidative phosphorylation, Ubiquinone biosynthesis |
| 119 | 23376 | AA851392 | i, x | |
| 119 | 23377 | AA851392 | x | |
| 120 | 13349 | AA851417 | General | |
| 121 | 21527 | AA851733 | r, u | |
| 122 | 4048 | AA851814 | i, o, u, General | |
| 123 | 10561 | AA851871 | bb | |
| 124 | 17411 | AA858621 | j, y | |
| 125 | 1801 | AA858636 | k, s, x, bb | |
| 126 | 18350 | AA858674 | p | |
| 127 | 19484 | AA858693 | e | |
| 128 | 6360 | AA858696 | d | |
| 129 | 17334 | AA858704 | p | |
| 130 | 6360 | AA858758 | q | |
| 131 | 13219 | AA858759 | a | |
| 132 | 6384 | AA858788 | l, m, General | |

TABLE 2-continued

| | | | PATHWAYS | |
|---|---|---|---|---|
| Sequence ID No. | Identifier | GenBank Acc/ Ref. Seq. ID No. | Model Code | Pathways |
| 134 | 13412 | AA858830 | p | |
| 135 | 7279 | AA858892 | f | |
| 136 | 18217 | AA858930 | t | |
| 137 | 5867 | AA858953 | v, General | Alanine and aspartate metabolism, Aminoacyl-tRNA biosynthesis |
| 138 | 14479 | AA858969 | r | |
| 139 | 6431 | AA859085 | t | |
| 140 | 17361 | AA859114 | o, General | |
| 141 | 21025 | AA859241 | General | |
| 142 | 10076 | AA859271 | c | |
| 143 | 21791 | AA859333 | k | |
| 144 | 16314 | AA859348 | cc, General | |
| 145 | 18862 | AA859520 | f | |
| 146 | 15059 | AA859545 | r | |
| 147 | 19894 | AA859581 | s | |
| 148 | 14353 | AA859585 | h | |
| 149 | 16318 | AA859648 | h | |
| 150 | 17316 | AA859652 | General | |
| 151 | 19067 | AA859663 | n, q | |
| 152 | 22406 | AA859680 | n | |
| 153 | 20599 | AA859690 | x | |
| 154 | 14261 | AA859693 | u | |
| 155 | 14138 | AA859700 | v | Porphyrin and chlorophyll metabolism |
| 155 | 14139 | AA859700 | v | Porphyrin and chlorophyll metabolism |
| 157 | 22374 | AA859804 | l | |
| 158 | 22385 | AA859805 | b, k | |
| 159 | 22773 | AA859885 | n | |
| 160 | 22816 | AA859898 | k, x, z | |
| 161 | 11891 | AA859926 | x | |
| 162 | 23070 | AA859942 | k | |
| 163 | 23121 | AA859948 | k | |
| 164 | 23166 | AA859954 | cc, General | |
| 165 | 18468 | AA859966 | aa | |
| 166 | 23336 | AA859981 | q | Inositol phosphate metabolism |
| 167 | 4222 | AA860024 | a, bb | |
| 168 | 13974 | AA860030 | u, x, General | |
| 169 | 7090 | AA860039 | x | |
| 170 | 23769 | AA860055 | k, x | |
| 171 | 16323 | AA866240 | w | |
| 172 | 4462 | AA866264 | General | |
| 173 | 15884 | AA866276 | k | |
| 174 | 17742 | AA866302 | c, y | Phenylalanine metabolism, Tyrosine metabolism |
| 175 | 16333 | AA866414 | a, h | |
| 176 | 18918 | AA866444 | p, q | |
| 177 | 16853 | AA866454 | j, l, m, y, z | |
| 178 | 18995 | AA866459 | h, m | |
| 179 | 16013 | AA866482 | s | |
| 180 | 26036 | AA874849 | r | |
| 181 | 16059 | AA874857 | h | |
| 182 | 16069 | AA874873 | r | |
| 183 | 21633 | AA874951 | f | |
| 184 | 16192 | AA874995 | w | |
| 185 | 16254 | AA875025 | j | |
| 186 | 16312 | AA875032 | cc, General | |
| 187 | 20701 | AA875097 | b | |
| 188 | 16416 | AA875098 | bb | |
| 189 | 16419 | AA875102 | bb | |
| 190 | 15313 | AA875126 | l, m, General | |
| 191 | 10936 | AA875146 | w | |
| 192 | 18084 | AA875186 | h | |
| 193 | 15371 | AA875205 | u | |
| 194 | 15401 | AA875257 | x, z | |
| 195 | 15410 | AA875268 | p, s | Oxidative phosphorylation, Ubiquinone biosynthesis |
| 196 | 15420 | AA875286 | f | |
| 197 | 15446 | AA875327 | s, w | |
| 198 | 7936 | AA875495 | b, General | |
| 199 | 17314 | AA875509 | i, l, m | |
| 200 | 24472 | AA875523 | k | |
| 201 | 15587 | AA875577 | j | |
| 202 | 15617 | AA875620 | General | |
| 202 | 15618 | AA875620 | General | |
| 203 | 5384 | AA891041 | f, cc, General | |

TABLE 2-continued

PATHWAYS

| Sequence ID No. | Identifier | GenBank Acc/ Ref. Seq. ID No. | Model Code | Pathways |
|---|---|---|---|---|
| 204 | 24814 | AA891209 | f, p | |
| 205 | 21930 | AA891322 | d | |
| 206 | 17225 | AA891553 | h | |
| 207 | 7522 | AA891571 | j, m | |
| 208 | 9071 | AA891578 | b | |
| 209 | 19321 | AA891666 | u | |
| 210 | 17693 | AA891737 | j, l, m, n, y, z | |
| 211 | 17256 | AA891739 | General | |
| 213 | 18269 | AA891769 | General | |
| 214 | 9905 | AA891774 | s, bb, General | |
| 215 | 17061 | AA891812 | d | |
| 216 | 7050 | AA891824 | h | |
| 217 | 4463 | AA891831 | General | |
| 218 | 14289 | AA891838 | i | |
| 219 | 20523 | AA891842 | r, cc | |
| 220 | 17779 | AA891914 | g, s, z | |
| 221 | 17438 | AA891943 | General | |
| 222 | 22862 | AA891944 | p | |
| 223 | 1159 | AA891949 | e, z | |
| 224 | 4473 | AA891965 | General | |
| 225 | 6362 | AA892053 | f, j, l, m | |
| 226 | 9037 | AA892066 | y | |
| 227 | 19469 | AA892112 | General | |
| 228 | 14595 | AA892128 | o, t, v | |
| 229 | 16527 | AA892154 | cc | |
| 230 | 4482 | AA892173 | bb | |
| 231 | 20917 | AA892238 | h | |
| 232 | 2357 | AA892268 | d | |
| 233 | 18183 | AA892271 | h | |
| 234 | 6523 | AA892299 | d | |
| 236 | 13647 | AA892367 | a | |
| 237 | 3473 | AA892378 | v | |
| 238 | 17682 | AA892382 | j, p, s, x, General | |
| 239 | 820 | AA892395 | g, s | Carbon fixation, Fructose and mannose metabolism, Glycolysis/ Gluconeogenesis, Inosital metabolism, Pentose phosphate cycle |
| 240 | 14754 | AA892414 | u | |
| 241 | 17439 | AA892446 | f | |
| 242 | 16469 | AA892462 | p | |
| 243 | 13609 | AA892468 | i, General | |
| 243 | 13610 | AA892468 | n, v, General | |
| 244 | 9254 | AA892470 | n, u | |
| 245 | 11991 | AA892483 | s | |
| 246 | 1522 | AA892486 | f | |
| 247 | 11994 | AA892507 | aa | |
| 248 | 23888 | AA892520 | w | |
| 248 | 23889 | AA892520 | h | |
| 249 | 8599 | AA892522 | p | |
| 250 | 15154 | AA892532 | p | |
| 251 | 17468 | AA892545 | r | |
| 252 | 11203 | AA892554 | f, h | |
| 253 | 18906 | AA892561 | a, bb, General | |
| 254 | 19327 | AA892562 | f, j, y, z | |
| 255 | 18274 | AA892572 | p | |
| 256 | 4512 | AA892578 | cc | |
| 257 | 15876 | AA892582 | w | |
| 258 | 19085 | AA892598 | General | |
| 258 | 19086 | AA892598 | General | |
| 259 | 20065 | AA892647 | l | |
| 260 | 20088 | AA892666 | a, n | |
| 261 | 23783 | AA892773 | n | |
| 262 | 17549 | AA892776 | f, z | |
| 263 | 13542 | AA892798 | b | |
| 264 | 22537 | AA892799 | General | Glyoxylate and dicarboxylate metabolism, Pyruvate metabolism |
| 264 | 22539 | AA892799 | v | Glyoxylate and dicarboxylate metabolism, Pyruvate metabolism |
| 264 | 22538 | AA892799 | General | Glyoxylate and dicarboxylate metabolism, Pyruvate metabolism |
| 265 | 6951 | AA892820 | h | |
| 266 | 23322 | AA892821 | j, z | |
| 267 | 17923 | AA892843 | f | |
| 268 | 22871 | AA892859 | m | |

TABLE 2-continued

PATHWAYS

| Sequence ID No. | Identifier | GenBank Acc/ Ref. Seq. ID No. | Model Code | Pathways |
|---|---|---|---|---|
| 269 | 9053 | AA892861 | p, v, General | |
| 270 | 16482 | AA892940 | w | |
| 271 | 12020 | AA893035 | j, y | |
| 272 | 3863 | AA893060 | General | |
| 273 | 13332 | AA893080 | i, General | |
| 274 | 21305 | AA893082 | General | |
| 275 | 16591 | AA893191 | j, z | |
| 276 | 17447 | AA893192 | General | |
| 277 | 3876 | AA893205 | n | |
| 278 | 3878 | AA893230 | General | |
| 279 | 20986 | AA893242 | q | Fatty acid metabolism |
| 280 | 16168 | AA893280 | i, z, General | |
| 281 | 3886 | AA893289 | j, m, y | |
| 282 | 15209 | AA893327 | y | |
| 283 | 17800 | AA893436 | cc | |
| 284 | 17836 | AA893626 | h | |
| 285 | 9084 | AA893717 | x | |
| 286 | 22731 | AA893743 | d | |
| 287 | 12031 | AA893860 | v | Aminoacyl-tRNA biosyntheis, Glycine, serine and threonine metabolism |
| 288 | 17897 | AA893905 | k | |
| 289 | 3447 | AA893982 | d | |
| 290 | 22583 | AA894009 | n | |
| 291 | 10540 | AA894027 | j | |
| 292 | 4569 | AA894059 | x | |
| 293 | 18419 | AA894130 | d | |
| 294 | 17336 | AA894297 | j | |
| 295 | 19120 | AA894318 | f, j | |
| 296 | 19762 | AA899113 | i | |
| 297 | 18286 | AA899219 | u | |
| 298 | 22051 | AA899498 | w | |
| 298 | 22052 | AA899498 | q | |
| 299 | 21628 | AA899563 | aa | |
| 300 | 4262 | AA899590 | i | |
| 301 | 4661 | AA899709 | t, General | |
| 302 | 21354 | AA899721 | q | |
| 303 | 17905 | AA899762 | General | |
| 304 | 15231 | AA899840 | r | |
| 305 | 23778 | AA899854 | c, k, x | |
| 306 | 22060 | AA899898 | b | |
| 307 | 9114 | AA899951 | v, General | |
| 308 | 8988 | AA900148 | f | |
| 309 | 11841 | AA900247 | v | |
| 310 | 4725 | AA900290 | cc | |
| 311 | 4747 | AA900465 | General | |
| 312 | 20988 | AA900562 | o | |
| 313 | 3822 | AA900863 | b, g, General | |
| 315 | 12420 | AA901017 | b | |
| 316 | 4849 | AA901155 | s | |
| 317 | 3959 | AA901338 | General | |
| 318 | 22846 | AA923982 | a, d | |
| 319 | 4895 | AA923999 | k | |
| 320 | 21546 | AA924188 | cc, General | |
| 321 | 24192 | AA924210 | n, General | |
| 322 | 4933 | AA924301 | g, l, General | |
| 323 | 4944 | AA924405 | l, General | |
| 324 | 4948 | AA924428 | r | |
| 325 | 4949 | AA924432 | General | |
| 326 | 18891 | AA924598 | e | |
| 327 | 22540 | AA924630 | v, General | Glyoxylate and dicarboxylate metabolism, Pyruvate metabolism |
| 327 | 22541 | AA924630 | General | Glyoxylate and dicarboxylate metabolism, Pyruvate metabolism |
| 328 | 14759 | AA924766 | k | |
| 329 | 23123 | AA924794 | x | |
| 330 | 4067 | AA924813 | g, p | |
| 331 | 2888 | AA924902 | r, General | |
| 332 | 18130 | AA924964 | d | |
| 333 | 23141 | AA925019 | r | |
| 334 | 23195 | AA925026 | General | |
| 335 | 21458 | AA925049 | f, aa, General | |
| 336 | 5073 | AA925061 | m | |
| 337 | 14790 | AA925087 | o, General | |
| 338 | 5089 | AA925126 | g | |

TABLE 2-continued

| Sequence ID No. | Identifier | GenBank Acc/ Ref. Seq. ID No. | Model Code | Pathways |
|---|---|---|---|---|
| 339 | 23261 | AA925145 | k, General | |
| 340 | 17363 | AA925150 | a | |
| 341 | 23448 | AA925167 | l | |
| 342 | 23159 | AA925318 | e | |
| 343 | 21500 | AA925353 | k | |
| 344 | 22479 | AA925418 | t | |
| 345 | 21151 | AA925539 | b | |
| 346 | 16944 | AA925541 | f | |
| 346 | 16945 | AA925541 | t | |
| 347 | 17514 | AA925554 | bb | Oxidative phosphorylation |
| 348 | 5183 | AA925662 | i, General | |
| 349 | 23189 | AA925844 | r | |
| 350 | 23190 | AA925863 | aa | |
| 351 | 5252 | AA926051 | General | |
| 352 | 22967 | AA926080 | h, cc | |
| 353 | 17157 | AA926129 | b | |
| 354 | 13411 | AA926196 | u, General | |
| 355 | 5295 | AA926247 | General | |
| 356 | 22928 | AA926262 | General | |
| 357 | 8948 | AA926316 | r | |
| 358 | 21798 | AA926365 | aa | |
| 359 | 9942 | AA942697 | s | |
| 360 | 6039 | AA942716 | x, General | |
| 361 | 11174 | AA942745 | g, o, w | |
| 362 | 23005 | AA942770 | g | |
| 363 | 21318 | AA942774 | General | |
| 364 | 6615 | AA942889 | v | |
| 365 | 6691 | AA943028 | c | |
| 366 | 22142 | AA943066 | p | |
| 367 | 21993 | AA943149 | v, General | |
| 368 | 9061 | AA943508 | General | |
| 369 | 24390 | AA943531 | b, j, n, y | |
| 370 | 13976 | AA943532 | f, s, x | |
| 371 | 22248 | AA943537 | cc, General | |
| 372 | 22257 | AA943558 | m | |
| 373 | 12673 | AA943773 | u, cc, General | |
| 374 | 13641 | AA944154 | u | |
| 375 | 2658 | AA944155 | f | |
| 376 | 12770 | AA944161 | d | |
| 377 | 20903 | AA944180 | i, x | |
| 378 | 13507 | AA944244 | v | |
| 379 | 15596 | AA944353 | General | |
| 380 | 22681 | AA944413 | i, v, cc, General | |
| 381 | 6711 | AA944439 | General | |
| 382 | 14763 | AA944481 | i, q, General | |
| 383 | 22466 | AA944605 | h | |
| 384 | 12301 | AA944727 | b | |
| 385 | 7023 | AA944792 | d, m, aa | Purine metabolism, Pyrimidine metabolism, RNA polymerase |
| 386 | 22536 | AA944803 | bb | |
| 387 | 22501 | AA944811 | g, l | |
| 388 | 23967 | AA944831 | s | |
| 389 | 26084 | AA944922 | i | |
| 390 | 11974 | AA944958 | General | |
| 391 | 22547 | AA944970 | aa | |
| 392 | 22554 | AA945076 | z, General | |
| 393 | 14352 | AA945181 | General | |
| 395 | 1798 | AA945569 | General | |
| 396 | 22050 | AA945604 | i, aa | |
| 397 | 19731 | AA945615 | d, o | |
| 398 | 22612 | AA945624 | a, General | |
| 399 | 22618 | AA945656 | aa | |
| 400 | 11871 | AA945679 | v | |
| 401 | 22656 | AA945818 | General | |
| 402 | 6720 | AA945828 | p | |
| 403 | 22351 | AA945867 | m | |
| 404 | 22665 | AA945877 | f | |
| 405 | 24243 | AA945950 | b | |
| 406 | 22689 | AA945962 | General | |
| 407 | 22692 | AA945986 | d | |
| 408 | 22696 | AA945996 | c, General | |
| 408 | 22697 | AA945996 | c, o | |
| 409 | 22658 | AA945998 | w | |
| 410 | 20832 | AA946040 | s | Oxidative phosphorylation |

TABLE 2-continued

| Sequence ID No. | Identifier | GenBank Acc/ Ref. Seq. ID No. | Model Code | Pathways |
|---|---|---|---|---|
| 411 | 18337 | AA946046 | General | |
| 412 | 825 | AA946108 | General | |
| 413 | 8639 | AA946221 | e, cc, General | |
| 414 | 23237 | AA946224 | f | |
| 415 | 15600 | AA946250 | o, aa | |
| 416 | 19387 | AA946275 | t | |
| 417 | 6351 | AA946344 | d | |
| 418 | 22057 | AA946348 | e | |
| 419 | 22069 | AA946349 | aa | |
| 420 | 13962 | AA946351 | General | |
| 421 | 18280 | AA946361 | g | |
| 422 | 18944 | AA946391 | v | |
| 424 | 21410 | AA946408 | t | |
| 425 | 643 | AA946439 | o, y | |
| 426 | 20736 | AA946443 | x | |
| 427 | 21878 | AA946448 | r | |
| 428 | 21947 | AA946451 | bb | |
| 429 | 17499 | AA946467 | General | |
| 430 | 1809 | AA946503 | x, General | |
| 431 | 23360 | AA955104 | f | |
| 432 | 23471 | AA955162 | General | |
| 433 | 9452 | AA955206 | b, General | |
| 434 | 23512 | AA955282 | General | |
| 435 | 22596 | AA955298 | General | |
| 436 | 23283 | AA955391 | h | |
| 437 | 23546 | AA955393 | General | |
| 438 | 12404 | AA955408 | b | |
| 439 | 23626 | AA955540 | aa | |
| 441 | 17540 | AA955914 | bb | |
| 442 | 24277 | AA955962 | General | |
| 443 | 19939 | AA955980 | General | |
| 444 | 24000 | AA956005 | i | |
| 445 | 11050 | AA956164 | s, v | |
| 446 | 498 | AA956278 | a, General | |
| 447 | 23409 | AA956294 | q | |
| 449 | 23773 | AA956476 | f, x | |
| 450 | 23799 | AA956530 | d | |
| 451 | 23800 | AA956534 | aa | |
| 452 | 23834 | AA956659 | cc, General | |
| 453 | 16425 | AA956688 | f, x | |
| 454 | 23847 | AA956723 | s | |
| 455 | 23852 | AA956746 | j, l, m, z | |
| 456 | 5989 | AA956907 | g, s | |
| 456 | 5990 | AA956907 | General | |
| 457 | 23957 | AA957123 | u, General | |
| 458 | 22357 | AA957264 | General | |
| 459 | 23314 | AA957270 | g, l, m, p, v, cc, General | |
| 460 | 23995 | AA957292 | a, b | |
| 461 | 2702 | AA957307 | General | Aminoacyl-tRNA biosynthesis, Glycine, serine and threonine metabolism |
| 462 | 24040 | AA957422 | c | |
| 463 | 12478 | AA957554 | m | |
| 464 | 21306 | AA957811 | v | |
| 465 | 24183 | AA957889 | t | |
| 466 | 24178 | AA957905 | d | |
| 467 | 17034 | AA953071 | e | |
| 468 | 24053 | AA963092 | General | |
| 469 | 2767 | AA963201 | o | |
| 470 | 2022 | AA963259 | g | |
| 471 | 2126 | AA963488 | d | |
| 472 | 24246 | AA963703 | b | |
| 473 | 2195 | AA963746 | General | |
| 474 | 19370 | AA963797 | i | |
| 475 | 2282 | AA964147 | e | |
| 476 | 2284 | AA964152 | x | |
| 478 | 2350 | AA964368 | g, General | |
| 479 | 18830 | AA964496 | aa | |
| 480 | 2392 | AA964541 | b | |
| 481 | 2395 | AA964554 | General | |
| 482 | 2410 | AA964589 | i, aa | |
| 483 | 19145 | AA964613 | t | |
| 484 | 2424 | AA964617 | g | |
| 485 | 3107 | AA964687 | General | |

TABLE 2-continued

| | | | PATHWAYS | |
|---|---|---|---|---|
| Sequence ID No. | Identifier | GenBank Acc/ Ref. Seq. ID No. | Model Code | Pathways |
| 486 | 2457 | AA964752 | q, t | |
| 487 | 6778 | AA964763 | b | |
| 489 | 2468 | AA964807 | l | |
| 490 | 2469 | AA964814 | w | Glutamate metabolism, Glutathione metabolism |
| 491 | 12561 | AA964815 | General | |
| 492 | 2326 | AA964892 | aa | |
| 493 | 21339 | AA964962 | General | |
| 494 | 21390 | AA964988 | General | |
| 495 | 12569 | AA965023 | g | |
| 496 | 2583 | AA965166 | bb | |
| 497 | 15885 | AA965207 | r | |
| 499 | 2905 | AA996727 | b, l, m, u, General | |
| 500 | 2915 | AA996782 | u, bb | |
| 501 | 2920 | AA996813 | d | |
| 502 | 19525 | AA996856 | aa, General | |
| 503 | 2984 | AA997015 | c | |
| 504 | 2986 | AA997028 | General | |
| 505 | 3145 | AA997237 | General | |
| 506 | 19249 | AA997342 | m | |
| 507 | 16883 | AA997345 | General | |
| 508 | 12598 | AA997362 | s | |
| 509 | 3470 | AA997374 | p | |
| 510 | 3180 | AA997425 | t | |
| 511 | 3245 | AA997608 | General | |
| 512 | 3020 | AA997656 | t | |
| 513 | 3269 | AA997800 | x, aa | |
| 514 | 3288 | AA997877 | f | |
| 515 | 23992 | AA998164 | k, x | |
| 516 | 17470 | AA998264 | b | |
| 517 | 3773 | AA998356 | General | |
| 518 | 19623 | AA998422 | General | |
| 519 | 3572 | AA998516 | x | |
| 520 | 2782 | AA998565 | c | |
| 521 | 26119 | AA998576 | i, r, w, General | |
| 522 | 22737 | AA998660 | aa | |
| 523 | 3696 | AA999030 | e | |
| 524 | 3079 | AA999169 | k, x, General | |
| 525 | 3081 | AA999171 | e, p, r | |
| 526 | 3082 | AA999172 | General | Glutamate metabolism, Purine metabolism |
| 527 | 17337 | AB000717 | k | |
| 528 | 1535 | AB000778 | a | |
| 529 | 1382 | AB002406 | k | |
| 530 | 20184 | AB003753 | d | |
| 531 | 4312 | AB010635 | c, i, j, k, y, z | |
| 532 | 21666 | AB012214 | k | Methionine metabolism |
| 533 | 15772 | AB015645 | g | |
| 534 | 1183 | AF013144 | h | |
| 535 | 1582 | AF015911 | h, z | |
| 536 | 11483 | AF020618 | u, cc, General | |
| 537 | 20595 | AF024712 | aa | |
| 538 | 19077 | AF030358 | y, z | |
| 539 | 23044 | AF034218 | General | |
| 540 | 25178 | AF035955 | d | |
| 541 | 1564 | AF035963 | x, bb, General | |
| 542 | 8426 | AF036335 | f | |
| 543 | 21817 | AF036537 | k | |
| 544 | 21145 | AF038571 | General | |
| 545 | 22062 | AF044574 | General | |
| 546 | 13464 | AF047707 | h | |
| 547 | 24024 | AF052695 | x | |
| 548 | 12259 | AF061266 | h | |
| 549 | 4589 | AF062389 | y, z | |
| 550 | 16007 | AF062594 | t | |
| 551 | 15761 | AF062741 | u | |
| 552 | 17426 | AF073839 | p | |
| 553 | 18615 | AF074608 | s | |
| 554 | 15797 | AF084205 | f | |
| 555 | 12932 | AF102552 | s | |
| 556 | 18603 | AI007649 | x | |
| 557 | 22733 | AI007668 | r | |
| 558 | 22746 | AI007672 | r | |
| 559 | 24109 | AI007725 | General | |
| 560 | 15848 | AI007820 | n, v | |

TABLE 2-continued

PATHWAYS

| Sequence ID No. | Identifier | GenBank Acc/ Ref. Seq. ID No. | Model Code | Pathways |
|---|---|---|---|---|
| 561 | 10108 | AI007857 | f | |
| 562 | 6804 | AI007877 | General | |
| 563 | 20099 | AI007893 | f, u | |
| 564 | 11368 | AI007948 | d | |
| 565 | 15849 | AI008074 | h | |
| 566 | 3121 | AI008160 | General | |
| 567 | 16646 | AI008190 | t | |
| 568 | 12683 | AI008203 | x | |
| 569 | 22018 | AI008309 | b | |
| 570 | 23917 | AI008441 | n | |
| 571 | 22599 | AI008458 | General | |
| 572 | 22698 | AI008578 | p, General | |
| 573 | 14405 | AI008579 | r, x | |
| 574 | 4086 | AI008629 | x | |
| 575 | 3808 | AI008643 | j, v, General | |
| 576 | 3931 | AI008697 | l | |
| 577 | 7785 | AI008758 | aa | |
| 578 | 16701 | AI008838 | q | |
| 579 | 21789 | AI008930 | k | |
| 580 | 21895 | AI008971 | General | |
| 581 | 410 | AI008974 | i, aa, General | |
| 582 | 21632 | AI009167 | General | |
| 583 | 21596 | AI009168 | General | |
| 584 | 22801 | AI009197 | General | |
| 585 | 11876 | AI009321 | cc, General | |
| 586 | 2506 | AI009341 | General | |
| 587 | 6382 | AI009362 | General | |
| 588 | 14370 | AI009427 | k | |
| 589 | 19275 | AI009460 | x | |
| 590 | 4154 | AI009467 | g | |
| 591 | 3464 | AI009589 | cc | |
| 592 | 3926 | AI009592 | e | |
| 593 | 19358 | AI009675 | c | |
| 594 | 22545 | AI009747 | g | |
| 595 | 15089 | AI009752 | cc, General | |
| 596 | 5458 | AI009756 | h | |
| 597 | 6844 | AI009770 | e, r, cc | |
| 598 | 15627 | AI009810 | aa | |
| 599 | 22619 | AI009825 | d | |
| 600 | 7857 | AI009898 | j, l, m, z | |
| 601 | 13259 | AI009946 | r | |
| 602 | 21105 | AI010067 | General | |
| 603 | 24627 | AI010102 | aa | |
| 604 | 12716 | AI010178 | General | |
| 605 | 18757 | AI010216 | aa | |
| 606 | 2912 | AI010220 | aa, General | |
| 607 | 3316 | AI010237 | t | |
| 608 | 15644 | AI010256 | General | |
| 609 | 657 | AI010262 | b | |
| 610 | 3271 | AI010303 | b | |
| 611 | 11081 | AI010407 | bb | |
| 612 | 16521 | AI010470 | c, s, t, General | Porphyrin and chlorophyll metabolism |
| 613 | 6927 | AI010542 | General | |
| 614 | 17524 | AI010568 | a, j, y, General | |
| 615 | 6946 | AI010642 | n | |
| 616 | 23509 | AI010962 | aa | |
| 617 | 6044 | AI011285 | t | |
| 618 | 13855 | AI011361 | o | |
| 619 | 21779 | AI011380 | cc | |
| 621 | 12534 | AI011460 | cc | |
| 622 | 12629 | AI011492 | e, f | |
| 623 | 735 | AI011560 | f | |
| 624 | 3941 | AI011598 | General | |
| 625 | 17550 | AI011607 | j, General | |
| 626 | 10636 | AI011634 | e | |
| 627 | 3995 | AI011678 | General | |
| 628 | 16112 | AI011706 | h | |
| 629 | 13354 | AI011757 | c | |
| 630 | 12745 | AI011799 | cc | |
| 631 | 18684 | AI011812 | t | |
| 632 | 4205 | AI011982 | b | |
| 633 | 6518 | AI012114 | General | |
| 634 | 17407 | AI012145 | General | |
| 635 | 13093 | AI012177 | r | |

TABLE 2-continued

PATHWAYS

| Sequence ID No. | Identifier | GenBank Acc/ Ref. Seq. ID No. | Model Code | Pathways |
|---|---|---|---|---|
| 636 | 15395 | AI012216 | f | |
| 637 | 21796 | AI012221 | d, General | |
| 638 | 3981 | AI012235 | i, General | |
| 639 | 6606 | AI012308 | i, r | |
| 640 | 3417 | AI012337 | w | |
| 641 | 24200 | AI012356 | b, t, General | |
| 642 | 7471 | AI012379 | cc | |
| 643 | 7247 | AI012438 | g | |
| 644 | 7127 | AI012464 | p, General | |
| 645 | 3304 | AI012471 | b | |
| 646 | 2311 | AI012485 | aa | |
| 647 | 20817 | AI012589 | g, n, q | Glutathione metabolism |
| 648 | 3493 | AI012590 | v, General | |
| 649 | 8975 | AI012613 | General | |
| 650 | 11335 | AI012619 | j | |
| 651 | 21409 | AI012637 | General | |
| 652 | 8015 | AI012638 | aa | |
| 653 | 8476 | AI012647 | w | |
| 654 | 4232 | AI012958 | e, p, General | |
| 655 | 23128 | AI013011 | General | |
| 656 | 20086 | AI013260 | General | |
| 657 | 11969 | AI013273 | k | |
| 658 | 26147 | AI013387 | aa | |
| 659 | 8815 | AI013437 | p | |
| 660 | 19722 | AI013508 | k | |
| 661 | 6674 | AI013568 | General | |
| 662 | 23145 | AI013647 | o, t | |
| 663 | 15130 | AI013676 | w | |
| 664 | 7274 | AI013715 | aa | |
| 665 | 7276 | AI013730 | e | |
| 666 | 7278 | AI013738 | y, z, aa | |
| 667 | 22592 | AI013740 | s, x, bb, General | |
| 668 | 16584 | AI013765 | w | |
| 669 | 24143 | AI013804 | j, l | |
| 670 | 15928 | AI013829 | a, General | |
| 671 | 21950 | AI013861 | j | Valine, leucine and isoleucine degradation |
| 672 | 3260 | AI013875 | t | |
| 673 | 2708 | AI013882 | d, q | |
| 674 | 8585 | AI013886 | i | |
| 675 | 7299 | AI013911 | p, r, t, General | |
| 676 | 15904 | AI013971 | General | |
| 677 | 12781 | AI014023 | w | |
| 678 | 19372 | AI014135 | aa | |
| 679 | 4241 | AI014140 | w | |
| 680 | 15247 | AI014169 | c, u | |
| 681 | 7315 | AI028831 | n | |
| 682 | 16631 | AI028856 | General | |
| 683 | 23297 | AI028953 | x | |
| 684 | 11326 | AI029015 | b | |
| 685 | 2866 | AI029058 | n, y | |
| 686 | 12812 | AI029126 | General | |
| 687 | 17602 | AI029156 | p | |
| 688 | 7392 | AI029185 | aa | |
| 689 | 6517 | AI029264 | d, k, x | |
| 690 | 7639 | AI029292 | b | |
| 691 | 3874 | AI029428 | i, General | |
| 692 | 12819 | AI029437 | f | |
| 693 | 7452 | AI029466 | r | |
| 694 | 7493 | AI029608 | b | |
| 696 | 7537 | AI029829 | o, General | |
| 697 | 2310 | AI029969 | v | |
| 698 | 7585 | AI030023 | x | |
| 699 | 7586 | AI030024 | b, n | |
| 700 | 14492 | AI030091 | cc | |
| 701 | 10673 | AI030134 | f | |
| 702 | 7615 | AI030163 | o, r | |
| 703 | 2370 | AI030179 | General | |
| 704 | 7681 | AI030449 | n | |
| 705 | 11559 | AI030472 | General | |
| 706 | 7665 | AI030668 | t, bb | |
| 707 | 24222 | AI030704 | k | |
| 708 | 10740 | AI030743 | h | |
| 709 | 10742 | AI030773 | e | |
| 711 | 16169 | AI030932 | General | |

TABLE 2-continued

PATHWAYS

| Sequence ID No. | Identifier | GenBank Acc/ Ref. Seq. ID No. | Model Code | Pathways |
|---|---|---|---|---|
| 712 | 19527 | AI030991 | f | |
| 713 | 22614 | AI031004 | r | |
| 714 | 3167 | AI031012 | e | |
| 715 | 5350 | AI043611 | a | |
| 716 | 7858 | AI043654 | t | |
| 717 | 10784 | AI043678 | d | |
| 718 | 9180 | AI043694 | aa | |
| 719 | 7867 | AI043695 | aa | Glutamate metabolism, Purine metabolism |
| 720 | 7584 | AI043724 | General | |
| 721 | 7895 | AI043768 | e | |
| 722 | 7903 | AI043805 | General | |
| 723 | 7913 | AI043849 | cc | |
| 724 | 3899 | AI043904 | l | |
| 725 | 6766 | AI043914 | f | |
| 726 | 10818 | AI043990 | g, l, m, General | |
| 727 | 7956 | AI044018 | f | |
| 728 | 5393 | AI044170 | p | |
| 729 | 5398 | AI044177 | q | |
| 730 | 5425 | AI044237 | a, d | |
| 731 | 8692 | AI044247 | r | |
| 732 | 5430 | AI044253 | i | |
| 733 | 5461 | AI044338 | g, p, General | |
| 734 | 5464 | AI044345 | i | |
| 735 | 3359 | AI044347 | aa | |
| 737 | 2695 | AI044396 | b | |
| 738 | 5494 | AI044425 | General | |
| 740 | 9882 | AI044588 | j, m | |
| 741 | 5575 | AI044688 | g | |
| 742 | 2348 | AI044794 | General | |
| 743 | 18205 | AI044836 | n | |
| 744 | 5626 | AI044864 | u | |
| 745 | 5630 | AI044869 | f | |
| 746 | 5634 | AI044883 | General | |
| 747 | 4047 | AI044947 | l, m | |
| 748 | 5654 | AI044976 | w | |
| 749 | 5684 | AI045056 | r | |
| 750 | 19235 | AI045074 | General | |
| 751 | 5689 | AI045075 | i, aa, General | |
| 752 | 5711 | AI045151 | General | |
| 753 | 19237 | AI045153 | c | |
| 754 | 9964 | AI045161 | f | |
| 755 | 5735 | AI045223 | f | |
| 756 | 5474 | AI045477 | a, General | |
| 757 | 5811 | AI045502 | d, e | |
| 758 | 5819 | AI045537 | General | |
| 759 | 5839 | AI045594 | i | |
| 760 | 6808 | AI045600 | s | |
| 761 | 17755 | AI045608 | y | |
| 763 | 10020 | AI045632 | a | |
| 764 | 5855 | AI045669 | General | |
| 765 | 5881 | AI045789 | i | |
| 766 | 5897 | AI045862 | General | |
| 767 | 5900 | AI045866 | y, z | |
| 768 | 7540 | AI045882 | o, t, General | |
| 769 | 5329 | AI045970 | p | |
| 770 | 15093 | AI058285 | d | |
| 771 | 8002 | AI058304 | i | |
| 772 | 8017 | AI058341 | c | |
| 773 | 6828 | AI058359 | General | |
| 774 | 8177 | AI058603 | aa | |
| 775 | 3090 | AI058730 | aa | |
| 776 | 10093 | AI058746 | g | |
| 777 | 8143 | AI058759 | General | |
| 778 | 18659 | AI058762 | f | |
| 779 | 8163 | AI058837 | aa | |
| 780 | 4789 | AI058889 | General | |
| 781 | 8221 | AI059061 | General | |
| 782 | 10159 | AI059147 | d | |
| 783 | 8245 | AI059154 | b | |
| 784 | 8283 | AI059290 | n | |
| 785 | 8314 | AI059386 | g, General | |
| 786 | 10200 | AI059444 | i | |
| 787 | 8347 | AI059519 | s | |
| 788 | 18359 | AI059675 | n | |

TABLE 2-continued

| | | PATHWAYS | | |
|---|---|---|---|---|
| Sequence ID No. | Identifier | GenBank Acc/ Ref. Seq. ID No. | Model Code | Pathways |
| 789 | 10281 | AI059947 | b, t | |
| 790 | 8494 | AI059968 | aa | |
| 791 | 8495 | AI059971 | General | |
| 792 | 8496 | AI059974 | General | |
| 793 | 10289 | AI060053 | i | |
| 794 | 8548 | AI060176 | k | |
| 795 | 8565 | AI060236 | t | |
| 796 | 18322 | AI060279 | i, y, z | |
| 797 | 8745 | AI069939 | r | |
| 798 | 8785 | AI070067 | o | |
| 799 | 17506 | AI070068 | cc | |
| 800 | 9067 | AI070087 | General | |
| 801 | 3551 | AI070122 | e | |
| 802 | 4967 | AI070179 | k | |
| 803 | 18 | AI070195 | General | |
| 804 | 24197 | AI070314 | General | |
| 805 | 8869 | AI070330 | r | |
| 806 | 8874 | AI070336 | b, cc | |
| 807 | 10417 | AI070410 | m | |
| 808 | 8901 | AI070419 | aa | |
| 809 | 14424 | AI070421 | l, p, General | |
| 810 | 10434 | AI070497 | General | |
| 811 | 8927 | AI070523 | v | |
| 812 | 8946 | AI070611 | q | |
| 813 | 8950 | AI070621 | w | |
| 814 | 8972 | AI070673 | General | |
| 815 | 8981 | AI070715 | bb | |
| 816 | 26184 | AI070784 | i, l | |
| 817 | 3007 | AI070824 | w | |
| 818 | 8999 | AI070839 | p | |
| 819 | 10477 | AI070868 | e, f | |
| 820 | 24301 | AI070911 | k | |
| 821 | 8721 | AI071024 | General | |
| 822 | 9212 | AI071098 | x | |
| 823 | 1831 | AI071137 | c | |
| 824 | 11005 | AI071139 | r | |
| 825 | 9104 | AI071173 | j, m | |
| 826 | 9583 | AI071185 | General | |
| 827 | 9644 | AI071410 | c | |
| 828 | 16058 | AI071490 | General | Sphingoglycolipid metabolism |
| 829 | 11057 | AI071509 | f, o | |
| 831 | 5695 | AI071566 | bb | |
| 832 | 9671 | AI071568 | w | |
| 833 | 22929 | AI071578 | General | |
| 834 | 9673 | AI071581 | General | |
| 835 | 9699 | AI071646 | General | |
| 837 | 9799 | AI072008 | q, y, z | |
| 838 | 9808 | AI072050 | d | |
| 839 | 22796 | AI072213 | General | |
| 840 | 9271 | AI072405 | v | |
| 841 | 10869 | AI072425 | w | |
| 842 | 21797 | AI072439 | General | |
| 843 | 9306 | AI072521 | r | |
| 844 | 9312 | AI072550 | j | |
| 845 | 10893 | AI072559 | x | |
| 846 | 1501 | AI072634 | cc, General | |
| 847 | 6548 | AI072658 | General | |
| 848 | 9363 | AI072695 | d | |
| 850 | 9409 | AI072841 | n | |
| 851 | 9410 | AI072842 | w | |
| 852 | 9468 | AI073021 | General | |
| 853 | 9518 | AI073223 | f | |
| 854 | 11183 | AI100768 | t | Nitrogen metabolism |
| 855 | 9190 | AI100835 | e | |
| 856 | 2029 | AI100842 | p | |
| 857 | 5687 | AI101006 | e | |
| 858 | 15192 | AI101099 | g, cc | |
| 859 | 17399 | AI101157 | o | |
| 860 | 9339 | AI101160 | l, m, o | |
| 861 | 6321 | AI101256 | General | |
| 862 | 5421 | AI101270 | c | |
| 863 | 11910 | AI101323 | General | |
| 864 | 23140 | AI101608 | e | |
| 865 | 4119 | AI101901 | General | |

TABLE 2-continued

PATHWAYS

| Sequence ID No. | Identifier | GenBank Acc/ Ref. Seq. ID No. | Model Code | Pathways |
|---|---|---|---|---|
| 866 | 16324 | AI102009 | b | |
| 867 | 18642 | AI102023 | o | |
| 868 | 19373 | AI102044 | a | |
| 869 | 7051 | AI102055 | h | |
| 870 | 6544 | AI102064 | c | |
| 871 | 10227 | AI102248 | w | |
| 872 | 23849 | AI102318 | e, q | |
| 873 | 11954 | AI102505 | g, j, s | Oxidative phosphorylation |
| 874 | 2125 | AI102519 | c, k | |
| 875 | 5967 | AI102520 | y | |
| 875 | 5969 | AI102520 | p, w | |
| 876 | 11563 | AI102560 | General | |
| 877 | 15190 | AI102562 | b, g, n, p, v | |
| 878 | 19769 | AI102570 | bb | |
| 879 | 22487 | AI102578 | General | |
| 880 | 19011 | AI102618 | General | |
| 881 | 23837 | AI102620 | q, t | |
| 882 | 23538 | AI102727 | g, General | |
| 883 | 17234 | AI102741 | c | |
| 884 | 5891 | AI102745 | k | |
| 885 | 6796 | AI102753 | General | |
| 886 | 8837 | AI102849 | o, p | |
| 887 | 15861 | AI102868 | i | |
| 888 | 3533 | AI102877 | g | |
| 889 | 13222 | AI102977 | General | |
| 890 | 6806 | AI103018 | o, u | |
| 891 | 10659 | AI103059 | w, cc, General | |
| 892 | 17400 | AI103097 | e | |
| 893 | 3584 | AI103106 | x, aa | |
| 894 | 13298 | AI103143 | r | |
| 895 | 15981 | AI103150 | i, x | |
| 896 | 3475 | AI103245 | w | |
| 898 | 23619 | AI103314 | p | |
| 899 | 24181 | AI103320 | e | |
| 901 | 4355 | AI103410 | General | |
| 902 | 7622 | AI103472 | General | |
| 903 | 20918 | AI103552 | n | |
| 904 | 21579 | AI103572 | General | |
| 905 | 2222 | AI103631 | o | |
| 906 | 2752 | AI103641 | e | |
| 907 | 4856 | AI103708 | i | |
| 908 | 8990 | AI103719 | l, m, y, z | |
| 909 | 15942 | AI103738 | r | |
| 910 | 22885 | AI103828 | e, General | |
| 911 | 15853 | AI103841 | x | |
| 912 | 15050 | AI103911 | j, y | Oxidative phosphorylation |
| 913 | 12376 | AI103939 | u | |
| 914 | 22271 | AI103947 | o, y | |
| 915 | 20833 | AI104035 | f, q | Oxidative phosphorylation |
| 916 | 7010 | AI104099 | w | |
| 917 | 22101 | AI104251 | General | |
| 918 | 22833 | AI104258 | General | |
| 919 | 22211 | AI104279 | g, m | |
| 920 | 10720 | AI104296 | l | |
| 921 | 15416 | AI104340 | i | |
| 922 | 10991 | AI104342 | a | |
| 923 | 18831 | AI104357 | p | |
| 924 | 7223 | AI104373 | e | |
| 925 | 23574 | AI104520 | e, g, s | Oxidative phosphorylation |
| 926 | 18509 | AI104528 | q | |
| 927 | 11680 | AI104605 | v | |
| 928 | 12342 | AI104658 | w | |
| 929 | 23689 | AI104685 | r | |
| 930 | 15377 | AI104821 | o, cc | |
| 931 | 22957 | AI104897 | General | |
| 932 | 18451 | AI104953 | o, s | Oxidative phosphorylation, Type III protein secretion system |
| 933 | 24375 | AI104979 | n, General | |
| 934 | 18278 | AI105080 | bb | |
| 935 | 2196 | AI105243 | g | |
| 936 | 5199 | AI105272 | bb, General | |
| 937 | 12901 | AI105301 | o, s | |
| 938 | 7700 | AI105383 | cc, General | |
| 939 | 13343 | AI105398 | u | |

TABLE 2-continued

PATHWAYS

| Sequence ID No. | Identifier | GenBank Acc/ Ref. Seq. ID No. | Model Code | Pathways |
|---|---|---|---|---|
| 940 | 22931 | AI105417 | e, General | |
| 941 | 23596 | AI105435 | bb | Fatty acid metabolism, Lysine degradation, Tryptophan metabolism |
| 942 | 15893 | AI105465 | o | |
| 943 | 12660 | AI111492 | c | |
| 944 | 4479 | AI111599 | General | |
| 945 | 24211 | AI111853 | k | |
| 946 | 2539 | AI111960 | r | |
| 947 | 5729 | AI111990 | k | |
| 948 | 4049 | AI112012 | i, q, u, General | |
| 949 | 12908 | AI112043 | i | |
| 950 | 20041 | AI112161 | t | |
| 951 | 12937 | AI112462 | General | |
| 952 | 3713 | AI112571 | b | |
| 953 | 12921 | AI112636 | General | |
| 954 | 12965 | AI112926 | General | |
| 955 | 7499 | AI112986 | General | |
| 956 | 4969 | AI113008 | r | |
| 957 | 11817 | AI136295 | f | |
| 959 | 11165 | AI136372 | c | |
| 960 | 4045 | AI136460 | cc | |
| 961 | 12782 | AI136493 | k | |
| 962 | 6850 | AI136665 | h | Purine metabolism, Pyrimidine metabolism |
| 963 | 20920 | AI136891 | p, v | |
| 964 | 6552 | AI137062 | o | |
| 965 | 22722 | AI137211 | i | |
| 966 | 13111 | AI137224 | o, General | |
| 967 | 15969 | AI137302 | e | |
| 968 | 14349 | AI137303 | d | |
| 969 | 9166 | AI137406 | General | |
| 970 | 9525 | AI137516 | r | |
| 971 | 6638 | AI137579 | General | |
| 972 | 7414 | AI137586 | General | |
| 973 | 11321 | AI137752 | z | |
| 974 | 23473 | AI137932 | l | |
| 975 | 13158 | AI138024 | i | |
| 976 | 13467 | AI138034 | cc | |
| 977 | 11377 | AI138105 | y | |
| 978 | 6790 | AI144801 | d, h | |
| 979 | 6506 | AI144919 | j, l, y | |
| 980 | 8027 | AI144958 | i | |
| 982 | 14458 | AI145095 | General | |
| 983 | 7476 | AI145202 | g | |
| 984 | 17545 | AI145384 | e | |
| 985 | 17479 | AI145385 | r | |
| 986 | 4194 | AI145387 | r | |
| 987 | 8634 | AI145722 | g | |
| 988 | 8339 | AI145761 | y, General | |
| 989 | 2059 | AI146005 | h, General | |
| 990 | 23224 | AI146033 | o | |
| 991 | 5232 | AI168942 | bb | Valine, leucine and isoleucine degradation |
| 992 | 18472 | AI168975 | u | |
| 992 | 18473 | AI168975 | u | |
| 993 | 13235 | AI169020 | r | |
| 994 | 11618 | AI169115 | o, y, General | |
| 995 | 17386 | AI169144 | o | |
| 996 | 10984 | AI169156 | o, u | |
| 997 | 8205 | AI169176 | e | |
| 998 | 12979 | AI169177 | e | |
| 999 | 2607 | AI169211 | c | |
| 1000 | 22661 | AI169265 | s, z | Oxidative phosphorylation, Type III protein secretion system |
| 1001 | 13239 | AI169278 | g, j, l, y, z | |
| 1002 | 24162 | AI169279 | m | |
| 1003 | 16879 | AI169284 | o | |
| 1004 | 24213 | AI169289 | p | |
| 1005 | 13240 | AI169311 | cc | |
| 1006 | 5931 | AI169324 | b | |
| 1007 | 20891 | AI169337 | d | |
| 1008 | 11979 | AI169365 | cc | |
| 1009 | 10947 | AI169372 | s | |
| 1010 | 20697 | AI169494 | o, u | |
| 1011 | 8234 | AI169517 | z | |
| 1012 | 18343 | AI169648 | o | |

TABLE 2-continued

PATHWAYS

| Sequence ID No. | Identifier | GenBank Acc/ Ref. Seq. ID No. | Model Code | Pathways |
|---|---|---|---|---|
| 1013 | 10839 | AI169655 | l, m | |
| 1014 | 24146 | AI169668 | j, l | |
| 1015 | 22575 | AI169728 | r | |
| 1016 | 804 | AI169756 | cc | |
| 1017 | 8213 | AI169883 | p | |
| 1018 | 3916 | AI169947 | i, bb | |
| 1019 | 3733 | AI170053 | u, General | |
| 1020 | 14179 | AI170224 | cc | |
| 1021 | 11406 | AI170263 | r | |
| 1022 | 3547 | AI170279 | General | |
| 1023 | 11524 | AI170340 | j, y, z | |
| 1024 | 2729 | AI170363 | e, j | |
| 1025 | 18811 | AI170525 | i | |
| 1026 | 22524 | AI170542 | h | |
| 1027 | 24048 | AI170570 | a, g | |
| 1028 | 5968 | AI170692 | y, aa | |
| 1029 | 9757 | AI170693 | b | |
| 1030 | 18905 | AI170770 | e, s | |
| 1031 | 16170 | AI170894 | i | |
| 1032 | 7089 | AI171185 | c | |
| 1033 | 17591 | AI171354 | b | |
| 1034 | 13285 | AI171361 | h | |
| 1035 | 4428 | AI171362 | a | Oxidative phosphorylation, Ubiquinone biosynthesis |
| 1036 | 18126 | AI171369 | w | |
| 1037 | 23253 | AI171448 | o | |
| 1038 | 4584 | AI171492 | m, General | |
| 1039 | 11158 | AI171542 | r, s | |
| 1040 | 15345 | AI171587 | l | |
| 1041 | 21183 | AI171676 | k | |
| 1042 | 8215 | AI171692 | i | |
| 1043 | 11437 | AI171794 | i | |
| 1044 | 2625 | AI171800 | cc | |
| 1045 | 23579 | AI171802 | v | |
| 1046 | 11708 | AI171807 | l, t | |
| 1047 | 17204 | AI171844 | s, y, z | Oxidative phosphorylation, Type III protein secretion system |
| 1048 | 4420 | AI171916 | m | |
| 1049 | 3266 | AI171948 | l, m | |
| 1050 | 19012 | AI172056 | t | |
| 1051 | 11205 | AI172057 | a, q, bb | |
| 1052 | 6057 | AI172102 | b | |
| 1053 | 19128 | AI172103 | m | |
| 1054 | 15673 | AI172107 | z | |
| 1055 | 6630 | AI172184 | n | |
| 1056 | 11968 | AI172208 | bb | |
| 1057 | 6974 | AI172263 | l, m | |
| 1058 | 23313 | AI172271 | d | |
| 1059 | 2140 | AI172272 | General | |
| 1060 | 15382 | AI172302 | l, p, General | |
| 1061 | 18689 | AI172329 | l | |
| 1062 | 17887 | AI172414 | o | |
| 1063 | 3042 | AI172447 | General | |
| 1064 | 17291 | AI172491 | bb | Citrate cycle (TCA cycle), Glutathione metabolism, Reductive carboxylate cycle (CO2 fixation) |
| 1065 | 26222 | AI172506 | p | |
| 1066 | 13095 | AI172595 | r | |
| 1067 | 8795 | AI172618 | General | |
| 1068 | 6454 | AI175342 | j, l, m, y | |
| 1070 | 4445 | AI175466 | x | |
| 1071 | 3418 | AI175475 | m | |
| 1072 | 18507 | AI175551 | bb | |
| 1073 | 10217 | AI175628 | w | |
| 1074 | 7262 | AI175833 | j, m, x | |
| 1075 | 19004 | AI175875 | r | |
| 1076 | 22352 | AI175959 | l, General | |
| 1077 | 7022 | AI176041 | h, n | |
| 1078 | 21467 | AI176061 | t | |
| 1079 | 18581 | AI176160 | General | |
| 1080 | 14159 | AI176169 | g | |
| 1081 | 21742 | AI176172 | w | |
| 1082 | 10182 | AI176185 | v | |
| 1083 | 22765 | AI176265 | General | |

TABLE 2-continued

| Sequence ID No. | Identifier | GenBank Acc/ Ref. Seq. ID No. | Model Code | Pathways |
|---|---|---|---|---|
| 1084 | 6905 | AI176275 | a | |
| 1085 | 12999 | AI176276 | cc | |
| 1086 | 16438 | AI176294 | e | |
| 1087 | 21130 | AI176298 | y | |
| 1088 | 3014 | AI176362 | e | |
| 1089 | 15015 | AI176363 | r | |
| 1090 | 19006 | AI176393 | x | |
| 1091 | 20001 | AI176396 | o | |
| 1092 | 12174 | AI176435 | j, m | |
| 1093 | 15191 | AI176456 | b, o, t, v, cc | |
| 1094 | 24236 | AI176473 | d, General | |
| 1095 | 16518 | AI176546 | v | |
| 1096 | 2161 | AI176592 | General | |
| 1097 | 12436 | AI176610 | General | |
| 1098 | 2536 | AI176616 | l, v, General | |
| 1099 | 18525 | AI176792 | u | |
| 1100 | 23449 | AI176828 | g | |
| 1101 | 23299 | AI176839 | General | |
| 1102 | 3580 | AI176848 | e | |
| 1103 | 22103 | AI176849 | d, General | |
| 1104 | 16036 | AI176855 | f | |
| 1105 | 15588 | AI176916 | General | |
| 1106 | 16917 | AI176951 | t | |
| 1107 | 16124 | AI176963 | cc | |
| 1108 | 15146 | AI176969 | b, General | |
| 1109 | 5786 | AI177058 | f | |
| 1110 | 2852 | AI177059 | c | |
| 1112 | 3156 | AI177092 | g | |
| 1113 | 14384 | AI177096 | a | Purine metabolism |
| 1114 | 13310 | AI177119 | General | |
| 1115 | 24049 | AI177341 | g, p, s, u | |
| 1116 | 15964 | AI177360 | o, General | |
| 1117 | 14989 | AI177366 | u | |
| 1118 | 7975 | AI177374 | aa | |
| 1119 | 3006 | AI177395 | k | |
| 1120 | 17570 | AI177683 | r | |
| 1121 | 9521 | AI177706 | b | |
| 1122 | 14425 | AI177755 | g, General | |
| 1123 | 10611 | AI177790 | j, m | |
| 1124 | 5356 | AI177813 | cc | |
| 1125 | 11791 | AI177843 | General | |
| 1126 | 14484 | AI177867 | General | |
| 1127 | 5780 | AI177869 | General | |
| 1128 | 19184 | AI178025 | General | |
| 1129 | 6059 | AI178245 | c, General | |
| 1130 | 23248 | AI178267 | y | |
| 1131 | 4073 | AI178272 | o | |
| 1132 | 7838 | AI178291 | e | |
| 1133 | 18996 | AI178326 | y | |
| 1134 | 22488 | AI178392 | b | |
| 1135 | 18800 | AI178504 | n, p, aa | |
| 1136 | 22197 | AI178527 | g, General | |
| 1137 | 3401 | AI178684 | bb | |
| 1138 | 17713 | AI178700 | m | |
| 1139 | 14874 | AI178735 | e | |
| 1140 | 23567 | AI178746 | v, General | |
| 1141 | 18907 | AI178971 | c | |
| 1142 | 20991 | AI178979 | i | |
| 1143 | 5887 | AI179099 | q, t | |
| 1144 | 8477 | AI179167 | b, e, General | |
| 1145 | 3348 | AI179288 | u, v | |
| 1146 | 13608 | AI179314 | e | |
| 1147 | 8849 | AI179315 | g, p | |
| 1148 | 13611 | AI179378 | v, General | |
| 1149 | 15438 | AI179399 | m, x | |
| 1150 | 13614 | AI179407 | e, t, General | |
| 1151 | 15042 | AI179422 | b, General | |
| 1152 | 2768 | AI179481 | i, General | |
| 1153 | 24041 | AI179580 | b, i | |
| 1154 | 19822 | AI179599 | o, General | |
| 1155 | 23270 | AI179601 | q, General | |
| 1156 | 5901 | AI179605 | e | |
| 1157 | 16081 | AI179610 | g, i, p | Porphyrin and chlorophyll metabolism |
| 1158 | 14564 | AI179717 | k | |

TABLE 2-continued

| | | | PATHWAYS | |
|---|---|---|---|---|
| Sequence ID No. | Identifier | GenBank Acc/ Ref. Seq. ID No. | Model Code | Pathways |
| 1159 | 7918 | AI179750 | General | |
| 1160 | 6647 | AI179795 | g | |
| 1161 | 9097 | AI179875 | o, General | |
| 1162 | 23989 | AI179953 | a | |
| 1163 | 12899 | AI179967 | b | |
| 1164 | 1687 | AI179971 | c | |
| 1165 | 22569 | AI179979 | General | |
| 1166 | 23514 | AI179986 | o, General | Glycine, serine and threonine metabolism |
| 1167 | 15892 | AI179988 | c, General | |
| 1168 | 12402 | AI180004 | g | |
| 1169 | 5443 | AI180165 | General | |
| 1170 | 5481 | AI180170 | General | |
| 1171 | 24028 | AI180239 | l | |
| 1172 | 17089 | AI180281 | g | |
| 1173 | 3701 | AI180306 | aa | |
| 1174 | 3352 | AI180334 | m | |
| 1175 | 24368 | AI180392 | l, m | |
| 1176 | 14337 | AI180414 | c | |
| 1177 | 19080 | AI227647 | j, y, z | |
| 1178 | 22838 | AI227667 | aa | |
| 1179 | 6765 | AI227761 | i, General | |
| 1180 | 24054 | AI227867 | General | |
| 1181 | 7324 | AI227885 | i | |
| 1182 | 23898 | AI227987 | d | |
| 1183 | 1651 | AI228068 | n, w | |
| 1184 | 14237 | AI228128 | e | |
| 1185 | 14242 | AI228197 | General | |
| 1186 | 16913 | AI228236 | o | |
| 1187 | 22915 | AI228299 | r | |
| 1188 | 8917 | AI228301 | General | |
| 1189 | 15879 | AI228313 | r, General | |
| 1190 | 13727 | AI228326 | o, General | |
| 1191 | 6102 | AI228335 | General | |
| 1192 | 13730 | AI228356 | a | |
| 1193 | 13745 | AI228494 | b, cc | |
| 1194 | 4217 | AI228587 | s | |
| 1195 | 16053 | AI228596 | cc | |
| 1196 | 3557 | AI228672 | e | |
| 1197 | 11605 | AI228682 | e | |
| 1198 | 13203 | AI228728 | r | |
| 1199 | 13771 | AI228848 | g | |
| 1200 | 5918 | AI229036 | r | |
| 1201 | 8235 | AI229154 | k | |
| 1202 | 16203 | AI229196 | r | |
| 1203 | 13826 | AI229304 | a | |
| 1204 | 13144 | AI229320 | g | |
| 1205 | 4640 | AI229404 | x, aa | |
| 1206 | 23563 | AI229421 | l | |
| 1207 | 15426 | AI229497 | s | |
| 1208 | 15193 | AI229508 | bb | |
| 1209 | 19243 | AI229638 | x | |
| 1210 | 23078 | AI229647 | p | |
| 1211 | 3099 | AI229680 | o | Oxidative phosphorylation, Ubiquinone biosynthesis |
| 1212 | 19508 | AI229698 | bb | |
| 1213 | 13977 | AI229707 | x | |
| 1214 | 23983 | AI229708 | v | |
| 1215 | 2688 | AI229793 | e | |
| 1216 | 13874 | AI229832 | g | |
| 1217 | 12587 | AI229979 | General | |
| 1218 | 20591 | AI229993 | l, m | |
| 1219 | 24042 | AI230002 | a, b, d, General | |
| 1220 | 13880 | AI230042 | u | |
| 1221 | 17672 | AI230074 | d | Oxidative phosphorylation, Ubiquinone biosynthesis |
| 1222 | 3652 | AI230113 | General | |
| 1223 | 18650 | AI230121 | aa | |
| 1224 | 13025 | AI230173 | c | |
| 1225 | 4280 | AI230247 | z | |
| 1226 | 18528 | AI230284 | General | |
| 1227 | 7084 | AI230362 | p | |
| 1228 | 20895 | AI230549 | b, n | |
| 1229 | 12961 | AI230554 | General | |
| 1230 | 15636 | AI230616 | r | |

TABLE 2-continued

PATHWAYS

| Sequence ID No. | Identifier | GenBank Acc/ Ref. Seq. ID No. | Model Code | Pathways |
|---|---|---|---|---|
| 1231 | 4121 | AI230647 | j, m | |
| 1232 | 14388 | AI230702 | General | |
| 1233 | 18529 | AI230716 | x, General | |
| 1234 | 13618 | AI230724 | General | |
| 1235 | 8304 | AI230746 | cc | |
| 1236 | 4731 | AI230773 | e | |
| 1237 | 14430 | AI230798 | c, k, x | |
| 1238 | 16627 | AI230822 | bb | Glycoprotein biosynthesis |
| 1239 | 3125 | AI231028 | General | |
| 1240 | 633 | AI231127 | k | |
| 1241 | 20846 | AI231140 | p | |
| 1242 | 6743 | AI231219 | d | |
| 1244 | 26292 | AI231391 | k | |
| 1245 | 12343 | AI231433 | w | |
| 1246 | 7337 | AI231465 | aa | |
| 1247 | 16321 | AI231506 | General | |
| 1248 | 8004 | AI231532 | j, l | |
| 1249 | 15171 | AI231792 | g | |
| 1250 | 6193 | AI231797 | i | |
| 1252 | 14227 | AI231999 | u | |
| 1253 | 24501 | AI232006 | w, y, bb | |
| 1254 | 3434 | AI232014 | g, q, z, cc, General | |
| 1255 | 19094 | AI232021 | n, General | |
| 1256 | 14020 | AI232076 | u | |
| 1257 | 6726 | AI232157 | d | |
| 1258 | 11549 | AI232174 | l, m | |
| 1259 | 23125 | AI232266 | j, s | |
| 1260 | 2085 | AI232270 | bb | |
| 1261 | 2913 | AI232272 | o | |
| 1262 | 14304 | AI232281 | g | |
| 1263 | 15955 | AI232294 | u, bb, General | |
| 1264 | 15122 | AI232303 | y | |
| 1265 | 4716 | AI232313 | y | |
| 1266 | 15246 | AI232332 | t, u | |
| 1267 | 24321 | AI232340 | o | |
| 1268 | 16172 | AI232341 | d | |
| 1269 | 11411 | AI232346 | h | |
| 1270 | 19287 | AI232379 | f | pdgf |
| 1271 | 5601 | AI232461 | n, General | |
| 1272 | 14051 | AI232489 | l, m | |
| 1273 | 5572 | AI232490 | i, t | |
| 1274 | 11157 | AI232494 | cc | |
| 1275 | 8709 | AI232534 | o | |
| 1276 | 20350 | AI232552 | j, v, y | |
| 1277 | 14069 | AI232631 | e | |
| 1278 | 4440 | AI232643 | w | |
| 1279 | 17695 | AI232784 | e | |
| 1280 | 15796 | AI232874 | v | |
| 1281 | 12467 | AI232924 | General | |
| 1282 | 12873 | AI232984 | i | |
| 1283 | 5355 | AI233031 | r | |
| 1284 | 18794 | AI233121 | c | |
| 1285 | 3823 | AI233147 | b, g, General | |
| 1286 | 11967 | AI233155 | c, k, General | |
| 1287 | 11561 | AI233182 | d | |
| 1288 | 3471 | AI233183 | g | |
| 1289 | 21948 | AI233191 | i | |
| 1290 | 13598 | AI233194 | g, p, y | |
| 1291 | 15552 | AI233195 | y | |
| 1292 | 17907 | AI233224 | bb | |
| 1293 | 14111 | AI233269 | cc | |
| 1294 | 12894 | AI233365 | d | |
| 1295 | 7161 | AI233407 | General | |
| 1296 | 15906 | AI233425 | q | |
| 1297 | 14120 | AI233433 | d | |
| 1298 | 14095 | AI233468 | a, d | |
| 1299 | 3075 | AI233494 | u, aa | |
| 1300 | 6046 | AI233530 | General | |
| 1301 | 18900 | AI233570 | General | |
| 1302 | 7888 | AI233583 | General | Aminoacyl-tRNA biosynthesis, Arginine and proline metabolism |
| 1303 | 16709 | AI233602 | General | Purine metabolism |
| 1304 | 5163 | AI233712 | y | |

TABLE 2-continued

PATHWAYS

| Sequence ID No. | Identifier | GenBank Acc/ Ref. Seq. ID No. | Model Code | Pathways |
|---|---|---|---|---|
| 1305 | 7243 | AI233717 | General | |
| 1306 | 3816 | AI233729 | g | |
| 1307 | 13023 | AI233740 | d, h, General | |
| 1308 | 14871 | AI233743 | g | |
| 1309 | 7469 | AI233767 | cc | |
| 1310 | 7804 | AI233771 | b | |
| 1311 | 13563 | AI233773 | e | |
| 1312 | 2154 | AI233818 | k, cc | |
| 1313 | 16616 | AI234079 | h | |
| 1314 | 13393 | AI234100 | a, d, General | |
| 1315 | 7071 | AI234162 | r | |
| 1316 | 14677 | AI234620 | General | |
| 1317 | 4443 | AI234629 | m | |
| 1318 | 22453 | AI234678 | b | |
| 1319 | 23964 | AI234748 | t, General | |
| 1320 | 19581 | AI234753 | f | |
| 1321 | 22152 | AI234822 | o, General | |
| 1322 | 18942 | AI234865 | d | |
| 1323 | 22662 | AI234939 | aa | Oxidative phosphorylation, Type III protein secretion system |
| 1324 | 3875 | AI235047 | o, General | |
| 1325 | 19479 | AI235135 | o | |
| 1326 | 14906 | AI235192 | g | |
| 1327 | 14718 | AI235210 | e | |
| 1328 | 15004 | AI235224 | b, General | |
| 1329 | 6632 | AI235277 | v | |
| 1330 | 14722 | AI235284 | x, z | |
| 1331 | 1462 | AI235585 | u, General | |
| 1332 | 21061 | AI235631 | l, m | |
| 1333 | 14665 | AI235646 | m | tgf-beta |
| 1334 | 19940 | AI235689 | General | |
| 1335 | 5698 | AI235692 | u | |
| 1336 | 23745 | AI235732 | k | |
| 1337 | 11164 | AI235739 | General | |
| 1338 | 5212 | AI235745 | d | |
| 1339 | 14768 | AI235912 | h | |
| 1340 | 14776 | AI235950 | m | |
| 1341 | 3091 | AI236027 | n, General | |
| 1342 | 14861 | AI236045 | r | |
| 1343 | 14862 | AI236048 | e | |
| 1344 | 16943 | AI236097 | p | |
| 1345 | 8336 | AI236101 | l | |
| 1346 | 23230 | AI236146 | v | |
| 1347 | 22855 | AI236150 | e | |
| 1348 | 14594 | AI236152 | i | |
| 1349 | 18406 | AI236168 | r | |
| 1350 | 15051 | AI236332 | General | |
| 1351 | 19298 | AI236338 | bb | |
| 1352 | 10667 | AI236366 | b | |
| 1353 | 10774 | AI236397 | f | |
| 1354 | 9407 | AI236402 | aa | |
| 1355 | 26335 | AI236460 | General | |
| 1356 | 17950 | AI236590 | t, General | |
| 1357 | 18259 | AI236601 | h, v | |
| 1358 | 11445 | AI236613 | j, y | |
| 1359 | 17248 | AI236635 | o, aa | |
| 1360 | 16859 | AI236753 | t, General | |
| 1361 | 5208 | AI236754 | g | |
| 1362 | 24388 | AI236772 | e, General | |
| 1363 | 15850 | AI236795 | n, v, w | |
| 1364 | 14800 | AI236856 | w | |
| 1366 | 11404 | AI237002 | m | |
| 1367 | 18151 | AI237212 | o, General | |
| 1368 | 21653 | AI237535 | t, General | |
| 1369 | 11208 | AI237586 | z | |
| 1370 | 21893 | AI237713 | i, k, aa | |
| 1371 | 14842 | AI237724 | r | |
| 1372 | 3467 | AI237835 | General | |
| 1373 | 25840 | AI638972 | u | |
| 1374 | 17108 | AI639017 | n | |
| 1375 | 16676 | AI639082 | c, k, x | |
| 1376 | 12400 | AI639107 | k | |
| 1377 | 19952 | AI639108 | q, v | |
| 1379 | 25907 | AI639167 | o, w | |

TABLE 2-continued

PATHWAYS

| Sequence ID No. | Identifier | GenBank Acc/ Ref. Seq. ID No. | Model Code | Pathways |
|---|---|---|---|---|
| 1381 | 18533 | AI639231 | n | |
| 1382 | 18353 | AI639233 | t, aa | |
| 1384 | 15330 | AI639285 | General | |
| 1385 | 20026 | AI639354 | g | |
| 1386 | 25971 | AI639365 | r | |
| 1388 | 19152 | AI639387 | u, General | |
| 1390 | 18338 | AI639422 | y | |
| 1392 | 20082 | AI639488 | i, m | |
| 1394 | 20056 | AI639504 | a, bb, General | |
| 1395 | 4713 | AI639518 | q | |
| 1396 | 14332 | AJ001044 | bb | |
| 1397 | 7602 | AJ001929 | k | |
| 1398 | 9867 | AJ005424 | u | |
| 1400 | 16351 | AJ011811 | General | |
| 1401 | 20116 | AJ011969 | l, General | |
| 1402 | 17635 | AJ223355 | v, w | |
| 1403 | 18686 | D00729 | q | Fatty acid metabolism |
| 1404 | 5049 | D10655 | n, w | |
| 1405 | 25257 | D13623 | j | |
| 1405 | 15281 | D13623 | h | |
| 1406 | 11434 | D14014 | cc | |
| 1407 | 1613 | D14076 | x | |
| 1408 | 1728 | D16479 | q | Bile acid biosynthesis, Fatty acid biosynthesis (path 2), Fatty acid metabolism, Phenylalanine metabolism, Valine, leucine and isoleucine degradation |
| 1409 | 3015 | D16554 | c, s, v, z | |
| 1410 | 472 | D26111 | d, s, bb | |
| 1412 | 16233 | D29960 | j, l | |
| 1413 | 9029 | D30804 | n | |
| 1414 | 1485 | D38222 | y, z | |
| 1415 | 9135 | D45247 | s | Proteasome |
| 1416 | 16354 | D50564 | u | Cysteine metabolism |
| 1417 | 1884 | D50695 | l, m, bb | |
| 1418 | 21147 | D63772 | General | |
| 1419 | 826 | D82928 | f | Glycerolipid metabolism |
| 1420 | 25306 | D84485 | u | |
| 1421 | 18867 | D88250 | t | |
| 1423 | 22543 | H31117 | r, v, General | |
| 1424 | 12360 | H31456 | w | |
| 1425 | 20514 | H31489 | h, j | |
| 1426 | 11358 | H31610 | h | |
| 1427 | 4360 | H31813 | bb, General | |
| 1428 | 9343 | H32169 | l | |
| 1429 | 4386 | H33093 | h, w | |
| 1430 | 4415 | H33636 | h | |
| 1431 | 15374 | H34186 | l | |
| 1432 | 17159 | J00797 | u, General | |
| 1433 | 16260 | J01878 | f | |
| 1434 | 17284 | J02827 | bb | Valine, leucine and isoleucine degradation |
| 1435 | 15017 | J03752 | n | |
| 1436 | 44 | J03819 | p, s | |
| 1437 | 21014 | J03914 | e, r, General | Glutathione metabolism |
| 1438 | 20429 | J05035 | f | Androgen and estrogen metabolism, Bile acid biosynthesis |
| 1439 | 1247 | J05181 | j, l, m, s, y, z | Glutamate metabolism, Glutathione metabolism |
| 1440 | 10464 | J05510 | n, u, General | |
| 1441 | 20149 | K03243 | q | |
| 1442 | 17758 | K03249 | q | |
| 1443 | 381 | L00124 | w | |
| 1444 | 2048 | L00382 | k, x | |
| 1445 | 10500 | L04619 | s | |
| 1447 | 108 | L14002 | p | |
| 1448 | 25366 | L14003 | t | |
| 1449 | 109 | L14004 | c, p | |
| 1450 | 20414 | L14323 | General | |
| 1451 | 25369 | L14937 | y | |
| 1452 | 16119 | L16532 | k | |
| 1453 | 25377 | L25387 | h | |
| 1453 | 12058 | L25387 | h | |
| 1455 | 21146 | L35558 | General | |
| 1456 | 106 | L37203 | w | |

TABLE 2-continued

PATHWAYS

| Sequence ID No. | Identifier | GenBank Acc/ Ref. Seq. ID No. | Model Code | Pathways |
|---|---|---|---|---|
| 1458 | 13682 | L38482 | f, j, k, m, z | |
| 1459 | 6405 | L38615 | p | Glutamate metabolism, Glutathione metabolism |
| 1461 | 15189 | M11794 | n, v | |
| 1462 | 17086 | M13011 | j | |
| 1464 | 21053 | M15481 | o | |
| 1465 | 25405 | M18330 | j, l | |
| 1466 | 25415 | M19648 | a | |
| 1468 | 14967 | M22366 | w | |
| 1469 | 20481 | M22631 | bb | |
| 1471 | 15048 | M24542 | q | Oxidative phospharylation |
| 1472 | 20921 | M29853 | m | |
| 1473 | 1224 | M31931 | u | |
| 1474 | 15579 | M33648 | q | |
| 1474 | 15580 | M33648 | q | |
| 1475 | 17211 | M34331 | g, n, q, v | |
| 1476 | 20699 | M35601 | b, x, bb | |
| 1476 | 20700 | M35601 | b, t, bb | |
| 1477 | 9223 | M36151 | o | |
| 1479 | 1585 | M57728 | j, m, y | |
| 1480 | 24844 | M58040 | c | |
| 1481 | 25057 | M58495 | h | |
| 1482 | 457 | M60666 | d, General | |
| 1483 | 1223 | M75281 | f | |
| 1484 | 5733 | M81855 | i, k, aa | |
| 1485 | 4198 | M83143 | m | |
| 1485 | 4199 | M83143 | m | |
| 1486 | 24651 | M83678 | k, x, z | |
| 1487 | 1430 | M84648 | General | Histidine metabolism, Phenylalanine metabolism, Tryptophan metabolism, Tyrosine metabolism |
| 1488 | 25467 | M93297 | c | Arginine and proline metabolism, Urea cycle and metabolism of amino groups |
| 1489 | 729 | M95762 | a, y | |
| 1490 | 23698 | NM_012489 | q | Bile acid biosynthesis, Fatty acid biosynthesis (path 2), Fatty acid metabolism, Phenylalanine metabolism, Valine, leucine and isoleucine degradation |
| 1490 | 23699 | NM_012489 | q | Bile acid biosynthesis, Fatty acid biosynthesis (path 2), Fatty acid metabolism, Phenylalanine metabolism, Valine, leucine and isoleucine degradation |
| 1491 | 7062 | NM_012495 | q | Carbon fixation, Fructose and mannose metabolism, Glycolysis/ Gluconeogenesis, Inositol metabolism, Pentose phosphate cycle |
| 1492 | 15511 | NM_012498 | u | Fructose and mannose metabolism, Galactose metabolism, Glycerolipid metabolism, Pentose and glucuronate interconversions, Pyruvate metabolism |
| 1494 | 7427 | NM_012515 | General | |
| 1495 | 24433 | NM_012527 | i | |
| 1496 | 4467 | NM_012529 | d | Arginine and proline metabolism, Urea cycle and metabolism of amino groups |
| 1497 | 16520 | NM_012532 | General | Porphyrin and chlorophyll metabolism |
| 1498 | 225 | NM_012544 | x, z | |
| 1499 | 1431 | NM_012545 | General | Histidine metabolism, Phenylalanine metabolism, Tryptophan metabolism, Tyrosine metabolism |
| 1500 | 23868 | NM_012551 | l, m, v, General | |
| 1500 | 23872 | NM_012551 | l, v, cc, General | |
| 1500 | 23869 | NM_012551 | v, General | |
| 1501 | 19407 | NM_012554 | z | Glycolysis/ Gluconeogenesis, Phenylalanine, tyrosine and tryptophan biosynthesis |
| 1501 | 19408 | NM_012554 | n, s, y, z | Glycolysis/ Gluconeogenesis, Phenylalanine, tyrosine and tryptophan biosynthesis |
| 1502 | 21836 | NM_012555 | k | |

TABLE 2-continued

PATHWAYS

| Sequence ID No. | Identifier | GenBank Acc/ Ref. Seq. ID No. | Model Code | Pathways |
|---|---|---|---|---|
| 1503 | 16895 | NM_012558 | g, s | Carbon fixation, Fructose and mannose metabolism, Glycolysis/ Gluconeogenesis, Pentose phosphate cycle |
| 1504 | 25317 | NM_012559 | bb | |
| 1504 | 6477 | NM_012559 | b, bb | |
| 1504 | 6478 | NM_012559 | bb | |
| 1505 | 11731 | NM_012561 | k | |
| 1507 | 4254 | NM_012564 | a | |
| 1508 | 16026 | NM_012578 | r | |
| 1508 | 16024 | NM_012578 | r | |
| 1508 | 16025 | NM_012578 | r | |
| 1509 | 16080 | NM_012580 | g, m | Porphyrin and chlorophyll metabolism |
| 1510 | 15098 | NM_012588 | bb | |
| 1511 | 4450 | NM_012592 | bb | Valine, leucine and isoleucine degradation |
| 1511 | 4451 | NM_012592 | i, bb | Valine, leucine and isoleucine degradation |
| 1511 | 4452 | NM_012592 | bb | Valine, leucine and isoleucine degradation |
| 1512 | 17198 | NM_012593 | a, x | |
| 1512 | 17197 | NM_012593 | x | |
| 1513 | 18749 | NM_012600 | a, h | Carbon fixation, Pyruvate metabolism |
| 1514 | 2628 | NM_012603 | General | |
| 1514 | 2629 | NM_012603 | x, General | |
| 1515 | 16849 | NM_012608 | n, o, q | |
| 1517 | 15540 | NM_012620 | General | |
| 1518 | 24568 | NM_012630 | General | |
| 1518 | 24566 | NM_012630 | General | |
| 1519 | 18553 | NM_012631 | k | |
| 1520 | 1844 | NM_012637 | General | |
| 1521 | 24668 | NM_012642 | f | |
| 1522 | 18632 | NM_012645 | a | |
| 1523 | 25435 | NM_012647 | g | |
| 1524 | 9423 | NM_012649 | b, cc | |
| 1525 | 24496 | NM_012654 | n | |
| 1526 | 7101 | NM_012679 | x, bb, General | |
| 1527 | 24707 | NM_012693 | i | Fatty acid metabolism, Tryptophan metabolism |
| 1528 | 1850 | NM_012696 | t | |
| 1528 | 1854 | NM_012696 | t | |
| 1529 | 1603 | NM_012697 | General | |
| 1530 | 1372 | NM_012734 | u | Aminosugars metabolism, Fructose and mannose metabolism, Galactose metabolism, Glycolysis/ Gluconeogenesis, Starch and sucrose metabolism |
| 1531 | 1478 | NM_012744 | bb, General | Alanine and aspartate metabolism, Citrate cycle (TCA cycle), Pyruvate metabolism |
| 1532 | 343 | NM_012747 | h, t | |
| 1533 | 8829 | NM_012749 | General | |
| 1534 | 20828 | NM_012752 | General | |
| 1534 | 20829 | NM_012752 | i, General | |
| 1534 | 20830 | NM_012752 | i, General | |
| 1535 | 15174 | NM_012756 | b | |
| 1536 | 21685 | NM_012760 | j, m, n | |
| 1537 | 18068 | NM_012762 | t | |
| 1538 | 1246 | NM_012770 | a, General | Purine metabolism |
| 1539 | 1348 | NM_012776 | f | |
| 1540 | 18135 | NM_012791 | w | |
| 1541 | 16947 | NM_012793 | p, bb | Arginine and proline metabolism, Glycine, serine and threonine metabolism, Urea cycle and metabolism of amino groups |
| 1542 | 960 | NM_012796 | u | Glutathione metabolism |
| 1543 | 260 | NM_012798 | f, u | |
| 1544 | 556 | NM_012803 | d | |
| 1545 | 21729 | NM_012804 | q | |
| 1546 | 15032 | NM_012816 | General | |
| 1547 | 24895 | NM_012817 | General | |
| 1548 | 18109 | NM_012823 | u, General | |
| 1549 | 373 | NM_012833 | h, l, q, General | |
| 1550 | 2855 | NM_012838 | e | |
| 1551 | 11136 | NM_012839 | s | |
| 1552 | 20885 | NM_012842 | a | egf |
| 1552 | 20884 | NM_012842 | a, bb | egf |
| 1553 | 18770 | NM_012857 | e | |
| 1554 | 20674 | NM_012861 | i | |
| 1555 | 13151 | NM_012862 | a, r, General | |

TABLE 2-continued

PATHWAYS

| Sequence ID No. | Identifier | GenBank Acc/ Ref. Seq. ID No. | Model Code | Pathways |
|---|---|---|---|---|
| 1556 | 24617 | NM_012870 | General | |
| 1557 | 20945 | NM_012875 | a, v | |
| 1558 | 15872 | NM_012879 | o, r | |
| 1559 | 495 | NM_012880 | z | |
| 1559 | 494 | NM_012880 | c | |
| 1560 | 23651 | NM_012881 | d, u, General | |
| 1562 | 19477 | NM_012891 | q | |
| 1563 | 18564 | NM_012899 | v, General | Porphyrin and chlorophyll metabolism |
| 1564 | 7197 | NM_012904 | f, r, cc, General | |
| 1564 | 7196 | NM_012904 | v, cc, General | |
| 1565 | 20202 | NM_012909 | b, r | |
| 1566 | 16581 | NM_012911 | c, j | |
| 1566 | 16582 | NM_012911 | c | |
| 1567 | 24431 | NM_012912 | General | |
| 1568 | 18118 | NM_012913 | p | Oxidative phosphorylation |
| 1569 | 6108 | NM_012915 | n | |
| 1570 | 20757 | NM_012923 | c, i, aa | |
| 1570 | 20755 | NM_012923 | i | |
| 1571 | 2830 | NM_012925 | f | |
| 1571 | 2831 | NM_012925 | f | |
| 1572 | 1977 | NM_012930 | q | Fatty acid metabolism, Glycerolipid metabolism |
| 1573 | 18694 | NM_012931 | j, l, m, z | |
| 1574 | 13723 | NM_012935 | n | |
| 1575 | 9109 | NM_012939 | j, y, z | |
| 1575 | 19398 | NM_012939 | aa | |
| 1576 | 223 | NM_012945 | b, cc | |
| 1577 | 15058 | NM_012950 | cc | |
| 1579 | 19111 | NM_012963 | g | |
| 1580 | 19374 | NM_012964 | x | |
| 1581 | 2554 | NM_012967 | t | |
| 1581 | 2555 | NM_012967 | t, cc, General | |
| 1582 | 24528 | NM_012973 | c | |
| 1583 | 956 | NM_012976 | c | |
| 1584 | 16417 | NM_012991 | g | |
| 1585 | 17393 | NM_012992 | d | |
| 1586 | 23544 | NM_013013 | s | |
| 1587 | 1588 | NM_013026 | k | |
| 1588 | 17894 | NM_013027 | m | |
| 1589 | 18300 | NM_013030 | s, v, General | |
| 1589 | 18076 | NM_013030 | g, s, z | |
| 1589 | 18078 | NM_013030 | s | |
| 1589 | 18077 | NM_013030 | e, s, z | |
| 1591 | 730 | NM_013040 | w | |
| 1592 | 17401 | NM_013043 | l, o, General | |
| 1593 | 16684 | NM_013052 | General | |
| 1594 | 14421 | NM_013053 | u | |
| 1595 | 15254 | NM_013058 | k | |
| 1596 | 14997 | NM_013059 | s, z | Folate biosynthesis, Glycerolipid metabolism |
| 1596 | 14996 | NM_013059 | General | Folate biosynthesis, Glycerolipid metabolism |
| 1597 | 25676 | NM_013069 | aa | |
| 1597 | 16924 | NM_013069 | o | |
| 1598 | 24748 | NM_013070 | h, q | |
| 1599 | 1529 | NM_013082 | d, General | |
| 1600 | 1521 | NM_013091 | j, l, z, General | |
| 1601 | 1685 | NM_013096 | c, aa | |
| 1601 | 26150 | NM_013096 | c, i | |
| 1601 | 1688 | NM_013096 | p | |
| 1601 | 1689 | NM_013096 | c, p | |
| 1601 | 1684 | NM_013096 | c, s, aa | |
| 1602 | 20886 | NM_013097 | u, x, bb | |
| 1602 | 20887 | NM_013097 | u, x, bb | |
| 1603 | 1321 | NM_013098 | c | Galactose metabolism, Glycolysis/ Gluconeogenesis, Starch and sucrose metabolism |
| 1604 | 15296 | NM_013102 | l, m | |
| 1606 | 23709 | NM_013113 | o, s, z, aa | |
| 1606 | 23711 | NM_013113 | p | |
| 1606 | 23710 | NM_013113 | s | |
| 1607 | 1976 | NM_013118 | u | |
| 1609 | 870 | NM_013130 | h | |
| 1610 | 16650 | NM_013132 | u, General | |
| 1611 | 650 | NM_013134 | h | Sterol biosynthesis |
| 1611 | 651 | NM_013134 | h, j, l | Sterol biosynthesis |

TABLE 2-continued

PATHWAYS

| Sequence ID No. | Identifier | GenBank Acc/ Ref. Seq. ID No. | Model Code | Pathways |
|---|---|---|---|---|
| 1612 | 1712 | NM_013138 | General | |
| 1613 | 16982 | NM_013144 | o, v, General | |
| 1614 | 21683 | NM_013154 | t, cc, General | |
| 1614 | 21682 | NM_013154 | cc | |
| 1615 | 3431 | NM_013156 | b, g, n | |
| 1615 | 25567 | NM_013156 | v, General | |
| 1615 | 3430 | NM_013156 | General | |
| 1616 | 1309 | NM_013159 | w | |
| 1616 | 1310 | NM_013159 | w | |
| 1617 | 21723 | NM_013174 | w | |
| 1618 | 1314 | NM_013181 | m | |
| 1619 | 17357 | NM_013183 | p, bb, General | |
| 1620 | 1300 | NM_013190 | y | Fructose and mannose metabolism, Galactose metabolism, Glycolysis/ Gluconeogenesis, Pentose phosphate cycle |
| 1621 | 16448 | NM_013197 | c | Glycine serine and threonine metabolism |
| 1622 | 20856 | NM_013200 | b | Fatty acid metabolism, Glycerolipid metabolism |
| 1623 | 397 | NM_013214 | f | |
| 1624 | 20864 | NM_013215 | g, n, y | |
| 1625 | 20728 | NM_013217 | v | |
| 1626 | 1396 | NM_013222 | j | |
| 1627 | 815 | NM_013224 | w | |
| 1628 | 18305 | NM_013226 | v | |
| 1629 | 21078 | NM_016986 | d | Fatty acid metabolism, Propanoate metabolism, Valine, leucine and isoleucine degradation, beta-Alanine metabolism |
| 1630 | 24649 | NM_016988 | v | Riboflavin metabolism |
| 1631 | 15239 | NM_016989 | q, w | |
| 1632 | 45 | NM_016996 | General | |
| 1633 | 20714 | NM_016999 | t | Fatty acid metabolism, Tryptophan metabolism |
| 1633 | 20713 | NM_016999 | t | Fatty acid metabolism, Tryptophan metabolism |
| 1633 | 20711 | NM_016999 | q, t | Fatty acid metabolism, Tryptophan metabolism |
| 1633 | 20715 | NM_016999 | q, t | Fatty acid metabolism, Tryptophan metabolism |
| 1634 | 1698 | NM_017000 | e, n, p, General | Sterol biosynthesis |
| 1635 | 1399 | NM_017006 | h, n, General | Glutathione metabolism, Pentose phosphate cycle |
| 1637 | 18989 | NM_017013 | n | Glutathione metabolism |
| 1638 | 21013 | NM_017014 | e, f | Glutathione metabolism |
| 1638 | 21015 | NM_017014 | e, General | Glutathione metabolism |
| 1639 | 11836 | NM_017023 | b | |
| 1639 | 5475 | NM_017023 | b | |
| 1639 | 25546 | NM_017023 | b, bb | |
| 1640 | 17807 | NM_017025 | i, General | Cysteine metabolism, Glycolysis/ Gluconeogenesis, Propanoate metabolism, Pyruvate metabolism |
| 1641 | 24597 | NM_017040 | u | |
| 1642 | 24696 | NM_017048 | f, j, z | |
| 1643 | 24695 | NM_017049 | u | |
| 1644 | 20876 | NM_017050 | j, n, z | |
| 1645 | 910 | NM_017059 | f, l, m | |
| 1645 | 912 | NM_017059 | i | |
| 1646 | 1946 | NM_017061 | h | |
| 1646 | 1942 | NM_017061 | t, General | |
| 1646 | 1943 | NM_017061 | t | |
| 1647 | 6062 | NM_017066 | d | |
| 1648 | 6654 | NM_017068 | w | |
| 1649 | 11153 | NM_017073 | s | Glutamate metabolism, Nitrogen metabolism |
| 1650 | 923 | NM_017076 | General | |
| 1651 | 1523 | NM_017079 | s | |
| 1652 | 23660 | NM_017080 | s | Androgen and estrogen metabolism, C21-Steroid hormone metabolism |
| 1653 | 275 | NM_017081 | b, d, General | Androgen and estrogen metabolism, C21-Steroid hormone metabolism |
| 1654 | 16211 | NM_017082 | j, s, z | |
| 1655 | 1552 | NM_017084 | j | Glycine, serine and threonine metabolism |
| 1655 | 1550 | NM_017084 | y | Glycine, serine and threonine metabolism |
| 1656 | 22552 | NM_017087 | a, k, x | |
| 1657 | 8888 | NM_017090 | m | Purine metabolism |

TABLE 2-continued

PATHWAYS

| Sequence ID No. | Identifier | GenBank Acc/ Ref. Seq. ID No. | Model Code | Pathways |
|---|---|---|---|---|
| 1658 | 10887 | NM_017094 | a, General | |
| 1659 | 4393 | NM_017101 | a, y | |
| 1660 | 24770 | NM_017111 | d | |
| 1661 | 20745 | NM_017113 | e | |
| 1661 | 20746 | NM_017113 | a | |
| 1662 | 1375 | NM_017122 | w | |
| 1663 | 12903 | NM_017124 | k | |
| 1664 | 24885 | NM_017138 | r | |
| 1664 | 24886 | NM_017138 | d, q | |
| 1665 | 15363 | NM_017147 | n, u | |
| 1666 | 13392 | NM_017148 | u, General | |
| 1667 | 5351 | NM_017150 | q | |
| 1668 | 16954 | NM_017151 | a, n | |
| 1669 | 21643 | NM_017152 | g | |
| 1670 | 1694 | NM_017153 | a, q | |
| 1671 | 17104 | NM_017160 | bb, General | |
| 1671 | 17106 | NM_017160 | u | |
| 1671 | 17107 | NM_017160 | d, e | |
| 1672 | 17686 | NM_017165 | n, q | Glutathione metabolism |
| 1673 | 20702 | NM_017166 | c | |
| 1674 | 3513 | NM_017177 | r | Glycerolipid metabolism |
| 1675 | 19031 | NM_017180 | v, General | |
| 1676 | 15437 | NM_017187 | x, z | |
| 1676 | 15433 | NM_017187 | y | |
| 1676 | 15434 | NM_017187 | x, z | |
| 1677 | 24437 | NM_017190 | p | |
| 1678 | 1542 | NM_017193 | j, l, m, z | |
| 1679 | 14695 | NM_017202 | q, s | Oxidative phosphorylation |
| 1679 | 14694 | NM_017202 | s, z | Oxidative phosphorylation |
| 1680 | 1428 | NM_017213 | m | |
| 1681 | 1622 | NM_017216 | g, j, s, z | |
| 1682 | 13642 | NM_017220 | v | |
| 1682 | 19976 | NM_017220 | w | |
| 1683 | 1510 | NM_017224 | General | |
| 1684 | 1811 | NM_017228 | j, l, m, z | |
| 1686 | 17563 | NM_017245 | a, c, e, q | |
| 1687 | 17502 | NM_017248 | r | |
| 1687 | 17501 | NM_017248 | x | |
| 1688 | 19 | NM_017258 | v, General | |
| 1689 | 15300 | NM_017259 | i, v, cc, General | |
| 1689 | 15301 | NM_017259 | l, m, v, aa, cc, General | |
| 1689 | 15299 | NM_017259 | l, y, cc, General | |
| 1690 | 15224 | NM_017264 | d | |
| 1691 | 3987 | NM_017280 | bb | Proteasome |
| 1692 | 1447 | NM_017281 | l | Proteasome |
| 1693 | 15535 | NM_017283 | s, bb | Proteasome |
| 1694 | 12349 | NM_017290 | General | Oxidative phosphorylation |
| 1695 | 15819 | NM_017298 | p | |
| 1696 | 23825 | NM_017299 | v | |
| 1696 | 23826 | NM_017299 | v | |
| 1697 | 14003 | NM_017305 | j, l, m, y, z | Glutamate metabolism, Glutathione metabolism |
| 1698 | 26109 | NM_017306 | q, s | |
| 1698 | 18687 | NM_017306 | q, t | Fatty acid metabolism |
| 1699 | 18142 | NM_017314 | g, s, aa | |
| 1700 | 1894 | NM_017320 | t | |
| 1701 | 20809 | NM_017326 | u | |
| 1702 | 355 | NM_017334 | cc | |
| 1703 | 16148 | NM_017340 | q, s | Fatty acid metabolism |
| 1703 | 16150 | NM_017340 | a | Fatty acid metabolism |
| 1704 | 20849 | NM_017343 | r, u, General | |
| 1704 | 20848 | NM_017343 | b, General | |
| 1705 | 606 | NM_017350 | b | |
| 1706 | 1581 | NM_017365 | General | |
| 1707 | 455 | NM_019131 | x | |
| 1707 | 456 | NM_019131 | y, z | |
| 1708 | 4532 | NM_019134 | b | |
| 1709 | 1608 | NM_019166 | j, y, z | |
| 1710 | 7489 | NM_019169 | c, General | |
| 1711 | 17066 | NM_019170 | p | Prostaglandin and leukotriene metabolism |
| 1712 | 23924 | NM_019174 | bb | Nitrogen metabolism |
| 1713 | 24019 | NM_019186 | t | |
| 1714 | 22063 | NM_019195 | d | |

TABLE 2-continued

PATHWAYS

| Sequence ID No. | Identifier | GenBank Acc/ Ref. Seq. ID No. | Model Code | Pathways |
|---|---|---|---|---|
| 1715 | 2079 | NM_019220 | j, k, z | |
| 1716 | 16284 | NM_019229 | l, m | |
| 1717 | 985 | NM_019233 | b, cc | |
| 1718 | 15503 | NM_019237 | k, x | |
| 1718 | 15504 | NM_019237 | k, x | |
| 1719 | 17908 | NM_019242 | l, v, cc, General | |
| 1720 | 11218 | NM_019247 | c | |
| 1721 | 15259 | NM_019259 | d, f | |
| 1722 | 21443 | NM_019262 | aa, General | |
| 1722 | 21444 | NM_019262 | t, General | |
| 1723 | 117 | NM_019266 | o, bb | |
| 1724 | 1145 | NM_019280 | w | |
| 1725 | 22220 | NM_019286 | c | Bile acid biosynthesis, Fatty acid metabolism, Glycerolipid metabolism, Glycolysis/ Gluconeogenesis, Tyrosine metabolism |
| 1726 | 10015 | NM_019289 | l, m, t, x, General | |
| 1726 | 10016 | NM_019289 | bb, General | |
| 1727 | 21651 | NM_019296 | c, f, x | |
| 1728 | 20751 | NM_019301 | s | |
| 1729 | 645 | NM_019345 | bb | |
| 1730 | 1301 | NM_019349 | c | |
| 1731 | 3776 | NM_019354 | a, u | |
| 1732 | 4592 | NM_019356 | General | |
| 1733 | 1324 | NM_019371 | w | |
| 1734 | 19577 | NM_019377 | e | |
| 1735 | 24626 | NM_019381 | s | |
| 1736 | 744 | NM_019622 | p | |
| 1737 | 20716 | NM_019623 | c | Fatty acid metabolism, Tryptophan metabolism |
| 1738 | 20709 | NM_019904 | x | |
| 1739 | 574 | NM_019905 | u, General | Glyoxylate and dicarboxylate metabolism |
| 1740 | 9096 | NM_019908 | j | |
| 1741 | 20457 | NM_020073 | i, General | |
| 1741 | 20458 | NM_020073 | General | |
| 1741 | 20460 | NM_020073 | General | |
| 1742 | 18713 | NM_020075 | r | |
| 1742 | 18715 | NM_020075 | r | |
| 1743 | 20493 | NM_020076 | p | Tryptophan metabolism |
| 1744 | 16375 | NM_020976 | g | |
| 1745 | 20816 | NM_021261 | k, General | |
| 1746 | 15335 | NM_021264 | a | |
| 1747 | 18729 | NM_021578 | k, z | |
| 1748 | 19060 | NM_021587 | cc | |
| 1749 | 17324 | NM_021593 | o, General | |
| 1750 | 19679 | NM_021653 | General | |
| 1750 | 19678 | NM_021653 | a, v, General | |
| 1751 | 19665 | NM_021688 | u, General | |
| 1752 | 19667 | NM_021690 | m | |
| 1754 | 22916 | NM_021740 | a | |
| 1755 | 19710 | NM_021744 | t | |
| 1755 | 19711 | NM_021744 | t | |
| 1756 | 19712 | NM_021745 | r | |
| 1757 | 1962 | NM_021750 | j, k, y, z | |
| 1757 | 19824 | NM_021750 | a, bb | Taurine and hypotaurine metabolism |
| 1758 | 25198 | NM_021754 | h | |
| 1758 | 20035 | NM_021754 | b, n, s, v, General | |
| 1759 | 20090 | NM_021757 | m | |
| 1760 | 17885 | NM_021765 | aa | |
| 1762 | 20161 | NM_021836 | cc, General | |
| 1764 | 1203 | NM_021997 | k, z | |
| 1765 | 23151 | NM_022005 | b | |
| 1767 | 17101 | NM_022179 | bb | Aminosugars metabolism, Fructose and mannose metabolism, Galactose metabolism, Glycolysis/ Gluconeogenesis, Starch and sucrose metabolism |
| 1767 | 17100 | NM_022179 | bb | Aminosugars metabolism, Fructose and mannose metabolism, Galactose metabolism, Glycolysis/ Gluconeogenesis, Starch and sucrose metabolism |
| 1768 | 20257 | NM_022180 | w, General | |
| 1768 | 25699 | NM_022180 | i | |

TABLE 2-continued

PATHWAYS

| Sequence ID No. | Identifier | GenBank Acc/ Ref. Seq. ID No. | Model Code | Pathways |
|---|---|---|---|---|
| 1768 | 10860 | NM_022180 | p | |
| 1769 | 23780 | NM_022183 | k, x | |
| 1770 | 20312 | NM_022224 | o | |
| 1771 | 6585 | NM_022266 | d, p, cc | |
| 1772 | 17161 | NM_022298 | i, v, cc, General | |
| 1772 | 17162 | NM_022298 | u | |
| 1772 | 17160 | NM_022298 | u | |
| 1772 | 17158 | NM_022298 | q | |
| 1773 | 11454 | NM_022381 | i, aa, General | |
| 1773 | 11455 | NM_022381 | l, General | |
| 1774 | 13480 | NM_022390 | s | Folate biosynthesis |
| 1775 | 15184 | NM_022391 | z | |
| 1776 | 22413 | NM_022392 | h | |
| 1776 | 22414 | NM_022392 | n | |
| 1777 | 22499 | NM_022393 | t | |
| 1779 | 24537 | NM_022399 | e | |
| 1779 | 24539 | NM_022399 | y | |
| 1780 | 1141 | NM_022401 | o, General | |
| 1781 | 1069 | NM_022402 | g | |
| 1782 | 8211 | NM_022500 | j, n, s | |
| 1782 | 8212 | NM_022500 | n, s | |
| 1783 | 6815 | NM_022503 | s | Oxidative phosphorylation |
| 1784 | 4259 | NM_022504 | q, w | |
| 1785 | 1611 | NM_022509 | j | |
| 1786 | 2236 | NM_022512 | y, z | Butanoate metabolism, Fatty acid metabolism, Valine, leucine and isoleucine degradation |
| 1787 | 3026 | NM_022514 | a | |
| 1787 | 3027 | NM_022514 | a, q, r, aa | |
| 1788 | 2696 | NM_022515 | a, d | |
| 1788 | 2697 | NM_022515 | n, w, aa | |
| 1789 | 3900 | NM_022516 | h | |
| 1790 | 4151 | NM_022518 | o | |
| 1791 | 4242 | NM_022521 | c | Arginine and proline metabolism, Urea cycle and metabolism of amino groups |
| 1792 | 4412 | NM_022523 | o | |
| 1793 | 6641 | NM_022533 | General | |
| 1794 | 8097 | NM_022536 | a | |
| 1795 | 8597 | NM_022538 | c, r, u | |
| 1795 | 8598 | NM_022538 | u | |
| 1796 | 9296 | NM_022541 | o | |
| 1797 | 21063 | NM_022585 | h | |
| 1799 | 20781 | NM_022591 | z | |
| 1800 | 20803 | NM_022592 | n | Carbon fixation, Pentose phosphate cycle |
| 1801 | 20925 | NM_022594 | q | |
| 1802 | 20944 | NM_022597 | aa | |
| 1803 | 21024 | NM_022599 | o, General | |
| 1804 | 2250 | NM_022643 | General | |
| 1805 | 17567 | NM_022672 | a, y | |
| 1806 | 17661 | NM_022674 | bb | |
| 1807 | 24563 | NM_022676 | b | |
| 1807 | 24564 | NM_022676 | b, x | |
| 1808 | 20506 | NM_022686 | l | |
| 1809 | 20508 | NM_022688 | g | |
| 1810 | 17586 | NM_022694 | k | |
| 1811 | 17730 | NM_022697 | a | |
| 1811 | 17729 | NM_022697 | q | |
| 1812 | 154 | NM_022849 | t | |
| 1813 | 127 | NM_022855 | h | |
| 1814 | 152 | NM_022858 | j | |
| 1816 | 18101 | NM_022948 | z | |
| 1816 | 18103 | NM_022948 | u | |
| 1817 | 21491 | NM_022951 | w | |
| 1818 | 15742 | NM_022958 | y | |
| 1819 | 9286 | NM_023027 | t, w | |
| 1820 | 23215 | NM_023102 | z | |
| 1821 | 21238 | NM_024125 | cc, General | il6, interact6-1 |
| 1821 | 21239 | NM_024125 | cc, General | il6, interact6-1 |
| 1822 | 353 | NM_024127 | i, n, General | |
| 1822 | 354 | NM_024127 | i, n, General | |
| 1822 | 352 | NM_024127 | h, General | |
| 1823 | 17227 | NM_024131 | x | |
| 1824 | 1598 | NM_024134 | l | |
| 1825 | 1162 | NM_024153 | d | Porphyrin and chlorophyll metabolism |

TABLE 2-continued

| | | | PATHWAYS | |
|---|---|---|---|---|
| Sequence ID No. | Identifier | GenBank Acc/ Ref. Seq. ID No. | Model Code | Pathways |
| 1826 | 7863 | NM_024156 | c | Oxidative phosphorylation, Type III protein secretion system |
| 1827 | 22079 | NM_024157 | x | |
| 1828 | 16476 | NM_024162 | General | |
| 1829 | 17765 | NM_024351 | b, s, v | |
| 1830 | 8879 | NM_024360 | h | |
| 1831 | 20772 | NM_024363 | x | |
| 1832 | 2812 | NM_024386 | c | Butanoate metabolism, Synthesis and degradation of ketone bodies, Valine, leucine and isoleucine degradation |
| 1833 | 335 | NM_024387 | j, y | Porphyrin and chlorophyll metabolism |
| 1834 | 21 | NM_024388 | cc | |
| 1834 | 22 | NM_024388 | cc | |
| 1836 | 9929 | NM_024392 | f | Androgen and estrogen metabolism |
| 1837 | 3582 | NM_024396 | aa | |
| 1838 | 19993 | NM_024398 | e, p, s, aa | |
| 1839 | 10789 | NM_024399 | o | |
| 1840 | 22626 | NM_024400 | cc, General | |
| 1841 | 13633 | NM_024403 | g, General | |
| 1841 | 13634 | NM_024403 | g, General | |
| 1842 | 23387 | NM_024404 | b, General | |
| 1843 | 21038 | NM_024484 | h | Glycine, serine and threonine metabolism |
| 1844 | 1853 | NM_030826 | s | Glutathione metabolism |
| 1845 | 15111 | NM_030827 | e, General | |
| 1845 | 15112 | NM_030827 | y, z | |
| 1845 | 15110 | NM_030827 | General | |
| 1846 | 808 | NM_030837 | k, m | |
| 1847 | 4057 | NM_030844 | k | |
| 1848 | 1221 | NM_030845 | t | |
| 1849 | 21509 | NM_030847 | x | |
| 1850 | 1928 | NM_030872 | v | |
| 1851 | 17342 | NM_030873 | u | |
| 1852 | 24648 | NM_030985 | u | |
| 1852 | 25453 | NM_030985 | General | |
| 1853 | 21802 | NM_030987 | h | |
| 1854 | 23109 | NM_031000 | f, s, z | Glycerolipid metabolism, Glycolysis/ Gluconeogenesis, Pentose and glucuronate interconversions |
| 1855 | 134 | NM_031003 | a, u | |
| 1856 | 25461 | NM_031009 | o | |
| 1857 | 1845 | NM_031010 | t | Prostaglandin and leukotriene metabolism |
| 1857 | 25517 | NM_031010 | c, t | Prostaglandin and leukotriene metabolism |
| 1858 | 16562 | NM_031020 | f | |
| 1859 | 1480 | NM_031021 | f | |
| 1860 | 1719 | NM_031024 | n | |
| 1861 | 1350 | NM_031030 | h | |
| 1862 | 16775 | NM_031031 | General | Arginine and proline metabolism, Glycine, serine and threonine metabolism, Urea cycle and metabolism of amino groups |
| 1863 | 691 | NM_031034 | w | |
| 1864 | 15886 | NM_031035 | z | |
| 1866 | 3608 | NM_031044 | k, General | Histidine metabolism |
| 1866 | 3610 | NM_031044 | d, General | Histidine metabolism |
| 1867 | 15137 | NM_031051 | s | |
| 1868 | 514 | NM_031056 | General | |
| 1869 | 17269 | NM_031057 | General | Inositol metabolism, Propanoate metabolism, Valine, leucine and isoleucine degradation |
| 1870 | 11849 | NM_031065 | a | |
| 1871 | 1855 | NM_031074 | h | |
| 1872 | 4683 | NM_031083 | d | |
| 1873 | 15202 | NM_031093 | a | |
| 1873 | 15201 | NM_031093 | a, n | |
| 1874 | 12639 | NM_031099 | aa | |
| 1875 | 20812 | NM_031100 | a | |
| 1876 | 16938 | NM_031103 | w | |
| 1877 | 19268 | NM_031104 | q | |
| 1878 | 16929 | NM_031108 | q | |
| 1879 | 10878 | NM_031110 | q, bb | |
| 1880 | 19162 | NM_031111 | aa | |
| 1880 | 19161 | NM_031111 | a, bb | |
| 1881 | 24615 | NM_031112 | a, y | |
| 1882 | 20839 | NM_031113 | a, q | |
| 1883 | 19040 | NM_031114 | l, m, General | |

TABLE 2-continued

PATHWAYS

| Sequence ID No. | Identifier | GenBank Acc/ Ref. Seq. ID No. | Model Code | Pathways |
|---|---|---|---|---|
| 1884 | 16349 | NM_031115 | u | |
| 1885 | 14970 | NM_031127 | General | |
| 1886 | 1814 | NM_031134 | n, q | |
| 1887 | 13359 | NM_031135 | General | |
| 1888 | 15052 | NM_031136 | a | |
| 1888 | 19359 | NM_031136 | a | |
| 1889 | 15185 | NM_031140 | General | |
| 1890 | 21625 | NM_031144 | a, e | |
| 1891 | 238 | NM_031152 | bb | |
| 1891 | 240 | NM_031152 | bb | |
| 1892 | 15277 | NM_031237 | g | |
| 1893 | 18083 | NM_031315 | q | |
| 1893 | 1858 | NM_031315 | q | |
| 1894 | 15663 | NM_031318 | General | |
| 1895 | 1422 | NM_031324 | bb, General | |
| 1896 | 18597 | NM_031325 | g, bb | Nucleotide sugars metabolism, Pentose and glucuronate interconversions, Starch and sucrose metabolism |
| 1897 | 11259 | NM_031327 | i, cc, General | |
| 1898 | 4235 | NM_031330 | General | |
| 1899 | 18375 | NM_031331 | l, m | |
| 1900 | 3519 | NM_031334 | cc | |
| 1901 | 20698 | NM_031357 | b | |
| 1903 | 634 | NM_031509 | n | Glutathione metabolism |
| 1903 | 25525 | NM_031509 | n | Glutathione metabolism |
| 1903 | 25069 | NM_031509 | b, n, w | |
| 1903 | 635 | NM_031509 | z | Glutathione metabolism |
| 1904 | 848 | NM_031517 | t | |
| 1905 | 1872 | NM_031523 | a | |
| 1905 | 16245 | NM_031523 | a, d, u | |
| 1905 | 16244 | NM_031523 | a | |
| 1906 | 9370 | NM_031527 | w | |
| 1907 | 20448 | NM_031530 | General | |
| 1907 | 20449 | NM_031530 | General | |
| 1908 | 14633 | NM_031533 | u | Androgen and estrogen metabolism, Pentose and glucuronate interconversions, Porphyrin and chlorophyll metabolism, Starch and sucrose metabolism |
| 1909 | 16048 | NM_031541 | f | |
| 1910 | 4011 | NM_031543 | c, q | Fatty acid metabolism, Tryptophan metabolism |
| 1910 | 4010 | NM_031543 | c, q | Fatty acid metabolism, Tryptophan metabolism |
| 1910 | 4012 | NM_031543 | q | Fatty acid metabolism, Tryptophan metabolism |
| 1911 | 28 | NM_031546 | General | |
| 1912 | 24640 | NM_031548 | h, cc | |
| 1913 | 17149 | NM_031549 | x | |
| 1913 | 17151 | NM_031549 | x | |
| 1914 | 13105 | NM_031552 | w | |
| 1915 | 15411 | NM_031559 | d, r | Fatty acid metabolism, Glycerolipid metabolism |
| 1916 | 16164 | NM_031563 | a, y | |
| 1917 | 9621 | NM_031570 | bb | |
| 1917 | 9620 | NM_031570 | w, bb | |
| 1918 | 546 | NM_031573 | f | |
| 1919 | 1921 | NM_031576 | f | |
| 1919 | 1920 | NM_031576 | r | |
| 1920 | 24219 | NM_031579 | i, General | |
| 1921 | 770 | NM_031584 | k, x | |
| 1922 | 18008 | NM_031588 | cc | |
| 1922 | 18005 | NM_031588 | h | |
| 1922 | 18011 | NM_031588 | cc, General | |
| 1923 | 1584 | NM_031595 | k | |
| 1924 | 24235 | NM_031614 | v | Pyrimidine metabolism |
| 1924 | 24234 | NM_031614 | General | Pyrimidine metabolism |
| 1925 | 1639 | NM_031627 | j, l, v | |
| 1926 | 1727 | NM_031642 | m, General | |
| 1927 | 20766 | NM_031643 | y | |
| 1929 | 1993 | NM_031655 | k, l, m, General | |
| 1930 | 2057 | NM_031660 | e | |
| 1931 | 15039 | NM_031672 | k, General | |

TABLE 2-continued

PATHWAYS

| Sequence ID No. | Identifier | GenBank Acc/ Ref. Seq. ID No. | Model Code | Pathways |
|---|---|---|---|---|
| 1932 | 15175 | NM_031682 | bb | Butanoate metabolism, Fatty acid biosynthesis (path 2), Fatty acid metabolism, Lysine degradation, Tryptophan metabolism. Valine, leucine and isoleucine degradation |
| 1933 | 1004 | NM_031685 | v | |
| 1934 | 19727 | NM_031687 | a, q, s | |
| 1935 | 20404 | NM_031700 | j, r, y | |
| 1935 | 20405 | NM_031700 | o, r | |
| 1936 | 811 | NM_031705 | General | Pantothenate and CoA biosynthesis, Pyrimidine metabolism, beta-Alanine metabolism |
| 1936 | 812 | NM_031705 | o, v, bb, General | Pantothenate and CoA biosynthesis, Pyrimidine metabolism, beta-Alanine metabolism |
| 1937 | 16204 | NM_031706 | q, bb | |
| 1937 | 16205 | NM_031706 | a, y | |
| 1938 | 24081 | NM_031708 | m | |
| 1939 | 16918 | NM_031709 | a, q | |
| 1940 | 1081 | NM_031712 | General | |
| 1941 | 1340 | NM_031715 | b, n, u, cc, General | Fructose and mannose metabolism, Galactose metabolism, Glycolysis/ Gluconeogenesis, Pentose phosphate cycle |
| 1942 | 23884 | NM_031731 | j, s | Arginine and proline metabolism, Ascorbate and aldarate metabolism, Bile acid biosynthesis, Butanoate metabolism, Fatty acid metabolism, Glycerolipid metabolism, Histidine metabolism, Lysine degradation, Propanoate metabolism, Pyruvate metabolism, Tryptophan metabolism, Valine, leucine and isoleucine degradation, beta-Alanine metabolism |
| 1943 | 10241 | NM_031740 | d | |
| 1944 | 1214 | NM_031741 | r | |
| 1944 | 1215 | NM_031741 | r | |
| 1945 | 20724 | NM_031753 | h | |
| 1946 | 20753 | NM_031763 | h | |
| 1946 | 20752 | NM_031763 | y | |
| 1947 | 14953 | NM_031774 | p | |
| 1948 | 14184 | NM_031776 | t, General | Purine metabolism |
| 1948 | 14185 | NM_031776 | d, o, t, General | Purine metabolism |
| 1949 | 1169 | NM_031789 | c | |
| 1950 | 16155 | NM_031810 | d, z | |
| 1950 | 16156 | NM_031810 | d | |
| 1951 | 17194 | NM_031814 | z | |
| 1952 | 17535 | NM_031816 | bb | |
| 1953 | 2655 | NM_031821 | i, j, m, aa | |
| 1954 | 10167 | NM_031830 | i | |
| 1955 | 22321 | NM_031832 | o, t, u, General | |
| 1956 | 4748 | NM_031834 | e, t | |
| 1956 | 4749 | NM_031834 | e, t | |
| 1957 | 7914 | NM_031835 | e | Alanine and aspartate metabolism, Glycine, serine and threonine metabolism |
| 1958 | 8385 | NM_031836 | h | |
| 1958 | 8384 | NM_031836 | h | |
| 1959 | 10268 | NM_031838 | a | |
| 1959 | 10269 | NM_031838 | aa | |
| 1959 | 10267 | NM_031838 | n, aa | |
| 1960 | 15077 | NM_031841 | b | |
| 1961 | 16726 | NM_031855 | x | Fructose and mannose metabolism |
| 1962 | 25802 | NM_031969 | a | |
| 1962 | 19191 | NM_031969 | c | |
| 1962 | 19195 | NM_031969 | r | |
| 1962 | 19190 | NM_031969 | p | |
| 1963 | 17734 | NM_031970 | v, General | |
| 1964 | 1475 | NM_031971 | v | |
| 1965 | 15470 | NM_031978 | f | |
| 1966 | 18502 | NM_031984 | c | |
| 1967 | 19768 | NM_031986 | v, aa, General | |
| 1968 | 723 | NM_032084 | n | |
| 1969 | 17935 | NM_032615 | a | |
| 1970 | 16831 | NM_033095 | n | |

TABLE 2-continued

PATHWAYS

| Sequence ID No. | Identifier | GenBank Acc/ Ref. Seq. ID No. | Model Code | Pathways |
|---|---|---|---|---|
| 1971 | 25468 | NM_033234 | c, z | |
| 1971 | 25469 | NM_033234 | c | |
| 1971 | 17832 | NM_033234 | c, p | |
| 1971 | 17829 | NM_033234 | c, z | |
| 1972 | 4723 | NM_033235 | z | |
| 1973 | 1409 | NM_033349 | p, General | Pyruvate metabolism |
| 1974 | 19998 | NM_033352 | General | |
| 1975 | 1410 | NM_052798 | d | |
| 1976 | 15028 | NM_052809 | f | Cysteine metabolism, Taurine and hypotaurine metabolism |
| 1977 | 5176 | NM_053297 | u | |
| 1978 | 7660 | NM_053299 | i | |
| 1979 | 5117 | NM_053310 | p | |
| 1981 | 17473 | NM_053319 | a, v | |
| 1982 | 25480 | NM_053329 | g | |
| 1982 | 21977 | NM_053329 | y | |
| 1983 | 14926 | NM_053330 | f | |
| 1983 | 14929 | NM_053330 | e, General | |
| 1984 | 16407 | NM_053332 | c, e | |
| 1985 | 15790 | NM_053341 | j, x | |
| 1986 | 6154 | NM_053356 | p | |
| 1987 | 9215 | NM_053374 | i | |
| 1988 | 6416 | NM_053380 | General | |
| 1989 | 19113 | NM_053395 | a | |
| 1990 | 2242 | NM_053433 | n, General | |
| 1991 | 5561 | NM_053438 | y | |
| 1992 | 14670 | NM_053439 | n, General | |
| 1993 | 17102 | NM_053440 | w | |
| 1994 | 24762 | NM_053442 | General | |
| 1995 | 8085 | NM_053453 | General | |
| 1996 | 4622 | NM_053463 | d | |
| 1997 | 21866 | NM_053472 | p | |
| 1998 | 9573 | NM_053475 | h | |
| 1999 | 16137 | NM_053480 | k | |
| 2000 | 15556 | NM_053483 | y | |
| 2001 | 16394 | NM_053485 | General | |
| 2002 | 4290 | NM_053487 | j, y | |
| 2004 | 18826 | NM_053523 | d | |
| 2005 | 7764 | NM_053525 | aa | |
| 2006 | 14199 | NM_053538 | c | |
| 2007 | 1058 | NM_053539 | c, d | |
| 2008 | 4327 | NM_053563 | General | |
| 2009 | 1342 | NM_053573 | h | |
| 2010 | 19254 | NM_053576 | h, s | Methane metabolism, Phenylalanine metabolism |
| 2010 | 19253 | NM_053576 | h | Methane metabolism, Phenylalanine metabolism |
| 2011 | 3049 | NM_053582 | p, cc, General | |
| 2011 | 3050 | NM_053582 | o, General | |
| 2012 | 21423 | NM_053586 | s, y | Oxidative phosphorylation |
| 2013 | 21445 | NM_053587 | t, v | |
| 2014 | 20871 | NM_053591 | j, l | |
| 2014 | 20870 | NM_053591 | l | |
| 2015 | 21044 | NM_053594 | d | |
| 2016 | 21709 | NM_053596 | k | |
| 2016 | 21708 | NM_053596 | z | |
| 2017 | 1597 | NM_053611 | t | |
| 2018 | 5565 | NM_053618 | General | |
| 2019 | 13004 | NM_053623 | t | Fatty acid metabolism |
| 2020 | 1127 | NM_053626 | g | Arginine and proline metabolism, D-Arginine and D-ornthine metabolism, Glycine, serine and threonine metabolism |
| 2021 | 18644 | NM_053648 | n | |
| 2022 | 21637 | NM_053653 | p | |
| 2023 | 3454 | NM_053662 | cc | |
| 2024 | 16121 | NM_053698 | h, j, z | |
| 2024 | 16122 | NM_053698 | h, j, z | |
| 2025 | 25379 | NM_053713 | General | |
| 2025 | 13622 | NM_053713 | General | |
| 2026 | 15376 | NM_053747 | h | |
| 2027 | 1218 | NM_053748 | b | |
| 2028 | 1137 | NM_053763 | y | |
| 2029 | 15996 | NM_053769 | cc | |
| 2030 | 8652 | NM_053774 | g | |

TABLE 2-continued

| Sequence ID No. | Identifier | GenBank Acc/ Ref. Seq. ID No. | Model Code | Pathways |
|---|---|---|---|---|
| 2031 | 14664 | NM_053806 | General | |
| 2032 | 4361 | NM_053812 | k | |
| 2034 | 15002 | NM_053819 | b, x, bb, General | |
| 2034 | 15003 | NM_053819 | b, l, x, bb, General | |
| 2035 | 16173 | NM_053822 | t | |
| 2036 | 17154 | NM_053835 | j, z | |
| 2037 | 20868 | NM_053843 | t | |
| 2037 | 20869 | NM_053843 | t | |
| 2040 | 714 | NM_053863 | y | |
| 2041 | 19781 | NM_053883 | b | |
| 2041 | 19780 | NM_053883 | b | |
| 2042 | 1454 | NM_053887 | General | |
| 2043 | 1660 | NM_053891 | g | |
| 2044 | 712 | NM_053896 | k | |
| 2045 | 753 | NM_053897 | k | |
| 2046 | 794 | NM_053902 | General | Tryptophan metabolism |
| 2047 | 17937 | NM_053911 | f | |
| 2048 | 8188 | NM_053927 | General | |
| 2050 | 1628 | NM_053936 | h | |
| 2051 | 13954 | NM_053955 | General | |
| 2052 | 408 | NM_053961 | General | |
| 2052 | 19991 | NM_053961 | a | |
| 2052 | 16190 | NM_053961 | q | |
| 2052 | 21355 | NM_053961 | j, l, y, z | |
| 2055 | 15136 | NM_053971 | aa | |
| 2055 | 15135 | NM_053971 | d | |
| 2056 | 1764 | NM_053974 | h | |
| 2057 | 1292 | NM_053980 | l | |
| 2058 | 15468 | NM_053982 | q | |
| 2059 | 15642 | NM_053985 | General | |
| 2060 | 21066 | NM_054001 | t | |
| 2061 | 17326 | NM_054008 | o | |
| 2061 | 17327 | NM_054008 | cc | |
| 2061 | 17329 | NM_054008 | g, o, cc | |
| 2062 | 25253 | NM_057099 | j, l, m, p, z | |
| 2062 | 22849 | NM_057099 | j, l | |
| 2063 | 19657 | NM_057103 | b, cc | |
| 2064 | 5492 | NM_057105 | w | Androgen and estrogen metabolism, Pentose and glucuronate interconversions, Porphyrin and chlorophyll metabolism, Starch and sucrose metabolism |
| 2064 | 15126 | NM_057105 | r | Androgen and estrogen metabolism, Pentose and glucuronate interconversions, Porphyrin and chlorophyll metabolism, Starch and sucrose metabolism |
| 2064 | 15125 | NM_057105 | s | Androgen and estrogen metabolism, Pentose and glucuronate interconversions, Porphyrin and chlorophyll metabolism, Starch and sucrose metabolism |
| 2066 | 15391 | NM_057114 | n | |
| 2067 | 727 | NM_057123 | m | |
| 2068 | 915 | NM_057124 | s | |
| 2069 | 15151 | NM_057131 | k | |
| 2070 | 1892 | NM_057144 | b | |
| 2071 | 12333 | NM_057155 | f | |
| 2071 | 12331 | NM_057155 | v, General | |
| 2071 | 12332 | NM_057155 | f, General | |
| 2072 | 17477 | NM_057194 | a, General | |
| 2073 | 15408 | NM_057197 | p, t | |
| 2073 | 15409 | NM_057197 | t | |
| 2074 | 7866 | NM_057198 | h | Glutamate metabolism, Purine metabolism |
| 2075 | 14125 | NM_057208 | h, j, y, z | |
| 2076 | 1743 | NM_057210 | k, s | |
| 2077 | 10498 | NM_078617 | a | |
| 2078 | 8820 | NM_080399 | n | |
| 2079 | 15701 | NM_080581 | j, m, y, z | |
| 2079 | 20105 | NM_080581 | aa | |
| 2080 | 16109 | NM_080585 | c | |
| 2081 | 1757 | NM_080766 | d | |
| 2082 | 7108 | NM_080778 | y | |
| 2083 | 132 | NM_080782 | k | |
| 2083 | 133 | NM_080782 | l | |
| 2084 | 20122 | NM_080887 | General | |

TABLE 2-continued

PATHWAYS

| Sequence ID No. | Identifier | GenBank Acc/ Ref. Seq. ID No. | Model Code | Pathways |
|---|---|---|---|---|
| 2085 | 6143 | NM_080892 | e | |
| 2086 | 9952 | NM_080902 | h | |
| 2087 | 17546 | NM_130401 | b | |
| 2088 | 21695 | NM_130411 | c, x | |
| 2089 | 21391 | NM_130416 | x, General | |
| 2090 | 20694 | NM_130430 | General | |
| 2090 | 19818 | NM_130430 | cc | |
| 2090 | 18810 | NM_130430 | e, s | |
| 2091 | 18293 | NM_130433 | q | Bile acid biosynthesis, Fatty acid biosysnthesis (path 2), Fatty acid metabolism, Phenylalanine metabolism, Valine, leucine and isoleucine degradation |
| 2092 | 25064 | S45392 | a, n | |
| 2093 | 3244 | S63519 | u | |
| 2094 | 25501 | S63521 | q | |
| 2095 | 16248 | S68135 | h | |
| 2096 | 18647 | S69316 | q | |
| 2097 | 24351 | S74257 | v | |
| 2098 | 25066 | S75280 | d | |
| 2099 | 1460 | S76054 | j, l, m, x, y, General | |
| 2100 | 25539 | S76742 | v | |
| 2101 | 16400 | S76779 | c | |
| 2102 | 24469 | S77858 | n | |
| 2103 | 25545 | S77900 | k, s | |
| 2103 | 21583 | S77900 | k | |
| 2104 | 10260 | S81497 | s | |
| 2105 | 3609 | S82579 | k | Histidine metabolism |
| 2106 | 111 | U02506 | u | |
| 2107 | 14959 | U03390 | a, q, General | |
| 2109 | 2010 | U05675 | b, x, bb | |
| 2110 | 15462 | U06230 | d | |
| 2112 | 1583 | U07201 | s, General | |
| 2113 | 627 | U09229 | h | |
| 2114 | 809 | U17035 | General | |
| 2115 | 16675 | U17565 | k, x, bb | |
| 2116 | 25587 | U20110 | r | |
| 2117 | 90 | U20796 | r | |
| 2118 | 25589 | U21718 | h, aa | |
| 2119 | 22196 | U21719 | h | |
| 2120 | 17118 | U25746 | s | |
| 2121 | 1537 | U27518 | g, h, n | |
| 2122 | 1558 | U28504 | bb | |
| 2123 | 16193 | U30831 | n | |
| 2124 | 17480 | U31598 | z | |
| 2125 | 18302 | U33500 | General | |
| 2126 | 25599 | U34897 | y | |
| 2127 | 1394 | U37099 | h | |
| 2128 | 244 | U38376 | n | |
| 2129 | 1623 | U41164 | h | |
| 2130 | 15851 | U42719 | f, t, x, General | |
| 2131 | 17886 | U47315 | s, z | |
| 2132 | 21654 | U53184 | i, t, General | |
| 2133 | 1439 | U57391 | w | |
| 2134 | 725 | U62316 | bb | |
| 2137 | 2153 | U75404 | b, cc, General | |
| 2139 | 4956 | U76714 | j, y | |
| 2140 | 4477 | U77829 | l, m | |
| 2141 | 21703 | U82591 | z | |
| 2142 | 977 | U89744 | s | |
| 2143 | 23282 | U90725 | h | |
| 2144 | 22005 | U96490 | m | |
| 2146 | 819 | X02284 | j, z | Carbon fixation, Fructose and mannose metabolism, Glycolysis/ Gluconeogenesis, Inositol metabolism, Pentose phosphate cycle |
| 2147 | 818 | X02291 | e, j, z | Carbon fixation, Fructose and mannose metabolism, Glycolysis/ Gluconeogenesis, Inositol metabolism, Pentose phosphate cycle |
| 2148 | 20818 | X02904 | n, q | Glutathione metabolism |
| 2149 | 16401 | X04979 | c | |

TABLE 2-continued

PATHWAYS

| Sequence ID No. | Identifier | GenBank Acc/ Ref. Seq. ID No. | Model Code | Pathways |
|---|---|---|---|---|
| 2150 | 20513 | X05684 | o, r | Carbon fixation, Glycolysis/ Gluconeogenesis, Purine metabolism, Pyruvate metabolism |
| 2151 | 25084 | X06769 | cc | |
| 2152 | 672 | X13722 | h | |
| 2153 | 25675 | X14181 | n | |
| 2153 | 20810 | X14181 | n, q, w | |
| 2154 | 18541 | X14671 | y | |
| 2155 | 25679 | X15013 | q | |
| 2155 | 19244 | X15013 | c, q, w | |
| 2156 | 15626 | X17665 | a | |
| 2157 | 1893 | X51529 | t | Glycerolipid metabolism, Phospholipid degradation, Prostaglandin, and leukotriene metabolism |
| 2158 | 25686 | X51536 | bb | |
| 2158 | 10819 | X51536 | aa, bb | |
| 2159 | 18250 | X51706 | a, q, w | |
| 2160 | 20872 | X51707 | a | |
| 2161 | 516 | X52711 | c | |
| 2162 | 25689 | X52815 | g | |
| 2163 | 20427 | X53378 | w | |
| 2164 | 18606 | X53504 | General | |
| 2165 | 1463 | X54467 | d, u, General | |
| 2166 | 24577 | X55153 | a, v | |
| 2167 | 10344 | X57405 | j, m | |
| 2168 | 15106 | X57529 | g, n, q | |
| 2169 | 5667 | X58200 | q, bb | |
| 2169 | 18611 | X58200 | a, v | |
| 2170 | 17175 | X58389 | w | |
| 2171 | 25702 | X58465 | w | |
| 2171 | 10109 | X58465 | c, q | |
| 2172 | 25705 | X59375 | c, i, aa, General | |
| 2173 | 25709 | X59737 | u | |
| 2174 | 18354 | X59859 | General | |
| 2174 | 18355 | X59859 | t | |
| 2175 | 21657 | X61381 | General | |
| 2176 | 25718 | X62145 | bb, General | |
| 2176 | 15875 | X62145 | a, q, v | |
| 2177 | 13646 | X62166 | bb | |
| 2178 | 25721 | X62325 | p | |
| 2179 | 16012 | X62875 | m, s, z | |
| 2180 | 25730 | X63369 | cc | |
| 2181 | 25089 | X63594 | General | |
| 2181 | 25090 | X63594 | cc, General | |
| 2182 | 20844 | X65228 | n, w | |
| 2183 | 20879 | X65296 | j, y | |
| 2184 | 25736 | X68782 | c | |
| 2185 | 16426 | X70369 | c | |
| 2186 | 16300 | X70706 | u | |
| 2187 | 24232 | X75207 | c | |
| 2188 | 16272 | X76456 | n, p | |
| 2189 | 25741 | X76489 | u | |
| 2190 | 23302 | X78949 | h | |
| 2191 | 25747 | X81448 | General | |
| 2192 | 24115 | X81449 | u | |
| 2193 | 25754 | X89696 | g | |
| 2194 | 25097 | X90642 | y, z | |
| 2195 | 12978 | X96437 | cc, General | |
| 2197 | 4594 | Y07704 | c | |
| 2198 | 25777 | Y08355 | g, p, General | |
| 2199 | 15986 | Y09945 | bb, General | |
| 2200 | 20890 | Y13275 | k | |
| 2201 | 21914 | Y13336 | d | |
| 2202 | 406 | Z11995 | o, General | |
| 2203 | 18352 | Z12298 | t | |
| 2204 | 17481 | Z49761 | k | |
| 2205 | 8664 | Z75029 | r, v | |
| 2206 | 2459 | AA964755 | cc | |
| 2207 | 23830 | AA956638 | aa | |
| 2208 | 6100 | X73524 | x | |
| 2209 | 439 | Z22607 | w | |
| 2210 | 8665 | AI071965 | v | |
| 2211 | 155 | U32681 | t | |

TABLE 2-continued

PATHWAYS

| Sequence ID No. | Identifier | GenBank Acc/ Ref. Seq. ID No. | Model Code | Pathways |
|---|---|---|---|---|
| 2212 | 19252 | AA892041 | s | Methane metabolism, Phenylalanine metabolism |
| 2213 | 15582 | AI232320 | q | |
| 2214 | 17541 | M26125 | n | |
| 2215 | 18609 | M30689 | i | |
| 2216 | 6262 | AI177125 | g | |
| 2217 | 23859 | AI072161 | f | |
| 2218 | 21011 | H32189 | e | Glutathione metabolism |
| 2220 | 2572 | AI177143 | b | |
| 2221 | 25419 | M22922 | a | |

TABLE 3

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1 | 6949 | AA012785 | q | | |
| 2 | 25098 | AA108277 | h, v | | |
| 3 | 17312 | AA108308 | r | | EST, Moderately similar to A Chain A, Mdm2 Bound To The Transactivation Domain Of P53 {SUB 17-125 [*H. sapiens*], mouse double minute 2, human homolog of; p53-binding protein |
| 4 | 16882 | AA684537 | o | | NADH dehydrogenase (ubiquinone) 1 beta subcomplex, 5 (16 kD, SGDH) |
| 5 | 6049 | AA685178 | y | | EST, Weakly similar to T30827 nascent polypeptide-associated complex alpha chain, non-muscle splice form - mouse [*M. musculus*], FKSG17, *Homo sapiens* alpha-NAC gene for nascent polypeptide-associated complex component, KIAA0363 protein, expressed sequence AL022831, nascent-polypeptide-associated complex alpha polypeptide |
| 6 | 4426 | AA685974 | l, m | | |
| 7 | 21815 | AA686423 | g | | EST, Weakly similar to T46390 hypothetical protein DKFZp434C1920.1 [*H. sapiens*], hepatocellular carcinoma-associated antigen 59 |
| 8 | 1600 | AA686470 | i | DNA-damage inducible transcript 3, DNA-damage-inducible transcript 3 | DNA-damage inducible transcript 3, EST, Moderately similar to GA15_HUMAN GROWTH ARREST AND DNA-DAMAGE-INDUCIBLE PROTEIN GADD153 [*H. sapiens*], myozenin |
| 8 | 1599 | AA686470 | i | DNA-damage inducible transcript 3, DNA-damage-inducible transcript 3 | DNA-damage inducible transcript 3, EST, Moderately similar to GA15_HUMAN GROWTH ARREST AND DNA-DAMAGE-INDUCIBLE PROTEIN GADD153 [*H. sapiens*], myozenin |
| 9 | 21997 | AA799325 | u | | |
| 10 | 18396 | AA799330 | v | | |
| 11 | 6581 | AA799412 | f, l | | ESTs, Highly similar to ERR3_HUMAN ESTROGEN-RELATED RECEPTOR GAMMA [*H. sapiens*], Untitled, estrogen related receptor, alpha, estrogen related receptor, beta, estrogen-related receptor beta |
| 12 | 16538 | AA799449 | k | | ESTs, Moderately similar to NPL4_HUMAN NUCLEOSOME ASSEMBLY PROTEIN 1-LIKE 4 [*H. sapiens*], ESTs, Weakly similar to NPL4_HUMAN NUCLEOSOME ASSEMBLY PROTEIN 1-LIKE 4 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | [*H. sapiens*], SET translocation, nucleosome assembly protein 1-like 1, nucleosome assembly protein 1-like 4 |
| 13 | 23294 | AA799472 | u | | CGI-116 protein |
| 14 | 18290 | AA799497 | r | | |
| 15 | 18981 | AA799523 | e | | DAZ associated protein 1, ESTs, Highly similar to ROA1 RAT HETEROGENEOUS NUCLEAR RIBONUCLEOPROTEIN A1 [*R. norvegicus*], ESTs, Moderately similar to Up1, The Two Rna-Recognition Motif Domain Of Hnmp A1 (SUB 3-184 [*H. sapiens*], ESTs, Weakly similar to ROA1 RAT HETEROGENEOUS NUCLEAR RIBONUCLEOPROTEIN A1 [*R. norvegicus*], ESTs, Weakly similar to ROA2 MOUSE HETEROGENEOUS NUCLEAR RIBONUCLEOPROTEINS A2/B1 [*M. musculus*], RIKEN cDNA 3010025E17 gene, Ras-GTPase activating protein SH3 domain-binding protein 2, Ras-GTPase-activating protein SH3-domain binding protein, cell death regulator aven, heterogeneous nuclear ribonucleoprotein A1, heterogeneous nuclear ribonucleoprotein A2/B1 |
| 16 | 20843 | AA799545 | h | | EST, Moderately similar to A38983 TCP1 ring complex protein TRiC5 [*H. sapiens*], T-complex 1, chaperonin containing TCP1, subunit 3 (gamma), expressed sequence AI528772, t-complex 1, t-complex protein 1 |
| 17 | 16993 | AA799560 | b | | |
| 18 | 16576 | AA799570 | d | | |
| 19 | 18361 | AA799591 | i | | EST, Moderately similar to I38369 beta tubulin [*H. sapiens*], ESTs, Highly similar to I38370 beta-tubulin [*H. sapiens*], ESTs, Highly similar to T08726 tubulin beta chain [*H. sapiens*], ESTs, Highly similar to TBB1 RAT TUBULIN BETA CHAIN [*R. norvegicus*], ESTs, Moderately similar to I38370 beta-tubulin [*H. sapiens*], RIKEN cDNA 2410129E14 gene, RIKEN cDNA 4930447K03 gene, RIKEN cDNA 4930542G03 gene, Rat mRNA for beta-tubulin T beta15, beta tubulin 1, class VI, tubulin, beta 3, tubulin, beta, 2 |
| 20 | 17712 | AA799598 | z | | |
| 22 | 18346 | AA799718 | f | | |
| 23 | 8768 | AA799726 | l | | |
| 24 | 11687 | AA799732 | w | | DiGeorge syndrome chromosome region 6, DiGeorge syndrome critical region gene 6, DiGeorge syndrome critical region gene 6 like |
| 25 | 18349 | AA799744 | u | | |
| 26 | 17494 | AA799751 | n | | |
| 27 | 18360 | AA799771 | General | | |
| 28 | 18880 | AA799801 | w | | |
| 29 | 20998 | AA799803 | z | | EST, Moderately similar to MAS2_HUMAN MANNAN-BINDING LECTIN SERINE PROTEASE 2 PRECURSOR [*H. sapiens*], *Rattus norvegicus* mRNA for serine protease, complete cds, complement C1r-like proteinase precursor,, complement component 1, r subcomponent, complement component 1, s subcomponent, protein C |
| 30 | 21006 | AA799861 | c | | interferon regulatory factor 7 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 31 | 15011 | AA799893 | General | | ESTs, Moderately similar to Up1, The Two Rna-Recognition Motif Domain Of Hnrnp A1 {SUB 3-184 [*H. sapiens*], ESTs, Weakly similar to ROA1 RAT HETEROGENEOUS NUCLEAR RIBONUCLEOPROTEIN A1 [*R. norvegicus*], ESTs, Weakly similar to heterogeneous ribonuclear particle protein A1 [*H. sapiens*], Human DNA sequence from clone RP11-51N22 on chromosome 13 Contains ESTs, STSs and GSSs. Contains an HNRPA1 (heterogeneous nuclear ribonucleoprotein A1) pseudogene, RIKEN cDNA 4930547K05 gene, heterogeneous nuclear ribonucleoprotein A1 |
| 32 | 20811 | AA799899 | a | | EST, Moderately similar to RL1X_HUMAN 60S RIBOSOMAL PROTEIN L18A [*H. sapiens*], EST, Weakly similar to RL1X_HUMAN 60S RIBOSOMAL PROTEIN L18A [*H. sapiens*], EST, Weakly similar to S47353 ribosomal protein L18a, cytosolic [*H. sapiens*], ESTs, Highly similar to RL1X_HUMAN 60S RIBOSOMAL PROTEIN L18A [*H. sapiens*], RIKEN cDNA 2510019J09 gene, ribosomal protein L18a |
| 33 | 23202 | AA799971 | General | | |
| 34 | 4832 | AA800190 | b | | ESTs, Moderately similar to 1701409A glycogen phosphorylase [*H. sapiens*], ESTs, Weakly similar to 1701409A glycogen phosphorylase [*H. sapiens*], phosphorylase, glycogen; brain |
| 35 | 21656 | AA800202 | d | | |
| 36 | 18433 | AA800218 | j, y, z | | |
| 37 | 6386 | AA800235 | u | | |
| 38 | 18442 | AA800258 | h, k | | |
| 39 | 21092 | AA800380 | y | | DNA segment, Chr 14, University of California at Los Angeles 2, Hydroxysteroid dehydrogenase, 11 beta type 1, expressed sequence C79874, hydroxysteroid (11-beta) dehydrogenase 1, hydroxysteroid 11-beta dehydrogenase 1, hydroxysteroid 17-beta dehydrogenase 11, retinal short-chain dehydrogenase/reductase retSDR2 |
| 40 | 17325 | AA800587 | General | | ESTs, Highly similar to GSHG_MOUSE GLUTATHIONE PEROXIDASE-GASTROINTESTINAL (GSHPX-GI) [*M. musculus*], Glutathione peroxidase 1, glutathione peroxidase 1, glutathione peroxidase 2 (gastrointestinal) |
| 41 | 13930 | AA800613 | cc, General | | zinc finger protein 36, zinc finger protein homologous to Zfp-36 in mouse |
| 42 | 21372 | AA800693 | v | | |
| 42 | 21373 | AA800693 | s | | |
| 43 | 18161 | AA800701 | k | | |
| 44 | 6595 | AA800753 | w | | |
| 45 | 13348 | AA800928 | General | | |
| 46 | 23115 | AA801165 | o, y | | EST, Weakly similar to H2AL_HUMAN HISTONE H2A.L (H2A/L) [*H. sapiens*], H2A histone family, member L, similar to H2A histone family, member A (*H. sapiens*) |
| 47 | 12399 | AA801307 | General | | |
| 48 | 7543 | AA801395 | General | | |
| 49 | 24237 | AA817726 | t, General | | |
| 50 | 11215 | AA817921 | o | | |
| 51 | 5985 | AA818005 | g | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 52 | 11338 | AA818016 | x | | EST, Weakly similar to RB6K MOUSE RABKINESIN-6 [*M. musculus*], RAB6 interacting, kinesin-like (rabkinesin 6), RIKEN cDNA 3110001D19 gene, Rab6, kinesin-like |
| 53 | 2845 | AA818026 | k, General | | COP9 (constitutive photomorphogenic), subunit 6 (*Arabidopsis*), Homo sapiens cDNA FLJ14833 fis, clone OVARC1001171, moderately similar to Homo sapiens translation initiation factor 3 47 kDa subunit mRNA, IFP38, RIKEN cDNA 0610037M02 gene, eukaryotic translation initiation factor 3, subunit 5 (epsilon, 47 kD), hypothetical protein MGC13045, proteasome (prosome, macropain) 26S subunit, non-ATPase, 7 |
| 54 | 16756 | AA818089 | i, k, General | | glycyl-tRNA synthetase |
| 55 | 17771 | AA818224 | e, g, p, General | | EST, Weakly similar to S45140 tubulin beta chain [*H. sapiens*], RIKEN cDNA 2410129E14 gene, RIKEN cDNA 4930542G03 gene, tubulin, beta 2, tubulin, beta 5, tubulin, beta polypeptide, tubulin, beta, 2 |
| 56 | 6522 | AA818261 | g, m | | |
| 57 | 5924 | AA818359 | y | | |
| 58 | 7806 | AA818421 | b, aa | | |
| 59 | 8237 | AA818512 | v | | |
| 60 | 17434 | AA818574 | h | | |
| 61 | 8728 | AA818615 | General | | |
| 62 | 6054 | AA818658 | b, v, cc, General | diphtheria toxin receptor (heparin-binding epidermal growth factor-like growth factor), heparin binding epidermal growth factor-like growth factor | diphtheria toxin receptor (heparin-binding epidermal growth factor-like growth factor), expressed sequence AW047313, heparin binding epidermal growth factor-like growth factor |
| 63 | 11590 | AA818721 | d | | |
| 64 | 4291 | AA818741 | q, General | | |
| 65 | 4330 | AA818747 | o, General | | |
| 66 | 19723 | AA818761 | v, General | | |
| 67 | 13684 | AA818770 | h, j, i, m | | |
| 68 | 6322 | AA818801 | k | | |
| 69 | 7690 | AA818875 | General | | expressed sequence AV066530, guanylate cyclase activator 2B (uroguanylin), guanylate cyclase activator 2b (retina) |
| 70 | 4952 | AA818907 | q, General | | |
| 71 | 6094 | AA818911 | t | | |
| 72 | 10985 | AA818998 | o, General | | |
| 73 | 6120 | AA819008 | t | | |
| 74 | 2586 | AA819081 | c | | CocoaCrisp, ESTs, Weakly similar to JC5308 testis-specific, vespid, and pathogenesis-related protein 1 precursor [*H. sapiens*], Homo sapiens, Similar to RIKEN cDNA 1700011E04 gene, clone MGC: 26856 IMAGE: 4822995, mRNA, complete cds, RIKEN cDNA 1200009H11 gene, RIKEN cDNA 1700011E04 gene, RIKEN cDNA 4921508O11 gene, acidic epididymal glycoprotein-like 1, glioma pathogenesis-related protein, specific granule protein (28 kDa), testis specific gene 1, testis specific protein 1, testis specific protein 1 (probe H4-1 p3-1) |
| 76 | 6438 | AA819269 | o | | |
| 77 | 24721 | AA819306 | d, w | | |
| 78 | 6250 | AA819376 | o, y | | ESTs, Weakly similar to T17246 hypothetical protein DKFZp586M0617.1 [*H. sapiens*], KIAA0263 gene product, mammalian inositol hexakisphosphate kinase 2 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 80 | 6281 | AA819517 | j | | HYA22 protein, conserved gene amplified in osteosarcoma, nuclear LIM interactor-interacting factor |
| 81 | 10141 | AA819526 | j | | |
| 82 | 6551 | AA819558 | t | | |
| 83 | 6723 | AA819653 | r | | |
| 84 | 14958 | AA819744 | aa | | |
| 85 | 19433 | AA819776 | v | | ESTs, Highly similar to HS9B RAT HEAT SHOCK PROTEIN HSP 90-BETA [R. norvegicus], expressed sequence AL024080, expressed sequence C81438, heat shock 90 kD protein 1, beta, heat shock protein, 84 kDa 1 |
| 86 | 6204 | AA819889 | aa | | |
| 87 | 22820 | AA848315 | General | | GMPR2 for guanosine monophosphate reductase isolog, IMP (inosine monophosphate) dehydrogenase 2, RIKEN cDNA 2310004P21 gene, RIKEN cDNA 5730544D12 gene, expressed sequence AA959850, guanosine monophosphate reductase, inosine 5'-phosphate dehydrogenase 2 |
| 88 | 6614 | AA848389 | bb | | |
| 89 | 21125 | AA848437 | General | | |
| 90 | 23504 | AA848496 | q | | ESTs, Moderately similar to IF4B_HUMAN EUKARYOTIC TRANSLATION INITIATION FACTOR 4B [H. sapiens], eukaryotic translation initiation factor 4B |
| 91 | 18532 | AA848675 | g | | ESTs, Highly similar to FMO2_HUMAN DIMETHYLANILINE MONOOXYGENASE [H. sapiens], Flavin-containing monooxygenase 1, flavin containing monooxygenase 1, flavin containing monooxygenase 2, flavin containing monooxygenase 3, hypothetical protein PRO1257 |
| 92 | 21140 | AA848738 | c | | |
| 93 | 16128 | AA848807 | o | | |
| 94 | 22923 | AA848929 | g | | |
| 95 | 17339 | AA849497 | General | | |
| 96 | 11727 | AA849518 | l | | |
| 97 | 21275 | AA849796 | i, l, m, General | | |
| 98 | 16678 | AA849827 | aa | | |
| 99 | 8515 | AA849917 | e | | |
| 100 | 18447 | AA849939 | General | | |
| 101 | 12130 | AA850037 | p | | |
| 102 | 23981 | AA850040 | x, aa | | RIKEN cDNA 2810452G09 gene, adenylyl cyclase-associated CAP protein homolog 1 (S. cerevisiae, S. pombe), adenylyl cyclase-associated protein |
| 103 | 13615 | AA850364 | t | | |
| 105 | 2637 | AA850893 | x | | DKFZP434O125 protein |
| 106 | 22093 | AA850909 | d | | |
| 107 | 21766 | AA850916 | c | | |
| 108 | 2847 | AA850919 | w | | ESTs, Highly similar to LB4D_HUMAN NADP-DEPENDENT LEUKOTRIENE B4 12-HYDROXYDEHYDROGENASE [H. sapiens], ESTs, Weakly similar to FAS RAT FATTY ACID SYNTHASE [R. norvegicus], ESTs, Weakly similar to LB4D_HUMAN NADP-DEPENDENT LEUKOTRIENE B4 12-HYDROXYDEHYDROGENASE [H. sapiens], crystallin, zeta, fatty acid synthase |
| 109 | 12162 | AA850975 | h | | |
| 110 | 9514 | AA850978 | General | | |
| 111 | 3924 | AA851017 | e, q | | |
| 111 | 3925 | AA851017 | o, General | | |
| 112 | 4490 | AA851184 | a, k | | cathepsin Z |
| 113 | 19187 | AA851230 | General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 114 | 19189 | AA851237 | c | | RIKEN cDNA 1110058H21 gene, ubiquitin specific protease 18 |
| 115 | 15386 | AA851241 | m | | breast cancer metastasis-suppressor 1, hypothetical protein MGC11296 |
| 116 | 21462 | AA851261 | g, l, General | | ART-4 protein |
| 117 | 21471 | AA851343 | General | | |
| 118 | 16902 | AA851379 | p | | NADH dehydrogenase (ubiquinone) Fe—S protein 8 (23 kD) (NADH-coenzyme Q reductase) |
| 119 | 23376 | AA851392 | i, x | | kinesin-like 4 |
| 119 | 23377 | AA851392 | x | | kinesin-like 4 |
| 120 | 13349 | AA851417 | General | | |
| 121 | 21527 | AA851733 | r, u | | |
| 122 | 4048 | AA851814 | i, o, u, General | | EST, Moderately similar to PM17 MOUSE MELANOCYTE PROTEIN PMEL 17 PRECURSOR [*M. musculus*], *Homo sapiens*, Similar to glycoprotein (transmembrane) nmb, clone MGC:1696 IMAGE:3345861, mRNA, complete cds, glycoprotein (transmembrane) nmb, silver |
| 123 | 10561 | AA851871 | bb | | signal sequence receptor, alpha (translocon-associated protein alpha) |
| 124 | 17411 | AA858621 | j, y | | ESTs, Weakly similar to A60021 tropomyosin-related protein, neuronal - rat [*R. norvegicus*], RIKEN cDNA 0710005K15 gene, expressed sequence R75279, reticulon 1, reticulon 3 |
| 125 | 1801 | AA858636 | k, s, x, bb | | expressed sequence AI747533, mini chromosome maintenance deficient 7 (*S. cerevisiae*), minichromosome maintenance deficient (*S. cerevisiae*) 7 |
| 126 | 18350 | AA858674 | p | | |
| 127 | 19484 | AA858693 | e | | |
| 128 | 6360 | AA858696 | d | | |
| 129 | 17334 | AA858704 | p | | exostoses (multiple) 1, exostoses (multiple)-like 1, expressed sequence AA409028 |
| 130 | 6380 | AA858758 | q | | |
| 131 | 13219 | AA858759 | a | | |
| 132 | 6384 | AA858788 | l, m, General | | |
| 134 | 13412 | AA858830 | p | | LanC (bacterial lantibiotic synthetase component C)-like, LanC (bacterial lantibiotic synthetase component C)-like 1, RIKEN cDNA 1700003F10 gene |
| 135 | 7279 | AA858892 | f | | |
| 136 | 18217 | AA858930 | t | | |
| 137 | 5867 | AA858953 | v, General | | asparaginyl-tRNA synthetase, hypothetical protein FLJ23441 |
| 138 | 14479 | AA858969 | r | | Interleukin 1 receptor accessory protein, *Mus musculus* IL-1Rrp2 mRNA, complete cds, interleukin 1 receptor accessory protein-like 2, interleukin 1 receptor, type I, interleukin 18 receptor 1 |
| 139 | 6431 | AA859085 | t | | |
| 140 | 17361 | AA859114 | o, General | | |
| 141 | 21025 | AA859241 | General | | EST, Highly similar to OM25_RAT MITOCHONDRIAL OUTER MEMBRANE PROTEIN 25 (NPW16) [*R. norvegicus*], EST, Weakly similar to OM25_RAT MITOCHONDRIAL OUTER MEMBRANE PROTEIN 25 (NPW16) [*R. norvegicus*], Erbb2 interacting protein, discs, large homolog 4 (*Drosophila*), expressed sequence AI118201, hypothetical protein FLJ11271, synaptojanin 2 binding protein |
| 142 | 10076 | AA859271 | c | | |
| 143 | 21791 | AA859333 | k | | EST, Moderately similar to CYSR RAT CYSTEINE-RICH PROTEIN 1 [*R. norvegicus*], ESTs, Weakly similar |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | to S12658 cysteine-rich protein [*H. sapiens*], cysteine and glycine-rich protein 1, cysteine and glycine-rich protein 3 (cardiac LIM protein), cysteine rich protein, cysteine-rich protein 2, cysteine-rich protein 3, thymus LIM protein |
| 144 | 16314 | AA859348 | cc, General | | |
| 145 | 18862 | AA859520 | f | | |
| 146 | 15059 | AA859545 | r | | |
| 147 | 19894 | AA859581 | s | | EST, Highly similar to SPERM-COATING GLYCOPROTEIN PRECURSOR [*R. norvegicus*], ESTs, Weakly similar to JC4131 glioma pathogenesis-related protein [*H. sapiens*], Human DNA sequence from clone RP5-881L22 on chromosome 20 Contains ESTs, GSSs, STSs and CpG islands, Contains a gene for a novel protein similar to a trypsin inhibitor and four other genes for novel proteins, RIKEN cDNA 1810049K24 gene, RIKEN cDNA 2410114O14 gene, RIKEN cDNA 9230112K08 gene, acidic epididymal glycoprotein 1, acidic epididymal glycoprotein 2, epididymal glycoprotein, glioma pathogenesis-related protein |
| 148 | 14353 | AA859585 | h | | |
| 149 | 16318 | AA859648 | h | | DnaJ (Hsp40) homolog, subfamily B, member 1, DnaJ (Hsp40) homolog, subfamily B, member 5, DnaJ (Hsp40) homolog, subfamily B, member 6, DnaJ (Hsp40) homolog, subfamily B, member 8, ESTs, Weakly similar to DnaJ-like protein [*M. musculus*], ESTs, Weakly similar to HS44 MOUSE HEAT SHOCK 40 KDA PROTEIN 4 [*R. norvegicus*], *Homo sapiens* cDNA FLJ13992 fis, clone Y79AA1002139, weakly similar to DNAJ PROTEIN HOMOLOG 1, RIKEN cDNA 1700029A20 gene, RIKEN cDNA 2010306G19 gene |
| 150 | 17316 | AA859652 | General | | |
| 151 | 19067 | AA859663 | n, q | | |
| 152 | 22406 | AA859680 | n | | |
| 153 | 20599 | AA859690 | x | | |
| 154 | 14261 | AA859693 | u | | |
| 155 | 14138 | AA859700 | v | | protoporphyrinogen oxidase |
| 155 | 14139 | AA859700 | v | | protoporphyrinogen oxidase |
| 157 | 22374 | AA859804 | l | | |
| 158 | 22385 | AA859805 | b, k | | ESTs, Weakly similar to PROTEIN-LYSINE 6-OXIDASE PRECURSOR [*R. norvegicus*], Lysyl oxidase, lysyl oxidase, lysyl oxidase-like, lysyl oxidase-like 1, lysyl oxidase-like 2 |
| 159 | 22773 | AA859885 | n | | |
| 160 | 22816 | AA859898 | k, x, z | | |
| 161 | 11891 | AA859926 | x | | |
| 162 | 23070 | AA859942 | k | | EST, Weakly similar to JC1343 glycylpeptide N-tetradecanoyltransferase [*H. sapiens*], N-myristoyltransferase 1 |
| 163 | 23121 | AA859948 | k | | |
| 164 | 23166 | AA859954 | cc, General | | |
| 165 | 18468 | AA859966 | aa | | *Homo sapiens* cDNA FLJ14666 fis, clone NT2RP2003000, weakly similar to TUMOR NECROSIS FACTOR, ALPHA-INDUCED PROTEIN 1, *Homo sapiens* polymerase delta-interacting protein 1 mRNA, complete cds, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 166 | 23336 | AA859981 | q | | MSTP028 protein, tumor necrosis factor, alpha-induced protein 1 (endothelial) ESTs, Moderately similar to A Chain A, Inositol Monophosphatase [*H. sapiens*], Inositol (myo)-1(or 4)-monophosphatase 1, RIKEN cDNA 2900059K10 gene, bisphosphate 3'-nucleotidase 1, inositol (myo)-1(or 4)-monophosphatase 1, inositol (myo)-1(or 4)-monophosphatase 2, inositol(myo)-1(or 4)-monophosphatase 1, inositol(myo)-1(or 4)-monophosphatase 2 |
| 167 | 4222 | AA860024 | a, bb | | EST, Moderately similar to EF1G_HUMAN ELONGATION FACTOR 1-GAMMA [*H. sapiens*], ESTs, Highly similar to EF1G_HUMAN ELONGATION FACTOR 1-GAMMA [*H. sapiens*], *Homo sapiens* cDNA FLJ11216 fis, clone PLACE1008002, eukaryotic translation elongation factor 1 gamma |
| 168 | 13974 | AA860030 | u, x, General | | EST, Moderately similar to I38369 beta tubulin [*H. sapiens*], EST, Weakly similar to I38369 beta-tubulin [*H. sapiens*], EST, Weakly similar to TUBULIN BETA-5 CHAIN [*M. musculus*], ESTs, Highly similar to A25113 tubulin beta chain 15 - rat [*R. norvegicus*], FK506-binding protein 1A (12 kD), RIKEN cDNA 2310061K05 gene, RIKEN cDNA 2410129E14 gene, tubulin, beta 2, tubulin, beta 5, tubulin, beta polypeptide |
| 169 | 7090 | AA860039 | x | hyaluronan mediated motility receptor (RHAMM), hyaluronan-mediated motility receptor (RHAMM) | *Mus musculus* 12 days embryo male wolffian duct includes surrounding region cDNA, RIKEN full-length enriched library, clone: 6720466F14, full insert sequence, RIKEN cDNA 0610027D24 gene, TRAF4 associated factor 1, hyaluronan mediated motility receptor (RHAMM), hyaluronan-mediated motility receptor (RHAMM) |
| 170 | 23769 | AA860055 | k, x | | DKFZP547E2110 protein, hypothetical protein FLJ10604 |
| 171 | 16323 | AA866240 | w | | |
| 172 | 4462 | AA866264 | General | | EST, Weakly similar to PE2R RAT 20-ALPHA-HYDROXYSTEROID DEHYDROGENASE [*R. norvegicus*], *Mus musculus* 10 days embryo cDNA, RIKEN full-length enriched library, clone: 2610528B18, full insert sequence, RIKEN cDNA 9430025F20 gene, *Rattus norvegicus* mRNA for 20-alpha-hydroxysteroid dehydrogenase (20-alpha-HSD), complete cds, aldo-keto reductase family 1, member C1, aldo-keto reductase family 1, member C4 (chlordecone reductase; 3-alpha hydroxysteroid dehydrogenase, type I; dihydrodiol dehydrogenase 4), expressed sequence AI315367, expressed sequence AI503553, hydroxysteroid (17-beta) dehydrogenase 5 |
| 173 | 15884 | AA866276 | k | | ESTs, Highly similar to A54602 microtubule-associated serine/threonine protein kinase MAST205 - mouse [*M. musculus*], ESTs, Moderately similar to A54602 microtubule-associated serine/threonine protein kinase MAST205 - mouse [*M. musculus*], |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | *Homo sapiens* cDNA: FLJ21699 fis, clone COL09829, KIAA0303 protein, KIAA0807 protein, *Mus musculus* adult male cecum cDNA, RIKEN full-length enriched library, clone: 9130026D18, full insert sequence, microtubule associated testis specific serine/threonine protein kinase, syntrophin associated serine/threonine kinase |
| 174 | 17742 | AA866302 | c, y | 4-hydroxyphenylpyruvate dioxygenase, 4-hydroxyphenylpyruvic acid dioxygenase | 4-hydroxyphenylpyruvate dioxygenase, 4-hydroxyphenylpyruvic acid dioxygenase, ESTs, Weakly similar to HPPD MOUSE 4-HYDROXYPHENYLPYRUVATE DIOXYGENASE [*M. musculus*], ESTs, Weakly similar to S32820 alloantigen F - rat [*R. norvegicus*], hypothetical protein MGC15668 |
| 175 | 16333 | AA866414 | a, h | solute carrier family 4 (anion exchanger), member 1, solute carrier family 4, (anion exchanger), member 1 (erythrocyte membrane protein band 3, Diego blood group) | ESTs, Highly similar to BAND 3 ANION EXCHANGE PROTEIN [*M. musculus*], ESTs, Weakly similar to B3HU band 3 anion transport protein, erythrocyte [*H. sapiens*], solute carrier family 4 (anion exchanger), member 1, solute carrier family 4, anion exchanger, member 1 (erythrocyte membrane protein band 3, Diego blood group) |
| 176 | 18918 | AA866444 | p, q | | |
| 177 | 16853 | AA866454 | j, l, m, y, z | | |
| 178 | 18995 | AA866459 | h, m | | |
| 179 | 16013 | AA866482 | s | | ESTs, Highly similar to FGD1_HUMAN PUTATIVE RHO/RAC GUANINE NUCLEOTIDE EXCHANGE FACTOR [*H. sapiens*], ESTs, Weakly similar to FGD1 MOUSE PUTATIVE RHO/RAC GUANINE NUCLEOTIDE EXCHANGE FACTOR [*M. musculus*], ESTs, Weakly similar to FGD1_HUMAN PUTATIVE RHO/RAC GUANINE NUCLEOTIDE EXCHANGE FACTOR [*H. sapiens*], FGD1 family, member 3, RIKEN cDNA 5830461L01 gene, faciogenital dysplasia (Aarskog-Scott syndrome), faciogenital dysplasia homolog, faciogenital dysplasia homolog 2 (human) |
| 180 | 26036 | AA874849 | r | | |
| 181 | 16059 | AA874857 | h | | |
| 182 | 16069 | AA874873 | r | | |
| 183 | 21633 | AA874951 | f | | ESTs, Weakly similar to RNA binding protein [*H. sapiens*] |
| 184 | 16192 | AA874995 | w | | |
| 185 | 16254 | AA875025 | j | | cellular retinoic acid-binding protein 1 |
| 186 | 16312 | AA875032 | cc, General | | |
| 187 | 20701 | AA875097 | b | fibrinogen, A alpha polypeptide | *Homo sapiens* clone HQ0582, expressed sequence AI303526, fibrinogen, A alpha polypeptide, fibrinogen, gamma polypeptide |
| 188 | 16416 | AA875098 | bb | | ADP-ribosylation factor 3, RIKEN cDNA 5430400P17 gene, *Rattus norvegicus* ADP-ribosylation factor 3 mRNA, complete cds, expressed sequence AA408731 |
| 189 | 16419 | AA875102 | bb | | expressed sequence AL022645, expressed sequence C76690, small nuclear ribonucleoprotein E, small nuclear ribonucleoprotein polypeptide E |
| 190 | 15313 | AA875126 | l, m, General | | |
| 191 | 10936 | AA875146 | w | | |
| 192 | 18084 | AA875186 | h | | |
| 193 | 15371 | AA875205 | u | | ESTs, Weakly similar to IF39_HUMAN EUKARYOTIC TRANSLATION |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | INITIATION FACTOR 3 SUBUNIT 9 [*H. sapiens*] |
| 194 | 15401 | AA875257 | x, z | | |
| 195 | 15410 | AA875268 | p, s | | NADH dehydrogenase (ubiquinone) Fe—S protein 7 (20 kD) (NADH-coenzyme Q reductase) |
| 196 | 15420 | AA875286 | f | | |
| 197 | 15446 | AA875327 | s, w | | |
| 198 | 7936 | AA875495 | b, General | | |
| 199 | 17314 | AA875509 | i, l, m | | EST, Moderately similar to A Chain A, Mdm2 Bound To The Transactivation Domain Of P53 {SUB 17-125 [*H. sapiens*], mouse double minute 2, human homolog of; p53-binding protein |
| 200 | 24472 | AA875523 | k | | EST, Weakly similar to MOHU6N myosin alkali light chain 6, nonmuscle form [*H. sapiens*], myosin light chain, alkali, nonmuscle, myosin, light polypeptide 6, alkali, smooth muscle and non-muscle |
| 201 | 15587 | AA875577 | j | | |
| 202 | 15617 | AA875620 | General | | |
| 202 | 15618 | AA875620 | General | | |
| 203 | 5384 | AA891041 | f, cc, General | | Jun-B oncogene, jun B proto-oncogene |
| 204 | 24814 | AA891209 | f, p | | |
| 205 | 21930 | AA891322 | d | | EST, Moderately similar to JH0148 nucleolin - rat [*R. norvegicus*], EST, Weakly similar to NUCL_HUMAN NUCLEOLIN [*H. sapiens*], ESTs, Highly similar to FUS_HUMAN RNA-BINDING PROTEIN FUS [*H. sapiens*], ESTs, Weakly similar to T17210 hypothetical protein DKFZp434N041.1 [*H. sapiens*], RIKEN cDNA 2700022N21 gene, fusion, derived from t(12; 16) malignant liposarcoma, poly(A) binding protein, nuclear 1, small nuclear ribonucleoprotein 70 kD polypeptide (RNP antigen) |
| 206 | 17225 | AA891553 | h | | EST, Weakly similar to IF37 MOUSE EUKARYOTIC TRANSLATION INITIATION FACTOR 3 SUBUNIT 7 [*M. musculus*], eukaryotic translation initiation factor 3, subunit 7 (zeta, 66/67 kDa), eukaryotic translation initiation factor 3, subunit 7 (zeta, 66/67 kD) |
| 207 | 7522 | AA891571 | j, m | | |
| 208 | 9071 | AA891578 | b | | |
| 209 | 19321 | AA891666 | u | melanoma antigen, family D, 1 | *Homo sapiens*, Similar to neurofilament, heavy polypeptide (200 kD), clone MGC: 20701 IMAGE: 4634024, mRNA, complete cds, MAGE-E1 protein, MAGEF1 protein, Neurofilament, heavy polypeptide, RIKEN cDNA 2010107K23 gene, RIKEN cDNA 3830417A13 gene, general transcription factor IIH, polypeptide 1 (62 kD subunit), melanoma antigen, family D, 1, melanoma antigen, family D, 2, necdin, neurofilament, heavy polypeptide, neurofilament, heavy polypeptide (200 kD) |
| 210 | 17693 | AA891737 | j, l, m, n, y, z | | |
| 211 | 17256 | AA891739 | General | | |
| 213 | 18269 | AA891769 | General | | ESTs, Highly similar to S03917 fibronectin ED-A [*H. sapiens*], ESTs, Moderately similar to Fourth And Fifth Fibronectin Type I Module Pair (SUB 183-275 [*H. sapiens*], Fibronectin 1, fibronectin 1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 214 | 9905 | AA891774 | s, bb, General | | |
| 215 | 17061 | AA891812 | d | | |
| 216 | 7050 | AA891824 | h | | ESTs, Highly similar to 2013348A Ser kinase SRPK1 [*H. sapiens*], *Mus musculus* 13 days embryo head cDNA, RIKEN full-length enriched library, clone: 3110005M20, full insert sequence, *Mus musculus* adult male lung cDNA, RIKEN full-length enriched library, clone: 1200011B22, full insert sequence, SFRS protein kinase 1, SFRS protein kinase 2, serine/arginine-rich protein specific kinase 2, serine/threonine kinase 23 |
| 217 | 4463 | AA891831 | General | | EST, Weakly similar to PE2R RAT 20-ALPHA-HYDROXYSTEROID DEHYDROGENASE [*R. norvegicus*], *Mus musculus* 10 days embryo cDNA, RIKEN full-length enriched library, clone: 2610528B18, full insert sequence, RIKEN cDNA 9430025F20 gene, *Rattus norvegicus* mRNA for 20-alpha-hydroxysteroid dehydrogenase (20-alpha-HSD), complete cds, aldo-keto reductase family 1, member C1, aldo-keto reductase family 1, member C4 (chlordecone reductase; 3-alpha hydroxysteroid dehydrogenase, type I; dihydrodiol dehydrogenase 4), expressed sequence AI315387, expressed sequence AI503553, hydroxysteroid (17-beta) dehydrogenase 5 |
| 218 | 14289 | AA891838 | i | | |
| 219 | 20523 | AA891842 | r, cc | | |
| 220 | 17779 | AA891914 | g, s, z | | EST, Weakly similar to ACY1_HUMAN AMINOACYLASE-1 [*H. sapiens*], aminoacylase 1 |
| 221 | 17438 | AA891943 | General | | |
| 222 | 22862 | AA891944 | p | | |
| 223 | 1159 | AA891949 | e, z | | |
| 224 | 4473 | AA891965 | General | | |
| 225 | 6362 | AA892053 | f, j, l, m | | |
| 226 | 9037 | AA892066 | y | | |
| 227 | 19469 | AA892112 | General | | EST, Weakly similar to PROD_HUMAN PROLINE OXIDASE, MITOCHONDRIAL PRECURSOR [*H. sapiens*], *Homo sapiens* mRNA for KIAA1653 protein, partial cds, proline dehydrogenase, proline dehydrogenase (proline oxidase), proline oxidase 1, proline oxidase homolog |
| 228 | 14595 | AA892128 | o, t, v | | |
| 229 | 16527 | AA892154 | cc | | |
| 230 | 4482 | AA892173 | bb | | |
| 231 | 20917 | AA892238 | h | | |
| 232 | 2357 | AA892268 | d | | Met proto-oncogene, RYK receptor-like tyrosine kinase, macrophage stimulating 1 receptor (c-met-related tyrosine kinase), met proto-oncogene |
| 233 | 18183 | AA892271 | h | | |
| 234 | 6523 | AA892299 | d | | |
| 236 | 13647 | AA892367 | a | | EST, Weakly similar to 60S RIBOSOMAL PROTEIN L3 [*R. norvegicus*], EST, Weakly similar to I84501 ribosomal protein L3 [*H. sapiens*], ESTs, Moderately similar to 60S RIBOSOMAL PROTEIN L3 [*R. norvegicus*], ESTs, Moderately similar to I84501 ribosomal protein L3 [*H. sapiens*], ESTs, Weakly similar to RL3 MOUSE 60S RIBOSOMAL PROTEIN L3 [*M. musculus*], RIKEN |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 237 | 3473 | AA892378 | v | | cDNA 1110057H16 gene, ribosomal protein L3, ribosomal protein L3-like |
| 238 | 17682 | AA892382 | j, p, s, x, General | | ESTs, Weakly similar to T44342 hypothetical protein TSC501 [H. sapiens], kidney- and liver-specific gene, putative N-acetyltransferase Camello 2 |
| 239 | 820 | AA892395 | g, s | aldolase 2, B isoform, aldolase B, fructose-bisphosphate | |
| 240 | 14754 | AA892414 | u | | |
| 241 | 17439 | AA892446 | f | | |
| 242 | 16469 | AA892462 | p | | ubiquinol-cytochrome c reductase (6.4 kD) subunit |
| 243 | 13609 | AA892468 | i, General | | EST, Weakly similar to MAST CELL PROTEASE 7 PRECURSOR [M. musculus], ESTs, Weakly similar to MCT7 RAT MAST CELL PROTEASE 7 PRECURSOR [R. norvegicus], RIKEN cDNA 2410039E18 gene, RIKEN cDNA 4933401F05 gene, marapsin, mast cell protease 7, protease, serine, 21 (testisin), protease, serine, 22, protease, serine, 8 (prostasin), tryptase delta 1, tryptase, alpha |
| 243 | 13610 | AA892468 | n, v, General | | EST, Weakly similar to MAST CELL PROTEASE 7 PRECURSOR [M. musculus], ESTs, Weakly similar to MCT7 RAT MAST CELL PROTEASE 7 PRECURSOR [R. norvegicus], RIKEN cDNA 2410039E18 gene, RIKEN cDNA 4933401F05 gene, marapsin, mast cell protease 7, protease, serine, 21 (testisin), protease, serine, 22, protease, serine, 8 (prostasin), tryptase delta 1, tryptase, alpha |
| 244 | 9254 | AA892470 | n, u | | EST, Weakly similar to histone H2A.F/Z variant [H. sapiens], H2A histone family, member Z, RIKEN cDNA C530002L11 gene, histone H2A.F/Z variant |
| 245 | 11991 | AA892483 | s | | |
| 246 | 1522 | AA892486 | f | | EST, Weakly similar to A32609 alpha-glucosidase [H. sapiens], ESTs, Weakly similar to LYAG MOUSE LYSOSOMAL ALPHA-GLUCOSIDASE PRECURSOR [M. musculus], alpha glucosidase 2, alpha neutral subunit, glucosidase, alpha, acid |
| 247 | 11994 | AA892507 | aa | | ESTs, Highly similar to DS1_HUMAN DS-1 PROTEI [H. sapiens], immature colon carcinoma transcript 1 |
| 248 | 23888 | AA892520 | w | | |
| 248 | 23889 | AA892520 | h | | |
| 249 | 8599 | AA892522 | p | | |
| 250 | 15154 | AA892532 | p | | expressed sequence AI987846, expressed sequence AL023058, expressed sequence C77895, hypothetical protein MGC3178, protein disulfide isomerase-related protein, quiescin Q6 |
| 251 | 17468 | AA892545 | r | | |
| 252 | 11203 | AA892554 | f, h | | |
| 253 | 18906 | AA892561 | a, bb, General | | |
| 254 | 19327 | AA892562 | f, j, y, z | | ESTs, Moderately similar to DKC1 RAT DYSKERIN [R. norvegicus], ESTs, Weakly similar to DKC1_HUMAN DYSKERIN [H. sapiens], RIKEN cDNA 9030425C13 gene, dyskeratosis congenita 1, dyskerin, hypothetical protein, MGC: 7014, nuclear factor of kappa light polypeptide gene enhancer in B-cells inhibitor-like 1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 255 | 18274 | AA892572 | p | | |
| 256 | 4512 | AA892578 | cc | | |
| 257 | 15876 | AA892582 | w | | EST, Highly similar to 60S RIBOSOMAL PROTEIN L8 [*R. norvegicus*], EST, Moderately similar to 60S RIBOSOMAL PROTEIN L8 [*R. norvegicus*], EST, Weakly similar to JN0923 ribosomal protein L8, cytosolic [*H. sapiens*], ESTs, Highly similar to 60S RIBOSOMAL PROTEIN L8 [*R. norvegicus*], ESTs, Highly similar to RL8_HUMAN 60S RIBOSOMAL PROTEIN L [*M. musculus*], ESTs, Moderately similar to RL8_HUMAN 60S RIBOSOMAL PROTEIN L [*M. musculus*], expressed sequence AL024098, ribosomal protein L8 |
| 258 | 19085 | AA892598 | General | | |
| 258 | 19086 | AA892598 | General | | |
| 259 | 20065 | AA892647 | l | | EST, Highly similar to HISTONE H4 [*R. norvegicus*], ESTs, Highly similar to HISTONE H4 [*R. norvegicus*], H4 histone family, member D, H4 histone family, member H, H4 histone family, member I, H4 histone family, member K, *Mus musculus* 10 day old male pancreas cDNA, RIKEN full-length enriched library, clone: 1810029H14, full insert sequence, *Mus musculus* 10 days embryo cDNA, RIKEN full-length enriched library, clone: 2610027B07, full insert sequence, *Mus musculus* adult male testis cDNA, RIKEN full-length enriched library, clone: 4930558J22, full insert sequence, *Mus musculus* adult male tongue cDNA, RIKEN full-length enriched library, clone: 2310067E17, full insert sequence, histone 4 protein |
| 260 | 20088 | AA892666 | a, n | | |
| 261 | 23783 | AA892773 | n | | |
| 262 | 17549 | AA892776 | f, z | | *Mus musculus*, Similar to solute carrier family 25 (mitochondrial carrier; phosphate carrier), member 3, clone MGC: 7631, mRNA, complete cds, expressed sequence W51672, solute carrier family 25 (mitochondrial carrier; phosphate carrier), member 3 |
| 263 | 13542 | AA892798 | b | | |
| 264 | 22537 | AA892799 | General | | 3-phosphoglycerate dehydrogenase, EST, Weakly similar to SERA RAT D-3-PHOSPHOGLYCERATE DEHYDROGENASE [*R. norvegicus*], ESTs, Moderately similar to SERA_HUMAN D-3-PHOSPHOGLYCERATE DEHYDROGENASE [*H. sapiens*], *Mus musculus* adult male testis cDNA, RIKEN full-length enriched library, clone: 4930404C15, full insert sequence, RIKEN cDNA 1110059D05 gene, RIKEN cDNA 6430629L09 gene, glyoxylate reductase/hydroxypyruvate reductase, phosphoglycerate dehydrogenase |
| 264 | 22539 | AA892799 | v | | 3-phosphoglycerate dehydrogenase, EST, Weakly similar to SERA RAT D-3-PHOSPHOGLYCERATE DEHYDROGENASE [*R. norvegicus*], ESTs, Moderately similar to SERA_HUMAN D-3-PHOSPHOGLYCERATE DEHYDROGENASE [*H. sapiens*], *Mus musculus* adult male testis cDNA, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 264 | 22538 | AA892799 | General | | RIKEN full-length enriched library, clone: 4930404C15, full insert sequence, RIKEN cDNA 1110059D05 gene, RIKEN cDNA 6430629L09 gene, glyoxylate reductase/hydroxypyruvate reductase, phosphoglycerate dehydrogenase 3-phosphoglycerate dehydrogenase, EST, Weakly similar to SERA_RAT D-3-PHOSPHOGLYCERATE DEHYDROGENASE [*R. norvegicus*], ESTs, Moderately similar to SERA_HUMAN D-3-PHOSPHOGLYCERATE DEHYDROGENASE [*H. sapiens*], *Mus musculus* adult male testis cDNA, RIKEN full-length enriched library, clone: 4930404C15, full insert sequence, RIKEN cDNA 1110059D05 gene, RIKEN cDNA 6430629L09 gene, glyoxylate reductase/hydroxypyruvate reductase, phosphoglycerate dehydrogenase |
| 265 | 6951 | AA892820 | h | | |
| 266 | 23322 | AA892821 | j, z | | ESTs, Highly similar to AR72_HUMAN AFLATOXIN B1 ALDEHYDE REDUCTASE 1 (AFB1-AR 1) (ALDOKETOREDUCTASE 7) [*H. sapiens*], ESTs, Moderately similar to AFAR_RAT AFLATOXIN B1 ALDEHYDE REDUCTASE [*R. norvegicus*], RIKEN cDNA 0610025K21 gene, aflatoxin B1 aldehyde reductase, aldo-keto reductase family 7, member A2 (aflatoxin aldehyde reductase), aldo-keto reductase family 7, member A3 (aflatoxin aldehyde reductase) |
| 267 | 17923 | AA892843 | f | | |
| 268 | 22871 | AA892859 | m | | RIKEN cDNA 2410042F05 gene, procollagen-lysine, 2-oxoglutarate 5-dioxygenase (lysine hydroxylase) 2, procollagen-lysine, 2-oxoglutarate 5-dioxygenase (lysine hydroxylase, Ehlers-Danlos syndrome type VI), procollagen-lysine, 2-oxoglutarate 5-dioxygenase 1 |
| 269 | 9053 | AA892861 | p, v, General | | |
| 270 | 16482 | AA892940 | w | | EST, Weakly similar to EFHU2 translation elongation factor eEF-2 [*H. sapiens*], ESTs, Highly similar to ELONGATION FACTOR 2 [*R. norvegicus*], U5 snRNP-specific protein, 116 kD, eukaryotic translation elongation factor 2, expressed sequence AI451340, hypothetical protein FLJ21661 |
| 271 | 12020 | AA893035 | j, y | | |
| 272 | 3863 | AA893060 | General | | |
| 273 | 13332 | AA893080 | i, General | | |
| 274 | 21305 | AA893082 | General | | |
| 275 | 16591 | AA893191 | j, z | | |
| 276 | 17447 | AA893192 | General | | |
| 277 | 3876 | AA893205 | n | | |
| 278 | 3878 | AA893230 | General | | Calmodulin 1 (phosphorylase kinase, delta), Calmodulin III, ESTs, Highly similar to A Chain A, Calmodulin Complexed With Calmodulin-Binding Peptide From Smooth Muscle Myosin Light Chain Kinase {SUB 2-148 [*H. sapiens*], RIKEN cDNA 2310068O22 gene, calmodulin, calmodulin 1, calmodulin 1 (phosphorylase kinase, delta), |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 279 | 20986 | AA893242 | q | fatty acid Coenzyme A ligase, long chain 2, fatty-acid-Coenzyme A ligase, long-chain 2 | calmodulin 2, calmodulin 2 (phosphorylase kinase, delta), calmodulin 3, calmodulin-like 3 ESTs, Weakly similar to LCFB MOUSE LONG-CHAIN-FATTY-ACID-COA LIGASE 2 [*M. musculus*], *Mus musculus*, Similar to fatty-acid-Coenzyme A ligase, long-chain 6, clone MGC: 28744 IMAGE: 4481949, mRNA, complete cds, *Rattus norvegicus* gonadotropin-regulated long chain acyl-CoA synthetase (GR-LACS) mRNA, complete cds, fatty acid Coenzyme A ligase, long chain 2, fatty acid Coenzyme A ligase, long chain 5, fatty-acid-Coenzyme A ligase, long-chain 1, fatty-acid-Coenzyme A ligase, long-chain 2, lipidosin |
| 280 | 16168 | AA893280 | i, z, General | | RIKEN cDNA 1300012C15 gene, RIKEN cDNA 2310076L09 gene, adipose differentiation related protein, adipose differentiation-related protein |
| 281 | 3886 | AA893289 | j, m, y | | |
| 282 | 15209 | AA893327 | y | | |
| 283 | 17800 | AA893436 | cc | | |
| 284 | 17836 | AA893626 | h | | Guanine nucleotide-binding protein beta 1, *Homo sapiens* mRNA for FLJ00083 protein, partial cds, *Mus musculus*, clone MGC: 7934 IMAGE: 3583848, mRNA, complete cds, RIKEN cDNA 5930415H02 gene, WD repeat domain 5, guanine nucleotide binding protein (G protein), beta polypeptide 1, guanine nucleotide binding protein beta subunit 4, guanine nucleotide binding protein, beta 1, guanine nucleotide binding protein, beta 4, hypothetical protein, recombination protein REC14 |
| 285 | 9084 | AA893717 | x | | |
| 286 | 22731 | AA893743 | d | | |
| 287 | 12031 | AA893860 | v | | ESTs, Highly similar to YSHUT threonine-tRNA ligase [*H. sapiens*], ESTs, Moderately similar to YSHUT threonine-tRNA ligase [*H. sapiens*], hypothetical protein FLJ12528, threonyl-tRNA synthetase |
| 288 | 17897 | AA893905 | k | | |
| 289 | 3447 | AA893982 | d | | |
| 290 | 22583 | AA894009 | n | | |
| 291 | 10540 | AA894027 | j | | |
| 292 | 4569 | AA894059 | x | | |
| 293 | 18419 | AA894130 | d | | Amyloid protein precursor-like protein 2, EST, Weakly similar to AMYLOID-LIKE PROTEIN 2 PRECURSOR [*R. norvegicus*], Human DNA sequence from clone RP3-461P17 on chromosome 20q12-13.2. Contains two novel genes, gene HE4 for Major Epididymis-specific protein E4 precursor (Epididymis Secretory protein E4), RPL5 (60S Ribosomal Protein L5), COX6C (Cytochrome C Oxidase subunit VIC) and HSPD1 (HSP60, Mitochondrial Matrix Protein P1 precursor, Heat Shock Protein 60, GROEL, HUCHA60) pseudogenes, the SPINT3 gene for Kunitz type serine protease inhibitor 3 (HKIB9), two genes for novel Kunitz/Bovine pancreatic trypsin inhibitor and WAP-type (Whey Acidic Protein) 'four-disulfide core' domains containing proteins and the gene for Eppin-1, -2 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | and -3. Contains ESTs, STSs, GSSs and a CpG island, RIKEN cDNA 1700024E17 gene, amyloid beta (A4) precursor-like protein 2, serine protease inhibitor, Kunitz type 2, tissue factor pathway inhibitor, tissue factor pathway inhibitor 2 |
| 294 | 17336 | AA894297 | j | | |
| 295 | 19120 | AA894318 | f, j | | |
| 296 | 19762 | AA899113 | i | | |
| 297 | 18286 | AA899219 | u | | EST, Weakly similar to S45140 tubulin beta chain [*H. sapiens*], ESTs, Highly similar to T08726 tubulin beta chain [*H. sapiens*], ESTs, Highly similar to TBB1 RAT TUBULIN BETA CHAIN [*R. norvegicus*], ESTs, Moderately similar to I38370 beta-tubulin [*H. sapiens*], ESTs, Moderately similar to TBB1 RAT TUBULIN BETA CHAIN [*R. norvegicus*], RIKEN cDNA 2410129E14 gene, RIKEN cDNA 4930447K03 gene, RIKEN cDNA 4930542G03 gene, tubulin, beta 3, tubulin, beta polypeptide |
| 298 | 22051 | AA899498 | w | | |
| 298 | 22052 | AA899498 | q | | |
| 299 | 21628 | AA899563 | aa | | |
| 300 | 4262 | AA899590 | i | | |
| 301 | 4661 | AA899709 | t, General | receptor (calcitonin) activity modifying protein 3 | receptor (calcitonin) activity modifying protein 3 |
| 302 | 21354 | AA899721 | q | | |
| 303 | 17905 | AA899762 | General | | EST, Moderately similar to EGFR_HUMAN EPIDERMAL GROWTH FACTOR RECEPTOR PRECURSOR [*H. sapiens*], Epidermal growth factor receptor, formerly avian erythroblastic leukemia viral (v-erbB) oncogene homolog (Erbb1), avian erythroblastosis oncogene B 3, epidermal growth factor receptor, epidermal growth factor receptor (avian erythroblastic leukemia viral (v-erb-b) oncogene homolog) |
| 304 | 15231 | AA899840 | r | | |
| 305 | 23778 | AA899854 | c, k, x | topoisomerase (DNA) II alpha, topoisomerase (DNA) II alpha (170 kD) | ESTs, Moderately similar to A40493 DNA topoisomerase [*H. sapiens*], ESTs, Moderately similar to TP2A MOUSE DNA TOPOISOMERASE II, ALPHA [*M. musculus*], topoisomerase (DNA) II alpha, topoisomerase (DNA) II beta, topoisomerase (DNA) II beta (180 kD) |
| 306 | 22060 | AA899898 | b | | |
| 307 | 9114 | AA899951 | v, General | | |
| 308 | 8988 | AA900148 | f | | |
| 309 | 11841 | AA900247 | v | | ESTs, Highly similar to IEFS_HUMAN TRANSFORMATION-SENSITIVE PROTEIN IEF SSP 3521 [*H. sapiens*], hypothetical protein FLJ12788 |
| 310 | 4725 | AA900290 | cc | | Alpha-2-macroglobulin, ESTs, Moderately similar to A2M2 MOUSE MURINOGLOBULIN 2 PRECURSOR [*M. musculus*], RIKEN cDNA 2610307I21 gene, alpha-2-macroglobulin, carbon catabolite repression 4 homolog (*S. cerevisiae*), expressed sequence AW456442, pregnancy-zone protein |
| 311 | 4747 | AA900465 | General | | |
| 312 | 20988 | AA900562 | o | | |
| 313 | 3822 | AA900863 | b, g, General | | DNA segment, Chr 17, human D6S81E 1, ESTs, Highly similar to S33681 translation initiation factor eIF-4A.I [*H. sapiens*], HLA-B associated |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 315 | 12420 | AA901017 | b | | transcript 1, Human clone 23933 mRNA sequence, eukaryotic translation initiation factor 4A, isoform 1, mitochondrial DEAD-box polypeptide 28, nuclear RNA helicase, DECD variant of DEAD box family *Mus musculus*, Similar to aspartyl-tRNA synthetase, clone MGC: 6719 IMAGE: 3586278, mRNA, complete cds, asparaginyl-tRNA synthetase, aspartyl-tRNA synthetase, hypothetical protein FLJ10514, hypothetical protein FLJ23441 |
| 316 | 4849 | AA901155 | s | | |
| 317 | 3959 | AA901338 | General | | |
| 318 | 22846 | AA923982 | a, d | | succinate-CoA ligase, ADP-forming, beta subunit |
| 319 | 4895 | AA923999 | k | | |
| 320 | 21546 | AA924188 | cc, General | | |
| 321 | 24192 | AA924210 | n, General | | |
| 322 | 4933 | AA924301 | g, l, General | | |
| 323 | 4944 | AA924405 | l, General | | ESTs, Weakly similar to NEUROFILAMENT TRIPLET H PROTEIN [*M. musculus*], RIKEN cDNA 0610009L18 gene, RIKEN cDNA 1300003A17 gene, RIKEN cDNA 2410142G14 gene, nucleolar protein (KKE/D repeat) |
| 324 | 4948 | AA924428 | r | | |
| 325 | 4949 | AA924432 | General | | ESTs, Weakly similar to NPT2_HUMAN RENAL SODIUM-DEPENDENT PHOSPHATE TRANSPORT PROTEIN 2 [*H. sapiens*], *Homo sapiens*, Similar to solute carrier family 34 (sodium phosphate), member 1, clone MGC: 18179 IMAGE: 4155326, mRNA, complete cds, *Rattus norvegicus* mRNA for NaPi-2 alpha, complete cds, Solute carrier family 17 (sodium/hydrogen exchanger), member 2, expressed sequence AI649385, solute carrier family 34 (sodium phosphate), member 1, solute carrier family 34 (sodium phosphate), member 2 |
| 326 | 18891 | AA924598 | e | | |
| 327 | 22540 | AA924630 | v, General | | 3-phosphoglycerate dehydrogenase, EST, Weakly similar to SERA RAT D-3-PHOSPHOGLYCERATE DEHYDROGENASE [*R. norvegicus*], ESTs, Moderately similar to SERA_HUMAN D-3-PHOSPHOGLYCERATE DEHYDROGENASE [*H. sapiens*], *Mus musculus* adult male testis cDNA, RIKEN full-length enriched library, clone: 4930404C15, full insert sequence, RIKEN cDNA 1110059D05 gene, RIKEN cDNA 6430629L09 gene, glyoxylate reductase/hydroxypyruvate reductase, phosphoglycerate dehydrogenase |
| 327 | 22541 | AA924630 | General | | 3-phosphoglycerate dehydrogenase, EST, Weakly similar to SERA RAT D-3-PHOSPHOGLYCERATE DEHYDROGENASE [*R. norvegicus*], ESTs, Moderately similar to SERA_HUMAN D-3-PHOSPHOGLYCERATE DEHYDROGENASE [*H. sapiens*], *Mus musculus* adult male testis cDNA, RIKEN full-length enriched library, clone: 4930404C15, full insert sequence, RIKEN cDNA 1110059D05 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | gene, RIKEN cDNA 6430629L09 gene, glyoxylate reductase/hydroxypyruvate reductase, phosphoglycerate dehydrogenase |
| 328 | 14759 | AA924766 | k | | |
| 329 | 23123 | AA924794 | x | | |
| 330 | 4067 | AA924813 | g, p | | |
| 331 | 2888 | AA924902 | r, General | | |
| 332 | 18130 | AA924964 | d | | |
| 333 | 23141 | AA925019 | r | | |
| 334 | 23195 | AA925026 | General | | ESTs, Weakly similar to A35863 tryptase [*H. sapiens*], ESTs, Weakly similar to MCT7 RAT MAST CELL PROTEASE 7 PRECURSOR [*R. norvegicus*], RIKEN cDNA 4733401N09 gene, mast cell protease 7, tryptase delta 1, tryptase gamma 1, tryptase, alpha |
| 335 | 21458 | AA925049 | f, aa, General | | |
| 336 | 5073 | AA925061 | m | | |
| 337 | 14790 | AA925087 | o, General | | |
| 338 | 5089 | AA925126 | g | | *Homo sapiens*, clone IMAGE: 3940519, mRNA, partial cds, hypothetical protein DKFZp762O076 |
| 339 | 23261 | AA925145 | k, General | | *Mus musculus* adult male testis cDNA, RIKEN full-length enriched library, clone: 4930572N12, full insert sequence, betaine-homocysteine methyltransferase, betaine-homocysteine methyltransferase 2 |
| 340 | 17363 | AA925150 | a | | KIAA0438 gene product, *Rattus norvegicus* mRNA for neurodegeneration associated protein 1, complete cds, expressed sequence AL022700, g1-related zinc finger protein, hypothetical protein, hypothetical protein FLJ11830 similar to Praja1, hypothetical protein, similar to (U06944) PRAJA1, praja1 |
| 341 | 23448 | AA925167 | l | | |
| 342 | 23159 | AA925318 | e | | EST, Weakly similar to TRI9__HUMAN THYROID RECEPTOR INTERACTING PROTEIN 9 [*H. sapiens*], ESTs, Highly similar to A44437 regenerating liver inhibitory factor RL/IF-1 - rat [*R. norvegicus*], ESTs, Weakly similar to I-kappa B alpha chain [*M. musculus*], nuclear factor of kappa light chain gene enhancer in B-cells inhibitor, alpha, nuclear factor of kappa light chain gene enhancer in B-cells inhibitor, beta, nuclear factor of kappa light polypeptide gene enhancer in B-cells inhibitor, alpha, nuclear factor of kappa light polypeptide gene enhancer in B-cells inhibitor, beta, nuclear factor of kappa light polypeptide gene enhancer in B-cells inhibitor, epsilon |
| 343 | 21500 | AA925353 | k | | |
| 344 | 22479 | AA925418 | t | | |
| 345 | 21151 | AA925539 | b | | |
| 346 | 16944 | AA925541 | f | heterogeneous nuclear ribonucleoprotein L | EST, Moderately similar to 1604358A nuclear RNP protein L [*H. sapiens*], ESTs, Highly similar to 1604358A nuclear RNP protein L [*H. sapiens*], ESTs, Moderately similar to 1604358A nuclear RNP protein L [*H. sapiens*], heterogeneous nuclear ribonucleoprotein L |
| 346 | 16945 | AA925541 | t | heterogeneous nuclear ribonucleoprotein L | EST, Moderately similar to 1604358A nuclear RNP protein L [*H. sapiens*], ESTs, Highly similar to 1604358A nuclear RNP protein L [*H. sapiens*], ESTs, Moderately similar to 1604358A |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 347 | 17514 | AA925554 | bb | | nuclear RNP protein L [*H. sapiens*], heterogeneous nuclear ribonucleoprotein L ESTs, Moderately similar to JX0336 succinate dehydrogenase [*H. sapiens*], succinate dehydrogenase complex, subunit A, flavoprotein (Fp) |
| 348 | 5183 | AA925662 | i, General | | |
| 349 | 23189 | AA925844 | r | | |
| 350 | 23190 | AA925863 | aa | | EST, Weakly similar to IMB3_HUMAN IMPORTIN BETA-3 SUBUNIT [*H. sapiens*], *Homo sapiens* cDNA FLJ12978 fis, clone NT2RP2006321, RAN binding protein 6, karyopherin (importin) beta 3 |
| 351 | 5252 | AA926051 | General | | |
| 352 | 22967 | AA926080 | h, cc | | |
| 353 | 17157 | AA926129 | b | | |
| 354 | 13411 | AA926196 | u, General | | |
| 355 | 5295 | AA926247 | General | | potassium channel, subfamily K, member 1 (TWIK-1), potassium channel, subfamily K, member 3 (TASK-1), potassium channel, subfamily K, member 6 (TWIK-2), potassium channel, subfamily K, member 7 |
| 356 | 22928 | AA926262 | General | | DNA segment, human D4S114, P311 protein |
| 357 | 8948 | AA926316 | r | | |
| 358 | 21798 | AA926365 | aa | | CGI-69 protein, EST, Moderately similar to T43493 hypothetical protein DKFZp434C119.1 [*H. sapiens*], mitochondrial carrier family protein, mitochondrial solute carrier |
| 359 | 9942 | AA942697 | s | | |
| 360 | 6039 | AA942716 | x, General | | DNA segment, Chr 17, ERATO Doi 441, expressed, hematological and neurological expressed 1 |
| 361 | 11174 | AA942745 | g, o, w | | |
| 362 | 23005 | AA942770 | g | | |
| 363 | 21318 | AA942774 | General | | |
| 364 | 6615 | AA942889 | v | | |
| 365 | 6691 | AA943028 | c | | RAT MACROPHAGE COLONY STIMULATING FACTOR I RECEPTOR PRECURSOR [*R. norvegicus*], colony stimulating factor 1 receptor, colony stimulating factor 1 receptor, formerly McDonough feline sarcoma viral (v-fms) oncogene homolog |
| 366 | 22142 | AA943066 | p | | DEAD (aspartate-glutamate-alanine-aspartate) box polypeptide 5, DEAD/H (Asp-Glu-Ala-Asp/His) box polypeptide 17 (72 kD), KIAA0801 gene product, RIKEN cDNA 2610007K22 gene, RIKEN cDNA 4921506D17 gene, RIKEN cDNA 9130430L19 gene, RNA helicase, *Rattus norvegicus* RNA helicase with arginine-serine-rich domain mRNA, complete cds, expressed sequence AI325430, hypothetical protein, prp28, U5 snRNP 100 kd protein |
| 367 | 21993 | AA943149 | v, General | | ALEX1 protein, ALEX3 protein, armadillo repeat protein ALEX2, hypothetical protein MGC3195 |
| 368 | 9061 | AA943508 | General | | TU3A protein, hypothetical protein MGC11034 |
| 369 | 24390 | AA943531 | b, j, n, y | | ESTs, Weakly similar to VIL1 MOUSE VILLIN [*M. musculus*], actin binding LIM protein 1, advillin, erythrocyte membrane protein band 4.9 (dematin), erythrocyte protein band 4.9, villin |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 370 | 13976 | AA943532 | f, s, x | | EST, Moderately similar to I38369 beta tubulin [*H. sapiens*], EST, Weakly similar to I38369 beta-tubulin [*H. sapiens*], EST, Weakly similar to TUBULIN BETA-5 CHAIN [*M. musculus*], ESTs, Highly similar to A25113 tubulin beta chain 15 - rat [*R. norvegicus*], FK506-binding protein 1A (12 kD), RIKEN cDNA 2310061K05 gene, RIKEN cDNA 2410129E14 gene, tubulin, beta 2, tubulin, beta 5, tubulin, beta polypeptide |
| 371 | 22248 | AA943537 | cc, General | | ajuba, expressed sequence AI481106, expressed sequence R75157, zyxin |
| 372 | 22257 | AA943558 | m | | TATA box binding protein (TBP)-associated factor, RNA polymerase II, J, 20 kD |
| 373 | 12673 | AA943773 | u, cc, General | | |
| 374 | 13641 | AA944154 | u | | |
| 375 | 2658 | AA944155 | f | | |
| 376 | 12770 | AA944161 | d | | |
| 377 | 20903 | AA944180 | i, x | | CDC28 protein kinase 2, RIKEN cDNA 1110038L14 gene, expressed sequence AI047807 |
| 378 | 13507 | AA944244 | v | | |
| 379 | 15596 | AA944353 | General | | |
| 380 | 22681 | AA944413 | i, v, cc, General | | |
| 381 | 6711 | AA944439 | General | | |
| 382 | 14763 | AA944481 | i, q, General | | ESTs, Highly similar to AGP2__RAT ANGIOPOIETIN-2 (ANG-2) [*R. norvegicus*], angiopoietin 1, angiopoietin 2, angiopoietin-like 3, angiopoietin-like 4, angiopoietin-like factor |
| 383 | 22466 | AA944605 | h | | |
| 384 | 12301 | AA944727 | b | | B-cell CLL/lymphoma 3, B-cell leukemia/lymphoma 3, ESTs, Highly similar to A44437 regenerating liver inhibitory factor RL/IF-1 - rat [*R. norvegicus*], ESTs, Weakly similar to I-kappa B alpha chain [*M. musculus*], molecule possessing ankyrin repeats induced by lipopolysaccharide (MAIL), homolog of mouse, nuclear factor of kappa light chain gene enhancer in B-cells 1, p105, nuclear factor of kappa light chain gene enhancer in B-cells inhibitor, alpha, nuclear factor of kappa light polypeptide gene enhancer in B-cells 2, p49/p100, nuclear factor of kappa light polypeptide gene enhancer in B-cells inhibitor, alpha, nuclear factor of kappa light polypeptide gene enhancer in B-cells inhibitor, epsilon, testis-specific ankyrin motif containing protein |
| 385 | 7023 | AA944792 | d, m, aa | | |
| 386 | 22536 | AA944803 | bb | | |
| 387 | 22501 | AA944811 | g, l | | CGI-89 protein, hypothetical protein DKFZp667O2416, hypothetical protein FLJ20984, leukocyte receptor cluster (LRC) member 4 |
| 388 | 23967 | AA944831 | s | | |
| 389 | 26084 | AA944922 | i | | |
| 390 | 11974 | AA944958 | General | | |
| 391 | 22547 | AA944970 | aa | | |
| 392 | 22554 | AA945076 | z, General | | |
| 393 | 14352 | AA945181 | General | | |
| 395 | 1798 | AA945569 | General | | |
| 396 | 22050 | AA945604 | i, aa | | |
| 397 | 19731 | AA945615 | d, o | | |
| 398 | 22612 | AA945624 | a, General | | Diaphorase (NADH/NADPH), NAD(P)H menadione oxidoreductase 2, dioxin inducible, NAD(P)H menadione |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | oxidoreductase 2, dioxin-inducible, diaphorase (NADH/NADPH) (cytochrome b-5 reductase), diaphorase 4 (NADH/NADPH) |
| 399 | 22618 | AA945656 | aa | | |
| 400 | 11871 | AA945679 | v | | |
| 401 | 22656 | AA945818 | General | | |
| 402 | 6720 | AA945828 | p | | |
| 403 | 22351 | AA945867 | m | | |
| 404 | 22665 | AA945877 | f | | |
| 405 | 24243 | AA945950 | b | | |
| 406 | 22689 | AA945962 | General | | |
| 407 | 22692 | AA945986 | d | | |
| 408 | 22696 | AA945996 | c, General | | |
| 408 | 22697 | AA945996 | c, o | | |
| 409 | 22658 | AA945998 | w | | |
| 410 | 20832 | AA946040 | s | | ESTs, Weakly similar to COXG MOUSE CYTOCHROME C OXIDASE POLYPEPTIDE VIB [*M. musculus*], Human DNA sequence from clone RP4-591N18 on chromosome 22q13.1-13.2 Contains a COX6B (Cytochrome C Oxidase subunit VIb (EC 1.9.3.1)) pseudogene, ESTs, GSSs and two putative CpG islands, RIKEN cDNA 2010000G05 gene, cytochrome c oxidase subunit VIb |
| 411 | 18337 | AA946046 | General | | |
| 412 | 825 | AA946108 | General | | EST, Highly similar to LMA3__HUMAN LAMININ ALPHA-3 CHAIN PRECURSOR [*H. sapiens*], ESTs, Highly similar to LMA3__HUMAN LAMININ ALPHA-3 CHAIN PRECURSOR [*H. sapiens*], *Homo sapiens* cDNA: FLJ21236 fis, clone COL01111, expressed sequence AI853660, laminin, alpha 3 (nicein (150 kD), kalinln (165 kD), BM600 (150 kD), epilegrin) |
| 413 | 8639 | AA946221 | e, cc, General | | |
| 414 | 23237 | AA946224 | f | | |
| 415 | 15600 | AA946250 | o, aa | | |
| 416 | 19387 | AA946275 | t | | actin related protein 2/3 complex, subunit 3 (21 kD) |
| 417 | 6351 | AA946344 | d | | EST, Weakly similar to JC5111 cyclin-dependent kinase-related protein 1b - rat [*R. norvegicus*], EST, Weakly similar to S10889 proline-rich protein [*H. sapiens*], ESTs, Highly similar to JC5111 cyclin-dependent kinase-related protein 1b - rat [*R. norvegicus*], *Homo sapiens* ALS2CR7 mRNA, complete cds, PCTAIRE protein kinase 1, PCTAIRE-motif protein kinase 1, PFTAIRE protein kinase 1 |
| 418 | 22057 | AA946348 | e | | |
| 419 | 22069 | AA946349 | aa | | |
| 420 | 13962 | AA946351 | General | | |
| 421 | 18280 | AA946361 | g | | EST, Moderately similar to 1923401A protein CBP [*M. musculus*], EST, Weakly similar to 1923401A protein CBP [*M. musculus*], ESTs, Highly similar to 1923401A protein CBP [*M. musculus*], ESTs, Weakly similar to 1923401A protein CBP [*M. musculus*], bromodomain, testis-specific, bromodomain-containing 2 |
| 422 | 18944 | AA946391 | v | | |
| 424 | 21410 | AA946408 | t | | |
| 425 | 643 | AA946439 | o, y | | EST, Highly similar to HISTONE H4 [*R. norvegicus*], H4 histone family, member D, H4 histone family, member H, H4 histone family, member I, H4 histone family, member K, *Mus* |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | *musculus* 10 day old male pancreas cDNA, RIKEN full-length enriched library, clone: 1810029H14, full insert sequence, *Mus musculus* 10 days embryo cDNA, RIKEN full-length enriched library, clone: 2610027B07, full insert sequence, *Mus musculus* adult male testis cDNA, RIKEN full-length enriched library, clone: 4930558J22, full insert sequence, *Mus musculus* adult male tongue cDNA, RIKEN full-length enriched library, clone: 2310067E17, full insert sequence, germinal histone H4 gene, histone 4 protein |
| 426 | 20736 | AA946443 | x | | EST, Weakly similar to NPD1_HUMAN NEURAL PROLIFERATION DIFFERENTIATION AND CONTROL PROTEIN-1 PRECURSOR (NPDC-1 PROTEIN) [*H. sapiens*], expressed sequence AI314472, neural proliferation, differentiation and control gene 1, neural proliferation, differentiation and control, 1 |
| 427 | 21878 | AA946448 | r | | |
| 428 | 21947 | AA946451 | bb | | EST, Highly similar to AF151863 1 CGI 105 protein [*H. sapiens*] |
| 429 | 17499 | AA946467 | General | | |
| 430 | 1809 | AA946503 | x, General | | |
| 431 | 23360 | AA955104 | f | | |
| 432 | 23471 | AA955162 | General | | |
| 433 | 9452 | AA955206 | b, General | | |
| 434 | 23512 | AA955282 | General | | |
| 435 | 22596 | AA955298 | General | | |
| 436 | 23283 | AA955391 | h | | high density lipoprotein binding protein (vigilin) |
| 437 | 23546 | AA955393 | General | | |
| 438 | 12404 | AA955408 | b | | ESTs, Weakly similar to SX10 RAT TRANSCRIPTION FACTOR SOX-10 [*R. norvegicus*], SRY (sex determining region Y)-box 10, SRY (sex determining region Y)-box 9 (campomelic dysplasia, autosomal sex-reversal), SRY-box containing gene 10, expressed sequence AV220920 |
| 439 | 23626 | AA955540 | aa | | |
| 441 | 17540 | AA955914 | bb | | EST, Highly similar to FBRL MOUSE FIBRILLARIN [*M. musculus*], EST, Weakly similar to A38712 fibrillarin [*H. sapiens*], ESTs, Highly similar to A38712 fibrillarin [*H. sapiens*], ESTs, Weakly similar to FBRL MOUSE FIBRILLARIN [*M. musculus*], expressed sequence AL022665, fibrillarin |
| 442 | 24277 | AA955962 | General | | |
| 443 | 19939 | AA955980 | General | | |
| 444 | 24000 | AA956005 | i | | ESTs, Weakly similar to PCB3_MOUSE POLY(RC)-BINDING PROTEIN 3 (ALPHA-CP3) [*M. musculus*], ESTs, Weakly similar to ROK_HUMAN HETEROGENEOUS NUCLEAR RIBONUCLEOPROTEIN K [*R. norvegicus*], IGF-II mRNA-binding protein 3, RIKEN cDNA 2610101N11 gene, coding region determinant-binding protein, heterogeneous nuclear ribonucleoprotein K, poly(rC)-binding protein 3, poly(rC)-binding protein 4 |
| 445 | 11050 | AA956164 | s, v | | EST, Weakly similar to T-COMPLEX PROTEIN 1, EPSILON SUBUNIT [*M. musculus*], ESTs, Moderately similar to T-COMPLEX PROTEIN 1, EPSILON SUBUNIT [*M. musculus*], T- |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | complex 1, chaperonin containing TCP1, subunit 5 (epsilon), chaperonin subunit 5 (epsilon), expressed sequence AI528772, t-complex 1, t-complex protein 1 |
| 446 | 498 | AA956278 | a, General | | |
| 447 | 23409 | AA956294 | q | | |
| 449 | 23773 | AA956476 | f, x | | |
| 450 | 23799 | AA956530 | d | | |
| 451 | 23800 | AA956534 | aa | | ESTs, Weakly similar to RNG1_HUMAN RING1 PROTEIN [*H. sapiens*], ring finger protein 1, ring finger protein 2 |
| 452 | 23834 | AA956659 | cc, General | | |
| 453 | 16425 | AA956688 | f, x | | gene rich cluster, C8 gene, hypothetical protein MGC2577 |
| 454 | 23847 | AA956723 | s | | |
| 455 | 23852 | AA956746 | j, l, m, z | | ESTs, Weakly similar to CHD4_HUMAN CHROMODOMAIN HELICASE-DNA-BINDING PROTEIN 4 [*H. sapiens*], KIAA1416 protein, KIAA1696 protein, chromodomain helicase DNA binding protein 4 |
| 456 | 5989 | AA956907 | g, s | | DnaJ (Hsp40) homolog, subfamily C, member 8, *Homo sapiens* mRNA; cDNA DKFZp434C2016 (from clone DKFZp434C2016), eukaryotic translation initiation factor 3, eukaryotic translation initiation factor 3, subunit 10 (theta, 150/170 kD), expressed sequence C85189, guanylate kinase membrane-associated inverted 1, hypothetical protein DKFZp434B227, nasopharyngeal epithelium specific protein 1 |
| 456 | 5990 | AA956907 | General | | DnaJ (Hsp40) homolog, subfamily C, member 8, *Homo sapiens* mRNA; cDNA DKFZp434C2016 (from clone DKFZp434C2016), eukaryotic translation initiation factor 3, eukaryotic translation initiation factor 3, subunit 10 (theta, 150/170 kD), expressed sequence C85189, guanylate kinase membrane-associated inverted 1, hypothetical protein DKFZp434B227, nasopharyngeal epithelium specific protein 1 |
| 457 | 23957 | AA957123 | u, General | | X-linked protein, brain expressed, X-linked 1, hypothetical protein FLJ10097, nerve growth factor receptor (TNFRSF16) associated protein 1 |
| 458 | 22357 | AA957264 | General | | EST, Weakly similar to T12456 hypothetical protein DKFZp564M2423.1 [*H. sapiens*], ESTs, Highly similar to T12456 hypothetical protein DKFZp564M2423.1 [*H. sapiens*], PAI-1 mRNA-binding protein, intracellular hyaluronan-binding protein |
| 459 | 23314 | AA957270 | g, l, m, p, v, cc, General | | |
| 460 | 23995 | AA957292 | a, b | | |
| 461 | 2702 | AA957307 | General | | EST, Moderately similar to G01026 serine - tRNA ligase [*H. sapiens*], hypothetical protein FLJ20450, seryl-tRNA synthetase, uncharacterized gastric protein YC12P |
| 462 | 24040 | AA957422 | c | | CD3 antigen, zeta polypeptide, CD3Z antigen, zeta polypeptide (TiT3 complex), Fc fragment of IgE, high affinity I, receptor for: gamma |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 463 | 12478 | AA957554 | m | | polypeptide, Fc receptor, IgE, high affinity I, gamma polypeptide, expressed sequence AI573376 EST, Weakly similar to S01696 gene P3 protein [*H. sapiens*], ESTs, Highly similar to P3 PROTEIN [*M. musculus*], Protein P3 |
| 464 | 21306 | AA957811 | v | | |
| 465 | 24183 | AA957889 | t | | |
| 466 | 24178 | AA957905 | d | | |
| 467 | 17034 | AA963071 | e | | ESTs, Moderately similar to COPE_HUMAN COATOMER EPSILON SUBUNIT [*H. sapiens*], ESTs, Highly similar to COPE_HUMAN COATOMER EPSILON SUBUNIT [*H. sapiens*], coatomer protein complex, subunit epsilon, hypothetical protein FLJ13241 |
| 468 | 24053 | AA963092 | General | | X-linked protein, brain expressed, X-linked 1, hypothetical protein FLJ10097, nerve growth factor receptor (TNFRSF16) associated protein 1 |
| 469 | 2767 | AA963201 | o | | |
| 470 | 2022 | AA963259 | g | | |
| 471 | 2126 | AA963488 | d | | |
| 472 | 24246 | AA963703 | b | | |
| 473 | 2195 | AA963746 | General | | |
| 474 | 19370 | AA963797 | i | | |
| 475 | 2282 | AA964147 | e | | |
| 476 | 2284 | AA964152 | x | | |
| 478 | 2350 | AA964368 | g, General | | ubiquitin specific protease 14 (tRNA-guanine transglycosylase) |
| 479 | 18830 | AA964496 | aa | | ESTs, Weakly similar to A29861 actin gamma [*H. sapiens*], ESTs, Weakly similar to I39393 alpha-actin [*H. sapiens*], ESTs, Weakly similar to S38782 actin beta' chain [*H. sapiens*], *Homo sapiens* mRNA; cDNA DKFZp434B2115 (from clone DKFZp434B2115), RIKEN cDNA 1700052K15 gene, RIKEN cDNA 1700061J02 gene, actin-like 7a, expressed sequence AL023024, expressed sequence AV259599, melanoma X-actin, uncharacterized hypothalamus protein HARP11 |
| 480 | 2392 | AA964541 | b | | |
| 481 | 2395 | AA964554 | General | | |
| 482 | 2410 | AA964589 | i, aa | | |
| 483 | 19145 | AA964613 | t | | |
| 484 | 2424 | AA964617 | g | | |
| 485 | 3107 | AA964687 | General | | |
| 486 | 2457 | AA964752 | q, t | | |
| 487 | 6778 | AA964763 | b | | |
| 489 | 2468 | AA964807 | l | | |
| 490 | 2469 | AA964814 | w | glutamate-cysteine ligase, modifier subunit, glutamate cysteine ligase, modifier subunit | ESTs, Highly similar to GSH0_HUMAN GLUTAMATE-CYSTEINE LIGASE REGULATORY SUBUNIT [*H. sapiens*], glutamate-cysteine ligase, modifier subunit, glutamate-cysteine ligase, modifier subunit |
| 491 | 12561 | AA964815 | General | | |
| 492 | 2326 | AA964892 | aa | | EST, Weakly similar to PROCOLLAGEN ALPHA 1(IV) CHAIN PRECURSOR [*M. musculus*], collagen, type IV, alpha 1, procollagen, type IV, alpha 1, procollagen, type IV, alpha 3, procollagen, type IV, alpha 5 |
| 493 | 21339 | AA964962 | General | | ATP-binding cassette, sub-family A (ABC1), member 1, ATP-binding cassette, sub-family A (ABC1), member 12, ATP-binding cassette, sub-family A (ABC1), member 7, EST, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | Moderately similar to ABC1_HUMAN ATP-BINDING CASSETTE, SUB-FAMILY A, MEMBER 1 [*H. sapiens*], EST, Weakly similar to ABC1 MOUSE ATP-BINDING CASSETTE, SUB-FAMILY A, MEMBER 1 [*M. musculus*], RIKEN cDNA 1810036E22 gene |
| 494 | 21390 | AA964988 | General | | |
| 495 | 12569 | AA965023 | g | | |
| 496 | 2583 | AA965166 | bb | | *Homo sapiens*, clone MGC: 8857 IMAGE: 3866266, mRNA, complete cds, inorganic pyrophosphatase, pyrophosphatase (inorganic) |
| 497 | 15885 | AA965207 | r | | EST, Highly similar to T14795 hypothetical protein DKFZp434E171.1 [*H. sapiens*] |
| 499 | 2905 | AA996727 | b, l, m, u, General | | |
| 500 | 2915 | AA996782 | u, bb | | ESTs, Moderately similar to LAMIN B3 [*M. musculus*], hypothetical protein MGC2721, lamin B1, lamin B2 |
| 501 | 2920 | AA996813 | d | | |
| 502 | 19525 | AA996856 | aa, General | | |
| 503 | 2984 | AA997015 | c | | |
| 504 | 2986 | AA997028 | General | | |
| 505 | 3145 | AA997237 | General | | |
| 506 | 19249 | AA997342 | m | | |
| 507 | 16883 | AA997345 | General | | |
| 508 | 12598 | AA997362 | s | | methylene tetrahydrofolate dehydrogenase (NAD+ dependent), methenyltetrahydrofolate cyclohydrolase, protease, serine, 15 |
| 509 | 3470 | AA997374 | p | | EST, Weakly similar to LIS1 MOUSE PLATELET-ACTIVATING FACTOR ACETYLHYDROLASE IB ALPHA SUBUNIT [*R. norvegicus*], ESTs, Weakly similar to LIS1 MOUSE PLATELET-ACTIVATING FACTOR ACETYLHYDROLASE IB ALPHA SUBUNIT [*R. norvegicus*], WD repeat domain 3, f-box and WD-40 domain protein 2, hypothetical protein MGC2655, platelet-activating factor acetylhydrolase beta subunit (PAF-AH beta), platelet-activating factor acetylhydrolase, isoform 1b, beta1 subunit, platelet-activating factor acetylhydrolase, isoform Ib, alpha subunit (45 kD) |
| 510 | 3180 | AA997425 | t | | |
| 511 | 3245 | AA997608 | General | | EST, Weakly similar to PLASMINOGEN ACTIVATOR INHIBITOR-2, TYPE A [*R. norvegicus*], expressed sequence AI876477, expressed sequence C76171, plasminogen activator inhibitor 2 type A, serine (or cysteine) proteinase inhibitor, clade B (ovalbumin), member 2, serine (or cysteine) proteinase inhibitor, clade B (ovalbumin), member 6, serine protease inhibitor 12 |
| 512 | 3020 | AA997656 | t | | |
| 513 | 3269 | AA997800 | x, aa | | *Homo sapiens*, clone IMAGE: 4810400, mRNA, antigen identified by monoclonal antibody Ki 67 |
| 514 | 3288 | AA997877 | f | | |
| 515 | 23992 | AA998164 | k, x | | DNA segment, Chr 4, ERATO Doi 639, expressed, EST, Moderately similar to CGB2 MOUSE G2/MITOTIC-SPECIFIC CYCLIN B2 [*M. musculus*], ESTs, Weakly similar to CGB1_HUMAN G2/MITOTIC-SPECIFIC CYCLIN B [*H. sapiens*], cyclin B1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 516 | 17470 | AA998264 | b | | biliverdin reductase B (flavin reductase (NADPH)) |
| 517 | 3773 | AA998356 | General | | B-cell CLL/lymphoma 3, molecule possessing ankyrin repeats induced by lipopolysaccharide (MAIL), homolog of mouse, nuclear factor of kappa light polypeptide gene enhancer in B-cells inhibitor, epsilon |
| 518 | 19623 | AA998422 | General | | |
| 519 | 3572 | AA998516 | x | | ESTs, Weakly similar to G2/MITOTIC-SPECIFIC CYCLIN B1 [*R. norvegicus*], cyclin A2, cyclin B1, cyclin B1, related sequence 1, cyclin B2 |
| 520 | 2782 | AA998565 | c | | cyclin-dependent kinase inhibitor 1C (P57), cyclin-dependent kinase inhibitor 1C (p57, Kip2) |
| 521 | 26119 | AA998576 | i, r, w, General | | |
| 522 | 22737 | AA998660 | aa | | |
| 523 | 3696 | AA999030 | e | | |
| 524 | 3079 | AA999169 | k, x, General | | |
| 525 | 3081 | AA999171 | e, p, r | signal transducer and activator of transcription 1, signal transducer and activator of transcription 1, 91 kD | Signal transducer and activator of transcription 3, expressed sequence AA408197, signal transducer and activator of transcription 1, signal transducer and activator of transcription 1, 91 kD, signal transducer and activator of transcription 2, signal transducer and activator of transcription 3, signal transducer and activator of transcription 3 (acute-phase response factor), signal transducer and activator of transcription 4 |
| 526 | 3082 | AA999172 | General | | ESTs, Moderately similar to A54847 GMP synthase [*H. sapiens*], guanine monophosphate synthetase |
| 527 | 17337 | AB000717 | k | | |
| 528 | 1535 | AB000778 | a | | phospholipase D1, phophatidylcholine-specific, phospholipase D2 |
| 529 | 1382 | AB002406 | k | RuvB (*E coli* homolog)-like 1, RuvB-like protein 1 | Homer, neuronal immediate early gene, 1B, Homer, neuronal immediate early gene, 2, homer, neuronal immediate early gene, 1, homer, neuronal immediate early gene, 2 |
| 530 | 20184 | AB003753 | d | | |
| 531 | 4312 | AB010635 | c, i, j, k, y, z | | EST, Weakly similar to JC5408 carboxylesterase [*H. sapiens*], ESTs, Moderately similar to ES22 MOUSE LIVER CARBOXYLESTERASE 22 PRECURSOR [*M. musculus*], ESTs, Weakly similar to A48809 carboxylesterase [*H. sapiens*], ESTs, Weakly similar to JC5408 carboxylesterase [*H. sapiens*], T-complex expressed gene 5, carboxylesterase 1, carboxylesterase 2 (intestine, liver), carboxylesterase 3, carboxylesterase 3 (brain), hypothetical protein FLJ21736 |
| 532 | 21666 | AB012214 | k | | DNA (cytosine-5-)-methyltransferase 1, DNA (cytosine-5-)-methyltransferase 2, DNA methyltransferase (cytosine-5) 1, EST, Weakly similar to JE0378 DNA [*R. norvegicus*], *Mus musculus* DNA cytosine methyltransferase mRNA, f-box and leucine-rich repeat protein 11, protein containing CXXC domain 2 |
| 533 | 15772 | AB015645 | g | | *Mus musculus* mouse-thyrotropin-releasing hormone receptor 2 (TRH-R2) mRNA, complete cds, thyrotropin releasing hormone receptor, thyrotropin-releasing hormone receptor |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 534 | 1183 | AF013144 | h | | ESTs, Weakly similar to DUS8_HUMAN DUAL SPECIFICITY PROTEIN PHOSPHATASE 8 [*H. sapiens*], Human DNA sequence from clone RP11-243J16 on chromosome 20 Contains parts of 2 isoforms of the BCL2L1 (BCL2-like 1) gene, the gene for a novel protein (FLS353), the gene for a protein similar to MYLK (myosin, light polypeptide kinase), the FKHL18 (forkhead (*Drosophila*)-like 18) gene, part of three novel genes, ESTs, STSs, GSSs and CpG islands, KIAA1725 protein, dual specificity phosphatase 13, dual specificity phosphatase 14, dual specificity phosphatase 5, expressed sequence BB104621, expressed sequence C79103, protein tyrosine phosphatase, non-receptor type 16 |
| 535 | 1582 | AF015911 | h, z | | B-cell CLL/lymphoma 6, member B (zinc finger protein), ESTs, Moderately similar to zinc finger protein [*H. sapiens*], *Homo sapiens*, Similar to RIKEN cDNA 0610020I02 gene, clone MGC: 23427 IMAGE: 4654320, mRNA, complete cds |
| 536 | 11483 | AF020618 | u, cc, General | | |
| 537 | 20295 | AF024712 | aa | | HLA-G histocompatibility antigen, class I, G |
| 538 | 19077 | AF030358 | y, z | | hypothetical protein, clone 1-53, small inducible cytokine subfamily D (Cys-X3 Cys), member 1 (fractalkine, neurotactin), small inducible cytokine subfamily D, 1 |
| 539 | 23044 | AF034218 | General | | RIKEN cDNA 4632428M18 gene, hyaluronidase 1, hyaluronidase 2, hyaluronoglucosaminidase 1, hyaluronoglucosaminidase 2, hyaluronoglucosaminidase 3, sperm adhesion molecule |
| 540 | 25178 | AF035955 | d | | |
| 541 | 1564 | AF035963 | x, bb, General | | ESTs, Moderately similar to hepatitis A virus cellular receptor 1 [*H. sapiens*], ESTs, Moderately similar to kidney injury molecule-1 [*R. norvegicus*], ESTs, Weakly similar to kidney injury molecule-1 [*R. norvegicus*] |
| 542 | 8426 | AF036335 | f | | ESTs, Moderately similar to NR54_HUMAN 54 KDA NUCLEAR RNA-BINDING PROTEIN [*H. sapiens*], ESTs, Moderately similar to p54nrb [*H. sapiens*], ESTs, Weakly similar to A54691 octamer-binding protein NonO - mouse [*M. musculus*], ESTs, Weakly similar to PSF_HUMAN PTB-ASSOCIATED SPLICING FACTOR [*H. sapiens*], RIKEN cDNA 5730470C09 gene, RIKEN cDNA 9030402K04 gene, non-POU-domain-containing, octamer-binding protein |
| 543 | 21817 | AF036537 | k | | ESTs, Highly similar to A55318 serine/threonine protein kinase [*M. musculus*], ESTs, Weakly similar to RIP MOUSE SERINE/THREONINE PROTEIN KINASE RIP [*M. musculus*], Human DNA sequence from clone RP5-1182A14 on chromosome 1 Contains part of a gene similar to rat Espin, a pseudogene similar to KIAA0454, a gene similar to MST1 (macrophage stimulating 1 (hepatocyte growth factor-like)), a pseudogene |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | similar to KIAA0445, two isoforms of a novel gene (isoform 2 is the gene for KIAA1245 protein), ESTs, STSs, GSSs and CpG islands, ankyrin repeat domain 3, cerebral cavernous malformations 1, mitogen activated protein kinase kinase kinase 12, mitogen-activated protein kinase kinase kinase 12, receptor (TNFRSF)-interacting serine-threonine kinase 1, receptor Interacting protein 3, receptor-interacting serine-threonine kinase 2 |
| 544 | 21145 | AF038571 | General | solute carrier family 1 (neuronal/epithelial high affinity glutamate transporter, system Xag), member 1, solute carrier family 1, member 1 | |
| 545 | 22602 | AF044574 | General | | 2,4-dienoyl CoA reductase 1, mitochondrial, 2,4-dienoyl CoA reductase 2, peroxisomal, 2-4-dienoyl-Coenzyme A reductase 2, peroxisomal, ESTs, Weakly similar to S11021 2,4-dienoyl-CoA reductase [*R. norvegicus*], *Homo sapiens* AS10 protein mRNA, partial cds, RIKEN cDNA 1200012F07 gene, RIKEN cDNA 2400003B18 gene, hydroxyprostaglandin dehydrogenase 15 (NAD), hydroxysteroid (17-beta) dehydrogenase 10, peroxisomal trans 2-enoyl CoA reductase; putative short chain alcohol dehydrogenase |
| 546 | 13464 | AF047707 | h | | UDP-glucose ceramide glucosyltransferase |
| 547 | 24024 | AF052695 | x | | |
| 548 | 12259 | AF061266 | h | | EST, Highly similar to JC5807 trp3 protein - rat [*R. norvegicus*], EST, Weakly similar to TRP1_MOUSE TRANSIENT RECEPTOR POTENTIAL CHANNEL 1 (TRANSIENT RECEPTOR PROTEIN 1) (MTRP1) (TRP-RELATED PROTEIN 1) [*M. musculus*], transient receptor potential channel 1, transient receptor protein 1, transient receptor protein 3, transient receptor protein 4, transient receptor protein 5 |
| 549 | 4589 | AF062389 | y, z | | EST, Highly similar to A61209 hypertension-associated protein SA - rat [*R. norvegicus*], ESTs, Highly similar to A61209 hypertension-associated protein SA - rat [*R. norvegicus*], ESTs, Weakly similar to I54401 hypertension-associated protein SA [*H. sapiens*], KIAA1504 protein, SA (rat hypertension-associated) homolog, SA rat hypertension-associated homolog, expressed sequence AI788978, hypothetical protein FLJ20581, medium-chain acyl-CoA synthetase, solute carrier family 27 (fatty acid transporter), member 1, solute carrier family 27 (fatty acid transporter), member 4 |
| 550 | 16007 | AF062594 | t | nucleosome assembly protein 1-like 1 | ESTs, Highly similar to 2008109A set gene [*R. norvegicus*], ESTs, Highly similar to SET_HUMAN SET PROTEIN [*H. sapiens*], SET translocation, SET translocation (myeloid leukemia-associated), nucleosome assembly |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 551 | 15761 | AF062741 | u | | protein 1-like 1, nucleosome assembly protein 1-like 2, nucleosome assembly protein 1-like 4 KIAA1348 protein, protein phosphatase 1G (formerly 2C), magnesium-dependent, gamma isoform |
| 552 | 17426 | AF073839 | p | | |
| 553 | 18615 | AF074608 | s | | |
| 554 | 15797 | AF084205 | f | | ESTs, Moderately similar to T17365 serine/threonine protein kinase TAO1 - rat [*R. norvegicus*], ESTs, Weakly similar to ST25_MOUSE SERINE/THREONINE PROTEIN KINASE 25 (STERILE 20/OXIDANT STRESS-RESPONSE KINASE 1) (STE20/OXIDANT STRESS RESPONSE KINASE-1) (SOK-1) (STE20-LIKE KINASE) [*M. musculus*], KIAA1361 protein, STE20-like kinase, expressed sequence AU020252, prostate derived STE20-like kinase PSK, serine/threonine kinase 10, thousand and one amino acid protein kinase |
| 555 | 12932 | AF102552 | s | | ESTs, Moderately similar to A55575 ankyrin 3, long splice form [*H. sapiens*], RIKEN cDNA 2310026G15 gene, RIKEN cDNA 2410004E01 gene, RIKEN cDNA 2410197A17 gene, RIKEN cDNA 4933400N19 gene, RIKEN cDNA 8430401K06 gene, RIKEN cDNA C430011H06 gene, ankyrin 3, node of Ranvier (ankyrin G), hypothetical protein FLJ20189, phospholipase A2, group VI, phospholipase A2, group VI (cytosolic, calcium-independent), proteasome (prosome, macropain) 26S subunit, non-ATPase, 10 |
| 556 | 18603 | AI007649 | x | | EST, Moderately similar to A49013 tumor cell suppression protein HTS1 [*H. sapiens*], KIAA1277 protein, hypothetical protein FLJ22457, suppression of tumorigenicity 5 |
| 557 | 22733 | AI007668 | r | | |
| 558 | 22746 | AI007672 | r | | |
| 559 | 24109 | AI007725 | General | | |
| 560 | 15848 | AI007820 | n, v | | EST, Highly similar to HS9B RAT HEAT SHOCK PROTEIN HSP 90-BETA [*R. norvegicus*], EST, Weakly similar to HHMS84 heat shock protein 84 - mouse [*M. musculus*], ESTs, Highly similar to T46243 hypothetical protein DKFZp761K0511.1 [*H. sapiens*], expressed sequence AL022974, expressed sequence C81438, heat shock 90 kD protein 1, beta, heat shock protein, 84 kDa 1 |
| 561 | 10108 | AI007857 | f | | HGF-regulated tyrosine kinase substrate, *Homo sapiens* cDNA FLJ13428 fis, clone PLACE1002493, highly similar to *Homo sapiens* signal transducing adaptor molecule 2A (STAM2) mRNA, Mouse 31-kDa proline-rich salivary protein, complete cds of clone pUMP125, *Mus musculus*, Similar to proline-rich protein BstNI subfamily 2, clone MGC: 18611 IMAGE: 4165240, mRNA, complete cds, RIKEN cDNA 1700120F24 gene, RIKEN cDNA 4930406E12 gene, *Rattus norvegicus* proline-rich proteoglycan (PRPG2) mRNA, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | complete cds, proline-rich protein HaeIII subfamily 2, signal transducing adaptor molecule (SH3 domain and ITAM motif) 2 |
| 562 | 6804 | AI007877 | General | | |
| 563 | 20099 | AI007893 | f, u | | |
| 564 | 11368 | AI007948 | d | | |
| 565 | 15849 | AI008074 | h | | EST, Highly similar to HS9B RAT HEAT SHOCK PROTEIN HSP 90-BETA [*R. norvegicus*], EST, Weakly similar to HHMS84 heat shock protein 84 - mouse [*M. musculus*], ESTs, Highly similar to T46243 hypothetical protein DKFZp761K0511.1 [*H. sapiens*], expressed sequence AL022974, expressed sequence C81438, heat shock 90 kD protein 1, beta, heat shock protein, 84 kDa 1 |
| 566 | 3121 | AI008160 | General | | CGI-83 protein |
| 567 | 16646 | AI008190 | t | | EST, Highly similar to JC7290 guanine nucleotide binding protein G gamma 2 chain [*H. sapiens*], EST, Weakly similar to GBG9 RAT GUANINE NUCLEOTIDE-BINDING PROTEIN G(I)/G(S)/G(O) GAMMA-9 SUBUNIT [*M. musculus*], EST, Weakly similar to JC7290 guanine nucleotide binding protein G gamma 2 chain [*H. sapiens*], RIKEN cDNA 1110003P13 gene, guanine nucleotide binding protein (G protein), gamma 12, guanine nucleotide binding protein (G protein), gamma 2, guanine nucleotide binding protein (G protein), gamma 2 subunit, guanine nucleotide binding protein (G protein), gamma 3 subunit, guanine nucleotide binding protein (G protein), gamma 4 subunit, guanine nucleotide binding protein 4 |
| 568 | 12683 | AI008203 | x | | EST, Moderately similar to CGB2 MOUSE G2/MITOTIC-SPECIFIC CYCLIN B2 [*M. musculus*], ESTs, Weakly similar to G2/MITOTIC-SPECIFIC CYCLIN B1 [*R. norvegicus*], *Homo sapiens* cDNA FLJ13342 fis, clone OVARC1001950, cyclin A1, cyclin B1, cyclin B1, related sequence 1, cyclin B2 |
| 569 | 22018 | AI008309 | b | | ESTs, Highly similar to PROTO-ONCOGENE SERINE/THREONINE-PROTEIN KINASE PIM-1 [*M. musculus*], ESTs, Highly similar to S55333 protein kinase pim-2 [*M. musculus*], ESTs, Moderately similar to S55333 protein kinase pim-2 [*M. musculus*], Pim-1 oncogene, pim-1 oncogene, pim-2 oncogene, proviral integration site 1, serine threonine kinase pim3 |
| 570 | 23917 | AI008441 | n | | phosphogluconate dehydrogenase |
| 571 | 22599 | AI008458 | General | | |
| 572 | 22698 | AI008578 | p, General | | |
| 573 | 14405 | AI008579 | r, x | | |
| 574 | 4086 | AI008629 | x | | EST, Weakly similar to JH0446 75K autoantigen [*H. sapiens*], polymyositis/scleroderma autoantigen 1 (75 kD) |
| 575 | 3808 | AI008643 | i, v, General | | DnaJ (Hsp40) homolog, subfamily B, member 1, DnaJ (Hsp40) homolog, subfamily B, member 12, DnaJ (Hsp40) homolog, subfamily B, member 4, DnaJ (Hsp40) homolog, subfamily B, member 5, ESTs, Weakly similar to HS4L__HUMAN HEAT |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | SHOCK 40 KDA PROTEIN 1 HOMOLOG [*H. sapiens*], RIKEN cDNA 1700029A20 gene, RIKEN cDNA 2010306G19 gene |
| 576 | 3931 | AI008697 | l | | |
| 577 | 7785 | AI008758 | aa | dipeptidylpeptidase 4, dipeptidylpeptidase IV (CD26, adenosine deaminase complexing protein 2) | ESTs, Weakly similar to DPP4 MOUSE DIPEPTIDYL PEPTIDASE IV [*M. musculus*], ESTs, Weakly similar to DPP4 RAT DIPEPTIDYL PEPTIDASE IV [*R. norvegicus*], *Homo sapiens* chromosome 19, cosmid R26894, *Homo sapiens*, clone IMAGE: 3447394, mRNA, partial cds, RIKEN cDNA 4932434F09 gene, dipeptidylpeptidase 4, dipeptidylpeptidase 6, dipeptidylpeptidase 8, fibroblast activation protein, fibroblast activation protein, alpha |
| 578 | 16701 | AI008838 | q | | |
| 579 | 21789 | AI008930 | k | | EST, Moderately similar to CYSR RAT CYSTEINE-RICH PROTEIN 1 [*R. norvegicus*], ESTs, Weakly similar to S12658 cysteine-rich protein [*H. sapiens*], cysteine and glycine-rich protein 1, cysteine and glycine-rich protein 3 (cardiac LIM protein), cysteine rich protein, cysteine-rich protein 2, cysteine-rich protein 3, thymus LIM protein |
| 580 | 21895 | AI008971 | General | | |
| 581 | 410 | AI008974 | i, aa, General | | |
| 582 | 21632 | AI009167 | General | | BCL2-associated athanogene 2, ESTs, Highly similar to T08764 hypothetical protein DKFZp586C021.1 [*H. sapiens*] |
| 583 | 21596 | AI009168 | General | | |
| 584 | 22801 | AI009197 | General | | |
| 585 | 11876 | AI009321 | cc, General | | |
| 586 | 2506 | AI009341 | General | | |
| 587 | 6382 | AI009362 | General | | |
| 588 | 14370 | AI009427 | k | | EST, Weakly similar to PRCF_HUMAN PROTEASOME COMPONENT MECL-1 PRECURSOR [*H. sapiens*], ESTs, Weakly similar to PRCF_HUMAN PROTEASOME COMPONENT MECL-1 PRECURSOR [*H. sapiens*], proteasome (prosome, macropain) subunit, beta type 10, proteasome (prosome, macropain) subunit, beta type 7, proteasome (prosome, macropain) subunit, beta type, 10, proteasome (prosome, macropain) subunit, beta type, 7 |
| 589 | 19275 | AI009460 | x | | EST, Moderately similar to ABP2_HUMAN ENDOTHELIAL ACTIN-BINDING PROTEIN [*H. sapiens*], ESTs, Moderately similar to ABP2_HUMAN ENDOTHELIAL ACTIN-BINDING PROTEIN [*H. sapiens*], filamin A, alpha (actin-binding protein-280), filamin B, beta (actin-binding protein-278) |
| 590 | 4154 | AI009467 | g | | |
| 591 | 3464 | AI009589 | cc | | |
| 592 | 3926 | AI009592 | e | | |
| 593 | 19358 | AI009675 | c | | |
| 594 | 22545 | AI009747 | g | | |
| 595 | 15089 | AI009752 | cc, General | | |
| 596 | 5458 | AI009756 | h | programmed cell death 6 interacting protein, programmed cell death 6-interacting protein | EST, Moderately similar to T14756 hypothetical protein DKFZp564F0923.1 [*H. sapiens*], EST, Weakly similar to A28996 proline-rich protein M14 precursor - mouse [*M. musculus*], EST, Weakly similar to PRP4_HUMAN SALIVARY PROLINE- |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | RICH PROTEIN PO PRECURSOR [*H. sapiens*], expressed sequence AI462446, poly(A)-binding protein, nuclear 1, proline rich protein, proline rich protein 2, proline-rich protein BstNI subfamily 4, protein tyrosine phosphatase, non-receptor type 23 |
| 597 | 6844 | AI009770 | e, r, cc | | |
| 598 | 15627 | AI009810 | aa | | EST AI317031, EST, Weakly similar to R3HU16 ribosomal protein S16, cytosolic [*H. sapiens*], expressed sequence AA420385, ribosomal protein S16 |
| 599 | 22619 | AI009825 | d | | |
| 600 | 7857 | AI009898 | j, l, m, z | | |
| 601 | 13259 | AI009946 | r | | |
| 602 | 21105 | AI010067 | General | | |
| 603 | 24627 | AI010102 | aa | testis enhanced gene transcript, testis enhanced gene transcript (BAX inhibitor 1) | CGI-119 protein, RIKEN cDNA 5031406P05 gene, testis enhanced gene transcript (BAX inhibitor 1) |
| 604 | 12716 | AI010178 | General | | CGI-100 protein |
| 605 | 18757 | AI010216 | aa | | |
| 606 | 2912 | AI010220 | aa, General | | RIKEN cDNA 6720456I16 gene, claudin 10, claudin 15, claudin 7 |
| 607 | 3316 | AI010237 | t | | |
| 608 | 15644 | AI010256 | General | | ESTs, Highly similar to HISTONE H3.3 [*R. norvegicus*], H3 histone, family 3A, H3 histone, family 3B, H3 histone, family 3B (H3.3B) |
| 609 | 657 | AI010262 | b | | colony stimulating factor 2 receptor, beta 1, low-affinity (granulocyte-macrophage), interleukin 4 receptor, interleukin 4 receptor, alpha |
| 610 | 3271 | AI010303 | b | | |
| 611 | 11081 | AI010407 | bb | | |
| 612 | 16521 | AI010470 | c, s, t, General | ceruloplasmin, ceruloplasmin (ferroxidase) | DNA segment, Chr 3, ERATO Doi 555, expressed, EST, Highly similar to 1012298A factor VIIIC [*H. sapiens*], ESTs, Weakly similar to CERU MOUSE CERULOPLASMIN PRECURSOR [*M. musculus*], ESTs, Weakly similar to CERU RAT CERULOPLASMIN PRECURSOR [*R. norvegicus*], ESTs, Weakly similar to KUHU ferroxidase [*H. sapiens*], Hermansky-Pudlak syndrome 3, ceruloplasmin, ceruloplasmin (ferroxidase), hephaestin |
| 613 | 6927 | AI010542 | General | | |
| 614 | 17524 | AI010568 | a, j, y, General | growth hormone receptor | growth hormone receptor |
| 615 | 6946 | AI010642 | n | | |
| 616 | 23509 | AI010962 | aa | | RIKEN cDNA 2510028H01 gene, sorting nexin 2, sorting nexin 3 |
| 617 | 6044 | AI011285 | t | | |
| 618 | 13855 | AI011361 | o | | |
| 619 | 21779 | AI011380 | cc | | |
| 621 | 12534 | AI011460 | cc | | |
| 622 | 12629 | AI011492 | e, f | | HYA22 protein, conserved gene amplified in osteosarcoma, nuclear LIM interactor-interacting factor |
| 623 | 735 | AI011560 | f | | *Homo sapiens*, Similar to RIKEN cDNA 2300002L21 gene, clone MGC: 17528 IMAGE: 3458906, mRNA, complete cds, RIKEN cDNA 2300002L21 gene, S100 calcium-binding protein A12 (calgranulin C), S100 calcium-binding protein, beta (neural), S100 protein, beta polypeptide, neural |
| 624 | 3941 | AI011598 | General | | ESTs, Moderately similar to 2113291A laminin: SUBUNIT, Usher syndrome 2A (autosomal recessive, mild) homolog (human), hypothetical protein, MGC: 8159, laminin, alpha 5 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 625 | 17550 | AI011607 | j, General | | butyrobetaine (gamma), 2-oxoglutarate dioxygenase (gamma-butyrobetaine hydroxylase) 1, epsilon-trimethyllysine hydroxylase |
| 626 | 10636 | AI011634 | e | | |
| 627 | 3995 | AI011678 | General | | |
| 628 | 16112 | AI011706 | h | | EST, Weakly similar to SPLICING FACTOR, ARGININE/SERINE-RICH 5 [*R. norvegicus*], *Mus musculus*, Similar to splicing factor, arginine/serine-rich 7 (35 kD), clone MGC: 6268 IMAGE: 2646366, mRNA, complete cds, neural-salient serine/arginine-rich, splicing factor, arginine/serine-rich 3, splicing factor, arginine/serine-rich 3 (SRp20), splicing factor, arginine/serine-rich 5, splicing factor, arginine/serine-rich 5 (SRp40, HRS) |
| 629 | 13354 | AI011757 | c | | Fc fragment of IgG, high affinity Ia, receptor for (CD64), Fc fragment of IgG, low affinity IIIa, receptor for (CD16), Fc fragment of IgG, low affinity IIIb, receptor for (CD16), Fc receptor, IgG, low affinity III, expressed sequence BB219290 |
| 630 | 12745 | AI011799 | cc | | |
| 631 | 18684 | AI011812 | t | | DKFZP564O123 protein, putative breast adenocarcinoma marker (32 kD) |
| 632 | 4205 | AI011982 | b | | |
| 633 | 6518 | AI012114 | General | | chromosome 1 open reading frame 25, hypothetical protein FLJ20244 |
| 634 | 17407 | AI012145 | General | | |
| 635 | 13093 | AI012177 | r | | FK506 binding protein 4 (59 kDa), FK506 binding protein 8 (38 kDa), FK506-binding protein 4 (59 kD), FK506-binding protein 6 (36 kD), FK506-binding protein like, RIKEN cDNA 2210019E14 gene |
| 636 | 15395 | AI012216 | f | | Fas-associated factor 1, ORF, RIKEN cDNA 2210404D11 gene, UBX domain containing 2, expressed sequence AA408698, expressed sequence AI196514, putative glialblastoma cell differentiation-related |
| 637 | 21796 | AI012221 | d, General | | EST X83352, ESTs, Highly similar to T17226 hypothetical protein DKFZp566G223.1 [*H. sapiens*], *Homo sapiens*, Similar to chloride intracellular channel 4, clone MGC: 8812 IMAGE: 3861372, mRNA, complete cds, RIKEN cDNA 5730531E12 gene, chloride intracellular channel 1, chloride intracellular channel 4, chloride intracellular channel 4 (mitochondrial), hypothetical protein DKFZp434N127, intracellular chloride ion channel protein p64H1 |
| 638 | 3981 | AI012235 | i, General | | |
| 639 | 6606 | AI012308 | i, r | | |
| 640 | 3417 | AI012337 | w | | ESTs, Weakly similar to NHPX RAT NHP2/RS6 FAMILY PROTEIN YEL026W HOMOLOG [*R. norvegicus*], RIKEN cDNA 2410130M07 gene, non-histone chromosome protein 2 (*S. cerevisiae*)-like 1, nucleolar protein family A, member 2 (H/ACA small nucleolar RNPs), sperm specific antigen 1 |
| 641 | 24200 | AI012356 | b, t, General | | |
| 642 | 7471 | AI012379 | cc | | |
| 643 | 7247 | AI012438 | g | | |
| 644 | 7127 | AI012464 | p, General | | |
| 645 | 3304 | AI012471 | b | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 646 | 2311 | AI012485 | aa | | |
| 647 | 20817 | AI012589 | g, n, q | | |
| 648 | 3493 | AI012590 | v, General | | |
| 649 | 8975 | AI012613 | General | | |
| 650 | 11335 | AI012619 | j | | |
| 651 | 21409 | AI012637 | General | | |
| 652 | 8015 | AI012638 | aa | | |
| 653 | 8476 | AI012647 | w | | EST, Weakly similar to S33710 ribosomal protein S20, cytosolic [*H. sapiens*], *Mus musculus*, Similar to ribosomal protein S20, clone MGC: 6876 IMAGE: 2651405, mRNA, complete cds, expressed sequence AL024076 |
| 654 | 4232 | AI012958 | e, p, General | | |
| 655 | 23128 | AI013011 | General | | |
| 656 | 20086 | AI013260 | General | | |
| 657 | 11969 | AI013273 | k | | ESTs, Highly similar to A26061 glia-derived neurite promoting factor precursor [*H. sapiens*], ESTs, Highly similar to A27496 glia-derived nexin I alpha precursor [*H. sapiens*], ESTs, Weakly similar to GLIA DERIVED NEXIN PRECURSOR [*R. norvegicus*], serine (or cysteine) proteinase inhibitor, clade E (nexin, plasminogen activator inhibitor type 1), member 2, serine (or cysteine) proteinase inhibitor, clade I (neuroserpin), member 1 |
| 658 | 26147 | AI013387 | aa | | |
| 659 | 8815 | AI013437 | p | | |
| 660 | 19722 | AI013508 | k | | |
| 661 | 6674 | AI013568 | General | | |
| 662 | 23145 | AI013647 | o, t | | |
| 663 | 15130 | AI013676 | w | | |
| 664 | 7274 | AI013715 | aa | | Bone morphogenetic protein 6, bone morphogenetic protein 5, bone morphogenetic protein 6, bone morphogenetic protein 7, bone morphogenetic protein 7 (osteogenic protein 1), growth differentiation factor 15 |
| 665 | 7276 | AI013730 | e | | |
| 666 | 7278 | AI013738 | y, z, aa | | |
| 667 | 22592 | AI013740 | s, x, bb, General | | ESTs, Weakly similar to S32567 A4 protein [*H. sapiens*], *Homo sapiens*, Similar to RIKEN cDNA 2900052H21 gene, clone MGC: 21625 IMAGE: 4214683, mRNA, complete cds, *Homo sapiens*, clone MGC: 19762 IMAGE: 3636045, mRNA, complete cds, proteolipid protein 2 (colonic epithelium-enriched) |
| 668 | 16584 | AI013765 | w | | *Mus musculus* retinal cone arrestin 3 (Arr3) mRNA, complete cds, RIKEN cDNA 1200006I17 gene, arrestin, beta 2, expressed sequence AI326910, retinal S-antigen |
| 669 | 24143 | AI013804 | j, l | | |
| 670 | 15928 | AI013829 | a, General | | |
| 671 | 21950 | AI013861 | j | | 3-hydroxyisobutyrate dehydrogenase, ESTs, Highly similar to D3HI_HUMAN 3-HYDROXYISOBUTYRATE DEHYDROGENASE, MITOCHONDRIAL PRECURSOR (HIBADH) [*H. sapiens*], cytokine-like nuclear factor n-pac |
| 672 | 3260 | AI013875 | t | | |
| 673 | 2708 | AI013882 | d, q | | |
| 674 | 8585 | AI013886 | i | | |
| 675 | 7299 | AI013911 | p, r, t, General | | *H. sapiens* PABII pseudogene, Human DNA sequence from PAC 560B9 on chromosome 1q24-1q25. Contains |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | profilin-like pseudogene, 60S ribosomal protein L4 pseudogene RNA binding protein, ESTs, GSS, *Mus musculus* adult male tongue cDNA, RIKEN full-length enriched library, clone: 2310074E15, full insert sequence, RNA binding motif protein 3, RNA binding motif protein, X chromosome, RNA binding motif protein, X chromosome retrogene, cold inducible RNA-binding protein, testes-specific heterogenous nuclear ribonucleoprotein G-T |
| 676 | 15904 | AI013971 | General | | |
| 677 | 12781 | AI014023 | w | | EST, Moderately similar to Y124_HUMAN HYPOTHETICAL PROTEIN KIAA0124 [*H. sapiens*], block of proliferation 1 |
| 678 | 19372 | AI014135 | aa | beta-carotene 15, 15'-dioxygenase, beta-carotene 15, 15'-dioxygenase | EST, Moderately similar to 0806162D protein COII [*M. musculus*], EST, Weakly similar to 810024D cytochrome oxidase II [*H. sapiens*] |
| 679 | 4241 | AI014140 | w | | DKFZP564A2416 protein, EST, Moderately similar to T14738 hypothetical protein DKFZp564A2416.1 [*H. sapiens*], *Homo sapiens* cDNA FLJ14138 fis, clone MAMMA1002765, hypothetical protein FLJ13117 |
| 680 | 15247 | AI014169 | c, u | | *Homo sapiens* cDNA: FLJ22783 fis, clone KAIA1993, *Homo sapiens* mRNA; cDNA DKFZp434B102 (from clone DKFZp434B102), KIAA1376 protein, expressed sequence AV216361, upregulated by 1,25-dihydroxyvitamin D-3 |
| 681 | 7315 | AI028831 | n | | ESTs, Highly similar to JE0363 mitogen-activated protein kinase kinase kinase [*H. sapiens*], mitogen activated protein kinase kinase kinase 5, mitogen-activated protein kinase kinase kinase 6 |
| 682 | 16631 | AI028856 | General | | |
| 683 | 23297 | AI028953 | x | | ESTs, Moderately similar to RUXG_HUMAN SMALL NUCLEAR RIBONUCLEOPROTEIN G [*H. sapiens*], small nuclear ribonucleoprotein polypeptide G |
| 684 | 11326 | AI029015 | b | | |
| 685 | 2866 | AI029058 | n, y | | |
| 686 | 12812 | AI029126 | General | | |
| 687 | 17602 | AI029156 | p | | |
| 688 | 7392 | AI029185 | aa | | |
| 689 | 6517 | AI029264 | d, k, x | | |
| 690 | 7639 | AI029292 | b | | |
| 691 | 3874 | AI029428 | i, General | | ESTs, Moderately similar to CB80_HUMAN 80 KDA NUCLEAR CAP BINDING PROTEIN [*H. sapiens*], *Homo sapiens* cDNA FLJ11599 fis, clone HEMBA1003879, nuclear cap binding protein subunit 1, 80 kD |
| 692 | 12819 | AI029437 | f | | |
| 693 | 7452 | AI029466 | r | | |
| 694 | 7493 | AI029608 | b | | |
| 696 | 7537 | AI029829 | o, General | | |
| 697 | 2310 | AI029969 | v | | |
| 698 | 7585 | AI030023 | x | | |
| 699 | 7586 | AI030024 | b, n | | |
| 700 | 14492 | AI030091 | cc | | |
| 701 | 10673 | AI030134 | f | | EST, Weakly similar to 1605244A erythrocyte ankyrin [*H. sapiens*], ESTs, Weakly similar to S68418 protein phosphatase 1M chain M110 isoform - rat [*R. norvegicus*], Human DNA |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | sequence from clone RP11-196N14 on chromosome 20 Contains ESTs, STSs, GSSs and CpG islands. Contains three novel genes, part of a gene for a novel protein similar to protein serine/threonine phosphatase 4 regulatory subunit 1 (PP4R1) and a gene for a novel protein with an ankyrin domain, RIKEN cDNA 1110058D09 gene, RIKEN cDNA 1600009D24 gene, RIKEN cDNA 4930539L19 gene, expressed sequence AA408090, hypothetical protein MGC5540, leukocyte receptor cluster (LRC) member 3, myosin phosphatase, target subunit 1, protein phosphatase 1, regulatory (inhibitor) subunit 12A, testis-specific ankyrin motif containing protein |
| 702 | 7615 | AI030163 | o, r | | |
| 703 | 2370 | AI030179 | General | | |
| 704 | 7681 | AI030449 | n | | |
| 705 | 11559 | AI030472 | General | | |
| 706 | 7665 | AI030668 | t, bb | nucleosome assembly protein 1-like 1 | ESTs, Highly similar to 2008109A set gene [*R. norvegicus*], ESTs, Highly similar to SET_HUMAN SET PROTEIN [*H. sapiens*], SET translocation, SET translocation (myeloid leukemia-associated), nucleosome assembly protein 1-like 1, nucleosome assembly protein 1-like 2, nucleosome assembly protein 1-like 4 |
| 707 | 24222 | AI030704 | k | | |
| 708 | 10740 | AI030743 | h | | |
| 709 | 10742 | AI030773 | e | | |
| 711 | 16169 | AI030932 | General | | RIKEN cDNA 1300012C15 gene, RIKEN cDNA 2310076L09 gene, adipose differentiation related protein, adipose differentiation-related protein |
| 712 | 19527 | AI030991 | f | | |
| 713 | 22614 | AI031004 | r | | |
| 714 | 3167 | AI031012 | e | | ClpP (caseinolytic protease, ATP-dependent, proteolytic subunit, *E. coli*) homolog, caseinolytic protease, ATP-dependent, proteolytic subunit homolog (*E. coli*) |
| 715 | 5350 | AI043611 | a | | |
| 716 | 7858 | AI043654 | t | | |
| 717 | 10784 | AI043678 | d | | |
| 718 | 9180 | AI043694 | aa | | |
| 719 | 7867 | AI043695 | aa | | ESTs, Highly similar to PUR1_HUMAN AMIDOPHOSPHORIBOSYLTRANSFERASE PRECURSOR [*H. sapiens*], ESTs, Moderately similar to PUR1_HUMAN AMIDOPHOSPHORIBOSYLTRANSFERASE PRECURSOR [*H. sapiens*], RIKEN cDNA 5730454C12 gene, expressed sequence AA675351, expressed sequence C79945, glutamine fructose-6-phosphate transaminase 2, glutamine-fructose-6-phosphate transaminase 2, phosphoribosyl pyrophosphate amidotransferase |
| 720 | 7584 | AI043724 | General | | |
| 721 | 7895 | AI043768 | e | | |
| 722 | 7903 | AI043805 | General | | |
| 723 | 7913 | AI043849 | cc | | ELL-RELATED RNA POLYMERASE II, ELONGATION FACTOR, ESTs, Highly similar to ELL2_HUMAN RNA POLYMERASE II ELONGATION FACTOR ELL2 [*H. sapiens*], ESTs, Weakly similar to ELL MOUSE RNA |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | POLYMERASE II ELONGATION FACTOR ELL [*M. musculus*], ESTs, Weakly similar to ELL2_HUMAN RNA POLYMERASE II ELONGATION FACTOR ELL2 [*H. sapiens*], *Mus musculus*, clone IMAGE: 3583970, mRNA, partial cds, *Mus musculus*, clone MGC: 11987 IMAGE: 3601737, mRNA, complete cds, eleven-nineteen lysine-rich leukemia gene, hypothetical protein FLJ22637 |
| 724 | 3899 | AI043904 | l | | |
| 725 | 6766 | AI043914 | f | | |
| 726 | 10818 | AI043990 | g, l, m, General | | |
| 727 | 7956 | AI044018 | f | | |
| 728 | 5393 | AI044170 | p | | |
| 729 | 5398 | AI044177 | q | | |
| 730 | 5425 | AI044237 | a, d | | EST, Weakly similar to S59856 collagen alpha 1(III) chain precursor - mouse [*M. musculus*], ESTs, Weakly similar to S59856 collagen alpha 1(III) chain precursor - mouse [*M. musculus*], *Homo sapiens*, Similar to hypothetical protein FLJ20783, clone MGC: 1005 IMAGE: 3139876, mRNA, complete cds, expressed sequence AW122071, hypothetical protein FLJ10355, procollagen, type XIX, alpha 1, sequence-specific single-stranded-DNA-binding protein, single-stranded DNA-binding protein 2 |
| 731 | 8692 | AI044247 | r | | 2,4-dienoyl CoA reductase 1, mitochondrial, 2,4-dienoyl CoA reductase 2, peroxisomal, ESTs, Weakly similar to LUNG CARBONYL REDUCTASE [*M. musculus*], ESTs, Weakly similar to S11021 2,4-dienoyl-CoA reductase [*R. norvegicus*], FabG (beta-ketoacyl-[acyl-carrier-protein] reductase, *E coli*) like, *Homo sapiens* AS10 protein mRNA, partial cds, RIKEN cDNA 1200012F07 gene, RIKEN cDNA 1810027P18 gene, carbonyl reductase, carbonyl reductase 2, oxidoreductase UCPA |
| 732 | 5430 | AI044253 | i | | |
| 733 | 5461 | AI044338 | g, p, General | | |
| 734 | 5464 | AI044345 | i | | |
| 735 | 3359 | AI044347 | aa | | |
| 737 | 2695 | AI044396 | b | | EST, Moderately similar to IL6B_HUMAN INTERLEUKIN-6 RECEPTOR BETA CHAIN PRECURSOR [*H. sapiens*], colony stimulating factor 3 receptor (granulocyte), cytokine receptor-like factor 1, interleukin 12 receptor, beta 2, interleukin 6 signal transducer, interleukin 6 signal transducer (gp130, oncostatin M receptor) |
| 738 | 5494 | AI044425 | General | | |
| 740 | 9882 | AI044588 | j, m | | |
| 741 | 5575 | AI044688 | g | | |
| 742 | 2348 | AI044794 | General | | |
| 743 | 18205 | AI044836 | n | | EST, Moderately similar to JH0148 nucleolin - rat [*R. norvegicus*], EST, Moderately similar to RBM8_HUMAN PUTATIVE RNA-BINDING PROTEIN 8 [*H. sapiens*], EST, Weakly similar to NUCL_HUMAN NUCLEOLIN [*H. sapiens*], ESTs, Highly similar to FUS_HUMAN RNA-BINDING PROTEIN FUS [*H. sapiens*], ESTs, Highly similar to RBM8_HUMAN PUTATIVE RNA-BINDING PROTEIN 8 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | [*H. sapiens*], ESTs, Moderately similar to RBM8_HUMAN PUTATIVE RNA-BINDING PROTEIN 8 [*H. sapiens*], *Mus musculus* pigpen protein mRNA, complete cds, RNA binding motif protein 8A, TATA box binding protein (TBP)-associated factor, RNA polymerase II, N, 68 kD (RNA-binding protein 56), fusion, derived from t(12; 16) malignant liposarcoma |
| 744 | 5626 | AI044864 | u | | |
| 745 | 5630 | AI044869 | f | | |
| 746 | 5634 | AI044883 | General | | |
| 747 | 4047 | AI044947 | l, m | | |
| 748 | 5654 | AI044976 | w | | |
| 749 | 5684 | AI045056 | r | | |
| 750 | 19235 | AI045074 | General | | ESTs, Highly similar to BGAL MOUSE BETA-GALACTOSIDASE PRECURSOR [*M. musculus*], ESTs, Weakly similar to BGAL MOUSE BETA GALACTOSIDASE PRECURSOR [*M. musculus*], *Homo sapiens*, clone IMAGE: 3502329, mRNA, partial cds, *Homo sapiens*, clone IMAGE: 3938286, mRNA, partial cds, RIKEN cDNA 4833408P15 gene, galactosidase, beta 1 |
| 751 | 5689 | AI045075 | i, aa, General | | |
| 752 | 5711 | AI045151 | General | | ESTs, Weakly similar to MCAT_HUMAN MITOCHONDRIAL CARNITINE/ACYLCARNITINE CARRIER PROTEIN [*H. sapiens*], expressed sequence AW108044, solute carrier family 25 (carnitine/acylcarnitine translocase), member 20, solute carrier family 25 (mitochondrial carnitine/acylcarnitine translocase), member 20, solute carrier family 25 (mitochondrial carrier, adenine nucleotide translocator), member 10, solute carrier family 25 (mitochondrial carrier; ornithine transporter), member 15, uncoupling protein 2 (mitochondrial, proton carrier), uncoupling protein 2, mitochondrial |
| 753 | 19237 | AI045153 | c | | ESTs, Moderately similar to K6B2_MOUSE RIBOSOMAL PROTEIN S6 KINASE BETA 2 (S6K-BETA 2) (70 KDA RIBOSOMAL PROTEIN S6 KINASE 2) (P70-S6KB) (P70 RIBOSOMAL S6 KINASE BETA) (P70 S6KBETA) (S6K2) [*M. musculus*], NIMA (never in mitosis gene a)-related expressed kinase 3, RIKEN cDNA 2610318I15 gene, expressed sequence AI256796, expressed sequence AW319595, ribosomal protein S6 kinase, 70 kD, polypeptide 2, serine/threonine kinase 5 |
| 754 | 9964 | AI045161 | f | | |
| 755 | 5735 | AI045223 | f | | |
| 756 | 5474 | AI045477 | a, General | | |
| 757 | 5811 | AI045502 | d, e | | |
| 758 | 5819 | AI045537 | General | | |
| 759 | 5839 | AI045594 | i | | |
| 760 | 6808 | AI045600 | s | | TRAM-like protein, translocating chain-associating membrane protein |
| 761 | 17755 | AI045608 | y | | |
| 763 | 10020 | AI045632 | a | | |
| 764 | 5855 | AI045669 | General | | |
| 765 | 5881 | AI045789 | i | | B aggressive lymphoma gene, DKFZP434J214 protein, KIAA1268 protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 766 | 5897 | AI045862 | General | | KIAA0138 gene product, hypothetical protein FLJ13213, scaffold attachment factor B |
| 767 | 5900 | AI045866 | y, z | | |
| 768 | 7540 | AI045882 | o, t, General | | EST, Weakly similar to C29149 proline-rich protein - mouse [*M. musculus*], ESTs, Weakly similar to C29149 proline-rich protein - mouse [*M. musculus*], KIAA0999 protein, Mouse 31-kDa proline-rich salivary protein, complete cds of clone pUMP125, *Mus musculus*, Similar to proline-rich protein BstNI subfamily 2, clone MGC: 18611 IMAGE: 4165240, mRNA, complete cds, RIKEN cDNA 6030468B19 gene, *Rattus norvegicus* proline-rich proteoglycan (PRPG2) mRNA, complete cds, proline-rich protein HaeIII subfamily 2 |
| 769 | 5329 | AI045970 | p | | |
| 770 | 15093 | AI058285 | d | | |
| 771 | 8002 | AI058304 | i | | |
| 772 | 8017 | AI058341 | c | | |
| 773 | 6828 | AI058359 | General | | Cdc42 effector protein 2, Cdc42 effector protein 3 |
| 774 | 8177 | AI058603 | aa | | |
| 775 | 3090 | AI058730 | aa | | |
| 776 | 10093 | AI058746 | g | | |
| 777 | 8143 | AI058759 | General | | |
| 778 | 18659 | AI058762 | f | | |
| 779 | 8163 | AI058837 | aa | | |
| 780 | 4789 | AI058889 | General | | |
| 781 | 8221 | AI059061 | General | | |
| 782 | 10159 | AI059147 | d | | |
| 783 | 8245 | AI059154 | b | | EST, Weakly similar to GBLP_HUMAN GUANINE NUCLEOTIDE-BINDING PROTEIN BETA SUBUNIT-LIKE PROTEIN 12.3 [*H. sapiens*], *Homo sapiens* mRNA for FLJ00083 protein, partial cds, IRA1 protein, *Rattus norvegicus* Sprague Dawley protein kinase C receptor mRNA, complete cds, WD repeat domain 5, expressed sequence AL033335, hypothetical protein, recombination protein REC14 |
| 784 | 8283 | AI059290 | n | | |
| 785 | 8314 | AI059386 | g, General | | |
| 786 | 10200 | AI059444 | i | | |
| 787 | 8347 | AI059519 | s | | DKFZP566D213 protein, EST, Moderately similar to EPIDERMAL GROWTH FACTOR PRECURSOR [*M. musculus*], ESTs, Weakly similar to mel [*M. musculus*], Epidermal growth factor, epidermal growth factor, epidermal growth factor (beta-urogastrone), hypothetical protein MGC11256, nel-like 2 homolog (chicken) |
| 788 | 18359 | AI059675 | n | | EST, Highly similar to TERA HUMAN [*H. sapiens*], EST, Weakly similar to T46437 hypothetical protein DKFZp434K0126.1 [*H. sapiens*], ESTs, Weakly similar to T46437 hypothetical protein DKFZp434K0126.1 [*H. sapiens*], ESTs, Weakly similar to TERA HUMAN [*H. sapiens*], ESTs, Weakly similar to TERA RAT TRANSITIONAL ENDOPLASMIC RETICULUM ATPASE [*R. norvegicus*], RIKEN cDNA 4833413G10 gene, RIKEN cDNA 5430414H02 gene, spermatogenesis associated factor, valosin containing protein, valosin-containing protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 789 | 10281 | AI059947 | b, t | | |
| 790 | 8494 | AI059968 | aa | | |
| 791 | 8495 | AI059971 | General | | *Homo sapiens* (clone NCD18) tumor necrosis factor receptor related protein mRNA, complete exon and repeat region, lymphotoxin B receptor, lymphotoxin beta receptor (TNFR superfamily, member 3), tumor necrosis factor receptor superfamily, member 8 |
| 792 | 8496 | AI059974 | General | | KIAA1685 protein, KIAA1713 protein |
| 793 | 10289 | AI060053 | i | | CGI-142, RIKEN cDNA 3930401K13 gene |
| 794 | 8548 | AI060176 | k | | |
| 795 | 8565 | AI060236 | t | | |
| 796 | 18322 | AI060279 | i, y, z | | |
| 797 | 8745 | AI069939 | r | | |
| 798 | 8785 | AI070067 | o | | IK cytokine, down-regulator of HLA II, *Mus musculus*, Similar to IK cytokine, down-regulator of HLA II, clone MGC: 25508 IMAGE: 4920184, mRNA, complete cds |
| 799 | 17506 | AI070068 | cc | | growth arrest and DNA-damage-inducible 45 beta, growth arrest and DNA-damage-inducible, alpha, growth arrest and DNA-damage-inducible, beta |
| 800 | 9067 | AI070087 | General | | ESTs, Highly similar to NUCL_HUMAN NUCLEOLIN [*H. sapiens*], Nucleolin, RIKEN cDNA 0610010A22 gene, eukaryotic translation initiation factor 3, subunit 4 (delta, 44 kDa), eukaryotic translation initiation factor 3, subunit 4 (delta, 44 kD), nucleolin |
| 801 | 3551 | AI070122 | e | | CGI-97 protein, EST, Weakly similar to YC97_HUMAN HYPOTHETICAL PROTEIN CGI-97 [*H. sapiens*], RIKEN cDNA 4733401P19 gene |
| 802 | 4967 | AI070179 | k | | glia maturation factor, gamma |
| 803 | 18 | AI070195 | General | | CGI-20 protein |
| 804 | 24197 | AI070314 | General | | armadillo repeat gene deletes in velocardiofacial syndrome, catenin (cadherin-associated protein), delta 1, catenin (cadherin-associated protein), delta 2 (neural plakophilin-related arm-repeat protein), plakophilin 4 |
| 805 | 8869 | AI070330 | r | | |
| 806 | 8874 | AI070336 | b, cc | | |
| 807 | 10417 | AI070410 | m | | |
| 808 | 8901 | AI070419 | aa | | toll-like receptor 1, toll-like receptor 10, toll-like receptor 2, toll-like receptor 6 |
| 809 | 14424 | AI070421 | l, p, General | | |
| 810 | 10434 | AI070497 | General | | |
| 811 | 8927 | AI070523 | v | | |
| 812 | 8946 | AI070611 | q | | |
| 813 | 8950 | AI070621 | w | | |
| 814 | 8972 | AI070673 | General | | |
| 815 | 8981 | AI070715 | bb | | |
| 816 | 26184 | AI070784 | i, l | | ESTs, Highly similar to I49636 DNA-binding protein - mouse [*M. musculus*], ESTs, Moderately similar to I49636 DNA-binding protein - mouse [*M. musculus*], ESTs, Weakly similar to B57785 zinc finger protein ZNF136 [*H. sapiens*], ESTs, Weakly similar to OZF_HUMAN ZINC FINGER PROTEIN OZF [*H. sapiens*], *Homo sapiens*, Similar to zinc finger protein 136 (clone pHZ-20), clone MGC: 10647 IMAGE: 4053041, mRNA, complete cds, RIKEN cDNA 2310011F05 gene, pancreas zinc finger protein, zinc |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 817 | 3007 | AI070824 | w | | finger protein 136 (clone pHZ-20), zinc finger protein 260, zinc finger protein 63, zinc finger protein 97 DKFZP564F0522 protein, ESTs, Weakly similar to T08675 hypothetical protein DKFZp564F0522.1 [*H. sapiens*] |
| 818 | 8999 | AI070839 | p | | |
| 819 | 10477 | AI070868 | e, f | | ESTs, Highly similar to NRP2_RAT NEUROPILIN-2 PRECURSOR (VASCULAR ENDOTHELIAL CELL GROWTH FACTOR 165 RECEPTOR 2) [*R. norvegicus*], neuropilin 2, neuropilin-2, platelet derived growth factor C |
| 820 | 24301 | AI070911 | k | | |
| 821 | 8721 | AI071024 | General | | |
| 822 | 9212 | AI071098 | x | | |
| 823 | 1831 | AI071137 | c | | cell division cycle 25 homolog B (*S. cerevisiae*), cell division cycle 25 homolog C (*S. cerevisiae*), cell division cycle 25B, cell division cycle 25C, expressed sequence AI604853 |
| 824 | 11005 | AI071139 | r | | |
| 825 | 9104 | AI071173 | j, m | | ESTs, Highly similar to ROG_HUMAN HETEROGENEOUS NUCLEAR RIBONUCLEOPROTEIN G [*H. sapiens*], Homo sapiens, Similar to RNA binding motif protein, X chromosome, clone MGC: 9398 IMAGE: 3875565, mRNA, complete cds, RIKEN cDNA 1700012H05 gene, RNA binding motif protein, X chromosome, RNA binding motif protein, X chromosome retrogene, RNA binding motif protein, Y chromosome, family 1, member A1, testes-specific heterogenous nuclear ribonucleoprotein G-T |
| 826 | 9583 | AI071185 | General | | |
| 827 | 9644 | AI071410 | c | | |
| 828 | 16058 | AI071490 | General | | serine palmitoyltransferase, long chain base subunit 2 |
| 829 | 11057 | AI071509 | f, o | | |
| 831 | 5695 | AI071566 | bb | | |
| 832 | 9671 | AI071568 | w | | |
| 833 | 22929 | AI071578 | General | | DNA segment, human D4S114, P311 protein |
| 834 | 9673 | AI071581 | General | | |
| 835 | 9699 | AI071646 | General | | |
| 837 | 9799 | AI072008 | q, y, z | | |
| 838 | 9808 | AI072050 | d | | |
| 839 | 22796 | AI072213 | General | | |
| 840 | 9271 | AI072405 | v | | |
| 841 | 10869 | AI072425 | w | | |
| 842 | 21797 | AI072439 | General | | EST X83352, ESTs, Highly similar to T17226 hypothetical protein DKFZp566G223.1 [*H. sapiens*], Homo sapiens, Similar to chloride intracellular channel 4, clone MGC: 8812 IMAGE: 3861372, mRNA, complete cds, RIKEN cDNA 5730531E12 gene, chloride intracellular channel 1, chloride intracellular channel 4, chloride intracellular channel 4 (mitochondrial), hypothetical protein DKFZp434N127, intracellular chloride ion channel protein p64H1 |
| 843 | 9306 | AI072521 | r | | |
| 844 | 9312 | AI072550 | j | | |
| 845 | 10893 | AI072559 | x | | |
| 846 | 1501 | AI072634 | cc, General | | |
| 847 | 6548 | AI072658 | General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 848 | 9363 | AI072695 | d | | DnaJ (Hsp40) homolog, subfamily C, member 4, Homo sapiens, clone MGC: 19482 IMAGE: 4309314, mRNA, complete cds, hypothetical protein FLJ11506 |
| 850 | 9409 | AI072841 | n | | |
| 851 | 9410 | AI072842 | w | | |
| 852 | 9468 | AI073021 | General | | |
| 853 | 9518 | AI073223 | f | | |
| 854 | 11183 | AI100768 | t | | EST, Moderately similar to CARBONIC ANHYDRASE II [R. norvegicus], carbonic anhydrase 2, carbonic anhydrase II, carbonic anhydrase VIII, carbonic anhydrase-like sequence 1 |
| 855 | 9190 | AI100835 | e | | |
| 856 | 2029 | AI100842 | p | | |
| 857 | 5687 | AI101006 | e | | |
| 858 | 15192 | AI101099 | g, cc | | ESTs, Moderately similar to AF078844 1 hqp0376 protein [H. sapiens], expressed sequence AA409533 |
| 859 | 17399 | AI101157 | o | | ATP synthase, H+ transporting, mitochondrial F0 complex, subunit f, isoform 2, EST, Weakly similar to ATPK_HUMAN ATP SYNTHASE F CHAIN, MITOCHONDRIAL [H. sapiens], ESTs, Highly similar to ATPK_HUMAN ATP SYNTHASE F CHAIN, MITOCHONDRIAL [H. sapiens] |
| 860 | 9339 | AI101160 | l, m, o | | |
| 861 | 6321 | AI101256 | General | | ESTs, Moderately similar to HETEROGENEOUS NUCLEAR RIBONUCLEOPROTEIN C [R. norvegicus], Mus musculus high-glycine/tyrosine protein type I E5 mRNA, complete cds, RNA binding protein p45AUF1, expressed sequence C85084, heterogeneous nuclear ribonucleoprotein A/B, heterogeneous nuclear ribonucleoprotein D, heterogeneous nuclear ribonucleoprotein D (AU-rich element RNA-binding protein 1, 37 kD), heterogeneous nuclear ribonucleoprotein D-like |
| 862 | 5421 | AI101270 | c | | Rho GDP dissociation inhibitor (GDI) beta, expressed sequence C87222, rho, GDP dissociation inhibitor (GDI) beta |
| 863 | 11910 | AI101323 | General | | ets variant gene 5 (ets-related molecule) |
| 864 | 23140 | AI101608 | e | | |
| 865 | 4119 | AI101901 | General | | |
| 866 | 16324 | AI102009 | b | | |
| 867 | 18642 | AI102023 | o | | brain-specific membrane-anchored protein, chromosome 1 open reading frame 8 |
| 868 | 19373 | AI102044 | a | beta-carotene 15, 15'-dioxygenase, beta-carotene 15, 15'-dioxygenase, frizzled (Drosophila) homolog 1, frizzled homolog 1, (Drosophila) | EST, Moderately similar to 0806162D protein COII [M. musculus], EST, Weakly similar to 810024D cytochrome oxidase II [H. sapiens] |
| 869 | 7051 | AI102055 | h | | ESTs, Highly similar to 2013348A Ser kinase SRPK1 [H. sapiens], Mus musculus 13 days embryo head cDNA, RIKEN full-length enriched library, clone: 3110005M20, full insert sequence, Mus musculus adult male lung cDNA, RIKEN full-length enriched library, clone: 1200011B22, full insert sequence, SFRS protein kinase 1, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | SFRS protein kinase 2, serine/arginine-rich protein specific kinase 2, serine/threonine kinase 23 |
| 870 | 6544 | AI102064 | c | | |
| 871 | 10227 | AI102248 | w | | |
| 872 | 23849 | AI102318 | e, q | | |
| 873 | 11954 | AI102505 | g, j, s | | |
| 874 | 2125 | AI102519 | c, k | | TYRO protein tyrosine kinase binding protein |
| 875 | 5967 | AI102520 | y | | ESTs, Weakly similar to GEF2_HUMAN GANGLIOSIDE EXPRESSION FACTOR 2 [*R. norvegicus*], GABA(A) receptor-associated protein-like 2, RIKEN cDNA 0610012F20 gene, ganglioside expression factor 2 |
| 875 | 5969 | AI102520 | p, w | | ESTs, Weakly similar to GEF2_HUMAN GANGLIOSIDE EXPRESSION FACTOR 2 [*R. norvegicus*], GABA(A) receptor-associated protein-like 2, RIKEN cDNA 0610012F20 gene, gamma-aminobutyric acid (GABA(A)) receptor-associated protein-like 1, ganglioside expression factor 2 |
| 876 | 11563 | AI102560 | General | | |
| 877 | 15190 | AI102562 | b, g, n, p, v | | EST, Moderately similar to Cd-7 Metallothionein-2 [*H. sapiens*], EST, Moderately similar to SMHU1E metallothionein 1E [*H. sapiens*] |
| 878 | 19769 | AI102570 | bb | | |
| 879 | 22487 | AI102578 | General | | EST, Highly similar to I49523 Mouse primary response gene B94 mRNA, 3'end - mouse [*M. musculus*], *Homo sapiens*, clone MGC: 16332 IMAGE: 3842543, mRNA, complete cds, RIKEN cDNA 1200009I06 gene, RIKEN cDNA 1600013K19 gene, similar to *S. cerevisiae* Sec6p and *R. norvegicus* rsec6, tumor necrosis factor, alpha-induced protein 2 |
| 880 | 19011 | AI102618 | General | | |
| 881 | 23837 | AI102620 | q, t | | |
| 882 | 23538 | AI102727 | g, General | | solute carrier family 20 (phosphate transporter), member 1, solute carrier family 20 (phosphate transporter), member 2, solute carrier family 20, member 1, solute carrier family 20, member 2 |
| 883 | 17234 | AI102741 | c | tissue inhibitor of metalloproteinase 3, tissue inhibitor of metalloproteinase 3 (Sorsby fundus dystrophy, pseudoinflammatory) | tissue inhibitor of metalloproteinase 3, tissue inhibitor of metalloproteinase 3 (Sorsby fundus dystrophy, pseudoinflammatory) |
| 884 | 5891 | AI102745 | k | | |
| 885 | 6796 | AI102753 | General | | |
| 886 | 8837 | AI102849 | o, p | | |
| 887 | 15861 | AI10288 | i | | phosphoserine aminotransferase |
| 888 | 3533 | AI102877 | g | | |
| 889 | 13222 | AI102977 | General | | |
| 890 | 6806 | AI103018 | o, u | | |
| 891 | 10659 | AI103059 | w, cc, General | | |
| 892 | 17400 | AI103097 | e | | ATP synthase, H+ transporting, mitochondrial F0 complex, subunit f, isoform 2, EST, Weakly similar to ATPK_HUMAN ATP SYNTHASE F CHAIN, MITOCHONDRIAL [*H. sapiens*], ESTs, Highly similar to ATPK_HUMAN ATP SYNTHASE F CHAIN, MITOCHONDRIAL [*H. sapiens*] |
| 893 | 3584 | AI103106 | x, aa | | |
| 894 | 13298 | AI103143 | r | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 895 | 15981 | AI103150 | i, x | | ESTs, Highly similar to S17516 hypothetical protein [*H. sapiens*], ESTs, Highly similar to UBIQUITIN-CONJUGATING ENZYME E2-17 KD [*R. norvegicus*], RIKEN cDNA 1110015A16 gene, RIKEN cDNA 2610301N02 gene, expressed sequence AI327276, ubiquitin conjugating enzyme, ubiquitin-conjugating enzyme E2A (RAD6 homolog), ubiquitin-conjugating enzyme E2B (RAD6 homolog), ubiquitin-conjugating enzyme E2B (RAD6 homology), ubiquitin-conjugating enzyme E2C, ubiquitin-conjugating enzyme E2G 2 |
| 896 | 3475 | AI103245 | w | | |
| 898 | 23619 | AI103314 | p | | |
| 899 | 24181 | AI103320 | e | | |
| 901 | 4355 | AI103410 | General | | |
| 902 | 7622 | AI103472 | General | | |
| 903 | 20918 | AI103552 | n | | |
| 904 | 21579 | AI103572 | General | | |
| 905 | 2222 | AI103631 | o | | |
| 906 | 2752 | AI103641 | e | | |
| 907 | 4856 | AI103708 | i | | |
| 908 | 8990 | AI103719 | l, m, y, z | | |
| 909 | 15942 | AI103738 | r | | |
| 910 | 22885 | AI103828 | e, General | | |
| 911 | 15853 | AI103841 | x | complement component 4 (within H-2S), complement component 4B | EST, Weakly similar to complement component C4A [*H. sapiens*] |
| 912 | 15050 | AI103911 | j, y | | EST, Moderately similar to UCRI RAT UBIQUINOL-CYTOCHROME C REDUCTASE IRON-SULFUR SUBUNIT, MITOCHONDRIAL PRECURSOR [*R. norvegicus*], EST, Weakly similar to UCRI_HUMAN UBIQUINOL-CYTOCHROME C REDUCTASE IRON-SULFUR SUBUNIT, MITOCHONDRIAL PRECURSOR [*H. sapiens*], ESTs, Moderately similar to UCRI_HUMAN UBIQUINOL-CYTOCHROME C REDUCTASE IRON-SULFUR SUBUNIT, MITOCHONDRIAL PRECURSOR [*H. sapiens*], Human DNA sequence from clone RP1-228J4 on chromosome 6 Contains a pseudogene similar to UQCRFS1 (ubiquinol-cytochrome c reductase, Rieske iron-sulfur polypeptide 1), ESTs, an STS and GSSs, RIKEN cDNA 4430402G14 gene, expressed sequence AI875505, ubiquinol-cytochrome c reductase, Rieske iron-sulfur polypeptide 1 |
| 913 | 12376 | AI103939 | u | | |
| 914 | 22271 | AI103947 | o, y | | |
| 915 | 20833 | AI104035 | f, q | | ESTs, Weakly similar to COXG MOUSE CYTOCHROME C OXIDASE POLYPEPTIDE VIB [*M. musculus*], Human DNA sequence from clone RP4-591N18 on chromosome 22q13.1-13.2 Contains a COX6B (Cytochrome C Oxidase subunit VIb (EC 1.9.3.1)) pseudogene, ESTs, GSSs and two putative CpG islands, RIKEN cDNA 2010000G05 gene, cytochrome c oxidase subunit VIb |
| 916 | 7010 | AI104099 | w | | |
| 917 | 22101 | AI104251 | General | | DKFZP564O243 protein |
| 918 | 22833 | AI104258 | General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 919 | 22211 | AI104279 | g, m | | EST, Weakly similar to IF6_HUMAN EUKARYOTIC TRANSLATION INITIATION FACTOR 6 [*H. sapiens*], *Mus musculus* 10 days neonate cerebellum cDNA, RIKEN full-length enriched library, clone: 6530402L05, full insert sequence, integrin beta 4 binding protein |
| 920 | 10720 | AI104296 | l | | |
| 921 | 15416 | AI104340 | i | | |
| 922 | 10991 | AI104342 | a | | |
| 923 | 18831 | AI104357 | p | | ESTs, Weakly similar to A29861 actin gamma [*H. sapiens*], ESTs, Weakly similar to I39393 alpha-actin [*H. sapiens*], ESTs, Weakly similar to S38782 actin beta' chain [*H. sapiens*], *Homo sapiens* mRNA; cDNA DKFZp434B2115 (from clone DKFZp434B2115), RIKEN cDNA 1700052K15 gene, RIKEN cDNA 1700061J02 gene, actin-like 7a, expressed sequence AL023024, expressed sequence AV259599, melanoma X-actin, uncharacterized hypothalamus protein HARP11 |
| 924 | 7223 | AI104373 | e | | |
| 925 | 23574 | AI104520 | e, g, s | cytochrome c oxidase subunit VIa polypeptide 1, cytochrome c oxidase, subunit VI a, polypetide 1 | |
| 926 | 18509 | AI104528 | q | | NADH dehydrogenase (ubiquinone) 1 beta subcomplex, 6 (17 kD, B17) |
| 927 | 11680 | AI104605 | v | | |
| 928 | 12342 | AI104658 | w | | ESTs, Weakly similar to RENAL TRANSCRIPTION FACTOR KID-1 [*R. norvegicus*], ESTs, Weakly similar to T42682 hypothetical protein DKFZp434G1221.1 [*H. sapiens*], *Homo sapiens*, clone MGC: 20975 IMAGE: 4634585, mRNA, complete cds, expressed sequence AA415813, expressed sequence AI839920, expressed sequence AL024263, hypothetical protein FLJ20531, transcription factor 17, transcription factor 17-like 1, zinc finger protein 91, zinc finger protein homologous to Zfp91 in mouse |
| 929 | 23689 | AI104685 | r | | |
| 930 | 15377 | AI104821 | o, cc | | hypothetical protein MGC10947, leucine rich repeat (in FLII) interacting protein 2 |
| 931 | 22957 | AI104897 | General | | |
| 932 | 18451 | AI104953 | o, s | | ATP synthase, H+ transporting, mitochondrial F1 complex, delta subunit, EST, Moderately similar to ATPD_HUMAN ATP SYNTHASE DELTA CHAIN, MITOCHONDRIAL PRECURSO [*H. sapiens*], RIKEN cDNA 0610008F14 gene, expressed sequence AA960090, expressed sequence AI876556, expressed sequence C85518 |
| 933 | 24375 | AI104979 | n, General | | |
| 934 | 18278 | AI105080 | bb | | 3-oxoacid CoA transferase, hypothetical protein FKSG25 |
| 935 | 2196 | AI105243 | g | | |
| 936 | 5199 | AI105272 | bb, General | | |
| 937 | 12901 | AI105301 | o, s | | |
| 938 | 7700 | AI105383 | cc, General | | |
| 939 | 13343 | AI105398 | u | | |
| 940 | 22931 | AI105417 | e, General | | DNA segment, human D4S114, P311 protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 941 | 23596 | AI105435 | bb | | expressed sequence D17825, glutaryl-Coenzyme A dehydrogenase |
| 942 | 15893 | AI105465 | o | | ESTs, Highly similar to DHSD_HUMAN SUCCINATE DEHYDROGENASE [*H. sapiens*], ESTs, Moderately similar to DHSD_HUMAN SUCCINATE DEHYDROGENASE [*H. sapiens*], succinate dehydrogenase complex, subunit D, integral membrane protein |
| 943 | 12660 | AI111492 | c | | |
| 944 | 4479 | AI111599 | General | | |
| 945 | 24211 | AI111853 | k | | EST, Moderately similar to 0710252A histone H3 [*H. sapiens*], ESTs, Highly similar to H33_HUMAN HISTONE H3.3 [*H. sapiens*], ESTs, Weakly similar to H33_HUMAN HISTONE H3.3 [*H. sapiens*], ESTs, Weakly similar to JQ1983 H3.3 like histone MH921 - mouse [*M. musculus*], H3 histone, family 3A, H3 histone, family 3B, H3 histone, family 3B (H3.3B) |
| 946 | 2539 | AI111960 | r | | |
| 947 | 5729 | AI111990 | k | | EGF-containing fibulin-like extracellular matrix protein 1, EGF-containing fibulin like extracellular matrix protein 2, EST, Weakly similar to FBL3_RAT EGF-CONTAINING FIBULIN-LIKE EXTRACELLULAR MATRIX PROTEIN 1 PRECURSOR (FIBULIN-3) (FIBL-3) (T16 PROTEIN) [*R. norvegicus*], ESTs, Highly similar to FBL3_RAT EGF-CONTAINING FIBULIN-LIKE EXTRACELLULAR MATRIX PROTEIN 1 PRECURSOR (FIBULIN-3) (FIBL-3) (T16 PROTEIN) [*R. norvegicus*], ESTs, Weakly similar to FBL3_RAT EGF-CONTAINING FIBULIN-LIKE EXTRACELLULAR MATRIX PROTEIN 1 PRECURSOR (FIBULIN-3) (FIBL-3) (T16 PROTEIN) [*R. norvegicus*], epidermal growth factor-containing fibulin-like extracellular matrix protein 1, epidermal growth factor-containing fibulin-like extracellular matrix protein 2 |
| 948 | 4049 | AI112012 | i, q, u, General | | EST, Moderately similar to PM17 MOUSE MELANOCYTE PROTEIN PMEL 17 PRECURSOR [*M. musculus*], *Homo sapiens*, Similar to glycoprotein (transmembrane) nmb, clone MGC: 1696 IMAGE: 3345861, mRNA, complete cds, glycoprotein (transmembrane) nmb, silver |
| 949 | 12908 | AI112043 | i | | |
| 950 | 20041 | AI112161 | t | | |
| 951 | 12937 | AI112462 | General | | |
| 952 | 3713 | AI112571 | b | | |
| 953 | 12921 | AI112636 | General | | *Homo sapiens* BAC clone RP11-335J18 from 2, RIKEN cDNA 1700124F02 gene, expressed sequence AI325217, uridine phosphorylase |
| 954 | 12965 | AI112926 | General | | |
| 955 | 7499 | AI112986 | General | | |
| 956 | 4969 | AI113008 | r | | |
| 957 | 11817 | AI136295 | f | | DKFZP564O123 protein, putative breast adenocarcinoma marker (32 kD) |
| 959 | 11165 | AI136372 | c | | |
| 960 | 4045 | AI136460 | cc | | |
| 961 | 12782 | AI136493 | k | | |
| 962 | 6850 | AI136665 | h | | RIKEN cDNA 2010320H07 gene, ectonucleoside triphosphate diphosphohydrolase 1, ectonucleoside triphosphate diphosphohydrolase 2, ectonucleoside triphosphate |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 963 | 20920 | AI136891 | p, v | butyrate response factor 1, zinc finger protein, C3H type, 36-like 1 | diphosphohydrolase 3, ectonucleoside triphosphate diphosphohydrolase 6 (putative function) ESTs, Moderately similar to TISB RAT TIS11B PROTEIN [*R. norvegicus*], ESTs, Weakly similar to TISB RAT TIS11B PROTEIN [*R. norvegicus*], butyrate response factor 1, butyrate response factor 1 (EGF-response factor 1), butyrate response factor 2, butyrate response factor 2 (EGF-response factor 2), expressed sequence AW742437 |
| 964 | 6552 | AI137062 | o | | 6.2 kd protein |
| 965 | 22722 | AI137211 | i | | |
| 966 | 13111 | AI137224 | o, General | | hypothetical protein FLJ20260, oxysterol binding protein 2 |
| 967 | 15969 | AI137302 | e | | DNA segment, Chr 17, ERATO Doi 197, expressed, EST, Weakly similar to ZF37_RAT ZINC FINGER PROTEIN 37 (ZFP-37) [*R. norvegicus*], ESTs, Weakly similar I38600 zinc finger protein ZNF135 [*H. sapiens*], ESTs, Weakly similar to ZINC FINGER PROTEIN ZFP-29 [*M. musculus*], *Homo sapiens* GIOT-1 mRNA for gonadotropin inducible transcription repressor-1, partial cds, expressed sequence AI449432, hypothetical protein FLJ14855, zinc finger protein 135 (clone pHZ-17), zinc finger protein 29, zinc finger protein 37, zinc finger protein homologous to Zfp37 in mouse |
| 968 | 14349 | AI137303 | d | | |
| 969 | 9166 | AI137406 | General | | protein C receptor, endothelial, protein C receptor, endothelial (EPCR) |
| 970 | 9525 | AI137516 | r | | EST, Weakly similar to ZF37_RAT ZINC FINGER PROTEIN 37 (ZFP-37) [*R. norvegicus*], ESTs, Weakly similar to B32891 finger protein 2, placental [*H. sapiens*], ESTs, Weakly similar to MLZ4 MOUSE ZINC FINGER PROTEIN MLZ-4 [*M. musculus*], *Homo sapiens* cDNA FLJ14967 fis, clone THYRO1000242, moderately similar to ZINC FINGER PROTEIN 84, expressed sequence AI854635, zinc finger protein 113, zinc finger protein 268, zinc finger protein 37, zinc finger protein 46, zinc finger protein 84 (HPF2), zinc finger protein homologous to Zfp37 in mouse |
| 971 | 6638 | AI137579 | General | | |
| 972 | 7414 | AI137586 | General | | EST, Weakly similar to IMB3_HUMAN IMPORTIN BETA-3 SUBUNIT [*H. sapiens*], *Homo sapiens* cDNA FLJ12978 fis, clone NT2RP2006321, RAN binding protein 6, karyopherin (importin) beta 3 |
| 973 | 11321 | AI137752 | z | | EST, Highly similar to R5HU7 ribosomal protein L7, cytosolic [*H. sapiens*], EST, Weakly similar to RL7 MOUSE 60S RIBOSOMAL PROTEIN L7 [*M. musculus*], ESTs, Highly similar to R5HU7 ribosomal protein L7, cytosolic [*H. sapiens*], calponin like transmembrane domain protein, ribosomal protein L7 |
| 974 | 23473 | AI137932 | l | | |
| 975 | 13158 | AI138024 | i | | |
| 976 | 13467 | AI138034 | cc | | UDP-glucose ceramide glucosyltransferase |
| 977 | 11377 | AI138105 | y | | |
| 978 | 6790 | AI144801 | d, h | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 979 | 6506 | AI144919 | j, l, y | | |
| 980 | 8027 | AI144958 | i | | |
| 982 | 14458 | AI145095 | General | | |
| 983 | 7476 | AI145202 | g | | |
| 984 | 17545 | AI145384 | e | | |
| 985 | 17479 | AI145385 | r | | |
| 986 | 4194 | AI145387 | r | | |
| 987 | 8634 | AI145722 | g | | |
| 988 | 8339 | AI145761 | y, General | | |
| 989 | 2059 | AI146005 | h, General | | RIKEN cDNA 2610020J05 gene, pseudouridine synthase 1, pseudouridylate synthase 1 |
| 990 | 23224 | AI146033 | o | | translocase of inner mitochondrial membrane 10 homolog (yeast), translocase of inner mitochondrial membrane 9 (yeast) homolog |
| 991 | 5232 | AI168942 | bb | branched chain keto acid dehydrogenase E1, beta polypeptide (maple syrup urine disease), branched chain ketoacid dehydrogenase E1, beta polypeptide | |
| 992 | 18472 | AI168975 | u | | |
| 992 | 18473 | AI168975 | u | | |
| 993 | 13235 | AI169020 | r | | |
| 994 | 11618 | AI169115 | o, y, General | | |
| 995 | 17386 | AI169144 | o | | |
| 996 | 10984 | AI169156 | o, u | | |
| 997 | 8205 | AI169176 | e | | |
| 998 | 12979 | AI169177 | e | | immediate early response 3 |
| 999 | 2607 | AI169211 | c | | *Homo sapiens* clone 24468 mRNA sequence, *Mus musculus* 0 day neonate skin cDNA, RIKEN full-length enriched library, clone: 4633401I22, full insert sequence, heterogeneous nuclear ribonucleoprotein C, heterogeneous nuclear ribonucleoprotein C (C1/C2), hnRNP-associated with lethal yellow |
| 1000 | 22661 | AI169265 | s, z | | ATPase, H+ transporting, lysosomal (vacuolar proton pump), subunit 1, EST, Weakly similar to I54197 hypothetical protein [*H. sapiens*], ESTs, Weakly similar to VAS1_RAT VACUOLAR ATP SYNTHASE SUBUNIT S1 PRECURSOR (V-ATPASE S1 SUBUNIT) (V-ATPASE S1 ACCESSORY PROTEIN) (V-ATPASE AC45 SUBUNIT) (C7-1 PROTEIN) [*R. norvegicus*], *Homo sapiens* cDNA FLJ12563 fis, clone NT2RM4000820, weakly similar to VACUOLAR ATP SYNTHASE SUBUNIT AC45 PRECURSOR (EC 3.6.1.34) |
| 1001 | 13239 | AI169278 | g, j, l, y, z | | |
| 1002 | 24162 | AI169279 | m | | |
| 1003 | 16879 | AI169284 | o | | ADP-ribosylation factor-like 6 interacting protein |
| 1004 | 24213 | AI169289 | p | | EST, Moderately similar to 0710252A histone H3 [*H. sapiens*], ESTs, Highly similar to H33_HUMAN HISTONE H3.3 [*H. sapiens*], ESTs, Weakly similar to H33_HUMAN HISTONE H3.3 [*H. sapiens*], ESTs, Weakly similar to JQ1983 H3.3 like histone MH921 - mouse [*M. musculus*], H3 histone, family 3A, H3 histone, family 3B, H3 histone, family 3B (H3.3B) |
| 1005 | 13240 | AI169311 | cc | | |
| 1006 | 5931 | AI169324 | b | | |
| 1007 | 20891 | AI169337 | d | | hypothetical protein |
| 1008 | 11979 | AI169365 | cc | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1009 | 10947 | AI169372 | s | | EST, Weakly similar to S13101 cytochrome P450 c117 - rat [*R. norvegicus*], RIKEN cDNA 2010301M18 gene, RIKEN cDNA 2010318C06 gene, RIKEN cDNA 2210009K14 gene, cytochrome P450, 2c29, cytochrome P450, subfamily IIC (mephenytoin 4-hydroxylase), polypeptide 19 |
| 1010 | 20697 | AI169494 | o, u | | ATPase, H+ transporting, lysosomal (vacuolar proton pump), 42 kDa, ATPase, H+ transporting, lysosomal (vacuolar proton pump), member D, ESTs, Moderately similar to VA0D_HUMAN VACUOLAR ATP SYNTHASE SUBUNIT D (V-ATPASE D SUBUNIT) (VACUOLAR PROTON PUMP D SUBUNIT) (V-ATPASE AC39 SUBUNIT) (V-ATPASE 40 KDA ACCESSORY PROTEIN) (P39) [*H. sapiens*] |
| 1011 | 8234 | AI169517 | z | | |
| 1012 | 18343 | AI169648 | o | | |
| 1013 | 10839 | AI169655 | l, m | | |
| 1014 | 24146 | AI169668 | j, l | | ATP-binding cassette, sub-family F (GCN20), member 1, ATP-binding cassette, sub-family F (GCN20), member 2, hypothetical protein FLJ11198 |
| 1015 | 22575 | AI169728 | r | | EST, Highly similar to T47184 hypothetical protein DKFZp434F1526.1 [*H. sapiens*], ESTs, Weakly similar to T47184 hypothetical protein DKFZp434F1526.1 [*H. sapiens*], hypothetical protein FLJ10889 |
| 1016 | 804 | AI169756 | cc | | Gene 33/Mig-6, RIKEN cDNA 1300002F13 gene |
| 1017 | 8213 | AI169883 | p | ferritin light chain 1, ferritin, light polypeptide | ESTs, Highly similar to FRHUL ferritin light chain [*H. sapiens*], ESTs, Moderately similar to FRHUL ferritin light chain [*H. sapiens*], PRO0470 protein, RIKEN cDNA 4933416E14 gene, ferritin light chain 2, ferritin, light polypeptide |
| 1018 | 3916 | AI169947 | i, bb | | |
| 1019 | 3733 | AI170053 | u, General | | |
| 1020 | 14179 | AI170224 | cc | | |
| 1021 | 11406 | AI170263 | r | | interleukin 20 receptor, alpha |
| 1022 | 3547 | AI170279 | General | | ESTs, Weakly similar to ZNT4_HUMAN ZINC TRANSPORTER 4 [*H. sapiens*], RIKEN cDNA 1810059J10 gene, hypothetical protein DKFZp547M236, hypothetical protein FLJ12496, solute carrier family 30 (zinc transporter), member 1, solute carrier family 30 (zinc transporter), member 4 |
| 1023 | 11524 | AI170340 | j, y, z | | PDZ and LIM domain 1 (elfin), PDZ and LIM domain 3, PDZ-LIM protein mystique, RIKEN cDNA 1110003B01 gene, *Rattus norvegicus* LIM-domain protein LMP-1 mRNA, complete cds, Z-band alternatively spliced PDZ-motif, actinin alpha 2 associated LIM protein, alpha-actinin-2-associated LIM protein, reversion induced LIM gene |
| 1024 | 2729 | AI170363 | e, i | | |
| 1025 | 18811 | AI170525 | i | | |
| 1026 | 22524 | AI170542 | h | | |
| 1027 | 24048 | AI170570 | a, g | | CGI-10 protein |
| 1028 | 5968 | AI170692 | y, aa | | GABA(A) receptor-associated protein-like 2, RIKEN cDNA 0610012F20 gene, gamma-aminobutyric acid |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1029 | 9757 | AI170693 | b | | (GABA(A)) receptor-associated protein-like 1, ganglioside expression factor 2 |
| 1030 | 18905 | AI170770 | e, s | | |
| 1031 | 16170 | AI170894 | i | | RIKEN cDNA 1300012C15 gene, RIKEN cDNA 2310076L09 gene, adipose differentiation related protein, adipose differentiation-related protein |
| 1032 | 7089 | AI171185 | c | hyaluronan mediated motility receptor (RHAMM), hyaluronan-mediated motility receptor (RHAMM) | Mus musculus 12 days embryo male wolffian duct includes surrounding region cDNA, RIKEN full-length enriched library, clone: 6720466F14, full insert sequence, RIKEN cDNA 0610027D24 gene, TRAF4 associated factor 1, hyaluronan mediated motility receptor (RHAMM), hyaluronan-mediated motility receptor (RHAMM) |
| 1033 | 17591 | AI171354 | b | | |
| 1034 | 13285 | AI171361 | h | | heterogeneous nuclear ribonucleoprotein A0 |
| 1035 | 4428 | AI171362 | a | | EST, Moderately similar to NUAM_HUMAN NADH-UBIQUINONE OXIDOREDUCTASE 75 KD SUBUNIT PRECURSOR [H. sapiens], NADH dehydrogenase (ubiquinone) Fe—S protein 1 (75 kD) (NADH-coenzyme Q reductase) |
| 1036 | 18126 | AI171369 | w | | |
| 1037 | 23253 | AI171448 | o | | RIKEN cDNA 2010107E04 gene, chromosome 14 open reading frame 2, expressed sequence AU043134, expressed sequence AV124504 |
| 1038 | 4584 | AI171492 | m, General | | |
| 1039 | 11158 | AI171542 | r, s | | EST, Moderately similar to NI2M_HUMAN NADH-UBIQUINONE OXIDOREDUCTASE B22 SUBUNIT [H. sapiens], NADH dehydrogenase (ubiquinone) 1 beta subcomplex, 9 (22 kD, B22) |
| 1040 | 15345 | AI171587 | l | | |
| 1041 | 21183 | AI171676 | k | | |
| 1042 | 8215 | AI171692 | i | ferritin light chain 1, ferritin, light polypeptide | ESTs, Highly similar to FRHUL ferritin light chain [H. sapiens], ESTs, Moderately similar to FRHUL ferritin light chain [H. sapiens], PRO0470 protein, RIKEN cDNA 2010009K05 gene, RIKEN cDNA 4933416E14 gene, cysteine conjugate-beta lyase; cytoplasmic (glutamine transaminase K, kyneurenine aminotransferase), ferritin light chain 2, ferritin, light polypeptide, hypothetical protein 669 |
| 1043 | 11437 | AI171794 | i | | |
| 1044 | 2625 | AI171800 | cc | | |
| 1045 | 23579 | AI171802 | v | | |
| 1046 | 11708 | AI171807 | l, t | | |
| 1047 | 17204 | AI171844 | s, y, z | | ATP synthase, H+ transporting, mitochondrial F1 complex, epsilon subunit, RIKEN cDNA 2410043G19 gene, expressed sequence AV000645 |
| 1048 | 4420 | AI171916 | m | | |
| 1049 | 3266 | AI171948 | l, m | | DKFZP564F0522 protein, ESTs, Weakly similar to T08675 hypothetical protein DKFZp564F0522.1 [H. sapiens] |
| 1050 | 19012 | AI172056 | t | | |
| 1051 | 11205 | AI172057 | a, q, bb | | |
| 1052 | 6057 | AI172102 | b | | |
| 1053 | 19128 | AI172103 | m | | |
| 1054 | 15673 | AI172107 | z | | KIAA1883 protein, sirtuin (silent mating type information regulation 2, S. cerevisiae, homolog) 2, sirtuin 2 (silent mating type information regulation 2, homolog) 2 (S. cerevisiae) |
| 1055 | 6630 | AI172184 | n | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1056 | 11968 | AI172208 | bb | | Alpha-fetoprotein, ESTs, Weakly similar to ALPHA-FETOPROTEIN PRECURSOR [*M. musculus*], ESTs, Weakly similar to FPHU alpha-fetoprotein precursor [*H. sapiens*], alpha fetoprotein, alpha-fetoprotein |
| 1057 | 6974 | AI172263 | l, m | | |
| 1058 | 23313 | AI172271 | d | | |
| 1059 | 2140 | AI172272 | General | | ESTs, Highly similar to JC4577 transcription elongation factor T1 [*H. sapiens*], expressed sequence AI326274, transcription elongation factor A (SII), 2 |
| 1060 | 15382 | AI172302 | l, p, General | | |
| 1061 | 18689 | AI172329 | l | | |
| 1062 | 17887 | AI172414 | o | | |
| 1063 | 3042 | AI172447 | General | | ESTs, Highly similar to BCL3 [*M. musculus*], ESTs, Weakly similar to I-kappa B alpha chain [*M. musculus*], hypothetical protein MGC15396, nuclear factor of kappa light chain gene enhancer in B-cells inhibitor, alpha, nuclear factor of kappa light chain gene enhancer in B-cells inhibitor, beta, nuclear factor of kappa light polypeptide gene enhancer in B-cells inhibitor, alpha, nuclear factor of kappa light polypeptide gene enhancer in B-cells inhibitor, epsilon, testis-specific ankyrin motif containing protein |
| 1064 | 17291 | AI172491 | bb | | ESTs, Highly similar to ISOCITRATE DEHYDROGENASE [*R. norvegicus*], Isocitrate dehydrogenase 1, soluble, isocitrate dehydrogenase 1 (NADP+), soluble, isocitrate dehydrogenase 2 (NADP+), mitochondrial |
| 1065 | 26222 | AI172506 | p | | |
| 1066 | 13095 | AI172595 | r | | |
| 1067 | 8795 | AI172618 | General | | |
| 1068 | 6454 | AI175342 | j, l, m, y, | | BACULOVIRAL IAP REPEAT-CONTAINING PROTEIN 6 (UBIQUITIN-CONJUGATING BIR-DOMAIN ENZYME APOLLON) [*H. sapiens*], ESTs, Moderately similar to T31067 BIR repeat containing ubiquitin-conjugating enzyme BRUCE - mouse [*M. musculus*], baculoviral IAP repeat-containing 6, hypothetical protein FLJ13855, likely ortholog of mouse ubiquitin-conjugating enzyme E2-230K |
| 1070 | 4445 | AI175466 | x | | EST, Highly similar to RASN RAT TRANSFORMING PROTEIN P21/N-RAS [*R. norvegicus*], EST, Weakly similar to TVHURR transforming protein R-ras [*H. sapiens*], Harvey rat sarcoma oncogene, subgroup R, RIKEN cDNA 2610016H24 gene, RIKEN cDNA 4930526B11 gene, Ris, expressed sequence AI573426, neuroblastoma RAS viral (v-ras) oncogene homolog, neuroblastoma ras oncogene, related RAS viral (r-ras) oncogene homolog, similar to mouse Ras, dexamethasone-induced 1 |
| 1071 | 3418 | AI175475 | m | | ESTs, Weakly similar to NHPX RAT NHP2/RS6 FAMILY PROTEIN YEL026W HOMOLOG [*R. norvegicus*], RIKEN cDNA 2410130M07 gene, non-histone chromosome protein 2 (*S. cerevisiae*)-like 1, nucleolar protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | family A, member 2 (H/ACA small nucleolar RNPs), sperm specific antigen 1 |
| 1072 | 18507 | AI175551 | bb | | ESTs, Highly similar to S25432 translation elongation factor eEF-1 beta chain [*H. sapiens*], eukaryotic translation elongation factor 1 beta 2 |
| 1073 | 10217 | AI175628 | w | | |
| 1074 | 7262 | AI175833 | j, m, x | | |
| 1075 | 19004 | AI175875 | r | | |
| 1076 | 22352 | AI175959 | l, General | | |
| 1077 | 7022 | AI176041 | h, n | | |
| 1078 | 21467 | AI176061 | t | | EST, Moderately similar to TIG2_HUMAN RETINOIC ACID RECEPTOR RESPONDER PROTEIN 2 PRECURSOR [*H. sapiens*], retinoic acid receptor responder (tazarotene induced) 2 |
| 1079 | 18581 | AI176160 | General | | |
| 1080 | 14159 | AI176169 | g | | |
| 1081 | 21742 | AI176172 | w | | |
| 1082 | 10182 | AI176185 | v | FBJ osteosarcoma oncogene, v-fos FBJ murine osteosarcoma viral oncogene homolog | |
| 1083 | 22765 | AI176265 | General | | |
| 1084 | 6905 | AI176275 | a | | EST, Moderately similar to T02747 phospholipid-hydroperoxide glutathione peroxidase [*H. sapiens*], EST, Weakly similar to T02747 phospholipid-hydroperoxide glutathione peroxidase [*H. sapiens*], ESTs, Weakly similar to GSHH RAT PHOSPHOLIPID HYDROPEROXIDE GLUTATHIONE PEROXIDASE [*R. norvegicus*], *Homo sapiens* PRO2893 mRNA, complete cds, RIKEN cDNA 2310016C16 gene, RIKEN cDNA 3110050F08 gene, glutathione peroxidase 4, glutathione peroxidase 4 (phospholipid hydroperoxidase) |
| 1085 | 12999 | AI176276 | cc | | *Homo sapiens* cDNA FLJ12570 fis, clone NT2RM4000895, UDP-N-acteylglucosamine pyrophosphorylase 1 |
| 1086 | 16438 | AI176294 | e | | ESTs, Weakly similar to B Chain B, Crystal Structure Of The D1d2 Sub-Complex From The Human Snmp Core Domain [*H. sapiens*], small nuclear ribonucleoprotein D2 polypeptide (16.5 kD) |
| 1087 | 21130 | AI176298 | y | | |
| 1088 | 3014 | AI176362 | e | | |
| 1089 | 15015 | AI176363 | r | | |
| 1090 | 19006 | AI176393 | x | | |
| 1091 | 20001 | AI176396 | o | | ESTs, Highly similar to C560_HUMAN SUCCINATE DEHYDROGENASE CYTOCHROME B560 SUBUNIT, MITOCHONDRIAL PRECURSOR [*H. sapiens*], succinate dehydrogenase complex, subunit C, integral membrane protein, 15 kD |
| 1092 | 12174 | AI176435 | j, m | | |
| 1093 | 15191 | AI176456 | b, o, t, v, cc | | ESTs, Moderately similar to AF078844 1 hqp0376 protein [*H. sapiens*], expressed sequence AA409533 |
| 1094 | 24236 | AI176473 | d, General | | |
| 1095 | 16518 | AI176546 | v | | ESTs, Highly similar to HS9B RAT HEAT SHOCK PROTEIN HSP 90-BETA [*R. norvegicus*], *Mus musculus*, clone IMAGE: 3584589, mRNA, partial cds, expressed sequence C81438, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | heat shock 90 kD protein 1, beta, heat shock protein, 84 kDa 1, heat shock protein, 86 kDa 1 |
| 1096 | 2161 | AI176592 | General | | |
| 1097 | 12436 | AI176610 | General | | ESTs, Weakly similar to SYC_HUMAN CYSTEINYL-TRNA SYNTHETASE [*H. sapiens*], cysteinyl-tRNA synthetase, hypothetical protein FLJ12118 |
| 1098 | 2536 | AI176616 | l, v, General | | |
| 1099 | 18525 | AI176792 | u | | |
| 1100 | 23449 | AI176828 | g | | |
| 1101 | 23299 | AI176839 | General | | |
| 1102 | 3580 | AI176848 | e | | |
| 1103 | 22103 | AI176849 | d, General | | |
| 1104 | 16036 | AI176855 | f | | |
| 1105 | 15588 | AI176916 | General | | phosphomannomutase 1 |
| 1106 | 16917 | AI176951 | t | | |
| 1107 | 16124 | AI176963 | cc | | with Glu/Asp-rich carboxy-terminal domain, 2, Cbp/p300-interacting transactivator, with Glu/Asp-rich carboxy-terminal domain, 4, ESTs, Weakly similar to MRG1_HUMAN MSG-RELATED PROTEIN 1 [*H. sapiens*], expressed sequence AW742964 |
| 1108 | 15146 | AI176969 | b, General | | |
| 1109 | 5786 | AI177058 | f | | |
| 1110 | 2852 | AI177059 | c | | |
| 1112 | 3156 | AI177092 | g | | |
| 1113 | 14384 | AI177096 | a | | EST, Moderately similar to APT RAT ADENINE PHOSPHORIBOSYLTRANSFERASE [*R. norvegicus*], Mouse adenine phosphoribosyltransferase (APRT), complete cds, adenine phosphoribosyl transferase, adenine phosphoribosyltransferase, expressed sequence C85684 |
| 1114 | 13310 | AI177119 | General | | ESTs, Weakly similar to COMPLEMENT C1Q SUBCOMPONENT, C CHAIN PRECURSOR [*M. musculus*], Homo sapiens, Similar to complement component 1, q subcomponent, c polypeptide, clone MGC: 17279 IMAGE: 4212772, mRNA, complete cds, complement component 1, q subcomponent, beta polypeptide, complement component 1, q subcomponent, c polypeptide, expressed sequence AI385742 |
| 1115 | 24049 | AI177341 | g, p, s, u | | CGI-10 protein |
| 1116 | 15964 | AI177360 | o, General | | |
| 1117 | 14989 | AI177366 | u | | ESTs, Highly similar to B27079 fibronectin receptor beta chain precursor [*H. sapiens*], integrin beta 1 (fibronectin receptor beta), integrin beta 2, integrin, beta 1 (fibronectin receptor, beta polypeptide, antigen CD29 includes MDF2, MSK12), integrin, beta 2 (antigen CD18 (p95), lymphocyte function-associated antigen 1; macrophage antigen 1 (mac-1) beta subunit) |
| 1118 | 7975 | AI177374 | aa | | |
| 1119 | 3006 | AI177395 | k | | dickkopf (*Xenopus laevis*) homolog 3, dickkopf (*Xenopus laevis*) homolog 4, soggy-1 gene |
| 1120 | 17570 | AI177683 | r | | ESTs, Highly similar to ROA3_HUMAN HETEROGENEOUS NUCLEAR RIBONUCLEOPROTEIN A3 [*H. sapiens*], ESTs, Highly similar to S12520 core protein A1 [*H. sapiens*], |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | ESTs, Weakly similar to ROA2 MOUSE HETEROGENEOUS NUCLEAR RIBONUCLEOPROTEINS A2/B1 [*M. musculus*], Human DNA sequence from clone 522P13 on chromosome 6p21.31-22.3. Contains a 60S Ribosomal Protein L21 pseudogene and an HNRNP A3 (Heterogenous Nuclear Riboprotein A3, FBRNP) pseudogene. Contains ESTs, STSs and GSSs, RIKEN cDNA 3010025E17 gene, Ras-GTPase-activating protein SH3-domain binding protein, heterogeneous nuclear ribonucleoprotein A1, heterogeneous nuclear ribonucleoprotein A2/B1, hypothetical protein 23851 |
| 1121 | 9521 | AI177706 | b | | |
| 1122 | 14425 | AI177755 | g, General | | ESTs, Moderately similar to PBEF_HUMAN PRE-B CELL ENHANCING FACTOR PRECURSO [*H. sapiens*], pre-B-cell colony-enhancing factor |
| 1123 | 10611 | AI177790 | j, m | | |
| 1124 | 5356 | AI177813 | cc | | modulator recognition factor I |
| 1125 | 11791 | AI177843 | General | | sarcoma amplified sequence |
| 1126 | 14484 | AI177867 | General | | EH-domain containing 3, EH-domain containing 4, ESTs, Highly similar to EP15 MOUSE EPIDERMAL GROWTH FACTOR RECEPTOR SUBSTRATE SUBSTRATE 15 [*M. musculus*], *Homo sapiens* cDNA FLJ13682 fis, clone PLACE2000015, weakly similar to EPIDERMAL GROWTH FACTOR RECEPTOR SUBSTRATE SUBSTRATE 15, *Mus musculus* adult male cecum cDNA, RIKEN full-length enriched library, clone: 9130014G17, full insert sequence, epidermal growth factor receptor pathway substrate 15, epidermal growth factor receptor substrate EPS15R |
| 1127 | 5780 | AI177869 | General | | EST, Weakly similar to TESTIN 2 [*M. musculus*], LIM and cysteine-rich domains 1, four and a half LIM domains 2, testis derived transcript, testis derived transcript (3 LIM domains), vascular Rab-GAP/TBC-containing |
| 1128 | 19184 | AI178025 | General | | ESTs, Weakly similar to TGIF MOUSE 5'-TG-3' INTERACTING FACTOR [*M. musculus*], *Homo sapiens* TGF beta induced transcription factor 2-like mRNA, partial sequence, RIKEN cDNA 5430405H02 gene, RIKEN cDNA 5730599O09 gene, TG interacting factor, TGFB-induced factor (TALE family homeobox), TGFB-induced factor 2 (TALE family homeobox) |
| 1129 | 6059 | AI178245 | c, General | | ESTs, Highly similar to T13963 formin related protein, lymphocyte specific - mouse [*M. musculus*], ESTs, Moderately similar to T13963 formin related protein, lymphocyte specific - mouse [*M. musculus*], *Homo sapiens* mRNA; cDNA DKFZp762B245 (from clone DKFZp762B245); partial cds, KIAA1902 protein, formin-like |
| 1130 | 23248 | AI178267 | y | | chromosome 1 open reading frame 9 |
| 1131 | 4073 | AI178272 | o | | |
| 1132 | 7838 | AI178291 | e | | |
| 1133 | 18996 | AI178326 | y | | |
| 1134 | 22488 | AI178392 | b | | EST, Highly similar to I49523 Mouse primary response gene B94 mRNA, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | 3'end - mouse [*M. musculus*], *Homo sapiens*, clone MGC: 16332 IMAGE: 3842543, mRNA, complete cds, RIKEN cDNA 1200009I06 gene, RIKEN cDNA 1600013K19 gene, similar to *S. cerevisiae* Sec6p and *R. norvegicus* rsec6, tumor necrosis factor, alpha-induced protein 2 |
| 1135 | 18800 | AI178504 | n, p, aa | | |
| 1136 | 22197 | AI178527 | g, General | | |
| 1137 | 3401 | AI178684 | bb | | ESTs, Weakly similar to MCM3_HUMAN DNA REPLICATION LICENSING FACTOR MCM3 [*H. sapiens*], minichromosome maintenance deficient (*S. cerevisiae*) 3 |
| 1138 | 17713 | AI178700 | m | | |
| 1139 | 14874 | AI178735 | e | | |
| 1140 | 23567 | AI178746 | v, General | | |
| 1141 | 18907 | AI178971 | c | | EST, Moderately similar to HART1 hemoglobin alpha-1 chain - rat [*R. norvegicus*], EST, Weakly similar to A45964 hemoglobin alpha chain - mouse [*M. musculus*], ESTs, Moderately similar to HART1 hemoglobin alpha-1 chain - rat [*R. norvegicus*], Hemoglobin, alpha 1, hemoglobin alpha, adult chain 1, hemoglobin, alpha 1, hemoglobin, alpha 2 |
| 1142 | 20991 | AI178979 | i | | |
| 1143 | 5887 | AI179099 | q, t | | biotinidase, vanin 1, vanin 2, vanin 3 |
| 1144 | 8477 | AI179167 | b, e, General | | |
| 1145 | 3348 | AI179288 | u, v | | |
| 1146 | 13608 | AI179314 | e | | |
| 1147 | 8849 | AI179315 | g, p | | |
| 1148 | 13611 | AI179378 | v, General | | EST, Weakly similar to MAST CELL PROTEASE 7 PRECURSOR [*M. musculus*], ESTs, Weakly similar to MCT7 RAT MAST CELL PROTEASE 7 PRECURSOR [*R. norvegicus*], RIKEN cDNA 2410039E18 gene, RIKEN cDNA 4933401F05 gene, marapsin, mast cell protease 7, protease, serine, 21 (testisin), protease, serine, 22, protease, serine, 8 (prostasin), tryptase delta 1, tryptase, alpha |
| 1149 | 15438 | AI179399 | m, x | collagen, type V, alpha 2, procollagen, type V, alpha 2 | EST, Highly similar to CA13_HUMAN COLLAGEN ALPHA 1(III) CHAIN PRECURSOR [*H. sapiens*], EST, Weakly similar to CA25_HUMAN COLLAGEN ALPHA 2(V) CHAIN PRECURSO [*H. sapiens*], EST, Weakly similar to I49607 procollagen type V alpha 2 - mouse [*M. musculus*], RIKEN cDNA 2810002D19 gene, collagen, type III, alpha 1 (Ehlers-Danlos syndrome type IV, autosomal dominant), collagen, type V, alpha 2, hypothetical protein DKFZp434F0318, hypothetical protein MGC12921, procollagen, type III, alpha 1, procollagen, type V, alpha 2, procollagen, type XIII, alpha 1 |
| 1150 | 13614 | AI179407 | e, t, General | | |
| 1151 | 15042 | AI179422 | b, General | | |
| 1152 | 2768 | AI179481 | i, General | | |
| 1153 | 24041 | AI179580 | b, i | | |
| 1154 | 19822 | AI179599 | o, General | | |
| 1155 | 23270 | AI179601 | q, General | | |
| 1156 | 5901 | AI179605 | e | | |
| 1157 | 16081 | AI179610 | g, i, p | heme oxygenase (decycling) 1 | heme oxygenase (decycling) 1 |
| 1158 | 14564 | AI179717 | k | | |
| 1159 | 7918 | AI179750 | General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1160 | 6647 | AI179795 | g | | |
| 1161 | 9097 | AI179875 | o, General | hypothetical protein similar to mouse aldehyde reductase 6 (renal), renal-specific oxido-reducatse | |
| 1162 | 23989 | AI179953 | a | | gap junction membrane channel protein beta 2, gap junction membrane channel protein beta 6, gap junction protein, beta 2, 26 kD (connexin 26), gap junction protein, beta 6 (connexin 30) |
| 1163 | 12899 | AI179967 | b | | |
| 1164 | 1687 | AI179971 | c | hemoglobin alpha, adult chain 2, hemoglobin, alpha 1 | EST, Moderately similar to HART1 hemoglobin alpha-1 chain - rat [*R. norvegicus*], ESTs, Moderately similar to HART1 hemoglobin alpha-1 chain - rat [*R. norvegicus*], RIKEN cDNA 2510042H12 gene, hemoglobin alpha, adult chain 1, hemoglobin, alpha 1, hemoglobin, alpha 2 |
| 1165 | 22569 | AI179979 | General | | |
| 1166 | 23514 | AI179986 | o, General | | phosphoserine phosphatase, phosphoserine phosphatase-like |
| 1167 | 15892 | AI179988 | c, General | | |
| 1668 | 12402 | AI180004 | g | | |
| 1669 | 5443 | AI180165 | General | | DnaJ (Hsp40) homolog, subfamily B, member 3, DnaJ (Hsp40) homolog, subfamily B, member 6, ESTs, Moderately similar to HSJ2_HUMAN DNAJ PROTEIN HOMOLOG 2 [*H. sapiens*], ESTs, Weakly similar to HSJ2_HUMAN DNAJ PROTEIN HOMOLOG 2 [*H. sapiens*], *Homo sapiens*, clone IMAGE: 3930327, mRNA, partial cds, RIKEN cDNA 2810451A06 gene, expressed sequence AU020082 |
| 1170 | 5481 | AI180170 | General | | eukaryotic translation termination factor 1 |
| 1171 | 24028 | AI180239 | l | | |
| 1172 | 17089 | AI180281 | g | | |
| 1173 | 3701 | AI180306 | aa | | KIAA0273 gene product, KIAA1796 protein |
| 1174 | 3352 | AI180334 | m | | |
| 1175 | 24368 | AI180392 | l, m | | ESTs, Highly similar to NBP_HUMAN NUCLEOTIDE-BINDING PROTEIN [*H. sapiens*], hypothetical protein FLJ12660, nucleotide binding protein 1 (*E. coli* MinD like), nucleotide binding protein 2 (*E. coli* MinD like) |
| 1176 | 14337 | AI180414 | c | | EST, Highly similar to T14106 probable GTPase-activating protein SPA-1 - rat [*R. norvegicus*], ESTs, Highly similar to T14106 probable GTPase-activating protein SPA-1 - rat [*R. norvegicus*], KIAA0440 protein, RIKEN cDNA 2610511M17 gene, expressed sequence AW213287, signal-induced proliferation associated gene 1 |
| 1177 | 19080 | AI227647 | j, y, z | | hypothetical protein, clone 1-53, small inducible cytokine subfamily D (Cys-X3 Cys), member 1 (fractalkine, neurotactin), small inducible cytokine subfamily D, 1 |
| 1178 | 22838 | AI227667 | aa | | |
| 1179 | 6765 | AI227761 | i, General | | KIAA0665 gene product, KIAA1821 protein |
| 1180 | 24054 | AI227867 | General | | X-linked protein, brain expressed, X-linked 1, hypothetical protein FLJ10097, nerve growth factor receptor (TNFRSF16) associated protein 1 |
| 1181 | 7324 | AI227885 | i | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1182 | 23898 | AI227987 | d | | |
| 1183 | 1651 | AI228068 | n, w | peptidylglycine alpha-amidating monooxygenase | peptidylglycine alpha-amidating monooxygenase |
| 1184 | 14237 | AI228128 | e | | |
| 1185 | 14242 | AI228197 | General | | ESTs, Moderately similar to C21I_HUMAN PUTATIVE PROTEIN C21ORF18 [*H. sapiens*], chromosome 21 open reading frame 18 |
| 1186 | 16913 | AI228236 | o | | |
| 1187 | 22915 | AI228299 | r | | |
| 1188 | 8917 | AI228301 | General | | |
| 1189 | 15879 | AI228313 | r, General | | |
| 1190 | 13727 | AI228326 | o, General | | |
| 1191 | 6102 | AI228335 | General | | |
| 1192 | 13730 | AI228356 | a | | ESTs, Highly similar to S70642 ubiquitin ligase Nedd4 - rat [*R. norvegicus*], ESTs, Moderately similar to S70642 ubiquitin ligase Nedd4 - rat [*R. norvegicus*], ESTs, Weakly similar to NED4 MOUSE NEDD-4 PROTEIN [*M. musculus*], RIKEN cDNA 2600016C11 gene, neural precursor cell expressed, developmentally down-regulated 4, neural precursor cell expressed, developmentally down-regulated gene 4a |
| 1193 | 13745 | AI228494 | b, cc | | |
| 1194 | 4217 | AI228587 | s | | hypothetical protein MGC4614, membrane component, chromosome 17, surface marker 2 (ovarian carcinoma antigen CA125), next to the Brca1, oxidative stress induced like, sequestosome 1 |
| 1195 | 16053 | AI228596 | cc | | |
| 1196 | 3557 | AI228672 | e | | |
| 1197 | 11605 | AI228682 | e | | |
| 1198 | 13203 | AI228728 | r | | |
| 1199 | 13771 | AI228848 | g | | DEAD/H (Asp-Glu-Ala-Asp/His) box binding protein 1, Protein inhibitor of activated STAT X, protein inhibitor of activated STAT protein PIASy, protein inhibitor of activated STAT3 |
| 1200 | 5918 | AI229036 | r | | |
| 1201 | 8235 | AI229154 | k | | |
| 1202 | 16203 | AI229196 | r | vesicle-associated membrane protein 1, vesicle-associated membrane protein 1 (synaptobrevin 1), vesicle-associated membrane protein 2, vesicle-associated membrane protein 2 (synaptobrevin 2) | *Rattus norvegicus* mRNA for vesicle associated membrane protein 2B, vesicle-associated membrane protein 1, vesicle-associated membrane protein 1 (synaptobrevin 1), vesicle-associated membrane protein 2, vesicle-associated membrane protein 2 (synaptobrevin 2), vesicle-associated membrane protein 5, vesicle-associated membrane protein 5 (myobrevin), vesicle-associated membrane protein 8, vesicle-associated membrane protein 8 (endobrevin) |
| 1203 | 13826 | AI229304 | a | | |
| 1204 | 13144 | AI229320 | g | | |
| 1205 | 4640 | AI229404 | x, aa | | |
| 1206 | 23563 | AI229421 | l | | MAP kinase-activated protein kinase 2, mitogen-activated protein kinase-activated protein kinase 3 |
| 1207 | 15426 | AI229497 | s | | NADH dehydrogenase (ubiquinone) 1 beta subcomplex, 10 (22 kD, PDSW) |
| 1208 | 15193 | AI229508 | bb | | |
| 1209 | 19243 | AI229638 | x | | thymidine kinase 1, thymidine kinase 1, soluble |
| 1210 | 23078 | AI229647 | p | | |
| 1211 | 3099 | AI229680 | o | | NADH dehydrogenase (ubiquinone) Fe—S protein 3 (30 kD) (NADH-coenzyme Q reductase) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1212 | 19508 | AI229698 | bb | | |
| 1213 | 13977 | AI229707 | x | | EST, Moderately similar to I38369 beta tubulin [*H. sapiens*], EST, Weakly similar to I38369 beta-tubulin [*H. sapiens*], EST, Weakly similar to TUBULIN BETA-5 CHAIN [*M. musculus*], ESTs, Highly similar to A25113 tubulin beta chain 15 - rat [*R. norvegicus*], FK506-binding protein 1A (12 kD), RIKEN cDNA 2310061K05 gene, RIKEN cDNA 2410129E14 gene, tubulin, beta 2, tubulin, beta 5, tubulin, beta polypeptide |
| 1214 | 23983 | AI229708 | v | | quinolinate phosphoribosyltransferase (nicotinate-nucleotide pyrophosphorylase (carboxylating)) |
| 1215 | 2688 | AI229793 | e | | |
| 1216 | 13874 | AI229832 | g | | |
| 1217 | 12587 | AI229979 | General | | ESTs, Weakly similar to MOT2 MOUSE MONOCARBOXYLATE TRANSPORTER 2 [*M. musculus*], monocarboxylate transporter, monocarboxylate transporter 4, solute carrier 16 (monocarboxylic acid transporters), member 8, solute carrier family 16 (monocarboxylic acid transporters), member 3, solute carrier family 16 (monocarboxylic acid transporters), member 7, solute carrier family 16 (monocarboxylic acid transporters), member 8 |
| 1218 | 20591 | AI229993 | l, m | | |
| 1219 | 24042 | AI230002 | a, b, d, General | | |
| 1220 | 13880 | AI230042 | u | | EST, Highly similar to CCAA MOUSE VOLTAGE-DEPENDENT P/Q-TYPE CALCIUM CHANNEL ALPHA-1A SUBUNIT [*M. musculus*], ESTs, Weakly similar to CCAA MOUSE VOLTAGE-DEPENDENT P/Q-TYPE CALCIUM CHANNEL ALPHA-1A SUBUNIT [*M. musculus*], *Homo sapiens* mRNA; cDNA DKFZp434M0223 (from clone DKFZp434M0223); partial cds, *Mus musculus* calcium channel mRNA, complete cds, calcium channel, P/Q type, alpha 1A, calcium channel, voltage-dependent, alpha 1G subunit, two-pore channel 1, homolog |
| 1221 | 17672 | AI230074 | d | | NADH dehydrogenase (ubiquinone) 1 alpha subcomplex, 1, NADH dehydrogenase (ubiquinone) 1 alpha subcomplex, 1 (7.5 kD, MWFE) |
| 1222 | 3652 | AI230113 | General | | ESTs, Highly similar to E2BE RAT TRANSLATION INITIATION FACTOR EIF-2B EPSILON SUBUNIT [*R. norvegicus*], HSPC028 protein, RIKEN cDNA 1200015E15 gene, *Rattus norvegicus* initiation factor eIF-2Be mRNA, complete cds, basic leucine-zipper protein BZAP45, eukaryotic translation initiation factor 2B, subunit 5 (epsilon, 82 kD), expressed sequence C81315 |
| 1223 | 18650 | AI230121 | aa | | EST, Weakly similar to ENPL_HUMAN ENDOPLASMIN PRECURSOR [*H. sapiens*], ESTs, Highly similar to HS9B RAT HEAT SHOCK PROTEIN HSP 90-BETA [*R. norvegicus*], ESTs, Weakly similar to ENPL_HUMAN ENDOPLASMIN PRECURSOR [*H. sapiens*], *Homo sapiens* mRNA; cDNA DKFZp564F053 (from clone DKFZp564F053), RIKEN cDNA |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1224 | 13025 | AI230173 | c | | 1810014B01 gene, RIKEN cDNA 2410002K23 gene, expressed sequence C81438, heat shock 90 kD protein 1, beta, heat shock protein, 84 kDa 1, tumor rejection antigen (gp96) 1, tumor rejection antigen gp96 ESTs, Moderately similar to CHD3_HUMAN CHROMODOMAIN HELICASE-DNA-BINDING PROTEIN 3 [*H. sapiens*], chromodomain helicase DNA binding protein 3 |
| 1225 | 4280 | AI230247 | z | selenoprotein P, plasma, 1 | ESTs, Highly similar to A47327 selenoprotein P precursor [*H. sapiens*], selenoprotein P, plasma, 1 |
| 1226 | 18528 | AI230284 | General | | |
| 1227 | 7084 | AI230362 | p | | *Homo sapiens*, clone IMAGE: 3845253, mRNA, partial cds |
| 1228 | 20895 | AI230549 | b, n | | |
| 1229 | 12961 | AI230554 | General | | |
| 1230 | 15636 | AI230616 | r | | EST, Moderately similar to GALECTIN-1 [*R. norvegicus*], Human HL14 gene encoding beta-galactoside-binding lectin, 3' end, clone 2, RIKEN cDNA 2200008F12 gene, beta-galactoside-binding lectin, lectin, galactose binding, soluble 1, lectin, galactoside-binding, soluble, 1 (galectin 1), lectin, galactoside-binding, soluble, 2 (galectin 2) |
| 1231 | 4121 | AI230647 | j, m | | |
| 1232 | 14388 | AI230702 | General | | DNA segment, Chr 17, ERATO Doi 441, expressed, hematological and neurological expressed 1 |
| 1233 | 18529 | AI230716 | x, General | | |
| 1234 | 13618 | AI230724 | General | | EST, Weakly similar to JW0105 synaptojanin 2 alpha protein - mouse [*M. musculus*], ESTs, Weakly similar to 2204390A synaptojanin [*R. norvegicus*], ESTs, Weakly similar to JW0105 synaptojanin 2 alpha protein - mouse [*M. musculus*], expressed sequence AA675315, inositol polyphosphate-5-phosphatase, 75 kD, putative phosphatase, suppressor of actin 1, synaptojanin 2 |
| 1235 | 8304 | AI230746 | cc | | |
| 1236 | 4731 | AI230773 | e | | |
| 1237 | 14430 | AI230798 | c, k, x | | |
| 1238 | 16627 | AI230822 | bb | | Alg5, *S. cerevisiae*, homolog of, dolichyl-phosphate mannosyltransferase polypeptide 1, catalytic subunit |
| 1239 | 3125 | AI231028 | General | | DNA segment, Chr 10, ERATO Doi 398, expressed, ESTs, Weakly similar to PTNL RAT PROTEIN TYROSINE PHOSPHATASE, NON-RECEPTOR TYPE 21 [*R. norvegicus*], *Homo sapiens*, Similar to erythrocyte membrane protein band 4.1-like 3, clone MGC: 12343 IMAGE: 4044866, mRNA, complete cds, *Mus musculus* adult male pituitary gland cDNA, RIKEN full-length enriched library, clone: 5330430I10, full insert sequence, *Rattus norvegicus* protein tyrosine phosphatase 2E (PTP2E) mRNA, complete cds, erythrocyte membrane protein band 4.1 (elliptocytosis 1, RH-linked), erythrocyte membrane protein band 4.1-like 1, erythrocyte membrane protein band 4.1-like 3, erythrocyte |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | protein band 4.1-like 1, erythrocyte protein band 4.1-like 3, protein tyrosine phosphatase, non-receptor type 21 |
| 1240 | 633 | AI231127 | k | | |
| 1241 | 20846 | AI231140 | p | | EST, Highly similar to 60S RIBOSOMAL PROTEIN L23A [*R. norvegicus*], ESTs, Highly similar to RL2B__HUMAN 60S RIBOSOMAL PROTEIN L23A [*H. sapiens*], ribosomal protein L23a |
| 1242 | 6743 | AI231219 | d | | |
| 1244 | 26292 | AI231391 | k | | |
| 1245 | 12343 | AI231433 | w | | |
| 1246 | 7337 | AI231465 | aa | | |
| 1247 | 16321 | AI231506 | General | | |
| 1248 | 8004 | AI231532 | j, l | | ESTs, Moderately similar to Z183__HUMAN ZINC FINGER PROTEIN 183 [*H. sapiens*], zinc finger protein 183 (RING finger, C3HC4 type) |
| 1249 | 15171 | AI231792 | g | | BCL2-associated athanogene 3, Bcl2-associated athanogene 3, RIKEN cDNA 1600025G07 gene, RIKEN cDNA 2410112I15 gene |
| 1250 | 6193 | AI231797 | i | | |
| 1252 | 14227 | AI231999 | u | | RIKEN cDNA 2810411G23 gene, tumor protein D52-like 1 |
| 1253 | 24501 | AI232006 | w, y, bb | | EST, Moderately similar to EF1D__HUMAN ELONGATION FACTOR 1-DELTA [*H. sapiens*], ESTs, Weakly similar to EF1D__HUMAN ELONGATION FACTOR 1-DELTA [*H. sapiens*], eukaryotic translation elongation factor 1 delta (guanine nucleotide exchange protein), hypothetical protein FLJ20897 |
| 1254 | 3434 | AI232014 | g, q, z, cc, General | | |
| 1255 | 19094 | AI232021 | n, General | | ESTs, Highly similar to Human Translation Initiation Factor Eif1, Nmr, 29 Structures [*H. sapiens*], RIKEN cDNA 1500010M16 gene, RIKEN cDNA 3110001N14 gene, putative translation initiation factor, suppressor of initiator codon mutations, related sequence 1 (*S. cerevisiae*) |
| 1256 | 14020 | AI232076 | u | | |
| 1257 | 6726 | AI232157 | d | | |
| 1258 | 11549 | AI232174 | l, m | | |
| 1259 | 23125 | AI232266 | j, s | | |
| 1260 | 2085 | AI232270 | bb | | |
| 1261 | 2913 | AI232272 | o | | |
| 1262 | 14304 | AI232281 | g | | |
| 1263 | 15955 | AI232294 | u, bb, General | | |
| 1264 | 15122 | AI232303 | y | | DKFZP566H073 protein, *Homo sapiens* chromosome 19, cosmid R31343, RIKEN cDNA 1700065B19 gene, RIKEN cDNA 5730408C10 gene, likely ortholog of mouse g1-related zinc finger protein, ring finger protein 13, zinc finger protein 103 |
| 1265 | 4716 | AI232313 | y | purinergic receptor P2X, ligand-gated ion channel 4, purinergic receptor P2X, ligand-gated ion channel, 4 | purinergic receptor P2X, ligand-gated ion channel 4, purinergic receptor P2X, ligand-gated ion channel, 1, purinergic receptor P2X, ligand-gated ion channel, 4 |
| 1266 | 15246 | AI232332 | t, u | | |
| 1267 | 24321 | AI232340 | o | stromal cell derived factor 1, stromal cell-derived factor 1 | stromal cell derived factor 1, stromal cell-derived factor 1 |
| 1268 | 16172 | AI232341 | d | | |
| 1269 | 11411 | AI232346 | h | | |
| 1270 | 19287 | AI232379 | f | platelet derived growth factor receptor, alpha | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | polypeptide, platelet-derived growth factor receptor, alpha polypeptide | |
| 1271 | 5601 | AI232461 | n, General | | Flavin-containing monooxygenase 1, flavin containing monooxygenase 1, flavin containing monooxygenase 2, flavin containing monooxygenase 3, flavin containing monooxygenase 4, hypothetical protein PRO1257 |
| 1272 | 14051 | AI232489 | l, m | | |
| 1273 | 5572 | AI232490 | i, t | | ESTs, Moderately similar to A27340 complement C7 precursor [*H. sapiens*], complement component 7 |
| 1274 | 11157 | AI232494 | cc | | |
| 1275 | 8709 | AI232534 | o | | DnaJ (Hsp40) homolog, subfamily B, member 3, DnaJ (Hsp40) homolog, subfamily B, member 6, ESTs, Moderately similar to HSJ2__HUMAN DNAJ PROTEIN HOMOLOG 2 [*H. sapiens*], ESTs, Weakly similar to HSJ2__HUMAN DNAJ PROTEIN HOMOLOG 2 [*H. sapiens*], *Homo sapiens*, clone IMAGE: 3930327, mRNA, partial cds, RIKEN cDNA 2810451A06 gene, expressed sequence AU020082 |
| 1276 | 20350 | AI232552 | j, v, y | | |
| 1277 | 14069 | AI232631 | e | | |
| 1278 | 4440 | AI232643 | w | | |
| 1279 | 17695 | AI232784 | e | | 2,4-dienoyl CoA reductase 1, mitochondrial, 2,4-dienoyl CoA reductase 2, peroxisomal, ESTs, Weakly similar to S11021 2,4-dienoyl-CoA reductase [*R. norvegicus*], FabG (beta-ketoacyl-[acyl-carrier-protein] reductase, *E coli*) like, H2-K region expressed gene 6, *Homo sapiens* AS10 protein mRNA, partial cds, *Mus musculus*, clone MGC: 6971 IMAGE: 3154595, mRNA, complete cds, RIKEN cDNA 0610039E24 gene, RIKEN cDNA 1810026B04 gene, carbonyl reductase, oxidoreductase UCPA, peroxisomal trans 2-enoyl CoA reductase; putative short chain alcohol dehydrogenase |
| 1280 | 15796 | AI232874 | v | | |
| 1281 | 12467 | AI232924 | General | | |
| 1282 | 12873 | AI232984 | i | | ESTs, Highly similar to I49636 DNA-binding protein - mouse [*M. musculusl*], ESTs, Moderately similar to I49636 DNA-binding protein - mouse [*M. musculus*], ESTs, Weakly similar to OZF__HUMAN ZINC FINGER PROTEIN OZF [*H. sapiens*], RIKEN cDNA 2310011F05 gene, pancreas zinc finger protein, zinc finger protein 260, zinc finger protein 36 (KOX 18), zinc finger protein 63, zinc finger protein 97 |
| 1283 | 5355 | AI233031 | r | | |
| 1284 | 18794 | AI233121 | c | | |
| 1285 | 3823 | AI233147 | b, g, General | | DNA segment, Chr 17, human D6S81E 1, ESTs, Highly similar to S33681 translation initiation factor eIF-4A.I [*H. sapiens*], HLA-B associated transcript 1, Human clone 23933 mRNA sequence, eukaryotic translation initiation factor 4A, isoform 1, mitochondrial DEAD-box polypeptide 28, nuclear RNA helicase, DECD variant of DEAD box family |
| 1286 | 11967 | AI233155 | c, k, General | | |
| 1287 | 11561 | AI233182 | d | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1288 | 3471 | AI233183 | g | | putative receptor protein |
| 1289 | 21948 | AI233191 | i | | |
| 1290 | 13598 | AI233194 | g, p, y | | |
| 1291 | 15552 | AI233195 | y | | |
| 1292 | 17907 | AI233224 | bb | | EST, Moderately similar to EGFR_HUMAN EPIDERMAL GROWTH FACTOR RECEPTOR PRECURSOR [*H. sapiens*], Epidermal growth factor receptor, formerly avian erythroblastic leukemia viral (v-erbB) oncogene homolog (Erbb1), avian erythroblastosis oncogene B 3, epidermal growth factor receptor, epidermal growth factor receptor (avian erythroblastic leukemia viral (v-erb-b) oncogene homolog) |
| 1293 | 14111 | AI233269 | cc | | |
| 1294 | 12894 | AI233365 | d | | |
| 1295 | 7161 | AI233407 | General | | |
| 1296 | 15906 | AI233425 | q | | |
| 1297 | 14120 | AI233433 | d | | |
| 1298 | 14095 | AI233468 | a, d | | |
| 1299 | 3075 | AI233494 | u, aa | | oxidase (cytochrome c) assembly 1-like |
| 1300 | 6046 | AI233530 | General | | |
| 1301 | 18900 | AI233570 | General | | EST, Moderately similar to S56108 26S proteasome regulatory complex chain p31 [*H. sapiens*], proteasome (prosome, macropain) 26S subunit, non-ATPase, 8 |
| 1302 | 7888 | AI233583 | General | | *Homo sapiens*, clone MGC: 14993 IMAGE: 3613406, mRNA, complete cds, arginyl-tRNA synthetase |
| 1303 | 16709 | AI233602 | General | adenosine kinase | adenosine kinase, expressed sequence AI255373 |
| 1304 | 5163 | AI233712 | y | | protein phosphatase 1D magnesium-dependent, delta isoform |
| 1305 | 7243 | AI233717 | General | | coatomer protein complex, subunit alpha, embryonic ectoderm development |
| 1306 | 3816 | AI233729 | g | | *Homo sapiens* cDNA FLJ10203 fis, clone HEMBA1004930, moderately similar to 26S PROTEASOME SUBUNIT S5B, proteasome (prosome, macropain) 26S subunit, non-ATPase, 5 |
| 1307 | 13023 | AI233740 | d, h, General | | Aldehyde reductase 1 (low Km aldose reductase) (5.8 kb PstI fragment, probably the functional gene), EST, Highly similar to Aldose Reductase (E.C.1.1.1.21) [*H. sapiens*], ESTs, Moderately similar to ALDOSE REDUCTASE [*R. norvegicus*], ESTs, Moderately similar to ALDOSE REDUCTASE-RELATED PROTEIN 2 [*M. musculus*], *Homo sapiens*, Similar to RIKEN cDNA 1110018J12 gene, clone IMAGE: 3865164, mRNA, partial cds, RIKEN cDNA 2310005E10 gene, aldo-keto reductase family 1, member A4 (aldehyde reductase), aldo-keto reductase family 1, member B1 (aldose reductase), aldo-keto reductase family 1, member B10 (aldose reductase), aldo-keto reductase family 1, member B3 (aldose reductase), fibroblast growth factor regulated protein |
| 1308 | 14871 | AI233743 | g | | |
| 1309 | 7469 | AI233767 | cc | | Golgi-associated, gamma-adaptin ear containing, ARF-binding protein 2 |
| 1310 | 7804 | AI233771 | b | | |
| 1311 | 13563 | AI233773 | e | | |
| 1312 | 2154 | AI233818 | k, cc | A kinase (PRKA) anchor protein (gravin) 12 | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1313 | 16616 | AI234079 | h | | |
| 1314 | 13393 | AI234100 | a, d, General | | EST, Moderately similar to CYSR RAT CYSTEINE-RICH PROTEIN 1 [*R. norvegicus*], ESTs, Weakly similar to CYSR RAT CYSTEINE-RICH PROTEIN 1 [*R. norvegicus*], ESTs, Weakly similar to S12658 cysteine-rich protein [*H. sapiens*], cysteine and glycine-rich protein 1, cysteine rich protein, cysteine-rich protein 2, cysteine-rich protein 3, epithelial protein lost in neoplasm beta, thymus LIM protein |
| 1315 | 7071 | AI234162 | r | | |
| 1316 | 14677 | AI234620 | General | | |
| 1317 | 4443 | AI234629 | m | | |
| 1318 | 22453 | AI234678 | b | | |
| 1319 | 23964 | AI234748 | t, General | | |
| 1320 | 19581 | AI234753 | f | | |
| 1321 | 22152 | AI234822 | o, General | RAS, dexamethasone-induced 1 | Harvey rat sarcoma oncogene, subgroup R, RAP1B, member of RAS oncogene family, RAP2B, member of RAS oncogene family, RIKEN cDNA 2610016H24 gene, RIKEN cDNA 4021402C18 gene, RIKEN cDNA 4930526B11 gene, RIKEN cDNA 5830461H18 gene, expressed sequence AI573426, rap2A-like protein, ras-related protein |
| 1322 | 18942 | AI234865 | d | | |
| 1323 | 22662 | AI234939 | aa | | ATPase, H+ transporting, lysosomal (vacuolar proton pump), subunit 1, EST, Weakly similar to I54197 hypothetical protein [*H. sapiens*], ESTs, Weakly similar to VAS1_RAT VACUOLAR ATP SYNTHASE SUBUNIT S1 PRECURSOR (V-ATPASE S1 SUBUNIT) (V-ATPASE S1 ACCESSORY PROTEIN) (V-ATPASE AC45 SUBUNIT) (C7-1 PROTEIN) [*R. norvegicus*], *Homo sapiens* cDNA FLJ12563 fis, clone NT2RM4000820, weakly similar to VACUOLAR ATP SYNTHASE SUBUNIT AC45 PRECURSOR (EC 3.6.1.34) |
| 1324 | 3875 | AI235047 | o, General | | ESTs, Moderately similar to CB80_HUMAN 80 KDA NUCLEAR CAP BINDING PROTEIN [*H. sapiens*], *Homo sapiens* cDNA FLJ11599 fis, clone HEMBA1003879, nuclear cap binding protein subunit 1, 80 kD |
| 1325 | 19479 | AI235135 | o | | |
| 1326 | 14906 | AI235192 | g | | ATP-binding cassette, sub-family F (GCN20), member 1, ATP-binding cassette, sub-family F (GCN20), member 2, hypothetical protein FLJ11198 |
| 1327 | 14718 | AI235210 | e | | |
| 1328 | 15004 | AI235224 | b, General | | EST, Moderately similar to TIM1 RAT METALLOPROTEINASE INHIBITOR 1 PRECURSOR [*R. norvegicus*], EST, Weakly similar to TIM1 RAT METALLOPROTEINASE INHIBITOR 1 PRECURSOR [*R. norvegicus*], tissue inhibitor of metalloproteinase, tissue inhibitor of metalloproteinase 1 (erythroid potentiating activity, collagenase inhibitor) |
| 1329 | 6632 | AI235277 | v | | |
| 1330 | 14722 | AI235284 | x, z | | ESTs, Highly similar to A60592 T-cell surface glycoprotein E2 precursor [*H. sapiens*], *Homo sapiens* cDNA FLJ13471 fis, clone PLACE1003566, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | antigen identified by monoclonal antibodies 12E7, F21 and O13, hypothetical protein DKFZp761H2024 |
| 1331 | 1462 | AI235585 | u, General | | |
| 1332 | 21061 | AI235631 | l, m | | |
| 1333 | 14665 | AI235646 | m | MAD (mothers against decapentaplegic, *Drosophila*) homolog 4, MAD homolog 4 (*Drosophila*) | MAD (mothers against decapentaplegic, *Drosophila*) homolog 4 |
| 1334 | 19940 | AI235689 | General | | |
| 1335 | 5698 | AI235692 | u | | |
| 1336 | 23745 | AI235732 | k | | ESTs, Weakly similar to LDVR RAT VERY LOW-DENSITY LIPOPROTEIN RECEPTOR PRECURSOR [*R. norvegicus*], RIKEN cDNA 4933405I11 gene, Very low density lipoprotein receptor, nidogen 2, secreted modular calcium-binding protein 1, secreted modular calcium-binding protein 2, very low density lipoprotein receptor |
| 1337 | 11164 | AI235739 | General | | ESTs, Highly similar to A56716 aromatic ester hydrolase [*H. sapiens*], biphenyl hydrolase-like (serine hydrolase; breast epithelial mucin-associated antigen) |
| 1338 | 5212 | AI235745 | d | | |
| 1339 | 14768 | AI235912 | h | | |
| 1340 | 14776 | AI235950 | m | | |
| 1341 | 3091 | AI236027 | n, General | | |
| 1342 | 14861 | AI236045 | r | | |
| 1343 | 14862 | AI236048 | e | | |
| 1344 | 16943 | AI236097 | p | | integral membrane protein 2 B, integral membrane protein 2B, integral membrane protein 3 |
| 1345 | 8336 | AI236101 | l | | |
| 1346 | 23230 | AI236146 | v | | |
| 1347 | 22855 | AI236150 | e | | Down syndrome critical region gene 5 |
| 1348 | 14594 | AI236152 | i | | |
| 1349 | 18406 | AI236168 | r | | |
| 1350 | 15051 | AI236332 | General | | ESTs, Weakly similar to ATDA_HUMAN DIAMINE ACETYLTRANSFERASE [*H. sapiens*], RIKEN cDNA 2610016A03 gene, RIKEN cDNA 4930404K22 gene, spermidine/spermine N1-acetyltransferase, spermidine/spermine N1-acetyltransferase |
| 1351 | 19298 | AI236338 | bb | | ESTs, Highly similar to NHPX RAT NHP2/RS6 FAMILY PROTEIN YEL026W HOMOLOG [*R. norvegicus*], RIKEN cDNA 2410130M07 gene, non-histone chromosome protein 2 (*S. cerevisiae*)-like 1, nucleolar protein family A, member 2 (H/ACA small nucleolar RNPs), sperm specific antigen 1 |
| 1352 | 10667 | AI236366 | b | | ELAV (embryonic lethal, abnormal vision, *Drosophila*)-like 4 (Hu antigen D), EST, Highly similar to 2201474A inducible poly(A)-binding protein [*H. sapiens*], ESTs, Weakly similar to 2201474A inducible poly(A)-binding protein [*H. sapiens*], ESTs, Highly similar to HUD RAT PARANEOPLASTIC ENCEPHALOMYELITIS ANTIGEN HUD HOMOLOG [*R. norvegicus*], ESTs, Moderately similar to HUD RAT PARANEOPLASTIC ENCEPHALOMYELITIS ANTIGEN HUD HOMOLOG [*R. norvegicus*], ESTs, Moderately similar to |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | POLYADENYLATE-BINDING PROTEIN 1 [*M. musculus*], *Mus musculus* adult male testis cDNA, RIKEN full-length enriched library, clone: 4933407N23, full insert sequence, RIKEN cDNA 4932702K14 gene, poly A binding protein, cytoplasmic 1, poly(A)-binding protein, cytoplasmic 4 (inducible form), siah binding protein 1; FBP interacting repressor; pyrimidine tract binding splicing factor; Ro ribonucleoprotein-binding protein 1 |
| 1353 | 10774 | AI236397 | f | | |
| 1354 | 9407 | AI236402 | aa | | |
| 1355 | 26335 | AI236460 | General | | |
| 1356 | 17950 | AI236590 | t, General | | |
| 1357 | 18259 | AI236601 | h, v | | |
| 1358 | 11445 | AI236613 | j, y | | |
| 1359 | 17248 | AI236635 | o, aa | | S-phase kinase-associated protein 1A (p19A), transcription elongation factor B (SIII), polypeptide 1 (15 kDa),-like, transcription elongation factor B (SIII), polypeptide 1-like |
| 1360 | 16859 | AI236753 | t, General | | |
| 1361 | 5208 | AI236754 | g | | chromosome 8 open reading frame 1 |
| 1362 | 24388 | AI236772 | e, General | | |
| 1363 | 15850 | AI236795 | n, v, w | | EST, Highly similar to HS9B RAT HEAT SHOCK PROTEIN HSP 90-BETA [*R. norvegicus*], EST, Weakly similar to HHMSB4 heat shock protein B4 - mouse [*M. musculus*], ESTs, Highly similar to T46243 hypothetical protein DKFZp761K0511.1 [*H. sapiens*], expressed sequence AL022974, expressed sequence C81438, heat shock 90 kD protein 1, beta, heat shock protein, 84 kDa 1 |
| 1364 | 14800 | AI236856 | w | | |
| 1366 | 11404 | AI237002 | m | | Human DNA sequence from clone RP5-1057D4 on chromosome 20 Contains a spermidine synthase (SPDSY) pseudogene, a CpG island, ESTs, STSs and GSSs, spermidine synthase |
| 1367 | 18151 | AI237212 | o, General | | hepatitis B virus x-interacting protein (9.6 kD) |
| 1368 | 21653 | AI237535 | t, General | | |
| 1369 | 11208 | AI237586 | z | | EST, Weakly similar to JC1241 beta-interferon-induced protein - rat [*R. norvegicus*], ESTs, Moderately similar to JC1241 beta-interferon-induced protein - rat [*R. norvegicus*], RIKEN cDNA 1110036C17 gene, RIKEN cDNA 4933438K12 gene, interferon induced transmembrane protein 2 (1-8D) |
| 1370 | 21893 | AI237713 | i, k, aa | | KIAA0101 gene product |
| 1371 | 14842 | AI237724 | r | | |
| 1372 | 3467 | AI237835 | General | | ESTs, Highly similar to MXI1 RAT MAX INTERACTING PROTEIN 1 [*R. norvegicus*], MAX dimerization protein, MAX-interacting protein 1, Max dimerization protein, Max interacting protein 1 |
| 1373 | 25840 | AI638972 | u | | |
| 1374 | 17108 | AI639017 | n | | EST, Highly similar to S30385 G9a protein [*H. sapiens*], ESTs, Weakly similar to T17453 ERG-associated protein ESET - mouse [*M. musculus*], HLA-B associated transcript 8, SET domain, bifurcated 1, expressed sequence C77070, hypothetical protein FLJ12879, suppressor of |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1375 | 16676 | AI639082 | c, k, x | mini chromosome maintenance deficient 6 (*S. cerevisiae*), minichromosome maintenance deficient (mis5, *S. pombe*) 6 | variegation 3-9 (*Drosophila*) homolog 2; hypothetical protein FLJ23414 mini chromosome maintenance deficient 6 (*S. cerevisiae*), minichromosome maintenance deficient (mis5, *S. pombe*) 6 |
| 1376 | 12400 | AI639107 | k | | |
| 1377 | 19952 | AI639108 | q, v | | |
| 1379 | 25907 | AI639167 | o, w | | |
| 1381 | 18533 | AI639231 | n | | hypothetical protein, hypothetical protein FLJ20333 |
| 1382 | 18353 | AI639233 | t, aa | decorin | ESTs, Moderately similar to dJ63G5.3 [*H. sapiens*], RIKEN cDNA 1700034K16 gene, RIKEN cDNA 5530600M07 gene, decorin |
| 1384 | 15330 | AI639285 | General | | |
| 1385 | 20026 | AI639354 | g | | |
| 1386 | 25971 | AI639365 | r | | |
| 1388 | 19152 | AI639387 | u, General | | |
| 1390 | 18338 | AI639422 | y | | EST, Weakly similar to CAQC RAT CALSEQUESTRIN, CARDIAC MUSCLE ISOFORM PRECURSOR [*R. norvegicus*], calsequestrin 1, calsequestrin 1 (fast-twitch, skeletal muscle), calsequestrin 2, calsequestrin 2 (cardiac muscle) |
| 1392 | 20082 | AI639488 | i, m | | EST, Moderately similar to A Chain A, Mdm2 Bound To The Transactivation Domain Of P53 {SUB 17-125 [*H. sapiens*], mouse double minute 2, human homolog of; p53-binding protein, transformed mouse 3T3 cell double minute 2 |
| 1394 | 20056 | AI639504 | a, bb, General | | |
| 1395 | 4713 | AI639518 | q | | |
| 1396 | 14332 | AJ001044 | bb | | EST, Moderately similar to T42215 zonadhesin - mouse [*M. musculus*], EST, Weakly similar to MUC2_HUMAN MUCIN 2 PRECURSOR [*H. sapiens*], *Homo sapiens* SIB 297 intestinal mucin (MUC3) mRNA, partial cds, RIKEN cDNA 3110056H04 gene, RIKEN cDNA 4931407G18 gene, *Rattus norvegicus* podocalyxin mRNA, complete cds, hepatitis A virus cellular receptor 1, hypothetical protein DKFZp434N185, lymphocyte antigen 64, mucin 1, transmembrane, mucin 2, intestinal/tracheal, zonadhesin |
| 1397 | 7602 | AJ001929 | k | | |
| 1398 | 9867 | AJ005424 | u | | EST, Weakly similar to CGHU3B collagen alpha 3(IV) chain precursor, long splice form [*H. sapiens*], EST, Weakly similar to D40750 proline-rich protein PRB1/2S [*H. sapiens*], RIKEN cDNA 1190004M21 gene, RIKEN cDNA 2410150I18 gene, RIKEN cDNA 6330577E15 gene, expressed sequence AI551093, mitogen-activated protein kinase 7, murine leukemia viral (bmi-1) oncogene homolog, nemo-like kinase, phospholipid scramblase 1 |
| 1400 | 16351 | AJ011811 | General | claudin 7 | ESTs, Weakly similar to CLD7 MOUSE CLAUDIN-7 [*M. musculus*], ESTs, Weakly similar to CLD7 RAT CLAUDIN 7 [*R. norvegicus*], claudin 10, claudin 15, claudin 16, claudin 7 |
| 1401 | 20116 | AJ011969 | l, General | growth differentiation factor 15, prostate differentiation factor | |
| 1402 | 17635 | AJ223355 | v, w | | ESTs, Moderately similar to BMCP_HUMAN BRAIN |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | MITOCHONDRIAL CARRIER PROTEIN-1 [*H. sapiens*], ESTs, Weakly similar to M2OM_HUMAN MITOCHONDRIAL 2-OXOGLUTARATE/MALATE CARRIER PROTEIN [*H. sapiens*], ESTs, Weakly similar to brain mitochondrial carrier protein BMCP1 [*M. musculus*], RIKEN cDNA 1810012H11 gene, expressed sequence AW108044, solute carrier family 25 (mitochondrial carrier; adenine nucleotide translocator), member 10, solute carrier family 25 (mitochondrial carrier; dicarboxylate transporter), member 10, solute carrier family 25 (mitochondrial carrier; ornithine transporter), member 15, solute carrier family 25 (mitochondrial carrier; oxoglutarate carrier), member 11, uncoupling protein 2, mitochondrial |
| 1403 | 18686 | D00729 | q | dodecenoyl-Coenzyme A delta isomerase (3,2 trans-enoyl-Coenzyme A isomerase), dodecenoyl-Coenzyme A delta isomerase (3,2 trans-enoyl-Coenzyme A isomerase) | ESTs, Highly similar to D3D2 RAT 3,2-TRANS-ENOYL-COA ISOMERASE, MITOCHONDRIAL PRECURSOR [*R. norvegicus*], *Homo sapiens*, Similar to dodecenoyl-Coenzyme A delta isomerase (3,2 trans-enoyl-Coenzyme A isomerase), clone MGC: 3903 IMAGE: 3630566, mRNA, complete cds, dodecenoyl-Coenzyme A delta isomerase (3,2 trans-enoyl-Coenyme A isomerase), dodecenoyl-Coenzyme A delta isomerase (3,2 trans-enoyl-Coenzyme A isomerase) |
| 1404 | 5049 | D10655 | n, w | | ESTs, Weakly similar to ODP2 RAT DIHYDROLIPOAMIDE ACETYLTRANSFERASE COMPONENT OF PYRUVATE DEHYDROGENASE COMPLEX [*R. norvegicus*], *Mus musculus*, clone IMAGE: 3586777, mRNA, partial cds, Pyruvate dehydrogenase complex, lipoyl-containing component X; E3-binding protein, RIKEN cDNA 1600017E01 gene, RIKEN cDNA 4930529O08 gene, dihydrolipoamide S acetyltransferase (E2 component of pyruvate dehydrogenase complex), dihydrolipoamide branched chain transacylase (E2 component of branched chain keto acid dehydrogenase complex; maple syrup urine disease), dihydrolipoamide branched chain transacylase E2 |
| 1405 | 25257 | D13623 | j | | |
| 1405 | 15281 | D13623 | h | | |
| 1406 | 11434 | D14014 | cc | | |
| 1407 | 1613 | D14076 | x | | EST, Moderately similar to DYN2 MOUSE DYNAMIN 2 [*M. musculus*], ESTs, Moderately similar to DYN2 MOUSE DYNAMIN 2 [*M. musculus*], KIAA0820 protein, dynamin 2 |
| 1408 | 1728 | D16479 | q | | |
| 1409 | 3015 | D16554 | c, s, v, z | | |
| 1410 | 472 | D26111 | d, s, bb | | |
| 1412 | 16233 | D29960 | j, l | | |
| 1413 | 9029 | D30804 | n | proteasome (prosome, macropain) subunit, alpha type 7, proteasome (prosome, macropain) subunit, alpha type, 7 | EST, Highly similar to PROTEASOME SUBUNIT RC6-1 [*R. norvegicus*], EST, Highly similar to PSA7_HUMAN PROTEASOME SUBUNIT ALPHA TYPE 7 (PROTEASOME SUBUNIT RC6-1) (PROTEASOME SUBUNIT XAPC7) [*H. sapiens*], ESTs, Highly similar to PROTEASOME SUBUNIT RC6-1 [*R. norvegicus*], ESTs, Weakly |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1414 | 1485 | D38222 | y, z | | similar to PSA7_HUMAN PROTEASOME SUBUNIT ALPHA TYPE 7 (PROTEASOME SUBUNIT RC6-1) (PROTEASOME SUBUNIT XAPC7) [*H. sapiens*], Human DNA sequence from clone RP11-180I4 on chromosome 9 Contains a proteasome subunit pseudogene, ESTs, STSs, GSSs and a CpG island, RIKEN cDNA 2410072D24 gene, proteasome (prosome, macropain) subunit, alpha type 7, proteasome (prosome, macropain) subunit, alpha type, 7 PROTEIN-TYROSINE PHOSPHATASE-LIKE N PRECURSOR [*H. sapiens*], protein tyrosine phosphatase, receptor type, N, protein tyrosine phosphatase, receptor-type, N |
| 1415 | 9135 | D45247 | s | proteasome (prosome, macropain) subunit, beta type 5, proteasome (prosome, macropain) subunit, beta type, 5 | EST, Moderately similar to PRCE RAT PROTEASOME EPSILON CHAIN PRECURSOR [*R. norvegicus*], RIKEN cDNA 5830406J20 gene, proteasome (prosome, macropain) subunit, beta type 5, proteasome (prosome, macropain) subunit, beta type, 5 |
| 1416 | 16354 | D50564 | u | | |
| 1417 | 1884 | D50695 | l, m, bb | | proteasome (prosome, macropain) 26S subunit, ATPase, 4 |
| 1418 | 21147 | D63772 | General | solute carrier family 1 (neuronal/epithelial high affinity glutamate transporter, system Xag), member 1, solute carrier family 1, member 1 | |
| 1419 | 826 | D82928 | f | | CDP-diacylglycerol-inositol 3-phosphatidyltransferase (phosphatidylinositol synthase) |
| 1420 | 25306 | D84485 | u | | |
| 1421 | 18867 | D88250 | t | | EST, Moderately similar to MAS2_HUMAN MANNAN-BINDING LECTIN SERINE PROTEASE 2 PRECURSOR [*H. sapiens*], EST, Weakly similar to JC6554 probable serine proteinase [*R. norvegicus*], ESTs, Weakly similar to JC6554 probable serine proteinase [*R. norvegicus*], MASP-2 protein, complement component 1, r subcomponent, complement component 1, s subcomponent, mannan-binding lectin serine protease 1, mannan-binding lectin serine protease 2 |
| 1423 | 22543 | H31117 | r, v, General | | |
| 1424 | 12360 | H31456 | w | | |
| 1425 | 20514 | H31489 | h, j | | |
| 1426 | 11358 | H31610 | h | | DNA segment, Chr 16, Indiana University Medical 21, expressed, ESTs, Highly similar to JC5020 tetratricopeptide repeat protein [*H. sapiens*], ESTs, Moderately similar to JW0059 mtprd protein - mouse [*M. musculus*], PRO1880 protein, g1-related zinc finger protein, tetratricopeptide repeat domain, tetratricopeptide repeat domain 3 |
| 1427 | 4360 | H31813 | bb, General | | DKFZP586B1621 protein |
| 1428 | 9343 | H32169 | l | | EST, Moderately similar to COF1_HUMAN COFILIN, NON-MUSCLE ISOFOR [*H. sapiens*], cofilin 1 (non-muscle), cofilin 1, non-muscle, cofilin 2 (muscle), cofilin 2, muscle |
| 1429 | 4386 | H33093 | h, w | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1430 | 4415 | H33636 | h | | |
| 1431 | 15374 | H34186 | l | | ESTs, Weakly similar to IF39__HUMAN EUKARYOTIC TRANSLATION INITIATION FACTOR 3 SUBUNIT 9 [*H. sapiens*] |
| 1432 | 17159 | J00797 | u, General | | ESTs, Highly similar to A23035 tubulin alpha chain [*H. sapiens*], tubulin alpha 1, tubulin alpha 2, tubulin alpha 3, tubulin alpha 6, tubulin, alpha 2, tubulin, alpha 3, tubulin, alpha, ubiquitous |
| 1433 | 16260 | J01878 | f | | |
| 1434 | 17284 | J02827 | bb | branched chain keto acid dehydrogenase E1, alpha polypeptide (maple syrup urine disease), branched chain ketoacid dehydrogenase E1, alpha polypeptide | |
| 1435 | 15017 | J03752 | n | | |
| 1436 | 44 | J03819 | p, s | thyroid hormone receptor beta, thyroid hormone receptor, beta (avian erythroblastic leukemia viral (v-erb-a) oncogene homolog 2) | |
| 1437 | 21014 | J03914 | e, r, General | glutathione S-transferase M2 (muscle), glutathione S-transferase, mu 2 | ESTs, Moderately similar to GLUTATHIONE S-TRANSFERASE YB1 [*R. norvegicus*], glutathione S-transferase M1, glutathione S-transferase, mu 1 |
| 1438 | 20429 | J05035 | f | steroid 5 alpha-reductase 1, steroid-5-alpha-reductase, alpha polypeptide 1 (3-oxo-5 alpha-steroid delta 4-dehydrogenase alpha 1) | steroid-5-alpha-reductase, alpha polypeptide 1 (3-oxo-5 alpha-steroid delta 4-dehydrogenase alpha 1) |
| 1439 | 1247 | J05181 | j, l, m, s, y, z | glutamate-cysteine ligase, catalytic subunit | glutamate-cysteine ligase, catalytic subunit |
| 1440 | 10464 | J05510 | n, u, General | inositol 1,4,5-triphosphate receptor 1, inositol 1,4,5-triphosphate receptor, type 1 | ESTs, Highly similar to A55713 inositol 1,4,5-triphosphate receptor type 1 [*H. sapiens*], ESTs, Weakly similar to IP3R MOUSE INOSITOL 1,4,5-TRISPHOSPHATE-BINDING PROTEIN TYPE 1 RECEPTOR [*M. musculus*], expressed sequence AI528790, inositol 1,4,5-triphosphate receptor 1, inositol 1,4,5-triphosphate receptor, type 1 |
| 1441 | 20149 | K03243 | q | | |
| 1442 | 17758 | K03249 | q | | ESTs, Highly similar to ECHP__HUMAN PEROXISOMAL BIFUNCTIONAL ENZYME [*H. sapiens*], enoyl-Coenzyme A, hydratase/3-hydroxyacyl Coenzyme A dehydrogenase |
| 1443 | 381 | L00124 | w | | |
| 1444 | 2048 | L00382 | k, x | | |
| 1445 | 10500 | L04619 | s | | |
| 1447 | 108 | L14002 | p | | |
| 1448 | 25366 | L14003 | t | | |
| 1449 | 109 | L14004 | c, p | | |
| 1450 | 20414 | L14323 | General | phosphoinositide-specific phospholipase C-beta 1, phospholipase C, beta 1 | ESTs, Highly similar to KIAA0581 protein [*H. sapiens*] |
| 1451 | 25369 | L14937 | y | | |
| 1452 | 16119 | L16532 | k | 2',3'-cyclic nucleotide 3' phosphodiesterase, cyclic nucleotide phosphodiesterase 1 | 2',3'-cyclic nucleotide 3' phosphodiesterase, cyclic nucleotide phosphodiesterase 1, hypothetical gene CG018 |
| 1453 | 25377 | L25387 | h | phosphofructokinase, platelet | |
| 1453 | 12058 | L25387 | h | phosphofructokinase, platelet | ESTs, Highly similar to JC2055 6-phosphofructokinase [*H. sapiens*], ESTs, Weakly similar to JC2055 6- |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | phosphofructokinase [*H. sapiens*], *Mus musculus* adult male stomach cDNA, RIKEN full-length enriched library, clone: 2210403E17, full insert sequence, expressed sequence AA407869, phosphofructokinase, liver, B-type, phosphofructokinase, muscle, phosphofructokinase, platelet |
| 1455 | 21146 | L35558 | General | solute carrier family 1 (neuronal/epithelial high affinity glutamate transporter, system Xag), member 1, solute carrier family 1, member 1 | |
| 1456 | 106 | L37203 | w | | |
| 1458 | 13682 | L38482 | f, j, k, m, z | | |
| 1459 | 6405 | L38615 | p | glutathione synthetase | |
| 1461 | 15189 | M11794 | n, v | | |
| 1462 | 17086 | M13011 | j | | |
| 1464 | 21053 | M15481 | o | | |
| 1465 | 25405 | M18330 | j, l | | |
| 1466 | 25415 | M19648 | a | | |
| 1468 | 14967 | M22366 | w | | |
| 1469 | 20481 | M22631 | bb | | |
| 1471 | 15048 | M24542 | q | | EST, Moderately similar to UCRI RAT UBIQUINOL-CYTOCHROME C REDUCTASE IRON-SULFUR SUBUNIT, MITOCHONDRIAL PRECURSOR [*R. norvegicus*], EST, Weakly similar to UCRI_HUMAN UBIQUINOL-CYTOCHROME C REDUCTASE IRON-SULFUR SUBUNIT, MITOCHONDRIAL PRECURSOR [*H. sapiens*], ESTs, Moderately similar to UCRI_HUMAN UBIQUINOL-CYTOCHROME C REDUCTASE IRON-SULFUR SUBUNIT, MITOCHONDRIAL PRECURSOR [*H. sapiens*], Human DNA sequence from clone RP1-228J4 on chromosome 6 Contains a pseudogene similar to UQCRFS1 (ubiquinol-cytochrome c reductase, Rieske iron-sulfur polypeptide 1), ESTs, an STS and GSSs, RIKEN cDNA 4430402G14 gene, expressed sequence AI875505, ubiquinol-cytochrome c reductase, Rieske iron-sulfur polypeptide 1 |
| 1472 | 20921 | M29853 | m | cytochrome P450, subfamily IV B, polypeptide 1, cytochrome P450, subfamily IVB, polypeptide 1 | *Mus musculus*, Similar to cytochrome P450, 4a10, clone MGC: 25972 IMAGE: 4240359, mRNA, complete cds, RIKEN cDNA A230105L22 gene, cytochrome P450, 4a10, cytochrome P450, 4a14, cytochrome P450, subfamily IVA, polypeptide 11 |
| 1473 | 1224 | M31931 | u | cytochrome P450, subfamily IIA (phenobarbital-inducible), polypeptide 13 | |
| 1474 | 15579 | M33648 | q | | |
| 1474 | 15580 | M33648 | q | | |
| 1475 | 17211 | M34331 | g, n, q, v | | EST, Moderately similar to 60S RIBOSOMAL PROTEIN L35 [*R. norvegicus*], EST, Moderately similar to G01477 ribosomal protein L35 [*H. sapiens*], EST, Weakly similar to 60S RIBOSOMAL PROTEIN L35 [*R. norvegicus*], ESTs, Highly similar to G01477 ribosomal protein L35 [*H. sapiens*], Human DNA sequence from clone RP1-34P24 on chromosome 22 Contains a pseudogene similar to ribosomal protein L35, ESTs, STSs and GSSs, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | RIKEN cDNA 2410039E09 gene, ribosomal protein L35 |
| 1476 | 20699 | M35601 | b, x, bb | fibrinogen, A alpha polypeptide | *Homo sapiens* clone HQ0582, expressed sequence AI303526, fibrinogen, A alpha polypeptide, fibrinogen, gamma polypeptide |
| 1476 | 20700 | M35601 | b, t, bb | fibrinogen, A alpha polypeptide | *Homo sapiens* clone HQ0582, expressed sequence AI303526, fibrinogen, A alpha polypeptide, fibrinogen, gamma polypeptide |
| 1477 | 9223 | M36151 | o | | H. sapiens DMA, DMB, HLA-Z1, IPP2, LMP2, TAP1, LMP7, TAP2, DOB, DQB2 and RING8, 9, 13 and 14 genes, expressed sequence AI845868 |
| 1479 | 1585 | M57728 | j, m, y | | |
| 1480 | 24844 | M58040 | c | | *Homo sapiens* mRNA; cDNA DKFZp434M2227 (from clone DKFZp434M2227), *Homo sapiens* prostate-specific membrane antigen PSM mRNA, exon 6 alternative splice variant, partial cds, RIKEN cDNA 2610028K12 gene, folate hydrolase, transferrin receptor, transferrin receptor (p90, CD71), transferrin receptor 2 |
| 1481 | 25057 | M58495 | h | | |
| 1482 | 457 | M60666 | d, General | tropomyosin 1, (alpha), tropomyosin 1, alpha | ESTs, Moderately similar to alpha-tropomyosin slow [*M. musculus*], tropomyosin 4 |
| 1483 | 1223 | M75281 | f | | |
| 1484 | 5733 | M81855 | i, k, aa | ATP-binding cassette, sub-family B (MDR/TAP), member 1, ATP-binding cassette, sub-family B (MDR/TAP), member 1B | ATP-binding cassette, sub-family B (MDR/TAP), member 1, ATP-binding cassette, sub-family B (MDR/TAP), member 10, ATP-binding cassette, sub-family B (MDR/TAP), member 8, EST, Highly similar to MDR3 MOUSE MULTIDRUG RESISTANCE PROTEIN 3 [*M. musculus*], EST, Weakly similar to MDR1 RAT MULTIDRUG RESISTANCE PROTEIN 1 [*R. norvegicus*], ESTs, Weakly similar to MDR1 MOUSE MULTIDRUG RESISTANCE PROTEIN 1 [*M. musculus*] |
| 1485 | 4198 | M83143 | m | | ESTs, Highly similar to A41734 beta-galactoside alpha-2,6-sialyltransferase [*H. sapiens*] |
| 1485 | 4199 | M83143 | m | | ESTs, Highly similar to A41734 beta-galactoside alpha-2,6-sialyltransferase [*H. sapiens*] |
| 1486 | 24651 | M83678 | k, x, z | | RAB13, member RAS oncogene family, RIKEN cDNA 0610007N03 gene, expressed sequence AW107754 |
| 1487 | 1430 | M84648 | General | dopa decarboxylase, dopa decarboxylase (aromatic L-amino acid decarboxylase) | EST, Highly similar to AROMATIC-L-AMINO-ACID DECARBOXYLASE [*R. norvegicus*], EST, Moderately similar to AROMATIC-L-AMINO-ACID DECARBOXYLASE [*R. norvegicus*], *Mus musculus* 10 days embryo cDNA, RIKEN full-length enriched library, clone: 2610109O21, full insert sequence, dopa decarboxylase, dopa decarboxylase (aromatic L-amino acid decarboxylase) |
| 1488 | 25467 | M93297 | c | | |
| 1489 | 729 | M95762 | a, y | | ESTs, Highly similar to NTG3 MOUSE SODIUM- AND CHLORIDE-DEPENDENT GABA TRANSPORTER 3 [*M. musculus*], ESTs, Weakly similar to NTG3_HUMAN SODIUM- AND CHLORIDE-DEPENDENT GABA TRANSPORTER 3 [*H. sapiens*], expressed sequence AA589632, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1490 | 23698 | NM_012489 | q | | solute carrier family 6 (neurotransmitter transporter, GABA), member 13 DNA segment, Chr 9, ERATO Doi 25, expressed, *Homo sapiens* clone 23623 mRNA, partial cds, *Homo sapiens*, Similar to Acetyl-CoA acyltransferase, 3-oxo acyl-CoA thiolase A, peroxisomal, clone MGC: 18173 IMAGE: 4155289, mRNA, complete cds, *Homo sapiens*, Similar to acetyl-Coenzyme A acyltransferase 1 (peroxisomal 3-oxoacyl-Coenzyme A thiolase), clone MGC: 23127 IMAGE: 4908159, mRNA, complete cds, RIKEN cDNA 0610011L04 gene, acetyl-Coenzyme A acyltransferase 1 (peroxisomal 3-oxoacyl-Coenzyme A thiolase), expressed sequence AI255831, expressed sequence AI265397, t-complex protein 1, related sequence 1 |
| 1490 | 23699 | NM_012489 | q | | DNA segment, Chr 9, ERATO Doi 25, expressed, *Homo sapiens* clone 23623 mRNA, partial cds, *Homo sapiens*, Similar to Acetyl-CoA acyltransferase, 3-oxo acyl-CoA thiolase A, peroxisomal, clone MGC: 18173 IMAGE: 4155289, mRNA, complete cds, *Homo sapiens*, Similar to acetyl-Coenzyme A acyltransferase 1 (peroxisomal 3-oxoacyl-Coenzyme A thiolase), clone MGC: 23127 IMAGE: 4908159, mRNA, complete cds, RIKEN cDNA 0610011L04 gene, acetyl-Coenzyme A acyltransferase 1 (peroxisomal 3-oxoacyl-Coenzyme A thiolase), expressed sequence AI255831, expressed sequence AI265397, t-complex protein 1, related sequence 1 |
| 1491 | 7062 | NM_012495 | q | aldolase 1, A isoform, aldolase A, fructose-bisphosphate | EST, Moderately similar to ADHUA fructose-bisphosphate aldolase [*H. sapiens*], EST, Weakly similar to ADHUA fructose-bisphosphate aldolase [*H. sapiens*], EST, Weakly similar to I39435 fructose-bisphosphate aldolase [*H. sapiens*], ESTs, Moderately similar to aldolase A [*M. musculus*], *Homo sapiens*, aldolase 1, A isoform, clone MGC: 18171 IMAGE: 4155253, mRNA, complete cds, RIKEN cDNA 4933425L11 gene, aldolase 1, A isoform, aldolase 3, C isoform, aldolase A, fructose-bisphosphate |
| 1492 | 15511 | NM_012498 | u | aldo-keto reductase family 1, member B1 (aldose reductase), aldo-keto reductase family 1, member B3 (aldose reductase) | |
| 1494 | 7427 | NM_012515 | General | benzodiazapine receptor (peripheral), benzodiazepine receptor, peripheral | Human DNA sequence from clone 34B21 on chromosome 6p12.1-21.1. Contains part of a gene for a novel protein with ZU5 domain similar to part of Tight Junction Protein ZO1 (TJP1) and UNC5 Homologs, the gene for a novel BZRP (peripheral benzodiazepine receptor (MBR, PBR, PBKS, IBP, Isoquinoline-binding protein)) LIKE protein, the gene for a novel protein similar to part of APOBEC1 (Phorbolin 1, Apolipoprotein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | B mRNA editing protein), and the NFYA gene for nuclear transcription factor Y, alpha (CCAAT-Binding transcription factor subunit B, CBF-B, CAAT-Box DNA binding protein subunit A). Contains ESTs, STSs, GSSs, two putative CpG Islands and a ca repeat polymorphism, RIKEN cDNA 2510027D20 gene, benzodiazapine receptor (peripheral), benzodiazepine receptor, peripheral |
| 1495 | 24433 | NM_012527 | i | cholinergic receptor, muscarinic 3, cholinergic receptor, muscarinic 3, cardiac | cholinergic receptor, muscarinic 1, CNS, cholinergic receptor, muscarinic 3, cholinergic receptor, muscarinic 3, cardiac |
| 1496 | 4467 | NM_012529 | d | creatine kinase, brain | EST, Moderately similar to CREATINE KINASE, B CHAIN [*R. norvegicus*], EST, Weakly similar to KIHUCB creatine kinase [*H. sapiens*], creatine kinase, brain |
| 1497 | 16520 | NM_012532 | General | ceruloplasmin, ceruloplasmin (ferroxidase) | DNA segment, Chr 3, ERATO Doi 555, expressed, EST, Highly similar to 1012298A factor VIIIC [*H. sapiens*], ESTs, Weakly similar to CERU MOUSE CERULOPLASMIN PRECURSOR [*M. musculus*], ESTs, Weakly similar to CERU RAT CERULOPLASMIN PRECURSOR [*R. norvegicus*], ESTs, Weakly similar to KUHU ferroxidase [*H. sapiens*], Hermansky-Pudlak syndrome 3, ceruloplasmin, ceruloplasmin (ferroxidase), hephaestin |
| 1498 | 225 | NM_012544 | x, z | angiotensin I converting enzyme (peptidyl-dipeptidase A) 1, angiotensin converting enzyme | ESTs, Highly similar to A31759 peptidyl-dipeptidase A [*H. sapiens*], ESTs, Highly similar to JC2038 peptidyl-dipeptidase A [*R. norvegicus*], *Mus musculus* adult male testis cDNA, RIKEN full-length enriched library, clone: 4933424D04, full insert sequence, RIKEN cDNA 2010305L05 gene, angiotensin I converting enzyme (peptidyl-dipeptidase A) 1, angiotensin converting enzyme |
| 1499 | 1431 | NM_012545 | General | dopa decarboxylase, dopa decarboxylase (aromatic L-amino acid decarboxylase) | EST, Highly similar to AROMATIC-L-AMINO-ACID DECARBOXYLASE [*R. norvegicus*], EST, Moderately similar to AROMATIC-L-AMINO-ACID DECARBOXYLASE [*R. norvegicus*], *Mus musculus* 10 days embryo cDNA, RIKEN full-length enriched library, clone: 2610109O21, full insert sequence, dopa decarboxylase, dopa decarboxylase (aromatic L-amino acid decarboxylase) |
| 1500 | 23868 | NM_012551 | l, m, v, General | early growth response 1 | ESTs, Weakly similar to I53869 zinc finger protein - mouse [*M. musculus*], early growth response 1, repressor of GATA, testis zinc finger protein |
| 1500 | 23872 | NM_012551 | l, v, cc, General | early growth response 1 | ESTs, Weakly similar to I53869 zinc finger protein - mouse [*M. musculus*], early growth response 1, repressor of GATA, testis zinc finger protein |
| 1500 | 23869 | NM_012551 | v, General | early growth response 1 | ESTs, Weakly similar to I53869 zinc finger protein - mouse [*M. musculus*], early growth response 1, repressor of GATA, testis zinc finger protein |
| 1501 | 19407 | NM_012554 | z | enolase 1, (alpha), enolase 1, alpha non-neuron | EST, Moderately similar to ALPHA ENOLASE [*R. norvegicus*], EST, Weakly similar to A29170 phosphopyruvate hydratase [*H. sapiens*], *Homo sapiens* cDNA FLJ12774 fis, clone NT2RP2001663, moderately similar to ENOLASE (EC |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1501 | 19408 | NM_012554 | n, s, y, z | enolase 1, (alpha), enolase 1, alpha non-neuron | 4.2.1.11), enolase 1, (alpha), enolase 1, alpha non-neuron, enolase alpha, lung-specific, expressed sequence AI427012 EST, Moderately similar to ALPHA ENOLASE [*R. norvegicus*], EST, Weakly similar to A29170 phosphopyruvate hydratase [*H. sapiens*], *Homo sapiens* cDNA FLJ12774 fis, clone NT2RP2001663, moderately similar to ENOLASE (EC 4.2.1.11), enolase 1, (alpha), enolase 1, alpha non-neuron, enolase alpha, lung-specific, expressed sequence AI427012 |
| 1502 | 21836 | NM_012555 | k | E26 avian leukemia oncogene 1, 5' domain, v-ets avian erythroblastosis virus E26 oncogene homolog 1 | E26 avian leukemia oncogene 1, 5' domain, ESTs, Moderately similar to FLI1 MOUSE RETROVIRAL INTEGRATION SITE PROTEIN FLI-1 [*M. musculus*], FEV protein, *Rattus norvegicus* ETS domain transcription factor Pet-1 mRNA, complete cds, v-ets avian erythroblastosis virus E26 oncogene homolog 1 |
| 1503 | 16895 | NM_012558 | g, s | | EST, Weakly similar to FRUCTOSE-1,6-BISPHOSPHATASE ISOZYME 2 [*M. musculus*], fructose bisphosphatase 1, fructose bisphosphatase 2, fructose-1,6-bisphosphatase 1, fructose-1,6-bisphosphatase 2 |
| 1504 | 25317 | NM_012559 | bb | | |
| 1504 | 6477 | NM_012559 | b, bb | fibrinogen, gamma polypeptide | EST, Moderately similar to FGHUGB fibrinogen gamma-B chain precursor [*H. sapiens*], EST, Moderately similar to Recombinant Human Gamma-Fibrinogen Carboxyl Terminal Fragment [*H. sapiens*], ESTs, Weakly similar to FIBG RAT FIBRINOGEN GAMMA-A/-B CHAIN PRECURSOR [*R. norvegicus*], RIKEN cDNA 1110007F23 gene, expressed sequence AI303526, fibrinogen, gamma polypeptide, fibrinogen-like 1, ficolin A, ficolin B |
| 1504 | 6478 | NM_012559 | bb | fibrinogen, gamma polypeptide | EST, Moderately similar to FGHUGB fibrinogen gamma-B chain precursor [*H. sapiens*], EST, Moderately similar to Recombinant Human Gamma-Fibrinogen Carboxyl Terminal Fragment [*H. sapiens*], ESTs, Weakly similar to FIBG RAT FIBRINOGEN GAMMA-A/-B CHAIN PRECURSOR [*R. norvegicus*], RIKEN cDNA 1110007F23 gene, expressed sequence AI303526, fibrinogen, gamma polypeptide, fibrinogen-like 1, ficolin A, ficolin B |
| 1505 | 11731 | NM_012561 | k | follistatin | follistatin, follistatin-like 3, follistatin-like 3 (secreted glycoprotein), transmembrane protein with EGF-like and two follistatin-like domains 1 |
| 1507 | 4254 | NM_012564 | a | group specific component, group-specific component (vitamin D binding protein) | |
| 1508 | 16026 | NM_012578 | r | H1 histone family, member 0 | H1 histone family, member 0 |
| 1508 | 16024 | NM_012578 | r | H1 histone family, member 0 | H1 histone family, member 0 |
| 1508 | 16025 | NM_012578 | r | H1 histone family, member 0 | H1 histone family, member 0 |
| 1509 | 16080 | NM_012580 | g, m | heme oxygenase (decycling) 1 | heme oxygenase (decycling) 1 |
| 1510 | 15098 | NM_012588 | bb | insulin-like growth factor binding protein 3 | insulin-like growth factor binding protein 3, protease, serine, 11 (Igf binding) |
| 1511 | 4450 | NM_012592 | bb | isovaleryl Coenzyme A dehydrogenase, isovaleryl | RIKEN cDNA 1300003O09 gene, RIKEN cDNA 2310016C19 gene, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | coenzyme A dehydrogenase | acetyl-Coenzyme A dehydrogenase, short chain, isovaleryl Coenzyme A dehydrogenase, isovaleryl coenzyme A dehydrogenase |
| 1511 | 4451 | NM_012592 | i, bb | isovaleryl Coenzyme A dehydrogenase, isovaleryl coenzyme A dehydrogenase | RIKEN cDNA 1300003O09 gene, RIKEN cDNA 2310016C19 gene, acetyl-Coenzyme A dehydrogenase, short chain, isovaleryl Coenzyme A dehydrogenase, isovaleryl coenzyme A dehydrogenase |
| 1511 | 4452 | NM_012592 | bb | isovaleryl Coenzyme A dehydrogenase, isovaleryl coenzyme A dehydrogenase | RIKEN cDNA 1300003O09 gene, RIKEN cDNA 2310016C19 gene, acetyl-Coenzyme A dehydrogenase, short chain, isovaleryl Coenzyme A dehydrogenase, isovaleryl coenzyme A dehydrogenase |
| 1512 | 17198 | NM_012593 | a, x | kallikrein 1, renal/pancreas/salivary, kallikrein 6 | kallikrein 1, renal/pancreas/salivary, kallikrein 21, kallikrein 24, kallikrein 27, kallikrein 5 |
| 1512 | 17197 | NM_012593 | x | kallikrein 1, renal/pancreas/salivary, kallikrein 6 | kallikrein 1, renal/pancreas/salivary, kallikrein 21, kallikrein 24, kallikrein 27, kallikrein 5 |
| 1513 | 18749 | NM_012600 | a, h | malic enzyme 1, NADP(+)-dependent, cytosolic, malic enzyme, supernatant | |
| 1514 | 2628 | NM_012603 | General | myelocytomatosis oncogene, v-myc avian myelocytomatosis viral oncogene homolog | |
| 1514 | 2629 | NM_012603 | x, General | myelocytomatosis oncogene, v-myc avian myelocytomatosis viral oncogene homolog | RIKEN cDNA 2900002K07 gene, myelocytomatosis oncogene, v-myc avian myelocytomatosis viral oncogene homolog |
| 1515 | 16849 | NM_012608 | n, o, q | membrane metallo endopeptidase, membrane metallo-endopeptidase (neutral endopeptidase, enkephalinase, CALLA, CD10) | endothelin converting enzyme-like 1, expressed sequence AW322500, mel transforming oncogene-like 1, membrane metallo endopeptidase, membrane metallo-endopeptidase (neutral endopeptidase, enkephalinase, CALLA, CD10), membrane metallo-endopeptidase-like 2 |
| 1517 | 15540 | NM_012620 | General | serine (or cysteine) proteinase inhibitor, clade E (nexin, plasminogen activator inhibitor type 1), member 1 | serine (or cysteine) proteinase inhibitor, clade E (nexin, plasminogen activator inhibitor type 1), member 1 |
| 1518 | 24568 | NM_012630 | General | prolactin receptor | cytokine receptor-like factor 1, interleukin 13 receptor, alpha 2, interleukin 5 receptor, alpha, prolactin receptor, prolactin receptor related sequence 1 |
| 1518 | 24566 | NM_012630 | General | prolactin receptor | cytokine receptor-like factor 1, interleukin 13 receptor, alpha 2, interleukin 5 receptor, alpha, prolactin receptor, prolactin receptor related sequence 1 |
| 1519 | 18553 | NM_012631 | k | prion protein, prion protein (p27-30) (Creutzfeld-Jakob disease, Gerstmann-Strausler-Scheinker syndrome, fatal familial insomnia) | prion protein, prion protein (p27-30) (Creutzfeld-Jakob disease, Gerstmann-Strausler-Scheinker syndrome, fatal familial insomnia) |
| 1520 | 1844 | NM_012637 | General | | ESTs, Highly similar to TPHUN1 protein-tyrosine-phosphatase [*H. sapiens*], protein tyrosine phosphatase, non-receptor type 1 |
| 1521 | 24668 | NM_012642 | f | renin, renin 1 structural | expressed sequence D19352, renin, renin 1 structural, renin 2 tandem duplication of Ren1 |
| 1522 | 18632 | NM_012645 | a | | |
| 1523 | 25435 | NM_012647 | g | | |
| 1524 | 9423 | NM_012649 | b, cc | syndecan 4, syndecan 4 (amphiglycan, ryudocan) | syndecan 4, syndecan 4 (amphiglycan, ryudocan) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1525 | 24496 | NM_012654 | n | solute carrier family 9 (sodium/hydrogen exchanger), isoform 3, solute carrier family 9 (sodium/hydrogen exchanger), member 3 | ESTs, Weakly similar to NAH1 MOUSE SODIUM/HYDROGEN EXCHANGER 1 [*M. musculus*], *Homo sapiens* mRNA; cDNA DKFZp434D0818 (from clone DKFZp434D0818), RIKEN cDNA 0610040A22 gene, RIKEN cDNA 6430709P13 gene, expressed sequence AI182282, solute carrier family 9 (sodium/hydrogen exchanger), isoform 3, solute carrier family 9 (sodium/hydrogen exchanger), isoform 6, solute carrier family 9 (sodium/hydrogen exchanger), member 1 |
| 1526 | 7101 | NM_012679 | x, bb, General | | DNA segment, Chr 14, University of California at Los Angeles 3, EST, Moderately similar to A41386 clusterin precursor [*H. sapiens*], ESTs, Moderately similar to A41386 clusterin precursor [*H. sapiens*], clusterin, clusterin (complement lysis inhibitor, SP-40, 40, sulfated glycoprotein 2, testosterone-repressed prostate message 2, apolipoprotein J), expressed sequence AI893575 |
| 1527 | 24707 | NM_012693 | i | | cytochrome P450, 2a12, cytochrome P450, subfamily IIA (phenobarbital-inducible), polypeptide 13, cytochrome P450, subfamily IIA (phenobarbital-inducible), polypeptide 7, pseudogene 1, cytochrome P450, subfamily IIA (phenobarbital-inducible), polypeptide 7, pseudogene 2 |
| 1528 | 1850 | NM_012696 | t | kininogen | EST, Weakly similar to KNG_MOUSE KININOGEN PRECURSOR [CONTAINS: BRADYKININ] [*M. musculus*], kininogen |
| 1528 | 1854 | NM_012696 | t | kininogen | EST, Weakly similar to KNG_MOUSE KININOGEN PRECURSOR [CONTAINS: BRADYKININ] [*M. musculus*], kininogen |
| 1529 | 1603 | NM_012697 | General | | EST, Weakly similar to OCN2 MOUSE ORGANIC CATION/CARNITINE TRANSPORTER 2 [*M. musculus*], ESTs, Highly similar to OCN2_HUMAN ORGANIC CATION/CARNITINE TRANSPORTER 2 [*H. sapiens*], solute carrier family 22 (organic cation transporter), member 1, solute carrier family 22 (organic cation transporter), member 4, solute carrier family 22 (organic cation transporter), member 5, solute carrier family 22 (organic cation transporter), member 9 |
| 1530 | 1372 | NM_012734 | u | hexokinase 1 | ESTs, Highly similar to HXK1 RAT HEXOKINASE, TYPE I [*R. norvegicus*], hexokinase 1, hypothetical protein FLJ22761 |
| 1531 | 1478 | NM_012744 | bb, General | | expressed sequence C79630, methylcrotonoyl-Coenzyme A carboxylase 1 (alpha), pyruvate carboxylase, pyruvate decarboxylase |
| 1532 | 343 | NM_012747 | h, t | | Signal transducer and activator of transcription 1, signal transducer and activator of transcription 1, signal transducer and activator of transcription 1, 91 kD, signal transducer and activator of transcription 3, signal transducer and activator of transcription 3 (acute-phase response factor) |
| 1533 | 8829 | NM_012749 | General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1534 | 20828 | NM_012752 | General | CD24 antigen (small cell lung carcinoma cluster 4 antigen), CD24a antigen | CD24 antigen (small cell lung carcinoma cluster 4 antigen), CD24a antigen |
| 1534 | 20829 | NM_012752 | i, General | CD24 antigen (small cell lung carcinoma cluster 4 antigen), CD24a antigen | CD24 antigen (small cell lung carcinoma cluster 4 antigen), CD24a antigen |
| 1534 | 20830 | NM_012752 | i, General | CD24 antigen (small cell lung carcinoma cluster 4 antigen), CD24a antigen | CD24 antigen (small cell lung carcinoma cluster 4 antigen), CD24a antigen |
| 1535 | 15174 | NM_012756 | b | | ESTs, Highly similar to 1312358A IGF II receptor [*H. sapiens*], expressed sequence AI661837, insulin-like growth factor 2 receptor |
| 1536 | 21685 | NM_012760 | j, m, n | | EST, Weakly similar to ZF37_RAT ZINC FINGER PROTEIN 37 (ZFP-37) [*R. norvegicus*], ESTs, Weakly similar to S59069 Z13 protein - mouse [*M. musculus*], *Homo sapiens* chromosome 19, BAC 273239 (CIT-B-320G13), *Homo sapiens*, clone MGC: 23189 IMAGE: 4854518, mRNA, complete cds, RIKEN cDNA 2410081M15 gene, RIKEN cDNA 2610019F01 gene, RIKEN cDNA 2810011C24 gene, hypothetical protein FLJ12488, hypothetical zinc finger protein MGC2396, zinc finger protein 37, zinc finger protein homologous to Zfp37 in mouse |
| 1537 | 18068 | NM_012762 | t | | CARD only protein, ESTs, Moderately similar to A56084 interleukin-1beta converting enzyme beta isozyme [*H. sapiens*], ESTs, Weakly similar to interleukin-1beta converting enzyme-gamma isozyme [*H. sapiens*], *Homo sapiens* mRNA; cDNA DKFZp586A181 (from clone DKFZp586A181); partial cds, ICEBERG caspase-1 inhibitor, caspase 1, caspase 1, apoptosis-related cysteine protease (interleukin 1, beta, convertase) |
| 1538 | 1246 | NM_012770 | a, General | | ESTs, Weakly similar to ANPA MOUSE ATRIAL NATRIURETIC PEPTIDE RECEPTOR A PRECURSOR [*M. musculus*], guanylate cyclase 1, soluble, alpha 3, guanylate cyclase 1, soluble, beta 2, guanylate cyclase 1, soluble, beta 3, natriuretic peptide receptor 1 |
| 1539 | 1348 | NM_012776 | f | adrenergic receptor kinase, beta 1, adrenergic, beta, receptor kinase 1 | G protein-coupled receptor kinase 2, groucho gene related (*Drosophila*), G protein-coupled receptor kinase 5, G protein-coupled receptor kinase 6, adrenergic, beta, receptor kinase 1, rhodopsin kinase |
| 1540 | 18135 | NM_012791 | w | dual-specificity tyrosine-(Y)-phosphorylation regulated kinase 1A, dual-specificity tyrosine-(Y)-phosphorylation regulated kinase 1a | ESTs, Moderately similar to DYRK RAT DUAL-SPECIFICITY TYROSINE-(Y)-PHOSPHORYLATION REGULATED KINASE [*R. norvegicus*], ESTs, Weakly similar to DYRK MOUSE DUAL-SPECIFICITY TYROSINE-(Y)-PHOSPHORYLATION REGULATED KINASE [*M. musculus*], *Homo sapiens* chromosome 19, CIT-HSP BAC 470n8, *Mus musculus*, clone MGC: 6699 IMAGE: 3584001, mRNA, complete cds, dual-specificity tyrosine-(Y)-phosphorylation regulated kinase 1A, dual-specificity tyrosine-(Y)-phosphorylation regulated kinase 1a, dual-specificity tyrosine-(Y)-phosphorylation regulated kinase 1b, dual-specificity tyrosine-(Y)-phosphorylation regulated kinase 2, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | homeodomain-interacting protein kinase 2 |
| 1541 | 16947 | NM_012793 | p, bb | guanidinoacetate N-methyltransferase, guanidinoacetate methyltransferase | GAMT_HUMAN GUANIDINOACETATE N-METHYLTRANSFERASE [*H. sapiens*], *Homo sapiens*, clone MGC: 14390 IMAGE: 4300887, mRNA, complete cds, guanidinoacetate N-methyltransferase, guanidinoacetate methyltransferase |
| 1542 | 960 | NM_012796 | u | glutathione S-transferase theta 2, glutathione S-transferase, theta 2 | ESTs, Highly similar to GTT2 RAT GLUTATHIONE S-TRANSFERASE YRS-YRS [*R. norvegicus*], *Homo sapiens* mRNA; cDNA DKFZp762N226 (from clone DKFZp762N226), expressed sequence AI266894, glutathione S-transferase theta 2, glutathione S-transferase, theta 2, hypothetical protein |
| 1543 | 260 | NM_012798 | f, u | mal, T-cell differentiation protein, myelin and lymphocyte protein; T-cell differentiation protein | BENE protein, *Mus musculus*, Similar to BENE protein, clone MGC: 19097 IMAGE: 4205488, mRNA, complete cds, RIKEN cDNA 2700018N07 gene, expressed sequence AI461653, mal, T-cell differentiation protein, mal, T-cell differentiation protein 2, myelin and lymphocyte protein; T-cell differentiation protein |
| 1544 | 556 | NM_012803 | d | protein C, protein C (inactivator of coagulation factors Va and VIIIa) | B-factor, properdin, DKFZP586H2123 protein, ESTs, Weakly similar to PRTC RAT VITAMIN-K DEPENDENT PROTEIN C PRECURSOR [*R. norvegicus*], protein C, protein C (inactivator of coagulation factors Va and VIIIa) |
| 1545 | 21729 | NM_012804 | q | ATP-binding cassette, sub-family D (ALD), member 3 | ATP-binding cassette, sub-family D (ALD), member 1, ATP-binding cassette, sub-family D (ALD), member 2, ATP-binding cassette, sub-family D (ALD), member 3, ESTs, Weakly similar to ABD3 RAT ATP-BINDING CASSETTE, SUB-FAMILY D, MEMBER 3 [*R. norvegicus*] |
| 1546 | 15032 | NM_012816 | General | | alpha-methylacyl-CoA racemase, hypothetical protein FLJ11808 |
| 1547 | 24895 | NM_012817 | General | insulin-like growth factor binding protein 5 | insulin-like growth factor binding protein 5 |
| 1548 | 18109 | NM_012823 | u, General | | EST, Weakly similar to ANXA_HUMAN ANNEXIN XI [*H. sapiens*], annexin A10, annexin A3 |
| 1549 | 373 | NM_012833 | h, l, q, General | ATP-binding cassette, sub-family C (CFTR/MRP), member 2 | ATP-binding cassette, sub-family C (CFTR/MRP), member 10, ATP-binding cassette, sub-family C (CFTR/MRP), member 1a, ATP-binding cassette, sub-family C (CFTR/MRP), member 2, ATP-binding cassette, sub-family C (CFTR/MRP), member 4, ATP-binding cassette, sub-family C (CFTR/MRP), member 6, ESTs, Weakly similar to A40303 cystic fibrosis transmembrane conductance regulator - mouse [*M. musculus*], expressed sequence AI132311 |
| 1550 | 2855 | NM_012838 | e | cystatin B, cystatin B (stefin B) | cystatin B, cystatin B (stefin B), expressed sequence AA960480 |
| 1551 | 11136 | NM_012839 | s | cytochrome c, cytochrome c, somatic | ESTs, Highly similar to 630485A cytochrome c [*H. sapiens*], ESTs, Weakly similar to CYTOCHROME C, SOMATIC [*M. musculus*], *Homo sapiens* pseudogene for cytochrome c-like protein, clone pHGC4E1, Human DNA sequence from clone RP11-169O17 on chromosome 13 Contains ESTs, GSSs, STSs and four CpG |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | islands. Contains a novel protein similar to cytochrome c, part of a novel gene similar to TPTE encoding a transmembrane phosphatase with tensin homology and the ADPRTL1 gene encoding ADP-ribosyltransferase (NAD+; poly (ADP-ribose) polymerase)-like protein 1 (vault protein, KIAA0177), cytochrome c, cytochrome c, somatic |
| 1552 | 20885 | NM_012842 | a | epidermal growth factor, epidermal growth factor (beta-urogastrone) | EST, Moderately similar to EPIDERMAL GROWTH FACTOR PRECURSOR [*M. musculus*], ESTs, Moderately similar to EPIDERMAL GROWTH FACTOR PRECURSOR [*M. musculus*], ESTs, Weakly similar to EGRT epidermal growth factor precursor - rat [*R. norvegicus*], *Homo sapiens* mRNA: cDNA DKFZp434O0213 (from clone DKFZp434O0213); partial cds, epidermal growth factor, epidermal growth factor (beta-urogastrone), nidogen 2 |
| 1552 | 20884 | NM_012842 | a, bb | epidermal growth factor, epidermal growth factor (beta-urogastrone) | EST, Moderately similar to EPIDERMAL GROWTH FACTOR PRECURSOR [*M. musculus*], ESTs, Moderately similar to EPIDERMAL GROWTH FACTOR PRECURSOR [*M. musculus*], ESTs, Weakly similar to EGRT epidermal growth factor precursor - rat [*R. norvegicus*], *Homo sapiens* mRNA; cDNA DKFZp434O0213 (from clone DKFZp434O0213); partial cds, epidermal growth factor, epidermal growth factor (beta-urogastrone), nidogen 2 |
| 1553 | 18770 | NM_012857 | e | lysosomal membrane glycoprotein 1, lysosomal-associated membrane protein 1 | CD68 antigen, ESTs, Weakly similar to LMP1 RAT LYSOSOME-ASSOCIATED MEMBRANE GLYCOPROTEIN 1 PRECURSOR [*R. norvegicus*], lysosomal membrane glycoprotein 1, lysosomal-associated membrane protein 1, similar to S68401 (cattle) glucose induced gene |
| 1554 | 20674 | NM_012861 | i | 0-6-methylguanine-DNA methyltransferase, O-6-methylguanine-DNA methyltransferase | ESTs, Highly similar to 1207289A reverse transcriptase related protein [*H. sapiens*], ESTs, Highly similar to S21348 probable pol polyprotein-related protein 4 - rat [*R. norvegicus*], ESTs, Moderately similar to GNMSLL retrovirus-related reverse transcriptase homolog - mouse retrotransposon [*M. musculus*], ESTs, Weakly similar to 1207289A reverse transcriptase related protein [*H. sapiens*], ESTs, Weakly similar to B34087 hypothetical protein [*H. sapiens*], *Homo sapiens* cDNA FLJ12202 fis, clone MAMMA1000908, *Mus musculus*, Similar to L1 repeat, Tf subfamily, member 30, clone MGC: 7372 IMAGE: 3487559, mRNA, complete cds, RIKEN cDNA 1700082M22 gene, T lymphoma oncogene, expressed sequence AI267024, hypothetical protein FLJ21032, pheromone receptor V3R4 |
| 1555 | 13151 | NM_012862 | a, r, General | matrix Gla protein, matrix gamma-carboxyglutamate (gla) protein | MATRIX GLA-PROTEIN PRECURSOR [*H. sapiens*], matrix Gla protein, matrix gamma-carboxyglutamate (gla) protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1556 | 24617 | NM_012870 | General | tumor necrosis factor receptor superfamily, member 11b (osteoprotegerin) | Nerve growth factor receptor, fast, RIKEN cDNA 2610311B09 gene, nerve growth factor receptor, nerve growth factor receptor (TNFR superfamily, member 16), tumor necrosis factor receptor superfamily, member 11b (osteoprotegerin), tumor necrosis factor receptor superfamily, member 21 |
| 1557 | 20945 | NM_012875 | a, v | | EST, Moderately similar to 60S RIBOSOMAL PROTEIN L39 [*R. norvegicus*], ESTs, Highly similar to 60S RIBOSOMAL PROTEIN L39 [*R. norvegicus*], ESTs, Highly similar to G02654 ribosomal protein L39 [*H. sapiens*], ESTs, Moderately similar to G02654 ribosomal protein L39 [*H. sapiens*], RIKEN cDNA 2810465O16 gene, RIKEN cDNA 4930517K11 gene, ribosomal protein L39, ribosomal protein L39-like 1 |
| 1558 | 15872 | NM_012879 | o, r | solute carrier family 2 (facilitated glucose transporter), member 2 | ESTs, Highly similar to A31318 glucose transporter-like protein [*H. sapiens*], ESTs, Weakly similar to GLUCOSE TRANSPORTER TYPE 2, LIVER [*R. norvegicus*], ESTs, Weakly similar to S05319 glucose transport protein, hepatic - mouse [*M. musculus*], solute carrier family 2 (facilitated glucose transporter), member 10, solute carrier family 2 (facilitated glucose transporter), member 2, solute carrier family 2, (facilitated glucose transporter) member 8 |
| 1559 | 495 | NM_012880 | z | superoxide dismutase 3, extracellular | RIKEN cDNA 1700105P06 gene, superoxide dismutase 3, extracellular |
| 1559 | 494 | NM_012880 | c | superoxide dismutase 3, extracellular | RIKEN cDNA 1700105P06 gene, superoxide dismutase 3, extracellular |
| 1560 | 23651 | NM_012881 | d, u, General | secreted phosphoprotein 1, secreted phosphoprotein 1 (osteopontin, bone sialoprotein I, early T-lymphocyte activation 1) | |
| 1562 | 19477 | NM_012891 | q | | |
| 1563 | 18564 | NM_012899 | v, General | aminolevulinate, delta-, dehydratase | aminolevulinate, delta-, dehydratase |
| 1564 | 7197 | NM_012904 | f, r, cc, General | annexin A1 | EST, Weakly similar to A Chain A, Nmr Solution Structure Of Domain 1 Of Human Annexin I {SUB 41-113 [*H. sapiens*], annexin A1 |
| 1564 | 7196 | NM_012904 | v, cc, General | annexin A1 | |
| 1565 | 20202 | NM_012909 | b, r | aquaporin 2, aquaporin 2 (collecting duct) | aquaporin 2, aquaporin 2 (collecting duct), aquaporin 6, aquaporin 6, kidney specific |
| 1566 | 16581 | NM_012911 | c, j | | *Mus musculus* retinal cone arrestin 3 (Arr3) mRNA, complete cds, RIKEN cDNA 1200006I17 gene, arrestin, beta 2, expressed sequence AI326910, retinal S-antigen |
| 1566 | 16582 | NM_012911 | c | | *Mus musculus* retinal cone arrestin 3 (Arr3) mRNA, complete cds, RIKEN cDNA 1200006I17 gene, arrestin, beta 2, expressed sequence AI326910, retinal S-antigen |
| 1567 | 24431 | NM_012912 | General | activating transcription factor 3 | ESTs, Highly similar to 1604249C transcription factor ATF3 [*H. sapiens*], ESTs, Weakly similar to ATF3 RAT CYCLIC-AMP-DEPENDENT TRANSCRIPTION FACTOR ATF-3 [*R. norvegicus*], Jun dimerization protein 2, activating transcription factor 3, basic leucine zipper transcription factor, ATF-like |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1568 | 18118 | NM_012913 | p | ATPase, Na+/K+ transporting, beta 3 polypeptide | ATPase, Na+/K+ transporting, beta 3 polypeptide, ESTs, Highly similar to G02485 Na+/K+-exchanging ATPase [*H. sapiens*], expressed sequence AI664000 |
| 1569 | 6108 | NM_012915 | n | | ATPase inhibitor, ATPase inhibitor precursor, ESTs, Moderately similar to ATPASE INHIBITOR, MITOCHONDRIAL PRECURSOR [*R. norvegicus*], *Mus musculus* 10 days embryo cDNA, RIKEN full-length enriched library, clone: 2610204M17, full insert sequence |
| 1570 | 20757 | NM_012923 | c, i, aa | cyclin G, cyclin G1 | cyclin G, cyclin G1, cyclin G2, cyclin I |
| 1570 | 20755 | NM_012923 | i | cyclin G, cyclin G1 | cyclin G, cyclin G1, cyclin G2, cyclin I |
| 1571 | 2830 | NM_012925 | f | CD59 antigen p18-20 (antigen identified by monoclonal antibodies 16.3A5, EJ16, EJ30, EL32 and G344), CD59a antigen | CD59 antigen p18-20 (antigen identified by monoclonal antibodies 16.3A5, EJ16, EJ30, EL32 and G344), CD59a antigen, ESTs, Weakly similar to CD59 RAT CD59 GLYCOPROTEIN PRECURSOR [*R. norvegicus*] |
| 1571 | 2831 | NM_012925 | f | CD59 antigen p18-20 (antigen identified by monoclonal antibodies 16.3A5, EJ16, EJ30, EL32 and G344), CD59a antigen | CD59 antigen p18-20 (antigen identified by monoclonal antibodies 16.3A5, EJ16, EJ30, EL32 and G344), CD59a antigen, ESTs, Weakly similar to CD59 RAT CD59 GLYCOPROTEIN PRECURSOR [*R. norvegicus*] |
| 1572 | 1977 | NM_012930 | q | carnitine palmitoyltransferase 2, carnitine palmitoyltransferase II | EST, Moderately similar to CPT2 RAT CARNITINE O-PALMITOYLTRANSFERASE II, MITOCHONDRIAL PRECURSOR [*R. norvegicus*], carnitine palmitoyltransferase 2, carnitine palmitoyltransferase II, expressed sequence AI323697 |
| 1573 | 18694 | NM_012931 | j, l, m, z | | CD2-associated protein, HEF like Protein, *Homo sapiens* cDNA FLJ14854 fis, clone PLACE1000972, breast cancer anti-estrogen resistance 1, enhancer of filamentation 1 (cas-like docking; Crk-associated substrate related), neural precursor cell expressed, developmentally down-regulated gene 9, v-crk-associated tyrosine kinase substrate |
| 1574 | 13723 | NM_012935 | n | crystallin, alpha B | |
| 1575 | 9109 | NM_012939 | j, y, z | cathepsin H | ESTs, Highly similar to KHHUH cathepsin H [*H. sapiens*], ESTs, Weakly similar to CATHEPSIN H PRECURSOR [R. norveglcus], *Homo sapiens* cDNA: FLJ22499 fis, clone HRC11250, highly similar to HSCATHH Human mRNA for cathepsin H (EC 3.4.22.16), cathepsin H, cathepsin W, cathepsin W (lymphopain) |
| 1575 | 19398 | NM_012939 | aa | | |
| 1576 | 223 | NM_012945 | b, cc | diphtheria toxin receptor (heparin-binding epidermal growth factor-like growth factor), heparin binding epidermal growth factor-like growth factor | diphtheria toxin receptor (heparin-binding epidermal growth factor-like growth factor), expressed sequence AW047313, heparin binding epidermal growth factor-like growth factor |
| 1577 | 15058 | NM_012950 | cc | coagulation factor II (thrombin) receptor | ESTs, Weakly similar to GPRY_MOUSE PROBABLE G PROTEIN-COUPLED RECEPTOR GPR34 [*M. musculus*], G protein-coupled receptor 41, G protein-coupled receptor 43, *Rattus norvegicus* protease activated receptor 3 mRNA, complete cds, coagulation factor II (thrombin) receptor |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1579 | 19111 | NM_012963 | g | high mobility group box 1, high-mobility group (nonhistone chromosomal) protein 1 | EST, Moderately similar to A Chain A, Crystal Structure Of Hmg1 Domain A Bound To A Cisplatin- Modified Dna Duplex [R. norvegicus], EST, Weakly similar to A Chain A, Crystal Structure Of Hmg1 Domain A Bound To A Cisplatin- Modified Dna Duplex [R. norvegicus], ESTs, Highly similar to S02826 nonhistone chromosomal protein HMG-1 [H. sapiens], ESTs, Moderately similar to HIGH MOBILITY GROUP PROTEIN HMG1 [M. musculus], RIKEN cDNA 4932431P20 gene, high mobility group box 1, high mobility group box 3, high-mobility group (nonhistone chromosomal) protein 1, high-mobility group (nonhistone chromosomal) protein 1-like 10, high-mobility group (nonhistone chromosomal) protein 1-like 3 |
| 1580 | 19374 | NM_012964 | x | hyaluronan mediated motility receptor (RHAMM), hyaluronan-mediated motility receptor (RHAMM) | Mus musculus 12 days embryo male wolffian duct includes surrounding region cDNA, RIKEN full-length enriched library, clone: 6720466F14, full insert sequence, RIKEN cDNA 0610027D24 gene, TRAF4 associated factor 1, hyaluronan mediated motility receptor (RHAMM), hyaluronan-mediated motility receptor (RHAMM) |
| 1581 | 2554 | NM_012967 | t | intercellular adhesion molecule, intercellular adhesion molecule 1 (CD54), human rhinovirus receptor | Homo sapiens mRNA; cDNA DKFZp434E0516 (from clone DKFZp434E0516), intercellular adhesion molecule, intercellular adhesion molecule 1 (CD54), human rhinovirus receptor, intercellular adhesion molecule 3, intercellular adhesion molecule 5, telencephalin |
| 1581 | 2555 | NM_012967 | t, cc, General | intercellular adhesion molecule, intercellular adhesion molecule 1 (CD54), human rhinovirus receptor | Homo sapiens mRNA; cDNA DKFZp434E0516 (from clone DKFZp434E0516), intercellular adhesion molecule, intercellular adhesion molecule 1 (CD54), human rhinovirus receptor, intercellular adhesion molecule 3, intercellular adhesion molecule 5, telencephalin |
| 1582 | 24528 | NM_012973 | c | potassium voltage-gated channel, lsk-related family, member 1, potassium voltage-gated channel, lsk-related subfamily, member 1 | potassium voltage-gated channel, lsk-related family, member 1, potassium voltage-gated channel, lsk-related subfamily, member 1 |
| 1583 | 956 | NM_012976 | c | | ESTs, Highly similar to LEG9 RAT GALECTIN-9 [R. norvegicus], ESTs, Highly similar to LEG9_HUMAN GALECTIN-9 [H. sapiens], ESTs, Weakly similar to LEG9 RAT GALECTIN-9 [R. norvegicus], expressed sequence AI265545, lectin, galactose binding, soluble 12, lectin, galactose binding, soluble 9, lectin, galactoside-binding, soluble, 9 (galectin 9) |
| 1584 | 16417 | NM_012991 | g | nucleoporin 50 kD, nucleoprotein 50 | nucleoporin 50 kD, nucleoprotein 50 |
| 1585 | 17393 | NM_012992 | d | nucleophosmin (nucleolar phosphoprotein B23, numatrin), nucleophosmin 1 | ESTs, Moderately similar to NPM_HUMAN NUCLEOPHOSMIN [H. sapiens], ESTs, Weakly similar to NPM_HUMAN NUCLEOPHOSMIN [H. sapiens], nucleophosmin (nucleolar phosphoprotein B23, numatrin), nucleophosmin 1, nucleophosmin/nucleoplasmin 3, nucleoplasmin 3 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1586 | 23544 | NM_013013 | s | prosaposin, prosaposin (variant Gaucher disease and variant metachromatic leukodystrophy) | ESTs, Weakly similar to 1504251A sphingolipid activator [*H. sapiens*], RIKEN cDNA 2310020A21 gene, prosaposin, prosaposin (variant Gaucher disease and variant metachromatic leukodystrophy) |
| 1587 | 1588 | NM_013026 | k | syndecan 1 | syndecan 1 |
| 1588 | 17894 | NM_013027 | m | selenoprotein W, 1, selenoprotein W, muscle 1 | ESTs, Weakly similar to SELW MOUSE SELENOPROTEIN W [*M. musculus*], selenoprotein W, 1, selenoprotein W, muscle 1 |
| 1589 | 18300 | NM_013030 | s, v, General | | ESTs, Weakly similar to NPT2 RAT RENAL SODIUM-DEPENDENT PHOSPHATE TRANSPORT PROTEIN 2 [*R. norvegicus*], ESTs, Weakly similar to NPT2_HUMAN RENAL SODIUM-DEPENDENT PHOSPHATE TRANSPORT PROTEIN 2 [*H. sapiens*], *Homo sapiens*, Similar to solute carrier family 34 (sodium phosphate), member 1, clone MGC: 18179 IMAGE: 4155326, mRNA, complete cds, Solute carrier family 17 (sodium/hydrogen exchanger), member 2, expressed sequence AI649385, solute carrier family 34 (sodium phosphate), member 1, solute carrier family 34 (sodium phosphate), member 2 |
| 1589 | 18076 | NM_013030 | g, s, z | solute carrier family 34 (sodium phosphate), member 1 | ESTs, Weakly similar to NPT2 RAT RENAL SODIUM-DEPENDENT PHOSPHATE TRANSPORT PROTEIN 2 [*R. norvegicus*], ESTs, Weakly similar to NPT2_HUMAN RENAL SODIUM-DEPENDENT PHOSPHATE TRANSPORT PROTEIN 2 [*H. sapiens*], *Homo sapiens*, Similar to solute carrier family 34 (sodium phosphate), member 1, clone MGC: 18179 IMAGE: 4155326, mRNA, complete cds, *Rattus norvegicus* mRNA for NaPi-2 alpha, complete cds, expressed sequence AI649385, solute carrier family 34 (sodium phosphate), member 1, solute carrier family 34 (sodium phosphate), member 2 |
| 1589 | 18078 | NM_013030 | s | solute carrier family 34 (sodium phosphate), member 1 | ESTs, Weakly similar to NPT2 RAT RENAL SODIUM-DEPENDENT PHOSPHATE TRANSPORT PROTEIN 2 [*R. norvegicus*], ESTs, Weakly similar to NPT2_HUMAN RENAL SODIUM-DEPENDENT PHOSPHATE TRANSPORT PROTEIN 2 [*H. sapiens*], *Homo sapiens*, Similar to solute carrier family 34 (sodium phosphate), member 1, clone MGC: 18179 IMAGE: 4155326, mRNA, complete cds, *Rattus norvegicus* mRNA for NaPi-2 alpha, complete cds, Solute carrier family 17 (sodium/hydrogen exchanger), member 2, expressed sequence AI649385, solute carrier family 34 (sodium phosphate), member 1, solute carrier family 34 (sodium phosphate), member 2 |
| 1589 | 18077 | NM_013030 | e, s, z | solute carrier family 34 (sodium phosphate), member 1 | ESTs, Weakly similar to NPT2 RAT RENAL SODIUM-DEPENDENT PHOSPHATE TRANSPORT PROTEIN 2 [*R. norvegicus*], ESTs, Weakly similar to NPT2_HUMAN RENAL SODIUM-DEPENDENT PHOSPHATE TRANSPORT PROTEIN 2 [*H. sapiens*], *Homo sapiens*, Similar to solute carrier family 34 (sodium phosphate), member 1, clone MGC: 18179 IMAGE: 4155326, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | mRNA, complete cds, *Rattus norvegicus* mRNA for NaPi-2 alpha, complete cds, expressed sequence AI649385, solute carrier family 34 (sodium phosphate), member 1, solute carrier family 34 (sodium phosphate), member 2 |
| 1591 | 730 | NM_013040 | w | ATP-binding cassette, sub-family C (CFTR/MRP), member 9 | ATP-binding cassette, sub-family C (CFTR/MRP), member 8, ATP-binding cassette, sub-family C (CFTR/MRP), member 9, ESTs, Highly similar to ACC8_HUMAN SULFONYLUREA RECEPTOR 1 [*H. sapiens*], ESTs, Weakly similar to T42728 sulfonylurea receptor 2, isoform B - mouse [*M. musculus*], *Mus musculus* adult male pituitary gland cDNA, RIKEN full-length enriched library, clone: 5330439B14, full insert sequence |
| 1592 | 17401 | NM_013043 | i, o, General | transforming growth factor beta 1 induced transcript 4, transforming growth factor beta-stimulated protein TSC-22 | ESTs, Moderately similar to DIP_HUMAN DIP PROTEIN [*H. sapiens*], delta sleep inducing peptide, immunoreactor, glucocorticoid induced leucine zipper, transforming growth factor beta 1 induced transcript 4, transforming growth factor beta-stimulated protein TSC-22 |
| 1593 | 16684 | NM_013052 | General | tyrosine 3-monooxygenase/tryptophan 5-monooxygenase activation protein, eta polypeptide | 3-monooxgenase/tryptophan 5-monooxgenase activation protein, gamma polypeptide, tyrosine 3-monooxygenase/tryptophan 5-monooxygenase activation protein, eta polypeptide |
| 1594 | 14421 | NM_013053 | u | | RIKEN cDNA 2700028P07 gene, tyrosine 3-monooxygenase/tryptophan 5-monooxygenase activation protein, theta polypeptide |
| 1595 | 15254 | NM_013058 | k | | inhibitor of DNA binding 3, inhibitor of DNA binding 3, dominant negative helix-loop-helix protein |
| 1596 | 14997 | NM_013059 | s, z | | alkaline phosphatase, liver/bone/kidney |
| 1596 | 14996 | NM_013059 | General | | alkaline phosphatase, liver/bone/kidney |
| 1597 | 25676 | NM_013069 | aa | | |
| 1597 | 16924 | NM_013069 | o | | CD74 antigen (invariant polypeptide of major histocompatibility complex, class II antigen-associated), Ia-associated invariant chain, KIAA0275 gene product, sparc/osteonectin, cwcv and kazal-like domains proteoglycan (testican), sparc/osteonectin, cwcv and kazal-like domains proteoglycan 1, sparc/osteonectin, cwcv and kazal-like domains proteoglycan 2 |
| 1598 | 24748 | NM_013070 | h, q | utrophin, utrophin (homologous to dystrophin) | Dystrophin, dystrophin (muscular dystrophy, Duchenne and Becker types), includes DXS142, DXS164, DXS206, DXS230, DXS239, DXS268, DXS269, DXS270, DXS272, dystrophin, muscular dystrophy, dystrophin-related protein 2 A-form splice variant, utrophin, utrophin (homologous to dystrophin) |
| 1599 | 1529 | NM_013082 | d, General | | syndecan 2, syndecan 2 (heparan sulfate proteoglycan 1, cell surface-associated, fibroglycan) |
| 1600 | 1521 | NM_013091 | j, i, z, General | | tumor necrosis factor receptor superfamily, member 12, tumor necrosis factor receptor superfamily, member 12 (translocating chain-association membrane protein), tumor necrosis factor receptor superfamily, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | member 1A, tumor necrosis factor receptor superfamily, member 1a, tumor necrosis factor receptor superfamily, member 1a-like 1, tumor necrosis factor receptor superfamily, member 1a-like 2 |
| 1601 | 1685 | NM_013096 | c, aa | hemoglobin alpha, adult chain 2, hemoglobin, alpha 1 | |
| 1601 | 26150 | NM_013096 | c, i | | |
| 1601 | 1688 | NM_013096 | p | hemoglobin alpha, adult chain 2, hemoglobin, alpha 1 | |
| 1601 | 1689 | NM_013096 | c, p | hemoglobin alpha, adult chain 2, hemoglobin, alpha 1 | EST, Moderately similar to HART1 hemoglobin alpha-1 chain - rat [*R. norvegicus*], ESTs, Moderately similar to HART1 hemoglobin alpha-1 chain - rat [*R. norvegicus*], RIKEN cDNA 2510042H12 gene, hemoglobin alpha, adult chain 1, hemoglobin, alpha 1, hemoglobin, alpha 2 |
| 1601 | 1684 | NM_013096 | c, s, aa | hemoglobin alpha, adult chain 2, hemoglobin, alpha 1 | EST, Moderately similar to HART1 hemoglobin alpha-1 chain - rat [*R. norvegicus*], ESTs, Moderately similar to HART1 hemoglobin alpha-1 chain - rat [*R. norvegicus*], RIKEN cDNA 2510042H12 gene, hemoglobin alpha, adult chain 1, hemoglobin, alpha 1, hemoglobin, alpha 2 |
| 1602 | 20886 | NM_013097 | u, x, bb | | |
| 1602 | 20887 | NM_013097 | u, x, bb | | ESTs, Weakly similar to DRN1 RAT DEOXYRIBONUCLEASE I PRECURSOR [*R. norvegicus*], *Mus musculus* DNaseI precursor mRNA, complete cds, RIKEN cDNA 4733401H14 gene, deoxyribonuclease I, expressed sequence AI788650 |
| 1603 | 1321 | NM_013098 | c | | ESTs, Weakly similar to G6PT RAT GLUCOSE-6-PHOSPHATASE [*R. norvegicus*], *Homo sapiens*, clone IMAGE: 3050476, mRNA, partial cds, RIKEN cDNA 0710001K01 gene, expressed sequence AW545836, glucose-6-phosphatase, catalytic, glucose-6-phosphatase, catalytic (glycogen storage disease type I, von Gierke disease), glucose-6-phosphatase, catalytic, related sequence, islet-specific glucose-6-phosphatase catalytic subunit-related protein |
| 1604 | 15296 | NM_013102 | l, m | FK506 binding protein 1a (12 kDa), FK506-binding protein 1A (12 kD) | ESTs, Moderately similar to 1613455A FK506 binding protein FKBP [*H. sapiens*], FK506 binding protein 1a (12 kDa), FK506 binding protein 1b (12.6 kDa), FK506 binding protein 2 (13 kDa), FK506 binding protein 4 (59 kDa), FK506 binding protein 5 (51 kDa), FK506-binding protein 1A (12 kD) |
| 1606 | 23709 | NM_013113 | o, s, z, aa | | ATPase, Na+/K+ transporting, beta 1 polypeptide |
| 1606 | 23711 | NM_013113 | p | | ATPase, Na+/K+ transporting, beta 1 polypeptide |
| 1606 | 23710 | NM_013113 | s | | ATPase, Na+/K+ transporting, beta 1 polypeptide |
| 1607 | 1976 | NM_013118 | u | | guanylate cyclase activator 1B (retina), guanylate cyclase activator 2 (guanylin 2, intestinal, heatstable), guanylate cyclase activator 2A (guanylin) |
| 1609 | 870 | NM_013130 | h | | MAD (mothers against decapentaplegic, *Drosophila*) homolog 1, MAD (mothers against decapentaplegic, *Drosophila*) homolog 5, MAD (mothers against decapentaplegic, *Drosophila*) homolog 9 |
| 1610 | 16650 | NM_013132 | u, General | annexin A5 | annexin A5 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1611 | 650 | NM_013134 | h | | 3-hydroxy-3-methylglutaryl-Coenzyme A reductase, ESTs, Moderately similar to hydroxymethylglutaryl-CoA reductase [*M. musculus*], SREBP CLEAVAGE-ACTIVATING PROTEIN |
| 1611 | 651 | NM_013134 | h, j, l | | 3-hydroxy-3-methylglutaryl-Coenzyme A reductase, ESTs, Moderately similar to hydroxymethylglutaryl-CoA reductase [*M. musculus*], SREBP CLEAVAGE-ACTIVATING PROTEIN |
| 1612 | 1712 | NM_013138 | General | inositol 1,4,5-triphosphate receptor 3, inositol 1,4,5-triphosphate receptor, type 3 | ESTs, Moderately similar to INOSITOL 1,4,5,-TRISPHOSPHATE-BINDING PROTEIN TYPE 1 RECEPTOR [*M. musculus*], Mus musculus, Similar to Purkinje cell protein 1, clone MGC: 11943 IMAGE: 3600031, mRNA, complete cds, RIKEN cDNA 9330127I20 gene, inositol 1,4,5-triphosphate receptor 1, inositol 1,4,5-triphosphate receptor 2, inositol 1,4,5-triphosphate receptor 5, inositol 1,4,5-triphosphate receptor, type 3 |
| 1613 | 16982 | NM_013144 | o, v, General | | insulin-like growth factor binding protein 1, protease, serine, 11 (IGF binding) |
| 1614 | 21683 | NM_013154 | t, cc, General | CCAAT/enhancer binding protein (C/EBP), delta | CCAAT/enhancer binding protein (C/EBP), delta |
| 1614 | 21682 | NM_013154 | cc | CCAAT/enhancer binding protein (C/EBP), delta | CCAAT/enhancer binding protein (C/EBP), delta |
| 1615 | 3431 | NM_013156 | b, g, n | cathepsin L | ESTs, Weakly similar to CATHEPSIN L PRECURSOR [*M. musculus*], RIKEN cDNA 2310051M13 gene, RIKEN cDNA 4930486L24 gene, cathepsin 7, cathepsin F, cathepsin L, cathepsin L2, cathepsin O |
| 1615 | 25567 | NM_013156 | v, General | | |
| 1615 | 3430 | NM_013156 | General | cathepsin L | ESTs, Weakly similar to CATHEPSIN L PRECURSOR [*M. musculus*], RIKEN cDNA 2310051M13 gene, RIKEN cDNA 4930486L24 gene, cathepsin 7, cathepsin F, cathepsin L, cathepsin L2, cathepsin O |
| 1616 | 1309 | NM_013159 | w | | RIKEN cDNA 4833415K22 gene, expressed sequence AA675336, insulin degrading enzyme, insulin-degrading enzyme |
| 1616 | 1310 | NM_013159 | w | | RIKEN cDNA 4833415K22 gene, expressed sequence AA675336, insulin degrading enzyme, insulin-degrading enzyme |
| 1617 | 21723 | NM_013174 | w | | TGF beta 2 protein, transforming growth factor, beta 2, transforming growth factor, beta 3 |
| 1618 | 1314 | NM_013181 | m | | EST, Moderately similar to CAMP-DEPENDENT PROTEIN KINASE TYPE I-ALPHA REGULATORY CHAIN [*R. norvegicus*], protein kinase, cAMP dependent regulatory, type 1, alpha, protein kinase, cAMP dependent regulatory, type I beta, protein kinase, cAMP-dependent, regulatory, type I, alpha (tissue specific extinguisher 1) |
| 1619 | 17357 | NM_013183 | p, bb, General | meprin 1 beta, meprin A, beta | expressed sequence C87576, meprin 1 beta, meprin A, beta |
| 1620 | 1300 | NM_013190 | y | | *Mus musculus* adult male stomach cDNA, RIKEN full-length enriched library, clone: 2210403E17, full insert sequence, expressed sequence AA407869, phosphofructokinase, liver, phosphofructokinase, liver, B-type, phosphofructokinase, muscle |
| 1621 | 16448 | NM_013197 | c | | EST, Highly similar to HEM0 RAT 5-AMINOLEVULINIC ACID SYNTHASE, ERYTHROID-SPECIFIC, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | MITOCHONDRIAL PRECURSOR [*R. norvegicus*], ESTs, Highly similar to SYHUAE 5-aminolevulinate synthase [*H. sapiens*], aminolevulinate, delta-, synthase 2 (sideroblastic/hypochromic anemia), aminolevulinic acid synthase 1, aminolevulinic acid synthase 2, erythroid, glycine C-acetyltransferase (2-amino-3-ketobutyrate coenzyme A ligase), glycine C-acetyltransferase (2-amino-3-ketobutyrate-coenzyme A ligase) |
| 1622 | 20856 | NM_013200 | b | carnitine palmitoyltransferase 1, muscle, carnitine palmitoyltransferase I, muscle | ESTs, Moderately similar to CPTM RAT CARNITINE O-PALMITOYLTRANSFERASE I, MITOCHONDRIAL MUSCLE ISOFORM [*R. norvegicus*], ESTs, Weakly similar to CPT1 MOUSE CARNITINE O-PALMITOYLTRANSFERASE I, MITOCHONDRIAL LIVER ISOFORM [*M. musculus*], carnitine palmitoyltransferase 1, liver, carnitine palmitoyltransferase 1, muscle, carnitine palmitoyltransferase I, muscle |
| 1623 | 397 | NM_013214 | f | | |
| 1624 | 20864 | NM_013215 | g, n, y | | ESTs, Highly similar to AR72_HUMAN AFLATOXIN B1 ALDEHYDE REDUCTASE 1 (AFB1-AR 1) (ALDOKETOREDUCTASE 7) [*H. sapiens*], ESTs, Moderately similar to AFAR RAT AFLATOXIN B1 ALDEHYDE REDUCTASE [*R. norvegicus*], RIKEN cDNA 0610025K21 gene, *Rattus norvegicus* aiar mRNA for androgen-inducible aldehyde reductase, complete cds, aldo-keto reductase family 7, member A2 (aflatoxin aldehyde reductase), aldo-keto reductase family 7, member A3 (aflatoxin aldehyde reductase) |
| 1625 | 20728 | NM_013217 | v | | ESTs, Moderately similar to T30989 serine/threonine protein kinase NIK - mouse [*M. musculus*], *Mus musculus*, Similar to zinc finger protein 347, clone MGC: 18913 IMAGE: 4242025, mRNA, complete cds, RIKEN cDNA 1500031A17 gene, mitogen-activated protein kinase kinase kinase kinase 4, mitogen-activated protein kinase kinase kinase kinase 6, myeloid/lymphoid or mixed-lineage leukemia (trithorax (*Drosophila*) homolog); translocated to, 4, syntaxin binding protein 4 |
| 1626 | 1396 | NM_013222 | j | growth factor, erv1 (*S. cerevisiae*)-like (augmenter of liver regeneration) | ESTs, Highly similar to ALR RAT AUGMENTER OF LIVER REGENERATION [*R. norvegicus*], growth factor, erv1 (*S. cerevisiae*)-like (augmenter of liver regeneration) |
| 1627 | 815 | NM_013224 | w | | ESTs, Highly similar to RS26_HUMAN 40S RIBOSOMAL PROTEIN S26 [*H. sapiens*], *Homo sapiens*, clone IMAGE: 4100953, mRNA, Human DNA sequence from PAC 384D21 on chromosome X contains ribosomal protein S26 pseudogene, STS, polymerase (RNA) II (DNA directed) polypeptide D, ribosomal protein S26 |
| 1628 | 18305 | NM_013226 | v | | |
| 1629 | 21078 | NM_016986 | d | acetyl-Coenzyme A dehydrogenase, medium chain, acyl-Coenzyme A dehydrogenase, C-4 to C- | ESTs, Highly similar to ACDM MOUSE ACYL-COA DEHYDROGENASE, MEDIUM-CHAIN SPECIFIC PRECURSOR [*M. musculus*], acetyl- |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | 12 straight chain | Coenzyme A dehydrogenase, medium chain, acyl-Coenzyme A dehydrogenase, C-4 to C-12 straight chain, expressed sequence AI987948 |
| 1630 | 24649 | NM_016988 | v | acid phosphatase 2, lysosomal | ESTs, Weakly similar to PPAL RAT LYSOSOMAL ACID PHOSPHATASE PRECURSOR [*R. norvegicus*], acid phosphatase 2, lysosomal, acid phosphatase 6, lysophosphatidic, acid phosphatase, prostate, acid phosphatase, testicular |
| 1631 | 15239 | NM_016989 | q, w | | EST, Weakly similar to RL15 RAT 60S RIBOSOMAL PROTEIN L15 [*R. norvegicus*], ESTs, Highly similar to RL15_HUMAN 60S RIBOSOMAL PROTEIN L15 [*H. sapiens*], ESTs, Moderately similar to RL15 RAT 60S RIBOSOMAL PROTEIN L15 [*R. norvegicus*], RIKEN cDNA 2510008H07 gene, ribosomal protein L15 |
| 1632 | 45 | NM_016996 | General | calcium-sensing receptor, calcium-sensing receptor (hypocalcluric hypercalcemia 1, severe neonatal hyperparathyroidism) | EST, Weakly similar to EXTRACELLULAR CALCIUM-SENSING RECEPTOR PRECURSOR [*R. norvegicus*], ESTs, Weakly similar to CASR_HUMAN EXTRACELLULAR CALCIUM-SENSING RECEPTOR PRECURSOR [*H. sapiens*], ESTs, Weakly similar to JC7160 metabotropic glutamate receptor subtype 3 precursor - mouse [*M. musculus*], G protein coupled receptor, family C, group 1, member A, G protein coupled receptor, family C, group 1, member C, calcium-sensing receptor (hypocalciuric hypercalcemia 1, severe neonatal hyperparathyroidism), vomeronasal 2, receptor, 11, vomeronasal 2, receptor, 12 |
| 1633 | 20714 | NM_016999 | t | cytochrome P450, subfamily IV B, polypeptide 1, cytochrome P450, subfamily IVB, polypeptide 1 | *Mus musculus*, Similar to cytochrome P450, 4a10, clone MGC: 25972 IMAGE: 4240359, mRNA, complete cds, RIKEN cDNA A230105L22 gene, cytochrome P450, 4a10, cytochrome P450, 4a14, cytochrome P450, subfamily IVA, polypeptide 11 |
| 1633 | 20713 | NM_016999 | t | cytochrome P450, subfamily IV B, polypeptide 1, cytochrome P450, subfamily IVB, polypeptide 1 | *Mus musculus*, Similar to cytochrome P450, 4a10, clone MGC: 25972 IMAGE: 4240359, mRNA, complete cds, RIKEN cDNA A230105L22 gene, cytochrome P450, 4a10, cytochrome P450, 4a14, cytochrome P450, subfamily IVA, polypeptide 11 |
| 1633 | 20711 | NM_016999 | q, t | cytochrome P450, subfamily IV B, polypeptide 1, cytochrome P450, subfamily IVB, polypeptide 1 | *Mus musculus*, Similar to cytochrome P450, 4a10, clone MGC: 25972 IMAGE: 4240359, mRNA, complete cds, RIKEN cDNA A230105L22 gene, cytochrome P450, 4a10, cytochrome P450, 4a14, cytochrome P450, subfamily IVA, polypeptide 11 |
| 1633 | 20715 | NM_016999 | q, t | cytochrome P450, subfamily IV B, polypeptide 1, cytochrome P450, subfamily IVB, polypeptide 1 | *Mus musculus*, Similar to cytochrome P450, 4a10, clone MGC: 25972 IMAGE: 4240359, mRNA, complete cds, RIKEN cDNA A230105L22 gene, cytochrome P450, 4a10, cytochrome P450, 4a14, cytochrome P450, subfamily IVA, polypeptide 11 |
| 1634 | 1698 | NM_017000 | e, n, p, General | diaphorase (NADH/NADPH) (cytochrome b-5 reductase), diaphorase 4 (NADH/NADPH) | ESTs, Weakly similar to DHQU RAT NAD(P)H DEHYDROGENASE [*R. norvegicus*], NAD(P)H menadione oxidoreductase 2, dioxin inducible, NAD(P)H menadione oxidoreductase 2, dioxin-inducible, diaphorase (NADH/NADPH) (cytochrome b-5 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | reductase), diaphorase 4 (NADH/NADPH) |
| 1635 | 1399 | NM_017006 | h, n, General | glucose-6-phosphate dehydrogenase, glucose-6-phosphate dehydrogenase X-linked | glucose-6-phosphate dehydrogenase, glucose-6-phosphate dehydrogenase 2, glucose-6-phosphate dehydrogenase X-linked, hexose-6-phosphate dehydrogenase (glucose 1-dehydrogenase) |
| 1637 | 18989 | NM_017013 | n | glutathione S-transferase A2, glutathione S-transferase, alpha 2 (Yc2) | glutathione S-transferase A2, glutathione S-transferase, alpha 2 (Yc2) |
| 1638 | 21013 | NM_017014 | e, f | glutathione S-transferase M2 (muscle), glutathione S-transferase, mu 2 | ESTs, Moderately similar to GLUTATHIONE S-TRANSFERASE YB1 [*R. norvegicus*], glutathione S-transferase M1, glutathione S-transferase, mu 1 |
| 1638 | 21015 | NM_017014 | e, General | glutathione S-transferase M2 (muscle), glutathione S-transferase, mu 2 | ESTs, Moderately similar to GLUTATHIONE S-TRANSFERASE YB1 [*R. norvegicus*], glutathione S-transferase M1, glutathione S-transferase, mu 1 |
| 1639 | 11836 | NM_017023 | b | potassium inwardly-rectifying channel, subfamily J, member 1 | EST, Weakly similar to IRKF MOUSE ATP-SENSITIVE INWARD RECTIFIER POTASSIUM CHANNEL 15 [*M. musculus*], potassium inwardly-rectifying channel, subfamily J, member 1, potassium inwardly-rectifying channel, subfamily J, member 10, potassium inwardly-rectifying channel, subfamily J, member 15 |
| 1639 | 5475 | NM_017023 | b | potassium inwardly-rectifying channel, subfamily J, member 1 | EST, Weakly similar to IRKF MOUSE ATP-SENSITIVE INWARD RECTIFIER POTASSIUM CHANNEL 15 [*M. musculus*], potassium inwardly-rectifying channel, subfamily J, member 1, potassium inwardly-rectifying channel, subfamily J, member 10, potassium inwardly-rectifying channel, subfamily J, member 15 |
| 1639 | 25546 | NM_017023 | b, bb | | |
| 1640 | 17807 | NM_017025 | i, General | lactate dehydrogenase 1, A chain, lactate dehydrogenase A | ESTs, Highly similar to DEHULM L-lactate dehydrogenase [*H. sapiens*], ESTs, Moderately similar to DEHULM L-lactate dehydrogenase [*H. sapiens*], ESTs, Moderately similar to L-LACTATE DEHYDROGENASE M CHAIN [*R. norvegicus*], ESTs, Weakly similar to DEMSLM L-lactate dehydrogenase [*M. musculus*], *Homo sapiens*, Similar to lactate dehydrogenase 1, A chain, clone MGC: 23940 IMAGE: 3935569, mRNA, complete cds, expressed sequence AI326310, lactate dehydrogenase 1, A chain, lactate dehydrogenase A, lactate dehydrogenase C |
| 1641 | 24597 | NM_017040 | u | protein phosphatase 2 (formerly 2A), catalytic subunit, beta isoform, protein phosphatase 2a, catalytic subunit, beta isoform | *Mus musculus* adult female placenta cDNA, RIKEN full-length enriched library, clone: 1600017J22, full insert sequence, RIKEN cDNA 2310003C10 gene, expressed sequence AI115466, protein phosphatase 2 (formerly 2A), catalytic subunit, beta isoform, protein phosphatase 2a, catalytic subunit, beta isoform, protein phosphatase 4, catalytic subunit |
| 1642 | 24696 | NM_017048 | f, j, z | solute carrier family 4 (anion exchanger), member 2, solute carrier family 4, anion exchanger, member 2 (erythrocyte membrane protein band 3- | ESTs, Moderately similar to A25104 band 3 protein, nonerythroid [*H. sapiens*], Human DNA sequence from clone RP4-794I6 on chromosome 20 Contains a gene for a putative oncogene protein, parts of 2 novel |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | like 1) | genes, ESTs, STSs, GSSs and CpG islands, solute carrier family 4 (anion exchanger), member 2, solute carrier family 4, anion exchanger, member 2 (erythrocyte membrane protein band 3-like 1), solute carrier family 4, sodium bicarbonate cotransporter, member 4, solute carrier family 4, sodium bicarbonate cotransporter, member 9, solute carrier family 4, sodium bicarbonate transporter-like, member 11 |
| 1643 | 24695 | NM_017049 | u | | EST, Highly similar to B3A3 RAT ANION EXCHANGE PROTEIN 3 [*R. norvegicus*], ESTs, Weakly similar to I38496 anion exchanger 3 brain isoform [*H. sapiens*], Human DNA sequence from clone RP4-794I6 on chromosome 20 Contains a gene for a putative oncogene protein, parts of 2 novel genes, ESTs, STSs, GSSs and CpG islands, solute carrier family 4 (anion exchanger), member 3, solute carrier family 4, anion exchanger, member 3, solute carrier family 4, sodium bicarbonate transporter-like, member 11 |
| 1644 | 20876 | NM_017050 | j, n, z | superoxide dismutase 1, soluble, superoxide dismutase 1, soluble (amyotrophic lateral sclerosis 1 (adult)) | ESTs, Moderately similar to SUPEROXIDE DISMUTASE [*M. musculus*], copper chaperone for superoxide dismutase, superoxide dismutase 1, soluble, superoxide dismutase 1, soluble (amyotrophic lateral sclerosis 1 (adult)) |
| 1645 | 910 | NM_017059 | f, l, m | BCL2-associated X protein, Bcl2-associated X protein | BCL2-associated X protein, Bcl2-associated X protein |
| 1645 | 912 | NM_017059 | i | BCL2-associated X protein, Bcl2-associated X protein | BCL2-associated X protein, Bcl2-associated X protein |
| 1646 | 1946 | NM_017061 | h | lysyl oxidase | ESTs, Moderately similar to LYOX_HUMAN PROTEIN-LYSINE 6-OXIDASE PRECURSOR [*H. sapiens*], ESTs, Moderately similar to PROTEIN-LYSINE 6-OXIDASE PRECURSOR [*R. norvegicus*], hypothetical protein FLJ21889, lysyl oxidase, lysyl oxidase-like, lysyl oxidase-like 1, lysyl oxidase-like 2 |
| 1646 | 1942 | NM_017061 | t, General | lysyl oxidase | ESTs, Moderately similar to LYOX_HUMAN PROTEIN-LYSINE 6-OXIDASE PRECURSOR [*H. sapiens*], ESTs, Moderately similar to PROTEIN-LYSINE 6-OXIDASE PRECURSOR [*R. norvegicus*], hypothetical protein FLJ21889, lysyl oxidase, lysyl oxidase-like, lysyl oxidase-like 1, lysyl oxidase-like 2 |
| 1646 | 1943 | NM_017061 | t | lysyl oxidase | ESTs, Moderately similar to LYOX_HUMAN PROTEIN-LYSINE 6-OXIDASE PRECURSOR [*H. sapiens*], ESTs, Moderately similar to PROTEIN-LYSINE 6-OXIDASE PRECURSOR [*R. norvegicus*], hypothetical protein FLJ21889, lysyl oxidase, lysyl oxidase-like, lysyl oxidase-like 1, lysyl oxidase-like 2 |
| 1647 | 6062 | NM_017066 | d | pleiotrophin, pleiotrophin (heparin binding growth factor 8, neurite growth-promoting factor 1) | EST, Moderately similar to JH0385 midkine precursor [*H. sapiens*], EST, Weakly similar to PTN MOUSE PLEIOTROPHIN PRECURSOR [*R. norvegicus*], midkine, midkine (neurite growth-promoting factor 2), pleiotrophin, pleiotrophin (heparin |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1648 | 6654 | NM_017068 | w | lysosomal membrane glycoprotein 2, lysosomal-associated membrane protein 2 | binding growth factor 8, neurite growth-promoting factor 1) CD68 antigen, ESTs, Highly similar to LMP2 RAT LYSOSOME-ASSOCIATED MEMBRANE GLYCOPROTEIN 2 PRECURSOR [R. norvegicus], ESTs, Weakly similar to A48042 lysosomal membrane glycoprotein lamp-2 homolog [H. sapiens], lysosomal membrane glycoprotein 2, lysosomal-associated membrane protein 2 |
| 1649 | 11153 | NM_017073 | s | glutamate-ammonia ligase (glutamine synthase), glutamine synthetase | glutamate-ammonia ligase (glutamine synthase), glutamine synthetase |
| 1650 | 923 | NM_017076 | General | | DNA segment, Chr 7, ERATO Doi 458, expressed, RIKEN cDNA 2610301B19 gene, RIKEN cDNA 3830421F03 gene, poliovirus receptor, poliovirus receptor-related 2 (herpesvirus entry mediator B), poliovirus receptor-related 3, poliovirus sensitivity, tumor-associated antigen 1 |
| 1651 | 1523 | NM_017079 | s | | CD1B antigen, b polypeptide, CD1D antigen, d polypeptide, CD1E antigen, e polypeptide, CD1d1 antigen, CD1d2 antigen |
| 1652 | 23660 | NM_017080 | s | hydroxysteroid (11-beta) dehydrogenase 1, hydroxysteroid 11-beta dehydrogenase 1 | DNA segment, Chr 14, University of California at Los Angeles 2, ESTs, Weakly similar to CORTICOSTEROID 11-BETA-DEHYDROGENASE, ISOZYME 1 [R. norvegicus], expressed sequence C79874, hydroxysteroid (11-beta) dehydrogenase 1, hydroxysteroid 11-beta dehydrogenase 1, hydroxysteroid 17-beta dehydrogenase 11, retinal short-chain dehydrogenase/reductase retSDR2 |
| 1653 | 275 | NM_017081 | b, d, General | hydroxysteroid (11-beta) dehydrogenase 2, hydroxysteroid 11-beta dehydrogenase 2 | Mus musculus, Similar to hydroxysteroid 11-beta dehydrogenase 2, clone MGC: 25647 IMAGE: 4235545, mRNA, complete cds, hydroxysteroid (11-beta) dehydrogenase 2 |
| 1654 | 16211 | NM_017082 | j, s, z | uromodulin, uromodulin (uromucoid, Tamm-Horsfall glycoprotein) | RIKEN cDNA 2310037I18 gene, tectorin beta, uromodulin, uromodulin (uromucoid, Tamm-Horsfall glycoprotein), zona pellucida glycoprotein 1 |
| 1655 | 1552 | NM_017084 | j | glycine N-methyltransferase | glycine N-methyltransferase |
| 1655 | 1550 | NM_017084 | y | glycine N-methyltransferase | glycine N-methyltransferase |
| 1656 | 22552 | NM_017087 | a, k, x | biglycan | ESTs, Weakly similar to BONE/CARTILAGE PROTEOGLYCAN I PRECURSOR [R. norvegicus], ESTs, Weakly similar to PGS1_HUMAN BONE/CARTILAGE PROTEOGLYCAN I PRECURSOR [H. sapiens], asporin, asporin (LRR class 1), biglycan, opticin |
| 1657 | 8888 | NM_017090 | m | guanylate cyclase 1, soluble, alpha 3 | ESTs, Weakly similar to ANPA MOUSE ATRIAL NATRIURETIC PEPTIDE RECEPTOR A PRECURSOR [M. musculus], ESTs, Weakly similar to GUANYLATE CYCLASE SOLUBLE, ALPHA-1 CHAIN [R. norvegicus], guanylate cyclase 1, soluble, alpha 2, guanylate cyclase 1, soluble, alpha 3, guanylate cyclase 1, soluble, beta 3, natriuretic peptide receptor 1, soluble guanylyl cyclase alpha2 subunit |
| 1658 | 10887 | NM_017094 | a, General | growth hormone receptor | growth hormone receptor |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1659 | 4393 | NM_017101 | a, y | peptidylprolyl isomerase A, peptidylprolyl isomerase A (cyclophilin A) | ESTs, Highly similar to A Chain A, Cyclophilin A [*H. sapiens*], ESTs, Weakly similar to PEPTIDYL-PROLYL CIS-TRANS ISOMERASE A [*R. norvegicus*], KIAA1228 protein, RIKEN cDNA 2310076N22 gene, RIKEN cDNA 4930520F12 gene, expressed sequence AI256741, expressed sequence AW457192, peptidylprolyl isomerase A, peptidylprolyl isomerase A (cyclophilin A), peptidylprolyl isomerase E (cyclophilin E) |
| 1660 | 24770 | NM_017111 | d | solute carrier family 21 (organic anion transporter), member 1 | blood-brain barrier specific anion transporter, solute carrier family (organic anion transporter) member 10, solute carrier family 21 (organic anion transporter), member 1, solute carrier family 21 (organic anion transporter), member 10, solute carrier family 21 (organic anion transporter), member 14, solute carrier family 21 (organic anion transporter), member 3, solute carrier family 21 (organic anion transporter), member 6, solute carrier family 21 (organic anion transporter), member 8 |
| 1661 | 20745 | NM_017113 | e | granulin | granulin |
| 1661 | 20746 | NM_017113 | a | granulin | granulin |
| 1662 | 1375 | NM_017122 | w | hippocalcin | DNA segment, Chr 15, ERATO Doi 412, expressed, ESTs, Highly similar to HIPP RAT NEURON SPECIFIC CALCIUM-BINDING PROTEIN HIPPOCALCIN [*R. norvegicus*], ESTs, Highly similar to VIS3 MOUSE VISININ LIKE PROTEIN 3 [*M. musculus*], hippocalcin, hippocalcin-like 1, hypothetical protein FLJ20481 |
| 1663 | 12903 | NM_017124 | k | CD37 antigen | CD37 antigen, EST, Highly similar to A47629 cell surface glycoprotein CD37 [*H. sapiens*], *Mus musculus*, Similar to CD37 antigen, clone MGC: 7983 IMAGE: 3585492, mRNA, complete cds, oculospanin |
| 1664 | 24885 | NM_017138 | r | laminin receptor 1 (67 kD, ribosomal protein SA) | EST, Moderately similar to 40S RIBOSOMAL PROTEIN SA [*R. norvegicus*], ESTs, Highly similar to A31233 ribosomal protein RS.40K, cytosolic [*H. sapiens*], ESTs, Highly similar to A56880 laminin receptor, 67K [*H. sapiens*], ESTs, Moderately similar to A29395 ribosomal protein RS.40K - mouse [*M. musculus*], ESTs, Weakly similar to 1405340A protein 40 kD [*M. musculus*], Homo sapiens laminin receptor-like protein LAMRL5 mRNA, complete cds, laminin receptor 1 (67 kD, ribosomal protein SA) |
| 1664 | 24886 | NM_017138 | d, q | laminin receptor 1 (67 kD, ribosomal protein SA) | EST, Moderately similar to 40S RIBOSOMAL PROTEIN SA [*R. norvegicus*], ESTs, Highly similar to A31233 ribosomal protein RS.40K, cytosolic [*H. sapiens*], ESTs, Highly similar to A56880 laminin receptor, 67K [*H. sapiens*], ESTs, Moderately similar to A29395 ribosomal protein RS.40K - mouse [*M. musculus*], ESTs, Weakly similar to 1405340A protein 40 kD [*M. musculus*], Homo sapiens laminin receptor-like protein LAMRL5 mRNA, complete cds, laminin receptor 1 (67 kD, ribosomal protein SA) |
| 1665 | 15363 | NM_017147 | n, u | cofilin 1 (non-muscle), cofilin 1, non-muscle | EST, Moderately similar to COF1_HUMAN COFILIN, NON- |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1666 | 13392 | NM_017148 | u, General | | MUSCLE ISOFOR [*H. sapiens*], ESTs, Highly similar to DEST_HUMAN DESTRIN [*H. sapiens*], ESTs, Moderately similar to COF1 RAT COFILIN, NON-MUSCLE ISOFORM [*R. norvegicus*], ESTs, Moderately similar to COF1_HUMAN COFILIN, NON-MUSCLE ISOFOR [*H. sapiens*], cofilin 1 (non-muscle), cofilin 1, non-muscle, cofilin 2 (muscle), cofilin 2, muscle, destrin<br>EST, Moderately similar to CYSR RAT CYSTEINE-RICH PROTEIN 1 [*R. norvegicus*], ESTs, Weakly similar to CYSR RAT CYSTEINE-RICH PROTEIN 1 [*R. norvegicus*], ESTs, Weakly similar to S12658 cysteine-rich protein [*H. sapiens*], cysteine and glycine-rich protein 1, cysteine rich protein, cysteine-rich protein 2, cysteine-rich protein 3, epithelial protein lost in neoplasm beta, thymus LIM protein |
| 1667 | 5351 | NM_017150 | q | ribosomal protein L29 | EST, Moderately similar to 60S RIBOSOMAL PROTEIN L29 [*R. norvegicus*], EST, Weakly similar to S65784 ribosomal protein L29, cytosolic [*H. sapiens*], ESTs, Highly similar to S65784 ribosomal protein L29, cytosolic [*H. sapiens*], ESTs, Weakly similar to 60S RIBOSOMAL PROTEIN L29 [*M. musculus*], Human DNA sequence from clone RP4-595K12 on chromosome 1p31.2-31.3 Contains a pseudogene similar to 60S RPL29 (ribosomal protein L29 (cell surface heparin binding protein HIP)), a chromosome 1 specific mRNA (KIAA0499), a novel mRNA (KIAA0433), ESTs, STSs, GSSs and a CpG Island, ribosomal protein L29 |
| 1668 | 16954 | NM_017151 | a, n | ribosomal protein S15 | EST, Moderately similar to R3HU15 ribosomal protein S15, cytosolic [*H. sapiens*], EST, Weakly similar to 40S RIBOSOMAL PROTEIN S15 [*R. norvegicus*], ESTs, Highly similar to R3HU15 ribosomal protein S15, cytosolic [*H. sapiens*], *Homo sapiens*, clone IMAGE: 4479080, mRNA, partial cds, ribosomal protein S15 |
| 1669 | 21643 | NM_017152 | g | ribosomal protein S17 | EST, Weakly similar to 40S RIBOSOMAL PROTEIN S17 [*M. musculus*], ESTs, Highly similar to R4HU17 ribosomal protein S17, cytosolic [*H. sapiens*], ESTs, Moderately similar to R4HU17 ribosomal protein S17, cytosolic [*H. sapiens*], ribosomal protein S17 |
| 1670 | 1694 | NM_017153 | a, q | ribosomal protein S3A, ribosomal protein S3a | EST, Weakly similar to RS3A MOUSE 40S RIBOSOMAL PROTEIN S3A [*M. musculus*], ESTs, Highly similar to JC4662 ribosomal protein S3a, cytosolic [*H. sapiens*], ribosomal protein S3A, ribosomal protein S3a |
| 1671 | 17104 | NM_017160 | bb, General | ribosomal protein S6 | EST, Moderately similar to R3HU6 ribosomal protein S6, cytosolic [*H. sapiens*], EST, Weakly similar to 40S RIBOSOMAL PROTEIN S6 [*R. norvegicus*], ESTs, Moderately similar to 40S RIBOSOMAL PROTEIN S6 [*M. musculus*], *Homo sapiens* cDNA: FLJ23534 fis, clone LNG06974, highly similar to HUMRPS6A Human ribosomal protein S6 mRNA, RIKEN |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1671 | 17106 | NM_017160 | u | ribosomal protein S6 | cDNA 5830405M20 gene, ribosomal protein S6 EST, Moderately similar to R3HU6 ribosomal protein S6, cytosolic [*H. sapiens*], EST, Weakly similar to 40S RIBOSOMAL PROTEIN S6 [*R. norvegicus*], ESTs, Moderately similar to 40S RIBOSOMAL PROTEIN S6 [*M. musculus*], *Homo sapiens* cDNA: FLJ23534 fis, clone LNG06974, highly similar to HUMRPS6A Human ribosomal protein S6 mRNA, RIKEN cDNA 5830405M20 gene, ribosomal protein S6 |
| 1671 | 17107 | NM_017160 | d, e | ribosomal protein S6 | EST, Moderately similar to R3HU6 ribosomal protein S6, cytosolic [*H. sapiens*], EST, Weakly similar to 40S RIBOSOMAL PROTEIN S6 [*R. norvegicus*], ESTs, Moderately similar to 40S RIBOSOMAL PROTEIN S6 [*M. musculus*], *Homo sapiens* cDNA: FLJ23534 fis, clone LNG06974, highly similar to HUMRPS6A Human ribosomal protein S6 mRNA, RIKEN cDNA 5830405M20 gene, ribosomal protein S6 |
| 1672 | 17686 | NM_017165 | n, q | glutathione peroxidase 4, glutathione peroxidase 4 (phospholipid hydroperoxidase) | EST, Moderately similar to T02747 phospholipid-hydroperoxide glutathione peroxidase [*H. sapiens*], EST, Weakly similar to T02747 phospholipid-hydroperoxide glutathione peroxidase [*H. sapiens*], ESTs, Weakly similar to GSHH RAT PHOSPHOLIPID HYDROPEROXIDE GLUTATHIONE PEROXIDASE [*R. norvegicus*], *Homo sapiens* PRO2893 mRNA, complete cds, RIKEN cDNA 2310016C16 gene, RIKEN cDNA 3110050F08 gene, glutathione peroxidase 4, glutathione peroxidase 4 (phospholipid hydroperoxidase) |
| 1673 | 20702 | NM_017166 | c | leukemia-associated gene, stathmin 1/oncoprotein 18 | ESTs, Weakly similar to STHM MOUSE STATHMIN [*M. musculus*], *Homo sapiens* (clone B3B3E13) Huntington's disease candidate region mRNA fragment, leukemia-associated gene, stathmin 1/oncoprotein 18 |
| 1674 | 3513 | NM_017177 | r | choline kinase-like, choline/ethanolamine kinase | EST, Weakly similar to KICE MOUSE CHOLINE/ETHANOLAMINE KINASE [*M. musculus*], ESTs, Weakly similar to KICE RAT CHOLINE/ETHANOLAMINE KINASE [*R. norvegicus*], *Homo sapiens*, Similar to hypothetical protein FLJ10761, clone MGC: 19512 IMAGE: 4329734, mRNA, complete cds, *Mus musculus* mRNA for choline/ethanolamine kinase, complete cds, RIKEN cDNA 4930555L11 gene, choline kinase-like, choline/ethanolamine kinase, ethanolamine kinase, hypothetical protein FLJ10761 |
| 1675 | 19031 | NM_017180 | v, General | T-cell death associated gene, pleckstrin homology-like domain, family A, member 1 | ESTs, Weakly similar to S58222 PQ-rich protein [*H. sapiens*], MARCKS-like protein, *Mus musculus* 8 days embryo cDNA, RIKEN full-length enriched library, clone: 5730519L10, full insert sequence, Myristoylated alanine-rich protein kinase C substrate, myristoylated alanine rich protein kinase C substrate, myristoylated alanine-rich protein kinase C substrate (MARCKS, 80K-L), pleckstrin |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1676 | 15437 | NM_017187 | x, z | | homology-like domain, family A, member 1, pleckstrin homology-like domain, family A, member 3, tumor suppressing subtransferable candidate 3 EST, Moderately similar to HMG2 RAT HIGH MOBILITY GROUP PROTEIN HMG2 [*R. norvegicus*], EST, Weakly similar to HMG2 RAT HIGH MOBILITY GROUP PROTEIN HMG2 [*R. norvegicus*], ESTs, Weakly similar to 2001363A high mobility group protein 2 [*H. sapiens*], ESTs, Weakly similar to HMG2 RAT HIGH MOBILITY GROUP PROTEIN HMG2 [*R. norvegicus*], Human DNA sequence from clone RP3-527B10 on chromosome 6q25.1-25.3 Contains a pseudogene similar to HMG (high mobility group) protein, STSs and GSSs, Human DNA sequence from clone RP5-1007G16 on chromosome 1p34.2-35.3. Contains part of the gene for a novel CUB and Sushi (SCR repeat) domain protein, a novel high-mobility group (nonhistone chromosomal) protein 2 (HMG2) like protein (pseudo) gene, a heat shock 60 kD protein 1 (chaperonin) (HSPD1) pseudogene, ESTs, STSs and GSSs, RIKEN cDNA 2610021J01 gene, expressed sequence AI326135, expressed sequence C80539, high mobility group box 2, high-mobility group (nonhistone chromosomal) protein 2 |
| 1676 | 15433 | NM_017187 | y | | EST, Moderately similar to HMG2 RAT HIGH MOBILITY GROUP PROTEIN HMG2 [*R. norvegicus*], EST, Weakly similar to HMG2 RAT HIGH MOBILITY GROUP PROTEIN HMG2 [*R. norvegicus*], ESTs, Weakly similar to 2001363A high mobility group protein 2 [*H. sapiens*], ESTs, Weakly similar to HMG2 RAT HIGH MOBILITY GROUP PROTEIN HMG2 [*R. norvegicus*], Human DNA sequence from clone RP3-527B10 on chromosome 6q25.1-25.3 Contains a pseudogene similar to HMG (high mobility group) protein, STSs and GSSs, Human DNA sequence from clone RP5-1007G16 on chromosome 1p34.2-35.3. Contains part of the gene for a novel CUB and Sushi (SCR repeat) domain protein, a novel high-mobility group (nonhistone chromosomal) protein 2 (HMG2) like protein (pseudo) gene, a heat shock 60 kD protein 1 (chaperonin) (HSPD1) pseudogene, ESTs, STSs and GSSs, RIKEN cDNA 2610021J01 gene, expressed sequence AI326135, expressed sequence C80539, high mobility group box 2, high-mobility group (nonhistone chromosomal) protein 2 |
| 1676 | 15434 | NM_017187 | x, z | | EST, Moderately similar to HMG2 RAT HIGH MOBILITY GROUP PROTEIN HMG2 [*R. norvegicus*], EST, Weakly similar to HMG2 RAT HIGH MOBILITY GROUP PROTEIN HMG2 [*R. norvegicus*], ESTs, Weakly similar to 2001363A high mobility group protein 2 [*H. sapiens*], ESTs, Weakly |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | similar to HMG2 RAT HIGH MOBILITY GROUP PROTEIN HMG2 [*R. norvegicus*], Human DNA sequence from clone RP3-527B10 on chromosome 6q25.1-25.3 Contains a pseudogene similar to HMG (high mobility group) protein, STSs and GSSs, Human DNA sequence from clone RP5-1007G16 on chromosome 1p34.2-35.3. Contains part of the gene for a novel CUB and Sushi (SCR repeat) domain protein, a novel high-mobility group (nonhistone chromosomal) protein 2 (HMG2) like protein (pseudo) gene, a heat shock 60 kD protein 1 (chaperonin) (HSPD1) pseudogene, ESTs, STSs and GSSs, RIKEN cDNA 2610021J01 gene, expressed sequence AI326135, expressed sequence C80539, high mobility group box 2, high-mobility group (nonhistone chromosomal) protein 2 |
| 1677 | 24437 | NM_017190 | p | malignancy-associated protein, myelin-associated glycoprotein | CD33 antigen, CD33 antigen (gp67), ESTs, Weakly similar to MYELIN-ASSOCIATED GLYCOPROTEIN PRECURSOR [*R. norvegicus*], *Homo sapiens* HSPC078 mRNA, partial cds, myelin associated glycoprotein, myelin-associated glycoprotein |
| 1678 | 1542 | NM_017193 | j, l, m, z | L-kynurenine/alpha-aminoadipate aminotransferase, kynurenine aminotransferase II | ESTs, Weakly similar to S48737 kynurenine aminotransferase - rat [*R. norvegicus*], cysteine conjugate-beta lyase; cytoplasmic (glutamine transaminase K, kyneurenine aminotransferase), hypothetical protein 669 |
| 1679 | 14695 | NM_017202 | q, s | | EST, Weakly similar to COX4_HUMAN CYTOCHROME C OXIDASE POLYPEPTIDE IV PRECURSO [*H. sapiens*], cytochrome c oxidase subunit IV, cytochrome c oxidase subunit IV isoform 2, cytochrome c oxidase subunit IV isoform 2 precursor, cytochrome c oxidase, subunit IVa, cytochrome c oxidase, subunit IVb, expressed sequence AL024441 |
| 1679 | 14694 | NM_017202 | s, z | | EST, Weakly similar to COX4_HUMAN CYTOCHROME C OXIDASE POLYPEPTIDE IV PRECURSO [*H. sapiens*], cytochrome c oxidase subunit IV, cytochrome c oxidase subunit IV isoform 2, cytochrome c oxidase subunit IV isoform 2 precursor, cytochrome c oxidase, subunit IVa, cytochrome c oxidase, subunit IVb, expressed sequence AL024441 |
| 1680 | 1428 | NM_017213 | m | outer dense fiber of sperm tails 2, outer dense fibre of sperm tails 2 | ESTs, Highly similar to T09400 outer dense fiber protein 2 - mouse [*M. musculus*], KIAA1229 protein, Myosin heavy chain 11, Myosin, heavy polypeptide 9, non-muscle, expressed sequence C80049, myosin, heavy polypeptide 9, non-muscle, outer dense fiber of sperm tails 2, outer dense fiber of sperm tails 2 |
| 1681 | 1622 | NM_017216 | g, j, s, z | solute carrier family 3 (cystine, dibasic and neutral amino acid transporters, activator of cystine, dibasic and neutral amino acid transport), | ESTs, Moderately similar to 1914205A AA transporter [*H. sapiens*], putative L-type neutral amino acid transporter, solute carrier family 3 (activators of dibasic and neutral amino acid transport), member 2, solute carrier |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | member 1, solute carrier family 3, member 1 | family 3 (cystine, dibasic and neutral amino acid transporters, activator of cystine, dibasic and neutral amino acid transport), member 1, solute carrier family 3, member 1 |
| 1682 | 13642 | NM_017220 | v | | |
| 1682 | 19976 | NM_017220 | w | | |
| 1683 | 1510 | NM_017224 | General | | EST, Moderately similar to JC4884 organic cation transporter protein 2 - rat [R. norvegicus], EST, Weakly similar to OCN2 MOUSE ORGANIC CATION/CARNITINE TRANSPORTER 2 [M. musculus], ESTs, Highly similar to OCN2_HUMAN ORGANIC CATION/CARNITINE TRANSPORTER 2 [H. sapiens], ESTs, Highly similar to organic cation transporter [H. sapiens], solute carrier family 22 (organic cation transporter), member 1, solute carrier family 22 (organic cation transporter), member 4, solute carrier family 22 (organic cation transporter), member 5, solute carrier family 22 (organic cation transporter), member 9, solute carrier family 22, member 2, solute carrier family 22, member 3 |
| 1684 | 1811 | NM_017228 | j, l, m, z | dentatorubral pallidoluysian atrophy, dentatorubral-pallidoluysian atrophy (atrophin-1) | ESTs, Moderately similar to DRPL RAT ATROPHIN-1 [R. norvegicus], ESTs, Weakly similar to G01763 atrophin-1 [H. sapiens], Homo sapiens, clone IMAGE: 4153246, mRNA, partial cds, RIKEN cDNA 2310009E07 gene, RIKEN cDNA 2810012K09 gene, arginine-glutamic acid dipeptide (RE) repeats, dentatorubral pallidoluysian atrophy, dentatorubral-pallidoluysian atrophy (atrophin-1), expressed sequence C78339, formin |
| 1686 | 17563 | NM_017245 | a, c, e, q | eukaryotic translation elongation factor 2 | EST, Weakly similar to EFHU2 translation elongation factor eEF-2 [H. sapiens], ESTs, Highly similar to ELONGATION FACTOR 2 [R. norvegicus], ESTs, Weakly similar to ELONGATION FACTOR 2 [R. norvegicus], G1 to phase transition 1, G1 to phase transition 2, RIKEN cDNA 4930594C11 gene, U5 snRNP-specific protein, 116 kD, eukaryotic translation elongation factor 1 alpha 1, eukaryotic translation elongation factor 2, expressed sequence AI451340, hypothetical protein FLJ21661 |
| 1687 | 17502 | NM_017248 | r | heterogeneous nuclear ribonucleoprotein A1 | ESTs, Highly similar to ROA1 RAT HETEROGENEOUS NUCLEAR RIBONUCLEOPROTEIN A1 [R. norvegicus], ESTs, Moderately similar to Up1, The Two Rna-Recognition Motif Domain Of Hnrnp A1 {SUB 3-184 [H. sapiens], ESTs, Weakly similar to ROA1 RAT HETEROGENEOUS NUCLEAR RIBONUCLEOPROTEIN A1 [R. norvegicus], ESTs, Weakly similar to heterogeneous ribonuclear particle protein A1 [H. sapiens], Human DNA sequence from clone RP11-51N22 on chromosome 13 Contains ESTs, STSs and GSSs. Contains an HNRPA1 (heterogeneous nuclear ribonucleoprotein A1) pseudogene, RIKEN cDNA 4930547K05 gene, heterogeneous nuclear ribonucleoprotein A1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1687 | 17501 | NM_017248 | x | heterogenous nuclear ribonucleoprotein A1 | ESTs, Highly similar to ROA1 RAT HETEROGENEOUS NUCLEAR RIBONUCLEOPROTEIN A1 [*R. norvegicus*], ESTs, Moderately similar to Up1, The Two Rna-Recognition Motif Domain Of Hnmp A1 {SUB 3-184 [*H. sapiens*], ESTs, Weakly similar to ROA1 RAT HETEROGENEOUS NUCLEAR RIBONUCLEOPROTEIN A1 [*R. norvegicus*], ESTs, Weakly similar to heterogeneous ribonuclear particle protein A1 [*H. sapiens*], Human DNA sequence from clone RP11-51N22 on chromosome 13 Contains ESTs, STSs and GSSs. Contains an HNRPA1 (heterogeneous nuclear ribonucleoprotein A1) pseudogene, RIKEN cDNA 4930547K05 gene, heterogeneous nuclear ribonucleoprotein A1 |
| 1688 | 19 | NM_017258 | v, General | B-cell translocation gene 1, anti-proliferative | B-cell translocation gene 1, anti-proliferative, ESTs, Weakly similar to BTG1 RAT BTG1 PROTEIN [*R. norvegicus*], transducer of ERBB2, 1, transducer of ERBB2, 2, transducer of ErbB-2.1 |
| 1689 | 15300 | NM_017259 | i, v, cc, General | B-cell translocation gene 2, anti-proliferative, BTG family, member 2 | B-cell translocation gene 2, anti-proliferative, B-cell translocation gene 3, B-cell translocation gene 4, BTG family, member 2, BTG family, member 3, BTG family, member 4, ESTs, Highly similar to BTG2_HUMAN BTG2 PROTEIN PRECURSOR [*H. sapiens*] |
| 1689 | 15301 | NM_017259 | l, m, v, cc, General | B-cell translocation gene 2, anti-proliferative BTG family, member 2 | B-cell translocation gene 2, anti-proliferative, B-cell translocation gene 3, B-cell translocation gene 4, BTG family, member 2, BTG family, member 3, BTG family, member 4, ESTs, Highly similar to BTG2_HUMAN BTG2 PROTEIN PRECURSOR [*H. sapiens*] |
| 1689 | 15299 | NM_017259 | l, y, cc, General | B-cell translocation gene 2, anti-proliferative, BTG family, member 2 | B-cell translocation gene 2, anti-proliferative, B-cell translocation gene 3, B-cell translocation gene 4, BTG family, member 2, BTG family, member 3, BTG family, member 4, ESTs, Highly similar to BTG2_HUMAN BTG2 PROTEIN PRECURSOR [*H. sapiens*] |
| 1690 | 15224 | NM_017264 | d | protease (prosome, macropain) 28 subunit, alpha, proteasome (prosome, macropain) activator subunit 1 (PA28 alpha) | EST, Moderately similar to A Chain A, Proteasome Activator Reg(Alpha) {SUB 4-63 [*H. sapiens*], proteasome (prosome, macropain) activator subunit 1 (PA28 alpha) |
| 1691 | 3987 | NM_017280 | bb | proteasome (prosome, macropain) subunit, alpha type 3, proteasome (prosome, macropain) subunit, alpha type, 3 | multicatalytic endopeptidase complex [*H. sapiens*], ESTs, Highly similar to PRC8 MOUSE PROTEASOME COMPONENT C8 [*M. musculus*], ESTs, Highly similar to PROTEASOME COMPONENT C8 [*R. norvegicus*], ESTs, Weakly similar to SNHUC8 multicatalytic endopeptidase complex [*H. sapiens*], proteasome (prosome, macropain) subunit, alpha type 3, proteasome (prosome, macropain) subunit, alpha type, 3 |
| 1692 | 1447 | NM_017281 | l | proteasome (prosome, macropain) subunit, alpha type 4, proteasome (prosome, macropain) | EST, Weakly similar to SNHUC9 multicatalytic endopeptidase complex [*H. sapiens*], proteasome (prosome, macropain) subunit, alpha type 4, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | subunit, alpha type, 4 | proteasome (prosome, macropain) subunit, alpha type, 4 |
| 1693 | 15535 | NM_017283 | s, bb | proteasome (prosome, macropain) subunit, alpha type 6, proteasome (prosome, macropain) subunit, alpha type, 6 | ESTs, Weakly similar to PRCI_HUMAN PROTEASOME IOTA CHAIN [*R. norvegicus*], proteasome (prosome, macropain) subunit, alpha type 6, proteasome (prosome, macropain) subunit, alpha type, 6 |
| 1694 | 12349 | NM_017290 | General | ATPase, Ca++ transporting, cardiac muscle, slow twitch 2 | |
| 1695 | 15819 | NM_017298 | p | calcium channel, voltage-dependent, L type, alpha 1D subunit | EST, Highly similar to CCAD MOUSE VOLTAGE-DEPENDENT L-TYPE CALCIUM CHANNEL ALPHA-1D SUBUNIT [*M. musculus*], EST, Moderately similar to CCAD MOUSE VOLTAGE-DEPENDENT L-TYPE CALCIUM CHANNEL ALPHA-1D SUBUNIT [*M. musculus*], EST, Moderately similar to CCAD RAT VOLTAGE-DEPENDENT L-TYPE CALCIUM CHANNEL ALPHA-1D SUBUNIT [*R. norvegicus*], RIKEN cDNA 8430418G19 gene, calcium channe, voltage-dependent, alpha 1F subunit, calcium channel, voltage-dependent, L type, alpha 1D subunit, calcium channel, voltage-dependent, alpha 1F subunit, polycystic kidney disease 2-like 2 |
| 1696 | 23825 | NM_017299 | v | solute carrier family 19 (folate transporter), member 1, solute carrier family 19 (sodium/hydrogen exchanger), member 1 | expressed sequence AW322295, solute carrier family 19 (folate transporter), member 1, solute carrier family 19 (sodium/hydrogen exchanger), member 1, solute carrier family 19 (sodium/hydrogen exchanger), member 3, solute carrier family 19 (thiamine transporter), member 2, solute carrier family 19, member 3 |
| 1696 | 23826 | NM_017299 | v | solute carrier family 19 (folate transporter), member 1, solute carrier family 19 (sodium/hydrogen exchanger), member 1 | expressed sequence AW322295, solute carrier family 19 (folate transporter), member 1, solute carrier family 19 (sodium/hydrogen exchanger), member 1, solute carrier family 19 (sodium/hydrogen exchanger), member 3, solute carrier family 19 (thiamine transporter), member 2, solute carrier family 19, member 3 |
| 1697 | 14003 | NM_017305 | j, l, m, y, z | glutamate-cysteine ligase, modifier subunit, glutamate-cysteine ligase, modifier subunit | ESTs, Highly similar to GSH0_HUMAN GLUTAMATE-CYSTEINE LIGASE REGULATORY SUBUNIT [*H. sapiens*], glutamate-cysteine ligase, modifier subunit, glutamate-cysteine ligase, modifier subunit |
| 1698 | 26109 | NM_017306 | q, s | | |
| 1698 | 18687 | NM_017306 | q, t | dodecenoyl-Coenzyme A delta isomerase (3,2 trans-enoyl-Coenyme A isomerase), dodecenoyl-Coenzyme A delta isomerase (3,2 trans-enoyl-Coenzyme A isomerase) | ESTs, Highly similar to D3D2 RAT 3,2-TRANS-ENOYL-COA ISOMERASE, MITOCHONDRIAL PRECURSOR [*R. norvegicus*], Homo sapiens, Similar to dodecenoyl-Coenzyme A delta isomerase (3,2 trans-enoyl-Coenzyme A isomerase), clone MGC: 3903 IMAGE: 3630566, mRNA, complete cds, dodecenoyl-Coenzyme A delta isomerase (3,2 trans-enoyl-Coenyme A isomerase), dodecenoyl-Coenzyme A delta isomerase (3,2 trans-enoyl-Coenzyme A isomerase) |
| 1699 | 18142 | NM_017314 | g, s, aa | | EST, Moderately similar to S12583 polyubiquitin 4 - mouse [*M. musculus*], EST, Weakly similar to JE0190 polyubiquitin unit [*H. sapiens*], Homo |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | sapiens UBBP2 pseudogene for ubiquitin UBB, RIKEN cDNA 2700054O04 gene, expressed sequence AI194771, expressed sequence AL033289, ubiquitin B, ubiquitin C |
| 1700 | 1894 | NM_017320 | t | | cathepsin S |
| 1701 | 20809 | NM_017326 | u | calmodulin 2, calmodulin 2 (phosphorylase kinase, delta) | Calmodulin 1 (phosphorylase kinase, delta), Calmodulin III, ESTs, Highly similar to A Chain A, Calmodulin Complexed With Calmodulin-Binding Peptide From Smooth Muscle Myosin Light Chain Kinase {SUB 2-148 [*H. sapiens*], *R. norvegicus* CaMII retropseudogene (clone lambda SC27), RIKEN cDNA 2310068O22 gene, calmodulin 1, calmodulin 1 (phosphorylase kinase, delta), calmodulin 2, calmodulin 2 (phosphorylase kinase, delta), calmodulin 3, calmodulin-like 3 |
| 1702 | 355 | NM_017334 | cc | | |
| 1703 | 16148 | NM_017340 | q, s | | ESTs, Highly similar to ACYL-COENZYME A OXIDASE, PEROXISOMAL [*R. norvegicus*], ESTs, Highly similar to CAOP_HUMAN ACYL-COENZYME A OXIDASE, PEROXISOMAL [*H. sapiens*], RIKEN cDNA 1300003O09 gene, RIKEN cDNA 2310016C19 gene, acetyl-Coenzyme A dehydrogenase, short chain, acyl-Coenzyme A oxidase 2, branched chain, isovaleryl coenzyme A dehydrogenase |
| 1703 | 16150 | NM_017340 | a | | ESTs, Highly similar to ACYL-COENZYME A OXIDASE, PEROXISOMAL [*R. norvegicus*], ESTs, Highly similar to CAOP_HUMAN ACYL-COENZYME A OXIDASE, PEROXISOMAL [*H. sapiens*], RIKEN cDNA 1300003O09 gene, RIKEN cDNA 2310016C19 gene, acetyl-Coenzyme A dehydrogenase, short chain, acyl-Coenzyme A oxidase 2, branched chain, isovaleryl coenzyme A dehydrogenase |
| 1704 | 20849 | NM_017343 | r, u, General | | ESTs, Weakly similar to MOHULP myosin regulatory light chain, placental [*H. sapiens*], RIKEN cDNA 2900073G15 gene, expressed sequence C77744, myosin, light polypeptide, regulatory, non-sarcomeric (20 kD) |
| 1704 | 20848 | NM_017343 | b, General | | ESTs, Weakly similar to MOHULP myosin regulatory light chain, placental [*H. sapiens*], RIKEN cDNA 2900073G15 gene, expressed sequence C77744, myosin, light polypeptide, regulatory, non-sarcomeric (20 kD) |
| 1705 | 606 | NM_017350 | b | | GPI-anchored metastasis-associated protein homolog, metastasis-associated GPI-anchored protein, plasminogen activator, urokinase receptor, urokinase plasminogen activator receptor |
| 1706 | 1581 | NM_017365 | General | PDZ and LIM domain 1 (elfin) | ESTs, Weakly similar to LIM PROTEIN CLP36 [*R. norvegicus*], PDZ and LIM domain 1 (elfin), PDZ and LIM domain 3, PDZ-LIM protein mystique, RIKEN cDNA 1110003B01 gene, *Rattus norvegicus* LIM-domain protein LMP-1 mRNA, complete cds, Z-band alternatively spliced PDZ-motif, actinin |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | alpha 2 associated LIM protein, alpha-actinin-2-associated LIM protein, reversion induced LIM gene |
| 1707 | 455 | NM_019131 | x | tropomyosin 1 (alpha), tropomyosin 1, alpha | ESTs, Moderately similar to alpha-tropomyosin slow [*M. musculus*], tropomyosin 4 |
| 1707 | 456 | NM_019131 | y, z | tropomyosin 1 (alpha), tropomyosin 1, alpha | ESTs, Moderately similar to alpha-tropomyosin slow [*M. musculus*], tropomyosin 4 |
| 1708 | 4532 | NM_019134 | b | solute carrier family 12 (sodium/potassium/chloride transporters), member 1, solute carrier family 12, member 1 | EST, Weakly similar to NKC2_HUMAN BUMETANIDE-SENSITIVE SODIUM-(POTASSIUM)-CHLORIDE COTRANSPORTER 2 (KIDNEY-SPECIFIC NA-K-CL SYMPORTER) [*H. sapiens*], expressed sequence AI788571, hypothetical protein FLJ23188, solute carrier family 12 (sodium/potassium/chloride transporters), member 1, solute carrier family 12, member 1, solute carrier family 12, member 2 |
| 1709 | 1608 | NM_019166 | j, y, z | synaptogyrin 1 | ESTs, Moderately similar to SNG1 RAT SYNAPTOGYRIN 1 [*R. norvegicus*], synaptogyrin 1, synaptogyrin 3, synaptogyrin 4 |
| 1710 | 7489 | NM_019169 | c, General | synuclein, alpha, synuclein, alpha (non A4 component of amyloid precursor) | synuclein, alpha, synuclein, alpha (non A4 component of amyloid precursor), synuclein, beta, synuclein, gamma |
| 1711 | 17066 | NM_019170 | p | | ESTs, Weakly similar to JC5284 carbonyl reductase (NADPH) (EC 1.1.1.184), inducible - rat [*R. norvegicus*], *Homo sapiens*, clone MGC: 23280 IMAGE: 4637504, mRNA, complete cds, RIKEN cDNA 1110001J05 gene, RIKEN cDNA 9430059D04 gene, carbonyl reductase 1, carbonyl reductase 3, expressed sequence C81353 |
| 1712 | 23924 | NM_019174 | bb | carbonic anhydrase 4, carbonic anhydrase IV | ESTs, Weakly similar to CARBONIC ANHYDRASE IV PRECURSOR [*R. norvegicus*], carbonic anhydrase 15, carbonic anhydrase 4, carbonic anhydrase IV, carbonic anhydrase XIV, expressed sequence AW456718 |
| 1713 | 24019 | NM_019186 | t | ADP-ribosylation factor-like 4, ADP-ribosylation-like 4 | ADP-ribosylation factor-like 4, ADP-ribosylation factor-like 7, ADP-ribosylation-like 4, ESTs, Weakly similar to ARL4 MOUSE ADP-RIBOSYLATION FACTOR-LIKE PROTEIN 4 [*M. musculus*], *Mus musculus*, Similar to ADP-ribosylation-like 4, clone MGC: 5774 IMAGE: 3599701, mRNA, complete cds |
| 1714 | 22063 | NM_019195 | d | CD47 antigen (Rh-related antigen, integrin-associated signal transducer), integrin-associated protein | |
| 1715 | 2079 | NM_019220 | j, k, z | | ESTs, Weakly similar to GRG MOUSE GRG PROTEIN [*R. norvegicus*], amino-terminal enhancer of split |
| 1716 | 16284 | NM_019229 | l, m | solute carrier family 12 (potassium/chloride transporters), member 4, solute carrier family 12, member 4 | EST, Moderately similar to T31429 K—Cl cotransport protein KCC1, furosemide-sensitive - rat [*R. norvegicus*], EST, Weakly similar to T31429 K—Cl cotransport protein KCC1, furosemide-sensitive - rat [*R. norvegicus*], ESTs, Highly similar to T17275 hypothetical protein DKFZp434D2135.1 [*H. sapiens*], *Mus musculus* strain ILS K—Cl cotransporter (Slc12a5) mRNA, complete cds, *Rattus norvegicus* ccc6 mRNA for |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | cation-chloride cotransporter 6, complete cds, expressed sequence AW546649, solute carrier family 12 (potassium/chloride transporters), member 4, solute carrier family 12 (potassium/chloride transporters), member 6, solute carrier family 12 (potassium/chloride transporters), member 7, solute carrier family 12, member 2, solute carrier family 12, member 4, solute carrier family 12, member 7 |
| 1717 | 985 | NM_019233 | b, cc | small inducible cytokine subfamily A (Cys-Cys), member 20, small inducible cytokine subfamily A20 | small inducible cytokine subfamily A (Cys-Cys), member 20, small inducible cytokine subfamily A20 |
| 1718 | 15503 | NM_019237 | k, x | procollagen C-endopeptidase enhancer, procollagen C-proteinase enhancer protein | EST, Weakly similar to PCO1_HUMAN PROCOLLAGEN C-PROTEINASE ENHANCER PROTEIN PRECURSOR [*H. sapiens*], *Homo sapiens* cDNA FLJ12558 fis, clone NT2RM4000787, *Mus musculus* CSMD1 (Csmd1) mRNA, complete cds, RIKEN cDNA 2400001O18 gene, expressed sequence AI043106, membrane-type frizzled-related protein, procollagen C-endopeptidase enhancer, procollagen C-endopeptidase enhancer 2, procollagen C-proteinase enhancer protein |
| 1718 | 15504 | NM_019237 | k, x | procollagen C-endopeptidase enhancer, procollagen C-proteinase enhancer protein | EST, Weakly similar to PCO1_HUMAN PROCOLLAGEN C-PROTEINASE ENHANCER PROTEIN PRECURSOR [*H. sapiens*], *Homo sapiens* cDNA FLJ12558 fis, clone NT2RM4000787, *Mus musculus* CSMD1 (Csmd1) mRNA, complete cds, RIKEN cDNA 2400001O18 gene, expressed sequence AI043106, membrane-type frizzled-related protein, procollagen C-endopeptidase enhancer, procollagen C-endopeptidase enhancer 2, procollagen C-proteinase enhancer protein |
| 1719 | 17908 | NM_019242 | l, v, cc, General | interferon-related developmental regulator 1 | ESTs, Weakly similar to INTERFERON RELATED PROTEIN PC4 [*R. norvegicus*], interferon-related developmental regulator 1, interferon-related developmental regulator 2 |
| 1720 | 11218 | NM_019247 | c | paired-like homeodomain transcription factor 3 | paired-like homeodomain transcription factor 1, paired-like homeodomain transcription factor 2, paired-like homeodomain transcription factor 3 |
| 1721 | 15259 | NM_019259 | d, f | complement component 1, q subcomponent binding protein | DNA segment, Chr 11, Wayne State University 182, expressed, complement component 1, q subcomponent binding protein, expressed sequence AA986492 |
| 1722 | 21443 | NM_019262 | aa, General | complement component 1, q subcomponent, beta polypeptide | C1q-related factor, *Homo sapiens*, Similar to complement component 1, q subcomponent, c polypeptide, clone MGC: 17279 IMAGE: 4212772, mRNA, complete cds, complement component 1, q subcomponent, beta polypeptide, complement component 1, q subcomponent, c polypeptide, expressed sequence AI385742 |
| 1722 | 21444 | NM_019262 | t, General | complement component 1, q subcomponent, beta polypeptide | C1q-related factor, *Homo sapiens*, Similar to complement component 1, q subcomponent, c polypeptide, clone MGC: 17279 IMAGE: 4212772, mRNA, complete cds, complement component 1, q subcomponent, beta polypeptide, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1723 | 117 | NM_019266 | o, bb | sodium channel, voltage gated, type VIII, alpha polypeptide, sodium channel, voltage-gated, type VIII, alpha polypeptide | complement component 1, q subcomponent, c polypeptide, expressed sequence AI385742 ESTs, Highly similar to voltage gated Na channel Scn8a [*M. musculus*], *Mus musculus* adult male hypothalamus cDNA, RIKEN full-length enriched library, clone: A230108N10, full insert sequence, hypothetical protein MGC15619, sodium channel, voltage gated, type VIII, alpha polypeptide, sodium channel, voltage-gated, type II, alpha 2 polypeptide, sodium channel, voltage-gated, type III, alpha polypeptide, sodium channel, voltage-gated, type VIII, alpha polypeptide |
| 1724 | 1145 | NM_019280 | w | gap junction membrane channel protein alpha 5, gap junction protein, alpha 5, 40 kD (connexin 40) | |
| 1725 | 22220 | NM_019286 | c | alcohol dehydrogenase 1, complex, alcohol dehydrogenase 1A (class I), alpha polypeptide | ESTs, Weakly similar to ADHA MOUSE ALCOHOL DEHYDROGENASE A CHAIN [*M. musculus*], alcohol dehydrogenase 1A (class I), alpha polypeptide, alcohol dehydrogenase 1B (class I), beta polypeptide, expressed sequence AI194826, nuclear receptor binding factor 1 |
| 1726 | 10015 | NM_019289 | l, m, t, x, General | | EST, Highly similar to AR41_HUMAN ARP2/3 COMPLEX 41 KDA SUBUNIT [*H. sapiens*], ESTs, Moderately similar to AR41_HUMAN ARP2/3 COMPLEX 41 KDA SUBUNIT [*H. sapiens*], actin related protein ⅔ complex, subunit 1A (41 kD), actin related protein ⅔ complex, subunit 1A (41 kDa), actin related protein ⅔ complex, subunit 1B (41 kDa), expressed sequence AA408064, suppressor of profilin/p41 of actin-related complex ⅔ |
| 1726 | 10016 | NM_019289 | bb, General | | EST, Highly similar to AR41_HUMAN ARP2/3 COMPLEX 41 KDA SUBUNIT [*H. sapiens*], ESTs, Moderately similar to AR41_HUMAN ARP2/3 COMPLEX 41 KDA SUBUNIT [*H. sapiens*], actin related protein ⅔ complex, subunit 1A (41 kD), actin related protein ⅔ complex, subunit 1A (41 kDa), actin related protein ⅔ complex, subunit 1B (41 kDa), expressed sequence AA408064, suppressor of profilin/p41 of actin-related complex ⅔ |
| 1727 | 21651 | NM_019296 | c, f, x | | RIKEN cDNA 2310015O17 gene, RIKEN cDNA 4933411O17 gene, cell division cycle 2 homolog A (*S. pombe*), cell division cycle 2, G1 to S and G2 to M, cyclin-dependent kinase-like 1 (CDC2-related kinase), cyclin-dependent kinase-like 2 (CDC2-related kinase), cyclin-dependent kinase-like 3, expressed sequence AI852479, serine/threonine kinase NKIATRE beta |
| 1728 | 20751 | NM_019301 | s | | CUB and Sushi multiple domains 1, ESTs, Highly similar to I73012 complement C3b/C4b receptor, membrane-bound form precursor [*H. sapiens*], ESTs, Weakly similar to JC2054 complement regulatory protein, 5I2 antigen precursor - rat [*R. norvegicus*], *Mus musculus* 8 days embryo cDNA, RIKEN full-length enriched library, clone: 5730478H20, full insert sequence, complement |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | component (3b/4b) receptor 1, including Knops blood group system, complement receptor related protein, decay accelerating factor 1, decay accelerating factor 2, membrane cofactor protein |
| 1729 | 645 | NM_019345 | bb | solute carrier family 12 (sodium/chloride transporters), member 3, solute carrier, family 12, member 3 | ESTs, Moderately similar to PC4180 thiazide-sensitive sodium-chloride cotransporter [*H. sapiens*], ESTs, Moderately similar to thiazide-sensitive Na—Cl cotransporter [*M. musculus*], ESTs, Weakly similar to BUMETANIDE-SENSITIVE SODIUM-(POTASSIUM)-CHLORIDE COTRANSPORTER 2 [*M. musculus*], expressed sequence AI788571, solute carrier family 12 (sodium/chloride transporters), member 3, solute carrier family 12, member 1, solute carrier family 12, member 3 |
| 1730 | 1301 | NM_019349 | c | | |
| 1731 | 3776 | NM_019354 | a, u | | ESTs, Moderately similar to BMCP_HUMAN BRAIN MITOCHONDRIAL CARRIER PROTEIN-1 [*H. sapiens*], RIKEN cDNA 3632410G24 gene, RIKEN cDNA 4933433O23 gene, expressed sequence AW108044, solute carrier family 25 (mitochondrial carrier, brain), member 14, solute carrier family 25 (mitochondrial carrier; adenine nucleotide translocator), member 10, solute carrier family 25 (mitochondrial carrier; ornithine transporter), member 15, uncoupling protein 2 (mitochondrial, proton carrier), uncoupling protein 2, mitochondrial |
| 1732 | 4592 | NM_019356 | General | | RIKEN cDNA 0910001O23 gene, eukaryotic translation initiation factor 2, subunit 1 (alpha, 35 kD), eukaryotic translation initiation factor 2A |
| 1733 | 1324 | NM_019371 | w | | EGL nine (*C. elegans*) homolog 1, EGL nine (*C. elegans*) homolog 2, EGL nine (*C. elegans*) homolog 3, EGL nine homolog 3 (*C. elegans*), ESTs, Moderately similar to A53770 growth factor-responsive protein, vascular smooth muscle - rat [*R. norvegicus*], ESTs, Weakly similar to A53770 growth factor-responsive protein, vascular smooth muscle - rat [*R. norvegicus*], SCAN domain-containing 2 |
| 1734 | 19577 | NM_019377 | e | tyrosine 3-monooxgenase/tryptophan 5-monooxgenase activation protein, beta polypeptide, tyrosine 3-monooxygenase/tryptophan 5-monooxygenase activation protein, beta polypeptide | |
| 1735 | 24626 | NM_019381 | s | testis enhanced gene transcript, testis enhanced gene transcript (BAX inhibitor 1) | CGI-119 protein, RIKEN cDNA 5031406P05 gene, testis enhanced gene transcript (BAX inhibitor 1) |
| 1736 | 744 | NM_019622 | p | | ESTs, Highly similar to T42716 ankyrin 3, splice form 4 - mouse [*M. musculus*], ESTs, Moderately similar to A55575 ankyrin 3, long splice form [*H. sapiens*], ESTs, Weakly similar to T42716 ankyrin 3, splice form 4 - mouse [*M. musculus*], RIKEN cDNA 2310026G15 gene, RIKEN cDNA |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1737 | 20716 | NM_019623 | c | | 4833425P12 gene, RIKEN cDNA 4930400E23 gene, RIKEN cDNA C430011H06 gene, ankyrin 3, node of Ranvier (ankyrin G), hypothetical protein FLJ20189, phospholipase A2, group VI, phospholipase A2, group VI (cytosolic, calcium-independent), proteasome (prosome, macropain) 26S subunit, non-ATPase, 10 EST, Weakly similar to CPF1 RAT CYTOCHROME P450 4F1 [*R. norvegicus*], ESTs, Weakly similar to S45702 leukotriene-B4 20-monooxygenase [*H. sapiens*], *Mus musculus*, Similar to RIKEN cDNA 1810054N16 gene, clone MGC: 7384 IMAGE: 3487830, mRNA, complete cds, RIKEN cDNA 2310021J05 gene, cytochrome P450 isoform 4F12, cytochrome P450, subfamily IV B, polypeptide 1, cytochrome P450, subfamily IVF, polypeptide 11, cytochrome P450, subfamily IVF, polypeptide 2, cytochrome P450, subfamily IVF, polypeptide 8, expressed sequence AI787289 |
| 1738 | 20709 | NM_019904 | x | lectin, galactose binding, soluble 1, lectin, galactoside-binding, soluble, 1 (galectin 1) | EST, Moderately similar to 1713410A beta galactoside soluble lectin [*H. sapiens*], EST, Moderately similar to GALECTIN-1 [*R. norvegicus*], Human HL14 gene encoding beta-galactoside-binding lectin, 3' end, clone 2, RIKEN cDNA 2200008F12 gene, *Rattus norvegicus* mRNA for galectin-2 related protein, complete cds, lectin, galactose binding, soluble 1, lectin, galactoside-binding, soluble, 1 (galectin 1), lectin, galactoside-binding, soluble, 2 (galectin 2) |
| 1739 | 574 | NM_019905 | u, General | hydroxyacid oxidase (glycolate oxidase) 3, hydroxyacid oxidase 3 (medium-chain) | ESTs, Highly similar to (S)-2-HYDROXY-ACID OXIDASE, PEROXISOMAL [*R. norvegicus*], ESTs, Highly similar to LUHU36 annexin II [*H. sapiens*], RIKEN cDNA 1110003P15 gene, RIKEN cDNA B430311C09 gene, annexin A2, annexin A2 pseudogene 2, caspase recruitment domain family, member 6, expressed sequence AW215814, hydroxyacid oxidase (glycolate oxidase) 3, hydroxyacid oxidase 1, liver, hydroxyacid oxidase 2 (long chain), nucleolar protein 3 (apoptosis repressor with CARD domain) |
| 1740 | 9096 | NM_019908 | j | hypothetical protein similar to mouse aldehyde reductase 6 (renal), renal-specific oxido-reducatse | |
| 1741 | 20457 | NM_020073 | i, General | | parathyroid hormone receptor, parathyroid hormone receptor 1 |
| 1741 | 20458 | NM_020073 | General | | parathyroid hormone receptor, parathyroid hormone receptor 1 |
| 1741 | 20460 | NM_020073 | General | | parathyroid hormone receptor, parathyroid hormone receptor 1 |
| 1742 | 18713 | NM_020075 | r | eukaryotic translation initiation factor 5 | DNA segment, Chr 12, ERATO Doi 549, expressed, KIAA1856 protein, eukaryotic translation initiation factor 5 |
| 1742 | 18715 | NM_020075 | r | eukaryotic translation initiation factor 5 | DNA segment, Chr 12, ERATO Doi 549, expressed, KIAA1856 protein, eukaryotic translation initiation factor 5 |
| 1743 | 20493 | NM_020076 | p | | 3-hydroxyanthranilate 3,4-dioxygenase, RIKEN cDNA 0610007K21 gene, RIKEN cDNA 0610012J07 gene |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1744 | 16375 | NM_020976 | g | | angiotensin I converting enzyme (peptidyl-dipeptidase A) 2, kidney-specific membrane protein |
| 1745 | 20816 | NM_021261 | k, General | | EST, Highly similar to THYMOSIN BETA-10 [*R. norvegicus*], ESTs, Highly similar to TYB4 MOUSE THYMOSIN BETA-4 [*M. musculus*], expressed sequence AW544206, thymosin, beta 10, thymosin, beta 4, X chromosome |
| 1746 | 15335 | NM_021264 | a | ribosomal protein L35a | EST, Weakly similar to 60S RIBOSOMAL PROTEIN L35A [*R. norvegicus*], EST, Weakly similar to R35A MOUSE 60S RIBOSOMAL PROTEIN L35A [*M. musculus*], EST, Weakly similar to R5HU35 ribosomal protein L35a [*H. sapiens*], *Homo sapiens* cDNA FLJ11509 fis, clone HEMBA1002166, RIKEN cDNA 2810431L15 gene, ribosomal protein L35a, uncharacterized hypothalamus protein HSMNP1 |
| 1747 | 18729 | NM_021578 | k, z | transforming growth factor, beta 1 | transforming growth factor, beta 1 |
| 1748 | 19060 | NM_021587 | cc | latent transforming growth factor beta binding protein 1 | EST, Weakly similar to TGFB_HUMAN LATENT TRANSFORMING GROWTH FACTOR BETA BINDING PROTEIN 1 PRECURSOR [*H. sapiens*], ESTs, Weakly similar to TGFB RAT LATENT TRANSFORMING GROWTH FACTOR BETA BINDING PROTEIN 1 PRECURSOR [*R. norvegicus*], RIKEN cDNA 2310046A13 gene, hypothetical protein MGC13010, latent transforming growth factor beta binding protein 1, latent transforming growth factor beta binding protein 2, latent transforming growth factor beta binding protein 3 |
| 1749 | 17324 | NM_021593 | o, General | | |
| 1750 | 19679 | NM_021653 | General | deiodinase, iodothyronine, type I | ESTs, Moderately similar to TYPE I IODOTHYRONINE DEIODINASE [*R. norvegicus*], deiodinase, iodothyronine, type I |
| 1750 | 19678 | NM_021653 | a, v, General | deiodinase, iodothyronine, type I | ESTs, Moderately similar to TYPE I IODOTHYRONINE DEIODINASE [*R. norvegicus*], deiodinase, iodothyronine, type I |
| 1751 | 19665 | NM_021688 | u, General | | potassium channel, subfamily K, member 1 (TWIK-1), potassium channel, subfamily K, member 3 (TASK-1), potassium channel, subfamily K, member 6 (TWIK-2), potassium channel, subfamily K, member 7 |
| 1752 | 19667 | NM_021690 | m | | EST, Highly similar to GUANINE NUCLEOTIDE RELEASING PROTEIN [*R. norvegicus*], EST, Weakly similar to 2009427A guanine nucleotide-releasing protein [*H. sapiens*], ESTs, Highly similar to 2009427A guanine nucleotide-releasing protein [*H. sapiens*], ESTs, Weakly similar to S28407 guanine nucleotide-exchange activator CDC25 homolog - mouse [*M. musculus*], RAS protein-specific guanine nucleotide-releasing factor 1, RAS protein-specific guanine nucleotide-releasing factor 2, RIKEN cDNA 4921528G01 gene, Rap1 guanine-nucleotide-exchange factor directly activated by cAMP, *Rattus norvegicus* strain Wistar RAS guanine nucleotide-releasing factor 1 (Rasgrf1) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1754 | 22916 | NM_021740 | a | prothymosin alpha, prothymosin, alpha (gene sequence 28) | mRNA, partial cds, guanine nucleotide-releasing factor 2 (specific for crk proto oncogene) ESTs, Highly similar to THYA_HUMAN PROTHYMOSIN ALPHA [*H. sapiens*], RIKEN cDNA 2610009E16 gene, prothymosin a14, prothymosin alpha, prothymosin, alpha (gene sequence 28) |
| 1755 | 19710 | NM_021744 | t | | CD14 antigen, ESTs, Weakly similar to CD14 RAT MONOCYTE DIFFERENTIATION ANTIGEN CD14 PRECURSOR [*R. norvegicus*] |
| 1755 | 19711 | NM_021744 | t | | CD14 antigen, ESTs, Weakly similar to CD14 RAT MONOCYTE DIFFERENTIATION ANTIGEN CD14 PRECURSOR [*R. norvegicus*] |
| 1756 | 19712 | NM_021745 | r | | EST, Weakly similar to I38975 nuclear orphan receptor LXR-alpha [*H. sapiens*], ESTs, Moderately similar to JC4014 steroid hormone-nuclear receptor NER [*H. sapiens*], expressed sequence AI957360, nuclear receptor subfamily 1, group H, member 3, nuclear receptor subfamily 1, group H, member 4 |
| 1757 | 1962 | NM_021750 | j, k, y, z | | |
| 1757 | 19824 | NM_021750 | a, bb | | *Homo sapiens*, clone MGC: 18185 IMAGE: 4155381, mRNA, complete cds, KIAA0251 hypothetical protein, RIKEN cDNA 1110027M19 gene, cysteine sulfinic acid decarboxylase-related protein 2, glutamic acid decarboxylase 2 |
| 1758 | 25198 | NM_021754 | h | | |
| 1758 | 20035 | NM_021754 | b, n, s, v, General | | DKFZP566J153 protein, ESTs, Moderately similar to T17299 hypothetical protein DKFZp564H2171.1 [*H. sapiens*], nucleolar protein NOP5/NOP58 |
| 1759 | 20090 | NM_021757 | m | pleiotropic regulator 1 (PRL1, *Arabidopsis* homolog), pleiotropic regulator 1, PRL1 homolog (*Arabidopsis*) | EST, Weakly similar to LIS1 MOUSE PLATELET-ACTIVATING FACTOR ACETYLHYDROLASE IB ALPHA SUBUNIT [*R. norvegicus*], ESTs, Weakly similar to LIS1 MOUSE PLATELET-ACTIVATING FACTOR ACETYLHYDROLASE IB ALPHA SUBUNIT [*R. norvegicus*], *Homo sapiens* mRNA for FLJ00083 protein, partial cds, WD repeat domain 5, f-box and WD-40 domain protein 2, hypothetical protein, platelet-activating factor acetylhydrolase beta subunit (PAF-AH beta), platelet-activating factor acetylhydrolase, isoform 1b, beta1 subunit, platelet-activating factor acetylhydrolase, isoform Ib, alpha subunit (45 kD), recombination protein REC14 |
| 1760 | 17885 | NM_021765 | aa | | ESTs, Weakly similar to COPP RAT COATOMER BETA' SUBUNIT [*R. norvegicus*], *Mus musculus*, Similar to RIKEN cDNA 1500041N16 gene, clone MGC: 12066 IMAGE: 3708188, mRNA, complete cds, RIKEN cDNA 2510040D07 gene, coatomer protein complex, subunit beta 2 (beta prime), expressed sequence AA408785, expressed sequence AI256832, expressed sequence C77982, glutamate rich WD repeat protein GRWD, platelet-activating factor acetylhydrolase, isoform 1b, beta1 subunit |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1762 | 20161 | NM_021836 | cc, General | | Jun-B oncogene, jun B proto-oncogene |
| 1764 | 1203 | NM_021997 | k, z | cytoplasmic linker 2 | DKFZP586N1922 protein, ESTs, Moderately similar to S22695 restin [*H. sapiens*], ESTs, Weakly similar to T42734 cytoplasmic linker protein CLIP-115 - rat [*R. norvegicus*], RIKEN cDNA 1500005P14 gene, RIKEN cDNA 4631429H07 gene, RIKEN cDNA 5830409B12 gene, cytoplasmic linker 2, hypothetical protein FLJ20364, restin (Reed-Steinberg cell-espressed intermediate filament-associated protein), restin (Reed-Steinberg cell-expressed intermediate filament-associated protein) |
| 1765 | 23151 | NM_022005 | b | FXYD domain-containing ion transport regulator 6 | EST, Moderately similar to PLM RAT PHOSPHOLEMMAN PRECURSOR [*R. norvegicus*], EST, Weakly similar to PLM_HUMAN PHOSPHOLEMMAN PRECURSOR [*H. sapiens*], FXYD domain-containing ion transport regulator 1, FXYD domain-containing ion transport regulator 1 (phospholemman), FXYD domain-containing ion transport regulator 3, FXYD domain-containing ion transport regulator 4, FXYD domain-containing ion transport regulator 6, FXYD domain-containing ion transport regulator 7, hypothetical protein MGC13186 |
| 1767 | 17101 | NM_022179 | bb | | EST, Moderately similar to HXK3_HUMAN HEXOKINASE TYPE III [*H. sapiens*], EST, Weakly similar to HXK2 MOUSE HEXOKINASE TYPE II [*M. musculus*], ESTs, Moderately similar to HXK2 MOUSE HEXOKINASE TYPE II [*M. musculus*], ESTs, Weakly similar to HXK2 MOUSE HEXOKINASE TYPE II [*M. musculus*], hexokinase 2, hexokinase 3 (white cell) |
| 1767 | 17100 | NM_022179 | bb | | EST, Moderately similar to HXK3_HUMAN HEXOKINASE TYPE III [*H. sapiens*], EST, Weakly similar to HXK2 MOUSE HEXOKINASE TYPE II [*M. musculus*], ESTs, Moderately similar to HXK2 MOUSE HEXOKINASE TYPE II [*M. musculus*], ESTs, Weakly similar to HXK2 MOUSE HEXOKINASE TYPE II [*M. musculus*], hexokinase 2, hexokinase 3 (white cell) |
| 1768 | 20257 | NM_022180 | w, General | | expressed sequence AA986699, hepatic nuclear factor 4, hepatocyte nuclear factor 4, alpha |
| 1768 | 25699 | NM_022180 | i | | expressed sequence AA986699, hepatic nuclear factor 4, hepatocyte nuclear factor 4, alpha |
| 1768 | 10860 | NM_022180 | p | | |
| 1769 | 23780 | NM_022183 | k, x | topoisomerase (DNA) II alpha, topoisomerase (DNA) II alpha (170 kD) | ESTs, Moderately similar to A40493 DNA topoisomerase [*H. sapiens*], ESTs, Moderately similar to TP2A MOUSE DNA TOPOISOMERASE II, ALPHA [*M. musculus*], topoisomerase (DNA) II alpha, topoisomerase (DNA) II beta, topoisomerase (DNA) II beta (180 kD) |
| 1770 | 20312 | NM_022224 | o | | expressed sequence AI790318, expressed sequence AI836570, phosphotriesterase related |
| 1771 | 6585 | NM_022266 | d, p, cc | | WNT1 inducible signaling pathway protein 1, WNT1 inducible signaling |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | pathway protein 2, WNT1 inducible signaling pathway protein 3, connective tissue growth factor |
| 1772 | 17161 | NM_022298 | i, v, cc, General | | ESTs, Highly similar to A23035 tubulin alpha chain [*H. sapiens*], tubulin alpha 1, tubulin alpha 2, tubulin alpha 3, tubulin alpha 6, tubulin, alpha 2, tubulin, alpha 3, tubulin, alpha, ubiquitous |
| 1772 | 17162 | NM_022298 | u | | ESTs, Highly similar to A23035 tubulin alpha chain [*H. sapiens*], tubulin alpha 1, tubulin alpha 2, tubulin alpha 3, tubulin alpha 6, tubulin, alpha 2, tubulin, alpha 3, tubulin, alpha, ubiquitous |
| 1772 | 17160 | NM_022298 | u | | ESTs, Highly similar to A23035 tubulin alpha chain [*H. sapiens*], tubulin alpha 1, tubulin alpha 2, tubulin alpha 3, tubulin alpha 6, tubulin, alpha 2, tubulin, alpha 3, tubulin, alpha, ubiquitous |
| 1772 | 17158 | NM_022298 | q | | ESTs, Highly similar to A23035 tubulin alpha chain [*H. sapiens*], tubulin alpha 1, tubulin alpha 2, tubulin alpha 3, tubulin alpha 6, tubulin, alpha 2, tubulin, alpha 3, tubulin, alpha, ubiquitous |
| 1773 | 11454 | NM_022381 | i, aa, General | | EST, Moderately similar to E Chain E, Human Pcn [*H. sapiens*], proliferating cell nuclear antigen |
| 1773 | 11455 | NM_022381 | l, General | | EST, Moderately similar to E Chain E, Human Pcn [*H. sapiens*], proliferating cell nuclear antigen |
| 1774 | 13480 | NM_022390 | s | | RIKEN cDNA 2610008L04 gene, quinoid dihydropteridine reductase |
| 1775 | 15184 | NM_022391 | z | pituitary tumor-transforming 1 | |
| 1776 | 22413 | NM_022392 | h | | EST, Highly similar to ISI1_HUMAN INSULIN-INDUCED PROTEIN 1 [*H. sapiens*], ESTs, Highly similar to INSULIN-INDUCED GROWTH RESPONSE PROTEIN CL-6 [*R. norvegicus*], *Mus musculus*, clone MGC: 18904 IMAGE: 4240711, mRNA, complete cds, insulin induced gene 1, insulin induced protein 2 |
| 1776 | 22414 | NM_022392 | n | | EST, Highly similar to ISI1_HUMAN INSULIN-INDUCED PROTEIN 1 [*H. sapiens*], ESTs, Highly similar to INSULIN-INDUCED GROWTH RESPONSE PROTEIN CL-6 [*R. norvegicus*], *Mus musculus*, clone MGC: 18904 IMAGE: 4240711, mRNA, complete cds, insulin induced gene 1, insulin induced protein 2 |
| 1777 | 22499 | NM_022393 | t | | C-type (calcium dependent, carbohydrate recognition domain) lectin, superfamily member 10, C-type (calcium dependent, carbohydrate recognition domain) lectin, superfamily member 6, C-type (calcium dependent, carbohydrate-recognition domain) lectin, superfamily member 6, CD72 antigen, *Mus musculus* Ly-49Q mRNA for NK receptor Ly-49Q, complete cds, *Mus musculus*, Similar to macrophage galactose N-acetyl-galactosamine specific lectin, clone MGC: 25983 IMAGE: 4456238, mRNA, complete cds, RIKEN cDNA 4930572L20 gene, asialoglycoprotein receptor 1, macrophage lectin 2 (calcium dependent) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1779 | 24537 | NM_022399 | e | | ESTs, Weakly similar to CALRETICULIN PRECURSOR [*R. norvegicus*], *Homo sapiens*, Similar to RIKEN cDNA 1700031L01 gene, clone MGC: 26577 IMAGE: 4822010, mRNA, complete cds, RIKEN cDNA 1700031L01 gene, RIKEN cDNA 6330586I20 gene, calreticulin |
| 1779 | 24539 | NM_022399 | y | | ESTs, Weakly similar to CALRETICULIN PRECURSOR [*R. norvegicus*], *Homo sapiens*, Similar to RIKEN cDNA 1700031L01 gene, clone MGC: 26577 IMAGE: 4822010, mRNA, complete cds, RIKEN cDNA 1700031L01 gene, RIKEN cDNA 6330586I20 gene, calreticulin |
| 1780 | 1141 | NM_022401 | o, General | | ESTs, Highly similar to I39161 dystonin isoform 2 [*H. sapiens*], ESTs, Weakly similar to T42725 actin binding protein ACF7, neural isoform 1 - mouse (fragment) [*M. musculus*], Leman coiled-coil protein, actin-crosslinking protein 7, expressed sequence AA591047, expressed sequence AW554249, plectin 1, intermediate filament binding protein, 500 kD, serologically defined colon cancer antigen 8 |
| 1781 | 1069 | NM_022402 | g | | EST, Highly similar to R5HUP0 acidic ribosomal protein P0, cytosolic [*H. sapiens*], EST, Moderately similar to RLA0 PAT 60S ACIDIC RIBOSOMAL PROTEIN P0 [*R. norvegicus*], ESTs, Highly similar to R5HUP0 acidic ribosomal protein P0, cytosolic [*H. sapiens*], ESTs, Highly similar to RLA0 MOUSE 60S ACIDIC RIBOSOMAL PROTEIN P0 [*M. musculus*], RIKEN cDNA 2610012O22 gene, acidic ribosomal phosphoprotein P0, hypothetical protein IMAGE3455200, ribosomal protein, large, P0 |
| 1782 | 8211 | NM_022500 | j, n, s | ferritin light chain 1, ferritin, light polypeptide | ESTs, Highly similar to FRHUL ferritin light chain [*H. sapiens*], ESTs, Moderately similar to FRHUL ferritin light chain [*H. sapiens*], PRO0470 protein, RIKEN cDNA 4933416E14 gene, ferritin light chain 2, ferritin, light polypeptide |
| 1782 | 8212 | NM_022500 | n, s | ferritin light chain 1, ferritin, light polypeptide | ESTs, Highly similar to FRHUL ferritin light chain [*H. sapiens*], ESTs, Moderately similar to FRHUL ferritin light chain [*H. sapiens*], PRO0470 protein, RIKEN cDNA 4933416E14 gene, ferritin light chain 2, ferritin, light polypeptide |
| 1783 | 6815 | NM_022503 | s | cytochrome c oxidase subunit VIIa polypeptide 3 (liver), cytochrome c oxidase, subunit VIIa 3 | EST, Moderately similar to OSHU7L cytochrome-c oxidase [*H. sapiens*], cytochrome c oxidase subunit VIIa polypeptide 2 (liver), cytochrome c oxidase, subunit VIIa 1, cytochrome c oxidase, subunit VIIa 3 |
| 1784 | 4259 | NM_022504 | q, w | ribosomal protein L36 | EST, Moderately similar to T08720 ribosomal protein L36 [*H. sapiens*], ESTs, Weakly similar to RL36_HUMAN 60S RIBOSOMAL PROTEIN L36 [*H. sapiens*], RIKEN cDNA 1110038G14 gene, ribosomal protein L36 |
| 1785 | 1611 | NM_022509 | j | | ESTs, Weakly similar to SMN1_HUMAN SURVIVAL MOTOR NEURON PROTEIN 1 [*H. sapiens*], RIKEN cDNA 2410004J23 gene, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | expressed sequence AI849087, expressed sequence AW122398, splicing factor 30, survival of motor neuron-related, survival motor neuron, survival motor neuron pseudogene, survival of motor neuron 1, telomeric, survival of motor neuron 2, centromeric |
| 1786 | 2236 | NM_022512 | y, z | | ESTs, Weakly similar to acyl-CoA dehydrogenase [*R. norvegicus*], RIKEN cDNA 1300003O09 gene, RIKEN cDNA 2310016C19 gene, acetyl-Coenzyme A dehydrogenase, short chain, acyl-Coenzyme A dehydrogenase family, member 8, acyl-Coenzyme A dehydrogenase, C-2 to C-3 short chain, hypothetical protein FLJ12592, hypothetical protein MGC5601, isovaleryl coenzyme A dehydrogenase |
| 1787 | 3026 | NM_022514 | a | | EST, Weakly similar to 60S RIBOSOMAL PROTEIN L27 [*R. norvegicus*], EST, Weakly similar to S43505 ribosomal protein L27, cytosolic [*H. sapiens*], ribosomal protein L27 |
| 1787 | 3027 | NM_022514 | a, q, r, aa | | EST, Weakly similar to 60S RIBOSOMAL PROTEIN L27 [*R. norvegicus*], EST, Weakly similar to S43505 ribosomal protein L27, cytosolic [*H. sapiens*], ribosomal protein L27 |
| 1788 | 2696 | NM_022515 | a, d | | ESTs, Highly similar to RL24_HUMAN 60S RIBOSOMAL PROTEIN L24 [*H. sapiens*], RIKEN cDNA 0610008L05 gene, ribosomal protein L24 |
| 1788 | 2697 | NM_022515 | n, w, aa | | ESTs, Highly similar to RL24_HUMAN 60S RIBOSOMAL PROTEIN L24 [*H. sapiens*], RIKEN cDNA 0610008L05 gene, ribosomal protein L24 |
| 1789 | 3900 | NM_022516 | h | neural polypyrimidine tract binding protein, polypyrimidine tract binding protein | ESTs, Moderately similar to S15552 polypyrimidine tract-binding protein 1 - rat [*R. norvegicus*], ESTs, Weakly similar to S15552 polypyrimidine tract-binding protein 1 - rat [*R. norvegicus*], RIKEN cDNA 2810036L13 gene, expressed sequence AW107884, heterogeneous nuclear ribonucleoprotein L, neural polypyrimidine tract binding protein, polypyrimidine tract binding protein, polypyrimidine tract binding protein 2 |
| 1790 | 4151 | NM_022518 | o | | ADP-ribosylation factor 1, ADP-ribosylation factor domain protein 1, 64 kD, ADP-ribosylation factor-like 1, ARF protein, *Homo sapiens*, Similar to DKFZP727C091 protein, clone MGC: 10677 IMAGE: 3948445, mRNA, complete cds |
| 1791 | 4242 | NM_022521 | c | | ESTs, Highly similar to ORNITHINE AMINOTRANSFERASE PRECURSOR [*R. norvegicus*], RIKEN cDNA 1300019H02 gene, RIKEN cDNA 2900006B13 gene, hypothetical protein MGC15875, ornithine aminotransferase, ornithine aminotransferase (gyrate atrophy) |
| 1792 | 4412 | NM_022523 | o | | CD151 antigen, *Homo sapiens* cDNA FLJ14609 fis, clone NT2RP1000944, RIKEN cDNA 1110014F12 gene, RIKEN cDNA 1110031P12 gene, RIKEN cDNA 2700063A19 gene, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1793 | 6641 | NM_022533 | General | | transmembrane 4 superfamily member (tetraspan NET-2), transmembrane 4 superfamily member 6 ESTs, Weakly similar to A55046 plasmolipin - rat [*R. norvegicus*], ESTs, Weakly similar to PLLP_HUMAN PLASMOLIPIN [*H. sapiens*], *Homo sapiens* cDNA FLJ14787 fis, clone NT2RP4000878, highly similar to MYELOID UPREGULATED PROTEIN, *Mus musculus*, Similar to BENE protein, clone MGC: 19097 IMAGE: 4205488, mRNA, complete cds, RIKEN cDNA 2700018N07 gene, expressed sequence AI461653, myelin and lymphocyte protein; T-cell differentiation protein, plasmolipin |
| 1794 | 8097 | NM_022536 | a | | ESTs, Moderately similar to A Chain A, Cyclophilin B Complexed With [*H. sapiens*], RIKEN cDNA 1110060O10 gene, RIKEN cDNA 3732410E19 gene, RIKEN cDNA 4833408F11 gene, expressed sequence AA408962, expressed sequence AA553318, peptidylprolyl isomerase B, peptidylprolyl isomerase B (cyclophilin B) |
| 1795 | 8597 | NM_022538 | c, r, u | | |
| 1795 | 8598 | NM_022538 | u | | |
| 1796 | 9296 | NM_022541 | o | | EST, Highly similar to IM8B_MOUSE MITOCHONDRIAL IMPORT INNER MEMBRANE TRANSLOCASE SUBUNIT TIM8 B (DEAFNESS DYSTONIA PROTEIN 2 HOMOLOG) [*R. norvegicus*], translocase of inner mitochondrial membrane 8 (yeast) homolog B, translocase of inner mitochondrial membrane 8 homolog b (yeast) |
| 1797 | 21063 | NM_022585 | h | ornithine decarboxylase antizyme inhibitor | ESTs, Weakly similar to A Chain A, Crystal Structure Ornithine Decarboxylase From Mouse, Truncated 37 Residues From The C-Terminus, To 1.6 Angstrom Resolution [*M. musculus*], ESTs, Weakly similar to ORNITHINE DECARBOXYLASE [*R. norvegicus*], Ornitine decarboxylase, ornithine decarboxylase 1, ornithine decarboxylase antizyme inhibitor, ornithine decarboxylase, structural, ornithine decarboxylase-like protein |
| 1799 | 20781 | NM_022591 | z | | apoptotic protease activating factor, telomerase associated protein 1, telomerase-associated protein 1 |
| 1800 | 20803 | NM_022592 | n | | RIKEN cDNA 4933401I19 gene. hypothetical protein DKFZp434L1717, transketolase, transketolase (Wernicke Korsakoff syndrome), transketolase-like 1 |
| 1801 | 20925 | NM_022594 | q | enoyl Coenzyme A hydratase 1, peroxisomal, enoyl coenzyme A hydratase 1, peroxisomal | AU RNA-binding protein/enoyl-coenzyme A hydratase, EST, Weakly similar to ECH1_HUMAN DELTA3,5-DELTA2,4-DIENOYL-COA ISOMERASE PRECURSO [*H. sapiens*], RIKEN cDNA 2610009M20 gene, enoyl Coenzyme A hydratase 1, peroxisomal, enoyl coenzyme A hydratase 1, peroxisomal, expressed sequence AA617331 |
| 1802 | 20944 | NM_022597 | aa | | cathepsin B, lipocalin 7, tubulointerstitial nephritis antigen |
| 1803 | 21024 | NM_022599 | o, General | | EST, Highly similar to OM25_RAT MITOCHONDRIAL OUTER |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | MEMBRANE PROTEIN 25 (NPW16) [*R. norvegicus*], EST, Weakly similar to OM25__RAT MITOCHONDRIAL OUTER MEMBRANE PROTEIN 25 (NPW16) [*R. norvegicus*], Erbb2 interacting protein, discs, large homolog 4 (*Drosophila*), expressed sequence AI118201, hypothetical protein FLJ11271, synaptojanin 2 binding protein |
| 1804 | 2250 | NM_022643 | General | | H2B histone family, member D, H2B histone family, member G, H2B histone family, member K, RIKEN cDNA 2610022J01 gene, expressed sequence AI413321, expressed sequence R74621 |
| 1805 | 17567 | NM_022672 | a, y | ribosomal protein S14 | EST, Moderately similar to 40S RIBOSOMAL PROTEIN S14 [*R. norvegicus*], EST, Weakly similar to A25220 ribosomal protein S14, cytosolic [*H. sapiens*], EST, Weakly similar to JE0129 ribosomal protein S14 - mouse [*M. musculus*], ESTs, Highly similar to A25220 ribosomal protein S14, cytosolic [*H. sapiens*], ribosomal protein S14 |
| 1806 | 17661 | NM_022674 | bb | H2A histone family, member Z | EST, Weakly similar to histone H2A.F/Z variant [*H. sapiens*], ESTs, Highly similar to HISTONE H2A.Z [*R. norvegicus*], H2A histone family, member Z, RIKEN cDNA C530002L11 gene, histone H2A.F/Z variant |
| 1807 | 24563 | NM_022676 | b | protein phosphatase 1, regulatory (inhibitor) subunit 1A | EST, Weakly similar to IPP1__HUMAN PROTEIN PHOSPHATASE INHIBITOR 1 [*H. sapiens*], ESTs, Weakly similar to IPP1__HUMAN PROTEIN PHOSPHATASE INHIBITOR 1 [*H. sapiens*], RIKEN cDNA 4930579P15 gene, protein phosphatase 1, regulatory (inhibitor) subunit 1A, protein phosphatase 1, regulatory (inhibitor) subunit 1B (dopamine and cAMP regulated phosphoprotein, DARPP-32) |
| 1807 | 24564 | NM_022676 | b, x | protein phosphatase 1, regulatory (inhibitor) subunit 1A | EST, Weakly similar to IPP1__HUMAN PROTEIN PHOSPHATASE INHIBITOR 1 [*H. sapiens*], ESTs, Weakly similar to IPP1__HUMAN PROTEIN PHOSPHATASE INHIBITOR 1 [*H. sapiens*], RIKEN cDNA 4930579P15 gene, protein phosphatase 1, regulatory (inhibitor) subunit 1A, protein phosphatase 1, regulatory (inhibitor) subunit 1B (dopamine and cAMP regulated phosphoprotein, DARPP-32) |
| 1808 | 20506 | NM_022686 | l | | |
| 1809 | 20508 | NM_022688 | g | | |
| 1810 | 17586 | NM_022694 | k | | EBNA-2 co-activator (100 kD), ESTs, Moderately similar to I38968 100 kDa coactivator [*H. sapiens*] |
| 1811 | 17730 | NM_022697 | a | | DNA segment, Chr 7, Wayne State University 21, expressed, EST, Highly similar to S55915 ribosomal protein L28 [*H. sapiens*], ESTs, Highly similar to S55915 ribosomal protein L28 [*H. sapiens*], ribosomal protein L28 |
| 1811 | 17729 | NM_022697 | q | | DNA segment, Chr 7, Wayne State University 21, expressed, EST, Highly similar to S55915 ribosomal protein L28 [*H. sapiens*], ESTs, Highly similar to S55915 ribosomal protein L28 [*H. sapiens*], ribosomal protein L28 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1812 | 154 | NM_022849 | t | crp-ductin, deleted in malignant brain tumors 1 | CD163 antigen, ESTs, Highly similar to I38005 M130 antigen precursor, splice form 4 [*H. sapiens*], KIAA1822 protein, apoptosis inhibitory 6, crp-ductin, deleted in malignant brain tumors 1, lectin, galactoside-binding, soluble, 3 binding protein, macrophage scavenger receptor 2, peptidylprolyl isomerase C-associated protein |
| 1813 | 127 | NM_022855 | h | | EST, Weakly similar to KC13 RAT CASEIN KINASE I, GAMMA 3 ISOFORM [*R. norvegicus*], ESTs, Highly similar to KC13 RAT CASEIN KINASE I, GAMMA 3 ISOFORM [*R. norvegicus*], ESTs, Weakly similar to casein kinase [*M. musculus*], RIKEN cDNA 2610208K14 gene, RIKEN cDNA 3300002K07 gene, casein kinase 1, alpha 1, casein kinase 1, delta, casein kinase 1, epsilon, casein kinase 1, gamma 1, casein kinase 1, gamma 3 |
| 1814 | 152 | NM_022858 | j | | ESTs, Highly similar to FXD3_HUMAN FORKHEAD BOX PROTEIN D3 [*H. sapiens*], ESTs, Weakly similar to FXD3_HUMAN FORKHEAD BOX PROTEIN D3 [*H. sapiens*], ESTs, Weakly similar to HFH1 RAT HEPATOCYTE NUCLEAR FACTOR 3 FORKHEAD HOMOLOG 1 [*R. norvegicus*], HNF-3/forkhead homolog 1 like, expressed sequence AI385632, forkhead box D1, forkhead box D2, forkhead box D3, winged helix/forkhead transcription factor |
| 1816 | 18101 | NM_022948 | z | | |
| 1816 | 18103 | NM_022948 | u | | |
| 1817 | 21491 | NM_022951 | w | | CAT56 protein, EST, Highly similar to CA13_HUMAN COLLAGEN ALPHA 1(III) CHAIN PRECURSOR [*H. sapiens*], EST, Weakly similar to A28996 proline-rich protein M14 precursor - mouse [*M. musculus*], EST, Weakly similar to JE0291 FB19 protein [*H. sapiens*], collagen, type III, alpha 1 (Ehlers-Danlos syndrome type IV, autosomal dominant), procollagen, type III, alpha 1, proline rich protein, proline rich protein 2, protein phosphatase 1, regulatory subunit 10 |
| 1818 | 15742 | NM_022958 | y | | ESTs, Moderately similar to S57219 phosphatidylinositol 3-kinase [*H. sapiens*], FK506 binding protein 12-rapamycin associated protein 1, *Homo sapiens* cDNA FLJ12591 fis, clone NT2RM4001313, moderately similar to PHOSPHATIDYLINOSITOL 3-KINASE VPS34-LIKE (EC 2.7.1.137), *Homo sapiens* cDNA FLJ14331 fis, clone PLACE4000320, RIKEN cDNA 2410099E07 gene, phosphatidylinositol 3-kinase catalytic delta polypeptide, phosphatidylinositol 3-kinase, catalytic, beta polypeptide, phosphoinositide-3-kinase, class 3, rapamycin and FKBP12 target-1 protein |
| 1819 | 9286 | NM_023027 | t, w | | ELAV (embryonic lethal, abnormal vision, *Drosophila*)-like 4 (Hu antigen D), ESTs, Highly similar to HUD RAT PARANEOPLASTIC ENCEPHALOMYELITIS ANTIGEN HUD HOMOLOG [*R. norvegicus*], ESTs, Moderately similar to HUD RAT |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | PARANEOPLASTIC ENCEPHALOMYELITIS ANTIGEN HUD HOMOLOG [R. norvegicus], ESTs, Moderately similar to POLYADENYLATE-BINDING PROTEIN 1 [M. musculus], Mus musculus adult male testis cDNA, RIKEN full-length enriched library, clone: 4933407N23, full insert sequence, RIKEN cDNA 4932702K14 gene, poly A binding protein, cytoplasmic 1 |
| 1820 | 23215 | NM_023102 | z | | RIKEN cDNA 2610208K14 gene, VRK3 for vaccinia related kinase 3, casein kinase 1, alpha 1, casein kinase 1, delta, casein kinase 1, epsilon, casein kinase 1, gamma 2 |
| 1821 | 21238 | NM_024125 | cc, General | CCAAT/enhancer binding protein (C/EBP), beta | CCAAT/enhancer binding protein (C/EBP), beta |
| 1821 | 21239 | NM_024125 | cc, General | CCAAT/enhancer binding protein (C/EBP), beta | CCAAT/enhancer binding protein (C/EBP), beta |
| 1822 | 353 | NM_024127 | i, n, General | growth arrest and DNA-damage-inducible 45 alpha, growth arrest and DNA-damage-inducible, alpha | growth arrest and DNA-damage-inducible 45 alpha, growth arrest and DNA-damage-inducible 45 beta, growth arrest and DNA-damage-inducible, alpha |
| 1822 | 354 | NM_024127 | i, n, General | growth arrest and DNA-damage-inducible 45 alpha, growth arrest and DNA-damage-inducible, alpha | growth arrest and DNA-damage-inducible 45 alpha, growth arrest and DNA-damage-inducible 45 beta, growth arrest and DNA-damage-inducible, alpha |
| 1822 | 352 | NM_024127 | h, General | growth arrest and DNA-damage-inducible 45 alpha, growth arrest and DNA-damage-inducible, alpha | growth arrest and DNA-damage-inducible 45 alpha, growth arrest and DNA-damage-inducible 45 beta, growth arrest and DNA-damage-inducible, alpha |
| 1823 | 17227 | NM_024131 | x | D-dopachrome tautomerase | D-dopachrome tautomerase, expressed sequence C78655 |
| 1824 | 1598 | NM_024134 | l | DNA-damage inducible transcript 3, DNA-damage-inducible transcript 3 | DNA-damage inducible transcript 3, EST, Moderately similar to GA15_HUMAN GROWTH ARREST AND DNA-DAMAGE-INDUCIBLE PROTEIN GADD153 [H. sapiens], myozenin |
| 1825 | 1162 | NM_024153 | d | | ferredoxin reductase |
| 1826 | 7863 | NM_024156 | c | | ATPase, H+ transporting, lysosomal (vacuolar proton pump) 16 kD, ATPase, H+ transporting, lysosomal (vacuolar proton pump) 21 kD, ESTs, Weakly similar to VACUOLAR ATP SYNTHASE 16 KD PROTEOLIPID SUBUNIT [R. norvegicus], Mus musculus, Similar to ATPase, H+ transporting, lysosomal (vacuolar proton pump) 21 kD, clone MGC: 6568 IMAGE: 2812497, mRNA, complete cds |
| 1827 | 22079 | NM_024157 | x | | EST, Weakly similar to A29154 complement factor I [H. sapiens], I factor, (complement), RIKEN cDNA 1300008A22 gene, complement component factor I, protease, serine, 7 (enterokinase), suppression of tumorigenicity 14 (colon carcinoma), transmembrane protease, serine 2 |
| 1828 | 16476 | NM_024162 | General | fatty acid binding protein 3, muscle and heart, fatty acid binding protein 3, muscle and heart (mammary-derived growth inhibitor) | EST, Moderately similar to FABH MOUSE FATTY ACID-BINDING PROTEIN, HEART [M. musculus], ESTs, Highly similar to PC4011 fatty acid-binding protein - mouse [M. musculus], fatty acid binding protein 3, muscle and heart, fatty acid binding protein 3, muscle and heart (mammary-derived growth inhibitor), fatty acid binding protein 3, pseudogene 2 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1829 | 17765 | NM_024351 | b, s, v | heat shock 70 kD protein 8 | EST, Moderately similar to A27077 dnaK-type molecular chaperone [*H. sapiens*], EST, Weakly similar to A27077 dnaK-type molecular chaperone [*H. sapiens*], EST, Weakly similar to A45935 dnaK-type molecular chaperone hsc70 - mouse [*M. musculus*], heat shock 70 kD protein 8, hypothetical protein MGC4859 similar to HSPA8 |
| 1830 | 8879 | NM_024360 | h | | bHLH factor Hes4, basic helix-loop-helix domain containing, class B, 2, basic helix-loop-helix domain containing, class B, 3, hairy (*Drosophila*)-homolog, hairy and enhancer of split 1, (*Drosophila*), hairy and enhancer of split 6, (*Drosophila*), hairy/enhancer-of-split related with YRPW motif 1, hairy/enhancer-of-split related with YRPW motif 2, likely ortholog of mouse Hes6 neuronal differentiation gene |
| 1831 | 20772 | NM_024363 | x | HMT1 (hnRNP methyltransferase, *S. cerevisiae*)-like 2, heterogeneous nuclear ribonucleoproteins methyltransferase-like 2 (*S. cerevisiae*) | ANM1_HUMAN PROTEIN ARGININE N-METHYLTRANSFERASE 1 [*H. sapiens*], EST, Weakly similar to ANM1_HUMAN PROTEIN ARGININE N-METHYLTRANSFERASE 1 [*H. sapiens*], ESTs, Moderately similar to ANM1_MOUSE PROTEIN ARGININE N-METHYLTRANSFERASE 1 [*M. musculus*], HMT1 (hnRNP methyltransferase, *S. cerevisiae*)-like 2, HMT1 (hnRNP methyltransferase, *S. cerevisiae*)-like 3, *Homo sapiens* cDNA: FLJ23133 fis, clone LNG08560, RIKEN cDNA 2410018A17 gene, coactivator-associated arginine methyltransferase-1, expressed sequence AW214366, heterogeneous nuclear ribonucleoproteins methyltransferase-like 2 (*S. cerevisiae*), heterogeneous nuclear ribonucleoproteins methyltransferase-like 2 (*S. cerevisiae*), related sequence, hypothetical protein FLJ10559 |
| 1832 | 2812 | NM_024386 | c | | 3-hydroxy-3-methylglutaryl-Coenzyme A lyase, 3-hydroxymethyl-3-methylglutaryl-Coenzyme A lyase (hydroxymethylglutaricaciduria), *Homo sapiens* clone 24959 mRNA sequence, partial cds, hypothetical protein |
| 1833 | 335 | NM_024387 | j, y | | RIKEN cDNA 2700048O17 gene, heme oxygenase (decycling) 2 |
| 1834 | 21 | NM_024388 | cc | | nuclear receptor subfamily 4, group A, member 1 |
| 1834 | 22 | NM_024388 | cc | | nuclear receptor subfamily 4, group A, member 1 |
| 1836 | 9929 | NM_024392 | f | | *Homo sapiens* cDNA FLJ13261 fis, clone OVARC1000885, weakly similar to OXIDOREDUCTASE UCPA (EC 1.—.—.—), Human DNA sequence from clone 1068E13 on chromosome 20p11.21-12.3. Contains two putative novel genes, the gene for a novel protein similar to bovine SCP2 (Sterol Carrier Protein 2) and part of HSD17B4 (hydroxysteroid (17-beta) dehydrogenase 4), an EEF1A1 (eukaryotic translation elongation factor 1 alpha 1) pseudogene, ESTs, STSs and GSSs, RIKEN cDNA 1110029G07 gene, RIKEN cDNA |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | 1700010M22 gene, RIKEN cDNA 1810026B04 gene, RIKEN cDNA 2610207I16 gene, expressed sequence AW208803, hydroxysteroid (17-beta) dehydrogenase 4, hydroxysteroid 17-beta dehydrogenase 4, hypothetical protein MGC10940, oxidoreductase UCPA, retinal short-chain dehydrogenase/reductase 1 |
| 1837 | 3582 | NM_024396 | aa | | ATP-binding cassette, sub-family A (ABC1), member 2, ATP-binding cassette, sub-family A (ABC1), member 3, ATP-binding cassette, sub-family A (ABC1), member 4, ATP-binding cassette, sub-family A (ABC1), member 7, ATP-binding cassette, sub-family A (ABC1), member 8, ESTs, Weakly similar to ABC2 MOUSE ATP-BINDING CASSETTE TRANSPORTER 2 [*M. musculus*], *Homo sapiens* mRNA for KIAA1888 protein, partial cds, hypothetical protein FLJ14297, hypothetical protein PRO2543 |
| 1838 | 19993 | NM_024398 | e, p, s, aa | | DNA segment, Chr 9, ERATO Doi 85, expressed, *Homo sapiens* aconitase precursor (ACON) mRNA, nuclear gene encoding mitochondrial protein, partial cds, RIKEN cDNA 5031409G22 gene, aconitase 1, aconitase 1, soluble, aconitase 2, mitochondrial, iron-responsive element-binding protein |
| 1839 | 10789 | NM_024399 | o | | *Homo sapiens*, RIKEN cDNA 0610006H10 gene, clone MGC: 17267 IMAGE: 4155233, mRNA, complete cds, *Homo sapiens*, Similar to RIKEN cDNA 0610006H10 gene, clone MGC: 9740 IMAGE: 3853707, mRNA, complete cds, aspartoacylase (aminoacylase 2, Canavan disease) |
| 1840 | 22626 | NM_024400 | cc, General | | ESTs, Weakly similar to T47158 hypothetical protein DXFZp762C1110.1 [*H. sapiens*], *Mus musculus* papilin mRNA, complete cds, *Mus musculus*, Similar to a disintegrin and metalloproteinase with thrombospondin motifs 1 (ADAMTS-1), clone IMAGE: 3491991, mRNA, partial cds, RIKEN cDNA 6720426B09 gene, RIKEN cDNA A930008K15 gene, a disintegrin-like and metalloprotease (reprolysin type) with thrombospondin type 1 motif, 1, a disintegrin-like and metalloprotease (reprolysin type) with thrombospondin type 1 motif, 4, a disintegrin-like and metalloprotease (reprolysin type) with thrombospondin type 1 motif, 8, a disintegrin-like and metalloprotease (reprolysin type) with thrombospondin type 1 motif, 9 |
| 1841 | 13633 | NM_024403 | g, General | | EST, Weakly similar to ATF4_HUMAN CYCLIC-AMP-DEPENDENT TRANSCRIPTION FACTOR ATF-4 [*H. sapiens*], activating transcription factor 4 (tax-responsive enhancer element B67), activating transcription factor 5 |
| 1841 | 13634 | NM_024403 | g, General | | EST, Weakly similar to ATF4_HUMAN CYCLIC-AMP-DEPENDENT TRANSCRIPTION FACTOR ATF-4 [*H. sapiens*], activating transcription factor 4 (tax-responsive enhancer |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1842 | 23387 | NM_024404 | b, General | | element B67), activating transcription factor 5 ESTs, Moderately similar to HETEROGENEOUS NUCLEAR RIBONUCLEOPROTEIN C [*R. norvegicus*], ESTs, Weakly similar to A44192 heterogeneous nuclear ribonucleoprotein C-like protein [*H. sapiens*], *Mus musculus* high-glycine/tyrosine protein type I E5 mRNA, complete cds, expressed sequence C85084, heterogeneous nuclear ribonucleoprotein A/B, heterogeneous nuclear ribonucleoprotein D, heterogeneous nuclear ribonucleoprotein D (AU-rich element RNA-binding protein 1, 37 kD) |
| 1843 | 21038 | NM_024484 | h | aminolevulinate, delta-, synthase 1, aminolevulinic acid synthase 1 | EST, Weakly similar to SYHUAL 5-aminolevulinate synthase [*H. sapiens*], ESTs, Moderately similar to 5-AMINOLEVULINIC ACID SYNTHASE MITOCHONDRIAL PRECURSOR, NONSPECIFIC [*R. norvegicus*], aminolevulinate, delta-, synthase 1, aminolevulinic acid synthase 1, aminolevulinic acid synthase 2, erythroid, serine palmitoyltransferase, long chain base subunit 1, serine palmitoyltransferase, long chain base subunit 2 |
| 1844 | 1853 | NM_030826 | s | glutathione peroxidase 1 | GSHG_MOUSE GLUTATHIONE PEROXIDASE-GASTROINTESTINAL (GSHPX-GI) [*M. musculus*], ESTs, Weakly similar to GSHC RAT GLUTATHIONE PEROXIDASE [*R. norvegicus*], glutathione peroxidase 1, glutathione peroxidase 2 (gastrointestinal) |
| 1845 | 15111 | NM_030827 | e, General | low density lipoprotein receptor-related protein 2, low density lipoprotein-related protein 2 | EST, Highly similar to LRP2 RAT LOW-DENSITY LIPOPROTEIN RECEPTOR-RELATED PROTEIN 2 PRECURSOR [*R. norvegicus*], EST, Moderately similar to S25111 alpha-2-macroglobulin receptor precursor - mouse [*M. musculus*], ESTs, Highly similar to S02392 alpha-2-macroglobulin receptor precursor [*H. sapiens*], ESTs, Highly similar to S25111 alpha-2-macroglobulin receptor precursor - mouse [*M. musculus*], ESTs, Weakly similar to I53413 calcium sensor protein [*H. sapiens*], expressed sequence C79313, low density lipoprotein receptor-related protein 1, low density lipoprotein receptor-related protein 2, low density lipoprotein-related protein 1B (deleted in tumors), low density lipoprotein-related protein 2 |
| 1845 | 15112 | NM_030827 | y, z | low density lipoprotein receptor-related protein 2, low density lipoprotein-related protein 2 | EST, Highly similar to LRP2 RAT LOW-DENSITY LIPOPROTEIN RECEPTOR-RELATED PROTEIN 2 PRECURSOR [*R. norvegicus*], EST, Moderately similar to S25111 alpha-2-macroglobulin receptor precursor - mouse [*M. musculus*], ESTs, Highly similar to S02392 alpha-2-macroglobulin receptor precursor [*H. sapiens*], ESTs, Highly similar to S25111 alpha-2-macroglobulin receptor precursor - mouse [*M. musculus*], ESTs, Weakly similar to I53413 calcium sensor protein [*H. sapiens*], expressed sequence |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1845 | 15110 | NM_030827 | General | low density lipoprotein receptor-related protein 2, low density lipoprotein-related protein 2 | C79313, low density lipoprotein receptor-related protein 1, low density lipoprotein receptor-related protein 2, low density lipoprotein-related protein 1B (deleted in tumors), low density lipoprotein-related protein 2 EST, Highly similar to LRP2 RAT LOW-DENSITY LIPOPROTEIN RECEPTOR-RELATED PROTEIN 2 PRECURSOR [*R. norvegicus*], EST, Moderately similar to S25111 alpha-2-macroglobulin receptor precursor - mouse [*M. musculus*], ESTs, Highly similar to S02392 alpha-2-macroglobulin receptor precursor [*H. sapiens*], ESTs, Highly similar to S25111 alpha-2-macroglobulin receptor precursor - mouse [*M. musculus*], ESTs, Weakly similar to I53413 calcium sensor protein [*H. sapiens*], expressed sequence C79313, low density lipoprotein receptor-related protein 1, low density lipoprotein receptor-related protein 2, low density lipoprotein-related protein 1B (deleted in tumors), low density lipoprotein-related protein 2 |
| 1846 | 808 | NM_030837 | k, m | | solute carrier family 21 (organic anion transporter), member 1, solute carrier family 21 (organic anion transporter), member 10, solute carrier family 21 (organic anion transporter), member 14, solute carrier family 21 (organic anion transporter), member 3, solute carrier family 21 (organic anion transporter), member 6 |
| 1847 | 4057 | NM_030844 | k | | ESTs, Weakly similar I65309 autoantigen p69 - rat [*R. norvegicus*], Homo sapiens ALS2CR15 mRNA, partial cds, RIKEN cDNA 1700030B17 gene, islet cell autoantigen 1 (69 kD), islet cell autoantigen 1, 69 kDa |
| 1848 | 1221 | NM_030845 | t | | GRO1 oncogene, GRO2 oncogene, *Rattus norvegicus* CXC chemokine RTCK1 (Rtck1) mRNA, complete cds, interleukin 8, platelet factor 4, pro-platelet basic protein, pro-platelet basic protein (includes platelet basic protein, beta-thromboglobulin, connective tissue-activating peptide III, neutrophil-activating peptide-2) |
| 1849 | 21509 | NM_030847 | x | | ESTs, Weakly similar to PERIPHERAL MYELIN PROTEIN 22 [*R. norvegicus*], Peripheral myelin protein, epithelial membrane protein 3, peripheral myelin protein 22, peripheral myelin protein, 22 kDa |
| 1850 | 1928 | NM_030872 | v | pyruvate dehydrogenase 2, pyruvate dehydrogenase kinase, isoenzyme 2 | EST, Highly similar to PDK2 RAT [*R. norvegicus*], expressed sequence AI035637, pyruvate dehydrogenase 2, pyruvate dehydrogenase kinase, isoenzyme 2 |
| 1851 | 17342 | NM_030873 | u | | EST, Weakly similar to A Chain A, Human Platelet Profilin Complexed With The L-Pro10 Peptide {SUB 3-140 [*H. sapiens*], ESTs, Weakly similar to profilin [*R. norvegicus*], RIKEN cDNA 1700012P12 gene, profilin, profilin 1, profilin 2 |
| 1852 | 24648 | NM_030985 | u | | G protein-coupled receptor 15, G-protein coupled receptor SALPR; somatostatin and angiotensin-like peptide receptor, angiotensin receptor 1, expressed sequence AI551199 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1852 | 25453 | NM_030985 | General | | |
| 1853 | 21802 | NM_030987 | h | | ESTs, Weakly similar to GBB1 RAT GUANINE NUCLEOTIDE-BINDING PROTEIN G(I)/G(S)/G(T) BETA SUBUNIT 1 [*R. norvegicus*], *Mus musculus*, clone MGC: 7934 IMAGE: 3583848, mRNA, complete cds, RIKEN cDNA 5930415H02 gene, constitutive photomorphogenic protein 1 (*Arabidopsis*), guanine nucleotide binding protein (G protein), beta polypeptide 1, guanine nucleotide binding protein beta subunit 4, guanine nucleotide binding protein, beta 1, guanine nucleotide binding protein, beta 4, similar to constitutive photomorphogenic protein 1 (*Arabidopsis*) |
| 1854 | 23109 | NM_031000 | f, s, z | | EST, Weakly similar to ALCOHOL DEHYDROGENASE [*R. norvegicus*], RIKEN cDNA 2310005E10 gene, aldo-keto reductase family 1, member A1 (aldehyde reductase), aldo-keto reductase family 1, member A4 (aldehyde reductase), aldo-keto reductase family 1, member E1 |
| 1855 | 134 | NM_031003 | a, u | | 4-aminobutyrate aminotransferase, RIKEN cDNA 1300019H02 gene, RIKEN cDNA 2900006B13 gene, ornithine aminotransferase |
| 1856 | 25461 | NM_031009 | o | | |
| 1857 | 1845 | NM_031010 | t | | ARACHIDONATE 12-LIPOXYGENASE [*R. norvegicus*], arachidonate 12-lipoxygenase, arachidonate 12-lipoxygenase pseudogene 2, arachidonate 15-lipoxygenase, expressed sequence AW259591 |
| 1857 | 25517 | NM_031010 | c, t | | ARACHIDONATE 12-LIPOXYGENASE [*R. norvegicus*], arachidonate 12-lipoxygenase, arachidonate 12-lipoxygenase pseudogene 2, arachidonate 15-lipoxygenase, expressed sequence AW259591 |
| 1858 | 16562 | NM_031020 | f | | ESTs, Weakly similar to MK14 RAT MITOGEN-ACTIVATED PROTEIN KINASE 14 [*R. norvegicus*], mitogen activated protein kinase 14, mitogen-activated protein kinase 11, mitogen-activated protein kinase 14 |
| 1859 | 1480 | NM_031021 | f | | casein kinase 2, beta polypeptide, casein kinase II, beta subunit |
| 1860 | 1719 | NM_031024 | n | drebrin 1 | ESTs, Moderately similar to T30989 serine/threonine protein kinase NIK - mouse [*M. musculus*], RIKEN cDNA 1500031A17 gene, drebrin 1, drebrin-like, hypothetical protein FLJ13154, mitogen-activated protein kinase kinase kinase kinase 4, mitogen-activated protein kinase kinase kinase kinase 6, src homology 3 domain-containing protein HIP-55 |
| 1861 | 1350 | NM_031030 | h | | DnaJ (Hsp40) homolog, subfamily B, member 6, EST, Moderately similar to NEK1 MOUSE SERINE/THREONINE-PROTEIN KINASE NEK1 [*M. musculus*], EST, Moderately similar to T31096 cyclin G-associated kinase GAK - rat [*R. norvegicus*], EST, Weakly similar to T31096 cyclin G-associated kinase GAK - rat [*R. norvegicus*], ESTs, Moderately similar to NEK1 MOUSE SERINE/THREONINE-PROTEIN |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | KINASE NEK1 [*M. musculus*], KIAA1048 protein, *Mus musculus*, Similar to cyclin G associated kinase, clone IMAGE: 3487931, mRNA, partial cds, NIMA (never in mitosis gene a)-related expressed kinase 1, RIKEN cDNA 4632401F23 gene, cyclin G associated kinase, hypothetical protein DKFZp434P0116, serine/threonine kinase 16 |
| 1862 | 16775 | NM_031031 | General | | ESTs, Highly similar to GLYCINE AMIDINOTRANSFERASE PRECURSOR [*R. norvegicus*], RIKEN cDNA 1810003P21 gene, glycine amidinotransferase (L-arginine: glycine amidinotransferase) |
| 1863 | 691 | NM_031034 | w | | ESTs, Highly simitar to GB12 RAT GUANINE NUCLEOTIDE-BINDING PROTEIN, ALPHA-12 SUBUNIT [*R. norvegicus*], guanine nucleotide binding protein (G protein) alpha 12, guanine nucleotide binding protein (G protein), alpha 13, guanine nucleotide binding protein, alpha 12, guanine nucleotide binding protein, alpha 13 |
| 1864 | 15886 | NM_031035 | z | | guanine nucleotide binding protein (G protein), alpha inhibiting activity polypeptide 2, guanine nucleotide binding protein, alpha inhibiting 2, guanine nucleotide binding protein, alpha inhibiting 3 |
| 1866 | 3608 | NM_031044 | k, General | | *Homo sapiens*, Similar to histamine N-methyltransferase, clone MGC: 14500 IMAGE: 4249496, mRNA, complete cds, expressed sequence AI788969, histamine N-methyltransferase |
| 1866 | 3610 | NM_031044 | d, General | | *Homo sapiens*, Similer to histamine N-methyltransferase, clone MGC: 14500 IMAGE: 4249496, mRNA, complete cds, expressed sequence AI788969, histamine N-methyltransferase |
| 1867 | 15137 | NM_031051 | s | | EST, Highly similar to C Chain C, Macrophage Migration Inhibitory Factor [*H. sapiens*], EST, Moderately similar to C Chain C, Macrophage Migration Inhibitory Factor [*H. sapiens*], EST, Moderately similar to MIF RAT MACROPHAGE MIGRATION INHIBITORY FACTOR [*R. norvegicus*], macrophage migration inhibitory factor, macrophage migration inhibitory factor (glycosylation-inhibiting factor) |
| 1868 | 514 | NM_031056 | General | | matrix metalloproteinase 14 (membrane-inserted), matrix metalloproteinase 19, vitronectin |
| 1869 | 17269 | NM_031057 | General | | RIKEN cDNA 1110038I05 gene, aldehyde dehydrogenase family 1, subfamily A4, expressed sequence AI427784, hypothetical protein FLJ23189, methylmalonate-semialdehyde dehydrogenase |
| 1870 | 11849 | NM_031065 | a | | EST, Moderately similar to R10A MOUSE 60S RIBOSOMAL, PROTEIN L10A [*M. musculus*], EST, Weakly similar to 60S RIBOSOMAL PROTEIN L10A [*R. norvegicus*], ESTs, Highly similar to R10A_HUMAN 60S RIBOSOMAL PROTEIN L10A [*H. sapiens*], ribosomal protein L10A, ribosomal protein L10a |
| 1871 | 1855 | NM_031074 | h | nucleoporin 98, nucleoporin 98 kD | EST, Highly similar to NU98 RAT NUCLEAR PORE COMPLEX PROTEIN NUP98 [*R. norvegicus*], ESTs, Weakly similar to NU98 RAT |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1872 | 4683 | NM_031083 | d | | NUCLEAR PORE COMPLEX PROTEIN NUP98 [R. norvegicus], RIKEN cDNA 0610038H21 gene, RIKEN cDNA 4930432K09 gene, RIKEN cDNA 5430432N15 gene, melanoma antigen, family D, 3, nucleoporin 98 kD, plasma membrane associated protein, S3-12, trophinin phosphatidylinositol 3-kinase, catalytic, alpha polypeptide, phosphatidylinositol 4-kinase, catalytic, beta polypeptide, phosphoinositide-3-kinase, catalytic, gamma polypeptide |
| 1873 | 15202 | NM_031093 | a | | EST, Weakly similar to RALA MOUSE RAS-RELATED PROTEIN RAL-A [M. musculus], Homo sapiens cDNA: FLJ23197 fis, clone REC00917, RIKEN cDNA 1110065D03 gene, v-ral simian leukemia viral oncogene homolog A (ras related), v-ral simian leukemia viral oncogene homolog B (ras related) |
| 1873 | 15201 | NM_031093 | a, n | | EST, Weakly similar to RALA MOUSE RAS-RELATED PROTEIN RAL-A [M. musculus], Homo sapiens cDNA: FLJ23197 fis, clone REC00917, RIKEN cDNA 1110065D03 gene, v-ral simian leukemia viral oncogene homolog A (ras related), v-ral simian leukemia viral oncogene homolog B (ras relaled) |
| 1874 | 12639 | NM_031099 | aa | | ESTs, Weakly similar to S55912 ribosomal protein L5, cytosolic [H. sapiens], ribosomal protein L5 |
| 1875 | 20812 | NM_031100 | a | | EST, Moderately similar to 60S RIBOSOMAL PROTEIN L10 [M. musculus], EST, Moderately similar to 60S RIBOSOMAL PROTEIN L10 [R. norvegicus], ESTs, Highly similar to A42735 ribosomal protein L10, cytosolic [H. sapiens], Homo sapiens, Similar to ribosomal protein L10, clone MGC: 22634 IMAGE: 3935452, mRNA, complete cds, Human DNA sequence from clone RP3-334F4 on chromosome 6 Contains ESTs, STSs and GSSs. Contains a LAMR1 (laminin receptor 1, ribosomal protein SA) pseudogene and an RPL10 (ribosomal protein L10) pseudogene, Mouse 24.6 kda protein mRNA, complete cds, ribosomal protein L10 |
| 1876 | 16938 | NM_031103 | w | | ESTs, Weakly similar to 60S RIBOSOMAL PROTEIN L19 [R. norvegicus], Homo sapiens mRNA; cDNA DKFZp434D115 (from clone DKFZp434D115), ribosomal protein L19 |
| 1877 | 19268 | NM_031104 | q | | ESTs, Highly similar to JC2120 heparin-binding protein 15 [H. sapiens], ESTs, Moderately similar to RL22 RAT 60S RIBOSOMAL PROTEIN L22 [R. norvegicus], Homo sapiens mRNA; cDNA DKFZp586E0524 (from clone DKFZp586E0524), Human DNA sequence from clone 581F12 on chromosome Xq21. Contains Eukaryotic Translation Initiation Factor EIF3 P35 Subunit and 60S Ribosomal protein L22 pseudogenes. Contains ESTs, RIKEN cDNA 2700038K18 gene, RIKEN cDNA 3110001N18 gene, expressed sequence AU041196, ribosomal protein L22 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1878 | 16929 | NM_031108 | q | | EST, Weakly similar to RS9 RAT 40S RIBOSOMAL PROTEIN S9 [*R. norvegicus*], EST, Weakly similar to S55917 ribosomal protein S9, cytosolic [*H. sapiens*], *Homo sapiens*, clone IMAGE: 4500773, mRNA, partial cds, RIKEN cDNA 3010033P07 gene, expressed sequence AL022771, expressed sequence AL022885, mitochondrial ribosomal protein S4, ribosomal protein S9 |
| 1879 | 10878 | NM_031110 | q, bb | | EST, Weakly similar to 40S RIBOSOMAL PROTEIN S11 [*R. norvegicus*], *Homo sapiens* mRNA; cDNA DKFZp434A0326 (from clone DKFZp434A0326), Human DNA sequence from clone RP5-1060K6 on chromosome 20p12.1-13. Contains an RPS11 (40S ribosomal protein S11) pseudogene, ESTs, STSs and GSSs, RAD21 homolog (*S. pombe*), ribosomal protein S11 |
| 1880 | 19162 | NM_031111 | aa | | EST, Moderately similar to 40S RIBOSOMAL PROTEIN S21 [*R. norvegicus*], Human DNA sequence from clone RP5-1116H23 on chromosome 20 Contains a novel gene, a 40S ribosomal protein S21 pseudogene, 2 CpG islands, ESTs, STSs and GSSs, RIKEN cDNA 1810049N11 gene, RIKEN cDNA 2410030A14 gene, ribosomal protein S21 |
| 1880 | 19161 | NM_031111 | a, bb | | EST, Moderately similar to 40S RIBOSOMAL PROTEIN S21 [*R. norvegicus*], Human DNA sequence from clone RP5-1116H23 on chromosome 20 Contains a novel gene, a 40S ribosomal protein S21 pseudogene, 2 CpG islands, ESTs, STSs and GSSs, RIKEN cDNA 1810049N11 gene, RIKEN cDNA 2410030A14 gene, ribosomal protein S21 |
| 1881 | 24615 | NM_031112 | a, y | | EST, Highly similar to 40S RIBOSOMAL PROTEIN S24 [*R. norvegicus*], EST, Weakly similar to JH0213 ribosomal protein S24, cytosolic [*H. sapiens*], EST, Weakly similar to RS24_HUMAN 40S RIBOSOMAL PROTEIN S24 [*M. musculus*], ESTs, Highly similar to JH0213 ribosomal protein S24, cytosolic [*H. sapiens*], ESTs, Weakly similar to RS24_HUMAN 40S RIBOSOMAL PROTEIN S24 [*H. sapiens*], ribosomal protein S24 |
| 1882 | 20839 | NM_031113 | a, q | | EST, Moderately similar to S12583 polyubiquitin 4 - mouse [*M. musculus*], EST, Moderately similar to ubiquitin/ ribosomal protein S27a [*R. norvegicus*], EST, Weakly similar to R27A_HUMAN 40S RIBOSOMAL PROTEIN S27A {SUB 77-156 [*H. sapiens*], *Homo sapiens* cDNA FLJ11603 fis, clone HEMBA1003926, RIKEN cDNA 0610006J14 gene, expressed sequence AI132487, ribosomal protein S27a, ubiquitin C |
| 1883 | 19040 | NM_031114 | l, m, General | S100 calcium binding protein A10 (calgizzarin), S100 calcium binding protein A10 (annexin II ligand, calpactin I, light | EST, Moderately similar to A Chain A, P11 [*H. sapiens*], EST, Moderately similar to CALPACTIN I LIGHT CHAIN [*R. noevegicus*], S100 calcium-binding protein A10 (annexin II ligand, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | polypeptide (p11)) | calpactin I, light polypeptide (p11)), calcium binding protein A11 (calgizzarin) |
| 1884 | 16349 | NM_031115 | u | | ESTs, Highly similar to 2111411A secretin receptor [*H. sapiens*], ESTs, Weakly similar to vasoactive intestinal polypeptide 1 [*M. musculus*], adenylate cyclase activating polypeptide 1 receptor 1, secretin receptor, vasoactive intestinal peptide receptor 1 |
| 1885 | 14970 | NM_031127 | General | | ESTs, Highly similar to SUOX RAT SULFITE OXIDASE PRECURSOR [*R. norvegicus*], RIKEN cDNA 0610009N12 gene, RIKEN cDNA 1810044O22 gene, RIKEN cDNA 2810034J18 gene, fatty acid desaturase 2, sulfite oxidase |
| 1886 | 1814 | NM_031134 | n, q | thyroid hormone receptor alpha, thyroid hormone receptor, alpha (avian erythroblastic leukemia viral (v-erb-a) oncogene homolog) | EST, Weakly similar to A30893 thyroid hormone receptor alpha, splice form 2 [*H. sapiens*], expressed sequence AW259572, expressed sequence R75201, thyroid hormone receptor, alpha (avian erythroblastic leukemia viral (v-erb-a) oncogene homolog) |
| 1887 | 13359 | NM_031135 | General | | Kruppel-like factor 15 (kidney), Kruppel like factor 9, RIKEN cDNA 4930480I16 gene, TGFB inducible early growth response, basic transcription element binding protein 1, trans-acting transcription factor 3, trans-acting transcription factor 6 |
| 1888 | 15052 | NM_031136 | a | | ESTs, Highly similar to A38682 thymosin beta-4 [*H. sapiens*], ESTs, Highly similar to TYB4 MOUSE THYMOSIN BETA-4 [*M. musculus*], ESTs, Highly similar to TYB4_HUMAN THYMOSIN BETA-4 [*H. sapiens*], Human interferon-inducible mRNA (cDNA 6-26), expressed sequence AW544206, thymosin, beta 10, thymosin, beta 4, X chromosome, thymosin, beta 4, Y chromosome |
| 1888 | 19359 | NM_031136 | a | | |
| 1889 | 15185 | NM_031140 | General | | EST, Moderately similar to A25074 vimentin [*H. sapiens*], EST, Weakly similar to A25074 vimentin [*H. sapiens*], ESTs, Moderately similar to VIME RAT VIMENTIN [*R. norvegicus*], ESTs, Weakly similar to A25074 vimentin [*H. sapiens*], ESTs, Weakly similar to VIME RAT VIMENTIN [*R. norvegicus*], vimentin |
| 1890 | 21625 | NM_031144 | a, e | | EST, Weakly similar to ACTB_HUMAN ACTIN, CYTOPLASMIC 1 [*R. norvegicus*], ESTs, Highly similar to ATHUB actin beta [*H. sapiens*], ESTs, Weakly similar to ACTB_HUMAN ACTIN, CYTOPLASMIC 1 [*R. norvegicus*], *Homo sapiens* FKSG30 (FKSG30) mRNA, complete cds, RIKEN cDNA 1700052K15 gene, RIKEN cDNA 1700061J02 gene, actin, beta, actin-like 7a, actin-related protein 3-beta, melanoma X-actin |
| 1891 | 238 | NM_031152 | bb | | CATX-8 protein, ESTs, Weakly similar to R11A_HUMAN RAS-RELATED PROTEIN RAB-11A [*R. norvegicus*], RAB, member of RAS oncogene family like 2A, RAB11A, member RAS oncogene family, RAB11a, member RAS oncogene family, RAB25, member RAS oncogene family, RIKEN cDNA 2700023P08 gene |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1891 | 240 | NM_031152 | bb | | CATX-8 protein, ESTs, Weakly similar to R11A_HUMAN RAS-RELATED PROTEIN RAB-11A [*R. norvegicus*], RAB, member of RAS oncogene family like 2A, RAB11A, member RAS oncogene family, RAB11a, member RAS oncogene family, RAB25, member RAS oncogene family, RIKEN cDNA 2700023P08 gene |
| 1892 | 15277 | NM_031237 | g | | EST, Moderately similar to UB5B_HUMAN UBIQUITIN-CONJUGATING ENZYME E2-17 KD 2 [*R. norvegicus*], ESTs, Moderately similar to I59365 ubiquitin conjugating enzyme [*H. sapiens*], ESTs, Moderately similar to UB5B_HUMAN UBIQUITIN-CONJUGATING ENZYME E2-17 KD 2 [*M. musculus*], RIKEN cDNA 1100001F19 gene, RIKEN cDNA 1600028I17 gene, RIKEN cDNA 2700084L22 gene, *Rattus norvegicus* clone ubc2e ubiquitin conjugating enzyme (E217kB) mRNA, complete cds, expressed sequence AL022654, ubiquitin-conjugating enzyme E2D 1 (homologous to yeast UBC4/5), ubiquitin-conjugating enzyme E2D 2, ubiquitin-conjugating enzyme E2D 2 (homologous to yeast UBC4/5), ubiquitin-conjugating enzyme E2D 3 (homologous to yeast UBC4/5) |
| 1893 | 18083 | NM_031315 | q | | ESTs, Weakly similar to YZ28_HUMAN HYPOTHETICAL PROTEIN ZAP128 [*H. sapiens*], *Mus musculus*, Similar to cytosolic acyl-CoA thioesterase 1, clone MGC: 27572 IMAGE: 4485973, mRNA, complete cds |
| 1893 | 1858 | NM_031315 | q | cytosolic acyl-CoA thioesterase 1, peroxisomal long-chain acyl-coA thioesterase | PTE2_HUMAN PEROXISOMAL ACYL-COENZYME A THIOESTER HYDROLASE 2 (PEROXISOMAL LONG-CHAIN ACYL-COA THIOESTERASE 2) (ZAP128) [*H. sapiens*], ESTs, Moderately similar to JE0267 long-chain fatty-acyl-CoA hydrolase (EC 3.1.2.—) peroxisome proliferator-inducible - rat [*R. norvegicus*], ESTs, Moderately similar to PTE2_HUMAN PEROXISOMAL ACYL-COENZYME A THIOESTER HYDROLASE 2 (PEROXISOMAL LONG-CHAIN ACYL-COA THIOESTERASE 2) (ZAP128) [*H. sapiens*], ESTs, Weakly similar to PTE2_HUMAN PEROXISOMAL ACYL-COENZYME A THIOESTER HYOROLASE 2 (PEROXISOMAL LONG-CHAIN ACYL-COA THIOESTERASE 2) (ZAP128) [*H. sapiens*], ESTs, Weakly similar to YZ28_HUMAN HYPOTHETICAL PROTEIN ZAP128 [*H. sapiens*], *Mus musculus*, Similar to cytosolic acyl-CoA thioesterase 1, clone MGC: 27572 IMAGE: 4485973, mRNA, complete cds, RIKEN cDNA 4632408A20 gene, cytosolic acyl-CoA thioesterase 1, expressed sequence AW108394, peroxisomal long-chain acyl-coA |
| 1894 | 15663 | NM_031318 | General | | t-complex testis expressed 1, t-complex-associated-testis-expressed 1 like 1 |
| 1895 | 1422 | NM_031324 | bb, General | | ESTs, Moderately similar to I38134 prolyl oligopeptidase [*H. sapiens*], prolyl endopeptidase |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1896 | 18597 | NM_031325 | g, bb | | UDP-glucose dehydrogenase |
| 1897 | 11259 | NM_031327 | i, cc, General | | ESTs, Moderately similar to CYR6 MOUSE CYR61 PROTEIN PRECURSOR [*M. musculus*], cysteine rich protein 61, cysteine-rich, angiogenic inducer, 61 |
| 1898 | 4235 | NM_031330 | General | heterogeneous nuclear ribonucleoprotein A/B | ESTs, Highly similar to WZHURS argininosuccinate lyase [*H. sapiens*], ESTs, Weakly similar to 1601424A argininosuccinate lyase [*R. norvegicus*], *Homo sapiens* cDNA FLJ14312 fis, clone PLACE3000322, Musashi-1 homolog (*Drosophila*), RIKEN cDNA 2510006M18 gene, RIKEN cDNA 4933434H11 gene, argininosuccinate lyase, heterogeneous nuclear ribonucleoprotein A/B, heterogeneous nuclear ribonucleoprotein D-like |
| 1899 | 18375 | NM_031331 | l, m | | EST, Weakly similar to PSD4_HUMAN 26S PROTEASOME REGULATORY SUBUNIT S5A [*H. sapiens*], ESTs, Moderately similar to PSD4_HUMAN 26S PROTEASOME REGULATORY SUBUNIT S5A [*H. sapiens*], proteasome (prosome, macropain) 26S subunit, non-ATPase, 4 |
| 1900 | 3519 | NM_031334 | cc | cadherin 1, cadherin 1, type 1, E-cadherin (epithelial) | ESTs, Weakly similar to I49556 cadherin-11 - mouse [*M. musculus*], RIKEN cDNA 2610005L07 gene, cadherin 1, type 1, E-cadherin (epithelial), cadherin 6, cadherin 6, type 2, K-cadherin (fetal kidney) |
| 1901 | 20698 | NM_031357 | b | | |
| 1903 | 634 | NM_031509 | n | | EST, Moderately similar to GTC MOUSE GLUTATHIONE S-TRANSFERASE YC [*M. musculus*], glutathione S-transferase A3, glutathione S-transferase, alpa 3 |
| 1903 | 25525 | NM_031509 | n | | |
| 1903 | 25069 | NM_031509 | b, n, w | | |
| 1903 | 635 | NM_031509 | z | | EST, Moderately similar to GTC MOUSE GLUTATHIONE S-TRANSFERASE YC [*M. musculus*], glutathione S-transferase A3, glutathione S-transferase, alpha 3 |
| 1904 | 848 | NM_031517 | t | met proto-oncogene, met proto-oncogene (hepatocyte growth factor receptor) | EST, Highly similar to RON_HUMAN MACROPHAGE-STIMULATING PROTEIN RECEPTOR PRECURSOR [*H. sapiens*], ESTs, Highly similar to TVHUME hepatocyte growth factor receptor precursor [*H. sapiens*], *Mus musculus* D86 mRNA, complete cds, *Rattus norvegicus* ryk mRNA for tyrosine kinase-related protein, partial cds, macrophage stimulating 1 receptor (c-met-related tyrosine kinase), met proto-oncogene, met photo-oncogene (hepatocyte growth factor receptor) |
| 1905 | 1872 | NM_031523 | a | | RIKEN cDNA 0610007D04 gene, kallikrein 1, renal/pancreas/salivary, kallikrein 5, kallikrein 9, nerve growth factor, alpha, nerve growth factor, gamma |
| 1905 | 16245 | NM_031523 | a, d, u | | EST, Moderately similar to epidermal growth factor binding protein type 1 [*M. musculus*], EST, Weakly similar to pre-pro-protein for kallikrein [*H. sapiens*] |
| 1905 | 16244 | NM_031523 | a | | EST, Moderately similar to epidermal growth factor binding protein type 1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1906 | 9370 | NM_031527 | w | protein phosphatase 1, catalytic subunit, alpha isoform | [*M. musculus*], EST, Weakly similar to pre-pro-protein for kallikrein [*H. sapiens*] EST, Weakly similar to JN0723 phosphoprotein phosphatase [*H. sapiens*], protein phosphatase 1, catalytic subunit, alpha isoform |
| 1907 | 20448 | NM_031530 | General | small inducible cytokine A2, small inducible cytokine A2 (monocyte chemotactic protein 1, homologous to mouse Sig-je) | EST, Weakly similar to SY02 RAT SMALL INDUCIBLE CYTOKINE A2 PRECURSOR [*R. norvegicus*], expressed sequence AI323594, expressed sequence AW987545, small inducible cytokine A2, small inducible cytokine A24, small inducible cytokine A7 (monocyte chemotactic protein 3), small inducible cytokine subfamily A (Cys-Cys), member 17 |
| 1907 | 20449 | NM_031530 | General | small inducible cytokine A2, small inducible cytokine A2 (monocyte chemotactic protein 1, homologous to mouse Sig-je) | EST, Weakly similar to SY02 RAT SMALL INDUCIBLE CYTOKINE A2 PRECURSOR [*R. norvegicus*], expressed sequence AI323594, expressed sequence AW987545, small inducible cytokine A2, small inducible cytokine A24, small inducible cytokine A7 (monocyte chemotactic protein 3), small inducible cytokine subfamily A (Cys-Cys), member 17 |
| 1908 | 14633 | NM_031533 | u | | ESTs, Moderately similar to UDP-GLUCURONOSYLTRANSFERASE 2B5 PRECURSOR, MICROSOMAL [*M. musculus*], ESTs, Weakly similar to UDB7_HUMAN UDP-GLUCURONOSYLTRANSFERASE 2B7 PRECURSOR, MICROSOMAL [*H. sapiens*], ESTs, Weakly similar to UDBH_HUMAN UDP-GLUCURONOSYLTRANSFERASE 2B17 PRECURSOR, MICROSOMAL [*H. sapiens*], RIKEN cDNA 0610033E06 gene, UDP glycosyltransferase 2 family, polypeptide B17, UDP-glucuronosyltransferase 2 family, member 5, expressed sequence AA986709 |
| 1909 | 16048 | NM_031541 | f | CD36 antigen (collagen type I receptor, thrombospondin receptor)-like 1, scavenger receptor class B1 | CD36 antigen (collagen type I receptor, thrombospondin receptor)-like 1, CD36 antigen (collagen type I receptor, thrombospondin receptor)-like 2, ESTs, Weakly similar to JC5533 scavenger receptor class B type I precursor - rat [*R. norvegicus*], *Homo sapiens* scavenger receptor class B type III SR-BIII mRNA, partial cds, scavenger receptor class B1 |
| 1910 | 4011 | NM_031543 | c, q | cytochrome P450, 2e1, ethanol inducible, cytochrome P450, subfamily IIE (ethanol-inducible) | cytochrome P450, 2e1, ethanol inducible, cytochrome P450, subfamily IIE (ethanol-inducible) |
| 1910 | 4010 | NM_031543 | c, q | cytochrome P450, 2e1, ethanol inducible, cytochrome P450, subfamily IIE (ethanol-inducible) | cytochrome P450, 2e1, ethanol inducible, cytochrome P450, subfamily IIE (ethanol-inducible) |
| 1910 | 4012 | NM_031543 | q | cytochrome P450, 2e1, ethanol inducible, cytochrome P450, subfamily IIE (ethanol-inducible) | cytochrome P450, 2e1, ethanol inducible, cytochrome P450, subfamily IIE (ethanol-inducible) |
| 1911 | 28 | NM_031546 | General | regucalcin, regucalcin (senescence marker protein-30) | regucalcin, regucalcin (senescence marker protein-30) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1912 | 24640 | NM_031548 | h, cc | sodium channel, nonvoltage-gated 1 alpha, sodium channel, nonvoltage-gated, type I, alpha polypeptide | expressed sequence AW742291, sodium channel, nonvoltage-gated 1 alpha, sodium channel, nonvoltage-gated 1, delta, sodium channel, nonvoltage-gated, type I, alpha polypeptide |
| 1913 | 17149 | NM_031549 | x | transgelin | transgelin |
| 1913 | 17151 | NM_031549 | x | transgelin | transgelin |
| 1914 | 13105 | NM_031552 | w | adducin 3 (gamma) | ESTs, Moderately similar to ADDG_MOUSE GAMMA ADDUCIN (ADDUCIN-LIKE PROTEIN 70) [*M. musculus*], adducin 3 (gamma) |
| 1915 | 15411 | NM_031559 | d, r | carnitine palmitoyltransferase 1, liver, carnitine palmitoyltransferase I, liver | ESTs, Weakly similar to CPT1 MOUSE CARNITINE O-PALMITOYLTRANSFERASE I, MITOCHONDRIAL LIVER ISOFORM [*M. musculus*], ESTs, Weakly similar to I59351 carnitine O-palmitoyltransferase [*H. sapiens*], ESTs, Weakly similar to MITOCHONDRIAL CARNITINE O-PALMITOYLTRANSFERASE I, LIVER ISOFORM [*R. norvegicus*], carnitine palmitoyltransferase 1, liver, carnitine palmitoyltransferase 1, muscle, carnitine palmitoyltransferase I, liver |
| 1916 | 16164 | NM_031563 | a, y | Y box protein 1, nuclease sensitive element binding protein 1 | ESTs, Highly similar to I39382 Y box-binding protein 1 - human [*H. sapiens*], RIKEN cDNA 1700102N10 gene |
| 1917 | 9621 | NM_031570 | bb | ribosomal protein S7 | EST, Moderately similar to 40S RIBOSOMAL PROTEIN S7 [*R. norvegicus*], EST, Weakly similar to 40S RIBOSOMAL PROTEIN S7 [*R. norvegicus*], EST, Weakly similar to RS7_HUMAN 40S RIBOSOMAL PROTEIN S7 [*M. musculus*], ESTs, Highly similar to JC4388 ribosomal protein S7, cytosolic [*H. sapiens*], ESTs, Highly similar to RS7_HUMAN 40S RIBOSOMAL PROTEIN S7 [*H. sapiens*], nuclear factor of kappa light polypeptide gene enhancer in B-cells inhibitor-like 2, ribosomal protein S7 |
| 1917 | 9620 | NM_031570 | w, bb | ribosomal protein S7 | EST, Moderately similar to 40S RIBOSOMAL PROTEIN S7 [*R. norvegicus*], EST, Weakly similar to 40S RIBOSOMAL PROTEIN S7 [*R. norvegicus*], EST, Weakly similar to RS7_HUMAN 40S RIBOSOMAL PROTEIN S7 [*M. musculus*], ESTs, Highly similar to JC4388 ribosomal protein S7, cytosolic [*H. sapiens*], ESTs, Highly similar to RS7_HUMAN 40S RIBOSOMAL PROTEIN S7 [*H. sapiens*], nuclear factor of kappa light polypeptide gene enhancer in B-cells inhibitor-like 2, ribosomal protein S7 |
| 1918 | 546 | NM_031573 | f | phosphorylase kinase gamma, phosphorylase kinase, gamma 1 (muscle) | ESTs, Moderately similar to KPBG_HUMAN PHOSPHORYLASE B KINASE GAMMA CATALYTIC CHAIN, SKELETAL MUSCLE ISOFORM [*H. sapiens*], ESTs, Moderately similar to PHOSPHORYLASE B KINASE GAMMA CATALYTIC CHAIN, SKELETAL MUSCLE ISOFORM [*R. norvegicus*], RIKEN cDNA 1500017I02 gene, endoplasmic reticulum (ER) to nucleus signalling 2, phosphorylase kinase gamma, phosphorylase kinase, gamma 1 (muscle) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1919 | 1921 | NM_031576 | f | P450 (cytochrome) oxidoreductase | ESTs, Highly similar to A Chain A, Crystal Structure Of The Fmn-Binding Domain Of Human Cytochrome P450 Reductase At 1.93a Resolution {SUB 61-241 [*H. sapiens*], NADPH-dependent FMN and FAD containing oxidoreductase, P450 (cytochrome) oxidoreductase, RIKEN cDNA 4930447P04 gene, hypothetical protein FLJ10900 |
| 1919 | 1920 | NM_031576 | r | P450 (cytochrome) oxidoreductose | ESTs, Highly similar to A Chain A, Crystal Structure Of The Fmn-Binding Domain Of Human Cytochrome P450 Reductase At 1.93a Resolution {SUB 61-241 [*H. sapiens*]. NADPH-dependent FMN and FAD containing oxidoreductase, P450 (cytochrome) oxidoreductase, RIKEN cDNA 4930447P04 gene, hypothetical protein FLJ10900 |
| 1920 | 24219 | NM_031579 | i, General | protein tyrosine phosphatase 4a1, protein tyrosine phosphatase type IVA, member 1 | protein tyrosine phosphatase 4a1, protein tyrosine phosphatase 4a2, protein tyrosine phosphatase type IVA, member 1, protein tyrosine phosphatase type IVA, member 2, protein tyrosine phosphatase type IVA, member 3 |
| 1921 | 770 | NM_031584 | k, x | solute carrier family 22 (organic cation transporter), member 2 | EST, Moderately similar to JC4884 organic cation transporter protein 2 - rat [*R. norvegicus*], EST, Weakly similar to OCN2 MOUSE ORGANIC CATION/CARNITINE TRANSPORTER 2 [*M. musculus*], ESTs, Highly similar to OCN2_HUMAN ORGANIC CATION/CARNITINE TRANSPORTER 2 [*H. sapiens*], ESTs, Highly similar to organic cation transporter [*H. sapiens*], organic cationic transporter-like 1, solute carrier family 22 (organic cation transporter), member 1, solute carrier family 22 (organic cation transporter), member 4, solute carrier family 22 (organic cation transporter), member 5, solute carrier family 22 (organic cation transporter), member 9, solute carrier family 22, member 3 |
| 1922 | 18008 | NM_031588 | cc | | ESTs, Highly similar to NRG2_MOUSE PRO-NEUREGULIN-2 PRECURSOR (PRO-NRG2) [CONTAINS: NEUREGULIN-2 (NRG-2) (DIVERGENT OF NEUREGULIN 1) (DON-1)] [*M. musculus*], ESTs, Weakly similar to NRG2_MOUSE PRO-NEUREGULIN-2 PRECURSOR (PRO-NRG2) [CONTAINS: NEUREGULIN-2 (NRG-2) (DIVERGENT OF NEUREGULIN 1) (DON-1)] [*M. musculus*], neuregulin 1 |
| 1922 | 18005 | NM_031588 | h | | ESTs, Highly similar to NRG2_MOUSE PRO-NEUREGULIN-2 PRECURSOR (PRO-NRG2) [CONTAINS: NEUREGULIN-2 (NRG-2) (DIVERGENT OF NEUREGULIN 1) (DON-1)] [*M. musculus*], ESTs, Weakly similar to NRG2_MOUSE PRO-NEUREGULIN-2 PRECURSOR (PRO-NRG2) [CONTAINS: NEUREGULIN-2 (NRG-2) (DIVERGENT OF NEUREGULIN 1) (DON-1)] [*M. musculus*], neuregulin 1 |
| 1922 | 18011 | NM_031588 | cc, General | | ESTs, Highly similar to NRG2_MOUSE PRO-NEUREGULIN-2 PRECURSOR (PRO-NRG2) [CONTAINS: NEUREGULIN-2 (NRG-2) |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | (DIVERGENT OF NEUREGULIN 1) (DON-1)] [*M. musculus*], ESTs, Weakly similar to NRG2_MOUSE PRO-NEUREGULIN-2 PRECURSOR (PRO-NRG2) [CONTAINS: NEUREGULIN-2 (NRG-2) (DIVERGENT OF NEUREGULIN 1) (DON-1)] [*M. musculus*], neuregulin 1 |
| 1923 | 1584 | NM_031595 | k | proteasome (prosome, macropain) 26S subunit, ATPase 3, proteasome (prosome, macropain) 26S subunit, ATPase, 3 | EST, Moderately similar to PRSA RAT 26S PROTEASE REGULATORY SUBUNIT 6A [*R. norvegicus*], EST, Weakly similar to PRS4 MOUSE 26S PROTEASE REGULATORY SUBUNIT 4 [*M. musculus*], EST, Weakly similar to PRSA RAT 26S PROTEASE REGULATORY SUBUNIT 6A [*R. norvegicus*], ESTs, Moderately similar to PRSA RAT 26S PROTEASE REGULATORY SUBUNIT 6A [*R. norvegicus*], expressed sequence AI325227, protease (prosome, macropain) 26S subunit, ATPase 1, proteasome (prosome, macropain) 26S subunit, ATPase 3, proteasome (prosome, macropain) 26S subunit, ATPase, 3 |
| 1924 | 24235 | NM_031614 | v | thioredoxin reductose 1 | *Mus musculus* adult male small intestine cDNA, RIKEN full-length enriched library, clone: 2010001F03, full insert sequence, glutathione reductase 1, thioredoxin reductase 1, thioredoxin reductase 2, thioredoxin reductase beta |
| 1924 | 24234 | NM_031614 | General | thioredoxin reductase 1 | *Mus musculus* adult male small intestine cDNA, RIKEN full-length enriched library, clone: 2010001F03, full insert sequence, glutathione reductase 1, thioredoxin reductase 1, thioredoxin reductase 2, thioredoxin reductase beta |
| 1925 | 1639 | NM_031627 | j, l, v | nuclear receptor subfamily 1, group H, member 3 | EST, Moderately similar to A56043 steroid hormone receptor-like protein RLD-1 - rat [*R. norvegicus*], expressed sequence AU018371, nuclear receptor subfamily 1, group H, member 3, nuclear receptor subfamily 1, group H, member 4 |
| 1926 | 1727 | NM_031642 | m, General | core promoter element binding protein | EST, Moderately similar to CPBP RAT CORE PROMOTER ELEMENT-BINDING PROTEIN [*R. norvegicus*], ESTs, Moderately similar to CPBP RAT CORE PROMOTER ELEMENT-BINDING PROTEIN [*R. norvegicus*], Kruppel-like factor 3 (basic), Kruppel-like factor 5, Kruppel-like factor 7 (ubiquitous), core promoter element binding protein |
| 1927 | 20766 | NM_031643 | y | mitogen activated protein kinase kinase 2, mitogen-activated protein kinase kinase 2 | ESTs, Highly similar to MPK1 MOUSE DUAL SPECIFICITY MITOGEN-ACTIVATED PROTEIN KINASE KINASE 1 [*M. musculus*], ESTs, Moderately similar to MPK1_HUMAN DUAL SPECIFICITY MITOGEN-ACTIVATED PROTEIN KINASE KINASE 1 [*H. sapiens*], *Mus musculus* 12 days embryo head cDNA, RIKEN full-length enriched library, clone: 3000002B10, full insert sequence, mitogen activated protein kinase kinase 1, mitogen activated protein kinase kinase 3, mitogen activated protein kinase kinase 7, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | mitogen-activated protein kinase kinase 1, mitogen-activated protein kinase kinase 7 |
| 1929 | 1993 | NM_031655 | k, l, m, General | latexin, latexin protein | latexin, latexin protein, retinoic acid receptor responder (tazarotene induced) 1 |
| 1930 | 2057 | NM_031660 | e | | Human DNA sequence from clone RP5-822J19 on chromosome 20. Contains an alpha-endosulfine pseudogene, STSs and GSSs, cyclic AMP phosphoprotein, 19 kD, cyclic AMP phosphoprotein, 19 kD, endosulfine alpha |
| 1931 | 15039 | NM_031672 | k, General | solute carrier family 15 (H+/peptide transporter), member 2 | EST, Moderately similar to PET2 RAT OLIGOPEPTIDE TRANSPORTER, KIDNEY ISOFORM [*R. norvegicus*], EST, Moderately similar to PET2_HUMAN OLIGOPEPTIDE TRANSPORTER, KIDNEY ISOFORM [*H. sapiens*], expressed sequence C78862, solute carrier family 15 (H+/peptide transporter), member 2 |
| 1932 | 15175 | NM_031682 | bb | | 2-4-dienoyl-Coenzyme A reductase 2, peroxisomal, ESTs, Weakly similar to HCD2 RAT 3-HYDROXYACYL-COA DEHYDROGENASE TYPE II [*R. norvegicus*], H2-K region expressed gene 6, hydroxyacyl-Coenzyme A dehydrogenase, type II, hydroxyprostaglandin dehydrogenase 15 (NAD), hydroxysteroid (17-beta) dehydrogenase 10, hypothetical protein FLJ14431, retinal short-chain dehydrogenase/reductase retSDR3 |
| 1933 | 1004 | NM_031685 | v | golgi SNAP receptor complex member 2 | golgi SNAP receptor complex member 2 |
| 1934 | 19727 | NM_031687 | a, q, s | ubiquitin A-52 residue ribosomal protein fusion product 1 | EST, Moderately similar to I65237 ubiquitin/ribosomal protein L40 - rat [*R. norvegicus*], Homo sapiens ubiquitin-like fusion protein mRNA, complete cds, RIKEN cDNA 0610006J14 gene, *Rattus norvegicus* RSD-7 mRNA, complete cds, ubiquitin A-52 residue ribosomal protein fusion product 1 |
| 1935 | 20404 | NM_031700 | j, r, y | claudin 3 | ESTs, Weakly similar to A39484 androgen-withdrawal apoptosis protein RVP1, prostatic - rat [*R. norvegicus*], claudin 12, claudin 3, expressed sequence AI182374 |
| 1935 | 20405 | NM_031700 | o, r | claudin 3 | ESTs, Weakly similar to A39484 androgen-withdrawal apoptosis protein RVP1, prostatic - rat [*R. norvegicus*], claudin 12, claudin 3, expressed sequence AI182374 |
| 1936 | 811 | NM_031705 | General | dihydropyrimidinase | PRO0195 protein, collapsin response mediator protein 5, collapsin response mediator protein-5; CRMP3-associated molecule, dihydropyrimidinase, dihydropyrimidinase-like 2, dihydropyrimidinase-related protein |
| 1936 | 812 | NM_031705 | o, v, bb, General | dihydropyrimidinase | PRO0195 protein, collapsin response mediator protein 5, collapsin response mediator protein-5; CRMP3-associated molecule, dihydropyrimidinase, dihydropyrimidinase-like 2, dihydropyrimidinase-related protein |
| 1937 | 16204 | NM_031706 | q, bb | | EST, Moderately similar to RS8_HUMAN 40S RIBOSOMAL PROTEIN S [*H. sapiens*], EST, Weakly similar to 40S RIBOSOMAL PROTEIN S8 [*M. musculus*], EST, Weakly similar to 40S RIBOSOMAL PROTEIN S8 [*R. norvegicus*], ESTs, Moderately |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1937 | 16205 | NM_031706 | a, y | | similar to RS8_HUMAN 40S RIBOSOMAL PROTEIN S [*H. sapiens*], RIKEN cDNA 1110008P08 gene, ribosomal protein S8 EST, Moderately similar to RS8_HUMAN 40S RIBOSOMAL PROTEIN S [*H. sapiens*], EST, Weakly similar to 40S RIBOSOMAL PROTEIN S8 [*M. musculus*], EST, Weakly similar to 40S RIBOSOMAL PROTEIN S8 [*R. norvegicus*], ESTs, Moderately similar to RS8_HUMAN 40S RIBOSOMAL PROTEIN S [*H. sapiens*], RIKEN cDNA 1110008P08 gene, ribosomal protein S8 |
| 1938 | 24081 | NM_031708 | m | | ESTs, Weakly similar to G100_HUMAN 110 KDA CELL MEMBRANE GLYCOPROTEIN [*H. sapiens*], cell membrane glycoprotein, 110000M(r) (surface antigen) |
| 1939 | 16918 | NM_031709 | a, q | | ESTs, Highly similar to R3HU12 ribosomal protein S12, cytosolic [*H. sapiens*], mitochondrial ribosomal protein L50, ribosomal protein S12 |
| 1940 | 1081 | NM_031712 | General | PDZ domain containing 1 | ESTs, Weakly similar to T30259 multiple PDZ domain protein - mouse [*M. musculus*], ESTs, Weakly similar to T46612 multi PDZ domain protein 1 - rat [*R. norvegicus*], PDZ domain containing 1, channel-interacting PDZ domain protein, hypothetical protein FLJ22756, multiple PDZ domain protein, semaF cytoplasmic domain associated protein 3, solute carrier family 9 (sodium/hydrogen exchanger), isoform 3 regulatory factor 1, solute carrier family 9 (sodium/hydrogen exchanger), isoform 3 regulatory factor 2, syntaxin binding protein 4 |
| 1941 | 1340 | NM_031715 | b, n, u, cc, General | phosphofructokinase, muscle | ESTs, Highly similar to S71429 phosphofructokinase, muscle - rat [*R. norvegicus*], *Mus musculus* adult male stomach cDNA, RIKEN full-length enriched library, clone: 2210403E17, full insert sequence, expressed sequence AA407869, phosphofructokinase, liver, B-type, phosphofructokinase, muscle |
| 1942 | 23884 | NM_031731 | j, s | aldehyde dehydrogenase 3 family, member A2, aldehyde dehydrogenase family 3, subfamily A2 | ESTs, Weakly similar to DHA4 RAT FATTY ALDEHYDE DEHYDROGENASE [*R. norvegicus*], RIKEN cDNA 1700001N19 gene, RIKEN cDNA 1700055N04 gene, aldehyde dehydrogenase 3 family, member A2, aldehyde dehydrogenase family 3, subfamily A2, expressed sequence AI848594 |
| 1943 | 10241 | NM_031740 | d | UDP-Gal: betaGlcNAc beta 1,4-galactosyltransferase, polypeptide 6, UDP-Gal: betaGlcNAc beta 1,4-galactosyltransferase, polypeptide 6 | ESTs, Highly similar to N-ACETYLLACTOSAMINE SYNTHASE [*M. musculus*], UDP-Gal: betaGlcNAc beta 1,4-galactosyltransferase, polypeptide 1, UDP-Gal: betaGlcNAc beta 1,4-galactosyltransferase, polypeptide 2, UDP-Gal: betaGlcNAc beta 1,4-galactosyltransferase, polypeptide 3, UDP-Gal: betaGlcNAc beta 1,4-galactosyltransferase, polypeptide 4, UDP-Gal: betaGlcNAc beta 1,4-galactosyltransferase, polypeptide 5, UDP-Gal: betaGlcNAc beta 1,4-galactosyltransferase, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | polypeptide 6, UDP-Gal: betaGlcNAc beta 1,4-galactosyltransferase, polypeptide 3 |
| 1944 | 1214 | NM_031741 | r | solute carrier family 2 (facilitated glucose transporter), member 5, solute carrier family 2 (facilitated glucose/fructose transporter), member 5 | Mus musculus, clone MGC: 8298 IMAGE: 3593581, mRNA, complete cds, glucose transporter protein 11, solute carrier family 2 (facilitated glucose transporter), member 5, solute carrier family 2 (facilitated glucose transporter), member 9, solute carrier family 2 (facilitated glucose/fructose transporter), member 5 |
| 1944 | 1215 | NM_031741 | r | solute carrier family 2 (facilitated glucose transporter), member 5, solute carrier family 2 (facilitated glucose/fructose transporter), member 5 | Mus musculus, clone MGC: 8298 IMAGE: 3593581, mRNA, complete cds, glucose transporter protein 11, solute carrier family 2 (facilitated glucose transporter), member 5, solute carrier family 2 (facilitated glucose transporter), member 9, solute carrier family 2 (facilitated glucose/fructose transporter), member 5 |
| 1945 | 20724 | NM_031753 | h | | ESTs, Highly similar to C166_HUMAN CD166 ANTIGEN PRECURSOR [H. sapiens], Lutheran blood group (Auberger b antigen included), activated leucocyte cell adhesion molecule, activated leukocyte cell adhesion molecule, advanced glycosylation end product-specific receptor, melanoma call adhesion molecule |
| 1946 | 20753 | NM_031763 | h | | EST, Weakly similar to LIS1 MOUSE PLATELET-ACTIVATING FACTOR ACETYLHYDROLASE IB ALPHA SUBUNIT [R. norvegicus], ESTs, Weakly similar to LIS1 MOUSE PLATELET-ACTIVATING FACTOR ACETYLHYDROLASE IB ALPHA SUBUNIT [R. norvegicus], ESTs, Weakly similar to LIS1_HUMAN PLATELET-ACTIVATING FACTOR ACETYLHYDROLASE IB ALPHA SUBUNIT [H. sapiens], F-box protein FBW7, KIAA0007 protein, U3 snoRNP-associated 55-kDa protein, f-box and WD-40 domain protein 2, platelet-activating factor acetylhydrolase, isoform 1b, beta 1 subunit, platelet-activating factor acetylhydrolase, Isoform Ib, alpha subunit (45 kD) |
| 1946 | 20752 | NM_031763 | y | | EST, Weakly similar to LIS1 MOUSE PLATELET-ACTIVATING FACTOR ACETYLHYDROLASE IB ALPHA SUBUNIT [R. norvegicus], ESTs, Weakly similar to LIS1 MOUSE PLATELET-ACTIVATING FACTOR ACETYLHYDROLASE IB ALPHA SUBUNIT [R. norvegicus], ESTs, Weakly similar to LIS1_HUMAN PLATELET-ACTIVATING FACTOR ACETYLHYDROLASE IB ALPHA SUBUNIT [H. sapiens], F-box protein FBW7, KIAA0007 protein, U3 snoRNP-associated 55-kDa protein, f-box and WD-40 domain protein 2, platelet-activating factor acetylhydrolase, isoform 1b, beta 1 subunit, platelet-activating factor acetylhydrolase, isoform Ib, alpha subunit (45 kD) |
| 1947 | 14953 | NM_031774 | p | Rab acceptor 1 (prenylated) | |
| 1948 | 14184 | NM_031776 | t, General | | guanine deaminase |
| 1948 | 14185 | NM_031776 | d, o, t, General | | guanine deaminase |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1949 | 1169 | NM_031789 | c | | ESTs, Highly similar to NFL2 RAT NUCLEAR FACTOR ERYTHROID 2 RELATED FACTOR 2 [*R. norvegicus*], ESTs, Weakly similar to NFL2 RAT NUCLEAR FACTOR ERYTHROID 2 RELATED FACTOR 2 [*R. norvegicus*], nuclear factor (erythroid-derived 2)-like 2, nuclear, factor, erythroid derived 2. like 2 |
| 1950 | 16155 | NM_031810 | d, z | | defensin beta 1, defensin beta 2, defensin, beta 1 |
| 1950 | 16156 | NM_031810 | d | | defensin beta 1, defensin beta 2, defensin, beta 1 |
| 1951 | 17194 | NM_031814 | z | G protein-coupled receptor kinase-interactor 1 | EST, Weakly similar to T42627 ADP-ribosylation factor-directed GTPase activating protein, isoform a - mouse [*M. musculus*], ESTs, Highly similar to T42627 ADP-ribosylation factor-directed GTPase activating protein, isoform a - mouse [*M. musculus*], G protein-coupled receptor kinase-interactor 1, G protein-coupled receptor kinase-interactor 2, *Homo sapiens* p95 paxillin-kinase linker mRNA, complete cds, RIKEN cDNA 1700030C10 gene, development and differentiation enhancing |
| 1952 | 17535 | NM_031816 | bb | | ESTs, Weakly similar to GBLP_HUMAN GUANINE NUCLEOTIDE-BINDING PROTEIN BETA SUBUNIT-LIKE PROTEIN 12.3 [*R. norvegicus*], *Homo sapiens* cDNA: FLJ21913 fis, clone HEP03888, *Homo sapiens*, clone IMAGE: 3502107, mRNA, partial cds, RAE1 (RNA export 1, *S. pombe*) homolog, WD repeat domain 10, expressed sequence AI173248, expressed sequence AI504353, guanine nucleotide binding protein (G protein), beta polypeptide 2-like 1, guanine nucleotide binding protein, beta 2, related sequence 1, retinoblastoma binding protein 7, retinoblastoma-binding protein 7, transducin (beta)-like 2 |
| 1953 | 2655 | NM_031821 | i, l, m, aa | serum-inducible kinase | ESTs, Highly similar to A57286 probable serine/threonine protein kinase [*M. musculus*], ESTs, Highly similar to SNK_RAT SERINE/THREONINE-PROTEIN KINASE SNK (SERUM INDUCIBLE KINASE) [*R. norvegicus*], ESTs, Weakly similar to SNK_RAT SERINE/THREONINE-PROTEIN KINASE SNK (SERUM INDUCIBLE KINASE) [*R. norvegicus*], cytokine-inducible kinase, serine/threonine kinase 18, serum-inducible kinase, tousted-like kinase 2 (*Arabidopsis*) |
| 1954 | 10167 | NM_031830 | i | | flotillin 1, flotillin 2 |
| 1955 | 22321 | NM_031832 | o, t, u, General | lectin, galactose binding, soluble 3, lectin, galactoside-binding. soluble, 3 (galectin 3) | EST, Weakly similar to X-Ray Crystal Structure Of The Human Galectin-3 Carbohydrate Recognition Domain [*H. sapiens*], galectin-related inter-fiber protein |
| 1956 | 4748 | NM_031834 | e, t | | expressed sequence AI266890, expressed sequence AI853643, sulfotransferase family 1A, phenol-preferring, member 1, sulfotransferase family 4A, member 1, sulfotransferase family, cytosolic, 1A, phenol-preferring, member 1, sulfotransferase family, cytosolic, 1A, phenol-preferring, member 2, sulfotransferase family, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1956 | 4749 | NM_031834 | e, t | | cytosolic, 1A, phenol-preferring, member 3 expressed sequence AI266890, expressed sequence AI853643, sulfotransferase family 1A, phenol-preferring, member 1, sulfotransferase family 4A, member 1, sulfotransferase family, cytosolic, 1A, phenol-preferring, member 1, sulfotransferase family, cytosolic, 1A, phenol-preferring, member 2, sulfotransferase family, cytosolic, 1A, phenol-preferring, member 3 |
| 1957 | 7914 | NM_031835 | e | | ESTs, Weakly similar to AGT2 RAT ALANINE-GLYOXYLATE AMINOTRANSFERASE 2 PRECURSOR [*R. norvegicus*], RIKEN cDNA 1300019H02 gene, RIKEN cDNA 2900006B13 gene, alanine-glyoxylate aminotransferase 2, alanine-glyoxylate aminotransferase 2-like 1, ornithine aminotransferase |
| 1958 | 8385 | NM_031836 | h | | c-fos induced growth factor (vascular endothelial growth factor D), vascular endothelial growth factor, vascular endothelial growth factor B |
| 1958 | 8384 | NM_031836 | h | | c-fos induced growth factor (vascular endothelial growth factor D), vascular endothelial growth factor, vascular endothelial growth factor B |
| 1959 | 10268 | NM_031838 | a | | EST, Highly similar to 40S RIBOSOMAL PROTEIN S2 [*M. musculus*], EST, Highly similar to 40S RIBOSOMAL PROTEIN S2 [*R. norvegicus*], EST, Moderately similar to S08228 ribosomal protein S2, cytosolic [*H. sapiens*], EST, Weakly similar to S08228 ribosomal protein S2, cytosolic [*H. sapiens*], ESTs, Highly similar to RS2_HUMAN 40S RIBOSOMAL PROTEIN S2 [*H. sapiens*], ESTs, Moderately similar to 40S RIBOSOMAL PROTEIN S2 [*M. musculus*], repeat family 3 gene, ribosomal protein S2 |
| 1959 | 10269 | NM_031838 | aa | | EST, Highly similar to 40S RIBOSOMAL PROTEIN S2 [*M. musculus*], EST, Highly similar to 40S RIBOSOMAL PROTEIN S2 [*R. norvegicus*], EST, Moderately similar to S08228 ribosomal protein S2, cytosolic [*H. sapiens*], EST, Weakly similar to S08228 ribosomal protein S2, cytosolic [*H. sapiens*], ESTs, Highly similar to RS2_HUMAN 40S RIBOSOMAL PROTEIN S2 [*H. sapiens*], ESTs, Moderately similar to 40S RIBOSOMAL PROTEIN S2 [*M. musculus*], repeat family 3 gene, ribosomal protein S2 |
| 1959 | 10267 | NM_031838 | n, aa | | EST, Highly similar to 40S RIBOSOMAL PROTEIN S2 [*M. musculus*], EST, Highly similar to 40S RIBOSOMAL PROTEIN S2 [*R. norvegicus*], EST, Moderately similar to S08228 ribosomal protein S2, cytosolic [*H. sapiens*], EST, Weakly similar to S08228 ribosomal protein S2, cytosolic [*H. sapiens*], ESTs, Highly similar to RS2_HUMAN 40S RIBOSOMAL PROTEIN S2 [*H. sapiens*], ESTs, Moderately similar |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1960 | 15077 | NM_031841 | b | | to 40S RIBOSOMAL PROTEIN S2 [*M. musculus*], repeat family 3 gene, ribosomal protein S2 expressed sequence AU022220, hypothetical protein FLJ21032, stearoyl-CoA desaturase (delta-9-desaturase), stearoyl-Coenzyme A desaturase 1, stearoyl-Coenzyme A desaturase 2, stearoyl-coenzyme A desaturase 3 |
| 1961 | 16726 | NM_031855 | x | ketohexokinase, ketohexokinase (fructokinase) | ketohexokinase, ketohexokinase (fructokinase) |
| 1962 | 25802 | NM_031969 | a | calmodulin 1, calmodulin 1 (phosphorylase kinase, delta) | |
| 1962 | 19191 | NM_031969 | c | calmodulin 1, calmodulin 1 (phosphorylase kinase, delta) | Calmodulin III, ESTs, Highly similar to A Chain A, Calmodulin Complexed With Calmodulin-Binding Peptide From Smooth Muscle Myosin Light Chain Kinase {SUB 2-148 [*H. sapiens*], *R. norvegicus* CaMII retropseudogene (clone lambda SC27), RIKEN cDNA 2310068O22 gene, calmodulin, calmodulin 1, calmodulin 1 (phosphorylase kinase, delta), calmodulin 2, calmodulin 2 (phosphorylase kinase, delta), calmodulin 3, calmodulin-like 3 |
| 1962 | 19195 | NM_031969 | r | calmodulin 1, calmodulin 1 (phosphorylase kinase, delta) | Calmodulin III, ESTs, Highly similar to A Chain A, Calmodulin Complexed With Calmodulin-Binding Peptide From Smooth Muscle Myosin Light Chain Kinase {SUB 2-148 [*H. sapiens*], *R. norvegicus* CaMII retropseudogene (clone lambda SC27), RIKEN cDNA 2310068O22 gene, calmodulin, calmodulin 1, calmodulin 1 (phosphorylase kinase, delta), calmodulin 2, calmodulin 2 (phosphorylase kinase, delta), calmodulin 3, calmodulin-like 3 |
| 1962 | 19190 | NM_031969 | p | calmodulin 1, calmodulin 1 (phosphorylase kinase, delta) | Calmodulin III, ESTs, Highly similar to A Chain A, Calmodulin Complexed With Calmodulin-Binding Peptide From Smooth Muscle Myosin Light Chain Kinase {SUB 2-148 [*H. sapiens*], *R. norvegicus* CaMII retropseudogene (clone lambda SC27), RIKEN cDNA 2310068O22 gene, calmodulin, calmodulin 1, calmodulin 1 (phosphorylase kinase, delta), calmodulin 2, calmodulin 2 (phosphorylase kinase, delta), calmodulin 3, calmodulin-like 3 |
| 1963 | 17734 | NM_031970 | v, General | | EST, Weakly similar to HHHU27 heat shock protein 27 [*H. sapiens*], ESTs, Moderately similar to HHHU27 heat shock protein 27 [*H. sapiens*], crystallin, alpha C, heat shock 27 kD protein 1, heat shock 27 kD protein 3 |
| 1964 | 1475 | NM_031971 | v | heat shock 70 kD protein 1B, heat shock protein, 70 kDa 1 | ESTs, Weakly similar to BCHUIA S-100 protein alpha chain [*H. sapiens*], ESTs, Weakly similar to S10A MOUSE S-100 PROTEIN, ALPHA CHAIN [*M. musculus*], *Homo sapiens* cDNA FLJ10018 fis, clone HEMBA1000531, RIKEN cDNA B230217N24 gene, S100 calcium binding protein A1, S100 calcium binding protein A11, S100 calcium-binding protein A1, S100 calcium-binding protein A11 (calgizzarin), S100 calcium-binding protein P, expressed sequence |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1965 | 15470 | NM_031978 | f | | AI266795, heat shock 70 kD protein 1A, heat shock 70 kD protein 1B proteasome (prosome, macropain) 26S subunit, non-ATPase, 1 |
| 1966 | 18502 | NM_031984 | c | calbindin 1, (28 KD), calbindin-28K | ESTs, Moderately similar to CALBINDIN [*M. musculus*], calbindin 1, (28 kD), calbindin-28K |
| 1967 | 19768 | NM_031986 | v, aa, General | | ESTs, Highly similar to APB1 RAT AMYLOID BETA A4 PRECURSOR PROTEIN-BINDING FAMILY A MEMBER 1 [*R. norvegicus*], *Mus musculus*, Similar to hypothetical protein, clone MGC: 11704 IMAGE: 3964815, mRNA, complete cds, RIKEN cDNA 2310008D10 gene, amyloid beta (A4) precursor protein-binding, family A, APBA1: amyloid beta (A4) precursor protein-binding, family A, member 1 (X11), amyloid beta (A4) precursor protein-binding, family A, member 1 (X11), amyloid beta (A4) precursor protein-binding, family A, member 3, syndecan binding protein, syndecan binding protein (syntenin), syntenin-2 protein |
| 1968 | 723 | NM_032084 | n | | ESTs, Weakly similar to T42724 p190-B protein - mouse [*M. musculus*], PTPL1-associated RhoGAP 1, RIKEN cDNA 1700026N20 gene, RIKEN cDNA 1700112L09 gene, chimerin (chimaerin) 2, minor histocompatibility antigen HA-1, oligophrenin 1, rho GTPase activating protein 5 |
| 1969 | 17935 | NM_032615 | a | membrane interacting protein of RGS16 | hypothetical protein FLJ20207, membrane interacting protein of RGS16 |
| 1970 | 16831 | NM_033095 | n | | |
| 1971 | 25468 | NM_033234 | c, z | | |
| 1971 | 25469 | NM_033234 | c | | |
| 1971 | 17832 | NM_033234 | c, p | hemoglobin beta chain complex, hemoglobin, beta | |
| 1971 | 17829 | NM_033234 | c, z | hemoglobin beta chain complex, hemoglobin, beta | |
| 1972 | 4723 | NM_033235 | z | | ESTs, Highly similar to LDHH_HUMAN L-LACTATE DEHYDROGENASE H CHAIN [*H. sapiens*], Lactate dehydrogenease B, RIKEN cDNA 1700124B08 gene, lactate dehydrogenase 2, B chain, lactate dehydrogenase B, malate dehydrogenase 1, NAD (soluble), malate dehydrogenase, soluble |
| 1973 | 1409 | NM_033349 | p, General | glyoxylase 2, hydroxyacyl glutathione hydrolase | *Mus musculus*, Similar to hydroxyacyl glutathione hydrolase, clone MGC: 6697 IMAGE: 3583919, mRNA, complete cds, RIKEN cDNA 1500017E18 gene, RIKEN cDNA 2810014I23 gene, RIKEN cDNA C330022E15 gene, hydroxyacyl glutathione hydrolase, hypothetical protein MGC2605, protein expressed in thyroid |
| 1974 | 19998 | NM_033352 | General | PDZ domain containing 1 | ESTs, Weakly similar to T30259 multiple PDZ domain protein - mouse [*M. musculus*], ESTs, Weakly similar to T46612 multi PDZ domain protein 1 - rat [*R. norvegicus*], PDZ domain containing 1, channel-interacting PDZ domain protein, hypothetical protein FLJ22756, multiple PDZ domain protein, semaF cytoplasmic domain associated protein 3, solute carrier family 9 (sodium/hydrogen exchanger), isoform 3 regulatory factor 1, solute |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | carrier family 9 (sodium/hydrogen exchanger), isoform 3 regulatory factor 2, syntaxin binding protein 4 |
| 1975 | 1410 | NM_052798 | d | zinc finger protein 354A | ESTs, Moderately similar to S47073 finger protein HZF2, Krueppel-related [*H. sapiens*], ESTs, Moderately similar to T12489 hypothetical protein DKFZp572P0920.1 [*H. sapiens*], ESTs, Weakly similar to TC17 MOUSE TRANSCRIPTION FACTOR 17 [*M. musculus*], ESTs, Weakly similar to Z184_HUMAN ZINC FINGER PROTEIN 184 [*H. sapiens*], expressed sequence AI875089, transcription factor 17, transcription factor 17-like 1, transcription factor 17-like 2 |
| 1976 | 15028 | NM_052809 | f | cysteine dioxygenase 1, cytosolic, cysteine dioxygenase, type I | RIKEN cDNA 2900092E17 gene, cysteine dioxygenase 1, cytosolic, cysteine dioxygenase, type I |
| 1977 | 5176 | NM_053297 | u | pyruvate kinase 3, pyruvate kinase, muscle | |
| 1978 | 7660 | NM_053299 | i | diubiquitin, ubiquitin D | EST, Moderately similar to S12583 polyubiquitin 4 - mouse [*M. musculus*], *Homo sapiens* UBBP2 pseudogene for ubiquitin UBB, RIKEN cDNA 2700054O04 gene, diubiquitin, expressed sequence AI194771, expressed sequence AL033289, ubiquitin B, ubiquitin C |
| 1979 | 5117 | NM_053310 | p | Homer, neuronal immediate early gene, 3, homer, neuronal immediate early gene, 3 | CAT56 protein, EST, Weakly similar to A28996 proline-rich protein M14 precursor - mouse [*M. musculus*], EST, Weakly similar to JE0291 FB19 protein [*H. sapiens*], Homer, neuronal immediate early gene, 1B, RuvB-like protein 1, homer, neuronal immediate early gene, 1, homer, neuronal immediate early gene, 2, proline rich protein, proline rich protein 2, protein phosphatase 1, regulatory subunit 10 |
| 1981 | 17473 | NM_053319 | a, v | dynein, cytoplasmic, light chain 1, dynein, cytoplasmic, light polypeptide | ESTs, Moderately similar to protein inhibitor of nitric oxide synthase [*M. musculus*], RIKEN cDNA 6720463E02 gene, *Rattus norvegicus* dynein light chain-2 (Dlc2) mRNA, complete cds, dynein, cytoplasmic, light chain 1, dynein, cytoplasmic, light polypeptide |
| 1982 | 25480 | NM_053329 | g | insulin-like growth factor binding protein, acid labile subunit | |
| 1982 | 21977 | NM_053329 | y | insulin-like growth factor binding protein, acid labile subunit | ESTs, Weakly similar to ALS RAT INSULIN-LIKE GROWTH FACTOR BINDING PROTEIN COMPLEX ACID LABILE CHAIN PRECURSOR [*R. norvegicus*], ESTs, Weakly similar to JC6128 insulin-like growth factor binding complex acid labile chain - mouse [*M. musculus*], ESTs, Weakly similar to membrane glycoprotein [*M. musculus*], KIAA0644 gene product, glycoprotein 1a, alpha polypeptide, hypothetical protein FLJ20156, insulin-like growth factor binding protein, acid labile subunit, nogo receptor, reticulon 4 receptor, toll-like receptor 6, tumor endothelial marker 5 precursor |
| 1983 | 14926 | NM_053330 | f | ribosomal protein L21 | EST, Moderately similar to 2113200B ribosomal protein L21 [*H. sapiens*], EST, Moderately similar to RL21 MOUSE 60S RIBOSOMAL PROTEIN L21 [*M. musculus*], EST, Weakly similar to 2113200B ribosomal protein |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 1983 | 14929 | NM_053330 | e, General | ribosomal protein L21 | L21 [*H. sapiens*], EST, Weakly similar to RL21 MOUSE 60S RIBOSOMAL PROTEIN L21 [*M. musculus*], EST, Weakly similar to RL21_HUMAN 60S RIBOSOMAL PROTEIN L21 [*H. sapiens*], ESTs, Moderately similar to RL21 RAT 60S RIBOSOMAL PROTEIN L21 [*R. norvegicus*], RIKEN cDNA 2700085M18 gene, ribosomal protein L21 EST, Moderately similar to 2113200B ribosomal protein L21 [*H. sapiens*], EST, Moderately similar to RL21 MOUSE 60S RIBOSOMAL PROTEIN L21 [*M. musculus*], EST, Weakly similar to 2113200B ribosomal protein L21 [*H. sapiens*], EST, Weakly similar to RL21 MOUSE 60S RIBOSOMAL PROTEIN L21 [*M. musculus*], EST, Weakly similar to RL21_HUMAN 60S RIBOSOMAL PROTEIN L21 [*H. sapiens*], ESTs, Moderately similar to RL21 RAT 60S RIBOSOMAL PROTEIN L21 [*R. norvegicus*], RIKEN cDNA 2700085M18 gene, ribosomal protein L21 |
| 1984 | 16407 | NM_053332 | c, e | cubilin (intrinsic factor-cobalamin receptor) | DNA segment, Chr 2, Wayne State University 88, expressed, EST, Weakly similar to T09456 intrinsic factor-B12 receptor Cubilin precursor [*H. sapiens*], ESTs, Moderately similar to T09456 intrinsic factor-B12 receptor Cubilin precursor [*H. sapiens*], Homo sapiens cDNA FLJ12558 fis, clone NT2RM4000787, bone morphogenetic protein 1, cubilin (intrinsic factor-cobalamin receptor), expressed sequence AL022750, platelet-derived growth factor, C polypeptide, tolloid-like, tolloid-like 2, tumor necrosis factor induced protein 6, tumor necrosis factor, alpha-induced protein 6 |
| 1985 | 15790 | NM_053341 | j, x | chromosome 19 open reading frame 3, regulator of G-protein signaling 19 interacting protein 1 | chromosome 19 open reading frame 3, hypothetical protein FLJ20075 |
| 1986 | 6154 | NM_053356 | p | collagen, type I, alpha 2, procollagen, type I, alpha 2 | ESTs, Weakly similar to CGHU2S collagen alpha 2(I) chain precursor [*H. sapiens*], KIAA1026 protein, RIKEN cDNA 1110030G05 gene, RIKEN cDNA 9030409G11 gene, collagen, type I, alpha 1, collagen, type I, alpha 2, collagen, type II, alpha 1 (primary osteoarthritis, spondyloepiphyseal dysplasia, congenital), hypothetical protein FLJ20654, nischarin, procollagen, type I, alpha 1, procollagen, type I, alpha 2, procollagen, type II, alpha 1 |
| 1987 | 9215 | NM_053374 | i | | interleukin 18 binding protein |
| 1988 | 6416 | NM_053380 | General | | ESTs, Weakly similar to NPT2 RAT RENAL SODIUM-DEPENDENT PHOSPHATE TRANSPORT PROTEIN 2 [*R. norvegicus*], ESTs, Weakly similar to NPT2_HUMAN RENAL SODIUM-DEPENDENT PHOSPHATE TRANSPORT PROTEIN 2 [*H. sapiens*], Homo sapiens, Similar to solute carrier family 34 (sodium phosphate), member 1, clone MGC: 18179 IMAGE: 4155326, mRNA, complete cds, *Rattus norvegicus* mRNA for NaPi-2 alpha, complete cds, Solute carrier family 17 (sodium/hydrogen exchanger), |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | member 2, expressed sequence AI649385, solute carrier family 34 (sodium phosphate), member 1, solute carrier family 34 (sodium phosphate), member 2 |
| 1989 | 19113 | NM_053395 | a | small muscle protein, X-linked | small muscle protein, X-linked |
| 1990 | 2242 | NM_053433 | n, General | | ESTs, Highly similar to FMO3_HUMAN DIMETHYLANILINE MONOOXYGENASE [*H. sapiens*], Flavin-containing monooxygenase 1, *Homo sapiens* DNA sequence from PAC 127D3 on chromosome 1q23-25. Contains FMO2 and FMO3 genes for Flavin-containing Monooxygenase 2 and Flavin-containing Monooxygenase 3 (Dimethylaniline Monooxygenase (N-Oxide 3, EC1.14.13.8, Dimethylaniline Oxidase 3, FMO II, FMO 3), and a gene for another, unknown, Flavin-containing Monooxygenase family protein. Contains ESTs and GSSs, flavin containing monooxygenase 1, flavin containing monooxygenase 2, flavin containing monooxygenase 3, hypothetical protein PRO1257 |
| 1991 | 5561 | NM_053438 | y | | RIKEN cDNA 1700065B19 gene, RIKEN cDNA 5730408C10 gene, zinc finger protein 103, zinc finger protein homologous to Zfp103 in mouse |
| 1992 | 14670 | NM_053439 | n, General | | ESTs, Highly similar to RAB7 RAT RAS-RELATED PROTEIN RAB-7 [*R. norvegicus*], RAB7, member RAS oncogene family, RAN, member RAS oncogene family, RIKEN cDNA 1700009N14 gene |
| 1993 | 17102 | NM_053440 | w | stathmin-like 2, superiorcervical ganglia, neural specific 10 | stathmin-like 2, stathmin-like 4, superiorcervical ganglia, neural specific 10 |
| 1994 | 24762 | NM_053442 | General | | ESTs, Weakly similar to 1615347A ras p21 GTPase activating protein [*M. musculus*], KIAA1938 protein, *Mus musculus*, Similar to RAS p21 protein activator, clone MGC: 7759 IMAGE: 3498774, mRNA, complete cds, RAS protein activator like 2, *Rattus norvegicus* DOC2/DAB2 interactive protein mRNA, complete cds, expressed sequence BB079060, hypothetical protein FLJ21438 |
| 1995 | 8085 | NM_053453 | General | | ESTs, Moderately similar to RGS8 RAT REGULATOR OF G-PROTEIN SIGNALING 8 [*R. norvegicus*], regulator of G-protein signaling 18, regulator of G-protein signaling 2, regulator of G-protein signaling 8, regulator of G-protein signalling 13, regulator of G-protein signalling 2, 24 kD, regulator of G-protein signalling 8 |
| 1996 | 4622 | NM_053463 | d | | NEFA precursor, expressed sequence AI607786, nucleobindin, nucleobindin 1, nucleobindin 2 |
| 1997 | 21866 | NM_053472 | p | cytochrome c oxidase subunit IV isoform 2, cytochrome c oxidase, subunit IVb | EST, Weakly similar to COX4_HUMAN CYTOCHROME C OXIDASE POLYPEPTIDE IV PRECURSO [*H. sapiens*], cytochrome c oxidase subunit IV, cytochrome c oxidase subunit IV isoform 2, cytochrome c oxidase, subunit IV, cytochrome c oxidase, subunit IVa, cytochrome c oxidase, subunit IVb, expressed sequence AL024441 |
| 1998 | 9573 | NM_053475 | h | | protein tyrosine phosphatase 4a1, protein tyrosine phosphatase 4a2, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | protein tyrosine phosphatase type IVA, member 1, protein tyrosine phosphatase type IVA, member 2, protein tyrosine phosphatase type IVA, member 3 |
| 1999 | 16137 | NM_053480 | k | | DNA polymerase alpha 2, 68 kDa, *Mus musculus*, Similar to DNA polymerase alpha 2, 68 kDa, clone MGC: 11533 IMAGE: 3602559, mRNA, complete cds, expressed sequence AI573378, polymerase (DNA-directed), alpha (70 kD) |
| 2000 | 15556 | NM_053483 | y | | ESTs, Weakly similar to A Chain A, Importin Alpha, Mouse [*M. musculus*], expressed sequence AW146299, karyopherin (importin) alpha 2, karyopherin alpha 2 (RAG cohort 1, importin alpha 1) |
| 2001 | 16394 | NM_053485 | General | | EST, Moderately similar to CALCYCLIN [*R. norvegicus*], S100 calcium-binding protein A6 (calcyclin), calcium binding protein A6 (calcyclin) |
| 2002 | 4290 | NM_053487 | j, y | | peroxisomal biogenesis factor 11A, peroxisomal biogenesis factor 11B |
| 2004 | 18826 | NM_053523 | d | | EST, Moderately similar to Y025_HUMAN HYPOTHETICAL PROTEIN KIAA0025 [*H. sapiens*], RIKEN cDNA 5031400M07 gene, homocysteine-inducible, endoplasmic reticulum stress-inducible, ubiquitin-like domain member 1, hypothetical protein FLJ22313 |
| 2005 | 7764 | NM_053525 | aa | | DEAD/H (Asp-Glu-Ala-Asp/His) box polypeptide, Y chromosome, DNA segment, Chr 1, Pasteur Institute 1, ESTs, Moderately similar to DDXY_HUMAN DEAD BOX PROTEIN 3, Y-CHROMOSOMAL [*H. sapiens*], KIAA0801 gene product, RNA helicase, *Rattus norvegicus* RNA helicase with arginine-serine-rich domain mRNA, complete cds, expressed sequence AI324246, expressed sequence AI325430, expressed sequence C86129 |
| 2006 | 14199 | NM_053538 | c | | Lysosomal-associated multispanning membrane protein-5, lysosomal-associated protein transmembrane 5 |
| 2007 | 1058 | NM_053539 | c, d | | |
| 2008 | 4327 | NM_053563 | General | | DNA segment, Chr 17, human D6S81E 1, EST, Weakly similar to HE47 RAT PROBABLE ATP-DEPENDENT RNA HELICASE P47 [*R. norvegicus*], HLA-B associated transcript 1, KIAA0111 gene product, *Mus musculus*, clone MGC: 6664 IMAGE: 3498954, mRNA, complete cds, RIKEN cDNA 2610307C23 gene, eukaryotic translation initiation factor 4A, isoform 2, eukaryotic translation initiation factor 4A1, eukaryotic translation initiation factor 4A2, nuclear RNA helicase, DECD variant of DEAD box family |
| 2009 | 1342 | NM_053573 | h | | ESTs, Weakly similar to JE0096 myocilin - mouse [*M. musculus*], *Homo sapiens* NOE3-4 (NOE3) mRNA, complete cds, alternatively spliced, expressed sequence AW742568, olfactomedin related ER localized protein |
| 2010 | 19254 | NM_053576 | h, s | anti-oxidant protein 2 (non-selenium glutathione peroxidase, acidic calcium- | ESTs, Moderately similar to AOP2_HUMAN ANTIOXIDANT PROTEIN 2 [*H. sapiens*], anti-oxidant |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | independent phospholipase A2), peroxiredoxin 5 | protein 2 (non-selenium glutathione peroxidase, acidic calcium-independent phospholipase A2), peroxiredoxin 5 |
| 2010 | 19253 | NM_053576 | h | anti-oxidant protein 2 (non-selenium glutathione peroxidase, acidic calcium-independent phospholipase A2), peroxiredoxin 5 | ESTs, Moderately similar to AOP2_HUMAN ANTIOXIDANT PROTEIN 2 [*H. sapiens*], anti-oxidant protein 2 (non-selenium glutathione peroxidase, acidic calcium-independent phospholipase A2), peroxiredoxin 5 |
| 2011 | 3049 | NM_053582 | p, cc, General | | ESTs, Highly similar to JC7189 tubulointerstitial nephritis antigen [*H. sapiens*], P3ECSL, cathepsin B, lipocalin 7, tubulointerstitial nephritis antigen |
| 2011 | 3050 | NM_053582 | o, General | | ESTs, Highly similar to JC7189 tubulointerstitial nephritis antigen [*H. sapiens*], P3ECSL, cathepsin B, lipocalin 7, tubulointerstitial nephritis antigen |
| 2012 | 21423 | NM_053586 | s, y | | EST, Moderately similar to CYTOCHROME C OXIDASE POLYPEPTIDE VB PRECURSOR [*R. norvegicus*], cytochrome c oxidase subunit Vb, cytochrome c oxidase, subunit Vb |
| 2013 | 21445 | NM_053587 | t, v | | |
| 2014 | 20871 | NM_053591 | j, l | | ESTs, Weakly similar to MDP1 MOUSE MICROSOMAL DIPEPTIDASE PRECURSOR [*M. musculus*], ESTs, Weakly similar to S33757 membrane dipeptidase [*M. musculus*], RIKEN cDNA 1700018F16 gene, dipeptidase 1 (renal), putative dipeptidase, putative metallopeptidase (family M19) |
| 2014 | 20870 | NM_053591 | l | | ESTs, Weakly similar to MDP1 MOUSE MICROSOMAL DIPEPTIDASE PRECURSOR [*M. musculus*], ESTs, Weakly similar to S33757 membrane dipeptidase [*M. musculus*], RIKEN cDNA 1700018F16 gene, dipeptidase 1 (renal), putative dipeptidase, putative metallopeptidase (family M19) |
| 2015 | 21044 | NM_053594 | d | | protein tyrosine phosphatase, receptor type, R |
| 2016 | 21709 | NM_053596 | k | | KIAA0604 gene product, endothelin converting enzyme 1, endothelin converting enzyme-like 1, expressed sequence AW322500, expressed sequence BB127715, mel transforming oncogene-like 1, membrane metalloendopeptidase |
| 2016 | 21708 | NM_053596 | z | | KIAA0604 gene product, endothelin converting enzyme 1, endothelin converting enzyme-like 1, expressed sequence AW322500, expressed sequence BB127715, mel transforming oncogene-like 1, membrane metalloendopeptidase |
| 2017 | 1597 | NM_053611 | t | nuclear proten 1, p8 protein (candidate of metastasis 1) | ESTs, Weakly similar to Gene product with similarity to Rat P8 [*H. sapiens*] |
| 2018 | 5565 | NM_053618 | General | Bardet-Biedl syndrome 2, Bardet-Biedl syndrome 2 (human) | |
| 2019 | 13004 | NM_053623 | t | fatty acid-Coenzyme A ligase, long chain 4, fatty-acid-Coenzyme A ligase, long-chain 4 | |
| 2020 | 1127 | NM_053626 | g | | D-amino acid oxidase, D-amino-acid oxidase, D-aspartate oxidase, EST, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | Weakly similar to OXDA RAT D-AMINO ACID OXIDASE [*R. norvegicus*], ESTs, Highly similar to OXDA RAT D-AMINO ACID OXIDASE [*R. norvegicus*], RIKEN cDNA 5330420D20 gene, RIKEN cDNA 5730402C02 gene |
| 2021 | 18644 | NM_053648 | n | beta-carotene 15, 15'-dioxygenase, beta-carotene 15, 15'-dioxygenase | EST, Moderately similar to 0806162D protein COII [*M. musculus*], EST, Weakly similar to 810024D cytochrome oxidase II [*H. sapiens*] |
| 2022 | 21637 | NM_053653 | p | | c-fos induced growth factor, c-fos induced growth factor (vascular endothelial growth factor D), vascular endothelial growth factor, vascular endothelial growth factor B, vascular endothelial growth factor C |
| 2023 | 3454 | NM_053662 | cc | | ESTs, Highly similar to CG1C RAT G1/S-SPECIFIC CYCLIN C [*R. norvegicus*], *Homo sapiens*, clone IMAGE: 3537447, mRNA, partial cds, RIKEN cDNA 1810009O10 gene, cyclin C, cyclin K, cyclin L, cyclin L ania-6a, cyclin T2 |
| 2024 | 16121 | NM_053698 | h, j, z | | with Glu/Asp-rich carboxy-terminal domain, 2, Cbp/p300-interacting transactivator, with Glu/Asp-rich carboxy-terminal domain, 4, ESTs, Weakly similar to MRG1_HUMAN MSG-RELATED PROTEIN 1 [*H. sapiens*], expressed sequence AW742964 |
| 2024 | 16122 | NM_053698 | h, j, z | | with Glu/Asp-rich carboxy-terminal domain, 2, Cbp/p300-interacting transactivator, with Glu/Asp-rich carboxy-terminal domain, 4, ESTs, Weakly similar to MRG1_HUMAN MSG-RELATED PROTEIN 1 [*H. sapiens*], expressed sequence AW742964 |
| 2025 | 25379 | NM_053713 | General | | |
| 2025 | 13622 | NM_053713 | General | | ESTs, Moderately similar to CPBP RAT CORE PROMOTER ELEMENT-BINDING PROTEIN [*R. norvegicus*], Kruppel-like factor 4 (gut), RIKEN cDNA 7420700M05 gene, core promoter element binding protein |
| 2026 | 15376 | NM_053747 | h | ubiquilin 1 | |
| 2027 | 1218 | NM_053748 | b | | expressed sequence C86324, hypothetical protein FLJ23590 |
| 2028 | 1137 | NM_053763 | y | | cytochrome P450, 40 (25-hydroxyvitamin D3 1 alpha-hydroxylase), cytochrome P450, subfamily XXVIIB (25-hydroxyvitamin D-1-alpha-hydroxylase), polypeptide 1 |
| 2029 | 15996 | NM_053769 | cc | dual specificity phosphatase 1, protein tyrosine phosphatase, non-receptor type 16 | MKP-1 like protein tyrosine phosphatase, dual specificity phosphatase 1, dual specificity phosphatase 13, dual specificity phosphatase 14, dual specificity phosphatase 2, expressed sequence BB104621, protein tyrosine phosphatase, non-receptor type 16 |
| 2030 | 8652 | NM_053774 | g | ubiquitin specific protease 2 | KIAA1453 protein, RIKEN cDNA 4930511O11 gene, expressed sequence AA409661, ubiquitin specific protease 2, ubiquitin specific protease 8 |
| 2031 | 14664 | NM_053806 | General | | |
| 2032 | 4361 | NM_053812 | k | | B cell lymphoma 2 like, BCL2-antagonist/killer 1, BCL2-like 1, Bcl-w protein, Bcl2-like, *Mus musculus* N-BAK1 (Bak1) mRNA, complete cds, alternatively spliced, RIKEN cDNA 0610031G08 gene |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2034 | 15002 | NM_053819 | b, x, bb, General | | EST, Moderately similar to TIM1 RAT METALLOPROTEINASE INHIBITOR 1 PRECURSOR [R. norvegicus], EST, Weakly similar to TIM1 RAT METALLOPROTEINASE INHIBITOR 1 PRECURSOR [R. norvegicus], tissue inhibitor of metalloproteinase, tissue inhibitor of metalloproteinase 1 (erythroid potentiating activity, collagenase inhibitor) |
| 2034 | 15003 | NM_053819 | b, l, x, bb, General | | EST, Moderately similar to TIM1 RAT METALLOPROTEINASE INHIBITOR 1 PRECURSOR [R. norvegicus], EST, Weakly similar to TIM1 RAT METALLOPROTEINASE INHIBITOR 1 PRECURSOR [R. norvegicus], tissue inhibitor of metalloproteinase, tissue inhibitor of metalloproteinase 1 (erythroid potentiating activity, collagenase inhibitor) |
| 2035 | 16173 | NM_053822 | t | | |
| 2036 | 17154 | NM_053835 | j, z | | |
| 2037 | 20868 | NM_053843 | t | | |
| 2037 | 20869 | NM_053843 | t | | |
| 2040 | 714 | NM_053863 | y | | ESTs, Highly similar to CNT1_HUMAN SODIUM/NUCLEOSIDE COTRANSPORTER 1 [H. sapiens], ESTs, Moderately similar to A54892 Na+-dependent nucleoside transport protein cNT1 - rat [R. norvegicus] |
| 2041 | 19781 | NM_053883 | b | | ESTs, Moderately similar to DUS6 RAT DUAL SPECIFICITY PROTEIN PHOSPHATASE 6 [R. norvegicus], ESTs, Weakly similar to DUS6 RAT DUAL SPECIFICITY PROTEIN PHOSPHATASE 6 [R. norvegicus], dual specificity phosphatase 10, dual specificity phosphatase 13, dual specificity phosphatase 14, dual specificity phosphatase 6, dual specificity phosphatase 9, expressed sequence BB104621, mitogen-activated protein kinase phosphatase x, protein tyrosine phosphatase, non-receptor type 16 |
| 2041 | 19780 | NM_053883 | b | | ESTs, Moderately similar to DUS6 RAT DUAL SPECIFICITY PROTEIN PHOSPHATASE 6 [R. norvegicus], ESTs, Weakly similar to DUS6 RAT DUAL SPECIFICITY PROTEIN PHOSPHATASE 6 [R. norvegicus], dual specificity phosphatase 10, dual specificity phosphatase 13, dual specificity phosphatase 14, dual specificity phosphatase 6, dual specificity phosphatase 9, expressed sequence BB104621, mitogen-activated protein kinase phosphatase x, protein tyrosine phosphatase, non-receptor type 16 |
| 2042 | 1454 | NM_053887 | General | | |
| 2043 | 1660 | NM_053891 | g | | ESTs, Moderately similar to CD5R MOUSE CYCLIN-DEPENDENT KINASE 5 ACTIVATOR 1 PRECURSOR [R. norvegicus], cyclin-dependent kinase 5, regulatory subunit (p35), cyclin-dependent kinase 5, regulatory subunit 1 (p35), cyclin-dependent kinase 5, regulatory subunit 2 (p39) |
| 2044 | 712 | NM_053896 | k | | |
| 2045 | 753 | NM_053897 | k | | coagulation factor II (thrombin) receptor-like 1, coagulation factor II (thrombin) receptor-like 2 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2046 | 794 | NM_053902 | General | | RIKEN cDNA 4432411A05 gene, kynureninase (L-kynurenine hydrolase) |
| 2047 | 17937 | NM_053911 | f | | ESTs, Weakly similar to ARNO_HUMAN ARF NUCLEOTIDE-BINDING SITE OPENER [*H. sapiens*] |
| 2048 | 8188 | NM_053927 | General | | DNA segment, Chr 10, ERATO Doi 398, expressed, ESTs, Weakly similar to PTNL RAT PROTEIN TYROSINE PHOSPHATASE, NON-RECEPTOR TYPE 21 [*R. norvegicus*], *Homo sapiens*, Similar to erythrocyte membrane protein band 4.1-like 3, clone MGC: 12343 IMAGE: 4044866, mRNA, complete cds, *Mus musculus* adult male pituitary gland cDNA, RIKEN full-length enriched library, clone: 5330430I10, full insert sequence, *Rattus norvegicus* protein tyrosine phosphatase 2E (PTP2E) mRNA, complete cds, erythrocyte membrane protein band 4.1 (elliptocytosis 1, RH-linked), erythrocyte membrane protein band 4.1-like 1, erythrocyte membrane protein band 4.1-like 3, erythrocyte protein band 4.1-like 1, erythrocyte protein band 4.1-like 3, protein tyrosine phosphatase, non-receptor type 21 |
| 2050 | 1628 | NM_053936 | h | | endothelial differentiation, lysophosphatidic acid G-protein-coupled receptor 4, endothelial differentiation, lysophosphatidic acid G-protein-coupled receptor 7, endothelial differentiation, lysophosphatidic acid G-protein-coupled receptor, 2, endothelial differentiation, lysophosphatidic acid G-protein-coupled receptor, 4, endothelial differentiation, lysophosphatidic acid G-protein-coupled receptor, 7, putative G protein-coupled receptor, snGPCR32 |
| 2051 | 13954 | NM_053955 | General | | ESTs, Highly similar to B46290 mu-crystallin [*H. sapiens*], crystallin, mu |
| 2052 | 408 | NM_053961 | General | | |
| 2052 | 19991 | NM_053961 | a | | DNA segment, Chr 9, ERATO Dol 85, expressed, *Homo sapiens* aconitase precursor (ACON) mRNA, nuclear gene encoding mitochondrial protein, partial cds, RIKEN cDNA 5031409G22 gene, aconitase 1, aconitase 1, soluble, aconitase 2, mitochondrial, iron-responsive element-binding protein |
| 2052 | 16190 | NM_053961 | q | | *Homo sapiens* hepatocellular carcinoma-associated antigen 64 (HCA64) mRNA, complete cds, RIKEN cDNA 1300014E15 gene, RIKEN cDNA 1300017C12 gene, RIKEN cDNA 1810022C23 gene, RIKEN cDNA 2610009M20 gene, RIKEN cDNA 4933417A18 gene, enoyl Coenzyme A hydratase, short chain, 1, mitochondrial, peroxisomal D3, D2-enoyl-CoA isomerase, peroxisomal delta3, delta2-enoyl-Coenzyme A isomerase |
| 2052 | 21355 | NM_053961 | j, l, y, z | | |
| 2055 | 15136 | NM_053971 | aa | | EST, Moderately similar to I51803 TAXREB107 [*H. sapiens*], ESTs, Highly similar to I51803 TAXREB107 [*H. sapiens*], ribosomal protein L6 |
| 2055 | 15135 | NM_053971 | d | | EST, Moderately similar to I51803 TAXREB107 [*H. sapiens*], ESTs, Highly |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2056 | 1764 | NM_053974 | h | | similar to I51803 TAXREB107 [*H. sapiens*], ribosomal protein L6 ESTs, Highly similar to A26411 translation initiation factor eIF-4E [*H. sapiens*], RIKEN cDNA 2700069E09 gene, eukaryotic translation initiation factor 4E |
| 2057 | 1292 | NM_053980 | l | | ADP-ribosylation factor related protein 1, RIKEN cDNA 1500006I01 gene |
| 2058 | 15468 | NM_053982 | q | | EST, Highly similar to 40S RIBOSOMAL PROTEIN S15A [*R. norvegicus*], EST, Weakly similar to RS1A_HUMAN 40S RIBOSOMAL PROTEIN S15A [*R. norvegicus*], ESTs, Weakly similar to RS1A_HUMAN 40S RIBOSOMAL PROTEIN S15A [*H. sapiens*] |
| 2059 | 15642 | NM_053985 | General | | ESTs, Highly similar to HISTONE H3.3 [*R. norvegicus*], H3 histone, family 3A, H3 histone, family 3B, H3 histone, family 3B (H3.3B) |
| 2060 | 21066 | NM_054001 | t | | CD36 antigen (collagen type I receptor, thrombospondin receptor)-like 2 (lysosomal integral membrane protein II), EST, Moderately similar to LYII_HUMAN LYSOSOME MEMBRANE PROTEIN II [*H. sapiens*] |
| 2061 | 17326 | NM_054008 | o | | RGC32 protein, RIKEN cDNA 1190002H23 gene |
| 2061 | 17327 | NM_054008 | cc | | RGC32 protein, RIKEN cDNA 1190002H23 gene |
| 2061 | 17329 | NM_054008 | g, o, cc | | RGC32 protein, RIKEN cDNA 1190002H23 gene |
| 2062 | 25253 | NM_057099 | j, l, m, p, z | proteasome (prosome, macropain) subunit, beta type 6, proteasome (prosome, macropain) subunit, beta type, 6 | EST, Weakly similar to S17522 multicatalytic endopeptidase complex [*H. sapiens*], ESTs, Weakly similar to PROTEASOME DELTA CHAIN PRECURSOR [*R. norvegicus*], proteasome (prosome, macropain) subunit, beta type 6, proteasome (prosome, macropain) subunit, beta type 7, proteasome (prosome, macropain) subunit, beta type, 6, proteasome (prosome, macropain) subunit, beta type, 7 |
| 2062 | 22849 | NM_057099 | j, l | proteasome (prosome, macropain) subunit, beta type 6, proteasome (prosome, macropain) subunit, beta type, 6 | EST, Weakly similar to S17522 multicatalytic endopeptidase complex [*H. sapiens*], ESTs, Weakly similar to PROTEASOME DELTA CHAIN PRECURSOR [*R. norvegicus*], proteasome (prosome, macropain) subunit, beta type 6, proteasome (prosome, macropain) subunit, beta type 7, proteasome (prosome, macropain) subunit, beta type, 6, proteasome (prosome, macropain) subunit, beta type, 7 |
| 2063 | 19657 | NM_057103 | b, cc | A kinase (PRKA) anchor protein (gravin) 12 | |
| 2064 | 5492 | NM_057105 | w | UDP glycosyltransferase 1 family, polypeptide A cluster, UDP glycosyltransferase 1 family, polypeptide A6, UDP-glucuronosyltransferase 1 family, member 1 | |
| 2064 | 15126 | NM_057105 | r | UDP glycosyltransferase 1 family, polypeptide A cluster, UDP glycosyltransferase 1 family, polypeptide A6, UDP- | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2064 | 15125 | NM_057105 | s | glucuronosyltransferase 1 family, member 1 UDP glycosyltransferase 1 family, polypeptide A cluster, UDP-glucuronosyltransferase 1 family, member 1 | |
| 2066 | 15391 | NM_057114 | n | | EST, Moderately similar to TDX2_HUMAN THIOREDOXIN PEROXIDASE 2 [*H. sapiens*], EST, Weakly similar to TDX2_HUMAN THIOREDOXIN PEROXIDASE 2 [*H. sapiens*], peroxiredoxin 1 |
| 2067 | 727 | NM_057123 | m | | BCS1 (yeast homolog)-like, ESTs, Highly similar to PRS4_HUMAN 26S PROTEASE REGULATORY SUBUNIT 4 [*H. sapiens*], ESTs, Weakly similar to A44468 26S proteasome regulatory chain 4 [*H. sapiens*], expressed sequence AI325227, protease (prosome, macropain) 26S subunit, ATPase 1, proteasome (prosome, macropain) 26S subunit, ATPase, 1 |
| 2068 | 915 | NM_057124 | s | | ESTs, Weakly similar to P2UR MOUSE P2U PURINOCEPTOR 1 [*M. musculus*], G protein-coupled receptor 35, purinergic receptor P2Y, G-protein coupled 2, pyrimidinergic receptor P2Y, G-protein coupled, 4, pyrimidinergic receptor P2Y, G-protein coupled, 6 |
| 2069 | 15151 | NM_057131 | k | | |
| 2070 | 1892 | NM_057144 | b | | cysteine and glycine-rich protein 3 (cardiac LIM protein), cysteine rich protein, cysteine-rich protein 2, cysteine-rich protein 3, thymus LIM protein |
| 2071 | 12333 | NM_057155 | f | | |
| 2071 | 12331 | NM_057155 | v, General | | |
| 2071 | 12332 | NM_057155 | f, General | | |
| 2072 | 17477 | NM_057194 | a, General | | EST, Weakly similar to B36298 proline-rich protein PRB3S [*H. sapiens*], EST, Weakly similar to CGHU3B collagen alpha 3(IV) chain precursor, long splice form [*H. sapiens*], EST, Weakly similar to D40750 proline-rich protein PRB1/2S [*H. sapiens*], EST, Weakly similar to JE0284 Mm-1 cell derived transplantability-associated protein 1b [*H. sapiens*], galectin-related inter-fiber protein, murine leukemia viral (bmi-1) oncogene homolog, phospholipid scramblase 1, phospholipid scramblase 2, phospholipid scramblase 3 |
| 2073 | 15408 | NM_057197 | p, t | | 2,4-dienoyl CoA reductase 1, mitochondrial, 2,4-dienoyl CoA reductase 2, peroxisomal, peroxisomal trans 2-enoyl CoA reductase; putative short chain alcohol dehydrogenase |
| 2073 | 15409 | NM_057197 | t | | 2,4-dienoyl CoA reductase 1, mitochondrial, 2,4-dienoyl CoA reductase 2, peroxisomal, peroxisomal trans 2-enoyl CoA reductase; putative short chain alcohol dehydrogenase |
| 2074 | 7866 | NM_057198 | h | | ESTs, Highly similar to PUR1_HUMAN AMIDOPHOSPHORIBOSYLTRANSFERASE PRECURSOR [*H. sapiens*], ESTs, Moderately similar to PUR1_HUMAN AMIDOPHOSPHORIBOSYLTRANSFERASE PRECURSOR [*H. sapiens*], RIKEN cDNA 5730454C12 gene, expressed sequence AA675351, |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | expressed sequence C79945, glutamine fructose-6-phosphate transaminase 2, glutamine-fructose-6-phosphate transaminase 2, phosphoribosyl pyrophosphate amidotransferase |
| 2075 | 14125 | NM_057208 | h, j, y, z | | ESTs, Highly similar to A25530 tropomyosin, fibroblast [*H. sapiens*] |
| 2076 | 1743 | NM_057210 | k, s | | |
| 2077 | 10498 | NM_078617 | a | | EST, Moderately similar to RS23_HUMAN 40S RIBOSOMAL PROTEIN S2 [*R. norvegicus*], EST, Weakly similar to RS23_HUMAN 40S RIBOSOMAL PROTEIN S2 [*R. norvegicus*], ESTs, Weakly similar to RS23_HUMAN 40S RIBOSOMAL PROTEIN S2 [*R. norvegicus*], *Mus musculus*, Similar to mitochondrial ribosomal protein S12, clone MGC: 13892 IMAGE: 4209358, mRNA, complete cds, RIKEN cDNA 2410044J15 gene, expressed sequence AI327385, mitochondrial ribosomal protein S12, ribosomal protein S23 |
| 2078 | 8820 | NM_080399 | n | | |
| 2079 | 15701 | NM_080581 | j, m, y, z | | ATP-binding cassette, sub-family C (CFTR/MRP), member 1 (multiple drug resistance-associated protein), ATP-binding cassette, sub-family C (CFTR/MRP), member 1a, ATP-binding cassette, sub-family C (CFTR/MRP), member 1b, ATP-binding cassette, sub-family C (CFTR/MRP), member 2, ATP-binding cassette, sub-family C (CFTR/MRP), member 3, ATP-binding cassette, sub-family C (CFTR/MRP), member 6, ESTs, Moderately similar to JE0336 canalicular multispecific organic anion transporter [*H. sapiens*], RIKEN cDNA 1700019L09 gene |
| 2079 | 20105 | NM_080581 | aa | | |
| 2080 | 16109 | NM_080585 | c | | |
| 2081 | 1757 | NM_080766 | d | | |
| 2082 | 7108 | NM_080778 | y | | ESTs, Highly similar to COT2 RAT COUP TRANSCRIPTION FACTOR 2 [*R. norvegicus*], *Homo sapiens* cDNA: FLJ22189 fis, clone HRC01043, RIKEN cDNA 2700033K02 gene, nuclear receptor subfamily 2, group E, member 3, nuclear receptor subfamily 2, group F, member 2 |
| 2083 | 132 | NM_080782 | k | | cyclin-dependent kinase inhibitor 1A (P21), cyclin-dependent kinase inhibitor 1A (p21, Cip1), cyclin-dependent kinase inhibitor 1B (p27, kip1), cyclin-dependent kinase inhibitor 1B (p27, Kip1) |
| 2083 | 133 | NM_080782 | l | | cyclin-dependent kinase inhibitor 1A (P21), cyclin-dependent kinase inhibitor 1A (p21, Cip1), cyclin-dependent kinase inhibitor 1B (p27, kip1), cyclin-dependent kinase inhibitor 1B (p27, Kip1) |
| 2084 | 20122 | NM_080887 | General | | HT014, *Homo sapiens* thioredoxin delta 3 (TXN delta 3) mRNA, partial cds, RIKEN cDNA 4930429J24 gene, expressed sequence AU021712, thioredoxin, thioredoxin domain-containing 2 (spermatozoa), thioredoxin-like (32 kD), thioredoxin-like, 32 kD |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2085 | 6143 | NM_080892 | e | | *Homo sapiens*, Similar to selenium binding protein 1, clone MGC: 17268 IMAGE: 4155238, mRNA, complete cds, selenium binding protein 1, selenium binding protein 2 |
| 2086 | 9952 | NM_080902 | h | | |
| 2087 | 17546 | NM_130401 | b | | epithelial protein up-regulated in carcinoma, membrane associated protein 17 |
| 2088 | 21695 | NM_130411 | c, x | | ESTs, Weakly similar to CO1A_MOUSE CORONIN-LIKE PROTEIN P57 (CORONIN 1A) [*M. musculus*], coronin, actin binding protein 1A, coronin, actin binding protein 1B, coronin, actin binding protein 1C, coronin, actin-binding protein, 1A, hypothetical protein DKFZp762I166 |
| 2089 | 21391 | NM_130416 | x, General | | annexin VII, long form [*H. sapiens*], ESTs, Moderately similar to ANX4 MOUSE ANNEXIN IV [*M. musculus*], ZAP 36/annexin IV, annexin A4, annexin A7 |
| 2090 | 20694 | NM_130430 | General | | |
| 2090 | 19818 | NM_130430 | cc | | |
| 2090 | 18810 | NM_130430 | e, s | | ATP synthase, H+ transporting, mitochondrial F1 complex, alpha subunit, isoform 1, ATP synthase, H+ transporting, mitochondrial F1 complex, alpha subunit, isoform 1, cardiac muscle, EST, Moderately similar to ATPA RAT ATP SYNTHASE ALPHA CHAIN, MITOCHONDRIAL PRECURSOR [*R. norvegicus*], expressed sequence AL022851, expressed sequence AL023067 |
| 2091 | 18293 | NM_130433 | q | | |
| 2092 | 25064 | S45392 | a, n | | |
| 2093 | 3244 | S63519 | u | | |
| 2094 | 25501 | S63521 | q | | |
| 2095 | 16248 | S68135 | h | | |
| 2096 | 18647 | S69316 | q | | EST, Weakly similar to ENPL_HUMAN ENDOPLASMIN PRECURSOR [*H. sapiens*], ESTs, Highly similar to HS9B RAT HEAT SHOCK PROTEIN HSP 90-BETA [*R. norvegicus*], ESTs, Weakly similar to ENPL_HUMAN ENDOPLASMIN PRECURSOR [*H. sapiens*], *Homo sapiens* mRNA; cDNA DKFZp564F053 (from clone DKFZp564F053), RIKEN cDNA 1810014B01 gene, RIKEN cDNA 2410002K23 gene, expressed sequence C81438, heat shock 90 kD protein 1, beta, heat shock protein, 84 kDa 1, tumor rejection antigen (gp96) 1, tumor rejection antigen gp96 |
| 2097 | 24351 | S74257 | v | | ATP-binding cassette, sub-family D (ALD), member 4, ESTs, Highly similar to JC5604 ABC-transporting peroxisomal membrane protein 69 [*H. sapiens*], ESTs, Moderately similar to JC5604 ABC-transporting peroxisomal membrane protein 69 [*H. sapiens*] |
| 2098 | 25066 | S75280 | d | | |
| 2099 | 1460 | S76054 | j, l, m, x, y, General | | DNA segment, Chr 15, Wayne State University 77, expressed, EST, Moderately similar to K2C8 RAT KERATIN, TYPE II CYTOSKELETAL 8 [*R. norvegicus*], EST, Weakly similar to I37982 Keratin 8 [*H. sapiens*], ESTs, Moderately similar to I37982 Keratin 8 [*H. sapiens*], ESTs, Weakly similar to |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | I37982 Keratin 8 [*H. sapiens*], *Homo sapiens* mRNA; cDNA DKFZp434C107 (from clone DKFZp434C107), RIKEN cDNA 1200016G03 gene, expressed sequence AL022697, expressed sequence AU019895, keratin 8, keratin complex 2, basic, gene 8 |
| 2100 | 25539 | S76742 | v | | |
| 2101 | 16400 | S76779 | c | | |
| 2102 | 24469 | S77858 | n | | EST, Weakly similar to MOHU6N myosin alkali light chain 6, nonmuscle form [*H. sapiens*], myosin light chain, alkali, nonmuscle, myosin, light polypeptide 6, alkali, smooth muscle and non-muscle |
| 2103 | 25545 | S77900 | k, s | | |
| 2103 | 21583 | S77900 | k | | EST, Weakly similar to MOHULP myosin regulatory light chain, placental [*H. sapiens*], ESTs, Moderately similar to MOHULP myosin regulatory light chain, placental [*H. sapiens*], myosin regulatory light chain, myosin, light polypeptide, regulatory, non-sarcomeric (20 kD) |
| 2104 | 10260 | S81497 | s | lipase A, lysosomal acid, cholesterol esterase (Wolman disease), lysosomal acid lipase 1 | |
| 2105 | 3609 | S82579 | k | | *Homo sapiens*, Similar to histamine N-methyltransferase, clone MGC: 14500 IMAGE: 4249496, mRNA, complete cds, expressed sequence AI788969, histamine N-methyltransferase |
| 2106 | 111 | U02506 | u | | |
| 2107 | 14959 | U03390 | a, q, General | | EST, Moderately similar to GBLP_HUMAN GUANINE NUCLEOTIDE-BINDING PROTEIN BETA SUBUNIT-LIKE PROTEIN 12.3 [*R. norvegicus*], EST, Weakly similar to B33928 GTP-binding protein beta chain homolog [*H. sapiens*], ESTs, Weakly similar to A36986 activated protein kinase C receptor RACK1 - rat [*R. norvegicus*], *Homo sapiens* cDNA: FLJ21913 fis, clone HEP03888, *Homo sapiens*, Similar to guanine nucleotide binding protein (G protein), beta polypeptide 2-like 1, clone MGC: 17239 IMAGE: 4155303, mRNA, complete cds, expressed sequence AW544865, guanine nucleotide binding protein (G protein), beta polypeptide 2-like 1, guanine nucleotide binding protein, beta 2, related sequence 1 |
| 2109 | 2010 | U05675 | b, x, bb | | EST, Weakly similar to beta-fibrinogen precursor [*H. sapiens*], ESTs, Moderately similar to AF125176 1 angiopoietin-related protein-2 [*M. musculus*], ESTs, Weakly similar to FIBB RAT FIBRINOGEN BETA CHAIN PRECURSOR [*R. norvegicus*], expressed sequence AI256424, fibrinogen, B beta polypeptide |
| 2110 | 15462 | U06230 | d | | |
| 2112 | 1583 | U07201 | s, General | asparagine synthetase | |
| 2113 | 627 | U09229 | h | | ESTs, Highly similar to CDP_HUMAN CCAAT DISPLACEMENT PROTEIN [*H. sapiens*], Hepatocyte nuclear factor 6, Human chromosome 17q21 mRNA clone 1046: 1-1, KIAA0293 protein, cut (*Drosophila*)-like 1, cut (*Drosophila*)-like 1 (CCAAT displacement protein), cut (*Drosophila*)-like 2, one cut domain, family member 1 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2114 | 809 | U17035 | General | | |
| 2115 | 16675 | U17565 | k, x, bb | mini chromosome maintenance deficient 6 (S. cerevisiae), minichromosome maintenance deficient (mis5, S. pombe) 6 | mini chromosome maintenance deficient 6 (S. cerevisiae), minichromosome maintenance deficient (mis5, S. pombe) 6 |
| 2116 | 25587 | U20110 | r | | |
| 2117 | 90 | U20796 | r | | Mus musculus, Similar to nuclear receptor subfamily 1, group D, member 1, clone MGC: 6402 IMAGE: 3585478, mRNA, complete cds, nuclear receptor subfamily 1, group D, member 2, thyroid hormone receptor alpha |
| 2118 | 25589 | U21718 | h, aa | | |
| 2119 | 22196 | U21719 | h | | |
| 2120 | 17118 | U25746 | s | | DEAD (aspartate-glutamate-alanine-aspartate) box polypeptide 5, ESTs, Moderately similar to A57514 RNA helicase HEL117 - rat [R. norvegicus], KIAA0801 gene product, RIKEN cDNA 2610007K22 gene, RIKEN cDNA 4921506D17 gene, RIKEN cDNA 9130430L19 gene, RNA helicase, expressed sequence AI325430 |
| 2121 | 1537 | U27518 | g, h, n | | |
| 2122 | 1558 | U28504 | bb | | EST, Weakly similar to NPT1 RAT RENAL SODIUM-DEPENDENT PHOSPHATE TRANSPORT PROTEIN 1 [R. norvegicus], ESTs, Weakly similar to NPT1 MOUSE RENAL SODIUM-DEPENDENT PHOSPHATE TRANSPORT PROTEIN 1 [M. musculus], expressed sequence AW261723, solute carrier family 17 (sodium phosphate), member 1, solute carrier family 17 (sodium phosphate), member 3, solute carrier family 17 (sodium phosphate), member 4, solute carrier family 17 (sodium/hydrogen exchanger), member 1 |
| 2123 | 16193 | U30831 | n | | B/K protein, EST, Moderately similar to S68695 B/K protein - rat [R. norvegicus], Mus musculus B/K mRNA for B/K protein, complete cds, strain: BALB/c, RIKEN cDNA C030008B15 gene, synaptotagmin 1, synaptotagmin 5 |
| 2124 | 17480 | U31598 | z | | |
| 2125 | 18302 | U33500 | General | | |
| 2126 | 25599 | U34897 | y | | |
| 2127 | 1394 | U37099 | h | | Homo sapiens, clone MGC: 4711 IMAGE: 3534915, mRNA, complete cds, RAB23, member RAS oncogene family, RAB3A, member RAS oncogene family, RAB3C, member RAS oncogene family, expressed sequence AI850886 |
| 2128 | 244 | U38376 | n | | ESTs, Highly similar to FGD1_HUMAN PUTATIVE RHO/RAC GUANINE NUCLEOTIDE EXCHANGE FACTOR [H. sapiens], ESTs, Weakly similar to B39898 phospholipase A2 [M. musculus], ESTs, Weakly similar to FGD1 MOUSE PUTATIVE RHO/RAC GUANINE NUCLEOTIDE EXCHANGE FACTOR [M. musculus], ESTs, Weakly similar to FGD1_HUMAN PUTATIVE RHO/RAC GUANINE NUCLEOTIDE EXCHANGE FACTOR [H. sapiens], FGD1 family, member 3, RIKEN cDNA 5830461L01 gene, faciogenital dysplasia (Aarskog-Scott syndrome), |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2129 | 1623 | U41164 | h | | faciogenital dysplasia homolog, faciogenital dysplasia homolog 2 (human) ESTs, Weakly similar to AF167320 1 zinc finger protein ZFP113 [*M. musculus*], ESTs, Weakly similar to Z135_HUMAN ZINC FINGER PROTEIN 13 [*H. sapiens*], ESTs, Weakly similar to ZF29 MOUSE ZINC FINGER PROTEIN 29 [*M. musculus*], RIKEN cDNA 2310040I01 gene, expressed sequence AI835008 |
| 2130 | 15851 | U42719 | f, t, x, General | complement component 4 (within H-2S), complement component 4B | EST, Weakly similar to complement component C4A [*H. sapiens*] |
| 2131 | 17886 | U47315 | s, z | | |
| 2132 | 21654 | U53184 | i, t, General | | |
| 2133 | 1439 | U57391 | w | | |
| 2134 | 725 | U62316 | bb | | expressed sequence AW146050, monocarboxylate transporter, solute carrier family 16 (monocarboxylic acid transporters), member 3, solute carrier family 16 (monocarboxylic acid transporters), member 7 |
| 2137 | 2153 | U75404 | b, cc, General | A kinase (PRKA) anchor protein (gravin) 12 | |
| 2139 | 4956 | U76714 | j, y | | |
| 2140 | 4477 | U77829 | l, m | | |
| 2141 | 21703 | U82591 | z | | expressed sequence C76683, putative c-Myc-responsive |
| 2142 | 977 | U89744 | s | | KIAA1683 protein, KIAA1802 protein, expressed sequence AA407558, lymphocyte antigen 64, polymerase (RNA) II (DNA directed) polypeptide A (220 kD), suppressor of Ty (*S. cerevisiae*) 5 homolog |
| 2143 | 23282 | U90725 | h | | high density lipoprotein binding protein (vigilin) |
| 2144 | 22005 | U96490 | m | | |
| 2146 | 819 | X02284 | j, z | | |
| 2147 | 818 | X02291 | e, j, z | aldolase 2, B isoform, aldolase B, fructose-bisphosphate | |
| 2148 | 20818 | X02904 | n, q | | |
| 2149 | 16401 | X04979 | c | | |
| 2150 | 20513 | X05684 | o, r | pyruvate kinase liver and red blood cell, pyruvate kinase, liver and RBC | |
| 2151 | 25084 | X06769 | cc | | |
| 2152 | 672 | X13722 | h | | |
| 2153 | 25675 | X14181 | n | | |
| 2153 | 20810 | X14181 | n, q, w | | EST, Moderately similar to RL1X_HUMAN 60S RIBOSOMAL PROTEIN L18A [*H. sapiens*], EST, Weakly similar to RL1X_HUMAN 60S RIBOSOMAL PROTEIN L18A [*H. sapiens*], EST, Weakly similar to S47353 ribosomal protein L18a, cytosolic [*H. sapiens*], ESTs, Highly similar to RL1X_HUMAN 60S RIBOSOMAL PROTEIN L18A [*H. sapiens*], RIKEN cDNA 2510019J09 gene, ribosomal protein L18a |
| 2154 | 18541 | X14871 | y | | ESTs, Highly similar to RL26_HUMAN 60S RIBOSOMAL PROTEIN L26 [*H. sapiens*], ESTs, Highly similar to S33713 ribosomal protein L26, cytosolic [*H. sapiens*], ESTs, Weakly similar to 60S RIBOSOMAL PROTEIN L25 [*R. norvegicus*], ribosomal protein L26, ribosomal protein L26 pseudogene 1 |
| 2155 | 25679 | X15013 | q | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2155 | 19244 | X15013 | c, q, w | | EST, Weakly similar to 60S RIBOSOMAL PROTEIN L7A [*M. musculus*], ESTs, Highly similar to R5HU7A ribosomal protein L7a, cytosolic [*H. sapiens*], *Homo sapiens* rpL7a pseudogene, clone 3a, Human DNA sequence from clone RP1-189G13 on chromosome 20. Contains an RPL7A (60S ribosomal protein L7A) (SURF3) pseudogene, an RPS4 (40S ribosomal protein S4) pseudogene, ESTs, STSs and GSSs, RIKEN cDNA 4632404N19 gene, ribosomal protein L7a |
| 2156 | 15626 | X17665 | a | | EST AI317031, EST, Weakly similar to R3HU16 ribosomal protein S16, cytosolic [*H. sapiens*], expressed sequence AA420385, ribosomal protein S16 |
| 2157 | 1893 | X51529 | t | phospholipase A2, group IIA (platelets, synovial fluid) | |
| 2158 | 25686 | X51536 | bb | | |
| 2158 | 10819 | X51536 | aa, bb | | EST, Moderately similar to R3RT3 ribosomal protein S3 - rat [*R. norvegicus*], EST, Weakly similar to R3RT3 ribosomal protein S3 - rat [*R. norvegicus*], hypothetical protein FLJ23059, ribosomal protein S3 |
| 2159 | 18250 | X51706 | a, q, w | ribosomal protein L9 | EST, Weakly similar to 60S RIBOSOMAL PROTEIN L9 [*R. norvegicus*], EST, Weakly similar to S42106 ribosomal protein L9 homolog [*H. sapiens*], ESTs, Highly similar to S42106 ribosomal protein L9 homolog [*H. sapiens*], ESTs, Moderately similar to 60S RIBOSOMAL PROTEIN L9 [*R. norvegicus*], RIKEN cDNA 4930401B11 gene, ribosomal protein L9 |
| 2160 | 20872 | X51707 | a | ribosomal protein S19 | EST, Moderately similar to 40S RIBOSOMAL PROTEIN S19 [*R. norvegicus*], EST, Weakly similar to RS19_HUMAN 40S RIBOSOMAL PROTEIN S19 [*H. sapiens*], ribosomal protein S19 |
| 2161 | 516 | X52711 | c | myxovirus (influenza virus) resistance 1, myxovirus (influenza) resistance 1, homolog of murine (interferon-inducible protein p78) | |
| 2162 | 25689 | X52815 | g | | |
| 2163 | 20427 | X53378 | w | | ESTs, Highly similar to RS13_HUMAN 40S RIBOSOMAL PROTEIN S13 [*H. sapiens*], ESTs, Moderately similar to RS13_HUMAN 40S RIBOSOMAL PROTEIN S13 [*H. sapiens*] |
| 2164 | 18606 | X53504 | General | | EST, Moderately similar to S35531 ribosomal protein L12, cytosolic [*H. sapiens*], EST, Weakly similar to 60S RIBOSOMAL PROTEIN L12 [*R. norvegicus*], hypothetical protein, ribosomal protein L12 |
| 2165 | 1463 | X54467 | d, u, General | | |
| 2166 | 24577 | X55153 | a, v | | EST, Weakly similar to 60S ACIDIC RIBOSOMAL PROTEIN P2 [*R. norvegicus*], EST, Weakly similar to R6HUP2 acidic ribosomal protein P2, cytosolic [*H. sapiens*], ESTs, Highly similar to 60S ACIDIC RIBOSOMAL PROTEIN P2 [*R. norvegicus*], ESTs, Highly similar to MTJ1 MOUSE DNAJ PROTEIN HOMOLOG MTJ1 [*M. musculus*], Human DNA sequence from clone RP3-408B20 on |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2167 | 10344 | X57405 | j, m | Notch (*Drosophila*) homolog 1 (translocation-associated), Notch gene homolog 1, (*Drosophila*) | chromosome 6 Contains ESTs, STSs and GSSs. Contains a gene and two pseudogenes for novel 7 transmembrane receptors (olfactory family) and a gene for a novel protein similar to 60S acidic ribosomal protein P2 (RPLP2), RIKEN cDNA 2700049I22 gene, ribosomal protein, large P2, ribosomal protein, large, P1 EST, Highly similar to A40043 notch protein homolog TAN-1 precursor [*H. sapiens*], EST, Weakly similar to A40043 notch protein homolog TAN-1 precursor [*H. sapiens*], ESTs, Weakly similar to NEUROGENIC LOCUS NOTCH HOMOLOG PROTEIN 1 PRECURSOR [*M. musculus*], *Homo sapiens* mRNA; cDNA DKFZp761G02121 (from clone DKFZp761G02121); partial cds, Notch (*Drosophila*) homolog 1 (translocation-associated), Notch (*Drosophila*) homolog 2, Notch (*Drosophila*) homolog 3, Notch 3, Notch gene homolog 1, (*Drosophila*), Notch gene homolog 3, (*Drosophila*), jagged 1 |
| 2168 | 15106 | X57529 | g, n, q | | EST, Weakly similar to S30393 ribosomal protein S18, cytosolic [*H. sapiens*], ESTs, Highly similar to S30393 ribosomal protein S18, cytosolic [*H. sapiens*], ribosomal protein S18 |
| 2169 | 5667 | X58200 | q, bb | ribosomal protein L23 | |
| 2169 | 18611 | X58200 | a, v | ribosomal protein L29 | EST, Moderately similar to 60S RIBOSOMAL PROTEIN L29 [*R. norvegicus*], EST, Weakly similar to S65784 ribosomal protein L29, cytosolic [*H. sapiens*], ESTs, Highly similar to S65784 ribosomal protein L29, cytosolic [*H. sapiens*], ESTs, Weakly similar to 60S RIBOSOMAL PROTEIN L29 [*M. musculus*], Human DNA sequence from clone RP4-595K12 on chromosome 1p31.2-31.3 Contains a pseudogene similar to 60S RPL29 (ribosomal protein L29 (cell surface heparin binding protein HIP)), a chromosome 1 specific mRNA (KIAA0499), a novel mRNA (KIAA0433), ESTs, STSs, GSSs and a CpG Island, ribosomal protein L29 |
| 2170 | 17175 | X58389 | w | | EST, Moderately similar to RL17_HUMAN 60S RIBOSOMAL PROTEIN L17 [*H. sapiens*], EST, Weakly similar to RL17 RAT 60S RIBOSOMAL PROTEIN L17 [*R. norvegicus*], EST, Weakly similar to RL17_HUMAN 60S RIBOSOMAL PROTEIN L17 [*H. sapiens*], ESTs, Weakly similar to R5HU22 ribosomal protein L17, cytosolic [*H. sapiens*] |
| 2171 | 25702 | X58465 | w | ribosomal protein S5 | EST, Moderately similar to 40S RIBOSOMAL PROTEIN S5 [*R. norvegicus*], ESTs, Weakly similar to S55916 ribosomal protein S5, cytosolic [*H. sapiens*], ribosomal protein S5 |
| 2171 | 10109 | X58465 | c, q | ribosomal protein S5 | EST, Moderately similar to 40S RIBOSOMAL PROTEIN S5 [*R. norvegicus*], ESTs, Weakly similar to S55916 ribosomal protein S5, cytosolic [*H. sapiens*], ribosomal protein S5 |
| 2172 | 25705 | X59375 | c, i, aa, General | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2173 | 25709 | X59737 | u | creatine kinase, mitochondrial 1 (ubiquitous), creatine kinase, mitochondrial 1, ubiquitous | |
| 2174 | 18354 | X59859 | General | decorin | ESTs, Moderately similar to dJ63G5.3 [*H. sapiens*], RIKEN cDNA 1700034K16 gene, RIKEN cDNA 5530600M07 gene, decorin |
| 2174 | 18355 | X59859 | t | decorin | ESTs, Moderately similar to dJ63G5.3 [*H. sapiens*], RIKEN cDNA 1700034K16 gene, RIKEN cDNA 5530600M07 gene, decorin |
| 2175 | 21657 | X61381 | General | | ESTs, Moderately similar to S17182 interferon-induced protein 1-8U [*H. sapiens*], ESTs, Weakly similar to putative haemopoietic membrane protein [*M. musculus*], Human DNA sequence from clone RP4-781L3 on chromosome 1p34.3-36.11 Contains a pseudogene similar to IFITM3 (interferon inducedntransmembrane protein 3 (1-8U)), STSs and GSSs, RIKEN cDNA 1110004C05 gene, interferon induced transmembrane protein 3 (1-8U), interferon induced transmembrane protein 3-like, interferon-inducible protein 16 |
| 2176 | 25718 | X62145 | bb, General | | |
| 2176 | 15875 | X62145 | a, q, v | | EST, Highly similar to 60S RIBOSOMAL PROTEIN L8 [*R. norvegicus*], EST, Moderately similar to 60S RIBOSOMAL PROTEIN L8 [*R. norvegicus*], EST, Weakly similar to JN0923 ribosomal protein L8, cytosolic [*H. sapiens*], ESTs, Highly similar to 60S RIBOSOMAL PROTEIN L8 [*R. norvegicus*], ESTs, Highly similar to RL8_HUMAN 60S RIBOSOMAL PROTEIN L [*M. musculus*], ESTs, Moderately similar to RL8_HUMAN 60S RIBOSOMAL PROTEIN L [*M. musculus*], expressed sequence AL024098, ribosomal protein L8 |
| 2177 | 13646 | X62166 | bb | | EST, Weakly similar to 60S RIBOSOMAL PROTEIN L3 [*R. norvegicus*], EST, Weakly similar to I84501 ribosomal protein L3 [*H. sapiens*], ESTs, Moderately similar to 60S RIBOSOMAL PROTEIN L3 [*R. norvegicus*], ESTs, Moderately similar to I84501 ribosomal protein L3 [*H. sapiens*], ESTs, Weakly similar to RL3 MOUSE 60S RIBOSOMAL PROTEIN L3 [*M. musculus*], RIKEN cDNA 1110057H16 gene, ribosomal protein L3, ribosomal protein L3-like |
| 2178 | 25721 | X62325 | p | | |
| 2179 | 16012 | X62875 | m, s, z | | high mobility group AT-hook 1, high-mobility group (nonhistone chromosomal) protein isoforms I and Y |
| 2180 | 25730 | X63369 | cc | | |
| 2181 | 25089 | X63594 | General | | |
| 2181 | 25090 | X63594 | cc, General | | |
| 2182 | 20844 | X65228 | n, w | | EST, Highly similar to 60S RIBOSOMAL PROTEIN L23A [*R. norvegicus*], ESTs, Highly similar to RL2B_HUMAN 60S RIBOSOMAL PROTEIN L23A [*H. sapiens*], ribosomal protein L23a |
| 2183 | 20879 | X65296 | j, y | | EST, Weakly similar to JC5408 carboxylesterase [*H. sapiens*], ESTs, Moderately similar to ES22 MOUSE LIVER CARBOXYLESTERASE 22 |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| | | | | | PRECURSOR [*M. musculus*], T-complex expressed gene 5, carboxylesterase 1, carboxylesterase 1 (monocyte/macrophage serine esterase 1), carboxylesterase 3, carboxylesterase 3 (brain) |
| 2184 | 25736 | X68782 | c | | |
| 2185 | 16426 | X70369 | c | collagen, type III, alpha 1 (Ehlers-Danlos syndrome type IV, autosomal dominant), procollagen, type III, alpha 1 | EST, Highly similar to CA13_HUMAN COLLAGEN ALPHA 1(III) CHAIN PRECURSOR [*H. sapiens*], EST, Moderately similar to CA13_HUMAN COLLAGEN ALPHA 1(III) CHAIN PRECURSOR [*H. sapiens*], EST, Weakly similar to CGHU7L collagen alpha 1(III) chain precursor [*H. sapiens*], ESTs, Highly similar to CA21_HUMAN COLLAGEN ALPHA 2(I) CHAIN PRECURSOR [*H. sapiens*], collagen type V, alpha 2, collagen, type III, alpha 1 (Ehlers-Danlos syndrome type IV, autosomal dominant), macrophage receptor with collagenous structure, procollagen, type III, alpha 1 |
| 2186 | 16300 | X70706 | u | | ESTs, Highly similar to A34789 T-plastin [*H. sapiens*], ESTs, Highly similar to PLSI_HUMAN I-PLASTIN [*H. sapiens*], expressed sequence AI115446, expressed sequence AI427122, expressed sequence AL024105, plastin 2, L |
| 2187 | 24232 | X75207 | c | | B-cell CLL/lymphoma 1, EST, Moderately similar to CGD1 RAT G1/S-SPECIFIC CYCLIN D1 [*R. norvegicus*], ESTs, Weakly similar to 1709356A cyclin PRAD1 [*H. sapiens*], cyclin D1, cyclin D1 (PRAD1: parathyroid adenomatosis 1), expressed sequence AI327039 |
| 2188 | 16272 | X76456 | n, p | | ESTs, Highly similar to alpha-albumin protein [*M. musculus*], *Mus musculus* mRNA for alpha-albumin protein, afamin |
| 2189 | 25741 | X76489 | u | | |
| 2190 | 23302 | X78949 | h | | ESTs, Weakly similar to DAHUA1 procollagen-proline dioxygenase [*H. sapiens*], expressed sequence AI853847, expressed sequence C76437, procollagen-proline, 2-oxoglutarate 4-dioxygenase (proline 4-hydroxylase), alpha 1 polypeptide, procollagen-proline, 2-oxoglutarate 4-dioxygenase (proline 4-hydroxylase), alpha polypeptide I, procollagen-proline, 2-oxoglutarate 4-dioxygenase (proline 4-hydroxylase), alpha polypeptide II |
| 2191 | 25747 | X81448 | General | | |
| 2192 | 24115 | X81449 | u | | EST, Weakly similar to KERATIN, TYPE I CYTOSKELETAL 19 [*M. musculus*], ESTs, Moderately similar to K1CJ_HUMAN KERATIN, TYPE I CYTOSKELETAL 10 [*H. sapiens*], ESTs, Weakly similar to S30433 keratin 17, type I, cytoskeletal [*H. sapiens*], *Homo sapiens* mRNA for keratin 19, partial cds, isolate: K19-141, keratin 19, keratin complex 1, acidic, gene 19, type I intermediate filament cytokeratin |
| 2193 | 25754 | X89696 | g | | |
| 2194 | 25097 | X90642 | y, z | | |
| 2195 | 12978 | X96437 | cc, General | | immediate early response 3 |
| 2197 | 4594 | Y07704 | c | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2198 | 25777 | Y08355 | g, p, General | | |
| 2199 | 15986 | Y09945 | bb, General | | EST, Weakly similar to OCN2 MOUSE ORGANIC CATION/CARNITINE TRANSPORTER 2 [*M. musculus*], ESTs, Highly similar to OCN2_HUMAN ORGANIC CATION/CARNITINE TRANSPORTER 2 [*H. sapiens*], ESTs, Weakly similar to JE0346 high-affinity carntine transporter, CT1 - rat [*R. norvegicus*], ion transporter protein, solute carrier family 22 (organic cation transporter), member 1, solute carrier family 22 (organic cation transporter), member 4, solute carrier family 22 (organic cation transporter), member 5, solute carrier family 22 (organic cation transporter), member 9 |
| 2200 | 20890 | Y13275 | k | | CD9 antigen, RIKEN cDNA 6330415F13 gene, RIKEN cDNA B230119D02 gene, expressed sequence C76990, transmembrane 4 superfamily member 3 |
| 2201 | 21914 | Y13336 | d | | ESTs, Weakly similar to DAD1_HUMAN DEFENDER AGAINST CELL DEATH 1 [*R. norvegicus*], defender against cell death 1, expressed sequence AI323713 |
| 2202 | 406 | Z11995 | o, General | | |
| 2203 | 18352 | Z12298 | t | decorin | ESTs, Moderately similar to dJ63G5.3 [*H. sapiens*], RIKEN cDNA 1700034K16 gene, RIKEN cDNA 5530600M07 gene, decorin |
| 2204 | 17481 | Z49761 | k | | |
| 2205 | 8664 | Z75029 | r, v | | ESTs, Highly similar to T17342 hypothetical protein DKFZp586K1924.1 [*H. sapiens*], ESTs, Moderately similar to T17342 hypothetical protein DKFZp586K1924.1 [*H. sapiens*] |
| 2206 | 2459 | AA964755 | cc | | |
| 2207 | 23830 | AA956638 | aa | | |
| 2208 | 6100 | X73524 | x | | |
| 2209 | 439 | Z22607 | w | bone morphogenetic protein 4 | bone morphogenetic protein 15, bone morphogenetic protein 4, endometrial bleeding associated factor, endometrial bleeding associated factor (left-right determination, factor A; transforming growth factor beta superfamily), growth differentiation factor 2, growth differentiation factor 5, hypothetical protein FLJ10314 |
| 2210 | 8665 | AI071965 | v | | ESTs, Highly similar to T17342 hypothetical protein DKFZp586K1924.1 [*H. sapiens*], ESTs, Moderately similar to T17342 hypothetical protein DKFZp586K1924.1 [*H. sapiens*] |
| 2211 | 155 | U32681 | t | crp-ductin, deleted in malignant brain tumors 1 | CD163 antigen, ESTs, Highly similar to I38005 M130 antigen precursor, splice form 4 [*H. sapiens*], KIAA1822 protein, apoptosis inhibitory 6, crp-ductin, deleted in malignant brain tumors 1, lectin, galactoside-binding, soluble, 3 binding protein, macrophage scavenger receptor 2, peptidylprolyl isomerase C-associated protein |
| 2212 | 19252 | AA892041 | s | anti-oxidant protein 2 (non-selenium glutathione peroxidase, acidic calcium-independent phospholipase A2), peroxiredoxin 5 | ESTs, Moderately similar to AOP2_HUMAN ANTIOXIDANT PROTEIN 2 [*H. sapiens*], anti-oxidant protein 2 (non-selenium glutathione peroxidase, acidic calcium-independent phospholipase A2), peroxiredoxin 5 |
| 2213 | 15582 | AI232320 | q | | |

TABLE 3-continued

HUMAN HOMOLOGUE ANNOTATIONS

| Seq. ID No. | Identifier | GenBank Acc./ Ref. Seq. ID No. | Model Code | Homologous Gene Name | Homologous Cluster Name |
|---|---|---|---|---|---|
| 2214 | 17541 | M26125 | n | epoxide hydrolase 1, microsomal, epoxide hydrolase 1, microsomal (xenobiotic) | EST, Moderately similar to HYEP_HUMAN EPOXIDE HYDROLASE 1 [*H. sapiens*], ESTs, Highly similar to HYEP_HUMAN EPOXIDE HYDROLASE 1 [*H. sapiens*], epoxide hydrolase 1, microsomal, epoxide hydrolase 1, microsomal (xenobiotic) |
| 2215 | 18609 | M30689 | i | | |
| 2216 | 6262 | AI177125 | g | | |
| 2217 | 23859 | AI072161 | f | | |
| 2218 | 21011 | H32189 | e | glutathione S-transferase M2 (muscle), glutathione S-transferase, mu 2 | ESTs, Moderately similar to GLUTATHIONE S-TRANSFERASE YB1 [*R. norvegicus*], glutathione S-transferase M1, glutathione S-transferase, mu 1 |
| 2220 | 2572 | AI177143 | b | | |
| 2221 | 25419 | M22922 | a | | |

TABLE 4

CODE KEY

| | Time (hrs) | Code |
|---|---|---|
| GENERAL TOXICITY | | General |
| ACYCLOVIR | 24, 168 | a |
| ACYCLOVIR | 6 | b |
| ADR | 120, 168 | c |
| AY | 360 | d |
| BEA | 6, 24 | e |
| CAPTOPRIL | 336 | f |
| CARBOPLATIN | 6 | g |
| CEPHALORIDINE | 6, 24 | h |
| CIDOFOVIR | 120 | i |
| CISPANcombined | 6, 24 | j |
| CISPLATIN | 168 | k |
| CISPLATIN | 6, 24 | l |
| CISPLATIN | 6, 24, 168 | m |
| CITRININ | 6, 24 | n |
| COLCHICINE | 6, 24, 48 | o |
| CYCLOPHOSPHAMIDE | 6 | p |
| DIFLUNISAL | 24 | q |
| HYDRALAZINE | 6 | r |
| IFOSFAMIDE | 6, 24, 48, 144 | s |
| INDOMETHACIN | 48, 72 | t |
| LITHIUMCHLORIDE | 120 | u |
| MERCURICCHLORIDE | 3, 6, 24 | v |
| PAMIDRONATE | 24 | w |
| PAN | 168 | x |
| PAN | 6, 24 | y |
| PAN | 6, 24, 168 | z |
| SEMUSTINE | 168 | aa |
| SULFADIAZINE | 24 | bb |
| SULFADIAZINE | 3, 6 | cc |

TABLE 5

GENERAL

| Identifier | NonToxMean | NonToxSD | Tox-Mean | ToxSD | LDAScore |
|---|---|---|---|---|---|
| 12979 | 326.05 | 98.48 | 729.13 | 345.15 | 83.46 |
| 23314 | -7.57 | 63.50 | 480.54 | 528.59 | 83.43 |
| 5461 | 161.65 | 48.19 | 368.42 | 210.09 | 82.70 |
| 9583 | 40.60 | 17.67 | 158.01 | 127.01 | 82.56 |
| 16982 | 59.51 | 36.53 | 506.74 | 577.57 | 81.34 |
| 1809 | 5.28 | 13.85 | 191.53 | 265.23 | 81.21 |
| 19184 | 59.98 | 26.06 | 191.02 | 128.18 | 81.04 |
| 24200 | 382.07 | 78.91 | 618.97 | 199.18 | 80.18 |
| 15003 | 13.42 | 14.74 | 154.63 | 217.73 | 79.83 |
| 2629 | 18.92 | 8.93 | 58.17 | 43.50 | 79.72 |
| 22321 | 82.69 | 25.99 | 192.94 | 130.47 | 79.58 |
| 15301 | 20.84 | 20.65 | 124.72 | 132.03 | 79.47 |
| 15032 | 280.18 | 50.93 | 183.93 | 78.32 | 79.33 |
| 7489 | 89.81 | 28.30 | 47.02 | 25.94 | 79.28 |
| 2242 | 2431.04 | 453.24 | 1658.86 | 711.96 | 79.26 |
| 3050 | 77.80 | 26.29 | 166.37 | 91.49 | 79.22 |
| 22681 | 170.38 | 56.88 | 497.37 | 377.15 | 79.20 |
| 24042 | 4.31 | 9.28 | 112.52 | 198.98 | 79.06 |
| 14425 | 191.57 | 51.38 | 315.84 | 117.32 | 79.05 |
| 15300 | 104.10 | 41.29 | 305.26 | 261.16 | 79.01 |
| 23651 | 487.82 | 171.51 | 1473.41 | 1227.36 | 78.44 |
| 15964 | 1274.63 | 262.79 | 824.24 | 343.96 | 78.27 |
| 16312 | 44.81 | 17.42 | 107.40 | 60.46 | 78.21 |
| 16168 | 305.21 | 53.33 | 588.32 | 425.68 | 78.12 |
| 5384 | 28.68 | 24.27 | 102.33 | 70.63 | 78.08 |
| 12978 | 92.29 | 28.22 | 178.30 | 79.32 | 77.90 |
| 21654 | 332.77 | 53.62 | 518.29 | 196.63 | 77.78 |
| 3874 | 934.64 | 159.07 | 672.84 | 188.60 | 77.60 |
| 3049 | 176.71 | 56.69 | 334.05 | 163.05 | 77.39 |
| 16314 | 33.02 | 22.70 | 103.37 | 67.81 | 77.39 |
| 23299 | 345.71 | 73.26 | 514.49 | 166.24 | 77.35 |
| 9166 | 13.09 | 10.08 | 40.42 | 28.18 | 77.33 |
| 14763 | 1.59 | 39.67 | 228.03 | 268.46 | 77.30 |
| 4479 | 133.60 | 62.59 | 233.57 | 86.27 | 77.27 |
| 15928 | 142.69 | 34.11 | 244.10 | 90.89 | 77.08 |
| 3941 | 229.39 | 59.58 | 325.62 | 88.12 | 76.99 |
| 28 | 540.29 | 128.18 | 342.30 | 188.50 | 76.94 |
| 14929 | 687.79 | 150.66 | 1358.82 | 807.54 | 76.87 |
| 22885 | 1229.56 | 342.00 | 1987.11 | 703.59 | 76.84 |
| 22765 | 15.12 | 10.37 | 52.20 | 40.27 | 76.68 |
| 19040 | 158.12 | 34.83 | 333.27 | 212.49 | 76.68 |
| 21239 | 98.57 | 31.29 | 190.62 | 93.31 | 76.57 |
| 2555 | 83.76 | 25.31 | 159.42 | 79.77 | 76.51 |
| 15051 | 558.01 | 156.42 | 953.70 | 424.38 | 76.38 |
| 22569 | 701.48 | 148.25 | 468.05 | 181.60 | 76.33 |
| 15299 | 73.40 | 22.15 | 164.49 | 121.44 | 76.17 |
| 20116 | 1.36 | 12.44 | 53.19 | 60.94 | 76.12 |
| 7299 | 141.75 | 59.67 | 363.99 | 279.53 | 75.86 |
| 11618 | 445.83 | 108.35 | 290.61 | 162.81 | 75.81 |

TABLE 5-continued

GENERAL

| Identifier | NonToxMean | NonToxSD | Tox-Mean | ToxSD | LDAScore |
|---|---|---|---|---|---|
| 23868 | 113.35 | 64.90 | 514.43 | 654.54 | 75.65 |
| 812 | 164.76 | 29.18 | 118.06 | 38.83 | 75.63 |
| 23166 | 116.47 | 37.76 | 215.89 | 104.73 | 75.55 |
| 19723 | 63.30 | 24.96 | 147.23 | 109.39 | 75.53 |
| 2161 | 10.89 | 22.79 | 40.17 | 28.34 | 75.53 |
| 22592 | 195.01 | 88.25 | 453.16 | 291.73 | 75.50 |
| 21683 | 27.66 | 14.45 | 65.00 | 37.84 | 75.44 |
| 7540 | 135.61 | 39.51 | 269.18 | 167.73 | 75.42 |
| 3121 | 1387.78 | 270.45 | 970.56 | 410.36 | 75.23 |
| 17325 | 37.68 | 26.79 | 190.12 | 198.72 | 75.23 |
| 4049 | 8.16 | 14.26 | 100.05 | 143.11 | 75.21 |
| 24219 | 294.84 | 62.68 | 415.01 | 115.05 | 75.14 |
| 7101 | 266.61 | 65.47 | 1024.56 | 1594.33 | 75.14 |
| 21462 | 246.43 | 47.45 | 320.88 | 67.53 | 75.11 |
| 21458 | 203.89 | 61.93 | 345.78 | 139.58 | 75.01 |
| 1460 | 178.45 | 37.93 | 302.50 | 171.15 | 74.92 |
| 23957 | 57.89 | 29.03 | 120.87 | 65.67 | 74.89 |
| 12921 | 92.69 | 31.09 | 174.99 | 86.55 | 74.88 |
| 24237 | 46.61 | 22.12 | 105.68 | 71.47 | 74.84 |
| 20830 | 482.35 | 118.55 | 717.12 | 282.77 | 74.80 |
| 14185 | 181.85 | 52.63 | 307.94 | 156.98 | 74.74 |
| 3091 | 821.34 | 154.51 | 616.81 | 215.94 | 74.73 |
| 6046 | 221.77 | 64.88 | 141.08 | 71.40 | 74.73 |
| 10818 | 509.63 | 159.26 | 301.00 | 207.18 | 74.63 |
| 18906 | 270.92 | 73.69 | 171.86 | 79.69 | 74.60 |
| 17361 | 160.53 | 54.00 | 92.22 | 55.73 | 74.60 |
| 574 | 297.07 | 48.04 | 543.78 | 340.56 | 74.58 |
| 1529 | 305.18 | 51.69 | 224.24 | 69.41 | 74.56 |
| 20161 | 30.38 | 21.73 | 80.33 | 56.50 | 74.54 |
| 22152 | −0.67 | 16.93 | 51.48 | 64.42 | 74.54 |
| 21391 | 183.11 | 55.68 | 391.43 | 249.63 | 74.34 |
| 20056 | 319.93 | 46.22 | 248.41 | 81.57 | 74.34 |
| 5711 | 402.83 | 114.80 | 268.76 | 100.84 | 74.34 |
| 16169 | 126.24 | 66.19 | 419.86 | 462.11 | 74.32 |
| 7196 | 160.17 | 37.22 | 297.55 | 159.08 | 74.29 |
| 13634 | 754.99 | 133.63 | 1123.83 | 475.68 | 74.29 |
| 10659 | 111.21 | 38.66 | 239.07 | 166.99 | 74.28 |
| 15089 | 162.94 | 57.42 | 271.19 | 109.36 | 74.26 |
| 2628 | 8.82 | 14.55 | 37.93 | 39.15 | 74.22 |
| 1521 | 7.84 | 37.91 | 80.00 | 74.26 | 74.20 |
| 17524 | 1225.79 | 235.19 | 927.05 | 284.85 | 74.20 |
| 14677 | 64.57 | 22.56 | 114.45 | 54.63 | 74.04 |
| 17357 | 284.47 | 66.73 | 189.90 | 103.16 | 73.97 |
| 15382 | 79.92 | 58.73 | 367.62 | 435.18 | 73.94 |
| 1141 | 226.12 | 47.74 | 315.88 | 93.78 | 73.94 |
| 3995 | 643.39 | 131.36 | 476.67 | 160.12 | 73.88 |
| 6804 | 1354.29 | 374.19 | 830.60 | 415.24 | 73.82 |
| 20694 | 1004.30 | 200.48 | 773.76 | 246.63 | 73.81 |
| 8477 | 493.77 | 117.87 | 724.70 | 226.98 | 73.80 |
| 13332 | 440.18 | 81.35 | 336.07 | 113.36 | 73.79 |
| 2912 | 2775.27 | 619.46 | 2040.05 | 590.49 | 73.79 |
| 8143 | 30.96 | 28.78 | 105.91 | 87.78 | 73.79 |
| 8639 | 351.67 | 79.66 | 468.70 | 121.28 | 73.78 |
| 354 | 191.57 | 43.15 | 335.31 | 175.98 | 73.77 |
| 2702 | 261.10 | 53.61 | 363.77 | 115.07 | 73.74 |
| 13411 | 857.90 | 304.76 | 508.64 | 242.77 | 73.71 |
| 23261 | 1651.29 | 316.95 | 1185.07 | 374.72 | 73.69 |
| 16775 | 1092.58 | 348.47 | 732.47 | 398.39 | 73.66 |
| 10016 | 191.31 | 45.71 | 298.01 | 134.57 | 73.59 |
| 353 | 154.16 | 43.72 | 275.53 | 149.36 | 73.59 |
| 5295 | 199.26 | 56.55 | 318.50 | 126.31 | 73.55 |
| 10015 | 215.25 | 41.54 | 323.40 | 147.43 | 73.54 |
| 20458 | 377.19 | 83.99 | 283.38 | 95.28 | 73.52 |
| 23869 | 24.11 | 23.82 | 132.98 | 190.30 | 73.49 |
| 20848 | 474.69 | 80.77 | 708.43 | 261.80 | 73.46 |
| 9067 | 645.45 | 126.00 | 841.67 | 201.55 | 73.45 |
| 923 | 10.66 | 7.41 | 32.76 | 27.77 | 73.40 |
| 4291 | 317.92 | 87.25 | 202.30 | 99.83 | 73.38 |
| 18529 | 184.43 | 47.69 | 306.78 | 139.66 | 73.35 |
| 22626 | 66.24 | 25.65 | 191.03 | 161.08 | 73.32 |
| 3823 | 488.87 | 101.91 | 709.19 | 233.23 | 73.30 |
| 15663 | 179.56 | 40.22 | 269.94 | 97.24 | 73.29 |
| 22929 | 927.47 | 283.23 | 548.56 | 310.91 | 73.27 |
| 373 | 20.21 | 24.84 | 107.75 | 123.23 | 73.25 |
| 4952 | 97.10 | 31.18 | 160.25 | 66.14 | 73.23 |
| 2905 | 221.02 | 70.67 | 379.00 | 165.35 | 73.23 |
| 7127 | 301.01 | 84.77 | 195.82 | 87.14 | 73.22 |
| 20035 | 157.82 | 53.67 | 318.27 | 196.89 | 73.21 |
| 14424 | 40.56 | 38.11 | 216.48 | 294.45 | 73.19 |
| 1501 | 46.55 | 22.43 | 125.28 | 104.55 | 73.19 |
| 811 | 268.35 | 42.34 | 201.54 | 69.48 | 73.14 |
| 3610 | 1272.79 | 264.85 | 879.10 | 411.90 | 73.12 |
| 9053 | 249.79 | 41.36 | 192.96 | 58.86 | 73.09 |
| 23538 | 85.95 | 40.73 | 190.24 | 133.78 | 73.07 |
| 18337 | 1699.33 | 315.35 | 1236.46 | 390.84 | 73.06 |
| 15002 | 119.96 | 26.12 | 252.22 | 220.20 | 73.06 |
| 21147 | 365.33 | 62.56 | 285.83 | 76.45 | 73.05 |
| 8721 | 208.57 | 63.43 | 132.86 | 65.90 | 73.01 |
| 1462 | 364.98 | 75.98 | 659.63 | 429.84 | 73.01 |
| 11483 | 54.82 | 19.42 | 118.04 | 81.85 | 72.90 |
| 2348 | 545.81 | 197.73 | 349.07 | 201.06 | 72.86 |
| 1564 | 6.71 | 7.78 | 209.28 | 375.95 | 72.86 |
| 12467 | 60.46 | 20.47 | 103.84 | 48.93 | 72.85 |
| 6638 | 104.00 | 28.03 | 76.61 | 32.45 | 72.83 |
| 19031 | 50.08 | 27.00 | 116.79 | 84.17 | 72.83 |
| 1246 | 98.28 | 29.26 | 60.78 | 37.90 | 72.82 |
| 23872 | 30.55 | 27.67 | 146.46 | 207.24 | 72.80 |
| 19678 | 121.25 | 48.99 | 54.47 | 69.08 | 72.78 |
| 23512 | 1086.33 | 216.78 | 839.09 | 240.27 | 72.77 |
| 6321 | 458.69 | 127.59 | 644.50 | 219.13 | 72.75 |
| 22596 | 57.04 | 17.25 | 81.28 | 26.16 | 72.75 |
| 24431 | 50.52 | 15.50 | 151.16 | 210.56 | 72.73 |
| 15110 | 663.97 | 145.61 | 479.15 | 149.17 | 72.73 |
| 15892 | 12.32 | 15.49 | 44.12 | 34.64 | 72.71 |
| 14458 | 29.92 | 20.00 | 71.32 | 39.77 | 72.67 |
| 6641 | 402.83 | 66.65 | 309.63 | 82.93 | 72.53 |
| 1422 | 315.77 | 80.70 | 215.58 | 83.38 | 72.53 |
| 21443 | 90.59 | 31.63 | 155.73 | 92.87 | 72.53 |
| 8829 | 264.33 | 62.24 | 350.44 | 106.21 | 72.51 |
| 21632 | 27.74 | 33.70 | 87.38 | 68.91 | 72.48 |
| 24388 | 173.36 | 44.15 | 275.21 | 119.72 | 72.47 |
| 15851 | 171.96 | 68.96 | 332.47 | 267.49 | 72.38 |
| 15042 | 55.43 | 27.40 | 117.95 | 81.96 | 72.32 |
| 17908 | 49.38 | 21.99 | 125.62 | 121.11 | 72.32 |
| 15618 | 90.24 | 22.13 | 124.19 | 32.66 | 72.27 |
| 21318 | 41.50 | 23.94 | 72.71 | 32.13 | 72.27 |
| 6054 | 18.00 | 9.60 | 85.39 | 126.27 | 72.24 |
| 1727 | 30.19 | 25.05 | 113.76 | 121.46 | 72.19 |
| 23202 | 169.96 | 36.51 | 126.76 | 36.17 | 72.16 |
| 22248 | 216.64 | 78.55 | 393.59 | 188.26 | 72.15 |
| 22612 | 487.17 | 110.76 | 359.48 | 126.14 | 72.14 |
| 17734 | 106.27 | 34.17 | 214.91 | 182.70 | 72.12 |
| 19235 | 1112.95 | 271.69 | 810.00 | 308.94 | 72.06 |
| 13618 | 96.22 | 26.36 | 137.92 | 45.79 | 72.04 |
| 19525 | 23.64 | 12.50 | 46.38 | 27.18 | 72.03 |
| 4584 | 76.41 | 22.50 | 109.66 | 36.31 | 71.98 |
| 22197 | 112.68 | 34.33 | 178.88 | 75.61 | 71.98 |
| 24762 | 1064.07 | 310.38 | 755.53 | 273.04 | 71.97 |
| 10985 | 1189.01 | 218.09 | 885.13 | 290.39 | 71.96 |
| 3145 | 466.94 | 133.08 | 330.71 | 144.92 | 71.93 |
| 20828 | 278.75 | 83.71 | 482.02 | 272.83 | 71.89 |
| 2395 | 172.58 | 47.67 | 175.81 | 100.28 | 71.86 |
| 13609 | 252.08 | 52.43 | 186.04 | 64.47 | 71.86 |
| 21339 | 29.51 | 15.60 | 53.28 | 32.70 | 71.78 |
| 3079 | 27.52 | 22.01 | 67.24 | 49.93 | 71.78 |
| 16321 | 219.91 | 42.72 | 273.17 | 55.96 | 71.77 |
| 4944 | 100.32 | 33.19 | 177.16 | 86.89 | 71.77 |
| 24568 | 162.64 | 51.57 | 105.85 | 46.68 | 71.75 |
| 3875 | 539.59 | 120.20 | 389.50 | 146.06 | 71.75 |
| 6382 | 117.04 | 33.24 | 171.65 | 55.00 | 71.73 |
| 3959 | 329.28 | 86.36 | 451.00 | 151.79 | 71.73 |
| 8795 | 14.06 | 10.71 | 26.30 | 13.30 | 71.72 |
| 17477 | 102.32 | 22.97 | 156.34 | 68.17 | 71.71 |
| 7700 | 74.32 | 20.26 | 138.56 | 92.87 | 71.68 |
| 17550 | 1380.51 | 319.12 | 1028.40 | 363.64 | 71.63 |
| 410 | 1155.16 | 215.31 | 918.14 | 252.51 | 71.63 |
| 17682 | 706.42 | 143.23 | 505.72 | 215.80 | 71.63 |
| 5897 | 20.54 | 16.83 | 45.41 | 23.66 | 71.63 |

TABLE 5-continued

GENERAL

| Identifier | NonToxMean | NonToxSD | Tox-Mean | ToxSD | LDAScore |
|---|---|---|---|---|---|
| 4661 | 288.80 | 58.15 | 408.62 | 120.87 | 71.59 |
| 16521 | 266.79 | 60.39 | 378.60 | 127.02 | 71.59 |
| 13610 | 371.99 | 53.12 | 283.18 | 88.22 | 71.55 |
| 22554 | 565.54 | 122.08 | 428.04 | 154.62 | 71.49 |
| 11910 | 25.51 | 35.83 | −5.43 | 31.38 | 71.47 |
| 15588 | −4.65 | 25.14 | 33.98 | 37.77 | 71.42 |
| 5601 | 1014.34 | 210.01 | 731.23 | 341.39 | 71.42 |
| 5780 | −23.15 | 27.07 | 32.19 | 62.08 | 71.38 |
| 21546 | −79.60 | 43.55 | 44.91 | 170.38 | 71.38 |
| 15039 | 285.29 | 65.31 | 206.99 | 101.12 | 71.38 |
| 18300 | 483.67 | 133.71 | 307.50 | 148.77 | 71.38 |
| 14970 | 215.37 | 35.86 | 161.84 | 54.69 | 71.32 |
| 13151 | 635.29 | 173.43 | 1103.53 | 626.81 | 71.31 |
| 7197 | 180.11 | 57.15 | 296.88 | 139.25 | 71.28 |
| 21238 | −24.44 | 33.42 | 22.20 | 43.34 | 71.27 |
| 25090 | 74.42 | 33.18 | 128.49 | 62.02 | 71.24 |
| 18564 | 225.23 | 44.60 | 181.56 | 58.17 | 71.23 |
| 1409 | 441.80 | 78.21 | 357.51 | 91.06 | 71.20 |
| 7903 | 526.91 | 184.33 | 331.16 | 186.75 | 71.18 |
| 24109 | 231.59 | 87.11 | 172.36 | 143.80 | 71.18 |
| 6416 | 108.18 | 41.02 | 234.59 | 190.53 | 71.17 |
| 2250 | 1462.04 | 256.17 | 1165.90 | 304.84 | 71.12 |
| 5867 | 157.83 | 35.87 | 210.76 | 63.63 | 71.11 |
| 17771 | 710.83 | 199.94 | 1089.58 | 460.00 | 71.09 |
| 5494 | 62.28 | 23.39 | 104.89 | 53.79 | 71.08 |
| 18269 | 729.55 | 160.51 | 578.31 | 143.90 | 71.07 |
| 14996 | 459.09 | 95.27 | 332.24 | 132.64 | 71.03 |
| 24617 | 27.48 | 28.57 | −0.27 | 26.14 | 71.02 |
| 23195 | 323.13 | 74.62 | 242.16 | 107.55 | 71.01 |
| 22656 | 113.29 | 44.19 | 184.20 | 80.34 | 70.99 |
| 8728 | 114.64 | 32.58 | 163.70 | 57.48 | 70.99 |
| 14664 | 56.90 | 24.89 | 82.06 | 31.36 | 70.98 |
| 22698 | 286.73 | 90.38 | 147.82 | 160.71 | 70.97 |
| 24053 | 35.17 | 15.83 | 56.32 | 29.72 | 70.97 |
| 6796 | 190.54 | 59.10 | 259.72 | 68.76 | 70.97 |
| 5474 | 783.73 | 210.50 | 556.59 | 211.13 | 70.96 |
| 22820 | 199.69 | 49.08 | 296.30 | 123.01 | 70.89 |
| 21796 | 666.75 | 117.72 | 898.08 | 374.38 | 70.88 |
| 25747 | 41.52 | 18.23 | 88.80 | 66.31 | 70.85 |
| 5443 | 12.36 | 13.98 | 34.29 | 27.55 | 70.84 |
| 12965 | 104.50 | 38.53 | 152.54 | 54.48 | 70.80 |
| 12332 | 602.96 | 147.89 | 428.95 | 204.34 | 70.77 |
| 3773 | 20.24 | 15.61 | 47.49 | 38.34 | 70.75 |
| 5990 | 310.53 | 65.78 | 375.84 | 76.70 | 70.73 |
| 18302 | 132.49 | 67.39 | 63.56 | 100.58 | 70.70 |
| 23964 | 9.67 | 12.94 | 24.20 | 18.71 | 70.68 |
| 9468 | 65.20 | 31.76 | 38.22 | 29.36 | 70.68 |
| 16631 | 14.50 | 12.00 | 57.40 | 80.51 | 70.66 |
| 21653 | 224.19 | 41.69 | 303.28 | 104.55 | 70.63 |
| 9097 | 272.42 | 76.73 | 194.27 | 78.59 | 70.61 |
| 11259 | 79.73 | 54.95 | 259.20 | 287.87 | 70.60 |
| 1081 | 515.94 | 100.86 | 394.77 | 126.28 | 70.58 |
| 18360 | 214.50 | 54.30 | 161.55 | 58.13 | 70.58 |
| 4789 | 35.91 | 18.80 | 60.76 | 25.85 | 70.56 |
| 1798 | 346.08 | 90.64 | 258.66 | 95.94 | 70.56 |
| 25089 | 69.92 | 34.04 | 119.62 | 57.66 | 70.55 |
| 24234 | 170.64 | 48.79 | 257.81 | 150.22 | 70.55 |
| 23270 | 197.31 | 46.26 | 264.06 | 80.46 | 70.54 |
| 8339 | 457.12 | 115.09 | 336.46 | 156.58 | 70.52 |
| 4119 | 104.13 | 29.50 | 142.73 | 41.65 | 70.50 |
| 18581 | 239.39 | 63.97 | 323.89 | 102.81 | 70.48 |
| 8188 | 429.99 | 130.68 | 311.19 | 123.41 | 70.46 |
| 17950 | 60.85 | 21.71 | 84.23 | 24.05 | 70.45 |
| 11967 | 1829.61 | 479.72 | 1293.20 | 638.27 | 70.45 |
| 5252 | 13.79 | 9.94 | 24.05 | 13.59 | 70.44 |
| 22928 | 235.05 | 79.02 | 162.79 | 64.64 | 70.38 |
| 16684 | 483.85 | 102.78 | 662.86 | 218.95 | 70.37 |
| 1463 | 562.00 | 123.95 | 959.70 | 610.46 | 70.36 |
| 8495 | 174.57 | 44.41 | 233.66 | 68.66 | 70.36 |
| 2195 | 94.72 | 37.50 | 60.02 | 37.89 | 70.35 |
| 3042 | 289.42 | 103.30 | 458.48 | 192.79 | 70.34 |
| 15330 | 96.55 | 24.69 | 69.31 | 26.59 | 70.32 |
| 12399 | 80.36 | 27.26 | 110.73 | 35.05 | 70.32 |
| 16351 | 67.79 | 22.25 | 109.53 | 54.61 | 70.27 |
| 3822 | 871.73 | 175.65 | 1184.82 | 469.53 | 70.26 |
| 21025 | 483.29 | 121.39 | 358.54 | 123.38 | 70.26 |
| 6548 | 93.61 | 35.75 | 138.74 | 52.86 | 70.23 |
| 12561 | 159.96 | 46.53 | 108.93 | 51.49 | 70.19 |
| 5481 | 36.03 | 51.29 | 102.88 | 72.89 | 70.19 |
| 3430 | 414.54 | 95.45 | 587.65 | 251.37 | 70.17 |
| 26335 | 940.03 | 330.95 | 625.84 | 337.88 | 70.16 |
| 352 | 77.57 | 33.06 | 132.92 | 75.36 | 70.14 |
| 23044 | 213.44 | 34.48 | 253.69 | 53.74 | 70.13 |
| 17161 | 1069.69 | 220.67 | 1639.92 | 740.76 | 70.11 |
| 14352 | 179.82 | 26.18 | 211.25 | 38.48 | 70.10 |
| 21993 | 71.93 | 19.33 | 98.79 | 30.29 | 70.09 |
| 16756 | 165.09 | 40.66 | 231.09 | 68.53 | 70.09 |
| 7537 | 240.15 | 64.50 | 185.74 | 68.65 | 70.09 |
| 15986 | 336.87 | 70.00 | 240.73 | 102.05 | 70.07 |
| 17256 | 428.03 | 84.39 | 329.02 | 149.16 | 70.04 |
| 18151 | 1182.11 | 241.37 | 915.26 | 244.04 | 70.03 |
| 18354 | 372.44 | 129.56 | 548.59 | 224.71 | 70.03 |
| 19152 | 155.28 | 37.87 | 219.58 | 85.40 | 70.01 |
| 8314 | 44.66 | 24.23 | 401.40 | 1027.51 | 70.01 |
| 13222 | 132.87 | 25.87 | 162.46 | 38.58 | 69.99 |
| 3808 | 157.93 | 29.12 | 224.59 | 103.04 | 69.99 |
| 25705 | 432.30 | 81.33 | 560.17 | 181.12 | 69.98 |
| 4360 | 341.32 | 51.71 | 279.62 | 90.37 | 69.97 |
| 15904 | 48.14 | 15.72 | 70.45 | 28.37 | 69.96 |
| 3733 | 307.48 | 109.96 | 502.42 | 242.20 | 69.95 |
| 12349 | 248.84 | 51.51 | 206.79 | 57.13 | 69.94 |
| 6039 | 293.57 | 52.57 | 404.95 | 147.79 | 69.94 |
| 16394 | 529.95 | 207.80 | 998.31 | 642.96 | 69.92 |
| 1340 | 194.50 | 26.68 | 172.82 | 51.16 | 69.92 |
| 13393 | 68.65 | 39.60 | 120.92 | 67.73 | 69.91 |
| 26119 | 115.29 | 35.39 | 165.90 | 63.73 | 69.91 |
| 21471 | −15.71 | 27.91 | 21.66 | 45.38 | 69.91 |
| 498 | 513.15 | 100.54 | 694.75 | 220.14 | 69.89 |
| 19 | 324.56 | 59.40 | 415.19 | 125.18 | 69.89 |
| 22599 | 40.60 | 18.16 | 65.55 | 34.14 | 69.84 |
| 7427 | 235.31 | 43.69 | 295.43 | 88.56 | 69.83 |
| 16520 | 82.42 | 40.09 | 151.39 | 91.91 | 69.83 |
| 15642 | 389.37 | 82.84 | 518.22 | 172.58 | 69.83 |
| 1430 | 171.08 | 83.75 | 102.96 | 99.73 | 69.82 |
| 7918 | 36.73 | 13.76 | 61.83 | 31.90 | 69.82 |
| 13633 | 276.86 | 77.72 | 463.55 | 259.47 | 69.80 |
| 7936 | 155.24 | 33.42 | 122.46 | 38.98 | 69.79 |
| 15004 | 132.61 | 42.50 | 344.40 | 385.03 | 69.78 |
| 15955 | 791.51 | 166.06 | 571.10 | 228.60 | 69.77 |
| 1478 | 366.90 | 66.96 | 278.05 | 99.94 | 69.75 |
| 7622 | 55.21 | 18.42 | 74.69 | 23.71 | 69.75 |
| 22796 | 7.01 | 12.41 | 21.99 | 21.24 | 69.73 |
| 17401 | 821.97 | 205.41 | 1398.10 | 790.55 | 69.73 |
| 7888 | 262.03 | 59.59 | 349.92 | 94.63 | 69.72 |
| 13392 | 181.47 | 36.33 | 245.35 | 76.20 | 69.70 |
| 22101 | 199.60 | 77.45 | 118.24 | 102.76 | 69.70 |
| 18 | 61.29 | 34.62 | 98.91 | 45.09 | 69.69 |
| 21657 | 407.16 | 79.73 | 529.18 | 177.19 | 69.69 |
| 20414 | 124.45 | 34.92 | 93.89 | 36.15 | 69.68 |
| 3652 | 40.90 | 23.02 | 80.54 | 43.90 | 69.64 |
| 12436 | 40.94 | 17.34 | 63.44 | 29.74 | 69.64 |
| 15011 | 90.81 | 29.75 | 122.02 | 40.98 | 69.63 |
| 3434 | 300.37 | 104.25 | 456.96 | 211.34 | 69.62 |
| 21444 | 10.25 | 27.61 | 65.55 | 77.70 | 69.62 |
| 3493 | 56.09 | 16.33 | 78.00 | 27.67 | 69.58 |
| 13727 | 133.95 | 49.99 | 86.22 | 54.51 | 69.58 |
| 17339 | 2512.73 | 596.97 | 1882.04 | 680.16 | 69.56 |
| 6518 | 108.28 | 26.66 | 143.55 | 38.12 | 69.55 |
| 14484 | 468.99 | 102.51 | 371.12 | 113.87 | 69.50 |
| 45 | 184.62 | 61.15 | 131.00 | 98.51 | 69.50 |
| 4235 | 383.35 | 65.78 | 479.39 | 109.87 | 69.47 |
| 2350 | 631.18 | 75.04 | 733.81 | 127.04 | 69.47 |
| 20816 | 359.20 | 71.33 | 589.66 | 361.06 | 69.47 |
| 20448 | 51.14 | 15.80 | 96.53 | 91.69 | 69.45 |
| 3608 | 354.31 | 96.17 | 240.45 | 122.08 | 69.45 |
| 20829 | 754.23 | 187.16 | 1139.64 | 525.74 | 69.43 |
| 14388 | 133.84 | 46.32 | 189.57 | 73.63 | 69.41 |
| 13974 | 269.51 | 60.19 | 455.96 | 331.84 | 69.41 |

TABLE 5-continued

GENERAL

| Identifier | NonToxMean | NonToxSD | Tox-Mean | ToxSD | LDAScore |
|---|---|---|---|---|---|
| 13611 | 289.40 | 97.62 | 194.81 | 124.78 | 69.39 |
| 9452 | 109.85 | 33.54 | 243.69 | 304.19 | 69.39 |
| 19679 | 744.23 | 156.00 | 548.50 | 220.11 | 69.38 |
| 23471 | 80.62 | 27.27 | 134.19 | 61.98 | 69.38 |
| 15596 | 200.04 | 61.45 | 269.73 | 83.16 | 69.38 |
| 17159 | 662.06 | 139.21 | 916.50 | 373.05 | 69.37 |
| 9114 | 907.26 | 198.07 | 711.93 | 216.95 | 69.36 |
| 7690 | 188.30 | 76.58 | 286.44 | 101.61 | 69.30 |
| 4462 | 896.55 | 240.26 | 700.53 | 283.12 | 69.30 |
| 15146 | 117.66 | 45.74 | 219.43 | 151.19 | 69.28 |
| 4747 | 52.09 | 18.56 | 76.30 | 30.54 | 69.28 |
| 4463 | 171.78 | 48.48 | 116.71 | 64.25 | 69.26 |
| 21275 | 208.39 | 53.25 | 293.29 | 120.48 | 69.26 |
| 22537 | 314.16 | 116.85 | 217.64 | 134.70 | 69.24 |
| 21015 | 224.01 | 149.40 | 523.06 | 502.39 | 69.21 |
| 14184 | 104.95 | 35.03 | 152.30 | 77.88 | 69.21 |
| 16859 | 113.00 | 39.98 | 171.46 | 70.52 | 69.20 |
| 13359 | 18.79 | 19.20 | 41.55 | 29.30 | 69.17 |
| 24192 | 65.10 | 27.46 | 107.06 | 63.04 | 69.17 |
| 22357 | 537.91 | 143.42 | 683.30 | 219.11 | 69.15 |
| 22540 | 1928.78 | 500.80 | 1396.93 | 518.89 | 69.15 |
| 15111 | 1008.00 | 256.31 | 739.45 | 278.04 | 69.15 |
| 23128 | 629.03 | 117.68 | 522.92 | 126.85 | 69.13 |
| 9905 | 702.23 | 115.37 | 558.07 | 156.97 | 69.13 |
| 23387 | 23.75 | 24.01 | 57.01 | 48.92 | 69.12 |
| 21797 | 316.03 | 77.43 | 447.83 | 179.03 | 69.12 |
| 20457 | 401.15 | 78.89 | 312.93 | 100.71 | 69.12 |
| 13954 | 1425.24 | 337.03 | 1039.20 | 391.69 | 69.12 |
| 2059 | 134.19 | 33.99 | 173.66 | 52.56 | 69.11 |
| 21125 | 163.43 | 45.61 | 120.34 | 59.14 | 69.08 |
| 4048 | −12.32 | 8.61 | 25.98 | 74.75 | 69.08 |
| 13349 | 122.00 | 33.87 | 171.03 | 54.95 | 69.08 |
| 20086 | 103.42 | 54.54 | 186.02 | 112.44 | 69.07 |
| 7414 | 177.49 | 39.38 | 246.64 | 72.25 | 69.07 |
| 4327 | 84.49 | 26.30 | 133.01 | 68.89 | 69.07 |
| 19011 | 389.45 | 84.42 | 492.01 | 130.94 | 69.04 |
| 6384 | 55.77 | 19.77 | 79.31 | 27.28 | 69.03 |
| 8221 | 192.95 | 91.60 | 123.84 | 72.63 | 69.02 |
| 11876 | 100.42 | 32.61 | 145.49 | 59.19 | 69.00 |
| 275 | 540.79 | 117.63 | 450.26 | 289.26 | 69.00 |
| 19940 | 19.25 | 13.33 | 32.95 | 17.53 | 68.99 |
| 21895 | 415.77 | 107.68 | 527.63 | 122.68 | 68.99 |
| 6674 | 2589.26 | 592.43 | 1970.28 | 559.33 | 68.97 |
| 4330 | 519.93 | 146.26 | 393.68 | 177.88 | 68.97 |
| 1698 | 59.46 | 33.76 | 154.33 | 156.35 | 68.96 |
| 6927 | 351.13 | 88.63 | 276.07 | 87.17 | 68.95 |
| 15879 | 389.05 | 88.44 | 309.88 | 89.07 | 68.94 |
| 17269 | 669.21 | 164.65 | 510.44 | 183.69 | 68.94 |
| 809 | 38.57 | 18.55 | 73.18 | 50.10 | 68.93 |
| 25567 | 429.75 | 132.83 | 636.76 | 280.62 | 68.91 |
| 6711 | 46.47 | 22.83 | 68.95 | 25.01 | 68.91 |
| 25777 | 370.17 | 112.15 | 585.45 | 351.28 | 68.90 |
| 22801 | 1309.01 | 233.61 | 1102.68 | 241.27 | 68.88 |
| 17447 | 912.03 | 226.33 | 708.62 | 297.79 | 68.88 |
| 1603 | 652.04 | 149.41 | 516.80 | 165.06 | 68.85 |
| 20460 | 363.41 | 114.33 | 257.61 | 112.54 | 68.84 |
| 21145 | 216.97 | 60.61 | 173.14 | 61.10 | 68.83 |
| 25453 | 225.18 | 45.75 | 181.00 | 63.32 | 68.81 |
| 14670 | 1156.99 | 219.65 | 1505.97 | 540.37 | 68.80 |
| 19623 | 56.27 | 29.98 | 87.15 | 39.31 | 68.80 |
| 12716 | 167.13 | 43.68 | 133.50 | 41.78 | 68.80 |
| 24236 | 75.95 | 22.54 | 104.28 | 32.01 | 68.79 |
| 15617 | 18.52 | 33.89 | 39.26 | 21.38 | 68.79 |
| 3925 | 498.78 | 107.84 | 390.92 | 113.69 | 68.77 |
| 20449 | 39.97 | 25.35 | 119.71 | 151.16 | 68.76 |
| 21390 | 89.77 | 28.23 | 115.10 | 33.69 | 68.76 |
| 23514 | 434.32 | 164.14 | 307.02 | 151.33 | 68.74 |
| 20849 | 259.38 | 58.40 | 370.11 | 145.72 | 68.74 |
| 794 | 224.09 | 52.71 | 162.86 | 64.32 | 68.71 |
| 4592 | 183.27 | 30.19 | 222.63 | 53.46 | 68.70 |
| 13614 | 325.22 | 70.14 | 423.70 | 138.23 | 68.70 |
| 12673 | 32.94 | 15.97 | 60.47 | 35.35 | 68.69 |
| 3125 | 347.43 | 89.73 | 270.34 | 103.82 | 68.67 |
| 4232 | 131.63 | 36.97 | 170.35 | 127.98 | 68.67 |
| 1399 | 187.08 | 41.04 | 289.41 | 156.72 | 68.66 |
| 13930 | 114.32 | 44.14 | 212.08 | 140.70 | 68.65 |
| 5689 | 9.09 | 13.75 | 27.68 | 24.99 | 68.63 |
| 2370 | 1158.46 | 172.59 | 949.24 | 224.94 | 68.63 |
| 4933 | 93.92 | 113.34 | 358.13 | 386.59 | 68.63 |
| 406 | 374.38 | 68.18 | 306.59 | 91.47 | 68.62 |
| 22957 | 165.92 | 62.59 | 266.91 | 150.55 | 68.62 |
| 2768 | 2026.25 | 370.26 | 1657.86 | 463.04 | 68.61 |
| 24197 | 243.13 | 77.12 | 185.53 | 85.38 | 68.60 |
| 16650 | 242.10 | 65.10 | 338.01 | 127.40 | 68.57 |
| 8085 | 36.42 | 17.42 | 58.09 | 26.97 | 68.57 |
| 1712 | 167.50 | 36.63 | 216.60 | 72.08 | 68.57 |
| 5565 | 407.17 | 100.35 | 305.41 | 133.21 | 68.56 |
| 16883 | 1543.18 | 301.38 | 1229.72 | 308.97 | 68.55 |
| 13622 | 45.42 | 26.78 | 87.87 | 76.11 | 68.55 |
| 17807 | 711.63 | 133.84 | 948.59 | 316.04 | 68.55 |
| 8496 | 39.06 | 20.93 | 64.65 | 32.09 | 68.53 |
| 11559 | 615.91 | 118.47 | 505.06 | 115.82 | 68.53 |
| 19094 | 1013.42 | 192.17 | 1274.36 | 327.89 | 68.53 |
| 7584 | 99.66 | 69.21 | 216.92 | 170.84 | 68.53 |
| 457 | 268.02 | 49.06 | 378.26 | 164.79 | 68.53 |
| 21105 | 323.39 | 54.03 | 270.87 | 64.06 | 68.52 |
| 18900 | 449.75 | 84.06 | 557.56 | 130.48 | 68.48 |
| 16709 | 858.46 | 172.57 | 709.82 | 176.49 | 68.46 |
| 1993 | 26.13 | 15.23 | 53.08 | 37.27 | 68.43 |
| 13348 | 116.50 | 39.71 | 170.35 | 84.06 | 68.43 |
| 11454 | 223.14 | 54.78 | 315.07 | 133.93 | 68.43 |
| 18606 | 608.53 | 116.39 | 789.92 | 267.15 | 68.43 |
| 2986 | 39.62 | 12.73 | 54.78 | 18.98 | 68.41 |
| 15644 | 1338.83 | 225.09 | 1588.45 | 345.24 | 68.39 |
| 22541 | 3613.59 | 853.73 | 2681.23 | 879.66 | 68.39 |
| 17905 | 902.96 | 243.00 | 654.49 | 232.60 | 68.38 |
| 408 | 201.66 | 67.43 | 144.70 | 78.36 | 68.37 |
| 21409 | 86.43 | 35.21 | 119.21 | 45.92 | 68.37 |
| 22543 | 721.16 | 195.27 | 540.47 | 258.13 | 68.36 |
| 3863 | 214.88 | 78.45 | 158.64 | 93.71 | 68.36 |
| 21596 | 100.77 | 27.25 | 132.16 | 47.14 | 68.33 |
| 1583 | 25.58 | 12.08 | 46.81 | 25.12 | 68.32 |
| 8917 | 41.59 | 14.82 | 56.19 | 17.88 | 68.31 |
| 17324 | 371.15 | 66.13 | 297.98 | 105.05 | 68.30 |
| 5199 | 641.61 | 169.29 | 484.54 | 199.84 | 68.29 |
| 11164 | 532.49 | 129.79 | 382.15 | 153.36 | 68.28 |
| 10887 | 76.37 | 24.73 | 54.29 | 25.72 | 68.28 |
| 15540 | 36.28 | 11.51 | 64.56 | 42.69 | 68.27 |
| 4949 | 1162.93 | 273.54 | 892.52 | 329.00 | 68.26 |
| 21024 | 596.29 | 101.41 | 489.27 | 121.68 | 68.26 |
| 19085 | 70.29 | 20.84 | 101.53 | 44.09 | 68.25 |
| 25718 | 380.48 | 63.33 | 465.71 | 138.80 | 68.25 |
| 3981 | 53.40 | 27.49 | 166.56 | 218.99 | 68.25 |
| 19939 | 176.96 | 53.69 | 235.92 | 70.52 | 68.24 |
| 21305 | 438.34 | 113.88 | 332.58 | 104.75 | 68.23 |
| 22833 | 431.45 | 106.61 | 540.94 | 147.67 | 68.23 |
| 13310 | 116.08 | 48.35 | 197.32 | 125.83 | 68.22 |
| 19187 | 102.48 | 30.70 | 135.61 | 50.44 | 68.21 |
| 18011 | 27.06 | 22.52 | 56.30 | 38.43 | 68.21 |
| 24895 | 78.92 | 42.28 | 60.83 | 59.54 | 68.21 |
| 11563 | 52.55 | 31.11 | 94.44 | 49.63 | 68.20 |
| 2506 | 78.97 | 20.73 | 98.29 | 25.44 | 68.20 |
| 10434 | 30.66 | 16.63 | 56.30 | 35.67 | 68.19 |
| 23546 | 749.61 | 138.38 | 631.19 | 195.15 | 68.19 |
| 17104 | 430.01 | 79.30 | 558.85 | 188.65 | 68.18 |
| 12587 | 236.86 | 55.30 | 189.70 | 64.51 | 68.17 |
| 17316 | 70.29 | 31.03 | 47.27 | 32.31 | 68.17 |
| 10464 | 136.34 | 32.97 | 104.50 | 38.05 | 68.15 |
| 15185 | 154.81 | 45.05 | 251.81 | 139.06 | 68.15 |
| 22689 | 44.68 | 18.28 | 64.87 | 29.10 | 68.14 |
| 5855 | 74.85 | 27.42 | 52.36 | 35.41 | 68.14 |
| 2140 | 160.37 | 40.29 | 131.23 | 57.33 | 68.11 |
| 1510 | 780.11 | 196.05 | 591.05 | 213.64 | 68.11 |
| 15313 | 6.84 | 9.54 | 24.57 | 23.36 | 68.10 |
| 8972 | 26.33 | 18.24 | 47.47 | 25.93 | 68.10 |
| 2888 | 2111.78 | 515.11 | 1569.20 | 595.26 | 68.10 |
| 23834 | 68.94 | 19.78 | 90.90 | 31.53 | 68.09 |
| 3082 | 244.35 | 47.01 | 302.78 | 72.37 | 68.09 |

TABLE 5-continued

GENERAL

| Identifier | NonToxMean | NonToxSD | Tox-Mean | ToxSD | LDAScore |
|---|---|---|---|---|---|
| 3467 | 738.89 | 191.34 | 549.12 | 221.95 | 68.09 |
| 16476 | 738.64 | 159.14 | 630.49 | 196.22 | 68.09 |
| 5819 | 230.72 | 47.15 | 189.99 | 56.21 | 68.08 |
| 1942 | 12.95 | 13.20 | 45.54 | 48.73 | 68.08 |
| 514 | 4.47 | 50.55 | 52.66 | 58.22 | 68.08 |
| 19768 | 683.61 | 138.87 | 883.43 | 263.72 | 68.06 |
| 5183 | 204.36 | 51.85 | 284.20 | 109.64 | 68.06 |
| 24375 | 107.65 | 26.73 | 157.63 | 66.73 | 68.05 |
| 6059 | 199.74 | 47.55 | 169.09 | 54.88 | 68.04 |
| 12937 | 20.23 | 21.04 | 62.89 | 58.77 | 68.04 |
| 3245 | 97.45 | 32.09 | 132.43 | 48.29 | 68.02 |
| 19469 | 376.00 | 72.62 | 300.86 | 98.78 | 68.02 |
| 22696 | 72.56 | 48.08 | 25.09 | 39.70 | 68.02 |
| 4355 | 116.49 | 44.14 | 163.32 | 82.62 | 68.01 |
| 21579 | 110.85 | 35.32 | 153.51 | 68.22 | 68.00 |
| 1431 | 521.93 | 166.42 | 374.89 | 194.57 | 67.99 |
| 9673 | 66.91 | 27.02 | 44.90 | 26.55 | 67.99 |
| 20257 | 137.10 | 42.30 | 102.53 | 48.53 | 67.99 |
| 12961 | 185.53 | 42.22 | 151.73 | 41.05 | 67.97 |
| 22538 | 338.12 | 80.15 | 255.39 | 90.87 | 67.97 |
| 7243 | 56.76 | 22.51 | 79.45 | 28.02 | 67.96 |
| 5634 | 64.78 | 29.00 | 96.85 | 47.59 | 67.96 |
| 17438 | 62.59 | 33.01 | 31.95 | 40.59 | 67.96 |
| 1581 | 70.58 | 17.49 | 93.61 | 30.37 | 67.96 |
| 25379 | 75.47 | 18.52 | 100.15 | 31.59 | 67.95 |
| 2153 | 153.35 | 49.73 | 361.58 | 346.41 | 67.94 |
| 7499 | 17.61 | 8.98 | 28.61 | 16.07 | 67.94 |
| 6102 | 150.29 | 40.49 | 187.75 | 46.70 | 67.94 |
| 3878 | 479.08 | 106.98 | 389.02 | 107.79 | 67.93 |
| 20122 | 174.65 | 39.83 | 214.44 | 52.37 | 67.93 |
| 6828 | 122.12 | 53.45 | 207.48 | 104.75 | 67.92 |
| 11455 | 106.22 | 31.64 | 162.96 | 86.72 | 67.92 |
| 16058 | 146.84 | 40.61 | 225.40 | 102.56 | 67.92 |
| 23567 | 42.81 | 36.02 | 114.42 | 124.08 | 67.90 |
| 19998 | 290.74 | 86.07 | 214.07 | 102.16 | 67.90 |
| 24054 | 25.17 | 14.49 | 39.46 | 20.61 | 67.89 |
| 22352 | 139.84 | 54.27 | 253.98 | 211.46 | 67.89 |
| 21146 | 119.46 | 36.34 | 92.66 | 39.95 | 67.89 |
| 11791 | 136.74 | 46.57 | 173.47 | 50.00 | 67.88 |
| 19086 | 102.38 | 32.93 | 153.92 | 65.34 | 67.87 |
| 13111 | 235.97 | 68.33 | 187.10 | 77.46 | 67.86 |
| 14959 | 595.43 | 107.90 | 761.75 | 241.85 | 67.86 |
| 22103 | 222.38 | 50.69 | 294.15 | 83.02 | 67.84 |
| 1454 | 110.82 | 42.51 | 160.57 | 70.87 | 67.83 |
| 1844 | 167.38 | 35.91 | 216.33 | 60.90 | 67.83 |
| 13023 | 110.03 | 149.11 | 607.48 | 946.55 | 67.81 |
| 22487 | 34.23 | 15.90 | 60.56 | 35.71 | 67.80 |
| 7543 | 268.34 | 96.90 | 185.92 | 86.13 | 67.80 |
| 3107 | 779.30 | 164.38 | 696.29 | 236.36 | 67.80 |
| 8975 | 102.89 | 42.50 | 68.46 | 48.06 | 67.80 |
| 825 | 59.44 | 21.82 | 42.35 | 25.50 | 67.80 |
| 4473 | 192.83 | 43.69 | 148.92 | 66.25 | 67.78 |
| 18109 | 15.28 | 14.01 | 39.23 | 36.39 | 67.78 |
| 2845 | 651.40 | 103.22 | 768.87 | 160.95 | 67.76 |
| 11974 | 247.17 | 76.60 | 176.82 | 86.10 | 67.73 |
| 3547 | 14.36 | 11.57 | 25.42 | 14.68 | 67.73 |
| 22931 | 87.38 | 47.83 | 52.96 | 42.09 | 67.72 |
| 7161 | 46.95 | 14.21 | 64.96 | 24.05 | 67.69 |
| 9061 | 1135.34 | 236.25 | 942.16 | 326.87 | 67.69 |
| 12331 | 618.37 | 134.26 | 483.61 | 182.86 | 67.69 |
| 13962 | 523.52 | 110.90 | 438.13 | 148.62 | 67.68 |
| 24277 | 134.73 | 41.18 | 181.65 | 55.29 | 67.67 |
| 14790 | 176.36 | 78.47 | 102.86 | 72.99 | 67.67 |
| 18528 | 361.23 | 136.11 | 589.25 | 331.81 | 67.66 |
| 19665 | 81.08 | 33.19 | 142.12 | 76.68 | 67.66 |
| 14242 | 32.67 | 14.37 | 49.07 | 20.85 | 67.64 |
| 17407 | 1713.79 | 374.66 | 1443.40 | 337.67 | 67.64 |
| 6765 | 820.06 | 183.88 | 653.70 | 231.97 | 67.62 |
| 9514 | 675.01 | 129.64 | 570.37 | 132.48 | 67.62 |
| 22602 | 334.13 | 94.17 | 237.80 | 117.01 | 67.57 |
| 19822 | 1669.92 | 376.25 | 1281.37 | 430.75 | 67.56 |
| 9699 | 58.47 | 18.16 | 42.68 | 19.82 | 67.55 |
| 12812 | 99.34 | 33.83 | 74.64 | 38.83 | 67.55 |
| 24566 | 200.15 | 82.45 | 135.98 | 77.12 | 67.54 |
| 17499 | 24.56 | 23.09 | 55.11 | 35.51 | 67.53 |
| 18447 | 1233.88 | 274.38 | 958.23 | 329.75 | 67.53 |
| 21014 | 142.85 | 40.94 | 210.35 | 117.97 | 67.52 |
| 2536 | 406.73 | 114.26 | 323.04 | 150.73 | 67.51 |

TABLE 5A

ACYCLOVIR
Timepoint(s): 24, 168 hrs

| Identifier | NonToxMean | NonToxSD | Tox-Mean | ToxSD | LDAScore |
|---|---|---|---|---|---|
| 25419 | 159.17 | 64.32 | 38.16 | 8.66 | 99.48 |
| 25415 | 169.94 | 67.00 | 36.68 | 10.41 | 99.48 |
| 1872 | 723.76 | 219.40 | 182.16 | 67.65 | 99.36 |
| 17198 | 814.88 | 264.22 | 145.60 | 82.51 | 99.14 |
| 17567 | 1172.88 | 345.04 | 2623.71 | 250.73 | 98.97 |
| 14959 | 616.48 | 139.00 | 1288.62 | 137.24 | 98.84 |
| 20945 | 896.18 | 242.10 | 1896.41 | 180.47 | 98.80 |
| 16245 | 387.31 | 114.26 | 41.23 | 45.70 | 98.80 |
| 10887 | 73.83 | 25.90 | 17.83 | 4.94 | 98.67 |
| 4222 | 544.00 | 97.71 | 1042.92 | 176.22 | 98.67 |
| 19161 | 1064.06 | 296.13 | 2360.57 | 327.19 | 98.63 |
| 15626 | 1281.17 | 347.65 | 3250.17 | 648.92 | 98.58 |
| 11849 | 701.03 | 165.94 | 1608.51 | 320.36 | 98.50 |
| 20872 | 832.75 | 216.84 | 1896.38 | 376.01 | 98.50 |
| 15875 | 1175.87 | 375.74 | 2630.93 | 347.24 | 98.45 |
| 10498 | 1085.24 | 333.50 | 2568.66 | 334.73 | 98.45 |
| 20884 | 639.33 | 257.31 | 46.55 | 54.58 | 98.37 |
| 13151 | 702.17 | 319.88 | 2212.94 | 511.24 | 98.32 |
| 18611 | 1409.99 | 440.83 | 2945.57 | 350.22 | 98.28 |
| 20885 | 538.89 | 188.67 | 83.65 | 54.88 | 98.28 |
| 16244 | 40.33 | 21.14 | −0.26 | 5.01 | 98.24 |
| 16918 | 1172.71 | 382.43 | 2977.59 | 742.16 | 98.15 |
| 3027 | 1121.82 | 319.93 | 2267.04 | 262.71 | 98.15 |
| 20056 | 309.42 | 59.71 | 118.77 | 41.29 | 98.11 |
| 16205 | 932.31 | 252.05 | 1896.76 | 307.48 | 98.02 |
| 20812 | 1107.00 | 305.73 | 2296.29 | 293.56 | 97.98 |
| 14384 | 375.87 | 76.79 | 604.80 | 58.76 | 97.94 |
| 24615 | 809.56 | 214.82 | 1799.64 | 368.34 | 97.94 |
| 17524 | 1175.90 | 282.46 | 541.39 | 119.09 | 97.85 |
| 20839 | 1037.63 | 274.92 | 2191.65 | 391.42 | 97.85 |
| 18250 | 1088.85 | 307.06 | 2058.50 | 257.28 | 97.77 |
| 22846 | 1492.71 | 284.92 | 855.87 | 120.77 | 97.68 |
| 3026 | 512.85 | 99.35 | 933.31 | 159.19 | 97.64 |
| 13647 | 864.69 | 256.24 | 2095.09 | 431.00 | 97.64 |
| 17563 | 1195.18 | 331.95 | 2542.06 | 387.04 | 97.59 |
| 17473 | 422.91 | 93.66 | 796.08 | 169.41 | 97.59 |
| 20746 | 673.25 | 126.38 | 1181.14 | 211.43 | 97.59 |
| 19359 | 1061.61 | 314.08 | 2336.47 | 601.88 | 97.51 |
| 15201 | 1478.32 | 513.09 | 3558.35 | 808.75 | 97.47 |
| 15052 | 1433.93 | 492.46 | 3597.61 | 980.31 | 97.42 |
| 4490 | 76.73 | 73.42 | 270.49 | 135.30 | 97.42 |
| 2696 | 773.00 | 225.06 | 1860.28 | 390.37 | 97.42 |
| 22552 | 313.47 | 90.91 | 645.46 | 155.87 | 97.38 |
| 1694 | 1139.80 | 326.74 | 2255.77 | 345.62 | 97.38 |
| 19824 | 224.99 | 67.29 | 73.65 | 27.54 | 97.34 |
| 16333 | 133.41 | 38.84 | 45.56 | 15.40 | 97.16 |
| 16150 | 495.73 | 119.09 | 217.15 | 50.78 | 97.16 |
| 15928 | 157.91 | 59.34 | 354.44 | 52.65 | 97.16 |
| 15335 | 424.77 | 103.56 | 772.54 | 127.56 | 96.99 |
| 15202 | 788.60 | 313.98 | 1866.58 | 266.92 | 96.99 |
| 18749 | 116.41 | 42.26 | 34.59 | 11.87 | 96.95 |
| 16164 | 1075.08 | 276.06 | 1925.19 | 293.15 | 96.86 |
| 20088 | 384.13 | 78.71 | 185.57 | 40.67 | 96.78 |
| 23989 | 1057.77 | 294.07 | 466.25 | 116.46 | 96.74 |
| 24048 | 695.95 | 214.73 | 269.65 | 68.66 | 96.65 |
| 4254 | 144.21 | 377.79 | 15.39 | 14.62 | 96.65 |
| 24577 | 1170.09 | 364.08 | 2400.41 | 380.56 | 96.65 |

TABLE 5B

ACYCLOVIR
Timepoint(s): 6 hrs

| Identifier | NonToxMean | NonToxSD | Tox-Mean | ToxSD | LDAScore |
|---|---|---|---|---|---|
| 2572 | 1079.22 | 272.72 | 292.63 | 34.53 | 99.96 |
| 657 | 325.86 | 85.70 | 825.82 | 55.34 | 99.96 |
| 15174 | 582.65 | 154.01 | 1160.30 | 40.29 | 99.96 |
| 22060 | 120.39 | 46.22 | 489.85 | 39.32 | 99.87 |
| 21151 | 108.89 | 64.20 | 1068.35 | 133.62 | 99.87 |
| 17546 | 542.45 | 131.44 | 1300.18 | 82.92 | 99.83 |
| 8477 | 528.52 | 158.91 | 1301.77 | 46.70 | 99.83 |
| 16993 | 147.03 | 72.47 | 5.04 | 12.16 | 99.79 |
| 10667 | 41.39 | 38.71 | −236.50 | 27.34 | 99.79 |
| 3822 | 915.99 | 266.90 | 2473.92 | 69.91 | 99.74 |
| 17157 | 50.71 | 97.99 | 182.37 | 23.19 | 99.70 |
| 4532 | 266.41 | 75.57 | 62.22 | 7.77 | 99.70 |
| 15004 | 160.24 | 140.85 | 1576.85 | 132.63 | 99.70 |
| 4832 | 149.39 | 47.92 | 32.65 | 11.70 | 99.70 |
| 11836 | 219.06 | 64.52 | 69.22 | 8.46 | 99.61 |
| 24390 | 165.64 | 111.19 | −250.24 | 60.63 | 99.61 |
| 24200 | 421.04 | 138.48 | 1131.90 | 38.93 | 99.61 |
| 15002 | 137.74 | 85.32 | 904.65 | 69.55 | 99.61 |
| 3713 | 1141.71 | 271.69 | 457.32 | 36.48 | 99.57 |
| 6778 | 109.70 | 31.47 | 262.53 | 25.12 | 99.57 |
| 7936 | 149.06 | 36.24 | 49.64 | 5.41 | 99.57 |
| 13542 | 446.95 | 133.65 | 59.60 | 28.78 | 99.57 |
| 22385 | 107.82 | 53.29 | 22.50 | 3.64 | 99.57 |
| 20700 | 74.63 | 363.62 | 3153.73 | 549.12 | 99.57 |
| 15190 | 1801.09 | 1118.86 | 7715.59 | 404.27 | 99.53 |
| 20698 | −0.10 | 63.70 | 407.01 | 114.99 | 99.53 |
| 9757 | 408.35 | 98.75 | 159.69 | 13.35 | 99.53 |
| 15077 | 87.92 | 41.66 | 6.25 | 3.82 | 99.53 |
| 12301 | 58.09 | 29.22 | 219.75 | 30.79 | 99.53 |
| 3304 | 881.73 | 218.32 | 247.94 | 48.65 | 99.53 |
| 24041 | 11.98 | 28.98 | 230.57 | 61.01 | 99.53 |
| 19780 | 47.97 | 40.89 | 251.97 | 31.79 | 99.53 |
| 12899 | −9.55 | 17.51 | 146.15 | 30.06 | 99.49 |
| 23387 | 29.40 | 30.63 | 203.21 | 32.17 | 99.49 |
| 20699 | 86.60 | 192.11 | 2061.40 | 288.42 | 99.49 |
| 606 | −48.26 | 30.91 | 77.22 | 17.44 | 99.49 |
| 8874 | 118.63 | 59.95 | 395.15 | 33.95 | 99.49 |
| 5475 | 445.78 | 146.14 | 115.95 | 22.16 | 99.49 |
| 985 | 21.00 | 43.98 | 281.44 | 50.96 | 99.49 |
| 24243 | 258.96 | 69.54 | 71.35 | 13.38 | 99.44 |
| 6057 | 104.47 | 44.96 | 358.76 | 52.20 | 99.44 |
| 1892 | −6.30 | 35.30 | 58.25 | 24.52 | 99.40 |
| 275 | 519.62 | 162.35 | 80.95 | 30.90 | 99.40 |
| 2695 | 210.32 | 124.89 | 613.77 | 27.62 | 99.40 |
| 7804 | 1764.46 | 393.34 | 898.61 | 69.66 | 99.40 |
| 20701 | 32.96 | 54.09 | 404.95 | 132.78 | 99.40 |
| 12420 | 23.45 | 48.04 | −131.74 | 28.29 | 99.36 |
| 15003 | 33.26 | 83.63 | 776.16 | 111.38 | 99.36 |
| 24564 | 568.95 | 174.41 | 66.56 | 19.02 | 99.36 |
| 24246 | 300.44 | 96.46 | 678.79 | 40.80 | 99.36 |
| 9423 | 939.03 | 252.01 | 2035.02 | 137.31 | 99.36 |
| 23151 | 380.64 | 125.08 | 82.73 | 15.55 | 99.36 |
| 9071 | 48.03 | 25.31 | 2.95 | 1.90 | 99.36 |
| 2905 | 244.95 | 103.58 | 780.68 | 56.20 | 99.36 |
| 20856 | 55.56 | 46.37 | −5.93 | 3.53 | 99.36 |
| 5931 | 182.37 | 66.37 | 9.61 | 8.36 | 99.36 |
| 24042 | 18.74 | 67.93 | 772.42 | 198.67 | 99.36 |
| 17765 | 1285.78 | 452.80 | 2557.67 | 63.52 | 99.31 |
| 17470 | 102.21 | 54.04 | 410.26 | 61.20 | 99.31 |
| 2010 | 32.91 | 314.74 | 355.60 | 90.97 | 99.31 |
| 20848 | 510.27 | 150.82 | 1095.65 | 24.39 | 99.31 |
| 17591 | 385.36 | 90.04 | 744.25 | 62.21 | 99.27 |
| 1340 | 192.09 | 49.88 | 96.02 | 6.73 | 99.27 |
| 7806 | 51.84 | 19.09 | 122.32 | 8.65 | 99.27 |
| 7493 | 78.12 | 36.73 | 174.58 | 4.92 | 99.27 |
| 20035 | 180.04 | 101.54 | 817.96 | 80.03 | 99.23 |
| 19657 | 3.30 | 17.67 | 125.30 | 19.29 | 99.23 |
| 24563 | 309.99 | 99.44 | 4.82 | 17.01 | 99.23 |
| 22453 | 171.10 | 46.39 | 60.55 | 10.10 | 99.23 |
| 23995 | 161.66 | 57.89 | 380.58 | 31.88 | 99.23 |
| 15191 | 1989.62 | 1126.31 | 8988.79 | 1157.81 | 99.23 |
| 11326 | 332.40 | 95.69 | 94.87 | 14.33 | 99.23 |
| 7586 | 793.77 | 201.98 | 306.02 | 29.21 | 99.23 |

TABLE 5B-continued

ACYCLOVIR
Timepoint(s): 6 hrs

| Identifier | NonToxMean | NonToxSD | Tox-Mean | ToxSD | LDAScore |
|---|---|---|---|---|---|
| 2392 | 154.00 | 87.41 | 1138.50 | 400.02 | 99.23 |
| 4205 | 222.66 | 72.63 | 591.81 | 54.59 | 99.23 |
| 8245 | 54.69 | 20.70 | 113.91 | 5.63 | 99.23 |
| 16324 | 194.65 | 61.24 | 42.04 | 11.21 | 99.23 |
| 12404 | 105.63 | 62.52 | 662.04 | 167.20 | 99.23 |
| 7639 | 753.14 | 166.01 | 339.14 | 44.82 | 99.23 |
| 20895 | 331.67 | 100.56 | 50.78 | 24.52 | 99.19 |
| 22018 | 158.66 | 41.98 | 360.67 | 50.74 | 99.19 |
| 3823 | 524.10 | 147.80 | 1250.81 | 97.60 | 99.14 |
| 6477 | 13.58 | 161.23 | 99.71 | 26.48 | 99.14 |
| 223 | 11.18 | 17.65 | 124.61 | 25.10 | 99.14 |
| 15146 | 130.31 | 69.77 | 744.71 | 139.52 | 99.14 |
| 25069 | 134.29 | 60.66 | 25.21 | 12.36 | 99.14 |
| 3431 | 1503.29 | 617.93 | 3867.63 | 202.46 | 99.14 |
| 3271 | 576.75 | 119.79 | 239.69 | 44.71 | 99.14 |
| 6054 | 26.29 | 47.50 | 386.77 | 134.53 | 99.14 |
| 20202 | 627.69 | 194.14 | 49.29 | 62.88 | 99.14 |
| 25546 | 473.74 | 139.13 | 145.65 | 40.29 | 99.14 |
| 19781 | 113.50 | 55.43 | 454.62 | 115.29 | 99.14 |
| 22488 | 58.52 | 53.30 | 334.10 | 50.62 | 99.10 |
| 10281 | 168.73 | 157.24 | 1702.50 | 591.27 | 99.10 |
| 9452 | 125.58 | 75.70 | 1560.61 | 720.48 | 99.10 |
| 2153 | 182.83 | 143.86 | 1201.51 | 175.46 | 99.10 |
| 13745 | 27.62 | 27.50 | 297.57 | 96.36 | 99.10 |
| 1218 | 198.28 | 37.55 | 92.30 | 12.70 | 99.10 |
| 15042 | 63.76 | 42.44 | 353.57 | 60.19 | 99.10 |
| 9521 | 95.05 | 24.96 | 222.10 | 33.80 | 99.10 |

TABLE 5C

ADR
Timepoint(s): 120, 168 hrs

| Identifier | NonToxMean | NonToxSD | Tox-Mean | ToxSD | LDAScore |
|---|---|---|---|---|---|
| 1688 | 5353.71 | 3830.70 | 26.75 | 39.23 | 99.44 |
| 25469 | 1577.10 | 747.53 | 25.91 | 13.98 | 99.44 |
| 1684 | 2831.22 | 1612.49 | 24.53 | 31.27 | 99.44 |
| 17829 | 2235.92 | 1102.19 | 68.14 | 58.70 | 99.44 |
| 25468 | 2186.32 | 1123.33 | 11.47 | 13.96 | 99.44 |
| 26150 | 783.82 | 532.35 | −38.06 | 15.15 | 99.40 |
| 1687 | 1894.26 | 855.11 | 45.95 | 32.94 | 99.31 |
| 1685 | 9226.22 | 7079.05 | 58.61 | 94.83 | 99.31 |
| 1689 | 4411.94 | 2221.14 | 43.26 | 28.59 | 99.31 |
| 17832 | 1976.64 | 870.20 | 17.22 | 14.67 | 99.18 |
| 19358 | 792.56 | 328.04 | 6.04 | 46.93 | 98.71 |
| 18907 | 102.84 | 49.44 | 17.51 | 7.82 | 97.33 |
| 25467 | 636.86 | 169.13 | 1263.84 | 257.87 | 97.25 |
| 4011 | 457.30 | 195.33 | 953.88 | 244.47 | 96.78 |
| 14199 | 71.52 | 35.30 | 26.74 | 5.48 | 96.09 |
| 2852 | 49.29 | 27.79 | 19.72 | 2.87 | 95.92 |
| 21140 | 109.12 | 47.83 | 38.53 | 9.71 | 95.83 |
| 4594 | 63.32 | 30.73 | 22.33 | 5.88 | 95.44 |
| 7089 | 102.25 | 41.59 | 48.02 | 7.26 | 95.40 |
| 2984 | 582.52 | 185.78 | 258.99 | 70.15 | 95.27 |
| 1831 | 49.81 | 23.36 | 10.63 | 6.34 | 94.67 |
| 25705 | 455.64 | 115.95 | 612.52 | 59.36 | 94.45 |
| 16109 | 414.49 | 75.48 | 556.38 | 45.14 | 94.28 |
| 11165 | 529.31 | 155.75 | 250.39 | 51.44 | 93.98 |
| 19237 | 77.59 | 39.42 | 10.97 | 14.64 | 93.68 |
| 16401 | 1239.09 | 805.30 | 2322.72 | 497.80 | 93.68 |
| 109 | 547.11 | 293.37 | 1681.21 | 571.81 | 93.63 |
| 4312 | 77.34 | 39.04 | 127.17 | 10.27 | 93.51 |
| 16400 | 580.43 | 474.95 | 1090.34 | 298.55 | 93.42 |
| 18794 | 138.50 | 77.18 | 48.95 | 11.54 | 93.38 |
| 7489 | 81.80 | 32.11 | 25.62 | 12.02 | 93.34 |
| 2586 | 52.04 | 30.18 | 14.65 | 5.97 | 93.04 |
| 17742 | 1059.53 | 304.09 | 1669.92 | 253.17 | 92.99 |
| 956 | 54.64 | 39.22 | 1.90 | 10.80 | 92.78 |

TABLE 5C-continued

ADR
Timepoint(s): 120, 168 hrs

| Identifier | NonToxMean | NonToxSD | Tox-Mean | ToxSD | LDAScore |
|---|---|---|---|---|---|
| 17563 | 1201.38 | 349.79 | 1590.38 | 101.68 | 92.69 |
| 2125 | 78.10 | 82.13 | −4.59 | 19.58 | 92.69 |
| 24844 | 32.09 | 22.37 | 8.57 | 2.19 | 92.65 |
| 16676 | 38.73 | 27.29 | 17.84 | 2.42 | 92.61 |
| 19189 | 60.60 | 62.41 | 14.86 | 7.74 | 92.61 |
| 16521 | 285.39 | 89.91 | 428.27 | 70.75 | 92.56 |
| 14430 | 34.74 | 32.18 | 3.43 | 3.27 | 92.48 |
| 1301 | 325.54 | 286.68 | 14.24 | 17.87 | 92.43 |
| 21006 | 55.98 | 36.26 | 16.33 | 6.58 | 92.39 |
| 23778 | 69.71 | 34.49 | 24.74 | 8.89 | 92.26 |
| 2812 | 193.71 | 46.19 | 284.99 | 38.81 | 92.22 |
| 16407 | 459.56 | 105.59 | 825.37 | 208.72 | 92.12 |
| 16426 | 280.85 | 109.78 | 118.35 | 49.48 | 91.79 |
| 24232 | 160.98 | 60.26 | 72.06 | 20.28 | 91.66 |
| 6059 | 193.61 | 50.50 | 116.52 | 21.50 | 91.40 |
| 17234 | 634.83 | 173.83 | 432.41 | 36.23 | 91.27 |
| 13025 | 335.88 | 84.38 | 224.82 | 24.51 | 91.23 |
| 20757 | 411.95 | 220.62 | 771.74 | 157.51 | 91.09 |
| 10076 | 105.84 | 50.96 | 140.17 | 10.04 | 91.06 |
| 4010 | 961.35 | 403.18 | 2024.17 | 546.67 | 91.05 |
| 22220 | 147.73 | 137.94 | 463.05 | 162.91 | 90.96 |
| 9644 | −4.86 | 27.32 | 39.61 | 11.58 | 90.93 |
| 8597 | 240.84 | 58.03 | 315.06 | 30.21 | 90.89 |
| 16582 | 56.67 | 19.30 | 29.31 | 5.28 | 90.89 |
| 1321 | 510.50 | 316.91 | 1496.60 | 371.84 | 90.88 |
| 14337 | 211.54 | 44.52 | 148.64 | 18.05 | 90.84 |
| 19191 | 1011.62 | 281.12 | 631.62 | 94.67 | 90.76 |
| 20716 | 652.51 | 142.58 | 1029.68 | 128.61 | 90.75 |
| 8017 | 188.58 | 76.89 | 406.11 | 152.05 | 90.66 |
| 18502 | 670.14 | 243.60 | 313.44 | 111.24 | 90.63 |
| 2782 | 214.23 | 97.42 | 522.66 | 132.70 | 90.62 |
| 13354 | 88.85 | 57.76 | 34.85 | 9.49 | 90.50 |
| 22696 | 62.39 | 50.49 | −5.66 | 12.94 | 90.50 |
| 4242 | 749.55 | 193.32 | 1337.17 | 268.80 | 90.49 |
| 12660 | 71.28 | 22.64 | 44.42 | 5.74 | 90.46 |
| 15892 | 18.01 | 22.79 | 36.39 | 7.65 | 90.46 |
| 25517 | 39.47 | 33.13 | 2.75 | 7.99 | 90.41 |
| 22697 | 59.68 | 40.43 | 15.77 | 10.73 | 90.33 |
| 16448 | 129.58 | 38.04 | 43.90 | 19.88 | 90.32 |
| 1058 | 75.84 | 35.86 | 30.65 | 8.83 | 90.24 |
| 7863 | 1200.90 | 307.30 | 1386.51 | 55.05 | 90.24 |
| 11967 | 1725.17 | 550.50 | 1088.97 | 237.35 | 90.20 |
| 516 | 55.59 | 33.01 | 17.20 | 9.40 | 90.11 |
| 25736 | 24.77 | 16.54 | 7.84 | 4.16 | 89.98 |
| 6544 | 53.15 | 110.52 | 379.03 | 173.46 | 89.89 |
| 21651 | 32.42 | 26.38 | 7.38 | 3.39 | 89.85 |
| 16581 | 39.86 | 19.57 | 17.01 | 3.68 | 89.72 |
| 2607 | 218.90 | 50.79 | 175.06 | 11.54 | 89.55 |
| 15247 | 637.26 | 192.10 | 1113.60 | 210.08 | 89.41 |
| 6691 | 119.56 | 54.62 | 32.51 | 16.76 | 89.41 |
| 20702 | 300.67 | 70.50 | 198.62 | 33.60 | 89.38 |
| 10109 | 1044.97 | 289.50 | 1362.38 | 117.72 | 89.34 |
| 24040 | 557.97 | 233.98 | 196.88 | 87.97 | 89.29 |
| 1169 | 90.18 | 28.72 | 92.58 | 4.98 | 89.21 |
| 5421 | 279.85 | 96.20 | 162.53 | 31.31 | 89.21 |
| 19244 | 1224.80 | 382.60 | 1678.75 | 173.86 | 89.17 |
| 3015 | 2307.62 | 994.19 | 2930.38 | 184.09 | 89.12 |
| 21695 | 60.82 | 36.14 | 4.02 | 14.39 | 89.03 |
| 11218 | 102.70 | 37.49 | 47.65 | 19.31 | 88.95 |
| 21766 | 286.32 | 76.11 | 204.08 | 26.91 | 88.95 |
| 494 | 698.84 | 215.82 | 1186.69 | 207.80 | 88.86 |
| 24528 | 61.08 | 25.93 | 19.77 | 8.13 | 88.81 |

TABLE 5D

AY
Timepoint(s): 360 hrs

| Identifier | NonToxMean | NonToxSD | Tox-Mean | ToxSD | LDAScore |
|---|---|---|---|---|---|
| 6360 | 7.76 | 5.80 | 30.12 | 3.08 | 99.36 |
| 18826 | 1069.51 | 321.45 | 473.21 | 31.01 | 99.32 |
| 24886 | 1264.06 | 371.77 | 2165.64 | 63.29 | 99.27 |
| 6517 | 233.00 | 158.96 | 437.46 | 12.19 | 99.19 |
| 16576 | 111.85 | 41.47 | 67.47 | 0.61 | 99.19 |
| 22846 | 1490.00 | 287.46 | 852.52 | 44.29 | 99.10 |
| 2708 | 383.37 | 87.00 | 425.82 | 1.07 | 98.97 |
| 14349 | 413.99 | 144.50 | 244.25 | 2.46 | 98.97 |
| 13023 | 187.03 | 420.15 | −22.68 | 5.86 | 98.85 |
| 6585 | 653.17 | 368.20 | 239.73 | 12.54 | 98.76 |
| 15093 | 35.54 | 16.49 | −7.39 | 3.34 | 98.76 |
| 25066 | 136.51 | 58.55 | 34.09 | 4.82 | 98.72 |
| 21796 | 696.51 | 210.24 | 1145.40 | 47.75 | 98.67 |
| 3610 | 1195.23 | 334.91 | 780.10 | 28.06 | 98.67 |
| 24236 | 80.80 | 27.74 | 39.65 | 1.30 | 98.67 |
| 16156 | 858.19 | 319.87 | 3220.95 | 1137.23 | 98.59 |
| 17672 | 2630.76 | 734.18 | 3325.88 | 12.22 | 98.59 |
| 472 | 658.60 | 175.52 | 1275.16 | 135.82 | 98.59 |
| 15462 | 86.01 | 35.25 | 28.41 | 2.70 | 98.55 |
| 10159 | 7.63 | 18.34 | 30.64 | 0.79 | 98.55 |
| 457 | 284.29 | 87.14 | 421.47 | 22.09 | 98.42 |
| 22093 | −21.77 | 38.66 | 56.32 | 5.98 | 98.37 |
| 5212 | 189.25 | 67.72 | 0.93 | 13.47 | 98.33 |
| 11368 | 20.04 | 24.02 | 29.17 | 0.30 | 98.29 |
| 22731 | 24.04 | 24.97 | 9.37 | 0.65 | 98.29 |
| 23313 | 404.59 | 87.09 | 292.34 | 2.67 | 98.29 |
| 25178 | 4.72 | 6.91 | 30.15 | 9.22 | 98.25 |
| 11561 | 389.44 | 87.17 | 225.68 | 12.21 | 98.25 |
| 14120 | 740.64 | 221.38 | 1485.37 | 218.95 | 98.20 |
| 4622 | 608.46 | 110.69 | 956.12 | 79.60 | 98.20 |
| 12894 | 141.35 | 34.03 | 72.48 | 5.99 | 98.12 |
| 3447 | 33.98 | 17.04 | 11.74 | 0.97 | 98.03 |
| 1410 | 99.49 | 46.40 | 23.57 | 5.02 | 97.99 |
| 22103 | 235.14 | 64.79 | 449.04 | 43.64 | 97.99 |
| 14185 | 204.58 | 95.56 | 321.83 | 10.61 | 97.99 |
| 24770 | 233.44 | 86.68 | 44.57 | 16.38 | 97.95 |
| 21044 | 24.56 | 22.71 | −11.37 | 2.16 | 97.95 |
| 24721 | 203.93 | 53.62 | 144.06 | 2.18 | 97.95 |
| 20184 | 11.29 | 9.18 | 20.17 | 0.35 | 97.95 |
| 6062 | 182.74 | 59.18 | 106.49 | 1.72 | 97.90 |
| 16172 | 467.00 | 120.07 | 308.58 | 10.28 | 97.86 |
| 19731 | 225.58 | 214.69 | 63.47 | 15.21 | 97.82 |
| 16155 | 1075.32 | 410.99 | 3024.24 | 951.97 | 97.82 |
| 5425 | 85.43 | 33.27 | 153.80 | 5.81 | 97.82 |
| 1463 | 620.25 | 296.25 | 1592.90 | 460.18 | 97.78 |
| 2696 | 777.90 | 238.27 | 1766.44 | 260.04 | 97.78 |
| 2126 | 223.21 | 75.66 | 478.73 | 56.24 | 97.78 |
| 16245 | 384.42 | 117.13 | 589.67 | 20.00 | 97.73 |
| 4683 | 211.56 | 40.44 | 323.17 | 13.38 | 97.73 |
| 11590 | 276.38 | 78.94 | 238.32 | 1.35 | 97.69 |
| 556 | 82.41 | 35.72 | 33.35 | 5.40 | 97.69 |
| 10241 | 67.50 | 27.73 | 4.65 | 11.47 | 97.69 |
| 275 | 516.42 | 162.40 | 1038.56 | 193.69 | 97.65 |
| 10784 | 24.89 | 30.12 | −21.79 | 6.29 | 97.65 |
| 6523 | 30.10 | 14.87 | 8.53 | 1.41 | 97.60 |
| 4467 | 656.82 | 156.93 | 1236.28 | 198.60 | 97.60 |
| 24042 | 21.86 | 84.61 | 58.64 | 10.50 | 97.56 |
| 15135 | 706.76 | 182.37 | 1034.39 | 31.17 | 97.52 |
| 6790 | 63.12 | 24.62 | 19.35 | 3.71 | 97.52 |
| 6743 | 1405.82 | 280.92 | 2262.37 | 206.08 | 97.52 |
| 6351 | 45.29 | 26.36 | 88.65 | 2.94 | 97.48 |
| 18942 | −11.45 | 10.37 | 24.19 | 16.98 | 97.43 |
| 6726 | 393.51 | 104.57 | 242.70 | 10.50 | 97.43 |
| 9808 | 30.77 | 14.74 | 50.69 | 1.63 | 97.39 |
| 21078 | 567.53 | 143.04 | 363.30 | 11.51 | 97.39 |
| 22619 | 371.47 | 90.93 | 316.17 | 2.78 | 97.39 |
| 1058 | 75.62 | 35.90 | 24.89 | 3.27 | 97.39 |
| 22692 | 209.08 | 63.35 | 106.95 | 5.50 | 97.39 |
| 21914 | 404.11 | 71.79 | 635.41 | 66.12 | 97.39 |
| 22063 | 68.58 | 25.03 | 47.50 | 0.52 | 97.35 |
| 1162 | 10.60 | 37.16 | 138.81 | 40.04 | 97.35 |
| 15224 | 689.92 | 152.18 | 1138.23 | 103.80 | 97.35 |
| 24178 | 2.75 | 9.42 | 20.42 | 4.02 | 97.31 |

TABLE 5D-continued

AY
Timepoint(s): 360 hrs

| Identifier | NonToxMean | NonToxSD | Tox-Mean | ToxSD | LDAScore |
|---|---|---|---|---|---|
| 20891 | 140.77 | 49.29 | 78.20 | 3.12 | 97.31 |
| 17393 | 145.61 | 59.87 | 87.56 | 1.63 | 97.31 |
| 17061 | 557.85 | 95.17 | 904.28 | 161.35 | 97.22 |
| 21656 | 54.49 | 25.08 | 22.60 | 1.43 | 97.18 |
| 23651 | 656.34 | 623.55 | 2317.09 | 936.44 | 97.18 |
| 2357 | 76.01 | 23.05 | 69.48 | 0.72 | 97.13 |
| 18130 | 378.79 | 74.65 | 591.90 | 50.88 | 97.13 |
| 23898 | 10.17 | 6.54 | 30.37 | 7.27 | 97.13 |
| 9363 | 89.83 | 29.45 | 164.93 | 13.77 | 97.09 |
| 2920 | 78.42 | 29.88 | 124.28 | 3.10 | 97.09 |
| 21930 | 597.55 | 127.69 | 1108.70 | 256.19 | 97.05 |
| 12770 | 600.59 | 229.99 | 230.85 | 29.99 | 97.05 |
| 23799 | 146.92 | 43.68 | 75.83 | 5.19 | 97.05 |
| 1757 | 23.41 | 13.46 | −0.34 | 3.13 | 97.05 |
| 18419 | 1317.37 | 373.39 | 2669.33 | 536.46 | 97.05 |
| 7023 | 364.44 | 77.23 | 413.76 | 3.42 | 97.01 |
| 5811 | 35.76 | 18.86 | 52.44 | 0.86 | 97.01 |
| 1529 | 290.79 | 62.32 | 164.72 | 18.30 | 97.01 |
| 15259 | 227.54 | 56.59 | 163.79 | 2.45 | 97.01 |
| 14095 | 379.89 | 98.99 | 246.75 | 8.11 | 97.01 |
| 17107 | 2200.10 | 722.73 | 4177.24 | 487.81 | 96.96 |
| 13393 | 76.83 | 46.83 | 166.60 | 16.98 | 96.96 |
| 15411 | 305.14 | 91.59 | 162.75 | 9.40 | 96.96 |

TABLE 5E

BEA
Timepoint(s): 6, 24 hrs

| Identifier | NonToxMean | NonToxSD | Tox-Mean | ToxSD | LDAScore |
|---|---|---|---|---|---|
| 21011 | 154.85 | 315.31 | 689.68 | 175.67 | 98.32 |
| 21015 | 271.80 | 338.52 | 933.97 | 202.57 | 97.98 |
| 21013 | 214.58 | 340.35 | 710.95 | 153.21 | 97.68 |
| 22057 | 349.60 | 55.08 | 477.85 | 22.42 | 97.33 |
| 8477 | 529.15 | 164.21 | 876.56 | 49.54 | 97.03 |
| 23849 | 285.73 | 136.63 | 521.70 | 61.30 | 96.65 |
| 15969 | 339.58 | 71.02 | 574.34 | 94.47 | 96.47 |
| 5901 | 92.67 | 50.17 | 176.54 | 31.37 | 96.43 |
| 17034 | 885.84 | 144.51 | 1193.98 | 93.26 | 95.36 |
| 23140 | 172.19 | 53.17 | 288.43 | 107.64 | 94.67 |
| 6143 | 560.24 | 135.28 | 861.03 | 122.25 | 94.20 |
| 22931 | 79.76 | 48.36 | 19.97 | 4.03 | 94.15 |
| 13608 | 21.70 | 23.78 | 64.61 | 13.40 | 94.07 |
| 3167 | 308.80 | 70.69 | 438.24 | 41.83 | 94.07 |
| 17771 | 769.01 | 307.47 | 1086.30 | 71.95 | 93.98 |
| 10477 | 87.73 | 37.06 | 137.33 | 14.74 | 93.42 |
| 17563 | 1206.59 | 350.63 | 917.80 | 32.07 | 92.99 |
| 3551 | 440.44 | 98.71 | 307.06 | 31.45 | 92.69 |
| 22885 | 1347.43 | 493.33 | 2161.55 | 380.96 | 92.61 |
| 8515 | 262.49 | 109.22 | 415.39 | 29.53 | 92.52 |
| 20745 | 471.03 | 70.08 | 354.88 | 30.48 | 92.30 |
| 4748 | 110.75 | 127.98 | 202.78 | 32.60 | 92.18 |
| 8639 | 368.78 | 99.86 | 530.10 | 59.33 | 91.92 |
| 14874 | 50.39 | 17.11 | 78.62 | 12.99 | 91.66 |
| 21625 | 2492.78 | 1106.79 | 1806.41 | 173.96 | 91.53 |
| 2729 | 638.00 | 170.57 | 841.33 | 45.73 | 91.53 |
| 6844 | 124.24 | 58.33 | 32.11 | 26.05 | 91.53 |
| 19993 | 2317.82 | 568.48 | 3182.90 | 249.42 | 91.36 |
| 10742 | 62.40 | 27.77 | 27.67 | 6.47 | 91.32 |
| 8205 | 398.00 | 113.24 | 583.05 | 83.76 | 91.23 |
| 17400 | 121.53 | 78.34 | 254.55 | 53.39 | 91.23 |
| 1698 | 73.83 | 75.94 | 197.90 | 43.39 | 91.22 |
| 3557 | 107.65 | 39.24 | 177.58 | 40.40 | 91.14 |
| 18905 | 1365.13 | 302.42 | 1751.48 | 71.12 | 91.06 |
| 7276 | 72.89 | 27.71 | 30.30 | 10.38 | 91.01 |
| 15111 | 954.53 | 281.39 | 581.40 | 91.29 | 90.97 |
| 14929 | 800.42 | 430.77 | 1096.37 | 215.26 | 90.80 |
| 18077 | 2620.17 | 1190.40 | 1912.67 | 180.40 | 90.28 |

TABLE 5E-continued

BEA
Timepoint(s): 6, 24 hrs

| Identifier | NonToxMean | NonToxSD | Tox-Mean | ToxSD | LDAScore |
|---|---|---|---|---|---|
| 14862 | 181.12 | 72.28 | 270.61 | 28.36 | 90.28 |
| 10636 | 369.25 | 95.44 | 241.19 | 39.11 | 90.24 |
| 2057 | 291.01 | 74.63 | 398.13 | 39.83 | 90.15 |
| 21014 | 155.16 | 80.93 | 268.20 | 58.44 | 90.15 |
| 4232 | 137.37 | 62.35 | 64.91 | 22.20 | 90.07 |
| 5687 | 189.73 | 55.56 | 278.09 | 42.24 | 90.03 |
| 13614 | 342.46 | 95.82 | 447.07 | 32.82 | 90.03 |
| 11605 | 98.56 | 37.96 | 208.10 | 79.38 | 89.97 |
| 17107 | 2202.25 | 730.97 | 2581.41 | 115.51 | 89.72 |
| 14069 | 29.03 | 14.66 | 50.58 | 9.56 | 89.68 |
| 16407 | 463.39 | 111.03 | 329.66 | 41.65 | 89.68 |
| 3014 | 29.07 | 15.66 | 43.28 | 5.07 | 89.64 |
| 4731 | 119.24 | 35.99 | 215.47 | 51.98 | 89.63 |
| 14718 | 38.97 | 27.26 | 103.83 | 29.32 | 89.63 |
| 818 | 4123.05 | 2816.44 | 2751.13 | 405.49 | 89.60 |
| 17545 | 74.49 | 49.29 | 192.85 | 48.58 | 89.59 |
| 17695 | 728.25 | 203.79 | 1236.56 | 236.71 | 89.59 |
| 5811 | 35.97 | 18.81 | 13.37 | 6.74 | 89.47 |
| 3081 | 387.79 | 84.55 | 253.14 | 37.34 | 89.46 |
| 7895 | 997.72 | 308.71 | 1503.83 | 263.73 | 89.46 |
| 3924 | 183.13 | 68.64 | 101.62 | 16.04 | 89.34 |
| 24181 | 85.08 | 27.22 | 145.70 | 16.84 | 89.33 |
| 2752 | 405.86 | 139.92 | 593.99 | 60.88 | 89.33 |
| 1159 | 886.55 | 231.02 | 611.65 | 64.43 | 89.29 |
| 24388 | 188.48 | 72.47 | 251.08 | 30.81 | 89.29 |
| 3926 | 176.00 | 56.73 | 103.17 | 18.22 | 89.25 |
| 18981 | 231.55 | 65.64 | 189.11 | 9.52 | 89.21 |
| 7838 | 19.58 | 15.00 | 21.80 | 3.33 | 89.17 |
| 24537 | 528.52 | 104.62 | 396.25 | 38.65 | 89.08 |
| 2688 | 173.21 | 54.36 | 243.95 | 28.16 | 89.08 |
| 19484 | 184.45 | 70.04 | 320.46 | 37.72 | 89.03 |
| 22855 | 561.72 | 144.30 | 886.81 | 141.20 | 89.03 |
| 12979 | 391.37 | 216.96 | 627.81 | 88.47 | 88.94 |
| 7223 | 88.64 | 27.62 | 152.72 | 24.63 | 88.94 |
| 23159 | 416.48 | 85.49 | 537.44 | 47.74 | 88.91 |
| 13563 | 1028.27 | 255.15 | 1603.62 | 170.06 | 88.86 |
| 3696 | 42.57 | 32.72 | 106.32 | 10.80 | 88.86 |
| 2855 | 920.64 | 212.77 | 1412.67 | 261.05 | 88.77 |
| 3580 | 9.48 | 10.46 | 22.09 | 6.90 | 88.74 |
| 12629 | 65.11 | 30.82 | 27.44 | 7.55 | 88.61 |
| 18810 | 1188.71 | 319.49 | 906.85 | 60.20 | 88.52 |
| 18770 | 1131.01 | 331.57 | 887.70 | 58.94 | 88.48 |
| 19577 | 494.98 | 92.34 | 376.82 | 38.52 | 88.48 |
| 18891 | 1378.10 | 409.91 | 1823.58 | 193.46 | 88.48 |
| 7914 | 1537.05 | 507.11 | 1256.25 | 91.53 | 88.44 |

TABLE 5F

CAPTOPRIL (336 hrs)

| Identifier | NonToxMean | NonToxSD | Tox-Mean | ToxSD | LDAScore |
|---|---|---|---|---|---|
| 23859 | −10.09 | 17.25 | 58.28 | 12.00 | 99.70 |
| 1522 | 181.53 | 92.60 | −79.60 | 14.77 | 99.40 |
| 24668 | 76.16 | 46.93 | 1110.08 | 605.52 | 99.10 |
| 19287 | 161.27 | 40.70 | 265.00 | 9.72 | 98.84 |
| 735 | 125.45 | 37.81 | 123.72 | 0.37 | 98.50 |
| 1348 | 29.21 | 17.75 | 0.23 | 1.09 | 98.12 |
| 16260 | 66.53 | 18.90 | 82.33 | 0.49 | 98.07 |
| 24696 | 69.96 | 48.08 | −11.83 | 7.33 | 98.07 |
| 826 | 182.43 | 53.09 | 63.46 | 18.28 | 97.90 |
| 15851 | 203.67 | 153.22 | 36.02 | 16.84 | 97.69 |
| 19120 | 32.71 | 25.65 | −8.80 | 2.19 | 97.43 |
| 1480 | 253.73 | 66.75 | 112.96 | 18.69 | 97.43 |
| 18659 | 51.26 | 29.25 | 80.08 | 1.30 | 97.43 |
| 15420 | 59.26 | 52.41 | −14.25 | 3.04 | 97.39 |
| 2830 | 654.10 | 146.54 | 933.86 | 42.78 | 96.92 |
| 2658 | 891.04 | 236.04 | 443.07 | 41.79 | 96.88 |
| 17937 | 86.63 | 42.53 | −12.26 | 22.60 | 96.83 |

TABLE 5F-continued

CAPTOPRIL (336 hrs)

| Identifier | NonToxMean | NonToxSD | ToxMean | ToxSD | LDAScore |
|---|---|---|---|---|---|
| 10108 | 146.26 | 35.48 | 61.17 | 17.32 | 96.70 |
| 1223 | 191.43 | 47.65 | 289.39 | 15.78 | 96.66 |
| 16048 | 28.62 | 52.28 | −8.09 | 3.07 | 96.66 |
| 10774 | 26.49 | 16.73 | 40.49 | 1.17 | 96.62 |
| 16944 | 848.22 | 191.45 | 550.56 | 29.83 | 96.58 |
| 546 | 173.90 | 50.96 | 271.42 | 13.74 | 96.53 |
| 12819 | 184.28 | 47.07 | 239.54 | 3.32 | 96.53 |
| 5735 | 56.51 | 21.12 | 63.63 | 0.57 | 96.45 |
| 7956 | 27.42 | 11.15 | 39.67 | 0.69 | 96.40 |
| 12332 | 567.22 | 177.99 | 328.76 | 21.43 | 96.32 |
| 18346 | 273.04 | 62.53 | 138.13 | 21.45 | 96.32 |
| 16425 | 20.91 | 30.81 | −13.41 | 3.05 | 96.23 |
| 8426 | 54.76 | 23.35 | 27.91 | 1.50 | 96.19 |
| 9964 | 14.13 | 28.09 | 41.16 | 1.54 | 96.15 |
| 15395 | 797.12 | 155.79 | 610.46 | 12.19 | 96.02 |
| 21458 | 229.75 | 104.67 | 360.26 | 20.40 | 95.93 |
| 15259 | 227.63 | 56.54 | 154.42 | 4.47 | 95.93 |
| 11057 | 33.19 | 29.92 | 61.96 | 3.13 | 95.89 |
| 397 | 116.22 | 33.32 | 88.25 | 1.44 | 95.89 |
| 20429 | 108.55 | 34.07 | 193.71 | 39.16 | 95.85 |
| 12333 | 218.47 | 76.94 | 109.09 | 10.32 | 95.85 |
| 12629 | 64.58 | 30.66 | 134.34 | 14.35 | 95.76 |
| 20833 | 1255.87 | 351.77 | 1350.26 | 16.51 | 95.68 |
| 10673 | 62.50 | 35.24 | 48.56 | 1.93 | 95.63 |
| 9518 | 29.88 | 23.15 | 73.23 | 8.73 | 95.59 |
| 5630 | 77.86 | 48.50 | 150.84 | 8.45 | 95.59 |
| 16036 | 64.27 | 20.66 | 37.81 | 2.46 | 95.55 |
| 23773 | 214.43 | 85.23 | 94.48 | 13.72 | 95.51 |
| 11817 | 64.91 | 20.17 | 98.04 | 3.96 | 95.46 |
| 13976 | 459.29 | 377.97 | 122.98 | 19.90 | 95.46 |
| 14926 | 95.90 | 28.06 | 158.69 | 14.69 | 95.46 |
| 21633 | 302.73 | 119.13 | 151.23 | 11.45 | 95.42 |
| 910 | 58.30 | 22.93 | 35.87 | 1.63 | 95.42 |
| 11203 | 75.66 | 25.37 | 58.05 | 1.05 | 95.38 |
| 16562 | 188.78 | 45.14 | 125.67 | 5.83 | 95.29 |
| 6362 | 63.63 | 39.69 | −15.88 | 19.50 | 95.25 |
| 23237 | 89.94 | 41.57 | 97.86 | 1.24 | 95.25 |
| 5384 | 41.70 | 44.55 | 1.71 | 2.18 | 95.25 |
| 22665 | 128.49 | 29.89 | 159.98 | 3.47 | 95.21 |
| 6581 | 76.47 | 26.45 | 43.08 | 2.63 | 95.12 |
| 260 | 417.04 | 114.29 | 636.83 | 72.47 | 95.12 |
| 24814 | 171.62 | 33.74 | 127.03 | 5.19 | 95.12 |
| 13682 | 178.68 | 62.82 | 61.54 | 20.17 | 95.08 |
| 15028 | 346.53 | 107.46 | 569.31 | 126.83 | 95.08 |
| 17439 | 218.65 | 47.89 | 292.03 | 10.02 | 94.95 |
| 15797 | 20.60 | 17.76 | −7.25 | 4.56 | 94.95 |
| 17549 | 1304.87 | 367.92 | 1416.98 | 24.18 | 94.95 |
| 17923 | 66.78 | 23.31 | 48.46 | 1.01 | 94.95 |
| 23360 | 178.74 | 46.59 | 218.52 | 2.99 | 94.91 |
| 20099 | 81.73 | 30.45 | 123.33 | 3.88 | 94.91 |
| 19327 | 89.68 | 29.52 | 50.76 | 3.50 | 94.86 |
| 5786 | 125.64 | 46.92 | 48.44 | 13.78 | 94.86 |
| 9929 | 531.71 | 124.53 | 680.04 | 14.58 | 94.82 |
| 2831 | 619.77 | 172.12 | 917.69 | 61.75 | 94.82 |
| 10477 | 88.24 | 37.19 | 51.43 | 2.96 | 94.82 |
| 21013 | 217.62 | 342.33 | 442.35 | 95.19 | 94.82 |
| 21651 | 32.33 | 26.35 | 2.01 | 3.21 | 94.78 |
| 19527 | 47.24 | 56.67 | 112.09 | 11.81 | 94.78 |
| 1921 | 178.67 | 59.48 | 97.23 | 10.49 | 94.73 |
| 8988 | 56.52 | 38.39 | 8.71 | 5.65 | 94.73 |
| 6766 | 481.24 | 157.08 | 653.99 | 16.43 | 94.73 |
| 18862 | 47.30 | 24.54 | 31.00 | 1.20 | 94.69 |
| 15470 | 328.11 | 71.27 | 198.29 | 29.91 | 94.69 |
| 3288 | 10.56 | 13.80 | 41.78 | 12.82 | 94.69 |
| 23109 | 2081.66 | 927.60 | 2211.62 | 60.64 | 94.61 |
| 7197 | 197.55 | 84.70 | 290.53 | 17.88 | 94.56 |
| 7279 | 201.88 | 88.54 | 108.84 | 9.39 | 94.52 |
| 19581 | 48.08 | 32.46 | 66.08 | 3.68 | 94.48 |

TABLE 5G

CARBOPLATIN
Timepoint(s): 6 hrs

| Identifier | NonToxMean | NonToxSD | ToxMean | ToxSD | LDAScore |
|---|---|---|---|---|---|
| 6262 | 739.41 | 208.31 | 1532.53 | 76.80 | 99.61 |
| 24048 | 689.96 | 212.19 | 1411.28 | 55.30 | 99.36 |
| 17089 | 1547.81 | 626.59 | 4737.22 | 696.74 | 98.93 |
| 16081 | 115.61 | 379.88 | 645.20 | 213.95 | 98.54 |
| 25777 | 403.77 | 181.40 | 901.96 | 112.12 | 98.37 |
| 4933 | 134.08 | 204.01 | 525.52 | 82.57 | 98.20 |
| 7476 | 90.92 | 58.14 | 272.77 | 23.70 | 98.11 |
| 15171 | 241.90 | 97.44 | 403.05 | 21.96 | 98.03 |
| 24049 | 1518.47 | 439.97 | 2590.21 | 123.80 | 98.03 |
| 16080 | 44.66 | 251.23 | 378.60 | 161.27 | 97.99 |
| 10093 | 342.04 | 117.93 | 656.06 | 50.76 | 97.86 |
| 1069 | 1820.60 | 698.77 | 1513.87 | 16.71 | 97.64 |
| 25480 | 92.27 | 34.63 | 148.37 | 3.30 | 97.43 |
| 6647 | 510.34 | 159.21 | 1020.51 | 105.54 | 97.39 |
| 7247 | 504.54 | 113.43 | 793.61 | 51.11 | 97.34 |
| 18532 | 285.39 | 90.75 | 560.36 | 75.34 | 97.04 |
| 4067 | 123.93 | 59.96 | 232.57 | 36.85 | 96.92 |
| 23449 | 124.24 | 104.63 | 362.40 | 83.14 | 96.83 |
| 8314 | 95.89 | 403.64 | 202.84 | 47.87 | 96.79 |
| 14159 | 87.59 | 36.45 | 200.11 | 36.34 | 96.74 |
| 18280 | 584.52 | 131.77 | 819.56 | 51.87 | 96.70 |
| 23314 | 71.21 | 275.95 | 495.11 | 153.82 | 96.70 |
| 3816 | 326.31 | 77.12 | 471.75 | 21.93 | 96.66 |
| 17329 | 215.35 | 107.06 | 443.46 | 37.86 | 96.62 |
| 5461 | 193.57 | 116.65 | 442.55 | 77.30 | 96.57 |
| 22501 | 257.26 | 67.93 | 377.18 | 25.53 | 96.53 |
| 15277 | 900.30 | 154.78 | 1210.05 | 42.20 | 96.49 |
| 23538 | 101.09 | 71.79 | 256.02 | 74.72 | 96.44 |
| 8849 | 222.08 | 71.82 | 422.51 | 61.76 | 96.36 |
| 17779 | 1949.63 | 787.42 | 1501.46 | 41.41 | 96.36 |
| 23574 | 2277.50 | 970.11 | 1768.74 | 46.20 | 96.23 |
| 1127 | 1190.78 | 434.96 | 1227.98 | 24.14 | 96.14 |
| 4154 | 247.57 | 87.35 | 387.82 | 17.78 | 95.80 |
| 3471 | 80.41 | 35.57 | 126.92 | 4.34 | 95.76 |
| 22211 | 768.41 | 165.76 | 1038.58 | 34.89 | 95.72 |
| 21815 | 248.67 | 55.97 | 320.59 | 9.43 | 95.67 |
| 18597 | 521.69 | 163.32 | 851.48 | 104.45 | 95.63 |
| 2196 | 564.46 | 104.22 | 713.81 | 13.18 | 95.54 |
| 13598 | 350.22 | 110.18 | 570.66 | 47.31 | 95.46 |
| 16895 | 2022.10 | 903.47 | 1796.87 | 31.07 | 95.42 |
| 6522 | 571.58 | 153.62 | 693.92 | 15.58 | 95.42 |
| 8652 | 228.95 | 114.23 | 482.75 | 43.58 | 95.37 |
| 20026 | 64.36 | 24.25 | 120.87 | 11.23 | 95.33 |
| 15192 | 169.06 | 132.74 | 389.95 | 89.37 | 95.29 |
| 1622 | 2067.46 | 903.52 | 1573.48 | 71.56 | 95.29 |
| 3823 | 526.02 | 154.25 | 801.75 | 71.28 | 95.20 |
| 5989 | 269.96 | 71.53 | 419.90 | 36.98 | 95.12 |
| 3434 | 324.23 | 140.30 | 584.57 | 69.17 | 95.07 |
| 3156 | 1279.17 | 207.18 | 1810.46 | 187.54 | 95.03 |
| 10818 | 464.74 | 186.59 | 181.34 | 44.19 | 95.03 |
| 5575 | 86.94 | 36.56 | 34.41 | 8.85 | 94.99 |
| 11174 | 54.05 | 51.84 | 117.20 | 14.24 | 94.99 |
| 14425 | 213.74 | 79.18 | 349.63 | 37.59 | 94.94 |
| 16417 | 72.79 | 29.59 | 142.55 | 15.55 | 94.90 |
| 17771 | 769.30 | 306.35 | 1273.57 | 156.68 | 94.86 |
| 5208 | 1055.01 | 435.10 | 2101.50 | 490.32 | 94.82 |
| 3431 | 1514.30 | 636.90 | 1297.11 | 34.77 | 94.82 |
| 21462 | 258.49 | 59.82 | 358.44 | 18.51 | 94.77 |
| 3822 | 921.02 | 284.55 | 1300.83 | 99.42 | 94.73 |
| 15190 | 1824.97 | 1183.78 | 2141.03 | 82.58 | 94.69 |
| 19111 | 1604.90 | 429.51 | 2027.13 | 89.10 | 94.64 |
| 14906 | 383.54 | 73.03 | 535.04 | 39.09 | 94.47 |
| 13144 | −27.27 | 17.64 | −54.47 | 5.38 | 94.43 |
| 18142 | 1995.09 | 839.14 | 1819.48 | 43.33 | 94.39 |
| 13634 | 827.03 | 282.41 | 1137.48 | 107.16 | 94.34 |
| 2350 | 646.60 | 103.17 | 832.07 | 60.88 | 94.30 |
| 1537 | 31.35 | 46.10 | 59.58 | 13.80 | 94.26 |
| 13239 | 110.05 | 49.12 | 151.36 | 7.79 | 94.17 |
| 20864 | 1582.67 | 662.32 | 1722.73 | 33.76 | 94.13 |
| 12402 | 540.97 | 155.59 | 755.78 | 32.87 | 94.13 |
| 2424 | 585.64 | 132.80 | 807.06 | 45.48 | 94.13 |
| 15106 | 1894.10 | 713.95 | 1463.01 | 37.13 | 94.09 |
| 12569 | 402.63 | 145.28 | 719.92 | 106.90 | 94.04 |

TABLE 5G-continued

CARBOPLATIN
Timepoint(s): 6 hrs

| Identifier | NonToxMean | NonToxSD | Tox-Mean | ToxSD | LDAScore |
|---|---|---|---|---|---|
| 2022 | 270.40 | 55.81 | 378.75 | 24.92 | 93.83 |
| 13633 | 310.40 | 151.71 | 490.70 | 80.01 | 93.79 |
| 22197 | 123.97 | 52.28 | 217.39 | 36.02 | 93.79 |
| 13874 | 42.03 | 18.39 | 51.72 | 2.31 | 93.74 |
| 3533 | 212.11 | 64.89 | 298.00 | 11.86 | 93.74 |
| 5985 | 44.47 | 68.11 | 62.07 | 10.39 | 93.74 |
| 21643 | 1185.08 | 370.10 | 960.79 | 22.49 | 93.74 |
| 5089 | 70.77 | 28.48 | 123.98 | 19.48 | 93.74 |
| 17211 | 1445.11 | 555.30 | 1017.49 | 34.14 | 93.70 |
| 15772 | 28.16 | 13.60 | 23.47 | 26.74 | 93.66 |
| 25689 | 1435.28 | 508.41 | 1360.96 | 40.18 | 93.66 |
| 22545 | 252.03 | 89.09 | 444.84 | 127.61 | 93.62 |
| 11954 | 3134.66 | 1692.86 | 2572.78 | 105.71 | 93.57 |
| 8634 | 343.04 | 96.04 | 542.29 | 61.79 | 93.53 |
| 13771 | 91.36 | 32.90 | 152.72 | 14.45 | 93.53 |
| 14871 | 688.13 | 217.01 | 1066.71 | 67.36 | 93.53 |
| 25435 | 69.69 | 23.87 | 116.39 | 11.28 | 93.49 |
| 18076 | 2539.23 | 1190.89 | 2104.90 | 81.41 | 93.49 |
| 1660 | 6.16 | 20.59 | 24.43 | 41.71 | 93.44 |
| 20817 | 1076.80 | 681.07 | 1252.44 | 51.53 | 93.36 |
| 22923 | 57.85 | 40.50 | 3.36 | 7.47 | 93.32 |
| 20508 | 16.41 | 9.30 | 22.98 | 0.98 | 93.27 |
| 14304 | 95.81 | 30.28 | 138.83 | 9.76 | 93.23 |
| 23005 | 911.26 | 224.88 | 1191.71 | 45.14 | 93.23 |
| 16375 | 1004.76 | 291.14 | 1452.05 | 94.00 | 93.23 |
| 25754 | 73.97 | 20.01 | 103.72 | 4.72 | 93.19 |
| 820 | 2460.91 | 1164.05 | 2043.71 | 81.32 | 93.19 |

TABLE 5H

CEPHALORIDINE
Timepoint(s): 6, 24 hrs

| Identifier | NonToxMean | NonToxSD | Tox-Mean | ToxSD | LDAScore |
|---|---|---|---|---|---|
| 1698 | 72.61 | 72.54 | 355.15 | 57.50 | 98.88 |
| 25057 | −16.00 | 13.42 | 28.61 | 15.15 | 98.84 |
| 23302 | 115.35 | 36.99 | 250.40 | 26.19 | 98.45 |
| 25098 | 44.75 | 40.56 | 161.77 | 39.01 | 98.45 |
| 7022 | 6.54 | 19.86 | 87.07 | 26.85 | 98.45 |
| 18005 | 16.30 | 11.61 | 71.95 | 28.31 | 97.64 |
| 16318 | 111.73 | 57.76 | 214.34 | 48.82 | 97.59 |
| 15849 | 181.68 | 73.50 | 381.77 | 34.83 | 97.29 |
| 23283 | 520.93 | 94.30 | 765.95 | 70.15 | 97.25 |
| 651 | 12.40 | 11.40 | 69.75 | 44.55 | 97.16 |
| 16112 | 56.89 | 23.53 | 146.28 | 35.70 | 97.12 |
| 25198 | 33.14 | 18.60 | 104.50 | 28.93 | 97.12 |
| 8879 | 109.65 | 35.18 | 198.92 | 13.77 | 97.03 |
| 19253 | 280.76 | 74.42 | 450.66 | 32.07 | 97.03 |
| 15376 | 140.99 | 45.51 | 267.24 | 27.71 | 96.90 |
| 21038 | 113.15 | 45.28 | 284.43 | 88.10 | 96.82 |
| 20917 | 114.76 | 34.55 | 219.65 | 37.89 | 96.69 |
| 650 | 17.69 | 13.01 | 74.86 | 36.83 | 96.47 |
| 11411 | 252.17 | 76.16 | 422.51 | 26.01 | 96.35 |
| 343 | 28.78 | 32.80 | 129.29 | 21.40 | 96.35 |
| 16248 | 128.59 | 52.73 | 293.26 | 99.85 | 96.30 |
| 20843 | 165.02 | 37.03 | 274.00 | 60.23 | 96.30 |
| 18995 | 61.26 | 23.28 | 126.99 | 20.34 | 96.17 |
| 7050 | 68.24 | 24.46 | 116.13 | 10.21 | 95.92 |
| 20753 | 128.41 | 31.77 | 231.50 | 37.70 | 95.83 |
| 18084 | 36.85 | 19.15 | 95.80 | 24.41 | 95.83 |
| 1764 | 97.37 | 32.56 | 181.11 | 28.78 | 95.83 |
| 22413 | 73.51 | 35.54 | 155.12 | 24.23 | 95.74 |
| 12162 | 313.72 | 69.35 | 466.55 | 53.66 | 95.57 |
| 9573 | 313.16 | 70.67 | 449.88 | 24.42 | 95.53 |
| 5458 | 521.55 | 111.52 | 766.69 | 82.52 | 95.49 |
| 23889 | 170.87 | 60.58 | 320.41 | 74.89 | 95.49 |
| 1623 | 84.54 | 20.77 | 130.31 | 10.23 | 95.44 |
| 19254 | 240.06 | 74.71 | 400.30 | 44.56 | 95.31 |

TABLE 5H-continued

CEPHALORIDINE
Timepoint(s): 6, 24 hrs

| Identifier | NonToxMean | NonToxSD | Tox-Mean | ToxSD | LDAScore |
|---|---|---|---|---|---|
| 1628 | 13.93 | 10.20 | 37.44 | 6.38 | 95.27 |
| 672 | −2.45 | 13.09 | 33.39 | 16.62 | 95.27 |
| 1855 | 13.51 | 8.02 | 32.00 | 4.11 | 95.18 |
| 3900 | 83.63 | 36.44 | 170.88 | 42.74 | 95.14 |
| 15281 | 172.53 | 45.57 | 282.14 | 34.03 | 95.10 |
| 1582 | 16.73 | 13.23 | 46.93 | 7.97 | 95.10 |
| 25589 | 154.39 | 37.33 | 240.89 | 33.81 | 95.10 |
| 627 | 63.31 | 19.85 | 119.93 | 25.90 | 95.06 |
| 17434 | 163.74 | 49.10 | 263.86 | 22.79 | 95.01 |
| 21063 | 75.00 | 25.88 | 144.62 | 27.06 | 94.97 |
| 14353 | 61.97 | 20.12 | 119.73 | 30.32 | 94.93 |
| 6850 | 87.12 | 29.12 | 157.80 | 23.31 | 94.93 |
| 2059 | 139.66 | 39.69 | 243.75 | 48.13 | 94.84 |
| 16333 | 132.19 | 38.88 | 212.16 | 19.97 | 94.71 |
| 25377 | 31.75 | 20.09 | 77.51 | 19.81 | 94.50 |
| 23282 | 277.48 | 51.59 | 385.61 | 37.11 | 94.50 |
| 12058 | 109.37 | 35.93 | 194.17 | 43.87 | 94.45 |
| 9952 | 163.81 | 35.63 | 235.14 | 38.00 | 94.37 |
| 22196 | 58.71 | 24.71 | 123.83 | 37.19 | 94.37 |
| 16121 | 110.03 | 60.28 | 208.77 | 16.39 | 94.33 |
| 24640 | 177.93 | 59.42 | 295.24 | 35.00 | 94.33 |
| 1946 | 46.78 | 14.37 | 67.25 | 3.13 | 94.28 |
| 12259 | −0.17 | 9.62 | 21.16 | 7.74 | 94.15 |
| 6790 | 62.58 | 24.20 | 118.33 | 27.25 | 94.07 |
| 21802 | 45.94 | 21.21 | 103.13 | 35.44 | 94.07 |
| 14125 | 128.30 | 50.32 | 211.96 | 15.22 | 94.07 |
| 18183 | 31.28 | 14.65 | 67.29 | 14.30 | 94.02 |
| 17225 | 162.76 | 46.10 | 264.51 | 40.73 | 93.94 |
| 20514 | 83.93 | 25.89 | 146.04 | 21.67 | 93.94 |
| 1342 | 31.31 | 15.65 | 72.08 | 26.80 | 93.81 |
| 16616 | 88.26 | 37.98 | 165.12 | 31.68 | 93.77 |
| 4386 | 55.88 | 26.02 | 117.38 | 28.79 | 93.77 |
| 13464 | 30.34 | 17.92 | 75.47 | 19.34 | 93.68 |
| 11358 | 82.35 | 33.88 | 151.50 | 27.12 | 93.59 |
| 7866 | 43.15 | 16.17 | 81.51 | 16.07 | 93.51 |
| 22967 | 163.95 | 54.65 | 241.59 | 15.86 | 93.47 |
| 8385 | 57.15 | 28.33 | 114.53 | 19.32 | 93.42 |
| 24748 | −23.01 | 37.80 | 49.31 | 11.34 | 93.38 |
| 16059 | 50.12 | 14.86 | 84.72 | 17.27 | 93.38 |
| 16122 | 117.41 | 41.42 | 186.27 | 14.87 | 93.34 |
| 1350 | 143.74 | 30.94 | 209.15 | 28.63 | 93.34 |
| 8384 | 39.05 | 17.03 | 73.91 | 10.64 | 93.29 |
| 18259 | 216.96 | 155.49 | 545.75 | 138.45 | 93.28 |
| 20724 | 48.65 | 21.46 | 90.26 | 16.90 | 93.25 |
| 352 | 87.58 | 53.82 | 157.16 | 24.98 | 93.21 |
| 10740 | 26.94 | 24.94 | 69.61 | 15.31 | 93.12 |
| 1394 | 24.70 | 11.31 | 42.23 | 3.80 | 93.12 |
| 22466 | 462.31 | 92.72 | 638.40 | 68.34 | 92.99 |
| 13684 | 467.12 | 135.55 | 762.39 | 150.04 | 92.99 |
| 14768 | 85.99 | 47.21 | 225.50 | 66.59 | 92.98 |
| 13285 | 71.32 | 19.47 | 109.95 | 16.43 | 92.91 |
| 1537 | 29.82 | 40.75 | 245.05 | 131.87 | 92.90 |
| 18442 | 38.53 | 17.21 | 75.30 | 16.45 | 92.86 |
| 1183 | 52.85 | 29.47 | 214.38 | 101.63 | 92.85 |
| 127 | 19.05 | 14.19 | 48.31 | 9.93 | 92.73 |
| 1399 | 200.20 | 80.01 | 449.25 | 95.96 | 92.68 |
| 11203 | 75.19 | 24.99 | 127.88 | 16.58 | 92.65 |
| 870 | 22.03 | 9.87 | 40.53 | 4.22 | 92.61 |
| 4415 | 38.66 | 18.55 | 77.02 | 14.75 | 92.61 |
| 373 | 32.60 | 56.68 | 306.93 | 119.81 | 92.60 |
| 22524 | 112.62 | 47.12 | 195.09 | 26.00 | 92.56 |
| 6951 | 88.94 | 34.80 | 155.83 | 27.94 | 92.56 |
| 13023 | 176.39 | 400.42 | 1491.81 | 754.76 | 92.55 |
| 17836 | 102.26 | 27.02 | 156.20 | 28.41 | 92.48 |
| 7051 | 62.10 | 22.11 | 105.49 | 19.48 | 92.48 |
| 18749 | 115.18 | 42.04 | 202.78 | 33.94 | 92.39 |

TABLE 5I

CIDOFOVIR
Timepoint(s): 120 hrs

| Identifier | NonToxMean | NonToxSD | Tox-Mean | ToxSD | LDAScore |
|---|---|---|---|---|---|
| 18609 | 203.96 | 70.15 | 541.22 | 19.78 | 99.70 |
| 20674 | 83.03 | 21.84 | 203.76 | 22.76 | 99.61 |
| 4312 | 76.73 | 35.26 | 365.78 | 59.40 | 99.57 |
| 24041 | 12.84 | 32.48 | 31.93 | 0.33 | 99.53 |
| 5733 | 10.73 | 30.54 | 617.55 | 122.19 | 99.44 |
| 2768 | 1962.14 | 417.45 | 933.17 | 95.15 | 99.32 |
| 2410 | 11.13 | 10.13 | 64.03 | 13.02 | 99.32 |
| 14289 | 62.53 | 19.54 | 95.56 | 0.76 | 99.27 |
| 5689 | 12.82 | 19.88 | 85.25 | 13.41 | 99.23 |
| 14594 | −17.87 | 24.41 | 86.07 | 17.70 | 99.23 |
| 24000 | 64.13 | 33.98 | 157.59 | 7.48 | 99.19 |
| 8027 | 0.11 | 26.38 | 29.41 | 3.47 | 99.19 |
| 18322 | 2666.91 | 812.51 | 1165.22 | 99.03 | 99.06 |
| 7324 | 97.12 | 49.43 | 271.43 | 20.08 | 99.06 |
| 20903 | 70.06 | 46.59 | 288.96 | 29.37 | 99.06 |
| 20757 | 410.75 | 211.87 | 1571.32 | 228.32 | 98.97 |
| 1599 | 22.63 | 26.70 | 62.22 | 8.06 | 98.97 |
| 5183 | 215.17 | 70.24 | 445.78 | 24.68 | 98.97 |
| 4856 | 122.81 | 48.54 | 241.75 | 6.99 | 98.97 |
| 2655 | 42.27 | 39.82 | 529.96 | 152.39 | 98.97 |
| 10167 | 189.75 | 100.26 | 305.25 | 11.81 | 98.97 |
| 21275 | 225.36 | 80.40 | 666.87 | 94.23 | 98.93 |
| 22722 | 73.37 | 39.40 | 290.14 | 53.00 | 98.93 |
| 20082 | 75.76 | 32.27 | 258.55 | 44.96 | 98.93 |
| 912 | 474.15 | 83.63 | 764.00 | 33.56 | 98.84 |
| 8002 | 13.99 | 15.79 | 47.18 | 4.09 | 98.84 |
| 13158 | 463.87 | 106.89 | 360.87 | 1.60 | 98.80 |
| 10200 | 41.90 | 30.39 | 92.98 | 6.46 | 98.76 |
| 5572 | 332.45 | 146.31 | 611.55 | 14.40 | 98.67 |
| 410 | 1097.88 | 255.30 | 605.30 | 42.31 | 98.63 |
| 20755 | 145.36 | 116.99 | 986.50 | 562.94 | 98.63 |
| 23376 | 14.61 | 16.79 | 37.95 | 1.52 | 98.63 |
| 1600 | 44.38 | 66.08 | 114.35 | 13.26 | 98.63 |
| 25705 | 454.53 | 109.40 | 1132.56 | 152.81 | 98.59 |
| 13609 | 240.24 | 60.23 | 98.11 | 9.83 | 98.59 |
| 24219 | 315.68 | 82.27 | 692.16 | 77.33 | 98.59 |
| 26184 | 204.20 | 70.54 | 454.10 | 35.35 | 98.54 |
| 16081 | 117.80 | 381.49 | 136.30 | 8.26 | 98.54 |
| 7660 | 57.70 | 87.65 | 653.31 | 318.06 | 98.54 |
| 22681 | 222.75 | 194.18 | 580.89 | 50.39 | 98.54 |
| 9215 | 90.03 | 33.75 | 158.07 | 6.56 | 98.50 |
| 25699 | 137.08 | 68.59 | −11.79 | 8.27 | 98.50 |
| 4048 | −6.15 | 31.92 | 56.08 | 15.06 | 98.50 |
| 2729 | 640.63 | 170.18 | 328.03 | 37.57 | 98.50 |
| 15981 | 75.77 | 29.60 | 148.46 | 12.15 | 98.46 |
| 133 | −43.58 | 39.29 | 55.82 | 20.14 | 98.37 |
| 24707 | 47.32 | 82.24 | 10.71 | 1.68 | 98.37 |
| 6193 | 192.02 | 179.55 | 250.16 | 3.55 | 98.37 |
| 3981 | 72.52 | 103.32 | 368.64 | 91.18 | 98.37 |
| 21893 | 51.03 | 33.90 | 172.83 | 32.83 | 98.37 |
| 16168 | 350.38 | 204.48 | 829.66 | 132.95 | 98.37 |
| 4262 | 43.72 | 51.67 | 193.22 | 27.67 | 98.33 |
| 10289 | 14.87 | 14.48 | 127.47 | 59.89 | 98.24 |
| 17161 | 1157.45 | 414.68 | 2144.64 | 136.59 | 98.24 |
| 26150 | 780.06 | 534.26 | 32.24 | 49.38 | 98.24 |
| 3916 | 737.83 | 188.48 | 383.68 | 38.35 | 98.24 |
| 5839 | 5.98 | 20.99 | 59.41 | 8.18 | 98.16 |
| 26084 | 113.22 | 92.96 | 448.40 | 70.70 | 98.16 |
| 21654 | 362.77 | 114.65 | 543.47 | 30.13 | 98.12 |
| 26119 | 124.48 | 46.50 | 204.85 | 9.09 | 98.12 |
| 17314 | 6.10 | 12.64 | 43.93 | 7.10 | 98.07 |
| 353 | 173.67 | 81.62 | 475.77 | 74.64 | 98.07 |
| 16756 | 177.77 | 53.62 | 345.26 | 28.00 | 98.07 |
| 11437 | 555.26 | 125.28 | 290.62 | 37.25 | 98.07 |
| 24433 | 35.92 | 17.39 | 77.13 | 4.05 | 98.03 |
| 5464 | 225.07 | 67.79 | 427.11 | 46.05 | 97.99 |
| 15416 | 49.65 | 20.05 | 91.41 | 3.94 | 97.99 |
| 21948 | 203.26 | 65.91 | 33.57 | 32.91 | 97.99 |
| 18361 | 460.95 | 159.60 | 865.38 | 68.10 | 97.95 |
| 4049 | 22.90 | 64.75 | 174.30 | 49.09 | 97.90 |
| 6765 | 788.37 | 204.50 | 462.53 | 19.06 | 97.90 |
| 17401 | 910.82 | 424.91 | 1651.59 | 134.17 | 97.90 |
| 20830 | 519.62 | 176.96 | 850.57 | 34.74 | 97.86 |

TABLE 5I-continued

CIDOFOVIR
Timepoint(s): 120 hrs

| Identifier | NonToxMean | NonToxSD | Tox-Mean | ToxSD | LDAScore |
|---|---|---|---|---|---|
| 12908 | 40.69 | 40.63 | 135.60 | 42.31 | 97.86 |
| 19762 | 4.99 | 10.67 | 25.14 | 2.42 | 97.82 |
| 20457 | 382.89 | 90.62 | 215.96 | 13.41 | 97.82 |
| 5430 | 136.50 | 60.64 | 401.60 | 97.31 | 97.82 |
| 15300 | 137.15 | 130.99 | 496.58 | 110.00 | 97.73 |
| 11259 | 107.70 | 137.96 | 508.22 | 165.85 | 97.73 |
| 3808 | 168.07 | 57.61 | 297.97 | 55.59 | 97.73 |
| 22050 | 3164.11 | 929.00 | 1779.72 | 124.06 | 97.73 |
| 4451 | 290.06 | 65.29 | 164.79 | 13.86 | 97.73 |
| 16170 | 38.98 | 26.45 | 97.44 | 18.88 | 97.69 |
| 13332 | 420.04 | 95.61 | 169.12 | 30.12 | 97.69 |
| 15861 | 460.82 | 148.89 | 174.40 | 29.65 | 97.69 |
| 6606 | 251.17 | 124.12 | 178.93 | 1.98 | 97.65 |
| 19370 | 308.80 | 74.48 | 551.57 | 63.31 | 97.65 |
| 3874 | 883.32 | 205.24 | 530.31 | 28.27 | 97.65 |
| 20991 | 224.15 | 69.07 | 195.44 | 2.64 | 97.60 |
| 18811 | 46.63 | 26.47 | 80.60 | 1.75 | 97.60 |
| 5881 | 103.14 | 35.12 | 184.15 | 16.55 | 97.60 |
| 354 | 214.95 | 93.98 | 490.19 | 69.08 | 97.56 |
| 11454 | 238.74 | 78.96 | 470.27 | 65.91 | 97.56 |
| 12873 | 122.01 | 67.80 | 366.63 | 64.37 | 97.56 |
| 20829 | 813.56 | 302.89 | 1539.75 | 129.65 | 97.56 |
| 17807 | 753.81 | 228.33 | 1314.67 | 146.81 | 97.56 |
| 8585 | 289.56 | 118.65 | 190.91 | 6.78 | 97.56 |
| 8215 | 1680.14 | 394.54 | 881.26 | 110.65 | 97.56 |
| 14763 | 38.37 | 132.57 | 554.64 | 221.30 | 97.52 |

TABLE 5J

CISPAN combined
Timepoint(s): 6, 24 hrs

| Identifier | NonToxMean | NonToxSD | Tox-Mean | ToxSD | LDAScore |
|---|---|---|---|---|---|
| 8990 | 276.73 | 75.18 | 522.76 | 68.28 | 96.93 |
| 1460 | 198.36 | 85.83 | 320.23 | 42.90 | 95.60 |
| 16853 | 67.12 | 22.69 | 121.67 | 21.69 | 95.08 |
| 13239 | 108.86 | 47.65 | 222.86 | 33.91 | 94.73 |
| 21355 | 373.47 | 117.15 | 627.82 | 92.43 | 94.69 |
| 6454 | 238.70 | 77.20 | 419.87 | 47.88 | 94.69 |
| 1247 | 1313.77 | 499.48 | 559.96 | 117.97 | 94.56 |
| 6506 | 233.04 | 59.13 | 375.55 | 54.15 | 94.34 |
| 1585 | 67.19 | 32.77 | 140.57 | 23.52 | 94.26 |
| 1962 | 33.04 | 26.70 | 76.49 | 11.48 | 94.17 |
| 18433 | 18.64 | 45.96 | 123.81 | 42.15 | 94.13 |
| 15050 | 638.79 | 181.52 | 459.28 | 26.53 | 94.04 |
| 17693 | 1261.20 | 375.03 | 651.01 | 91.79 | 93.87 |
| 4956 | 78.53 | 37.78 | 155.47 | 25.21 | 93.65 |
| 16233 | 68.67 | 88.34 | 117.42 | 12.47 | 93.18 |
| 11445 | 435.55 | 103.48 | 642.14 | 86.21 | 92.62 |
| 8004 | 125.10 | 43.16 | 255.80 | 43.43 | 92.37 |
| 1811 | 10.62 | 25.84 | 83.04 | 26.96 | 92.28 |
| 1542 | 929.09 | 263.76 | 560.16 | 66.12 | 91.97 |
| 16591 | 151.89 | 47.44 | 236.90 | 29.21 | 91.84 |
| 18694 | 52.90 | 48.32 | 176.24 | 47.08 | 91.68 |
| 11524 | −14.63 | 24.06 | 46.43 | 29.33 | 91.59 |
| 19080 | 75.03 | 55.99 | 212.58 | 72.04 | 91.20 |
| 20514 | 83.88 | 26.10 | 127.69 | 12.79 | 91.19 |
| 15701 | 37.45 | 16.42 | 79.72 | 13.34 | 91.16 |
| 16122 | 116.73 | 39.95 | 217.85 | 62.09 | 90.99 |
| 2079 | 303.23 | 81.83 | 406.18 | 33.43 | 90.98 |
| 19327 | 88.79 | 28.83 | 152.22 | 21.27 | 90.86 |
| 335 | 95.54 | 44.88 | 191.73 | 23.12 | 90.86 |
| 14003 | 817.87 | 211.94 | 491.17 | 61.11 | 90.86 |
| 9104 | 138.43 | 38.55 | 221.59 | 41.76 | 90.69 |
| 25253 | 291.50 | 63.92 | 430.49 | 54.59 | 90.69 |
| 23322 | 1169.44 | 284.23 | 807.96 | 73.20 | 90.67 |
| 24696 | 68.34 | 46.61 | 180.46 | 53.14 | 90.60 |
| 1552 | 71.02 | 83.66 | 121.56 | 15.30 | 90.54 |

TABLE 5J-continued

CISPAN combined
Timepoint(s): 6, 24 hrs

| Identifier | NonToxMean | NonToxSD | Tox-Mean | ToxSD | LDAScore |
|---|---|---|---|---|---|
| 19120 | 31.87 | 24.91 | 90.61 | 26.26 | 90.51 |
| 17411 | 78.54 | 53.72 | 189.16 | 45.14 | 90.51 |
| 16121 | 109.00 | 58.08 | 258.63 | 87.07 | 90.47 |
| 1639 | 96.38 | 22.51 | 149.03 | 17.77 | 90.43 |
| 1622 | 2080.70 | 896.54 | 796.36 | 153.89 | 90.41 |
| 9882 | 487.60 | 181.11 | 245.48 | 60.74 | 90.41 |
| 23852 | 261.73 | 101.88 | 487.29 | 97.17 | 90.38 |
| 13684 | 465.64 | 134.08 | 778.77 | 108.34 | 90.38 |
| 7857 | 51.80 | 45.32 | 150.23 | 38.24 | 90.38 |
| 6281 | 232.74 | 67.04 | 343.63 | 49.82 | 90.34 |
| 15790 | 45.82 | 25.45 | 87.17 | 18.57 | 90.24 |
| 23884 | 40.55 | 32.64 | 101.67 | 19.55 | 90.21 |
| 17682 | 673.97 | 178.07 | 455.67 | 77.33 | 90.16 |
| 16581 | 39.15 | 19.04 | 83.46 | 15.21 | 90.12 |
| 24390 | 161.41 | 112.42 | 367.16 | 79.88 | 90.08 |
| 3886 | 57.66 | 28.30 | 124.53 | 24.81 | 90.08 |
| 13682 | 176.78 | 61.74 | 302.10 | 50.60 | 90.04 |
| 7262 | 1113.30 | 393.42 | 1879.06 | 245.81 | 90.00 |
| 11954 | 3158.62 | 1682.02 | 952.13 | 425.90 | 89.98 |
| 818 | 4151.32 | 2802.74 | 902.92 | 257.41 | 89.94 |
| 819 | 3116.95 | 1659.72 | 925.18 | 255.80 | 89.90 |
| 16211 | 2269.84 | 1132.19 | 853.70 | 212.63 | 89.90 |
| 1521 | 20.42 | 50.86 | 117.89 | 40.21 | 89.78 |
| 23125 | 4625.10 | 2534.40 | 1935.15 | 332.35 | 89.77 |
| 9109 | 1022.92 | 338.20 | 736.62 | 48.42 | 89.77 |
| 10141 | 53.73 | 45.97 | 150.14 | 52.96 | 89.69 |
| 152 | 72.28 | 26.46 | 108.76 | 14.84 | 89.68 |
| 17154 | 198.73 | 57.61 | 281.13 | 33.91 | 89.59 |
| 6362 | 62.35 | 38.95 | 146.74 | 29.87 | 89.56 |
| 10540 | 19.51 | 18.83 | 64.08 | 25.25 | 89.52 |
| 651 | 12.58 | 12.76 | 33.89 | 11.18 | 89.52 |
| 17086 | 151.38 | 43.21 | 214.56 | 21.12 | 89.51 |
| 12020 | 167.06 | 60.45 | 260.26 | 34.23 | 89.51 |
| 4121 | 62.05 | 23.29 | 113.40 | 19.65 | 89.43 |
| 8211 | 2875.40 | 1605.55 | 956.21 | 247.45 | 89.38 |
| 20404 | 53.25 | 45.78 | 130.86 | 32.28 | 89.35 |
| 7522 | 31.59 | 18.74 | 75.54 | 18.10 | 89.30 |
| 20879 | 87.24 | 50.13 | 179.14 | 40.07 | 89.26 |
| 17550 | 1318.67 | 366.65 | 860.58 | 175.55 | 89.25 |
| 21950 | 727.03 | 149.84 | 534.23 | 70.97 | 89.21 |
| 25405 | 77.77 | 28.49 | 139.55 | 22.89 | 89.17 |
| 14125 | 127.72 | 49.56 | 229.81 | 40.28 | 89.17 |
| 1611 | 8.22 | 23.65 | 52.29 | 18.59 | 89.13 |
| 21685 | 122.94 | 42.72 | 207.33 | 33.76 | 89.13 |
| 17524 | 1176.52 | 284.08 | 761.61 | 160.07 | 89.09 |
| 10611 | 10.59 | 27.29 | 104.61 | 49.13 | 89.06 |
| 22849 | 197.26 | 50.25 | 298.83 | 40.93 | 89.00 |
| 1608 | 12.43 | 29.83 | 56.08 | 17.26 | 89.00 |
| 4312 | 76.57 | 37.18 | 172.28 | 72.36 | 88.97 |
| 1396 | 47.24 | 18.54 | 84.98 | 24.01 | 88.92 |
| 20871 | 52.42 | 25.81 | 108.86 | 22.74 | 88.92 |
| 10344 | 22.14 | 21.48 | 62.29 | 12.19 | 88.83 |
| 15587 | 38.29 | 19.07 | 66.30 | 11.60 | 88.82 |
| 9096 | 9634.12 | 6768.62 | 2697.48 | 901.04 | 88.82 |
| 4290 | 94.06 | 28.34 | 144.64 | 19.10 | 88.79 |
| 24143 | 192.56 | 96.48 | 385.57 | 70.47 | 88.74 |
| 12174 | 80.77 | 29.46 | 139.07 | 31.48 | 88.74 |
| 17336 | 65.85 | 21.84 | 107.99 | 13.40 | 88.74 |
| 25257 | 101.83 | 34.03 | 168.25 | 31.38 | 88.74 |
| 20350 | 154.58 | 49.68 | 245.00 | 41.28 | 88.70 |
| 11335 | 661.49 | 162.55 | 459.38 | 57.71 | 88.64 |
| 24146 | 219.42 | 50.91 | 370.23 | 55.30 | 88.63 |
| 16254 | 5.55 | 11.81 | 26.92 | 12.39 | 88.61 |
| 20879 | 1683.23 | 611.09 | 940.93 | 123.03 | 88.60 |
| 9312 | 31.90 | 15.15 | 74.64 | 21.22 | 88.58 |

TABLE 5K

CISPLATIN
Timepoint(s): 168 hrs

| Identifier | NonToxMean | NonToxSD | Tox-Mean | ToxSD | LDAScore |
|---|---|---|---|---|---|
| 14458 | 36.84 | 28.40 | 100.33 | 0.26 | 99.96 |
| 22385 | 106.64 | 51.70 | 345.64 | 8.69 | 99.87 |
| 11731 | 43.29 | 24.10 | 393.30 | 43.69 | 99.87 |
| 23745 | 201.94 | 65.06 | 823.60 | 110.42 | 99.83 |
| 12903 | 53.64 | 18.74 | 124.32 | 6.90 | 99.83 |
| 15503 | 124.27 | 37.32 | 319.29 | 21.43 | 99.79 |
| 8235 | 43.83 | 34.77 | 145.95 | 18.00 | 99.79 |
| 16756 | 177.83 | 53.82 | 327.44 | 3.02 | 99.74 |
| 16119 | 15.30 | 15.19 | 84.22 | 6.17 | 99.74 |
| 11967 | 1725.18 | 546.07 | 289.45 | 25.19 | 99.74 |
| 3608 | 333.84 | 110.50 | 62.62 | 5.74 | 99.70 |
| 18729 | 19.92 | 29.07 | 174.49 | 19.16 | 99.61 |
| 5891 | −53.03 | 47.69 | 106.02 | 18.28 | 99.61 |
| 2048 | 31.69 | 20.74 | 125.19 | 16.43 | 99.61 |
| 4490 | 76.73 | 72.26 | 462.55 | 50.86 | 99.61 |
| 1743 | 29.35 | 16.21 | 72.89 | 1.22 | 99.61 |
| 1584 | 162.19 | 43.70 | 307.85 | 8.25 | 99.57 |
| 16137 | 6.75 | 397.82 | 87.49 | 8.36 | 99.53 |
| 23778 | 68.99 | 34.04 | 179.58 | 9.21 | 99.53 |
| 23261 | 1568.96 | 389.70 | 925.80 | 13.87 | 99.53 |
| 808 | 468.33 | 143.61 | 160.94 | 9.90 | 99.53 |
| 1962 | 33.33 | 26.74 | 101.07 | 4.72 | 99.53 |
| 21789 | 34.67 | 30.58 | 177.40 | 21.84 | 99.53 |
| 23769 | −6.24 | 8.69 | 33.99 | 6.30 | 99.53 |
| 23070 | 125.37 | 31.23 | 218.44 | 4.95 | 99.49 |
| 12400 | 13.19 | 10.48 | 74.60 | 11.18 | 99.49 |
| 16676 | 38.33 | 26.96 | 110.79 | 5.32 | 99.49 |
| 23780 | 25.07 | 35.93 | 95.20 | 12.81 | 99.44 |
| 25545 | 94.29 | 48.16 | 306.94 | 34.66 | 99.44 |
| 15254 | 209.66 | 67.16 | 447.21 | 21.22 | 99.44 |
| 23992 | 5.39 | 7.25 | 34.45 | 3.17 | 99.44 |
| 14430 | 34.19 | 31.78 | 125.29 | 8.54 | 99.40 |
| 11969 | 96.84 | 38.48 | 303.71 | 38.83 | 99.40 |
| 4312 | 77.16 | 37.99 | 241.97 | 24.41 | 99.40 |
| 4967 | 33.46 | 19.94 | 94.30 | 3.72 | 99.36 |
| 2079 | 303.69 | 81.26 | 527.92 | 20.78 | 99.32 |
| 22816 | 23.12 | 15.17 | 89.33 | 8.69 | 99.32 |
| 3609 | 407.50 | 148.70 | 67.97 | 9.33 | 99.32 |
| 4361 | 90.16 | 30.77 | 193.28 | 10.19 | 99.32 |
| 13682 | 177.74 | 62.54 | 333.83 | 4.20 | 99.32 |
| 15504 | 129.02 | 50.62 | 447.33 | 63.50 | 99.27 |
| 633 | 271.13 | 101.41 | 110.07 | 15.08 | 99.27 |
| 21183 | 22.62 | 26.03 | 134.40 | 19.53 | 99.27 |
| 24222 | 101.20 | 52.50 | 460.48 | 61.63 | 99.27 |
| 8548 | 63.06 | 30.22 | 6.09 | 1.52 | 99.27 |
| 24301 | 109.26 | 35.74 | 248.67 | 13.48 | 99.27 |
| 18442 | 38.61 | 17.15 | 99.87 | 5.14 | 99.27 |
| 14370 | 32.54 | 45.58 | 189.80 | 11.25 | 99.23 |
| 21500 | 80.36 | 76.69 | 471.24 | 73.44 | 99.23 |
| 24211 | 148.45 | 87.73 | 552.73 | 49.74 | 99.23 |
| 770 | 798.02 | 219.52 | 248.56 | 33.80 | 99.23 |
| 21791 | 84.31 | 36.00 | 242.62 | 24.88 | 99.23 |
| 24651 | 100.74 | 23.52 | 203.14 | 12.02 | 99.23 |
| 17897 | 53.72 | 25.98 | 111.75 | 3.84 | 99.23 |
| 20890 | 101.09 | 46.35 | 342.52 | 50.55 | 99.19 |
| 712 | 1.36 | 9.08 | 60.25 | 14.12 | 99.19 |
| 18553 | 54.23 | 33.42 | 166.80 | 12.30 | 99.19 |
| 15884 | 183.00 | 57.89 | 383.85 | 23.01 | 99.19 |
| 19722 | 168.71 | 55.03 | 336.25 | 15.95 | 99.19 |
| 17481 | 26.11 | 28.66 | 137.39 | 13.89 | 99.19 |
| 5733 | 12.25 | 46.24 | 172.15 | 34.99 | 99.19 |
| 4895 | 232.18 | 95.74 | 44.77 | 8.48 | 99.14 |
| 15151 | 153.83 | 39.15 | 302.83 | 29.57 | 99.14 |
| 14759 | 21.72 | 15.86 | 78.25 | 9.50 | 99.14 |
| 15039 | 272.18 | 79.33 | 101.53 | 6.80 | 99.14 |
| 12782 | 20.00 | 43.24 | 135.93 | 6.16 | 99.14 |
| 23121 | 19.80 | 13.92 | 60.40 | 2.66 | 99.14 |
| 26292 | 22.82 | 12.83 | 85.01 | 11.49 | 99.14 |
| 2154 | 59.03 | 121.05 | 244.16 | 33.75 | 99.14 |
| 21583 | 125.87 | 40.62 | 270.04 | 27.65 | 99.14 |
| 3006 | 26.57 | 35.44 | 81.75 | 9.18 | 99.10 |
| 1203 | 5.08 | 18.58 | 86.62 | 14.26 | 99.10 |
| 24472 | 234.56 | 47.65 | 380.85 | 13.16 | 99.10 |

TABLE 5K-continued

CISPLATIN
Timepoint(s): 168 hrs

| Identifier | NonToxMean | NonToxSD | Tox-Mean | ToxSD | LDAScore |
|---|---|---|---|---|---|
| 5729 | 87.49 | 38.35 | 274.95 | 40.90 | 99.10 |
| 132 | −24.93 | 23.56 | 50.93 | 12.76 | 99.10 |
| 1801 | 97.64 | 29.41 | 197.50 | 14.44 | 99.10 |
| 1993 | 30.09 | 21.86 | 117.89 | 9.03 | 99.10 |
| 16675 | 33.74 | 34.04 | 112.81 | 11.29 | 99.10 |
| 1382 | 57.80 | 21.22 | 127.59 | 5.60 | 99.10 |
| 17586 | 115.18 | 35.27 | 246.61 | 21.48 | 99.06 |
| 21666 | 22.81 | 17.92 | 87.38 | 6.42 | 99.06 |
| 2125 | 76.55 | 80.69 | 345.60 | 72.31 | 99.06 |
| 21709 | 142.70 | 29.95 | 215.46 | 6.19 | 99.06 |
| 16538 | 132.96 | 36.43 | 245.73 | 9.25 | 99.06 |
| 2845 | 667.61 | 123.51 | 1098.14 | 42.15 | 99.02 |
| 753 | 42.04 | 16.33 | 120.03 | 23.17 | 99.02 |
| 21893 | 50.92 | 33.48 | 203.93 | 25.50 | 99.02 |
| 21836 | 29.24 | 16.81 | 91.95 | 8.44 | 99.02 |
| 21817 | 10.63 | 13.30 | 59.28 | 7.00 | 99.02 |
| 6517 | 231.85 | 156.64 | 721.49 | 128.57 | 99.02 |
| 1588 | 61.92 | 22.15 | 122.71 | 6.97 | 99.02 |
| 14564 | 48.33 | 23.27 | 104.89 | 3.20 | 99.02 |
| 3079 | 34.64 | 46.77 | 152.78 | 26.18 | 98.97 |
| 7602 | 193.69 | 43.89 | 364.34 | 31.12 | 98.97 |
| 20816 | 393.33 | 173.56 | 774.42 | 37.69 | 98.97 |
| 6322 | 18.88 | 17.54 | 122.95 | 22.89 | 98.97 |
| 17337 | 510.70 | 139.07 | 253.28 | 6.67 | 98.97 |
| 18161 | 114.11 | 43.86 | 244.42 | 22.79 | 98.97 |
| 4057 | 64.54 | 20.73 | 139.42 | 12.02 | 98.97 |
| 22552 | 314.43 | 92.85 | 696.18 | 70.05 | 98.93 |

TABLE 5L

CISPLATIN
Timepoint(s): 6, 24 hrs

| Identifier | NonToxMean | NonToxSD | Tox-Mean | ToxSD | LDAScore |
|---|---|---|---|---|---|
| 20082 | 75.47 | 31.84 | 228.60 | 43.28 | 98.84 |
| 1598 | 47.75 | 56.92 | 133.89 | 25.63 | 98.58 |
| 15313 | 11.08 | 24.34 | 53.59 | 5.89 | 98.54 |
| 2655 | 43.13 | 48.31 | 177.30 | 66.12 | 98.20 |
| 14424 | 66.72 | 130.96 | 272.03 | 63.86 | 97.85 |
| 17314 | 5.89 | 11.89 | 63.70 | 27.83 | 97.85 |
| 21275 | 225.06 | 80.71 | 528.11 | 144.80 | 97.68 |
| 4047 | 85.85 | 50.33 | 190.04 | 23.02 | 97.60 |
| 20116 | 9.55 | 31.45 | 124.39 | 50.70 | 97.38 |
| 15382 | 122.93 | 203.50 | 341.43 | 85.17 | 97.34 |
| 1521 | 20.82 | 51.01 | 148.25 | 24.41 | 97.30 |
| 24146 | 220.17 | 51.83 | 396.31 | 40.61 | 97.30 |
| 8990 | 278.10 | 77.14 | 540.97 | 69.47 | 97.21 |
| 1884 | 178.33 | 37.79 | 272.14 | 18.27 | 97.17 |
| 4933 | 134.55 | 205.15 | 335.87 | 89.54 | 97.04 |
| 6506 | 233.65 | 59.50 | 415.92 | 45.52 | 97.04 |
| 4944 | 112.31 | 56.05 | 264.36 | 39.37 | 96.95 |
| 8004 | 125.79 | 44.06 | 271.11 | 40.68 | 96.95 |
| 1993 | 30.02 | 21.93 | 91.88 | 19.85 | 96.91 |
| 20506 | 21.57 | 7.97 | 46.99 | 7.30 | 96.82 |
| 21462 | 257.92 | 58.72 | 424.63 | 52.75 | 96.78 |
| 6974 | 129.50 | 46.90 | 236.12 | 28.32 | 96.78 |
| 11549 | 243.07 | 64.12 | 425.53 | 38.72 | 96.74 |
| 2905 | 245.79 | 107.78 | 488.69 | 56.33 | 96.74 |
| 1811 | 10.99 | 26.26 | 94.19 | 25.01 | 96.70 |
| 10839 | 313.60 | 67.83 | 533.54 | 83.77 | 96.70 |
| 2468 | 252.35 | 62.46 | 433.73 | 70.78 | 96.61 |
| 373 | 33.94 | 61.41 | 162.88 | 51.32 | 96.57 |
| 19040 | 186.25 | 107.25 | 258.19 | 19.20 | 96.57 |
| 15299 | 87.98 | 61.10 | 206.62 | 59.64 | 96.57 |
| 13684 | 467.21 | 135.45 | 831.58 | 69.76 | 96.52 |
| 910 | 57.76 | 21.93 | 136.53 | 45.93 | 96.35 |
| 4477 | 11.91 | 8.60 | 37.00 | 7.79 | 96.27 |
| 20871 | 52.68 | 25.99 | 122.97 | 14.46 | 96.22 |
| 16853 | 67.36 | 22.84 | 136.28 | 21.27 | 96.18 |
| 23473 | 156.94 | 56.94 | 338.21 | 73.37 | 96.18 |
| 2536 | 393.91 | 124.60 | 585.25 | 20.89 | 96.14 |
| 10015 | 232.29 | 77.80 | 340.64 | 28.00 | 96.14 |
| 18694 | 53.51 | 48.91 | 198.02 | 43.87 | 96.09 |
| 16284 | 40.93 | 27.58 | 129.79 | 27.84 | 96.09 |
| 18375 | 121.97 | 28.16 | 198.57 | 23.40 | 96.05 |
| 23314 | 70.46 | 275.32 | 498.55 | 211.58 | 96.05 |
| 651 | 12.67 | 12.78 | 40.79 | 8.43 | 95.97 |
| 3266 | 133.11 | 36.44 | 247.88 | 45.93 | 95.97 |
| 1460 | 198.97 | 85.95 | 340.15 | 49.64 | 95.97 |
| 20065 | 86.81 | 30.90 | 170.50 | 27.85 | 95.97 |
| 15301 | 38.37 | 68.10 | 96.58 | 21.67 | 95.92 |
| 23448 | 169.78 | 101.84 | 327.19 | 44.52 | 95.92 |
| 15003 | 36.27 | 96.97 | 63.65 | 10.34 | 95.88 |
| 26184 | 203.75 | 69.61 | 423.29 | 118.85 | 95.88 |
| 8336 | 26.96 | 37.28 | 139.71 | 61.60 | 95.79 |
| 6362 | 62.77 | 39.27 | 160.35 | 23.77 | 95.75 |
| 14003 | 815.94 | 212.81 | 484.61 | 51.19 | 95.67 |
| 9339 | 357.63 | 88.22 | 598.27 | 74.10 | 95.62 |
| 6384 | 60.88 | 59.65 | 127.67 | 27.22 | 95.54 |
| 15345 | 201.66 | 67.69 | 322.91 | 40.01 | 95.45 |
| 22849 | 197.75 | 50.59 | 318.11 | 30.11 | 95.41 |
| 23868 | 178.04 | 289.84 | 277.77 | 47.26 | 95.41 |
| 16233 | 68.93 | 88.14 | 123.52 | 11.88 | 95.36 |
| 6454 | 239.80 | 78.37 | 418.57 | 35.68 | 95.36 |
| 21061 | 58.86 | 27.77 | 128.21 | 17.87 | 95.36 |
| 24143 | 193.56 | 97.20 | 413.21 | 53.39 | 95.32 |
| 15296 | 137.87 | 56.84 | 269.21 | 33.23 | 95.32 |
| 22374 | 148.45 | 41.20 | 247.50 | 28.04 | 95.28 |
| 13239 | 109.46 | 48.17 | 236.67 | 36.75 | 95.28 |
| 8768 | 64.97 | 26.90 | 141.33 | 30.56 | 95.28 |
| 1542 | 927.15 | 264.15 | 512.83 | 50.15 | 95.28 |
| 22352 | 156.66 | 103.69 | 254.35 | 25.00 | 95.24 |
| 14051 | 133.17 | 35.29 | 219.32 | 28.80 | 95.24 |
| 9343 | 189.65 | 67.21 | 349.25 | 44.44 | 95.24 |
| 1247 | 1309.30 | 501.39 | 550.55 | 103.22 | 95.19 |
| 7857 | 52.35 | 45.86 | 156.83 | 28.07 | 95.19 |
| 11727 | 230.50 | 78.02 | 409.08 | 59.02 | 95.19 |
| 1639 | 96.67 | 22.79 | 153.44 | 17.91 | 95.11 |
| 15374 | 138.74 | 36.97 | 231.57 | 31.99 | 95.02 |
| 3899 | 141.45 | 61.33 | 242.19 | 14.71 | 94.98 |
| 25405 | 78.08 | 28.73 | 149.92 | 18.38 | 94.98 |
| 23872 | 49.59 | 92.93 | 101.10 | 24.53 | 94.98 |
| 24368 | 244.08 | 80.76 | 439.99 | 52.18 | 94.98 |
| 10818 | 465.48 | 185.96 | 140.29 | 49.38 | 94.98 |
| 17693 | 1257.86 | 376.37 | 596.02 | 96.76 | 94.98 |
| 25253 | 292.22 | 64.49 | 449.51 | 58.18 | 94.89 |
| 11708 | 319.92 | 92.39 | 486.60 | 46.21 | 94.89 |
| 17908 | 63.14 | 60.90 | 124.23 | 27.40 | 94.89 |
| 24028 | 407.75 | 96.21 | 644.04 | 67.17 | 94.85 |
| 11455 | 115.78 | 48.10 | 202.56 | 32.14 | 94.85 |
| 20870 | 19.10 | 29.21 | 92.31 | 26.59 | 94.81 |
| 3931 | 94.55 | 29.06 | 155.45 | 15.94 | 94.68 |
| 6581 | 76.02 | 26.19 | 132.63 | 10.11 | 94.68 |
| 1447 | 208.86 | 37.67 | 272.57 | 11.93 | 94.64 |
| 22501 | 257.01 | 67.60 | 383.79 | 63.10 | 94.64 |
| 10720 | 153.08 | 43.55 | 217.97 | 97.98 | 94.64 |
| 20591 | 25.22 | 22.60 | 68.79 | 11.62 | 94.59 |
| 1292 | 62.12 | 24.60 | 116.95 | 15.58 | 94.55 |
| 21355 | 374.95 | 118.50 | 635.77 | 102.99 | 94.51 |
| 23852 | 262.89 | 102.86 | 519.85 | 100.21 | 94.51 |
| 18689 | 360.99 | 81.71 | 541.28 | 55.93 | 94.51 |
| 4426 | 222.88 | 38.63 | 305.45 | 29.97 | 94.51 |
| 23563 | 24.57 | 33.24 | 96.80 | 28.33 | 94.46 |

TABLE 5M

CISPLATIN
Timepoint(s): 6, 24, 168 hrs

| Identifier | NonToxMean | NonToxSD | Tox-Mean | ToxSD | LDAScore |
|---|---|---|---|---|---|
| 1521 | 20.35 | 50.42 | 152.11 | 27.16 | 97.37 |
| 1884 | 178.00 | 37.40 | 272.66 | 21.76 | 97.03 |
| 16284 | 40.57 | 26.94 | 134.66 | 25.22 | 96.99 |
| 18694 | 52.96 | 48.08 | 203.55 | 35.96 | 96.77 |
| 10839 | 312.93 | 66.86 | 524.22 | 78.99 | 96.77 |
| 11549 | 242.48 | 63.43 | 420.82 | 36.27 | 96.73 |
| 8990 | 277.44 | 76.38 | 515.35 | 72.77 | 96.60 |
| 6362 | 62.37 | 38.73 | 167.05 | 23.05 | 96.60 |
| 1811 | 10.74 | 25.96 | 89.58 | 21.97 | 96.60 |
| 4477 | 11.83 | 8.50 | 36.45 | 6.35 | 96.55 |
| 4047 | 85.57 | 50.18 | 181.03 | 26.48 | 96.55 |
| 16853 | 67.12 | 22.50 | 136.44 | 18.16 | 96.55 |
| 3266 | 132.70 | 35.81 | 249.33 | 37.38 | 96.47 |
| 13684 | 466.14 | 134.44 | 811.93 | 63.86 | 96.47 |
| 2905 | 244.60 | 105.83 | 525.71 | 99.02 | 96.43 |
| 1460 | 198.53 | 85.75 | 335.50 | 43.05 | 96.38 |
| 23314 | 69.18 | 274.82 | 477.84 | 185.93 | 96.25 |
| 17693 | 1260.38 | 374.54 | 570.60 | 88.76 | 96.21 |
| 15301 | 38.18 | 68.12 | 96.20 | 20.88 | 96.12 |
| 17894 | 46.77 | 18.63 | 103.03 | 28.25 | 96.08 |
| 10015 | 231.46 | 76.52 | 389.17 | 82.89 | 95.99 |
| 19040 | 185.68 | 106.97 | 292.78 | 52.89 | 95.95 |
| 18375 | 121.75 | 27.96 | 193.24 | 20.67 | 95.74 |
| 4426 | 222.53 | 38.25 | 311.48 | 25.65 | 95.74 |
| 7857 | 51.97 | 45.46 | 159.10 | 25.13 | 95.65 |
| 6454 | 239.16 | 77.72 | 421.14 | 34.72 | 95.65 |
| 15296 | 137.17 | 55.52 | 295.99 | 61.04 | 95.56 |
| 10818 | 467.00 | 184.46 | 97.87 | 70.28 | 95.52 |
| 23852 | 261.84 | 101.45 | 536.68 | 85.55 | 95.52 |
| 1542 | 928.65 | 263.36 | 505.79 | 51.94 | 95.48 |
| 20090 | 122.37 | 27.65 | 178.94 | 11.38 | 95.31 |
| 1247 | 1312.52 | 499.20 | 486.71 | 136.84 | 95.31 |
| 13682 | 176.87 | 61.56 | 326.18 | 46.83 | 95.26 |
| 14003 | 817.40 | 211.66 | 451.12 | 81.85 | 95.26 |
| 12478 | 82.11 | 29.97 | 149.88 | 36.04 | 95.22 |
| 1585 | 67.31 | 32.78 | 148.67 | 23.18 | 95.22 |
| 9339 | 357.01 | 87.72 | 575.84 | 68.74 | 95.13 |
| 23868 | 177.77 | 290.29 | 269.73 | 44.26 | 95.09 |
| 20591 | 25.06 | 22.48 | 69.25 | 11.11 | 95.05 |
| 3352 | 439.29 | 115.94 | 757.04 | 153.95 | 95.00 |
| 6974 | 129.29 | 46.84 | 219.21 | 32.67 | 94.88 |
| 8888 | 58.70 | 29.09 | 133.86 | 26.30 | 94.88 |
| 21061 | 58.67 | 27.62 | 123.00 | 16.55 | 94.83 |
| 7262 | 1114.68 | 393.99 | 1942.97 | 210.00 | 94.83 |
| 24368 | 243.52 | 80.33 | 427.84 | 45.50 | 94.70 |
| 25253 | 291.81 | 64.18 | 436.10 | 53.03 | 94.53 |
| 20921 | 26.87 | 19.97 | 73.82 | 15.18 | 94.44 |
| 15438 | 65.27 | 31.97 | 154.80 | 42.05 | 94.36 |
| 12174 | 80.78 | 29.36 | 153.45 | 25.53 | 94.32 |
| 808 | 469.71 | 142.88 | 210.55 | 55.06 | 94.23 |
| 19667 | 34.63 | 16.92 | 74.26 | 11.91 | 94.19 |
| 3886 | 57.79 | 28.39 | 128.86 | 25.08 | 94.19 |
| 20082 | 75.08 | 31.10 | 214.13 | 47.37 | 94.08 |
| 14051 | 132.96 | 35.15 | 209.45 | 29.46 | 94.01 |
| 5073 | 188.58 | 69.99 | 346.14 | 69.21 | 93.93 |
| 10344 | 22.23 | 21.56 | 63.33 | 9.18 | 93.84 |
| 15386 | 93.23 | 133.87 | 380.59 | 101.27 | 93.76 |
| 9882 | 486.99 | 181.36 | 244.23 | 35.18 | 93.76 |
| 4443 | 259.36 | 71.87 | 429.91 | 75.00 | 93.76 |
| 16080 | 44.85 | 252.23 | 176.73 | 162.58 | 93.76 |
| 22005 | 63.42 | 50.09 | 187.23 | 39.58 | 93.71 |
| 15313 | 10.94 | 24.26 | 52.72 | 7.91 | 93.65 |
| 6384 | 60.76 | 59.71 | 117.04 | 26.05 | 93.63 |
| 15701 | 37.60 | 16.66 | 75.18 | 12.81 | 93.58 |
| 22257 | 33.56 | 15.61 | 61.03 | 7.13 | 93.54 |
| 2655 | 42.88 | 48.17 | 155.13 | 62.85 | 93.52 |
| 4198 | 698.17 | 161.70 | 448.59 | 56.51 | 93.50 |
| 6522 | 569.21 | 150.95 | 877.20 | 111.47 | 93.28 |
| 19128 | 112.63 | 38.66 | 180.82 | 19.01 | 93.15 |
| 17314 | 5.74 | 11.53 | 57.89 | 29.34 | 93.13 |
| 22871 | 101.59 | 29.83 | 165.82 | 22.84 | 93.11 |
| 21275 | 224.35 | 79.76 | 492.77 | 134.59 | 93.09 |
| 1727 | 43.38 | 60.84 | 96.90 | 23.97 | 93.07 |
| 19249 | 264.62 | 60.02 | 356.76 | 20.60 | 93.07 |
| 1993 | 29.72 | 21.35 | 101.33 | 20.81 | 93.04 |
| 4584 | 82.33 | 29.05 | 125.60 | 12.25 | 92.98 |
| 24162 | 523.84 | 133.30 | 788.13 | 85.20 | 92.94 |
| 7522 | 31.71 | 18.92 | 74.24 | 15.00 | 92.89 |
| 17713 | 134.82 | 29.04 | 191.13 | 21.86 | 92.85 |
| 1428 | −7.27 | 15.96 | 40.03 | 16.58 | 92.83 |
| 14776 | 99.41 | 35.18 | 153.67 | 26.50 | 92.81 |
| 3418 | 333.44 | 86.68 | 495.74 | 46.58 | 92.81 |
| 4199 | 529.94 | 132.34 | 301.96 | 61.95 | 92.64 |
| 21685 | 123.15 | 42.92 | 207.52 | 32.56 | 92.64 |
| 7023 | 363.44 | 76.61 | 483.68 | 29.43 | 92.55 |
| 4420 | 40.76 | 32.16 | 92.81 | 27.98 | 92.48 |
| 4121 | 62.21 | 23.49 | 110.83 | 18.20 | 92.42 |
| 18995 | 61.31 | 23.53 | 109.28 | 20.56 | 92.42 |
| 14665 | 151.38 | 37.30 | 219.57 | 23.41 | 92.33 |
| 11404 | 134.16 | 54.82 | 304.44 | 53.63 | 92.14 |
| 910 | 57.47 | 21.40 | 138.17 | 36.81 | 92.10 |
| 24081 | 117.08 | 63.79 | 235.77 | 50.20 | 92.03 |
| 22351 | 45.44 | 32.53 | 86.73 | 20.28 | 91.99 |
| 16012 | 72.47 | 31.00 | 153.59 | 33.17 | 91.97 |
| 22211 | 766.80 | 164.47 | 1061.59 | 90.34 | 91.95 |
| 727 | 210.80 | 38.94 | 274.04 | 15.91 | 91.90 |
| 9104 | 138.35 | 38.03 | 253.38 | 40.14 | 91.88 |
| 10417 | 43.82 | 25.97 | 125.71 | 32.61 | 91.88 |
| 10611 | 10.74 | 27.42 | 115.20 | 49.23 | 91.84 |
| 1314 | 262.03 | 49.07 | 394.88 | 48.07 | 91.79 |

TABLE 5N

CITRININ
Timepoint(s): 6, 24 hrs

| Identifier | NonToxMean | NonToxSD | Tox-Mean | ToxSD | LDAScore |
|---|---|---|---|---|---|
| 17541 | 622.47 | 209.71 | 2524.98 | 697.44 | 98.92 |
| 6108 | 533.46 | 112.70 | 1024.58 | 102.59 | 98.62 |
| 25064 | 962.08 | 317.37 | 2651.31 | 379.95 | 98.58 |
| 1698 | 70.27 | 55.64 | 598.98 | 232.89 | 98.49 |
| 8820 | 130.72 | 105.90 | 755.03 | 221.60 | 98.41 |
| 23917 | 725.54 | 174.69 | 1782.62 | 536.25 | 98.36 |
| 20817 | 1043.62 | 545.12 | 5020.35 | 2088.07 | 98.32 |
| 15391 | 756.64 | 170.28 | 1510.23 | 272.65 | 98.24 |
| 20864 | 1562.02 | 620.45 | 4051.37 | 596.98 | 98.19 |
| 24192 | 70.11 | 37.23 | 212.99 | 53.54 | 97.93 |
| 20818 | 665.29 | 354.08 | 2965.76 | 1254.63 | 97.93 |
| 1340 | 192.34 | 49.85 | 114.30 | 11.66 | 97.76 |
| 20035 | 180.50 | 107.18 | 446.34 | 61.98 | 97.72 |
| 25525 | 1057.73 | 339.31 | 2228.58 | 326.32 | 97.55 |
| 18989 | 782.09 | 261.73 | 1560.14 | 205.30 | 97.46 |
| 3431 | 1496.13 | 608.90 | 3517.88 | 499.00 | 97.42 |
| 13723 | 734.46 | 282.33 | 1643.16 | 339.11 | 97.29 |
| 353 | 173.42 | 82.57 | 323.18 | 43.00 | 97.25 |
| 15848 | 1318.65 | 418.94 | 2622.73 | 442.07 | 97.16 |
| 634 | 1135.42 | 374.65 | 2281.52 | 441.32 | 96.86 |
| 354 | 214.25 | 93.76 | 406.34 | 75.12 | 96.77 |
| 7681 | 101.15 | 43.91 | 212.89 | 41.46 | 96.64 |
| 13610 | 357.22 | 70.16 | 213.99 | 29.24 | 96.56 |
| 5601 | 970.57 | 259.22 | 473.69 | 102.75 | 96.47 |
| 3876 | 30.44 | 14.34 | 1.17 | 8.63 | 96.13 |
| 24375 | 115.03 | 40.98 | 208.88 | 57.88 | 96.04 |
| 8212 | 2232.57 | 1104.98 | 5289.94 | 717.26 | 95.96 |
| 15106 | 1878.08 | 698.66 | 3540.36 | 359.29 | 95.74 |
| 14670 | 1214.56 | 325.29 | 1917.56 | 318.04 | 95.70 |
| 15189 | 1735.59 | 1153.61 | 4557.38 | 1226.17 | 95.70 |
| 24496 | 122.73 | 40.31 | 47.99 | 15.89 | 95.57 |
| 20895 | 332.13 | 100.81 | 137.61 | 37.56 | 95.52 |
| 20876 | 1661.97 | 599.79 | 3113.86 | 382.39 | 95.52 |
| 18533 | 35.68 | 17.84 | 5.09 | 4.52 | 95.52 |

TABLE 5N-continued

CITRININ
Timepoint(s): 6, 24 hrs

| Identifier | NonToxMean | NonToxSD | Tox-Mean | ToxSD | LDAScore |
|---|---|---|---|---|---|
| 6630 | 1393.25 | 256.89 | 913.59 | 112.68 | 95.48 |
| 20844 | 837.88 | 286.57 | 1606.81 | 216.13 | 95.44 |
| 15850 | 1209.74 | 343.26 | 2046.05 | 316.40 | 95.44 |
| 7315 | −13.72 | 19.65 | 37.49 | 20.35 | 95.44 |
| 9254 | 247.89 | 49.11 | 157.69 | 17.49 | 95.44 |
| 15363 | 443.12 | 132.07 | 716.96 | 123.62 | 95.31 |
| 18359 | 245.00 | 113.72 | 546.56 | 83.87 | 95.22 |
| 8211 | 2822.70 | 1582.68 | 6312.46 | 772.17 | 95.22 |
| 16831 | 42.34 | 13.79 | 13.06 | 7.30 | 95.22 |
| 18644 | 2209.11 | 1246.61 | 5017.03 | 698.10 | 95.14 |
| 15190 | 1803.71 | 1156.33 | 4453.59 | 1177.82 | 95.09 |
| 15201 | 1480.71 | 527.22 | 2864.67 | 616.92 | 95.09 |
| 18205 | 277.90 | 58.81 | 408.93 | 34.56 | 95.09 |
| 19094 | 1054.85 | 243.62 | 1623.72 | 219.27 | 95.05 |
| 17108 | 219.63 | 44.77 | 132.90 | 13.45 | 95.01 |
| 10464 | 131.59 | 35.74 | 68.61 | 13.81 | 94.84 |
| 9409 | 102.66 | 32.91 | 171.76 | 24.78 | 94.84 |
| 7586 | 795.05 | 201.44 | 401.14 | 109.74 | 94.79 |
| 18800 | 2701.84 | 1144.69 | 5340.05 | 791.36 | 94.79 |
| 25675 | 688.20 | 206.46 | 1130.86 | 172.21 | 94.75 |
| 2697 | 1222.06 | 354.81 | 1908.51 | 176.60 | 94.75 |
| 10267 | 2101.59 | 872.11 | 4127.29 | 650.25 | 94.71 |
| 22773 | 230.97 | 52.31 | 131.59 | 26.18 | 94.54 |
| 1651 | 880.31 | 240.55 | 631.98 | 31.80 | 94.19 |
| 17494 | 219.24 | 41.89 | 138.20 | 23.13 | 94.15 |
| 244 | 51.19 | 35.18 | 14.03 | 8.20 | 94.15 |
| 17693 | 1247.25 | 372.94 | 2027.18 | 231.36 | 94.10 |
| 6946 | 389.05 | 103.41 | 200.78 | 37.64 | 94.02 |
| 23783 | 436.13 | 76.56 | 298.50 | 28.57 | 93.93 |
| 19408 | 1997.30 | 674.69 | 2937.88 | 154.93 | 93.89 |
| 20088 | 383.97 | 79.45 | 244.56 | 32.48 | 93.89 |
| 16272 | 192.25 | 63.76 | 102.37 | 22.94 | 93.89 |
| 2866 | 642.47 | 211.99 | 276.00 | 84.07 | 93.85 |
| 16954 | 48.70 | 79.17 | 202.92 | 44.32 | 93.80 |
| 21685 | 124.50 | 43.36 | 59.69 | 10.37 | 93.72 |
| 1719 | 145.21 | 38.11 | 80.93 | 12.30 | 93.67 |
| 20810 | 1256.69 | 398.25 | 2088.75 | 313.45 | 93.63 |
| 5049 | 298.40 | 65.65 | 175.28 | 28.59 | 93.63 |
| 1814 | 172.31 | 47.40 | 99.15 | 13.17 | 93.63 |
| 16193 | 101.42 | 30.67 | 44.23 | 15.12 | 93.59 |
| 15017 | 1007.41 | 395.69 | 2150.49 | 484.37 | 93.58 |
| 17686 | 1014.59 | 265.55 | 1558.32 | 151.72 | 93.50 |
| 20803 | 432.89 | 100.25 | 912.31 | 140.76 | 93.49 |
| 1537 | 29.21 | 35.65 | 294.59 | 185.42 | 93.45 |
| 1399 | 198.89 | 71.28 | 576.63 | 288.99 | 93.45 |
| 22583 | 26.67 | 14.48 | 3.43 | 7.60 | 93.37 |
| 3091 | 784.77 | 186.23 | 457.77 | 105.80 | 93.37 |
| 9029 | 430.46 | 93.52 | 614.72 | 63.36 | 93.37 |
| 16849 | 114.53 | 44.11 | 44.12 | 13.14 | 93.33 |
| 22414 | 58.52 | 33.14 | 101.78 | 22.01 | 93.33 |
| 8283 | 122.89 | 43.92 | 338.56 | 122.17 | 93.32 |
| 20918 | 440.21 | 126.29 | 269.42 | 29.15 | 93.29 |
| 25069 | 131.62 | 55.06 | 390.27 | 136.77 | 93.28 |
| 19067 | 175.20 | 51.04 | 88.87 | 21.48 | 93.24 |
| 7022 | 6.12 | 16.94 | 127.93 | 68.30 | 93.24 |
| 723 | 32.80 | 15.28 | 8.05 | 5.98 | 93.20 |
| 2242 | 2295.34 | 607.45 | 1325.08 | 393.96 | 93.16 |
| 24390 | 165.35 | 113.57 | −9.44 | 39.74 | 93.07 |
| 17211 | 1434.51 | 548.50 | 2462.85 | 274.87 | 93.03 |
| 22406 | 79.97 | 30.24 | 31.26 | 10.08 | 92.90 |
| 24469 | 1169.56 | 333.98 | 1827.58 | 165.96 | 92.86 |

TABLE 5O

COLCHICINE
Timepoint(s): 6, 24, 48 hrs

| Identifier | NonToxMean | NonToxSD | Tox-Mean | ToxSD | LDAScore |
|---|---|---|---|---|---|
| 23166 | 132.81 | 58.53 | 371.64 | 112.54 | 97.29 |
| 4412 | 377.59 | 61.12 | 558.75 | 77.91 | 96.99 |
| 18151 | 1133.81 | 261.37 | 563.27 | 117.10 | 96.47 |
| 15964 | 1187.13 | 325.69 | 508.38 | 159.50 | 96.12 |
| 11618 | 419.37 | 129.59 | 119.80 | 80.64 | 96.12 |
| 16882 | 177.88 | 54.70 | 82.96 | 14.87 | 95.78 |
| 24321 | 722.16 | 202.93 | 318.04 | 123.60 | 95.43 |
| 9097 | 258.85 | 82.10 | 115.52 | 31.47 | 95.05 |
| 20001 | 1683.96 | 373.32 | 1059.37 | 114.60 | 94.92 |
| 16913 | 1386.59 | 297.09 | 894.57 | 81.02 | 94.75 |
| 17887 | 1461.63 | 317.71 | 838.24 | 208.19 | 94.70 |
| 16924 | 445.74 | 155.90 | 188.36 | 46.16 | 94.57 |
| 20988 | 1221.44 | 211.78 | 853.97 | 84.52 | 94.49 |
| 22271 | 275.62 | 66.08 | 156.87 | 37.40 | 94.32 |
| 2222 | 802.84 | 200.86 | 537.76 | 35.92 | 94.06 |
| 6806 | 1236.90 | 342.77 | 566.10 | 189.93 | 94.01 |
| 13855 | 22.06 | 28.83 | 139.05 | 42.55 | 93.95 |
| 20513 | 57.97 | 25.96 | 166.84 | 71.44 | 93.82 |
| 9296 | 1306.96 | 257.77 | 840.48 | 105.26 | 93.80 |
| 643 | 62.16 | 32.97 | 14.32 | 5.63 | 93.71 |
| 16982 | 128.17 | 257.40 | 1462.72 | 552.54 | 93.60 |
| 20312 | 405.72 | 95.10 | 209.02 | 92.75 | 93.58 |
| 4073 | 562.17 | 184.40 | 230.54 | 83.32 | 93.58 |
| 3925 | 477.10 | 119.06 | 265.65 | 66.28 | 93.45 |
| 2913 | 736.68 | 160.48 | 481.77 | 40.00 | 93.24 |
| 10984 | 2020.41 | 564.71 | 1032.75 | 348.86 | 92.98 |
| 22321 | 100.73 | 64.58 | 321.87 | 131.71 | 92.96 |
| 2767 | 44.79 | 40.13 | 182.37 | 66.23 | 92.91 |
| 4151 | 563.27 | 167.25 | 920.16 | 111.75 | 92.89 |
| 7615 | 90.46 | 40.50 | 169.26 | 27.71 | 92.81 |
| 17399 | 1980.57 | 449.65 | 1255.63 | 187.29 | 92.64 |
| 6552 | 1594.49 | 296.14 | 1077.60 | 126.50 | 92.64 |
| 13111 | 228.20 | 73.35 | 132.80 | 17.16 | 92.59 |
| 13727 | 124.04 | 53.37 | 38.71 | 19.99 | 92.55 |
| 18642 | 974.76 | 203.55 | 664.60 | 62.35 | 92.55 |
| 3050 | 91.21 | 49.08 | 313.78 | 134.78 | 92.53 |
| 6438 | 114.03 | 57.15 | 38.70 | 14.25 | 92.51 |
| 20405 | 33.56 | 28.74 | 132.47 | 64.39 | 92.48 |
| 14185 | 202.17 | 89.20 | 491.51 | 237.69 | 92.48 |
| 16849 | 114.55 | 44.14 | 48.23 | 13.11 | 92.46 |
| 12901 | 1626.70 | 415.03 | 1002.61 | 177.27 | 92.42 |
| 20697 | 1421.26 | 277.19 | 931.95 | 163.03 | 92.25 |
| 8837 | 359.37 | 91.36 | 235.96 | 24.61 | 92.25 |
| 17361 | 145.97 | 59.92 | 56.10 | 14.57 | 92.20 |
| 17329 | 213.41 | 103.82 | 524.01 | 86.38 | 92.18 |
| 15600 | 774.27 | 210.27 | 435.87 | 107.62 | 92.08 |
| 16879 | 1207.58 | 276.77 | 796.63 | 98.39 | 92.03 |
| 4330 | 500.26 | 160.51 | 241.64 | 84.25 | 92.03 |
| 22152 | 7.72 | 33.71 | 81.27 | 38.69 | 91.79 |
| 21053 | 105.50 | 59.69 | 39.98 | 16.30 | 91.69 |
| 17324 | 360.96 | 79.01 | 153.55 | 65.98 | 91.58 |
| 7540 | 155.81 | 94.07 | 328.58 | 92.44 | 91.58 |
| 16128 | 286.68 | 62.49 | 192.02 | 31.18 | 91.56 |
| 14790 | 165.31 | 84.94 | 49.50 | 20.48 | 91.52 |
| 23115 | 570.61 | 171.16 | 295.42 | 91.28 | 91.47 |
| 11057 | 32.46 | 28.53 | 120.72 | 43.20 | 91.41 |
| 7537 | 230.23 | 69.42 | 125.41 | 29.85 | 91.34 |
| 19822 | 1596.44 | 410.54 | 942.00 | 210.50 | 91.26 |
| 17386 | 303.88 | 93.74 | 128.16 | 41.06 | 91.02 |
| 17248 | 2568.34 | 534.75 | 1704.94 | 295.46 | 91.00 |
| 15191 | 2013.99 | 1219.17 | 2599.48 | 219.23 | 90.96 |
| 1141 | 240.56 | 63.32 | 390.27 | 85.33 | 90.93 |
| 3099 | 966.22 | 189.19 | 660.01 | 95.36 | 90.70 |
| 21024 | 577.99 | 113.27 | 331.56 | 66.79 | 90.59 |
| 8709 | 148.12 | 48.57 | 78.15 | 19.09 | 90.57 |
| 19731 | 226.36 | 215.21 | 98.99 | 29.40 | 90.57 |
| 6250 | 492.94 | 104.90 | 372.14 | 23.59 | 90.53 |
| 117 | 21.16 | 17.56 | −5.10 | 9.54 | 90.44 |
| 17401 | 907.31 | 422.69 | 1550.66 | 328.51 | 90.42 |
| 15377 | 25.87 | 15.51 | 55.07 | 8.41 | 90.42 |
| 17326 | 22.55 | 24.06 | 93.51 | 28.61 | 90.42 |
| 22697 | 59.78 | 40.38 | 12.83 | 13.23 | 90.35 |
| 14595 | 87.77 | 36.04 | 175.49 | 38.60 | 90.29 |

TABLE 5O-continued

COLCHICINE
Timepoint(s): 6, 24, 48 hrs

| Identifier | NonToxMean | NonToxSD | ToxMean | ToxSD | LDAScore |
|---|---|---|---|---|---|
| 9223 | 150.65 | 64.81 | 54.19 | 23.82 | 90.27 |
| 8785 | 209.90 | 55.55 | 288.76 | 24.92 | 90.22 |
| 9339 | 360.32 | 89.43 | 226.70 | 47.31 | 90.22 |
| 23253 | 624.10 | 163.49 | 380.42 | 78.17 | 90.09 |
| 25907 | 19.74 | 25.13 | 47.86 | 14.93 | 90.09 |
| 15893 | 1733.99 | 343.83 | 1225.85 | 165.26 | 90.05 |
| 23514 | 407.55 | 167.53 | 162.38 | 70.14 | 89.97 |
| 3875 | 510.89 | 136.65 | 232.91 | 81.51 | 89.90 |
| 406 | 362.17 | 77.76 | 250.18 | 48.87 | 89.88 |
| 18343 | 437.98 | 107.72 | 280.49 | 46.68 | 89.79 |
| 25461 | 49.71 | 22.92 | 20.96 | 5.68 | 89.75 |
| 10789 | 326.18 | 107.75 | 117.23 | 67.68 | 89.73 |
| 23145 | 44.09 | 20.22 | 87.09 | 15.12 | 89.73 |
| 4048 | −7.14 | 26.09 | 121.21 | 153.77 | 89.66 |
| 11174 | 53.20 | 50.67 | 171.90 | 46.40 | 89.64 |
| 23709 | 2491.22 | 1205.88 | 2706.26 | 145.13 | 89.45 |
| 23224 | 194.78 | 48.70 | 129.40 | 19.04 | 89.41 |
| 11215 | 143.29 | 71.54 | 28.34 | 56.76 | 89.23 |
| 19479 | 276.88 | 106.02 | 134.33 | 36.73 | 89.23 |
| 15872 | 152.44 | 63.81 | 467.24 | 163.94 | 89.23 |
| 10985 | 1146.00 | 265.29 | 633.75 | 164.98 | 89.17 |
| 18451 | 1444.75 | 418.00 | 943.24 | 132.82 | 89.10 |
| 812 | 157.19 | 35.17 | 88.26 | 32.94 | 89.04 |

TABLE 5P

CYCLOP
Timepoint(s): 6 hrs

| Identifier | NonToxMean | NonToxSD | ToxMean | ToxSD | LDAScore |
|---|---|---|---|---|---|
| 17089 | 1545.78 | 604.39 | 6128.97 | 335.19 | 99.53 |
| 16081 | 113.02 | 372.25 | 1532.22 | 184.12 | 99.40 |
| 23619 | 327.35 | 96.06 | 660.24 | 21.96 | 99.32 |
| 5393 | −31.45 | 22.77 | 27.35 | 9.29 | 99.32 |
| 24049 | 1517.02 | 432.93 | 3280.45 | 348.50 | 99.10 |
| 22698 | 261.92 | 112.70 | −415.61 | 188.19 | 99.06 |
| 26222 | 371.68 | 149.80 | 1265.79 | 372.61 | 98.76 |
| 18118 | 895.16 | 271.71 | 2268.31 | 465.94 | 98.67 |
| 16469 | 1143.78 | 291.23 | 1083.34 | 3.98 | 98.67 |
| 17066 | 37.10 | 19.62 | −6.41 | 5.49 | 98.67 |
| 7084 | 123.08 | 117.51 | 622.25 | 118.49 | 98.59 |
| 24213 | 1604.12 | 394.78 | 3341.49 | 503.25 | 98.54 |
| 3470 | 143.86 | 59.86 | 458.18 | 196.11 | 98.54 |
| 23711 | 4518.75 | 2192.54 | 16927.73 | 3240.54 | 98.50 |
| 18831 | 4165.13 | 1320.79 | 10676.69 | 1466.84 | 98.50 |
| 108 | 289.68 | 144.40 | 164.86 | 3.48 | 98.46 |
| 1409 | 425.27 | 87.17 | 260.86 | 8.34 | 98.46 |
| 8815 | 664.61 | 111.50 | 420.20 | 41.92 | 98.46 |
| 12130 | 90.83 | 34.97 | 39.25 | 3.30 | 98.42 |
| 8213 | 3583.64 | 1528.59 | 10080.02 | 1528.73 | 98.42 |
| 109 | 556.91 | 312.14 | 239.04 | 32.06 | 98.42 |
| 21637 | 28.01 | 19.25 | −16.57 | 5.06 | 98.29 |
| 15819 | 42.77 | 22.12 | −47.81 | 46.21 | 98.16 |
| 44 | 34.58 | 17.78 | −3.41 | 3.04 | 98.16 |
| 6154 | 256.83 | 383.44 | −1506.42 | 1100.74 | 98.12 |
| 13412 | 28.40 | 24.99 | 148.78 | 61.50 | 98.12 |
| 6720 | 68.84 | 60.28 | 240.34 | 21.68 | 98.12 |
| 5117 | 162.84 | 78.90 | 364.60 | 35.27 | 98.07 |
| 5329 | 47.29 | 21.30 | 10.39 | 2.22 | 98.07 |
| 21866 | 109.05 | 73.32 | 379.42 | 172.12 | 98.03 |
| 14953 | 482.64 | 76.56 | 311.16 | 19.07 | 97.99 |
| 18350 | 90.05 | 49.29 | 301.03 | 46.70 | 97.99 |
| 2029 | 305.29 | 103.47 | 350.85 | 2.68 | 97.99 |
| 8837 | 358.84 | 91.24 | 173.81 | 19.49 | 97.95 |
| 25721 | 83.34 | 54.43 | 240.21 | 44.54 | 97.95 |
| 16272 | 191.69 | 64.06 | 131.07 | 3.08 | 97.95 |
| 5969 | 1516.76 | 347.22 | 2916.15 | 354.10 | 97.90 |
| 1689 | 4338.65 | 2126.09 | 15982.97 | 5400.06 | 97.90 |

TABLE 5P-continued

CYCLOP
Timepoint(s): 6 hrs

| Identifier | NonToxMean | NonToxSD | ToxMean | ToxSD | LDAScore |
|---|---|---|---|---|---|
| 4232 | 137.19 | 62.23 | 27.42 | 11.32 | 97.90 |
| 3049 | 202.76 | 101.21 | 529.19 | 69.46 | 97.86 |
| 18800 | 2711.70 | 1148.84 | 6417.82 | 556.95 | 97.86 |
| 14424 | 67.07 | 130.91 | 324.02 | 83.71 | 97.86 |
| 8849 | 222.06 | 71.45 | 477.43 | 62.77 | 97.77 |
| 25777 | 404.46 | 182.63 | 824.09 | 102.83 | 97.77 |
| 16902 | 66.96 | 91.89 | −172.67 | 27.28 | 97.77 |
| 23078 | 147.27 | 46.50 | 55.48 | 8.60 | 97.77 |
| 5461 | 193.94 | 117.20 | 396.91 | 37.67 | 97.73 |
| 24814 | 171.74 | 33.51 | 92.18 | 13.93 | 97.73 |
| 10860 | 46.07 | 29.90 | −6.09 | 2.93 | 97.69 |
| 1698 | 74.37 | 76.29 | 197.25 | 24.89 | 97.69 |
| 15408 | 193.87 | 58.16 | 69.92 | 11.05 | 97.69 |
| 17832 | 1948.88 | 851.66 | 5675.58 | 2032.21 | 97.65 |
| 7127 | 280.56 | 95.94 | 21.98 | 52.78 | 97.65 |
| 744 | 334.35 | 68.28 | 208.28 | 11.29 | 97.60 |
| 3081 | 387.30 | 84.71 | 227.05 | 31.49 | 97.56 |
| 18918 | 31.10 | 27.35 | −32.80 | 10.09 | 97.56 |
| 15154 | 267.93 | 62.29 | 131.15 | 21.56 | 97.52 |
| 17771 | 768.98 | 305.15 | 1490.79 | 130.43 | 97.52 |
| 20493 | 460.39 | 110.11 | 297.05 | 12.72 | 97.47 |
| 24437 | 68.49 | 25.43 | 175.35 | 41.14 | 97.47 |
| 8999 | 47.02 | 23.49 | 1.97 | 4.96 | 97.47 |
| 15382 | 122.71 | 202.12 | 570.78 | 188.00 | 97.47 |
| 8599 | 378.10 | 107.09 | 181.07 | 19.58 | 97.47 |
| 17682 | 672.30 | 178.35 | 399.02 | 29.34 | 97.43 |
| 22862 | 103.01 | 36.20 | 42.20 | 6.28 | 97.39 |
| 20920 | 626.34 | 183.56 | 421.78 | 11.19 | 97.39 |
| 17334 | 173.83 | 58.72 | 358.42 | 40.10 | 97.39 |
| 4067 | 123.98 | 59.95 | 245.14 | 32.72 | 97.39 |
| 17357 | 269.19 | 82.48 | 105.14 | 28.10 | 97.39 |
| 23314 | 72.17 | 276.94 | 318.28 | 105.05 | 97.35 |
| 19190 | 534.12 | 144.15 | 283.73 | 32.84 | 97.35 |
| 16943 | 2759.04 | 872.63 | 5041.36 | 392.40 | 97.35 |
| 16947 | 319.84 | 80.34 | 186.33 | 13.16 | 97.35 |
| 6405 | 380.95 | 93.60 | 241.49 | 11.37 | 97.35 |
| 9053 | 239.61 | 50.65 | 135.66 | 11.51 | 97.35 |
| 25253 | 293.63 | 65.17 | 155.93 | 16.09 | 97.30 |
| 1688 | 5256.90 | 3710.90 | 21624.32 | 7449.14 | 97.30 |
| 19993 | 2319.53 | 566.29 | 3763.82 | 221.97 | 97.30 |
| 20846 | 2377.64 | 663.94 | 3619.10 | 135.20 | 97.30 |
| 22142 | 32.37 | 17.29 | 0.24 | 3.37 | 97.26 |
| 17602 | 131.67 | 36.83 | 52.59 | 13.48 | 97.26 |
| 18274 | 300.34 | 63.28 | 159.26 | 25.71 | 97.26 |
| 15410 | 504.68 | 101.83 | 257.23 | 33.63 | 97.22 |
| 7299 | 181.01 | 153.33 | 372.36 | 39.71 | 97.22 |
| 6585 | 649.58 | 366.37 | 1390.92 | 91.78 | 97.17 |
| 17426 | 537.84 | 84.20 | 386.94 | 14.48 | 97.13 |
| 15190 | 1818.28 | 1175.28 | 4173.32 | 371.68 | 97.13 |
| 13598 | 349.78 | 108.22 | 755.01 | 165.06 | 97.09 |

TABLE 5Q

DIFLUNISAL
Timepoint(s): 24 hrs

| Identifier | NonToxMean | NonToxSD | ToxMean | ToxSD | LDAScore |
|---|---|---|---|---|---|
| 15582 | 98.54 | 389.02 | 523.22 | 20.51 | 99.87 |
| 23699 | 325.81 | 88.09 | 984.09 | 67.68 | 99.79 |
| 1858 | 165.70 | 50.67 | 468.35 | 55.34 | 99.66 |
| 18687 | 415.65 | 168.60 | 1876.04 | 173.83 | 99.66 |
| 20810 | 1260.74 | 402.11 | 2154.96 | 30.08 | 99.44 |
| 23698 | 272.98 | 101.50 | 824.56 | 62.23 | 99.44 |
| 15906 | 73.43 | 105.60 | 328.56 | 63.09 | 99.40 |
| 21354 | 414.86 | 118.96 | 1273.64 | 189.63 | 99.36 |
| 16918 | 1181.89 | 410.28 | 2103.00 | 56.71 | 99.36 |
| 15048 | 861.35 | 213.04 | 1349.81 | 15.30 | 99.32 |
| 17758 | 126.22 | 53.45 | 567.25 | 114.93 | 99.14 |
| 23504 | 176.69 | 49.53 | 287.50 | 5.80 | 99.14 |

TABLE 5Q-continued

DIFLUNISAL  
Timepoint(s): 24 hrs  
Atty. Docket No. 44921-5089US  
Doc. No. 1803440.1

| Identifier | NonToxMean | NonToxSD | Tox-Mean | ToxSD | LDAScore |
|---|---|---|---|---|---|
| 18686 | 468.60 | 214.77 | 2050.51 | 247.31 | 99.14 |
| 5351 | 711.19 | 145.06 | 979.89 | 15.97 | 99.06 |
| 18083 | 48.75 | 24.85 | 148.28 | 10.77 | 99.06 |
| 1977 | 142.19 | 40.33 | 293.78 | 26.17 | 98.97 |
| 20833 | 1254.24 | 350.22 | 1826.03 | 17.16 | 98.84 |
| 4012 | 650.38 | 267.26 | 1484.68 | 174.94 | 98.84 |
| 18250 | 1093.45 | 315.54 | 1684.15 | 30.30 | 98.80 |
| 26109 | 69.08 | 76.43 | 458.33 | 59.25 | 98.76 |
| 4049 | 23.28 | 65.36 | 63.64 | 6.15 | 98.76 |
| 23837 | 101.76 | 41.27 | 57.70 | 0.48 | 98.76 |
| 25679 | 901.31 | 261.02 | 1610.91 | 63.61 | 98.76 |
| 5887 | 79.37 | 88.10 | 285.80 | 15.29 | 98.63 |
| 23409 | 535.77 | 161.09 | 346.74 | 3.30 | 98.54 |
| 6380 | 135.92 | 123.74 | 459.26 | 82.61 | 98.54 |
| 2457 | 289.86 | 77.14 | 519.55 | 38.45 | 98.42 |
| 5667 | 744.60 | 177.74 | 1191.89 | 49.47 | 98.42 |
| 18293 | 770.57 | 235.09 | 1635.35 | 158.85 | 98.37 |
| 15579 | 32.24 | 115.84 | 189.18 | 29.09 | 98.33 |
| 18647 | 251.55 | 67.39 | 138.00 | 4.76 | 98.29 |
| 16849 | 114.09 | 44.40 | 66.30 | 1.36 | 98.20 |
| 15580 | 95.99 | 152.88 | 276.60 | 38.55 | 98.20 |
| 11205 | 594.93 | 193.66 | 371.24 | 5.25 | 98.20 |
| 17211 | 1440.25 | 553.34 | 2327.85 | 45.31 | 98.16 |
| 19244 | 1224.59 | 378.82 | 2305.53 | 135.95 | 98.16 |
| 1728 | 351.65 | 81.13 | 555.88 | 47.36 | 98.16 |
| 4010 | 965.06 | 407.94 | 2268.41 | 360.66 | 98.12 |
| 17563 | 1201.51 | 347.34 | 2039.09 | 80.83 | 98.07 |
| 19067 | 174.78 | 51.26 | 80.87 | 6.55 | 98.03 |
| 14763 | 38.55 | 133.68 | 500.64 | 63.55 | 98.03 |
| 17158 | 240.63 | 83.07 | 105.20 | 10.26 | 97.99 |
| 19727 | 1326.99 | 416.44 | 2052.69 | 41.43 | 97.90 |
| 2708 | 383.06 | 86.76 | 506.29 | 10.15 | 97.90 |
| 16204 | 755.43 | 187.45 | 1101.24 | 54.31 | 97.90 |
| 24748 | −22.65 | 38.12 | 33.61 | 1.39 | 97.86 |
| 15239 | 567.21 | 132.24 | 803.19 | 32.26 | 97.82 |
| 22052 | 256.34 | 73.77 | 451.80 | 35.28 | 97.77 |
| 20715 | 135.54 | 60.66 | 373.16 | 45.27 | 97.73 |
| 19268 | 940.57 | 273.83 | 1595.25 | 83.86 | 97.73 |
| 17686 | 1016.62 | 266.11 | 1780.84 | 121.15 | 97.69 |
| 20986 | 36.18 | 25.28 | 113.63 | 23.08 | 97.65 |
| 3027 | 1127.48 | 331.63 | 1758.65 | 53.48 | 97.65 |
| 23849 | 287.19 | 137.85 | 391.28 | 6.74 | 97.60 |
| 4952 | 108.82 | 48.80 | 171.37 | 6.32 | 97.60 |
| 1814 | 171.85 | 47.69 | 123.88 | 1.67 | 97.56 |
| 20839 | 1043.73 | 290.47 | 1565.67 | 42.99 | 97.52 |
| 16190 | 288.78 | 81.68 | 502.75 | 35.87 | 97.52 |
| 15875 | 1183.10 | 392.02 | 1973.54 | 86.87 | 97.35 |
| 16701 | 830.81 | 197.66 | 1528.91 | 267.69 | 97.35 |
| 15106 | 1887.41 | 709.31 | 3311.08 | 123.87 | 97.26 |
| 3434 | 326.00 | 140.86 | 131.21 | 15.66 | 97.26 |
| 21729 | 582.55 | 246.48 | 1512.04 | 499.79 | 97.26 |
| 19952 | 67.28 | 24.42 | 23.96 | 3.74 | 97.26 |
| 20818 | 681.56 | 422.22 | 1663.94 | 317.99 | 97.17 |
| 20149 | 1324.01 | 582.48 | 2795.60 | 215.42 | 97.17 |
| 14959 | 619.74 | 147.94 | 1010.98 | 113.74 | 97.13 |
| 16148 | 762.99 | 195.12 | 1313.23 | 188.91 | 97.13 |
| 24886 | 1263.69 | 371.87 | 2046.76 | 132.13 | 97.13 |
| 10878 | 952.87 | 253.83 | 1373.59 | 38.24 | 97.09 |
| 8946 | 207.89 | 87.83 | 74.88 | 7.06 | 97.09 |
| 19477 | 112.98 | 54.74 | 250.89 | 20.66 | 97.00 |
| 15468 | 734.22 | 179.64 | 1032.19 | 49.88 | 96.96 |
| 10109 | 1045.52 | 288.55 | 1597.93 | 74.73 | 96.96 |
| 3924 | 182.19 | 68.67 | 273.97 | 5.41 | 96.92 |
| 18918 | 31.02 | 27.50 | −11.16 | 3.27 | 96.88 |
| 17729 | 878.67 | 224.12 | 1508.83 | 163.08 | 96.83 |
| 14695 | 1736.29 | 632.39 | 2885.22 | 95.16 | 96.79 |
| 9799 | 145.87 | 50.77 | 85.38 | 3.80 | 96.79 |
| 20925 | 337.86 | 103.37 | 649.53 | 101.58 | 96.79 |
| 25501 | 102.21 | 56.92 | 20.07 | 8.06 | 96.79 |
| 7062 | 686.14 | 173.76 | 1144.72 | 115.88 | 96.79 |
| 5398 | 0.40 | 12.35 | 33.62 | 24.14 | 96.75 |
| 20711 | 43.78 | 42.18 | 150.73 | 22.20 | 96.75 |
| 373 | 34.25 | 61.71 | 167.08 | 44.08 | 96.70 |
| 16929 | 956.64 | 234.98 | 1405.43 | 58.88 | 96.70 |

TABLE 5Q-continued

DIFLUNISAL  
Timepoint(s): 24 hrs  
Atty. Docket No. 44921-5089US  
Doc. No. 1803440.1

| Identifier | NonToxMean | NonToxSD | Tox-Mean | ToxSD | LDAScore |
|---|---|---|---|---|---|
| 20817 | 1073.65 | 677.30 | 2215.68 | 400.07 | 96.70 |
| 4291 | 295.13 | 101.25 | 151.24 | 8.90 | 96.70 |
| 23336 | 141.91 | 43.60 | 268.14 | 38.59 | 96.66 |
| 23270 | 209.26 | 61.36 | 302.15 | 9.89 | 96.66 |
| 4259 | 700.25 | 158.48 | 1007.49 | 53.89 | 96.66 |
| 18509 | 418.06 | 82.28 | 584.02 | 27.38 | 96.62 |
| 1694 | 1145.19 | 337.82 | 1796.01 | 81.50 | 96.58 |
| 4011 | 459.62 | 198.95 | 896.31 | 148.45 | 96.53 |
| 6949 | 1.61 | 27.50 | 36.30 | 10.98 | 96.49 |
| 4713 | 107.84 | 37.11 | 71.04 | 3.04 | 96.40 |

TABLE 5R

HYDRALAZINE  
Timepoint(s): 6 hrs

| Identifier | NonToxMean | NonToxSD | Tox-Mean | ToxSD | LDAScore |
|---|---|---|---|---|---|
| 23230 | 381.93 | 101.69 | 164.86 | 3.08 | 99.83 |
| 7299 | 180.37 | 151.55 | 684.70 | 26.37 | 99.66 |
| 11005 | 71.62 | 20.88 | 31.26 | 0.53 | 99.66 |
| 18715 | 190.60 | 53.82 | 312.84 | 2.17 | 99.66 |
| 18713 | 300.35 | 70.22 | 564.29 | 26.19 | 99.62 |
| 9306 | 45.76 | 18.52 | 121.89 | 7.27 | 99.62 |
| 19004 | 788.98 | 306.09 | 794.75 | 1.65 | 99.57 |
| 9525 | 5.08 | 44.31 | 64.20 | 2.12 | 99.57 |
| 19712 | 98.45 | 32.90 | 58.61 | 0.21 | 99.53 |
| 16203 | 66.52 | 16.97 | 45.27 | 0.17 | 99.53 |
| 20513 | 58.53 | 27.11 | 242.01 | 35.67 | 99.49 |
| 5918 | 26.70 | 40.82 | 72.84 | 4.20 | 99.44 |
| 14479 | 473.36 | 112.67 | 261.32 | 4.86 | 99.44 |
| 4194 | 34.33 | 17.04 | 74.46 | 0.76 | 99.40 |
| 8948 | 217.22 | 104.91 | 343.57 | 1.20 | 99.40 |
| 15015 | 503.71 | 91.72 | 339.92 | 3.82 | 99.36 |
| 22746 | 534.33 | 197.34 | 312.42 | 2.15 | 99.36 |
| 13235 | 16.43 | 13.42 | 75.50 | 8.64 | 99.32 |
| 90 | 93.87 | 50.03 | 147.79 | 0.44 | 99.32 |
| 16069 | 59.01 | 26.48 | 31.64 | 0.25 | 99.32 |
| 20523 | 549.70 | 152.39 | 1021.93 | 29.01 | 99.23 |
| 15872 | 155.66 | 71.91 | 53.38 | 1.82 | 99.23 |
| 3513 | 171.87 | 35.63 | 273.79 | 6.58 | 99.19 |
| 7452 | 8.04 | 13.04 | 37.85 | 2.68 | 99.19 |
| 15059 | 92.43 | 24.57 | 82.57 | 0.16 | 99.14 |
| 8597 | 241.04 | 57.82 | 387.68 | 12.70 | 99.14 |
| 20849 | 277.59 | 87.41 | 309.60 | 0.68 | 99.06 |
| 13298 | 101.48 | 29.62 | 51.68 | 1.68 | 99.06 |
| 11406 | 242.13 | 50.08 | 177.73 | 0.85 | 99.02 |
| 7071 | 133.86 | 64.50 | 98.99 | 0.88 | 99.02 |
| 23189 | 330.92 | 72.72 | 460.60 | 3.57 | 98.97 |
| 15411 | 303.87 | 90.07 | 657.96 | 59.65 | 98.97 |
| 8692 | 1045.40 | 309.78 | 638.87 | 9.02 | 98.97 |
| 22614 | 17.91 | 87.18 | 86.87 | 14.83 | 98.93 |
| 4969 | −18.84 | 34.82 | 77.79 | 30.12 | 98.89 |
| 3081 | 387.16 | 84.82 | 227.51 | 15.13 | 98.89 |
| 15231 | 100.29 | 44.00 | 233.89 | 22.19 | 98.85 |
| 15942 | 230.65 | 65.79 | 294.11 | 1.11 | 98.85 |
| 18406 | 33.60 | 18.22 | 70.49 | 1.79 | 98.85 |
| 16024 | 239.14 | 63.32 | 487.33 | 52.09 | 98.85 |
| 2539 | 46.96 | 51.90 | 304.80 | 46.42 | 98.85 |
| 26119 | 124.62 | 46.64 | 176.21 | 1.26 | 98.80 |
| 6723 | 200.38 | 72.05 | 91.78 | 10.99 | 98.76 |
| 21878 | 144.05 | 35.94 | 106.39 | 0.58 | 98.76 |
| 8664 | 106.71 | 250.43 | 160.02 | 4.54 | 98.72 |
| 21014 | 155.47 | 80.73 | 369.94 | 37.53 | 98.72 |
| 14842 | 122.80 | 45.94 | 280.85 | 20.55 | 98.72 |
| 13093 | 700.37 | 165.48 | 367.14 | 36.76 | 98.72 |
| 20404 | 53.45 | 44.01 | 336.92 | 98.70 | 98.72 |
| 15126 | 792.34 | 224.59 | 1256.68 | 25.48 | 98.67 |
| 4948 | 153.55 | 61.38 | 307.30 | 11.57 | 98.63 |
| 6844 | 123.76 | 58.60 | 32.99 | 3.47 | 98.63 |

TABLE 5R-continued

HYDRALAZINE
Timepoint(s): 6 hrs

| Identifier | NonToxMean | NonToxSD | Tox-Mean | ToxSD | LDAScore |
|---|---|---|---|---|---|
| 16025 | 150.51 | 42.20 | 268.08 | 8.85 | 98.59 |
| 7615 | 90.87 | 40.61 | 221.25 | 17.10 | 98.55 |
| 22575 | 20.61 | 15.66 | 10.19 | 0.32 | 98.50 |
| 23141 | 239.29 | 55.53 | 490.92 | 129.05 | 98.50 |
| 15636 | 39.88 | 26.09 | 4.00 | 1.07 | 98.50 |
| 15885 | 93.27 | 28.63 | 182.42 | 15.91 | 98.46 |
| 5355 | 1164.75 | 345.23 | 1050.46 | 4.54 | 98.46 |
| 13151 | 711.00 | 343.67 | 1290.08 | 71.04 | 98.46 |
| 19195 | 1555.05 | 374.36 | 1121.86 | 8.23 | 98.42 |
| 6606 | 249.66 | 121.42 | 743.36 | 159.90 | 98.42 |
| 2888 | 2015.72 | 588.67 | 1201.76 | 29.67 | 98.42 |
| 20405 | 34.08 | 29.57 | 195.15 | 62.34 | 98.42 |
| 7197 | 197.58 | 84.65 | 309.34 | 7.55 | 98.42 |
| 1215 | 67.05 | 49.57 | 246.66 | 40.98 | 98.42 |
| 17479 | 157.69 | 34.71 | 89.24 | 4.57 | 98.37 |
| 22733 | 21.90 | 14.11 | 64.22 | 8.36 | 98.37 |
| 1920 | 426.50 | 112.57 | 740.10 | 44.20 | 98.37 |
| 8745 | 57.56 | 19.95 | 100.05 | 2.83 | 98.33 |
| 22915 | 171.30 | 47.15 | 114.08 | 2.66 | 98.33 |
| 25587 | 24.39 | 16.37 | 17.05 | 0.15 | 98.33 |
| 13259 | 68.80 | 25.82 | 161.38 | 28.29 | 98.33 |
| 17468 | 396.41 | 77.87 | 278.70 | 4.37 | 98.29 |
| 14405 | 465.44 | 308.54 | 1276.71 | 188.93 | 98.25 |
| 14861 | 48.74 | 17.37 | 75.52 | 1.15 | 98.25 |
| 3027 | 1129.44 | 333.52 | 1205.87 | 5.52 | 98.25 |
| 1214 | 165.46 | 52.58 | 424.14 | 92.45 | 98.20 |
| 11158 | 1023.54 | 302.35 | 1115.38 | 6.37 | 98.20 |
| 20202 | 624.37 | 196.92 | 959.56 | 18.31 | 98.20 |
| 18290 | 275.55 | 78.31 | 420.92 | 7.75 | 98.16 |
| 21527 | 239.85 | 60.68 | 369.29 | 12.50 | 98.16 |
| 24885 | 1107.60 | 334.53 | 1092.86 | 5.80 | 98.16 |
| 23689 | 0.64 | 11.77 | 22.99 | 3.94 | 98.16 |
| 8869 | 8.35 | 21.59 | 31.83 | 0.60 | 98.16 |
| 17502 | 147.76 | 53.99 | 264.34 | 13.12 | 98.16 |
| 13203 | −15.66 | 28.87 | 51.81 | 11.94 | 98.12 |
| 25971 | 106.47 | 34.61 | 50.27 | 2.15 | 98.12 |
| 13095 | 60.49 | 15.80 | 32.26 | 1.41 | 98.12 |
| 26036 | 34.25 | 17.22 | 19.79 | 0.49 | 98.12 |
| 17570 | 230.73 | 71.54 | 273.93 | 2.11 | 98.08 |
| 22543 | 689.99 | 222.20 | 447.42 | 9.98 | 98.08 |
| 17312 | 26.98 | 34.41 | 42.60 | 0.40 | 98.08 |
| 16026 | 221.52 | 75.94 | 411.54 | 26.17 | 98.08 |
| 5684 | 333.75 | 76.46 | 482.85 | 10.21 | 98.03 |
| 15879 | 374.14 | 93.39 | 276.43 | 3.61 | 98.03 |

TABLE 5S

IFOSFAMIDE
Timepoint(s): 6, 24, 48, 144 hrs

| Identifier | NonToxMean | NonToxSD | Tox-Mean | ToxSD | LDAScore |
|---|---|---|---|---|---|
| 19252 | 647.94 | 142.98 | 520.93 | 34.13 | 89.74 |
| 1622 | 2071.83 | 907.04 | 1625.21 | 143.87 | 88.88 |
| 16148 | 767.65 | 197.63 | 575.47 | 57.95 | 86.32 |
| 17779 | 1952.57 | 790.85 | 1617.53 | 137.53 | 85.80 |
| 12932 | 153.85 | 49.70 | 108.04 | 13.75 | 85.63 |
| 11158 | 1027.66 | 302.42 | 759.65 | 56.80 | 85.37 |
| 10947 | 1800.32 | 754.28 | 1416.69 | 180.51 | 85.28 |
| 19408 | 2011.57 | 680.23 | 1580.63 | 160.66 | 85.24 |
| 16013 | 58.91 | 18.74 | 71.23 | 5.22 | 85.11 |
| 19254 | 241.32 | 76.35 | 239.54 | 14.43 | 85.06 |
| 17886 | 1504.90 | 495.37 | 1122.51 | 90.54 | 84.72 |
| 16895 | 2027.64 | 906.56 | 1603.00 | 189.71 | 84.63 |
| 18300 | 450.17 | 150.80 | 316.95 | 39.08 | 84.33 |
| 8211 | 2862.98 | 1618.85 | 2138.69 | 273.26 | 84.29 |
| 23710 | 1141.57 | 367.03 | 897.82 | 79.04 | 84.20 |
| 11954 | 3141.99 | 1699.73 | 2471.68 | 314.40 | 83.90 |
| 1853 | 2014.76 | 833.49 | 1614.19 | 220.80 | 83.90 |

TABLE 5S-continued

IFOSFAMIDE
Timepoint(s): 6, 24, 48, 144 hrs

| Identifier | NonToxMean | NonToxSD | Tox-Mean | ToxSD | LDAScore |
|---|---|---|---|---|---|
| 14695 | 1746.72 | 637.07 | 1297.75 | 126.83 | 83.77 |
| 8212 | 2267.04 | 1143.40 | 1689.07 | 186.62 | 83.42 |
| 13976 | 453.36 | 377.22 | 783.29 | 266.52 | 83.38 |
| 14997 | 2596.32 | 1029.67 | 2216.17 | 249.47 | 83.20 |
| 23709 | 2500.59 | 1207.33 | 1994.07 | 261.44 | 83.16 |
| 22592 | 234.68 | 168.43 | 397.15 | 108.13 | 83.08 |
| 18142 | 2001.91 | 840.95 | 1479.52 | 180.12 | 82.99 |
| 9135 | 719.00 | 131.99 | 601.54 | 43.95 | 82.90 |
| 14694 | 2326.49 | 1072.07 | 1849.47 | 243.07 | 82.69 |
| 18810 | 1189.60 | 320.47 | 979.08 | 72.74 | 82.60 |
| 18077 | 2627.05 | 1191.54 | 1778.68 | 232.31 | 82.56 |
| 15125 | 1303.70 | 426.26 | 1007.41 | 95.34 | 82.55 |
| 20751 | 706.77 | 161.80 | 835.79 | 96.53 | 82.51 |
| 44 | 34.24 | 17.91 | 48.60 | 8.82 | 82.47 |
| 23544 | 1515.02 | 495.50 | 1325.70 | 110.75 | 82.17 |
| 19993 | 2320.17 | 574.10 | 2616.44 | 234.66 | 82.03 |
| 9942 | 443.45 | 98.80 | 518.47 | 38.50 | 81.95 |
| 17682 | 673.25 | 179.30 | 543.60 | 51.66 | 81.95 |
| 23574 | 2282.20 | 973.76 | 1808.58 | 200.84 | 81.82 |
| 6815 | 1138.28 | 344.89 | 837.60 | 73.20 | 81.65 |
| 11050 | 671.41 | 139.50 | 791.75 | 84.37 | 81.60 |
| 1247 | 1310.50 | 504.69 | 915.02 | 93.84 | 81.60 |
| 18078 | 1152.53 | 545.02 | 1014.06 | 139.87 | 81.56 |
| 1801 | 97.60 | 29.90 | 123.36 | 20.25 | 81.43 |
| 12901 | 1613.41 | 414.49 | 2126.00 | 326.75 | 81.39 |
| 20035 | 182.08 | 110.21 | 229.47 | 33.04 | 81.39 |
| 17118 | 53.61 | 19.28 | 66.07 | 6.68 | 81.30 |
| 17204 | 1733.32 | 660.21 | 1299.09 | 155.20 | 81.26 |
| 23847 | 47.46 | 36.72 | 90.72 | 17.29 | 81.21 |
| 10500 | 24.88 | 31.73 | 53.21 | 18.49 | 81.17 |
| 8347 | 76.96 | 46.62 | 110.08 | 23.49 | 81.13 |
| 3015 | 2318.93 | 997.42 | 1869.25 | 225.78 | 81.04 |
| 20832 | 722.84 | 197.13 | 591.89 | 72.43 | 81.00 |
| 18615 | 521.90 | 148.77 | 363.34 | 55.31 | 80.95 |
| 5989 | 269.37 | 71.43 | 354.20 | 68.39 | 80.91 |
| 19894 | 40.81 | 20.31 | 62.51 | 16.62 | 80.83 |
| 18076 | 2548.69 | 1193.37 | 1768.87 | 244.55 | 80.83 |
| 21423 | 1355.89 | 429.81 | 1080.04 | 115.43 | 80.78 |
| 1523 | 89.47 | 23.47 | 100.14 | 7.66 | 80.70 |
| 11991 | 57.24 | 22.13 | 76.61 | 11.20 | 80.65 |
| 23109 | 2089.70 | 930.42 | 1566.07 | 197.88 | 80.44 |
| 19727 | 1331.92 | 420.23 | 1162.29 | 117.79 | 80.44 |
| 18451 | 1434.72 | 418.40 | 1801.12 | 288.28 | 80.39 |
| 23884 | 41.09 | 33.35 | 54.46 | 12.98 | 80.39 |
| 472 | 662.53 | 178.22 | 500.21 | 63.31 | 80.35 |
| 11153 | 1474.65 | 500.35 | 1320.86 | 134.33 | 80.35 |
| 23125 | 4577.67 | 2547.90 | 5632.15 | 1198.40 | 80.31 |
| 12598 | 545.25 | 95.85 | 644.01 | 73.00 | 80.31 |
| 915 | 30.40 | 17.20 | 53.68 | 14.78 | 80.26 |
| 6808 | 698.18 | 193.62 | 893.93 | 94.12 | 80.26 |
| 10260 | 85.57 | 33.38 | 94.71 | 10.64 | 80.18 |
| 25545 | 94.20 | 49.43 | 150.75 | 32.71 | 80.09 |
| 23660 | 1281.20 | 383.06 | 1072.18 | 89.30 | 80.09 |
| 15410 | 504.96 | 102.87 | 427.16 | 47.59 | 80.05 |
| 977 | 16.73 | 10.91 | 41.99 | 18.19 | 80.01 |
| 15137 | 1520.02 | 496.49 | 1254.30 | 128.20 | 80.00 |
| 26109 | 69.41 | 79.57 | 138.16 | 53.60 | 79.96 |
| 11136 | 1003.50 | 311.85 | 725.42 | 110.05 | 79.92 |
| 4217 | 519.77 | 126.27 | 592.35 | 45.95 | 79.92 |
| 13480 | 650.24 | 137.90 | 533.92 | 69.48 | 79.83 |
| 15535 | 448.65 | 83.59 | 358.13 | 46.40 | 79.79 |
| 15426 | 411.88 | 86.42 | 342.56 | 30.90 | 79.66 |
| 16012 | 73.15 | 32.18 | 78.40 | 10.56 | 79.65 |
| 4849 | 773.73 | 168.65 | 929.55 | 91.93 | 79.61 |
| 17765 | 1296.75 | 460.31 | 914.95 | 107.23 | 79.61 |
| 23967 | 383.11 | 92.35 | 484.27 | 65.27 | 79.53 |
| 9905 | 673.59 | 140.94 | 588.24 | 39.94 | 79.53 |
| 1583 | 30.08 | 18.99 | 43.08 | 7.71 | 79.53 |
| 1743 | 29.18 | 16.19 | 50.78 | 15.93 | 79.40 |
| 15446 | 370.71 | 93.07 | 266.06 | 61.63 | 79.40 |
| 18905 | 1363.50 | 302.26 | 1680.54 | 182.30 | 79.36 |
| 24049 | 1519.32 | 446.29 | 1776.05 | 182.78 | 79.31 |
| 24626 | 1504.58 | 431.27 | 1251.16 | 114.87 | 79.31 |

TABLE 5S-continued

IFOSFAMIDE
Timepoint(s): 6, 24, 48, 144 hrs

| Identifier | NonToxMean | NonToxSD | ToxMean | ToxSD | LDAScore |
|---|---|---|---|---|---|
| 820 | 2467.06 | 1167.88 | 1920.44 | 339.35 | 79.22 |
| 1684 | 2833.17 | 1621.88 | 1212.60 | 870.83 | 79.22 |
| 21373 | 373.62 | 85.16 | 332.82 | 32.95 | 79.22 |
| 16211 | 2261.75 | 1141.46 | 1652.93 | 320.55 | 79.18 |
| 16521 | 285.41 | 90.61 | 359.56 | 55.31 | 79.14 |
| 22661 | 1309.12 | 421.45 | 1003.73 | 117.38 | 79.01 |

TABLE 5T

INDOMETHACIN
Timepoint(s): 48, 72 hrs

| Identifier | NonToxMean | NonToxSD | ToxMean | ToxSD | LDAScore |
|---|---|---|---|---|---|
| 155 | 21.42 | 16.98 | 101.88 | 13.61 | 99.53 |
| 154 | 112.29 | 36.99 | 249.23 | 25.25 | 99.27 |
| 16173 | 14.63 | 13.08 | 179.81 | 66.16 | 99.18 |
| 13614 | 340.21 | 88.42 | 786.72 | 118.82 | 99.01 |
| 1850 | 46.85 | 347.25 | 309.01 | 159.03 | 98.93 |
| 22499 | 8.20 | 11.83 | 58.62 | 9.91 | 98.88 |
| 1893 | 29.44 | 20.17 | 163.67 | 70.52 | 98.84 |
| 1221 | 0.23 | 15.64 | 193.08 | 98.35 | 98.80 |
| 21445 | 0.99 | 14.21 | 203.14 | 86.78 | 98.75 |
| 1854 | 43.31 | 289.94 | 282.61 | 143.16 | 98.67 |
| 25517 | 38.27 | 31.10 | 173.50 | 50.20 | 98.58 |
| 19710 | 43.43 | 20.81 | 132.45 | 42.06 | 98.54 |
| 6431 | 51.07 | 32.99 | 209.15 | 53.95 | 98.50 |
| 2457 | 288.90 | 75.46 | 543.74 | 54.46 | 98.45 |
| 7299 | 177.44 | 143.66 | 797.13 | 276.35 | 98.41 |
| 23964 | 12.50 | 18.01 | 63.92 | 17.10 | 98.37 |
| 1943 | 31.78 | 14.21 | 86.66 | 15.03 | 98.15 |
| 13615 | 253.23 | 68.59 | 560.03 | 77.71 | 98.15 |
| 20713 | 215.61 | 108.00 | 606.67 | 98.17 | 98.11 |
| 24237 | 56.39 | 37.15 | 281.98 | 103.56 | 98.07 |
| 8565 | 31.85 | 16.10 | 105.94 | 38.19 | 98.02 |
| 7540 | 154.84 | 89.44 | 535.02 | 179.10 | 98.02 |
| 1845 | -7.69 | 24.61 | 109.59 | 48.06 | 98.02 |
| 18684 | 137.77 | 49.02 | 305.11 | 48.29 | 97.98 |
| 7858 | -4.71 | 7.47 | 47.48 | 40.75 | 97.98 |
| 15408 | 192.19 | 56.59 | 376.55 | 44.39 | 97.98 |
| 10281 | 172.58 | 185.66 | 567.51 | 296.37 | 97.94 |
| 18867 | 103.82 | 49.82 | 263.24 | 51.22 | 97.94 |
| 18353 | 112.33 | 68.84 | 349.21 | 48.50 | 97.94 |
| 20715 | 134.85 | 59.63 | 354.19 | 34.91 | 97.90 |
| 6551 | 576.57 | 201.46 | 1150.85 | 135.93 | 97.90 |
| 7665 | 282.66 | 95.03 | 609.80 | 128.48 | 97.90 |
| 20868 | 22.06 | 17.54 | 98.66 | 30.62 | 97.85 |
| 343 | 28.72 | 32.40 | 151.55 | 21.38 | 97.85 |
| 20869 | 21.84 | 21.14 | 111.52 | 32.81 | 97.85 |
| 20711 | 43.08 | 40.65 | 197.85 | 41.42 | 97.77 |
| 16521 | 283.95 | 85.02 | 655.14 | 127.79 | 97.59 |
| 21444 | 19.93 | 43.02 | 180.28 | 49.29 | 97.51 |
| 21683 | 33.96 | 22.93 | 127.35 | 39.46 | 97.47 |
| 3180 | 309.65 | 80.63 | 524.23 | 45.30 | 97.47 |
| 1942 | 17.90 | 24.48 | 99.74 | 38.19 | 97.47 |
| 14184 | 113.17 | 49.05 | 251.46 | 48.41 | 97.42 |
| 1894 | 202.61 | 73.39 | 421.42 | 64.64 | 97.42 |
| 15851 | 200.88 | 151.27 | 525.10 | 94.05 | 97.38 |
| 20700 | 85.68 | 416.32 | 391.89 | 193.02 | 97.38 |
| 4749 | 234.65 | 200.18 | 431.09 | 62.04 | 97.38 |
| 6094 | 138.21 | 54.26 | 356.45 | 88.21 | 97.38 |
| 2555 | 96.41 | 46.12 | 235.98 | 52.95 | 97.34 |
| 3260 | 193.81 | 71.46 | 443.67 | 108.75 | 97.34 |
| 19012 | 483.92 | 149.86 | 930.52 | 98.29 | 97.21 |
| 5887 | 77.25 | 81.17 | 491.60 | 169.72 | 97.16 |
| 20041 | 192.79 | 82.66 | 490.91 | 119.03 | 97.16 |
| 16007 | 26.63 | 17.31 | 92.50 | 26.48 | 97.04 |
| 21653 | 236.04 | 61.07 | 399.34 | 79.22 | 97.04 |
| 13004 | 142.59 | 42.21 | 275.32 | 36.65 | 96.99 |

TABLE 5T-continued

INDOMETHACIN
Timepoint(s): 48, 72 hrs

| Identifier | NonToxMean | NonToxSD | ToxMean | ToxSD | LDAScore |
|---|---|---|---|---|---|
| 19387 | 667.36 | 146.95 | 1017.20 | 82.56 | 96.99 |
| 2554 | 53.34 | 18.18 | 111.59 | 20.52 | 96.99 |
| 4661 | 307.32 | 90.25 | 543.97 | 56.72 | 96.91 |
| 21467 | 13.64 | 131.26 | 140.69 | 60.68 | 96.86 |
| 18352 | 162.12 | 85.33 | 437.38 | 90.35 | 96.86 |
| 15191 | 2030.38 | 1211.92 | 434.31 | 67.70 | 96.86 |
| 24183 | 68.30 | 35.60 | 194.82 | 48.12 | 96.82 |
| 4748 | 110.39 | 127.49 | 266.50 | 52.38 | 96.82 |
| 19711 | 83.58 | 22.63 | 149.45 | 21.04 | 96.82 |
| 848 | 18.09 | 11.05 | 45.15 | 4.76 | 96.65 |
| 10015 | 231.63 | 76.39 | 422.68 | 89.46 | 96.65 |
| 11708 | 319.08 | 90.36 | 587.03 | 103.59 | 96.65 |
| 22321 | 101.90 | 68.06 | 234.02 | 51.42 | 96.61 |
| 1597 | 50.19 | 41.89 | 187.05 | 63.28 | 96.61 |
| 6120 | 511.17 | 159.69 | 914.05 | 106.73 | 96.52 |
| 20714 | 178.33 | 78.97 | 430.20 | 87.05 | 96.52 |
| 24200 | 421.16 | 141.29 | 847.55 | 177.88 | 96.52 |
| 3316 | 8.48 | 11.20 | 32.02 | 7.24 | 96.48 |
| 14595 | 87.99 | 36.42 | 175.31 | 16.47 | 96.39 |
| 21654 | 362.19 | 114.34 | 536.63 | 59.58 | 96.22 |
| 22479 | 433.07 | 146.06 | 846.76 | 137.55 | 96.18 |
| 18687 | 418.98 | 188.38 | 661.54 | 59.97 | 96.13 |
| 5572 | 330.93 | 144.21 | 692.30 | 98.63 | 96.09 |
| 3020 | 292.14 | 93.53 | 549.45 | 92.30 | 96.09 |
| 25366 | 52.69 | 46.59 | 140.27 | 34.35 | 96.01 |
| 11183 | 98.16 | 39.08 | 183.02 | 34.74 | 96.01 |
| 19145 | 363.77 | 71.33 | 513.30 | 38.33 | 95.96 |
| 15409 | 399.23 | 98.94 | 637.09 | 62.27 | 95.88 |
| 17950 | 64.06 | 23.04 | 112.35 | 10.61 | 95.79 |
| 16945 | 934.12 | 162.35 | 1222.61 | 66.01 | 95.79 |
| 16917 | 755.96 | 258.94 | 1351.72 | 135.35 | 95.75 |
| 9286 | 205.05 | 59.59 | 354.73 | 51.76 | 95.66 |
| 18217 | 15.31 | 19.01 | 63.19 | 16.35 | 95.62 |
| 14185 | 203.46 | 94.18 | 411.57 | 81.62 | 95.62 |
| 16646 | 28.33 | 20.91 | 71.67 | 15.31 | 95.58 |
| 23837 | 100.89 | 40.39 | 206.26 | 37.38 | 95.53 |
| 21066 | 43.85 | 16.28 | 90.93 | 15.15 | 95.53 |
| 18068 | 82.30 | 21.15 | 125.33 | 8.28 | 95.49 |
| 21410 | 183.82 | 61.54 | 326.34 | 61.71 | 95.45 |
| 18355 | 56.83 | 27.50 | 129.21 | 39.86 | 95.36 |
| 6044 | 327.15 | 91.24 | 520.74 | 70.39 | 95.36 |
| 23145 | 44.14 | 20.10 | 96.23 | 26.84 | 95.32 |
| 16859 | 122.48 | 51.26 | 241.14 | 54.89 | 95.27 |
| 15246 | 63.40 | 20.73 | 113.00 | 17.39 | 95.19 |
| 24019 | 27.09 | 25.66 | 86.45 | 18.38 | 95.19 |

TABLE 5U

LITHIUM CHLORIDE
Timepoint(s): 120 hrs

| Identifier | NonToxMean | NonToxSD | ToxMean | ToxSD | LDAScore |
|---|---|---|---|---|---|
| 24019 | 27.07 | 25.30 | 127.00 | 8.27 | 99.61 |
| 14421 | 418.40 | 87.55 | 639.64 | 12.93 | 99.57 |
| 13641 | 47.49 | 30.07 | 145.93 | 13.26 | 99.53 |
| 1463 | 619.17 | 296.16 | 1455.45 | 46.93 | 99.53 |
| 16300 | 61.51 | 20.88 | 147.76 | 15.29 | 99.49 |
| 13974 | 296.90 | 139.79 | 1260.41 | 77.75 | 99.49 |
| 3244 | 127.45 | 30.43 | 40.35 | 2.64 | 99.36 |
| 10464 | 131.43 | 35.68 | 41.70 | 2.59 | 99.36 |
| 1462 | 407.93 | 201.27 | 1216.38 | 60.80 | 99.36 |
| 18525 | 246.32 | 66.03 | 97.58 | 6.10 | 99.27 |
| 14227 | 72.35 | 65.02 | 265.04 | 34.60 | 99.23 |
| 25741 | 185.55 | 57.43 | 490.81 | 62.92 | 99.23 |
| 1224 | 3.70 | 11.53 | 50.50 | 8.69 | 99.23 |
| 13880 | 679.69 | 204.44 | 295.39 | 24.01 | 99.14 |
| 14261 | 39.73 | 17.42 | 113.90 | 16.40 | 99.14 |
| 18472 | 1551.82 | 378.09 | 827.52 | 66.71 | 99.10 |

TABLE 5U-continued

LITHIUM CHLORIDE
Timepoint(s): 120 hrs

| Identifier | NonToxMean | NonToxSD | ToxMean | ToxSD | LDAScore |
|---|---|---|---|---|---|
| 15363 | 446.56 | 133.55 | 187.16 | 15.68 | 99.06 |
| 8598 | 139.25 | 41.61 | 362.49 | 73.57 | 99.01 |
| 5176 | 217.77 | 121.65 | 603.36 | 60.94 | 98.93 |
| 14754 | 99.93 | 24.11 | 228.47 | 44.23 | 98.93 |
| 20849 | 276.44 | 85.41 | 565.38 | 36.71 | 98.93 |
| 15955 | 750.17 | 198.73 | 371.84 | 30.56 | 98.89 |
| 14633 | 97.72 | 88.30 | −1.97 | 5.36 | 98.84 |
| 15371 | 378.04 | 55.30 | 593.66 | 40.88 | 98.80 |
| 17342 | 202.36 | 532.80 | 480.79 | 60.48 | 98.80 |
| 20809 | 317.42 | 60.81 | 558.00 | 56.79 | 98.80 |
| 16650 | 256.32 | 82.88 | 614.21 | 64.30 | 98.80 |
| 18109 | 19.25 | 21.24 | 92.33 | 9.99 | 98.76 |
| 18286 | 10.51 | 10.22 | 41.67 | 5.33 | 98.76 |
| 24049 | 1526.25 | 442.84 | 773.94 | 52.98 | 98.76 |
| 16245 | 386.32 | 115.78 | 64.71 | 31.63 | 98.76 |
| 23651 | 656.57 | 627.85 | 1600.29 | 142.54 | 98.76 |
| 574 | 335.41 | 164.90 | 679.82 | 42.41 | 98.71 |
| 20099 | 81.48 | 29.97 | 171.81 | 18.17 | 98.71 |
| 1976 | 24.82 | 21.34 | 269.98 | 118.48 | 98.71 |
| 23294 | 244.42 | 55.35 | 115.25 | 8.35 | 98.71 |
| 3733 | 340.43 | 153.36 | 790.69 | 47.48 | 98.67 |
| 23957 | 68.22 | 41.24 | 264.04 | 43.03 | 98.67 |
| 3348 | 496.09 | 130.59 | 245.12 | 25.78 | 98.67 |
| 20697 | 1418.84 | 278.90 | 908.67 | 36.86 | 98.67 |
| 260 | 415.71 | 110.33 | 903.01 | 137.68 | 98.63 |
| 19321 | 313.57 | 55.98 | 464.14 | 23.58 | 98.63 |
| 8597 | 240.21 | 54.94 | 523.47 | 111.57 | 98.63 |
| 17159 | 699.06 | 218.26 | 1124.72 | 53.18 | 98.63 |
| 18103 | 58.33 | 28.29 | 149.64 | 17.07 | 98.59 |
| 5698 | 1169.95 | 220.06 | 1885.00 | 141.61 | 98.59 |
| 24648 | 40.24 | 20.33 | 6.76 | 1.40 | 98.59 |
| 14020 | 277.14 | 68.14 | 152.09 | 12.77 | 98.54 |
| 15246 | 63.64 | 21.09 | 87.26 | 0.84 | 98.54 |
| 24115 | 68.51 | 36.48 | 345.37 | 126.46 | 98.54 |
| 21997 | 28.94 | 25.26 | 95.22 | 19.06 | 98.54 |
| 960 | 191.35 | 46.71 | 93.10 | 7.12 | 98.50 |
| 22321 | 100.55 | 58.87 | 629.47 | 166.32 | 98.50 |
| 20886 | 711.00 | 279.64 | 2114.90 | 382.05 | 98.50 |
| 16354 | 280.15 | 119.74 | −118.26 | 64.76 | 98.50 |
| 12376 | 19.26 | 124.98 | 83.39 | 19.10 | 98.50 |
| 17106 | 81.66 | 24.82 | 36.82 | 2.74 | 98.50 |
| 18473 | 2589.69 | 916.99 | 1318.66 | 52.24 | 98.50 |
| 9254 | 246.49 | 48.78 | 393.24 | 20.14 | 98.46 |
| 1340 | 191.26 | 49.84 | 289.47 | 26.83 | 98.46 |
| 17162 | 6.69 | 16.97 | 58.11 | 15.91 | 98.46 |
| 6806 | 1233.36 | 345.85 | 586.60 | 42.84 | 98.41 |
| 25840 | −2.65 | 12.34 | 54.97 | 27.90 | 98.41 |
| 20887 | 784.36 | 296.51 | 2396.08 | 485.51 | 98.37 |
| 1372 | 199.45 | 51.98 | 391.46 | 35.86 | 98.33 |
| 18349 | 140.08 | 38.43 | 262.92 | 23.80 | 98.33 |
| 14989 | 500.36 | 106.29 | 910.22 | 99.63 | 98.33 |
| 4049 | 23.03 | 65.14 | 113.93 | 24.17 | 98.29 |
| 11483 | 65.04 | 45.49 | 132.25 | 10.90 | 98.29 |
| 9867 | 29.07 | 22.58 | −38.05 | 11.94 | 98.29 |
| 13411 | 789.51 | 324.70 | 239.08 | 27.46 | 98.29 |
| 25709 | 267.20 | 83.61 | 591.14 | 81.21 | 98.29 |
| 17160 | 1038.70 | 287.67 | 1872.62 | 168.15 | 98.24 |
| 12673 | 37.66 | 22.70 | 116.03 | 13.02 | 98.24 |
| 25306 | 27.76 | 21.91 | −55.70 | 19.66 | 98.24 |
| 16349 | 47.04 | 14.11 | 94.68 | 13.74 | 98.24 |
| 13392 | 190.93 | 48.80 | 355.59 | 34.39 | 98.24 |
| 4048 | −6.11 | 32.04 | 34.41 | 10.44 | 98.20 |
| 2915 | 87.49 | 36.50 | 176.88 | 18.22 | 98.20 |
| 15761 | 90.06 | 42.30 | 20.08 | 3.24 | 98.20 |
| 111 | 590.89 | 237.37 | 1115.91 | 164.07 | 98.20 |
| 24695 | 63.72 | 21.72 | 13.53 | 4.47 | 98.16 |
| 19152 | 164.93 | 52.20 | 401.36 | 74.04 | 98.16 |
| 24597 | 585.04 | 105.40 | 935.83 | 83.53 | 98.16 |
| 21527 | 239.33 | 59.62 | 438.09 | 50.65 | 98.16 |
| 3776 | 377.17 | 93.88 | 689.18 | 68.23 | 98.16 |
| 5626 | 26.84 | 18.16 | 84.22 | 9.81 | 98.11 |
| 3075 | 524.14 | 179.66 | 209.94 | 19.92 | 98.11 |
| 15511 | 214.84 | 128.36 | 897.69 | 308.94 | 98.11 |
| 6386 | 20.45 | 18.01 | −5.75 | 1.87 | 98.07 |
| 134 | 69.64 | 33.24 | 7.05 | 4.13 | 98.07 |
| 19665 | 91.84 | 47.87 | 296.74 | 33.57 | 98.07 |
| 10984 | 2015.62 | 568.01 | 964.72 | 141.17 | 98.03 |
| 15247 | 637.80 | 190.94 | 1369.01 | 148.83 | 98.03 |
| 2905 | 246.54 | 108.85 | 410.67 | 11.79 | 98.03 |
| 13343 | 210.51 | 55.05 | 72.01 | 21.01 | 98.03 |

TABLE 5V

MERCURIC CHLORIDE
Timepoints(s): 3, 6, 24 hrs

| Identifier | NonToxMean | NonToxSD | ToxMean | ToxSD | LDAScore |
|---|---|---|---|---|---|
| 8865 | 332.39 | 171.86 | 5197.14 | 2943.02 | 99.44 |
| 1475 | 136.94 | 103.32 | 3940.87 | 1974.36 | 99.18 |
| 20035 | 178.08 | 98.83 | 635.50 | 155.87 | 98.10 |
| 19723 | 74.87 | 55.61 | 273.03 | 109.44 | 98.02 |
| 15191 | 1988.23 | 1177.92 | 5041.11 | 935.19 | 96.55 |
| 14139 | 80.54 | 27.01 | 25.59 | 13.59 | 95.47 |
| 8664 | 86.42 | 70.91 | 2082.06 | 1352.81 | 95.23 |
| 12331 | 594.25 | 155.97 | 254.07 | 138.26 | 94.96 |
| 17734 | 119.63 | 75.92 | 566.88 | 280.56 | 94.84 |
| 23579 | 734.95 | 158.66 | 430.76 | 80.03 | 94.78 |
| 23983 | 544.27 | 150.95 | 220.82 | 131.74 | 94.48 |
| 14138 | 84.72 | 29.10 | 33.29 | 12.42 | 94.31 |
| 16518 | 826.45 | 273.09 | 2395.53 | 930.51 | 94.24 |
| 17635 | 651.30 | 148.78 | 358.62 | 92.32 | 93.79 |
| 7196 | 178.22 | 77.07 | 494.09 | 205.98 | 93.68 |
| 15850 | 1203.52 | 323.32 | 2507.97 | 545.30 | 93.68 |
| 24235 | 433.60 | 163.10 | 1038.60 | 349.80 | 93.55 |
| 21445 | 2.08 | 22.76 | 30.67 | 12.91 | 93.51 |
| 24649 | 122.93 | 28.55 | 76.77 | 12.19 | 93.49 |
| 5867 | 166.42 | 48.13 | 259.79 | 50.17 | 93.49 |
| 3348 | 497.46 | 129.58 | 259.25 | 78.88 | 93.45 |
| 15848 | 1313.68 | 402.72 | 2886.50 | 676.70 | 93.42 |
| 19768 | 706.30 | 166.91 | 1328.43 | 290.35 | 93.42 |
| 17161 | 1144.51 | 381.55 | 2737.15 | 723.56 | 93.33 |
| 1004 | 108.90 | 32.28 | 56.68 | 10.23 | 92.84 |
| 15190 | 1789.26 | 1124.32 | 5409.42 | 1117.57 | 92.73 |
| 14595 | 89.23 | 36.64 | 26.57 | 16.82 | 92.67 |
| 15189 | 1722.10 | 1120.12 | 5391.29 | 1462.09 | 92.60 |
| 15300 | 135.69 | 130.01 | 397.39 | 125.33 | 92.60 |
| 23314 | 67.33 | 271.41 | 622.50 | 259.52 | 92.43 |
| 15301 | 37.59 | 67.32 | 147.90 | 49.32 | 92.39 |
| 18944 | 202.65 | 68.48 | 458.00 | 181.57 | 92.30 |
| 6054 | 27.38 | 53.50 | 71.68 | 29.34 | 92.26 |
| 13642 | 209.02 | 74.04 | 85.92 | 29.90 | 92.24 |
| 23230 | 378.13 | 96.00 | 695.07 | 177.40 | 92.17 |
| 17211 | 1433.79 | 549.05 | 2360.95 | 279.33 | 91.85 |
| 3493 | 58.50 | 20.07 | 107.74 | 26.19 | 91.82 |
| 23825 | 283.86 | 49.04 | 166.00 | 50.35 | 91.78 |
| 18564 | 219.22 | 49.05 | 95.46 | 32.77 | 91.74 |
| 11680 | 360.19 | 81.92 | 233.52 | 34.79 | 91.68 |
| 17765 | 1277.82 | 438.77 | 2585.84 | 579.12 | 91.65 |
| 16982 | 138.22 | 290.89 | 380.00 | 223.17 | 91.57 |
| 13610 | 357.65 | 69.18 | 196.18 | 80.11 | 91.26 |
| 21993 | 76.47 | 25.96 | 129.83 | 18.36 | 91.26 |
| 8927 | 745.07 | 166.28 | 377.77 | 106.17 | 91.01 |
| 11871 | 55.24 | 129.01 | 197.33 | 57.60 | 90.91 |
| 11050 | 670.06 | 136.16 | 972.43 | 147.61 | 90.88 |
| 13507 | 422.59 | 99.12 | 659.30 | 138.95 | 90.83 |
| 9271 | 102.44 | 54.22 | 21.68 | 25.82 | 90.82 |
| 19031 | 59.98 | 47.58 | 145.41 | 39.97 | 90.79 |
| 24577 | 1168.59 | 364.98 | 2135.75 | 393.09 | 90.79 |
| 10182 | 2.45 | 99.29 | 78.59 | 59.67 | 90.75 |
| 18300 | 451.47 | 147.74 | 136.58 | 90.13 | 90.75 |
| 18259 | 207.76 | 78.23 | 1353.31 | 770.76 | 90.72 |

TABLE 5V-continued

MERCURIC CHLORIDE
Timepoints(s): 3, 6, 24 hrs

| Identifier | NonToxMean | NonToxSD | Tox-Mean | ToxSD | LDAScore |
|---|---|---|---|---|---|
| 1928 | 485.55 | 106.87 | 208.21 | 110.11 | 90.66 |
| 6632 | 171.87 | 58.89 | 288.22 | 64.66 | 90.53 |
| 13611 | 273.95 | 107.44 | 57.12 | 66.20 | 90.45 |
| 25098 | 43.26 | 30.01 | 276.68 | 179.66 | 90.37 |
| 22539 | 71.67 | 46.78 | −27.28 | 37.71 | 90.36 |
| 20945 | 897.15 | 248.57 | 1469.22 | 277.42 | 90.32 |
| 19678 | 110.11 | 57.05 | −19.38 | 53.40 | 90.32 |
| 23567 | 52.11 | 60.74 | 235.62 | 105.54 | 90.29 |
| 23868 | 159.82 | 189.43 | 1997.17 | 1212.75 | 90.24 |
| 812 | 157.29 | 34.98 | 83.70 | 36.70 | 90.19 |
| 23872 | 44.34 | 60.45 | 587.85 | 460.34 | 90.16 |
| 21372 | 276.72 | 65.43 | 134.32 | 44.54 | 90.10 |
| 18611 | 1409.94 | 446.15 | 2438.75 | 459.58 | 90.10 |
| 21306 | 126.88 | 54.43 | 52.78 | 18.76 | 90.09 |
| 3808 | 166.04 | 48.80 | 407.80 | 212.39 | 90.07 |
| 12031 | 145.86 | 38.78 | 225.16 | 30.38 | 90.06 |
| 23869 | 36.50 | 52.75 | 579.45 | 394.24 | 90.03 |
| 3015 | 2289.14 | 964.34 | 4534.92 | 1150.81 | 89.97 |
| 17908 | 60.79 | 49.95 | 325.35 | 238.47 | 89.90 |
| 25539 | 125.13 | 35.09 | 45.76 | 23.16 | 89.89 |
| 3473 | 120.74 | 34.02 | 69.52 | 20.97 | 89.83 |
| 2536 | 397.05 | 123.98 | 201.50 | 73.82 | 89.83 |
| 23826 | 344.12 | 55.78 | 225.14 | 47.99 | 89.80 |
| 9114 | 870.77 | 222.15 | 416.13 | 221.53 | 89.80 |
| 1639 | 97.37 | 22.99 | 62.34 | 12.37 | 89.70 |
| 20920 | 617.66 | 155.43 | 1397.16 | 623.36 | 89.60 |
| 20350 | 156.72 | 49.50 | 53.00 | 45.87 | 89.58 |
| 6615 | 279.24 | 84.15 | 96.62 | 96.14 | 89.50 |
| 19952 | 67.58 | 24.21 | 24.03 | 11.92 | 89.41 |
| 8237 | 102.59 | 36.73 | 179.81 | 51.98 | 89.37 |
| 11841 | 886.79 | 192.09 | 1632.36 | 479.53 | 89.34 |
| 2310 | −47.82 | 40.85 | 36.34 | 37.62 | 89.32 |
| 15796 | 337.30 | 87.85 | 156.28 | 76.95 | 89.24 |
| 22681 | 216.80 | 177.12 | 918.02 | 459.53 | 89.21 |
| 22543 | 694.25 | 216.61 | 217.39 | 263.73 | 89.20 |
| 19433 | 110.29 | 59.85 | 445.41 | 230.04 | 89.17 |
| 22540 | 1828.95 | 538.43 | 794.41 | 586.09 | 89.07 |
| 17473 | 421.95 | 90.69 | 764.49 | 230.12 | 89.04 |
| 15875 | 1177.56 | 384.90 | 1982.41 | 472.79 | 88.98 |
| 18396 | 74.08 | 26.23 | 124.23 | 18.90 | 88.94 |
| 19 | 336.88 | 73.75 | 628.54 | 175.62 | 88.82 |
| 25567 | 456.18 | 167.99 | 922.98 | 373.29 | 88.65 |
| 20728 | 538.10 | 99.95 | 327.92 | 109.45 | 88.59 |
| 24351 | −2.24 | 8.36 | 22.30 | 16.23 | 88.56 |
| 9053 | 240.22 | 50.14 | 146.06 | 39.78 | 88.55 |
| 18305 | 1364.98 | 457.67 | 2297.19 | 462.10 | 88.51 |

TABLE 5W

PAMIDRONATE
Timepoint(s): 24 hrs

| Identifier | NonToxMean | NonToxSD | Tox-Mean | ToxSD | LDAScore |
|---|---|---|---|---|---|
| 439 | 55.65 | 23.09 | 35.13 | 0.15 | 99.49 |
| 381 | 23.05 | 20.96 | 4.85 | 0.20 | 98.80 |
| 1439 | 233.12 | 46.90 | 167.13 | 1.64 | 98.63 |
| 24501 | 526.65 | 117.76 | 477.38 | 1.09 | 98.50 |
| 815 | 1161.46 | 344.32 | 1840.91 | 46.72 | 98.50 |
| 21723 | 24.61 | 15.80 | 18.81 | 0.26 | 98.37 |
| 25907 | 19.98 | 25.22 | 27.99 | 0.55 | 98.33 |
| 4440 | 320.37 | 110.50 | 249.77 | 1.69 | 98.33 |
| 8950 | 91.09 | 33.83 | 64.54 | 0.45 | 98.29 |
| 1145 | 59.20 | 26.43 | 36.98 | 0.67 | 98.25 |
| 20257 | 130.93 | 45.11 | 78.91 | 1.23 | 98.20 |
| 12781 | 189.97 | 49.11 | 273.46 | 3.66 | 98.12 |
| 20427 | 796.69 | 192.75 | 1119.78 | 17.38 | 97.90 |
| 16938 | 1322.80 | 411.98 | 1887.43 | 31.46 | 97.90 |
| 1324 | 63.66 | 31.18 | 28.89 | 2.88 | 97.82 |

TABLE 5W-continued

PAMIDRONATE
Timepoint(s): 24 hrs

| Identifier | NonToxMean | NonToxSD | Tox-Mean | ToxSD | LDAScore |
|---|---|---|---|---|---|
| 16584 | 115.91 | 45.04 | 161.39 | 2.19 | 97.73 |
| 17102 | 47.91 | 18.57 | 30.16 | 0.64 | 97.73 |
| 10227 | 447.34 | 108.01 | 244.96 | 13.58 | 97.69 |
| 1310 | 152.06 | 33.32 | 86.35 | 7.14 | 97.69 |
| 8476 | 3812.40 | 1012.46 | 4862.16 | 57.22 | 97.65 |
| 22051 | 151.18 | 44.26 | 223.47 | 4.06 | 97.65 |
| 5049 | 297.65 | 66.21 | 180.38 | 7.11 | 97.60 |
| 16323 | 68.35 | 35.92 | 36.63 | 1.47 | 97.56 |
| 6654 | 166.71 | 45.74 | 158.83 | 0.92 | 97.43 |
| 1651 | 878.67 | 240.75 | 692.24 | 5.18 | 97.39 |
| 16192 | 41.41 | 14.72 | 34.35 | 0.38 | 97.31 |
| 12343 | 50.68 | 18.55 | 31.84 | 0.83 | 97.31 |
| 691 | 133.51 | 42.32 | 62.52 | 3.81 | 97.26 |
| 17635 | 648.73 | 151.15 | 484.36 | 6.12 | 97.22 |
| 9286 | 205.78 | 60.59 | 319.19 | 10.41 | 97.22 |
| 14800 | 36.39 | 23.63 | 34.69 | 0.41 | 97.22 |
| 23888 | 105.90 | 50.58 | 91.90 | 1.08 | 97.13 |
| 5969 | 1521.63 | 357.02 | 1485.82 | 9.84 | 97.13 |
| 3475 | 384.13 | 98.77 | 465.98 | 4.26 | 97.05 |
| 11174 | 54.15 | 51.85 | 121.54 | 7.12 | 97.01 |
| 26119 | 124.47 | 45.67 | 234.96 | 195.06 | 97.01 |
| 18250 | 1094.73 | 316.96 | 1382.93 | 14.86 | 96.96 |
| 25069 | 133.97 | 60.97 | 77.32 | 2.29 | 96.88 |
| 18135 | 133.61 | 28.59 | 96.51 | 1.97 | 96.88 |
| 21742 | 33.31 | 18.06 | 25.78 | 0.33 | 96.83 |
| 25702 | 579.55 | 128.85 | 805.98 | 44.29 | 96.79 |
| 10936 | 207.62 | 43.60 | 191.02 | 1.12 | 96.79 |
| 12342 | 96.27 | 49.48 | 87.13 | 1.04 | 96.75 |
| 19976 | 47.03 | 15.83 | 30.77 | 0.70 | 96.75 |
| 9620 | 530.95 | 116.93 | 770.14 | 47.74 | 96.71 |
| 20810 | 1262.30 | 404.25 | 1842.66 | 50.26 | 96.71 |
| 24721 | 203.81 | 53.70 | 187.98 | 1.38 | 96.71 |
| 14967 | 49.34 | 21.65 | 19.69 | 1.41 | 96.58 |
| 1309 | 43.01 | 16.54 | 30.28 | 0.59 | 96.54 |
| 730 | 112.34 | 33.32 | 65.78 | 2.57 | 96.49 |
| 15876 | 1174.15 | 310.95 | 1565.93 | 37.98 | 96.49 |
| 16482 | 195.58 | 40.06 | 132.17 | 5.76 | 96.45 |
| 5654 | 41.42 | 24.77 | 86.94 | 5.20 | 96.45 |
| 15850 | 1216.75 | 351.89 | 1264.63 | 16.42 | 96.45 |
| 4259 | 700.70 | 159.00 | 935.48 | 29.71 | 96.36 |
| 7010 | 309.13 | 55.63 | 255.94 | 3.25 | 96.36 |
| 18880 | 36.99 | 12.90 | 31.14 | 0.58 | 96.32 |
| 3007 | 126.64 | 42.37 | 192.91 | 7.32 | 96.28 |
| 1375 | 84.74 | 20.63 | 55.45 | 2.98 | 96.28 |
| 19244 | 1227.03 | 383.14 | 1715.96 | 64.01 | 96.28 |
| 6595 | 76.76 | 35.41 | 102.22 | 2.83 | 96.19 |
| 18126 | 701.66 | 166.62 | 548.76 | 14.64 | 96.19 |
| 10869 | 11.30 | 60.29 | 123.69 | 15.83 | 96.15 |
| 15239 | 567.46 | 132.45 | 783.53 | 43.73 | 96.11 |
| 4241 | 114.51 | 43.66 | 203.36 | 162.90 | 96.11 |
| 12360 | 55.02 | 27.32 | 35.03 | 1.44 | 96.11 |
| 11687 | 25.88 | 23.50 | 35.95 | 1.69 | 96.11 |
| 5492 | 97.03 | 47.49 | 24.35 | 5.81 | 96.11 |
| 9671 | 124.41 | 52.83 | 135.25 | 1.91 | 96.11 |
| 9410 | 62.57 | 24.27 | 60.98 | 0.84 | 95.98 |
| 13105 | 64.62 | 26.94 | 43.02 | 1.19 | 95.98 |
| 10659 | 132.22 | 90.74 | 258.54 | 43.13 | 95.94 |
| 106 | 59.79 | 20.18 | 35.91 | 1.62 | 95.89 |
| 2697 | 1226.39 | 358.41 | 1822.86 | 80.35 | 95.85 |
| 10217 | 310.63 | 90.28 | 201.72 | 7.38 | 95.85 |
| 22658 | 275.00 | 67.48 | 237.14 | 2.73 | 95.85 |
| 3417 | 445.05 | 113.12 | 533.98 | 7.67 | 95.81 |
| 15446 | 369.04 | 93.58 | 428.95 | 2.94 | 95.81 |
| 2847 | 62.77 | 31.28 | 81.96 | 1.81 | 95.81 |
| 2469 | 1383.42 | 482.22 | 963.09 | 26.57 | 95.81 |
| 17175 | 619.05 | 156.40 | 867.90 | 59.01 | 95.77 |
| 4386 | 56.38 | 26.60 | 45.57 | 0.72 | 95.77 |
| 21491 | 110.61 | 27.92 | 90.43 | 1.09 | 95.77 |
| 20844 | 843.25 | 294.01 | 1309.53 | 64.24 | 95.72 |
| 9370 | 773.72 | 201.87 | 676.25 | 8.78 | 95.72 |
| 15130 | 274.69 | 83.28 | 262.79 | 4.56 | 95.64 |

TABLE 5X

PAN
Timepoint(s): 168 hrs

| Identifier | NonToxMean | NonToxSD | ToxMean | ToxSD | LDAScore |
|---|---|---|---|---|---|
| 6100 | −24.28 | 62.27 | 70.39 | 19.04 | 99.79 |
| 2048 | 31.63 | 20.68 | 119.91 | 5.57 | 99.79 |
| 24024 | 32.82 | 21.87 | 144.74 | 15.76 | 99.79 |
| 14722 | 658.73 | 219.20 | 1717.84 | 115.16 | 99.74 |
| 21651 | 31.52 | 24.04 | 198.29 | 19.08 | 99.74 |
| 15401 | 75.65 | 26.38 | 220.16 | 14.55 | 99.70 |
| 15503 | 124.16 | 37.19 | 305.20 | 27.55 | 99.70 |
| 7090 | 16.70 | 14.04 | 114.99 | 16.69 | 99.70 |
| 10893 | −30.66 | 62.67 | 46.11 | 19.29 | 99.70 |
| 23780 | 24.98 | 35.81 | 102.35 | 16.07 | 99.66 |
| 16726 | 944.95 | 205.53 | 460.40 | 16.03 | 99.61 |
| 14430 | 33.41 | 27.29 | 289.53 | 65.58 | 99.61 |
| 15434 | 132.29 | 53.11 | 374.76 | 31.01 | 99.53 |
| 17198 | 812.71 | 267.14 | 249.19 | 36.68 | 99.53 |
| 15437 | 38.33 | 22.07 | 168.45 | 19.74 | 99.53 |
| 225 | 123.21 | 34.21 | 276.57 | 21.70 | 99.49 |
| 3584 | 64.34 | 31.89 | 290.58 | 28.71 | 99.49 |
| 9084 | 46.92 | 17.70 | 134.77 | 13.50 | 99.49 |
| 20736 | 331.77 | 100.84 | 748.89 | 43.21 | 99.49 |
| 19374 | −8.73 | 12.21 | 63.84 | 14.49 | 99.44 |
| 20699 | 94.34 | 231.80 | 255.20 | 18.42 | 99.44 |
| 22816 | 23.08 | 15.16 | 83.31 | 4.90 | 99.44 |
| 23297 | 384.07 | 96.58 | 840.46 | 53.16 | 99.44 |
| 15002 | 140.16 | 98.17 | 338.90 | 19.21 | 99.44 |
| 3269 | 75.61 | 36.41 | 365.17 | 72.48 | 99.44 |
| 23773 | 212.24 | 81.04 | 629.63 | 48.29 | 99.40 |
| 23992 | 5.27 | 6.59 | 56.95 | 14.22 | 99.36 |
| 17682 | 673.28 | 176.72 | 223.65 | 27.55 | 99.36 |
| 3079 | 34.49 | 46.53 | 164.24 | 20.61 | 99.36 |
| 23778 | 68.50 | 31.99 | 270.34 | 37.08 | 99.36 |
| 19006 | 642.56 | 208.65 | 1445.68 | 75.63 | 99.31 |
| 20887 | 793.69 | 313.68 | 218.40 | 48.36 | 99.31 |
| 6039 | 310.04 | 86.04 | 693.54 | 28.37 | 99.27 |
| 15003 | 35.50 | 95.84 | 254.52 | 23.59 | 99.27 |
| 17227 | 873.36 | 191.79 | 476.74 | 33.25 | 99.27 |
| 1801 | 97.51 | 29.11 | 207.98 | 12.46 | 99.27 |
| 10015 | 231.53 | 75.18 | 560.75 | 25.13 | 99.27 |
| 12683 | 60.85 | 40.62 | 505.60 | 124.63 | 99.23 |
| 16675 | 33.50 | 33.48 | 151.49 | 16.04 | 99.23 |
| 1809 | 36.19 | 128.09 | 267.84 | 32.82 | 99.23 |
| 15981 | 75.09 | 25.95 | 290.62 | 83.27 | 99.23 |
| 2637 | 124.84 | 42.73 | 270.38 | 22.27 | 99.23 |
| 2284 | 99.14 | 37.28 | 252.45 | 25.44 | 99.23 |
| 11338 | 39.20 | 31.91 | 342.99 | 92.86 | 99.19 |
| 16425 | 19.78 | 26.43 | 256.34 | 69.36 | 99.19 |
| 9212 | 1017.57 | 301.78 | 2309.86 | 189.18 | 99.19 |
| 13977 | 281.63 | 142.69 | 1144.78 | 134.21 | 99.19 |
| 3572 | 33.77 | 17.83 | 169.37 | 47.47 | 99.19 |
| 22079 | 78.37 | 356.23 | 216.47 | 49.64 | 99.19 |
| 13974 | 298.69 | 149.15 | 842.98 | 65.09 | 99.19 |
| 24564 | 568.47 | 175.61 | 176.63 | 24.26 | 99.14 |
| 18603 | −45.88 | 67.13 | 192.24 | 18.99 | 99.14 |
| 2010 | 33.66 | 315.34 | 180.93 | 36.19 | 99.14 |
| 17501 | 31.72 | 17.98 | 94.02 | 6.17 | 99.14 |
| 23376 | 14.35 | 15.90 | 95.17 | 30.08 | 99.14 |
| 6517 | 231.39 | 155.95 | 730.29 | 101.68 | 99.14 |
| 20599 | 22.90 | 12.70 | 74.26 | 5.67 | 99.14 |
| 23377 | 61.42 | 52.07 | 359.41 | 62.64 | 99.14 |
| 14405 | 459.81 | 287.63 | 2264.76 | 369.05 | 99.14 |
| 1564 | 38.78 | 169.92 | 459.31 | 64.11 | 99.10 |
| 16676 | 38.17 | 26.57 | 134.01 | 11.56 | 99.10 |
| 21695 | 59.83 | 35.43 | 188.55 | 18.05 | 99.10 |
| 20886 | 719.56 | 292.49 | 116.56 | 44.10 | 99.10 |
| 17151 | 16.05 | 62.27 | 445.34 | 138.38 | 99.06 |
| 770 | 798.22 | 219.65 | 310.69 | 35.90 | 99.06 |
| 7262 | 1116.47 | 390.83 | 2517.22 | 160.89 | 99.06 |
| 23981 | 809.28 | 155.43 | 1417.26 | 153.29 | 99.06 |
| 22552 | 314.65 | 94.11 | 570.75 | 29.08 | 99.06 |
| 20709 | 162.15 | 69.62 | 483.04 | 60.17 | 99.06 |
| 7585 | −91.46 | 37.80 | 142.97 | 84.57 | 99.01 |
| 15853 | 5.82 | 59.90 | 258.64 | 131.89 | 99.01 |
| 22592 | 233.64 | 160.86 | 1028.66 | 111.76 | 98.97 |
| 4445 | 514.32 | 117.31 | 988.03 | 63.78 | 98.97 |

TABLE 5X-continued

PAN
Timepoint(s): 168 hrs

| Identifier | NonToxMean | NonToxSD | ToxMean | ToxSD | LDAScore |
|---|---|---|---|---|---|
| 4086 | 14.01 | 16.98 | 152.91 | 75.32 | 98.97 |
| 21509 | 88.80 | 92.91 | 448.20 | 56.16 | 98.97 |
| 24651 | 100.64 | 23.29 | 204.63 | 19.93 | 98.97 |
| 7101 | 389.56 | 671.41 | 1218.47 | 165.33 | 98.93 |
| 15851 | 200.60 | 148.70 | 784.83 | 83.88 | 98.93 |
| 23769 | −6.25 | 8.68 | 29.51 | 10.78 | 98.93 |
| 15504 | 128.87 | 50.45 | 417.46 | 77.64 | 98.93 |
| 1613 | −7.12 | 28.04 | 117.88 | 29.33 | 98.93 |
| 15438 | 65.66 | 32.54 | 171.12 | 14.45 | 98.93 |
| 1460 | 198.26 | 83.19 | 563.02 | 70.47 | 98.93 |
| 13976 | 449.17 | 351.62 | 2551.95 | 498.75 | 98.93 |
| 20903 | 69.41 | 42.80 | 397.90 | 116.45 | 98.89 |
| 23123 | 310.66 | 118.21 | 861.54 | 70.50 | 98.89 |
| 15790 | 45.93 | 25.16 | 134.46 | 10.51 | 98.89 |
| 21391 | 213.21 | 127.55 | 742.74 | 58.03 | 98.89 |
| 455 | 137.60 | 153.63 | 269.32 | 29.16 | 98.89 |
| 20772 | 149.52 | 40.53 | 313.83 | 28.96 | 98.89 |
| 19275 | 726.18 | 191.87 | 1580.61 | 140.07 | 98.84 |
| 17149 | 81.87 | 40.60 | 328.14 | 60.26 | 98.84 |
| 19243 | 76.71 | 48.71 | 359.48 | 105.52 | 98.84 |
| 17197 | 1903.25 | 828.79 | 668.38 | 83.11 | 98.84 |
| 11891 | −15.63 | 11.78 | 25.77 | 9.49 | 98.84 |
| 4640 | 80.30 | 30.25 | 184.62 | 15.77 | 98.80 |
| 4569 | 0.89 | 6.39 | 34.18 | 10.37 | 98.80 |
| 2629 | 25.55 | 23.81 | 70.08 | 4.98 | 98.80 |
| 18529 | 202.36 | 80.95 | 572.14 | 48.95 | 98.80 |

TABLE 5Y

PAN
Timepoint(s): 6, 24 hrs

Atty. Docket No. 44921-5089US
Doc. No. 1803440.1

| Identifier | NonToxMean | NonToxSD | ToxMean | ToxSD | LDAScore |
|---|---|---|---|---|---|
| 410 | 1099.85 | 252.82 | 487.89 | 71.66 | 99.01 |
| 1137 | 58.38 | 18.64 | 128.72 | 40.53 | 97.55 |
| 18322 | 2669.23 | 812.57 | 1422.54 | 109.34 | 97.47 |
| 15433 | 67.21 | 32.38 | 147.81 | 13.69 | 97.04 |
| 8990 | 278.32 | 77.85 | 504.55 | 67.10 | 96.35 |
| 23115 | 565.35 | 169.43 | 1013.53 | 113.02 | 96.22 |
| 1460 | 199.21 | 86.34 | 300.32 | 24.45 | 95.97 |
| 335 | 96.10 | 45.37 | 194.53 | 15.33 | 95.92 |
| 2866 | 637.05 | 212.44 | 1020.97 | 43.03 | 95.75 |
| 15701 | 37.69 | 16.68 | 82.72 | 11.76 | 95.75 |
| 16853 | 67.54 | 23.29 | 107.06 | 8.27 | 95.58 |
| 17693 | 1257.20 | 377.49 | 705.99 | 42.86 | 95.41 |
| 6250 | 490.36 | 103.66 | 731.52 | 54.23 | 95.36 |
| 19327 | 89.22 | 29.33 | 144.42 | 10.71 | 95.28 |
| 21977 | 88.79 | 52.26 | 163.28 | 17.00 | 95.11 |
| 1962 | 33.32 | 26.88 | 74.11 | 7.81 | 95.06 |
| 19080 | 75.82 | 57.08 | 219.58 | 56.51 | 95.06 |
| 13598 | 349.80 | 109.75 | 578.05 | 60.94 | 95.02 |
| 11524 | −14.25 | 24.65 | 43.36 | 19.72 | 95.02 |
| 729 | 90.40 | 35.70 | 171.30 | 19.74 | 94.98 |
| 15552 | 175.81 | 40.06 | 237.25 | 9.67 | 94.98 |
| 4312 | 77.28 | 38.83 | 150.22 | 19.98 | 94.94 |
| 18996 | 137.86 | 44.69 | 250.58 | 35.37 | 94.85 |
| 17411 | 79.24 | 54.48 | 184.11 | 25.15 | 94.76 |
| 20752 | 13.07 | 11.34 | 26.51 | 2.40 | 94.76 |
| 11445 | 436.52 | 103.96 | 686.40 | 101.03 | 94.42 |
| 17755 | 393.23 | 102.51 | 214.27 | 40.93 | 94.42 |
| 19077 | 208.94 | 51.22 | 306.89 | 24.65 | 94.25 |
| 21355 | 375.05 | 118.77 | 619.86 | 88.05 | 94.21 |
| 6454 | 239.78 | 78.25 | 421.17 | 60.75 | 94.16 |
| 21092 | 392.44 | 225.02 | 575.95 | 55.98 | 94.12 |
| 11618 | 414.89 | 130.79 | 694.32 | 108.18 | 94.03 |
| 18338 | 72.29 | 20.32 | 112.46 | 9.87 | 94.03 |
| 15050 | 637.68 | 181.55 | 464.30 | 24.18 | 94.03 |
| 1608 | 12.70 | 29.99 | 54.74 | 9.39 | 93.99 |
| 24539 | 613.90 | 163.40 | 344.65 | 53.69 | 93.99 |

TABLE 5Y-continued

PAN Timepoint(s): 6, 24 hrs  
Atty. Docket No. 44921-5089US  
Doc. No. 1803440.1

| Identifier | NonToxMean | NonToxSD | ToxMean | ToxSD | LDAScore |
|---|---|---|---|---|---|
| 5900 | 265.48 | 65.87 | 137.54 | 40.46 | 93.99 |
| 13239 | 109.63 | 48.60 | 209.05 | 26.39 | 93.99 |
| 5163 | 20.12 | 13.08 | 44.33 | 7.38 | 93.82 |
| 21130 | 78.12 | 26.32 | 110.79 | 5.99 | 93.73 |
| 2236 | 140.10 | 38.70 | 215.23 | 16.78 | 93.69 |
| 5967 | 1225.74 | 339.49 | 1876.92 | 202.57 | 93.65 |
| 9799 | 145.09 | 50.35 | 241.50 | 35.40 | 93.56 |
| 16205 | 940.52 | 264.48 | 668.73 | 24.99 | 93.56 |
| 456 | 869.99 | 317.52 | 515.38 | 44.20 | 93.56 |
| 25097 | 4.68 | 10.99 | 25.79 | 8.52 | 93.52 |
| 12020 | 167.47 | 60.50 | 285.05 | 31.13 | 93.52 |
| 5924 | 162.21 | 46.91 | 256.59 | 29.67 | 93.52 |
| 4716 | 156.93 | 40.11 | 238.10 | 25.26 | 93.48 |
| 8339 | 432.55 | 130.90 | 704.91 | 90.15 | 93.43 |
| 5561 | 167.91 | 55.87 | 283.83 | 41.10 | 93.39 |
| 15112 | 1549.68 | 531.98 | 736.99 | 111.89 | 93.39 |
| 7278 | 1467.27 | 341.78 | 1077.40 | 67.94 | 93.35 |
| 7108 | 53.62 | 29.56 | 116.16 | 20.84 | 93.30 |
| 4956 | 79.01 | 38.21 | 153.60 | 24.20 | 93.30 |
| 20404 | 53.75 | 46.18 | 126.25 | 22.59 | 93.26 |
| 6049 | 621.00 | 123.14 | 541.13 | 9.05 | 93.22 |
| 9109 | 1021.28 | 337.87 | 723.36 | 26.27 | 93.22 |
| 4393 | 1268.21 | 369.74 | 824.30 | 42.57 | 93.18 |
| 18541 | 1081.46 | 298.74 | 758.66 | 24.93 | 93.13 |
| 15556 | 208.38 | 83.99 | 333.56 | 45.17 | 93.09 |
| 4589 | 1213.38 | 369.83 | 790.80 | 42.48 | 93.09 |
| 22271 | 273.68 | 65.98 | 411.42 | 75.15 | 93.05 |
| 21423 | 1355.28 | 427.17 | 786.98 | 56.19 | 93.05 |
| 6506 | 234.14 | 60.71 | 335.18 | 21.90 | 93.05 |
| 4290 | 94.34 | 28.53 | 147.53 | 19.36 | 93.05 |
| 20350 | 155.10 | 50.13 | 248.15 | 31.72 | 93.05 |
| 714 | 46.67 | 31.34 | 115.67 | 27.05 | 93.05 |
| 1485 | 93.58 | 57.35 | 198.96 | 32.55 | 93.00 |
| 18433 | 19.39 | 46.95 | 105.10 | 24.21 | 93.00 |
| 17567 | 1185.38 | 364.09 | 750.70 | 33.02 | 93.00 |
| 24615 | 817.72 | 230.83 | 583.06 | 24.71 | 92.96 |
| 15742 | 33.17 | 14.60 | 56.07 | 3.60 | 92.96 |
| 20766 | 56.29 | 20.07 | 93.49 | 10.52 | 92.92 |
| 15209 | 164.94 | 33.20 | 220.88 | 12.45 | 92.92 |
| 20879 | 87.79 | 50.58 | 180.08 | 38.06 | 92.88 |
| 19408 | 2011.27 | 675.11 | 1014.96 | 97.93 | 92.88 |
| 1247 | 1309.18 | 501.52 | 569.36 | 138.91 | 92.83 |
| 15299 | 88.50 | 61.88 | 119.48 | 12.69 | 92.83 |
| 11377 | 116.76 | 30.96 | 177.28 | 17.37 | 92.79 |
| 9037 | 22.39 | 16.20 | 56.28 | 11.77 | 92.79 |
| 24390 | 162.85 | 113.82 | 331.70 | 49.97 | 92.79 |
| 1550 | 30.09 | 69.61 | 60.64 | 8.26 | 92.79 |
| 1300 | 156.68 | 44.76 | 234.60 | 19.19 | 92.75 |
| 1585 | 67.71 | 33.38 | 128.60 | 16.01 | 92.70 |
| 25599 | 56.14 | 20.41 | 91.99 | 8.79 | 92.66 |
| 17524 | 1173.79 | 285.74 | 801.36 | 115.86 | 92.62 |
| 15122 | 420.86 | 89.65 | 588.05 | 45.81 | 92.58 |
| 25369 | 18.36 | 10.68 | 38.74 | 6.19 | 92.58 |
| 3886 | 58.10 | 28.84 | 117.74 | 22.59 | 92.53 |
| 643 | 61.37 | 32.91 | 119.52 | 18.91 | 92.53 |
| 14003 | 815.86 | 212.90 | 497.74 | 73.28 | 92.49 |
| 16164 | 1083.28 | 283.92 | 680.99 | 54.84 | 92.49 |
| 20864 | 1587.98 | 660.11 | 798.40 | 87.84 | 92.45 |
| 17742 | 1066.26 | 308.06 | 723.12 | 37.02 | 92.45 |
| 23248 | 37.67 | 17.23 | 53.27 | 3.03 | 92.45 |
| 17204 | 1732.06 | 656.42 | 888.59 | 86.53 | 92.45 |
| 24501 | 525.70 | 117.48 | 664.66 | 34.25 | 92.40 |
| 14125 | 128.41 | 50.32 | 217.38 | 25.88 | 92.36 |
| 5968 | 962.02 | 263.60 | 1474.27 | 231.26 | 92.36 |

TABLE 5Z

PAN Timepoint(s): 6, 24, 168 hrs  
Atty. Docket No. 44921-5089US  
Doc. No. 1803440.1

| Identifier | NonToxMean | NonToxSD | ToxMean | ToxSD | LDAScore |
|---|---|---|---|---|---|
| 15433 | 66.69 | 31.46 | 164.15 | 24.65 | 97.20 |
| 1962 | 33.08 | 26.68 | 80.19 | 11.69 | 95.26 |
| 16122 | 116.83 | 40.09 | 224.79 | 57.88 | 94.96 |
| 1247 | 1312.82 | 499.50 | 526.34 | 127.30 | 94.87 |
| 16853 | 67.23 | 22.82 | 120.51 | 22.86 | 94.83 |
| 17693 | 1260.09 | 375.71 | 656.50 | 74.07 | 94.78 |
| 13239 | 108.92 | 47.30 | 236.00 | 58.32 | 94.57 |
| 15112 | 1553.39 | 530.07 | 717.14 | 110.65 | 94.35 |
| 18433 | 18.80 | 46.13 | 126.18 | 39.27 | 94.35 |
| 16121 | 109.21 | 58.36 | 264.16 | 84.47 | 94.18 |
| 15701 | 37.56 | 16.60 | 76.48 | 12.40 | 94.05 |
| 19077 | 208.57 | 51.01 | 301.25 | 21.97 | 94.01 |
| 4723 | 1721.81 | 624.78 | 922.60 | 68.61 | 93.58 |
| 25097 | 4.60 | 10.95 | 24.13 | 7.34 | 93.23 |
| 7278 | 1469.82 | 340.27 | 993.59 | 122.75 | 93.23 |
| 1159 | 888.08 | 229.69 | 532.18 | 82.33 | 93.19 |
| 15184 | −80.88 | 50.16 | 76.70 | 82.34 | 93.07 |
| 456 | 871.69 | 317.12 | 499.51 | 56.17 | 92.97 |
| 1608 | 12.56 | 29.97 | 50.60 | 9.98 | 92.93 |
| 15437 | 38.06 | 21.84 | 118.82 | 46.29 | 92.69 |
| 225 | 122.71 | 33.55 | 235.76 | 49.22 | 92.51 |
| 14997 | 2605.00 | 1019.08 | 1218.22 | 195.95 | 92.46 |
| 15401 | 75.23 | 25.84 | 175.78 | 44.88 | 92.39 |
| 19408 | 2015.21 | 673.87 | 1049.53 | 100.77 | 92.20 |
| 18076 | 2552.08 | 1185.85 | 1116.73 | 165.36 | 91.90 |
| 18077 | 2630.74 | 1183.04 | 1067.76 | 130.98 | 91.72 |
| 15434 | 131.68 | 52.58 | 292.95 | 80.76 | 91.61 |
| 16211 | 2268.34 | 1131.65 | 761.93 | 145.25 | 91.51 |
| 11208 | 322.94 | 110.75 | 642.67 | 141.37 | 91.48 |
| 24651 | 100.37 | 23.09 | 169.86 | 33.73 | 91.48 |
| 16012 | 72.52 | 31.21 | 141.73 | 32.89 | 91.35 |
| 1542 | 928.57 | 263.76 | 548.27 | 84.14 | 91.34 |
| 14722 | 656.51 | 217.90 | 1314.74 | 367.97 | 91.31 |
| 4589 | 1215.64 | 368.99 | 748.52 | 72.66 | 91.21 |
| 17886 | 1506.14 | 491.91 | 843.64 | 96.88 | 91.16 |
| 17829 | 2232.91 | 1111.68 | 900.83 | 138.88 | 91.16 |
| 15673 | 804.12 | 164.51 | 1076.89 | 78.92 | 91.16 |
| 4312 | 76.92 | 38.49 | 154.79 | 22.22 | 91.09 |
| 2079 | 303.47 | 81.98 | 400.13 | 28.12 | 90.99 |
| 18694 | 53.10 | 48.50 | 177.05 | 53.91 | 90.96 |
| 18322 | 2673.81 | 811.21 | 1499.15 | 181.85 | 90.79 |
| 16168 | 350.70 | 206.64 | 479.34 | 84.79 | 90.78 |
| 17779 | 1958.43 | 783.05 | 911.49 | 158.95 | 90.73 |
| 8990 | 277.74 | 77.38 | 465.89 | 83.79 | 90.57 |
| 3434 | 322.35 | 138.05 | 614.67 | 136.42 | 90.57 |
| 18729 | 19.67 | 29.33 | 96.11 | 37.87 | 90.57 |
| 14003 | 817.64 | 211.58 | 458.34 | 85.08 | 90.53 |
| 22816 | 22.96 | 15.10 | 59.89 | 23.04 | 90.49 |
| 9799 | 144.50 | 49.47 | 258.44 | 54.08 | 90.49 |
| 1521 | 20.40 | 50.29 | 136.10 | 71.19 | 90.49 |
| 15886 | 302.74 | 61.73 | 436.98 | 44.28 | 90.45 |
| 16155 | 1084.95 | 423.63 | 632.04 | 54.95 | 90.43 |
| 1485 | 92.98 | 56.73 | 213.05 | 31.14 | 90.36 |
| 17204 | 1735.18 | 656.07 | 938.01 | 109.72 | 90.30 |
| 1203 | 4.95 | 18.70 | 44.90 | 22.64 | 90.27 |
| 19080 | 75.38 | 56.65 | 202.18 | 64.18 | 90.27 |
| 1622 | 2078.05 | 898.00 | 838.34 | 144.28 | 90.26 |
| 17712 | 858.75 | 187.72 | 604.46 | 57.40 | 90.26 |
| 19407 | 1533.63 | 471.44 | 919.83 | 109.37 | 90.26 |
| 4280 | 1275.34 | 435.07 | 698.85 | 97.31 | 90.22 |
| 635 | 1254.34 | 431.22 | 723.36 | 97.99 | 90.17 |
| 22554 | 544.56 | 150.27 | 343.47 | 69.26 | 90.17 |
| 11524 | −14.44 | 24.49 | 37.71 | 21.53 | 90.14 |
| 21703 | 16.32 | 12.14 | 42.83 | 13.13 | 90.10 |
| 14125 | 127.72 | 48.99 | 246.62 | 72.21 | 90.06 |
| 17480 | 119.30 | 33.27 | 190.90 | 31.79 | 90.01 |
| 23322 | 1169.31 | 283.61 | 760.72 | 114.86 | 89.96 |
| 8234 | 49.37 | 21.69 | 92.92 | 31.52 | 89.93 |
| 13682 | 176.92 | 61.79 | 309.18 | 50.37 | 89.89 |
| 11321 | 175.44 | 50.38 | 286.20 | 55.16 | 89.89 |
| 25253 | 291.91 | 64.62 | 414.09 | 38.27 | 89.71 |
| 23852 | 262.19 | 102.61 | 480.31 | 78.92 | 89.71 |
| 20781 | 57.13 | 21.07 | 88.06 | 13.32 | 89.70 |
| 1582 | 16.67 | 13.15 | 45.26 | 13.10 | 89.67 |

TABLE 5Z-continued

PAN  
Timepoint(s): 6, 24, 168 hrs  
Atty. Docket No. 44921-5089US  
Doc. No. 1803440.1

| Identifier | NonToxMean | NonToxSD | ToxMean | ToxSD | LDAScore |
|---|---|---|---|---|---|
| 24696 | 68.64 | 47.19 | 170.78 | 42.12 | 89.67 |
| 818 | 4144.91 | 2804.50 | 980.91 | 271.23 | 89.66 |
| 9109 | 1022.78 | 337.79 | 702.34 | 58.34 | 89.66 |
| 21708 | 36.51 | 16.01 | 73.22 | 15.22 | 89.63 |
| 17549 | 1309.92 | 366.25 | 854.17 | 88.86 | 89.61 |
| 16591 | 151.86 | 47.16 | 253.45 | 36.23 | 89.54 |
| 17154 | 198.88 | 57.70 | 280.48 | 33.03 | 89.53 |
| 14694 | 2332.83 | 1063.34 | 1038.43 | 256.02 | 89.48 |
| 23109 | 2093.27 | 924.06 | 1002.79 | 195.59 | 89.48 |
| 2236 | 139.93 | 38.69 | 200.68 | 21.94 | 89.48 |
| 22661 | 1310.36 | 418.55 | 756.78 | 88.01 | 89.48 |
| 7857 | 51.98 | 45.43 | 149.29 | 46.95 | 89.45 |
| 20876 | 1681.76 | 611.63 | 958.77 | 99.56 | 89.44 |
| 25468 | 2183.54 | 1132.38 | 823.42 | 189.02 | 89.44 |
| 23215 | 106.03 | 29.48 | 169.54 | 21.53 | 89.41 |
| 5900 | 265.96 | 65.56 | 144.68 | 40.70 | 89.41 |
| 1811 | 10.93 | 26.49 | 65.20 | 23.39 | 89.37 |
| 23709 | 2507.78 | 1197.86 | 1088.40 | 231.11 | 89.35 |
| 495 | 135.24 | 83.30 | 303.90 | 57.27 | 89.32 |
| 20998 | 161.29 | 73.65 | 276.37 | 48.32 | 89.32 |
| 17194 | 46.75 | 27.72 | 107.07 | 19.66 | 89.32 |
| 19327 | 88.98 | 29.10 | 144.83 | 20.18 | 89.28 |
| 18101 | 81.85 | 27.96 | 121.65 | 14.02 | 89.27 |
| 819 | 3112.24 | 1661.98 | 1015.34 | 283.90 | 89.27 |
| 3015 | 2325.38 | 988.40 | 1058.04 | 289.77 | 89.22 |
| 21355 | 374.22 | 118.21 | 598.37 | 91.02 | 89.20 |

TABLE 5AA

SEMUSTINE  
Timepoint(s): 168 hrs  
Atty. Docket No. 44921-5089US  
Doc. No. 1803440.1

| Identifier | NonToxMean | NonToxSD | ToxMean | ToxSD | LDAScore |
|---|---|---|---|---|---|
| 23830 | -3.74 | 14.74 | 24.13 | 2.44 | 98.46 |
| 2655 | 43.68 | 49.43 | 103.83 | 13.87 | 98.07 |
| 22547 | 15.31 | 164.20 | 55.98 | 7.70 | 97.99 |
| 21893 | 51.15 | 34.39 | 119.77 | 15.62 | 97.86 |
| 7806 | 52.07 | 19.62 | 68.71 | 1.17 | 97.73 |
| 7785 | 1830.12 | 494.30 | 1054.17 | 67.70 | 97.69 |
| 25705 | 455.94 | 115.83 | 667.36 | 30.91 | 97.64 |
| 22050 | 3163.82 | 930.45 | 2122.73 | 41.59 | 97.47 |
| 21443 | 103.90 | 53.37 | 35.53 | 5.08 | 97.26 |
| 23981 | 812.67 | 160.21 | 626.66 | 12.41 | 97.13 |
| 5733 | 12.64 | 47.16 | 51.31 | 11.73 | 97.13 |
| 8494 | 276.36 | 53.17 | 213.99 | 3.26 | 97.13 |
| 8901 | 25.65 | 33.31 | 2.82 | 0.93 | 97.13 |
| 7023 | 364.88 | 77.19 | 291.07 | 3.81 | 97.09 |
| 18353 | 113.25 | 70.77 | 275.16 | 28.92 | 97.04 |
| 3027 | 1129.65 | 333.83 | 1127.48 | 12.54 | 97.04 |
| 8177 | 3894.73 | 1495.61 | 2320.07 | 89.57 | 96.92 |
| 19398 | 4332.61 | 2167.49 | 2566.57 | 72.18 | 96.83 |
| 23626 | 71.43 | 37.20 | 159.26 | 19.40 | 96.83 |
| 18650 | 804.69 | 246.36 | 518.86 | 13.70 | 96.74 |
| 15627 | 5054.50 | 1946.06 | 3041.20 | 96.69 | 96.62 |
| 20757 | 413.88 | 222.48 | 607.95 | 51.66 | 96.53 |
| 2410 | 11.25 | 10.57 | 25.63 | 2.99 | 96.49 |
| 7274 | 576.90 | 150.70 | 364.54 | 16.30 | 96.44 |
| 26147 | 1030.83 | 225.21 | 645.26 | 49.87 | 96.32 |
| 3359 | 119.66 | 57.61 | 290.85 | 65.10 | 96.27 |
| 11994 | 104.13 | 23.52 | 63.18 | 4.39 | 96.06 |
| 7867 | 64.06 | 34.54 | 163.76 | 30.00 | 96.02 |
| 3701 | 90.19 | 44.20 | 111.89 | 2.06 | 95.93 |
| 23800 | 32.07 | 18.29 | 77.92 | 15.10 | 95.84 |
| 1684 | 2810.78 | 1628.26 | 2548.66 | 84.69 | 95.84 |
| 19162 | 2230.57 | 613.60 | 1498.90 | 56.20 | 95.84 |
| 14958 | 138.49 | 48.09 | 181.53 | 4.13 | 95.80 |
| 11454 | 238.93 | 79.65 | 379.87 | 38.25 | 95.76 |
| 7764 | 6.68 | 15.73 | 27.19 | 3.33 | 95.76 |
| 19993 | 2327.93 | 570.40 | 1514.68 | 94.53 | 95.76 |
| 9407 | 350.93 | 216.90 | 167.34 | 16.19 | 95.76 |

TABLE 5AA-continued

SEMUSTINE  
Timepoint(s): 168 hrs  
Atty. Docket No. 44921-5089US  
Doc. No. 1803440.1

| Identifier | NonToxMean | NonToxSD | ToxMean | ToxSD | LDAScore |
|---|---|---|---|---|---|
| 15600 | 772.34 | 211.63 | 480.10 | 25.98 | 95.76 |
| 22662 | 137.98 | 35.08 | 116.24 | 1.67 | 95.72 |
| 18142 | 1994.46 | 839.22 | 1965.70 | 25.18 | 95.63 |
| 7278 | 1466.77 | 341.68 | 1037.78 | 55.91 | 95.59 |
| 1685 | 9177.09 | 7104.79 | 4192.02 | 442.45 | 95.59 |
| 15136 | 720.68 | 229.89 | 618.26 | 7.44 | 95.50 |
| 17248 | 2563.75 | 537.86 | 1741.86 | 94.90 | 95.46 |
| 15301 | 38.66 | 68.20 | 52.95 | 4.33 | 95.46 |
| 24627 | 5024.80 | 1714.05 | 3187.73 | 133.28 | 95.46 |
| 16678 | 192.60 | 90.16 | 295.43 | 9.43 | 95.37 |
| 21798 | 2088.65 | 441.72 | 1574.36 | 40.27 | 95.37 |
| 3582 | 396.47 | 105.41 | 299.17 | 10.26 | 95.29 |
| 22618 | 28.62 | 11.98 | 54.72 | 9.80 | 95.24 |
| 20295 | 23.12 | 13.39 | -1.42 | 5.25 | 95.20 |
| 10269 | 1868.08 | 422.77 | 1408.13 | 42.28 | 95.16 |
| 7975 | 744.31 | 175.27 | 709.93 | 7.00 | 95.12 |
| 3090 | 308.90 | 80.19 | 389.68 | 9.44 | 95.07 |
| 8163 | 105.92 | 55.18 | 246.10 | 47.62 | 95.03 |
| 7337 | 130.17 | 35.83 | 72.98 | 11.19 | 95.03 |
| 5689 | 12.93 | 20.23 | 44.79 | 8.55 | 94.99 |
| 22737 | 204.61 | 104.35 | 375.42 | 54.48 | 94.94 |
| 4640 | 80.47 | 30.73 | 144.33 | 17.03 | 94.82 |
| 10819 | 1187.21 | 363.05 | 1125.76 | 18.01 | 94.82 |
| 3269 | 76.54 | 40.97 | 147.76 | 18.49 | 94.77 |
| 18468 | 90.58 | 33.19 | 99.23 | 1.85 | 94.77 |
| 6204 | 39.16 | 12.29 | 53.01 | 1.67 | 94.77 |
| 19372 | 61.97 | 54.00 | 9.74 | 2.20 | 94.73 |
| 21628 | 116.51 | 45.00 | 204.96 | 26.35 | 94.69 |
| 3075 | 523.79 | 180.19 | 291.98 | 21.30 | 94.69 |
| 8015 | 52.45 | 36.45 | 80.79 | 2.30 | 94.64 |
| 20105 | 80.00 | 53.71 | 27.37 | 3.94 | 94.64 |
| 18830 | 5928.33 | 2277.75 | 3404.34 | 229.07 | 94.60 |
| 12639 | 1231.40 | 359.71 | 1328.85 | 25.82 | 94.60 |
| 2697 | 1227.29 | 359.86 | 1375.72 | 25.94 | 94.56 |
| 2326 | 1442.32 | 399.30 | 866.19 | 98.10 | 94.56 |
| 9180 | 82.53 | 35.16 | 153.13 | 21.13 | 94.47 |
| 22838 | 1383.85 | 399.86 | 912.16 | 54.21 | 94.47 |
| 23509 | 2234.19 | 462.51 | 1771.07 | 42.02 | 94.47 |
| 23709 | 2494.50 | 1202.87 | 2200.91 | 59.43 | 94.34 |
| 2912 | 2618.16 | 709.02 | 1838.26 | 100.99 | 94.34 |
| 20944 | 1191.93 | 395.05 | 1322.96 | 34.77 | 94.30 |
| 25589 | 154.92 | 38.08 | 184.54 | 2.96 | 94.30 |
| 18800 | 2730.47 | 1166.13 | 1296.14 | 149.09 | 94.26 |
| 2311 | 22.96 | 16.01 | 54.56 | 12.04 | 94.17 |
| 410 | 1097.48 | 256.27 | 795.24 | 44.26 | 94.17 |
| 17885 | 246.73 | 58.07 | 148.75 | 13.01 | 94.13 |
| 21458 | 229.64 | 104.63 | 360.82 | 32.46 | 94.13 |
| 22069 | 689.12 | 145.53 | 514.75 | 17.18 | 94.13 |
| 3584 | 65.13 | 35.08 | 106.58 | 9.75 | 94.13 |
| 5968 | 966.61 | 265.81 | 609.81 | 49.16 | 94.04 |
| 19525 | 27.97 | 21.00 | 56.08 | 10.20 | 94.04 |
| 18757 | 250.38 | 72.47 | 327.68 | 9.19 | 94.00 |
| 19768 | 711.98 | 179.77 | 874.96 | 22.13 | 94.00 |
| 7392 | 29.06 | 15.76 | 62.61 | 15.61 | 94.00 |
| 10267 | 2119.14 | 891.88 | 2056.03 | 48.77 | 94.00 |
| 23190 | 70.87 | 28.52 | 103.79 | 5.80 | 93.96 |
| 25676 | 218.79 | 80.22 | 97.09 | 19.62 | 93.96 |

TABLE 5BB

SULFADIAZINE  
Timepoint(s): 24 hrs

| Identifier | NonToxMean | NonToxSD | ToxMean | ToxSD | LDAScore |
|---|---|---|---|---|---|
| 13158 | 464.71 | 105.53 | 185.18 | 11.81 | 99.83 |
| 2010 | 31.95 | 313.46 | 578.42 | 46.88 | 99.79 |
| 15535 | 445.86 | 80.88 | 792.83 | 41.28 | 99.74 |
| 1564 | 34.77 | 147.30 | 1395.56 | 106.27 | 99.70 |
| 4452 | 989.99 | 248.64 | 328.14 | 43.97 | 99.70 |

TABLE 5BB-continued

SULFADIAZINE
Timepoint(s): 24 hrs

| Identifier | NonToxMean | NonToxSD | ToxMean | ToxSD | LDAScore |
|---|---|---|---|---|---|
| 4450 | 282.32 | 50.39 | 113.73 | 16.34 | 99.61 |
| 20700 | 81.27 | 404.57 | 1604.45 | 209.39 | 99.61 |
| 20481 | 208.68 | 44.26 | 81.56 | 7.25 | 99.57 |
| 25686 | 666.44 | 155.98 | 1348.56 | 47.39 | 99.53 |
| 5695 | 1559.28 | 402.43 | 636.16 | 43.80 | 99.53 |
| 6477 | 13.20 | 160.91 | 187.40 | 49.13 | 99.53 |
| 17101 | 352.23 | 77.89 | 621.28 | 16.27 | 99.49 |
| 15175 | 318.83 | 49.56 | 153.62 | 12.70 | 99.49 |
| 20699 | 90.33 | 220.48 | 1192.64 | 109.71 | 99.49 |
| 6478 | 22.55 | 383.52 | 251.88 | 88.78 | 99.44 |
| 725 | 117.71 | 45.62 | 14.15 | 2.76 | 99.44 |
| 645 | 151.16 | 54.99 | 17.82 | 6.85 | 99.44 |
| 3987 | 192.50 | 47.15 | 465.13 | 55.22 | 99.44 |
| 21947 | 752.67 | 136.25 | 319.39 | 29.30 | 99.40 |
| 17291 | 1389.57 | 412.30 | 482.86 | 101.58 | 99.40 |
| 238 | 227.68 | 51.22 | 496.72 | 69.45 | 99.36 |
| 20887 | 794.18 | 312.69 | 103.79 | 42.68 | 99.36 |
| 1558 | 203.57 | 58.77 | 553.28 | 64.74 | 99.36 |
| 17661 | 255.29 | 58.73 | 540.05 | 70.79 | 99.36 |
| 16947 | 320.42 | 79.17 | 77.47 | 19.86 | 99.36 |
| 16204 | 752.56 | 177.92 | 1702.82 | 145.45 | 99.36 |
| 18906 | 255.45 | 83.89 | 55.16 | 8.36 | 99.36 |
| 17357 | 269.77 | 81.23 | 2.53 | 12.73 | 99.31 |
| 17514 | 859.90 | 174.50 | 359.55 | 37.03 | 99.31 |
| 16416 | 22.83 | 18.51 | 84.23 | 3.30 | 99.27 |
| 2085 | 688.34 | 191.75 | 339.59 | 20.82 | 99.27 |
| 7101 | 380.51 | 644.25 | 3330.36 | 683.13 | 99.27 |
| 18278 | 1896.72 | 507.81 | 639.93 | 108.91 | 99.27 |
| 25718 | 392.38 | 80.21 | 851.19 | 103.08 | 99.23 |
| 1478 | 352.13 | 79.44 | 88.92 | 22.22 | 99.23 |
| 9621 | 292.01 | 59.49 | 563.88 | 51.66 | 99.23 |
| 23596 | 1491.59 | 375.55 | 487.23 | 90.69 | 99.23 |
| 20884 | 637.92 | 258.49 | 19.93 | 9.59 | 99.23 |
| 10016 | 207.78 | 73.01 | 590.63 | 39.54 | 99.23 |
| 7665 | 282.42 | 91.44 | 861.31 | 113.78 | 99.19 |
| 472 | 661.53 | 177.31 | 345.51 | 23.33 | 99.19 |
| 18597 | 521.43 | 162.83 | 914.02 | 31.92 | 99.19 |
| 4222 | 545.41 | 102.20 | 1014.25 | 79.67 | 99.19 |
| 20886 | 719.84 | 291.88 | 50.84 | 41.81 | 99.19 |
| 1884 | 178.24 | 37.12 | 331.54 | 22.95 | 99.19 |
| 1422 | 297.77 | 88.40 | 75.68 | 10.49 | 99.19 |
| 17104 | 449.21 | 107.90 | 1060.31 | 149.95 | 99.14 |
| 17907 | 1319.66 | 300.38 | 623.40 | 49.85 | 99.14 |
| 17284 | 229.07 | 60.08 | 77.02 | 16.01 | 99.14 |
| 8981 | 142.60 | 87.32 | 716.17 | 136.32 | 99.14 |
| 4451 | 290.54 | 64.21 | 76.77 | 27.51 | 99.14 |
| 15955 | 751.14 | 196.31 | 146.28 | 35.67 | 99.10 |
| 16419 | 306.72 | 58.43 | 562.97 | 56.12 | 99.10 |
| 16627 | 97.46 | 34.41 | 213.43 | 14.92 | 99.10 |
| 22592 | 234.18 | 163.38 | 903.10 | 59.07 | 99.10 |
| 19824 | 224.78 | 67.21 | 32.81 | 20.42 | 99.10 |
| 9905 | 674.04 | 138.26 | 279.49 | 36.23 | 99.10 |
| 15002 | 139.13 | 94.64 | 580.42 | 72.97 | 99.10 |
| 812 | 157.04 | 34.99 | 39.35 | 14.07 | 99.10 |
| 15193 | 172.71 | 60.15 | 463.80 | 40.10 | 99.10 |
| 11205 | 596.04 | 192.04 | 155.98 | 25.86 | 99.10 |
| 17535 | 246.41 | 64.45 | 529.14 | 76.63 | 99.06 |
| 4360 | 330.80 | 65.83 | 138.60 | 23.78 | 99.06 |
| 5667 | 742.84 | 172.36 | 1513.63 | 136.63 | 99.06 |
| 20056 | 309.09 | 59.92 | 81.20 | 26.34 | 99.06 |
| 11081 | 352.98 | 113.10 | 740.48 | 49.43 | 99.06 |
| 3916 | 738.87 | 186.54 | 212.10 | 43.88 | 99.06 |
| 1801 | 97.49 | 29.02 | 212.29 | 21.51 | 99.06 |
| 25317 | 15.28 | 68.43 | 72.14 | 39.26 | 99.06 |
| 24501 | 524.69 | 114.42 | 955.66 | 63.01 | 99.06 |
| 19508 | 100.97 | 41.09 | 11.48 | 5.01 | 99.06 |
| 19769 | 63.82 | 80.07 | 487.54 | 129.83 | 99.01 |
| 25546 | 473.54 | 139.58 | 193.05 | 34.65 | 99.01 |
| 10878 | 951.05 | 250.12 | 1714.95 | 105.09 | 99.01 |
| 10819 | 1183.30 | 358.76 | 2036.62 | 53.76 | 99.01 |
| 18507 | 701.19 | 159.97 | 1396.26 | 108.52 | 98.97 |
| 2915 | 87.36 | 36.13 | 206.79 | 19.36 | 98.97 |
| 15003 | 34.41 | 91.73 | 507.05 | 83.25 | 98.97 |
| 2583 | 369.08 | 148.55 | 848.08 | 90.80 | 98.97 |
| 9620 | 529.25 | 111.98 | 1071.29 | 125.35 | 98.97 |
| 19298 | 364.57 | 96.71 | 819.01 | 116.31 | 98.97 |
| 6614 | 478.70 | 150.19 | 97.33 | 35.20 | 98.97 |
| 15986 | 320.13 | 83.84 | 46.97 | 24.78 | 98.97 |
| 13646 | 727.39 | 191.95 | 1634.83 | 174.87 | 98.93 |
| 240 | 184.44 | 53.70 | 394.90 | 58.94 | 98.93 |
| 16675 | 33.18 | 31.66 | 226.87 | 74.32 | 98.93 |
| 11968 | 297.46 | 82.47 | 94.28 | 17.16 | 98.93 |
| 17540 | 561.49 | 199.04 | 1593.99 | 230.39 | 98.93 |
| 19161 | 1068.85 | 309.26 | 2020.78 | 120.96 | 98.93 |
| 23924 | 208.78 | 62.50 | 465.78 | 53.25 | 98.93 |
| 4482 | 227.17 | 73.35 | 67.19 | 17.67 | 98.93 |
| 5199 | 611.50 | 182.04 | 158.54 | 39.19 | 98.93 |
| 117 | 21.06 | 17.59 | -12.77 | 2.61 | 98.89 |
| 22536 | 1715.17 | 473.49 | 3319.42 | 278.50 | 98.89 |
| 17100 | 819.32 | 235.74 | 1519.10 | 85.28 | 98.89 |
| 14332 | 537.23 | 133.39 | 1143.62 | 152.21 | 98.89 |
| 5232 | 365.72 | 93.58 | 160.50 | 9.58 | 98.89 |
| 10561 | 78.49 | 36.71 | 188.47 | 14.45 | 98.89 |
| 15098 | 185.41 | 66.49 | 32.78 | 6.96 | 98.89 |
| 3401 | 14.24 | 21.17 | 144.41 | 52.94 | 98.89 |

TABLE 5CC

SULFADIAZINE
Timepoint(s): 3, 6 hrs

| Identifier | NonToxMean | NonToxSD | ToxMean | ToxSD | LDAScore |
|---|---|---|---|---|---|
| 2459 | 327.82 | 133.31 | 1186.99 | 180.16 | 99.44 |
| 985 | 18.91 | 23.49 | 435.93 | 226.01 | 99.36 |
| 6054 | 24.46 | 35.46 | 463.67 | 144.11 | 99.18 |
| 21546 | -60.81 | 78.07 | 461.08 | 143.78 | 99.14 |
| 11259 | 101.27 | 105.67 | 1117.26 | 304.40 | 99.05 |
| 223 | 10.81 | 16.39 | 121.57 | 31.76 | 99.05 |
| 13745 | 27.17 | 26.30 | 236.39 | 104.08 | 99.05 |
| 8304 | 263.66 | 68.46 | 104.04 | 18.52 | 99.05 |
| 2154 | 54.19 | 102.13 | 766.15 | 271.93 | 98.93 |
| 6585 | 635.65 | 314.22 | 2778.88 | 622.70 | 98.80 |
| 17506 | 33.02 | 28.55 | 170.00 | 54.28 | 98.80 |
| 2153 | 179.20 | 124.41 | 1217.91 | 474.19 | 98.75 |
| 23872 | 47.29 | 87.73 | 387.10 | 112.60 | 98.71 |
| 15301 | 35.41 | 55.60 | 466.69 | 146.16 | 98.67 |
| 15192 | 164.68 | 117.96 | 858.98 | 208.00 | 98.67 |
| 17327 | 209.40 | 86.17 | 531.34 | 65.50 | 98.62 |
| 15300 | 131.96 | 108.91 | 967.46 | 264.07 | 98.62 |
| 7700 | 80.97 | 38.43 | 377.20 | 103.65 | 98.58 |
| 13930 | 128.33 | 69.33 | 520.74 | 123.87 | 98.54 |
| 10659 | 128.90 | 79.62 | 602.71 | 192.55 | 98.54 |
| 7197 | 195.08 | 78.35 | 557.25 | 113.13 | 98.37 |
| 19060 | 150.81 | 79.81 | 399.19 | 134.24 | 98.32 |
| 15299 | 86.11 | 52.88 | 422.06 | 161.10 | 98.28 |
| 355 | 10.95 | 13.39 | 102.92 | 40.18 | 98.28 |
| 7196 | 178.85 | 80.11 | 517.52 | 81.96 | 98.28 |
| 25730 | 196.00 | 64.30 | 513.70 | 106.95 | 98.24 |
| 5356 | -12.88 | 18.58 | 46.77 | 19.05 | 98.19 |
| 19657 | 3.19 | 17.88 | 84.23 | 34.61 | 98.15 |
| 25084 | -12.38 | 22.65 | 46.65 | 25.44 | 98.11 |
| 1501 | 58.67 | 53.51 | 250.18 | 120.56 | 98.02 |
| 17908 | 62.13 | 58.89 | 240.27 | 66.39 | 97.98 |
| 16314 | 43.27 | 38.63 | 240.75 | 61.16 | 97.94 |
| 2555 | 95.85 | 44.10 | 292.92 | 71.25 | 97.94 |
| 21682 | -35.82 | 31.41 | 50.22 | 26.54 | 97.89 |
| 5384 | 40.19 | 41.73 | 218.67 | 41.90 | 97.89 |
| 22626 | 83.22 | 71.71 | 465.98 | 192.17 | 97.85 |
| 11483 | 64.30 | 44.10 | 197.71 | 47.03 | 97.85 |
| 16053 | 229.00 | 93.51 | 658.28 | 200.15 | 97.81 |
| 4045 | 93.63 | 47.19 | 244.15 | 46.42 | 97.81 |

TABLE 5CC-continued

SULFADIAZINE
Timepoint(s): 3, 6 hrs

| Identifier | NonToxMean | NonToxSD | ToxMean | ToxSD | LDAScore |
|---|---|---|---|---|---|
| 804 | 454.28 | 182.83 | 934.61 | 83.33 | 97.76 |
| 8874 | 118.37 | 60.25 | 305.67 | 73.98 | 97.76 |
| 23314 | 62.72 | 247.80 | 1403.77 | 543.62 | 97.76 |
| 21 | 69.73 | 31.90 | 161.45 | 47.41 | 97.76 |
| 22681 | 218.11 | 182.12 | 981.97 | 310.38 | 97.72 |
| 7471 | 219.05 | 63.97 | 421.52 | 40.74 | 97.72 |
| 13240 | 475.09 | 362.91 | 2390.71 | 790.75 | 97.68 |
| 1340 | 192.32 | 49.81 | 108.32 | 15.13 | 97.64 |
| 16312 | 54.74 | 33.76 | 197.76 | 42.24 | 97.59 |
| 11876 | 107.52 | 40.42 | 242.85 | 40.07 | 97.46 |
| 20161 | 38.17 | 33.28 | 150.28 | 32.80 | 97.46 |
| 15996 | 49.41 | 38.61 | 170.53 | 42.38 | 97.42 |
| 12978 | 105.07 | 45.80 | 334.16 | 95.16 | 97.42 |
| 14179 | 49.88 | 26.28 | 132.84 | 24.19 | 97.38 |
| 12534 | 87.91 | 36.00 | 223.28 | 65.14 | 97.38 |
| 21779 | 147.51 | 35.16 | 262.54 | 35.74 | 97.29 |
| 11979 | 210.67 | 69.55 | 85.98 | 17.52 | 97.25 |
| 17161 | 1152.09 | 406.69 | 2288.34 | 334.10 | 97.25 |
| 11434 | 326.14 | 103.27 | 663.21 | 132.01 | 97.12 |
| 6844 | 124.34 | 58.18 | 17.91 | 11.06 | 97.12 |
| 22 | 53.08 | 46.64 | 206.89 | 59.81 | 97.12 |
| 3464 | 165.60 | 53.31 | 329.80 | 63.59 | 97.08 |
| 3434 | 322.01 | 136.13 | 755.72 | 108.22 | 97.08 |
| 22248 | 243.91 | 118.15 | 625.27 | 179.46 | 97.03 |
| 9423 | 937.34 | 251.31 | 1765.27 | 274.26 | 97.03 |
| 21683 | 34.05 | 23.48 | 105.62 | 26.60 | 96.95 |
| 16527 | 51.16 | 16.84 | 24.15 | 3.25 | 96.90 |
| 4512 | 1.04 | 32.53 | 73.93 | 19.11 | 96.86 |
| 4725 | 81.40 | 55.94 | 245.03 | 66.25 | 96.78 |
| 21239 | 114.57 | 59.35 | 256.57 | 37.93 | 96.78 |
| 17329 | 213.88 | 104.30 | 531.44 | 105.41 | 96.65 |
| 13467 | 37.67 | 24.44 | 111.98 | 36.67 | 96.56 |
| 15089 | 179.58 | 77.35 | 389.68 | 58.33 | 96.56 |
| 3454 | 86.52 | 35.67 | 198.35 | 31.79 | 96.47 |
| 20523 | 547.69 | 149.96 | 965.84 | 112.80 | 96.43 |
| 15058 | 197.84 | 70.39 | 377.22 | 46.94 | 96.35 |
| 14492 | 613.89 | 164.78 | 1076.44 | 162.75 | 96.35 |
| 12999 | 128.09 | 33.18 | 203.14 | 17.45 | 96.30 |
| 22967 | 163.84 | 54.49 | 255.51 | 13.19 | 96.26 |
| 18008 | 1.51 | 16.75 | 42.22 | 12.38 | 96.26 |
| 24640 | 177.45 | 57.95 | 357.46 | 73.86 | 96.26 |
| 7913 | 55.20 | 20.69 | 108.16 | 18.70 | 96.17 |
| 2625 | 141.92 | 31.66 | 87.09 | 9.03 | 96.17 |
| 3049 | 201.89 | 100.36 | 461.30 | 105.24 | 96.17 |
| 18011 | 31.95 | 28.60 | 105.17 | 25.57 | 96.13 |
| 23834 | 71.40 | 23.40 | 137.38 | 25.69 | 96.09 |
| 19818 | 32.37 | 21.21 | 85.97 | 15.20 | 96.04 |
| 12673 | 37.51 | 22.58 | 99.74 | 25.41 | 96.04 |
| 15377 | 25.91 | 15.53 | 56.38 | 6.78 | 96.00 |
| 12745 | 330.67 | 112.37 | 623.69 | 81.74 | 96.00 |
| 14111 | 150.33 | 66.27 | 327.97 | 47.79 | 96.00 |
| 11157 | 681.75 | 178.91 | 356.49 | 80.44 | 96.00 |
| 23166 | 134.04 | 62.51 | 266.56 | 54.48 | 95.96 |
| 3519 | 375.54 | 125.21 | 690.15 | 176.36 | 95.87 |
| 16124 | 420.65 | 131.40 | 193.12 | 32.21 | 95.83 |
| 17800 | 204.49 | 42.25 | 108.97 | 22.01 | 95.79 |
| 8639 | 368.08 | 97.97 | 620.44 | 125.57 | 95.79 |
| 25090 | 83.00 | 43.32 | 203.07 | 48.58 | 95.79 |
| 15191 | 2005.55 | 1208.87 | 3819.43 | 343.39 | 95.74 |
| 7469 | 286.95 | 67.51 | 149.39 | 36.61 | 95.70 |
| 21238 | −17.22 | 39.01 | 55.57 | 20.45 | 95.70 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07426441B2). An electronic copy of the "Sequence Listing" will also be available from the USPTO upon request and payment of the fee set forth in 37 CFR 1.19(b)(3).

We claim:

1. A method for predicting the renal toxicity of a test compound, comprising:
   (a) preparing a normalized gene expression profile of at least ten genes for a rat kidney tissue or rat kidney cell sample, wherein the gene expression profile contains the differential gene expression values for said at least ten genes upon exposure to the test compound, and wherein said at least ten genes are listed in one of Tables 5-5CC;
   (b) comparing the gene expression profile to a renal toxicity model, the renal toxicity model comprising:
      (i) the normalized mean expression levels of said at least ten genes in kidney tissue or kidney cells exposed to a known renal toxin, and
      (ii) the normalized mean expression levels of said at least ten genes in unexposed kidney tissue or kidney cells; and
      (iii) information from one or more of Tables 5-5CC;
   (c) scoring the comparison to predict whether the test compound is a renal toxin; and
   (d) presenting the prediction.

2. The method of claim 1, wherein the gene expression profile comprises the levels of expression for at least 50 genes from Tables 5-5CC.

3. The method of claim 1, wherein the gene expression profile comprises the levels of expression for at least 100 genes from Tables 5-5CC.

4. The method of claim 1, wherein the kidney tissue or kidney cells are exposed to the test compound in vivo.

5. The method of claim 1, wherein the known renal toxin is associated with one or more of nephritis, kidney necrosis, glomerular or tubular injury, and focal segmental glomerulosclerosis.

6. The method of claim 1, wherein the known renal toxin is selected from the group consisting of cephaloridine, cisplatin, puromycin aminonucleoside (PAN), bromoethylamine hydrobromide (BEA), ifosfamide, cyclophosphamide, carboplatin, AY-25329, indomethacin, acyclovir, citrinin, mercuric chloride, diflunisal, cidofovir, pamidronate, lithium chloride, hydralazine, colchicine, sulfadiazine, captopril, semustine and adriamycin.

7. The method of claim 1, wherein the gene expression profile and the renal toxicity model are produced by hybridization of nucleic acids to a microarray.

8. The method of claim 1, wherein the scoring comprises determining whether the test compound induces a change in the expression of each of said at least ten genes in the same direction as the known renal toxin.

9. The method of claim 1, wherein preparing a normalized gene expression profile comprises hybridizing RNA from the kidney tissue or kidney cell sample to a panel of nucleic acid probes.

10. The method of claim 6, wherein the gene expression profile and the renal toxicity model are produced by hybridization of nucleic acids to a microarray.

11. The method of claim 6, wherein the scoring comprises determining whether the test compound induces a change in the expression of each of said at least ten genes in the same direction as the known renal toxin.

12. The method of claim 6, wherein preparing a normalized gene expression profile comprises hybridizing RNA from the kidney tissue or kidney cell sample to a panel of nucleic acid probes.

13. The method of claim 6, wherein said information from one or more of Tables 5-5CC are Tox and NonTox mean values.

14. The method of claim 6, wherein the renal toxicity model comprises the Tox and NonTox mean values in Tables 5-5CC.

* * * * *